(12) United States Patent
Bursavich et al.

(10) Patent No.: US 11,174,228 B2
(45) Date of Patent: *Nov. 16, 2021

(54) ANTAGONISTS OF HUMAN INTEGRIN (α4)(β7)

(71) Applicant: Morphic Therapeutic, Inc., Waltham, MA (US)

(72) Inventors: Matthew G. Bursavich, Needham, MA (US); Dawn M. Troast, Bedford, MA (US); Bryce A. Harrison, Framingham, MA (US); Blaise S. Lippa, Newton, MA (US); Bruce N. Rogers, Belmont, MA (US); Kyle D. Konze, Brooklyn, NY (US); Aleksey I. Gerasyuto, Flemington, NJ (US); Tyler Day, New York, NY (US); Fu-Yang Lin, Sudbury, MA (US); Kristopher N. Hahn, Medford, MA (US); Mats A. Svensson, New York, NY (US); Byungchan Kim, West New York, NJ (US); Cheng Zhong, Belmont, MA (US); Alexey A. Lugovskoy, Belmont, MA (US); Brian Sosa, Cambridge, MA (US)

(73) Assignee: Morphic Therapeutic, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/939,812

(22) Filed: Jul. 27, 2020

(65) Prior Publication Data

US 2020/0385352 A1 Dec. 10, 2020

Related U.S. Application Data

(63) Continuation of application No. 16/382,512, filed on Apr. 12, 2019, now Pat. No. 10,759,756.

(60) Provisional application No. 62/656,742, filed on Apr. 12, 2018.

(51) Int. Cl.
| | | |
|---|---|---|
| C07D 401/12 | (2006.01) |
| A61K 31/4545 | (2006.01) |
| C07D 213/64 | (2006.01) |
| C07D 401/06 | (2006.01) |
| C07D 413/14 | (2006.01) |
| C07D 401/14 | (2006.01) |
| C07D 241/18 | (2006.01) |
| C07D 413/12 | (2006.01) |
| C07D 487/04 | (2006.01) |
| C07D 239/90 | (2006.01) |
| C07D 237/32 | (2006.01) |
| C07D 205/08 | (2006.01) |
| C07D 471/04 | (2006.01) |

(52) U.S. Cl.
CPC ........ *C07D 213/64* (2013.01); *C07D 205/08* (2013.01); *C07D 237/32* (2013.01); *C07D 239/90* (2013.01); *C07D 241/18* (2013.01); *C07D 401/06* (2013.01); *C07D 401/12* (2013.01); *C07D 401/14* (2013.01); *C07D 413/12* (2013.01); *C07D 413/14* (2013.01); *C07D 471/04* (2013.01); *C07D 487/04* (2013.01)

(58) Field of Classification Search
CPC C07D 401/12; C07D 401/14; A61K 31/4545; A61K 31/444
USPC .......... 546/194, 261; 544/238; 514/318, 335
See application file for complete search history.

(56) References Cited

U.S. PATENT DOCUMENTS

| | | |
|---|---|---|
| 5,721,366 A | 2/1998 | Abood et al. |
| 5,981,492 A | 11/1999 | Zoller et al. |
| 6,294,562 B1 | 9/2001 | Stilz et al. |
| 6,645,939 B1 | 11/2003 | Durette et al. |
| 6,723,711 B2 | 4/2004 | Biediger et al. |
| 6,972,296 B2 | 12/2005 | Biediger et al. |
| 7,807,167 B2 | 10/2010 | Taylor et al. |
| 7,972,775 B2 | 7/2011 | Rubin et al. |
| 9,493,567 B2 | 11/2016 | Lieberburg |
| 9,873,742 B2 | 1/2018 | Keir et al. |
| 10,233,245 B2 | 3/2019 | Lieberburg |
| 10,246,451 B2 | 4/2019 | Biediger et al. |
| 10,273,542 B2 | 4/2019 | Hackney et al. |
| 10,494,367 B2 | 12/2019 | Biediger et al. |
| 10,759,756 B2 * | 9/2020 | Bursavich ............ C07D 239/90 |
| 2003/0199692 A1 | 10/2003 | Biediger et al. |
| 2004/0009169 A1 | 1/2004 | Taylor et al. |
| 2004/0010023 A1 | 1/2004 | Stahle et al. |
| 2007/0025989 A1 | 2/2007 | Taylor et al. |
| 2011/0064729 A1 | 3/2011 | Taylor et al. |
| 2014/0120084 A1 | 5/2014 | Anand et al. |

(Continued)

FOREIGN PATENT DOCUMENTS

| | | |
|---|---|---|
| EP | 1213288 A1 | 6/2002 |
| WO | WO-98/16524 A1 | 4/1998 |

(Continued)

OTHER PUBLICATIONS

Form 2 "VLA-4 Antagonists," The Patents Act 1970 (39 of 1970 & The Patent Rule, 2003), Ranbaxy Laboratories Limited 1-19 (2005).

(Continued)

*Primary Examiner* — Charanjit Aulakh
(74) *Attorney, Agent, or Firm* — Foley Hoag LLP; Dana M. Gordon; Lawrence P. Tardibono

(57) ABSTRACT

Disclosed are small molecule antagonists of α4β7 integrin, and methods of using them to treat a number of specific diseases or conditions.

20 Claims, 57 Drawing Sheets

(56) References Cited

U.S. PATENT DOCUMENTS

| | | |
|---|---|---|
| 2015/0152182 A1 | 6/2015 | Taylor et al. |
| 2017/0306026 A1 | 10/2017 | Taylor et al. |
| 2018/0086833 A1 | 3/2018 | Hassanali et al. |
| 2020/0148773 A1 | 5/2020 | Taylor et al. |
| 2020/0385352 A1 | 12/2020 | Bursavich et al. |

FOREIGN PATENT DOCUMENTS

| | | |
|---|---|---|
| WO | WO-98/16547 A1 | 4/1998 |
| WO | WO-99/36393 A1 | 7/1999 |
| WO | WO-2000/068188 A1 | 11/2000 |
| WO | WO-01/21584 A1 | 3/2001 |
| WO | WO-2002/16328 A1 | 2/2002 |
| WO | WO-2003/040173 A1 | 5/2003 |
| WO | WO-03/072040 A2 | 9/2003 |
| WO | WO-2006/026759 A2 | 3/2006 |
| WO | WO-2006/126529 A1 | 11/2006 |
| WO | WO-2006/126637 A1 | 11/2006 |
| WO | WO-2006/131200 A1 | 12/2006 |
| WO | WO-2010/091411 A1 | 8/2010 |
| WO | WO-2012/135589 A1 | 10/2012 |
| WO | WO-2016/011940 A1 | 1/2016 |
| WO | WO-2016/138207 A1 | 9/2016 |
| WO | WO-2019/200202 A1 | 10/2019 |
| WO | WO-2020/092375 A1 | 5/2020 |
| WO | WO-2020/092383 A1 | 5/2020 |
| WO | WO-2020/092394 A1 | 5/2020 |
| WO | WO-2020/092401 A1 | 5/2020 |
| WO | WO-2021/076890 A1 | 4/2021 |
| WO | WO-2021/076902 A1 | 4/2021 |

OTHER PUBLICATIONS

International Search Report and Written Opinion for International Application No. PCT/US2019/27141 dated Aug. 16, 2019.
Sattigeri et al., "Synthesis and biological evaluation of ureido derivatives as VLA-4 antagonists," Ind J Chem 45B:2534-2541 (2006).
Sircar et al., "Synthesis and SAR of N-Benzoyl-I-Biphenylalanine Derivatives: Discovery of TR-14035, A Dual a4β7/a4β1 Integrin Antagonist," Bioorganic & Medicinal Chemistry, 10(6): 2051-2066 (2002).
Stilz et al., "Discovery of an Orally Active Non-Peptide Fibrinogen Receptor Antagonist," J Med Chem 39:2118-2122 (1996).
Wong et al., "Morphic persents positive preclinical data supporting MORF-057 as an oral inhibitor of the α4β7 integrin and potential treatment for inflammatory bowel disease," Morphic Therapeutic, Feb. 14, 2020.
Wong et al., "Morphic therapeutic presents positive preclinical data supporting development of MORF-057 in inflammatory bowel disease at digestive disease week 2020," Morphic Therapeutic, Jun. 29, 2020.
Wong et al., "Preclinical characterization of an oral small molecule inhibitor targeting the integrin A4B7 for the treatment of inflammatory bowel diseases (IBD)," May 20, 2020.
"Athena Neurosciences Antibody Shows Progress in MS Model," Dow Jones News Service Nov. 14, 1994.
Bjorkesten et al., "Surrogate markers and clinical indices, alone or combined, as indicators for endoscopic remission in anti-TNF-treated luminal Crohn's disease," Scandinavian Journal of Gastroenterology, 47(5): 528-537 (2012).
ClinicalTrials.gov, "Study of MORF 057 to Evaluate Single and Multi Ascending Doses in Healthy Volunteers," Identifier: NCT04580745, Publication date: Oct. 8, 2020.
Ferrante et al., "Validation of Endoscopic Activity Scores in Patients With Crohn's Disease Based on a Post Hoc Analysis of Data From SONIC," Gastroenterology, 145: 978-986 (2013).
International Search Report and Written Opinion for International Application No. PCT/US2020/056001 dated Dec. 8, 2020.
Invitation to Pay Additional Fees for International Application No. PCT/US2020/055986 dated Dec. 8, 2020.
Kapp et al., "Integrin modulators: a patent review," Expert Opinion on Therapeutic Patents, 23(10): 1273-1295 (2013).
Kent et al., "A monoclonal antibody to α4-integrin reverses the MR-detectable signs of experimental allergic encephalomyelitis in the Guinea pig," JMRI, 5(5): 535-540 (1995).
Li et al., "α4β7 integrin inhibitors: a patent review," Expert Opinion on Therapeutic Patents, 28(12): 903-917 (2018).
Moskovotz et al., "Defining and Validating Cut-Off's for the Simple Endoscopic Score for Crohn's Disease," Gastroenterology, 132:S1097 (2007).
PubChem CID 10162717, "(3S)-3-[2-(3-Benzyl-5-methyl-2-oxopyridin-1-yl)hexanoylamino]-3-(3-fluorophenyl)propanoic acid," Created Oct. 25, 2006.
Tubridy et al., "The effect of anti-α4 integrin antibody on brain lesion activity in MS," Neurology, 53(3): 466-472 (1999).
Written Opinion for International Application No. PCT/US2019/058573 dated May 7, 2020.
Notice of Allowance for U.S. Appl. No. 17/072,797 dated Jun. 16, 2021.
Arndt et al., "Peptide derived non-peptidic α4β7-integrin antagonists," Peptides 2002: 4 pages (2002).
Gottschling et al., "Combinatorial and Rational Strategies to Develop Nonpeptidic α4β7-Integrin Antagonists from Cyclic Peptides," Angew. Chem. Int. Ed., 41 (16): 3007-3011 (2002).
Notice of Allowance for U.S. Appl. No. 17/072,797 dated Mar. 3, 2021.
Mangada et al., "Translational Biomarkers For Selective, Oral, Small Molecule α4β7 Inhibitor MORF-057," Morphic Therapeutic, UEG Week 2020 Abstract Submission: 2 pages (2020).
International Search Report and Written Opinion for International Application No. PCT/US2020/055986 dated Feb. 9, 2021.
Pubchem, SID 245847741, Modify Date: Jun. 25, 2015 [retrieved on Jan. 15, 2021], Retrieved from the Internet <URL:https://pubchem.ncbi.nlm.nih.gov/substance/245847741>.

\* cited by examiner

α4β7 IC₅₀ Values
A: 0.5 nM < IC$_{50}$ < 10 nM
B: 10 nM < IC$_{50}$ < 50 nM
C: 50 nM < IC$_{50}$ < 100 nM
D: 100 nM < IC$_{50}$ < 500 nM
| COMPOUNDS | IC50 [nM] |
|---|---|
| 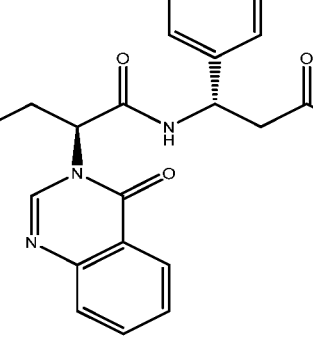 | A |
| 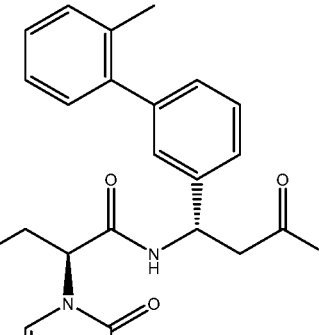 | B |
| 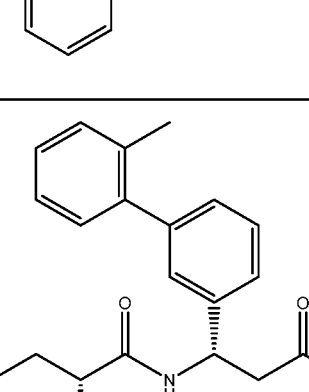 | D |

(cont.)
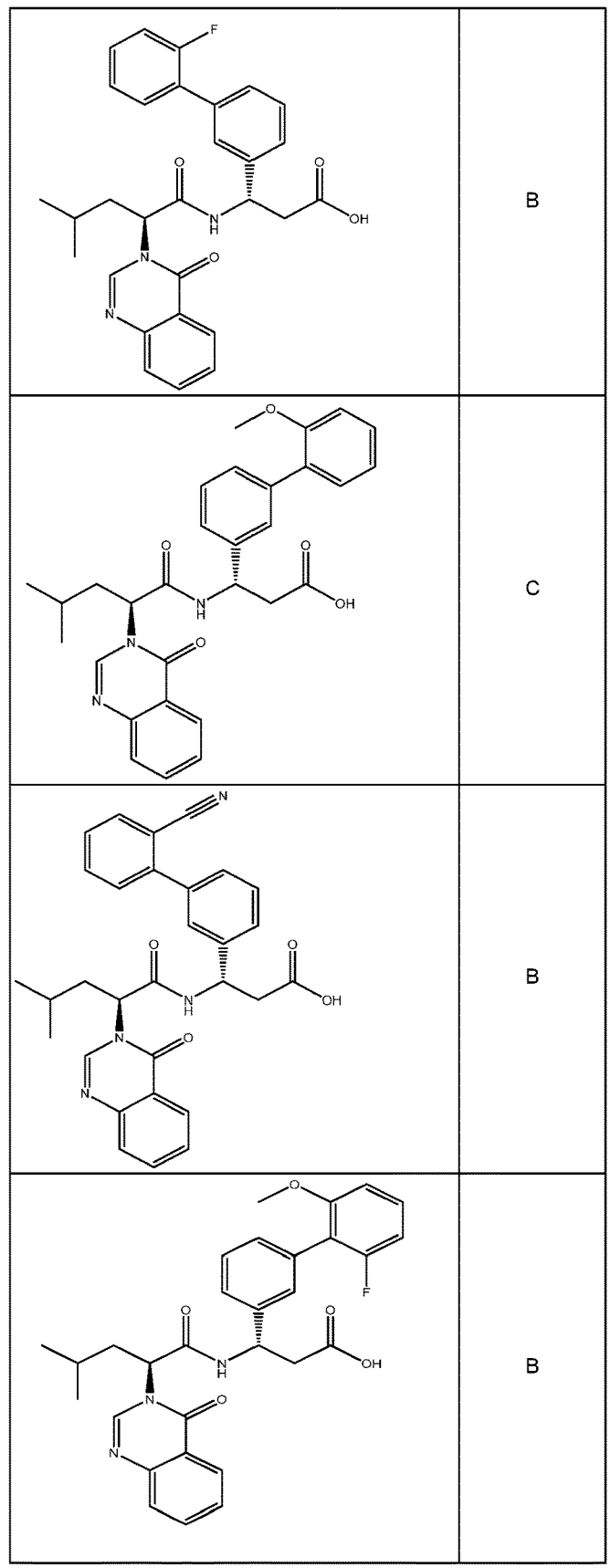

(cont.)
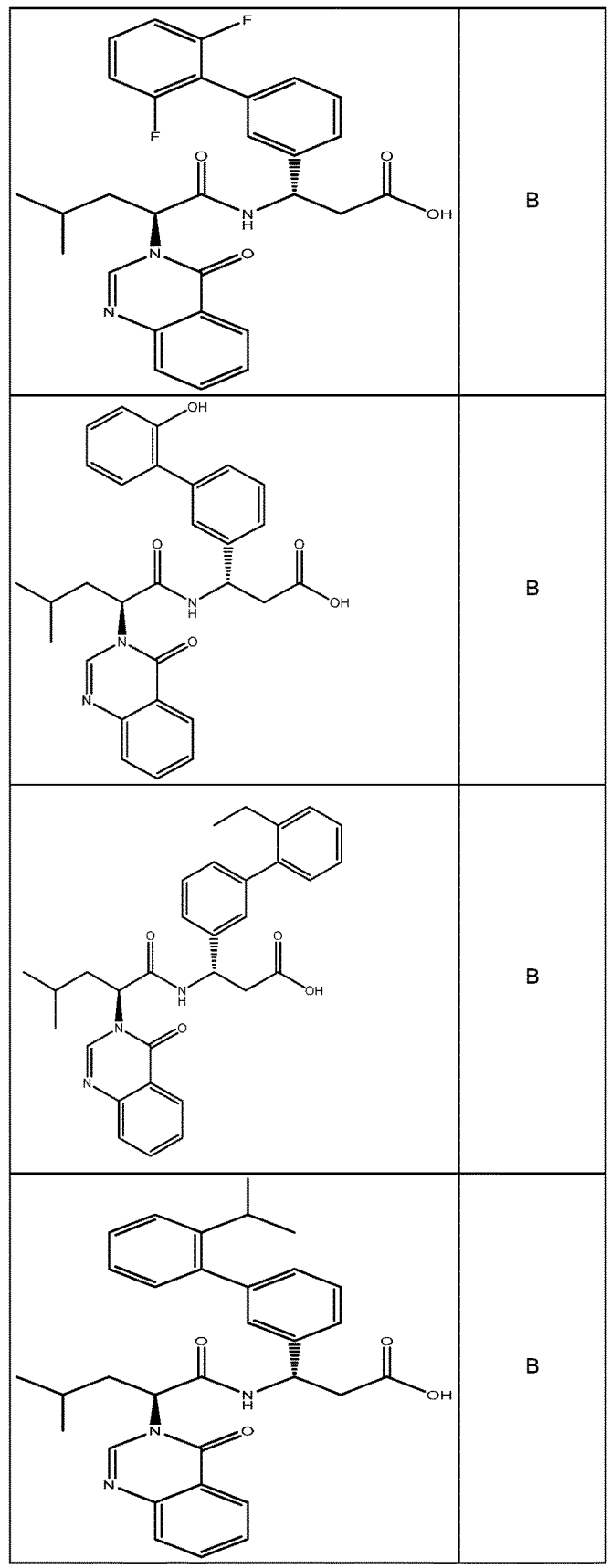

(cont.)
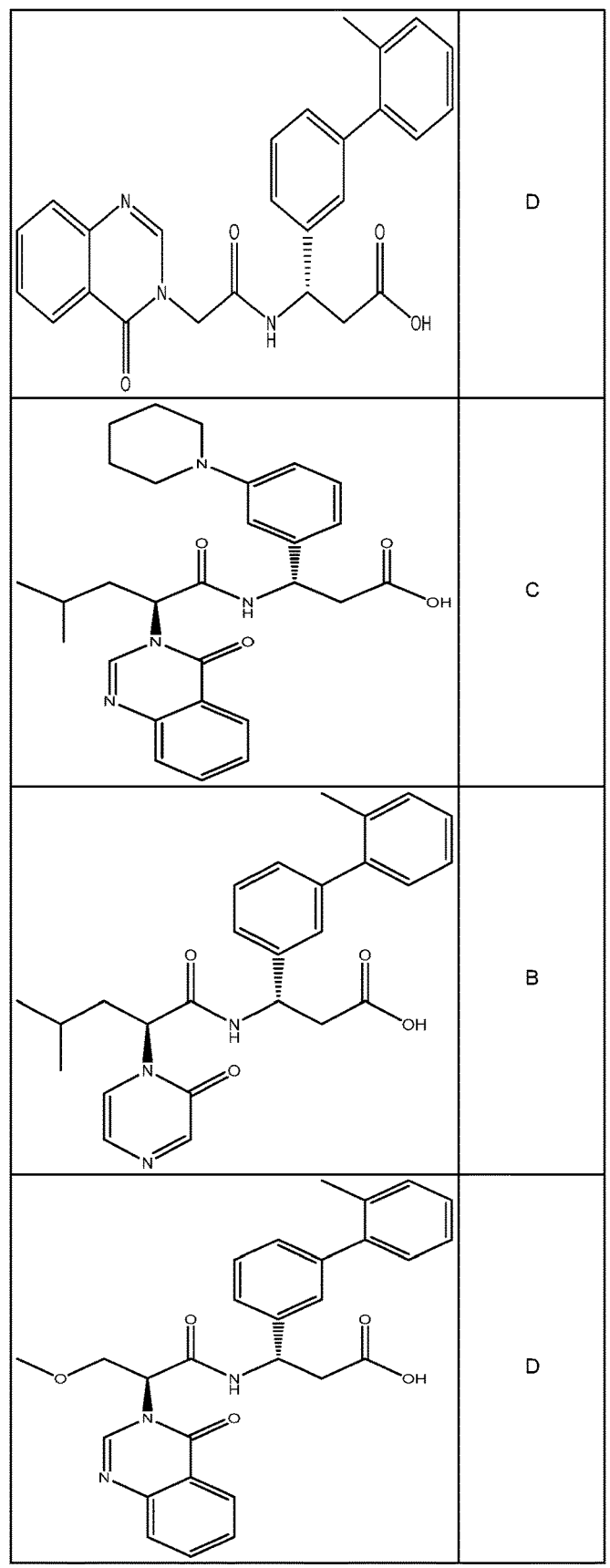

(cont.)
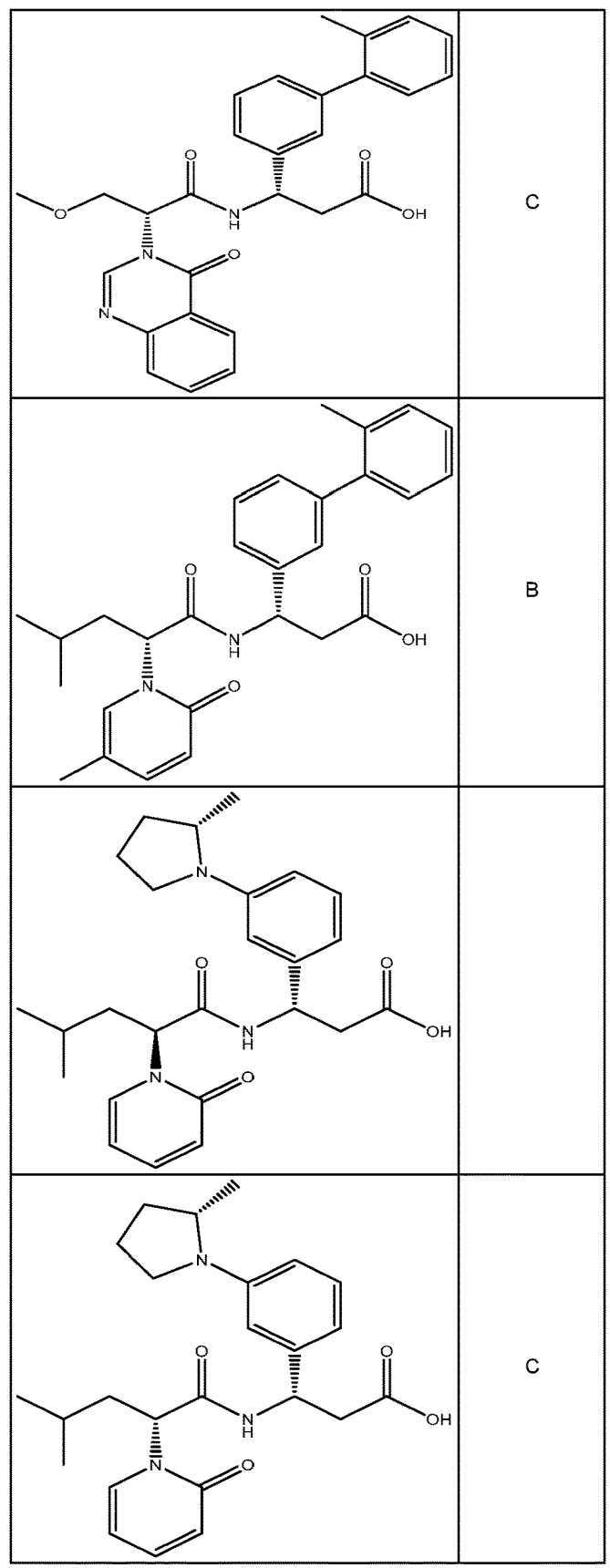

(cont.)
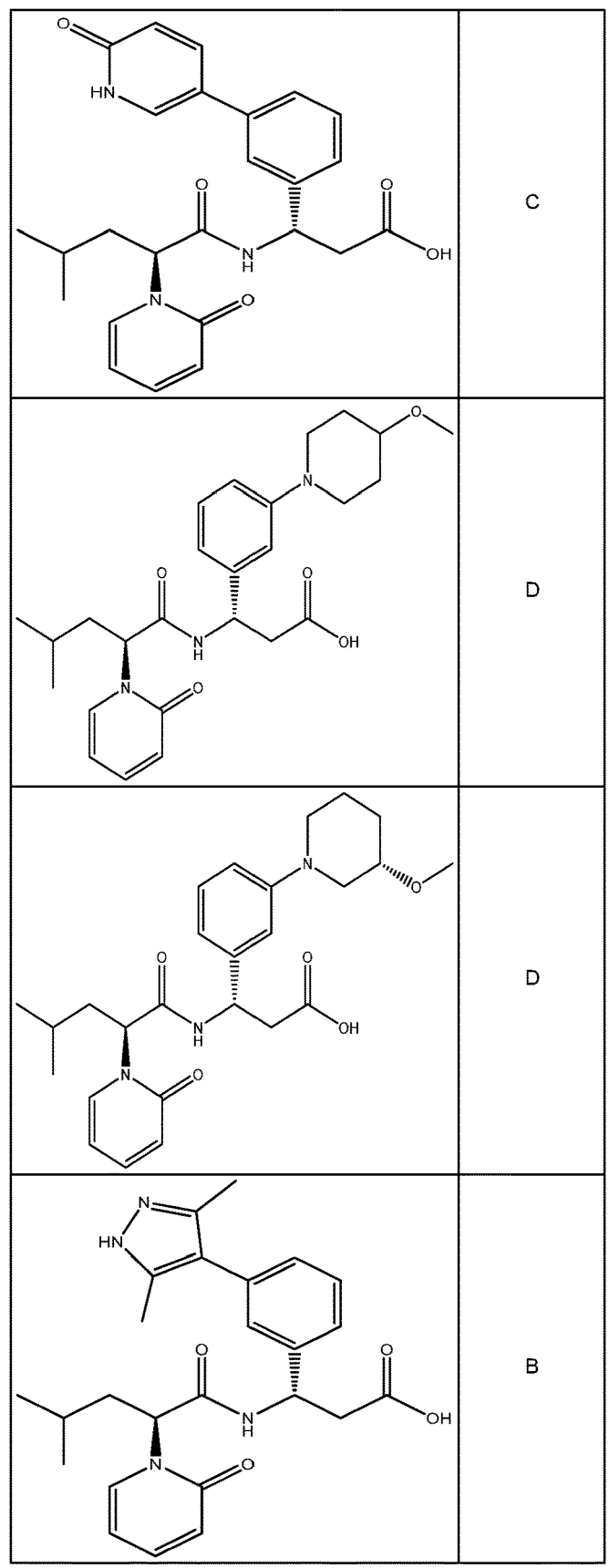

(cont.)
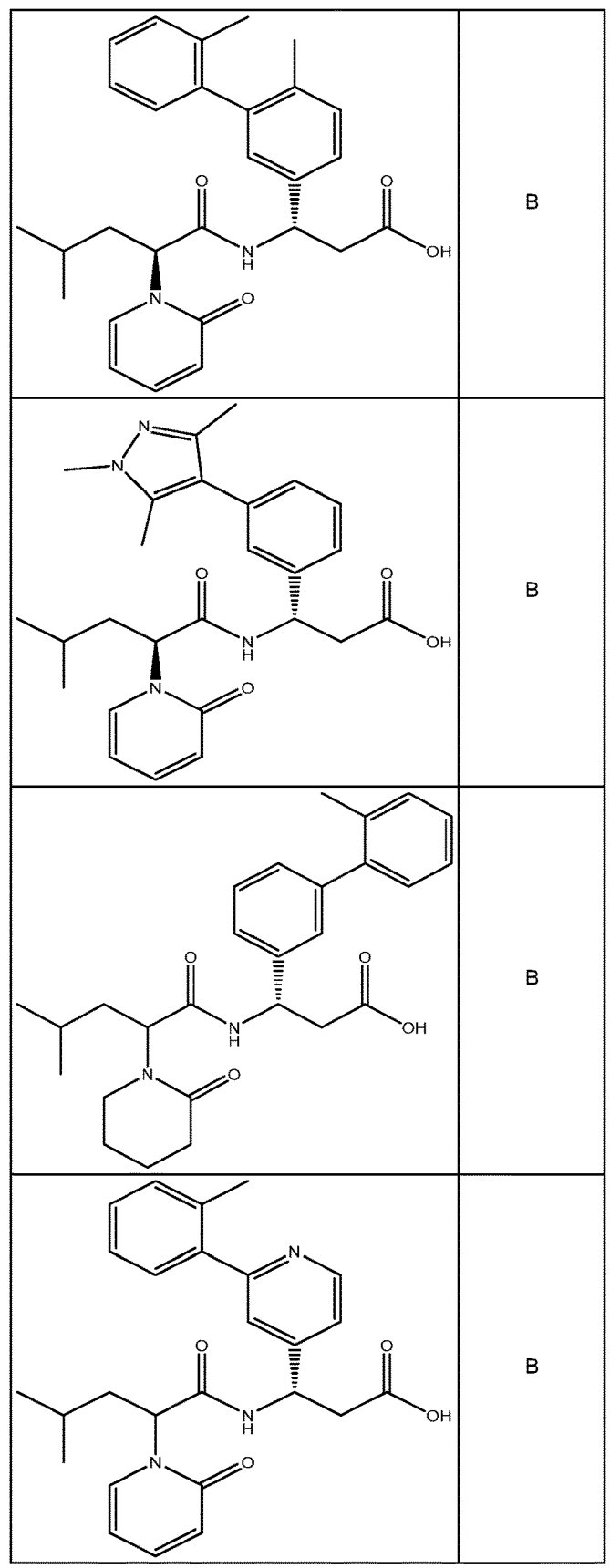

(cont.)
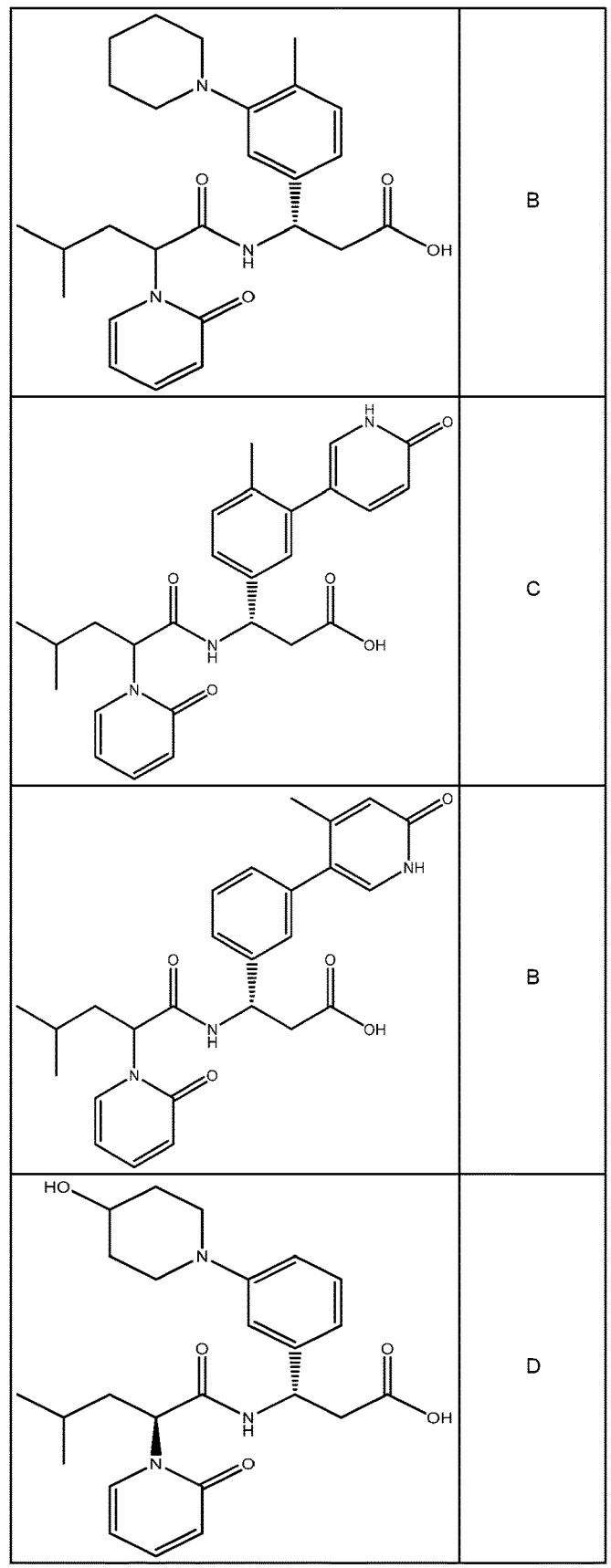

(cont.)
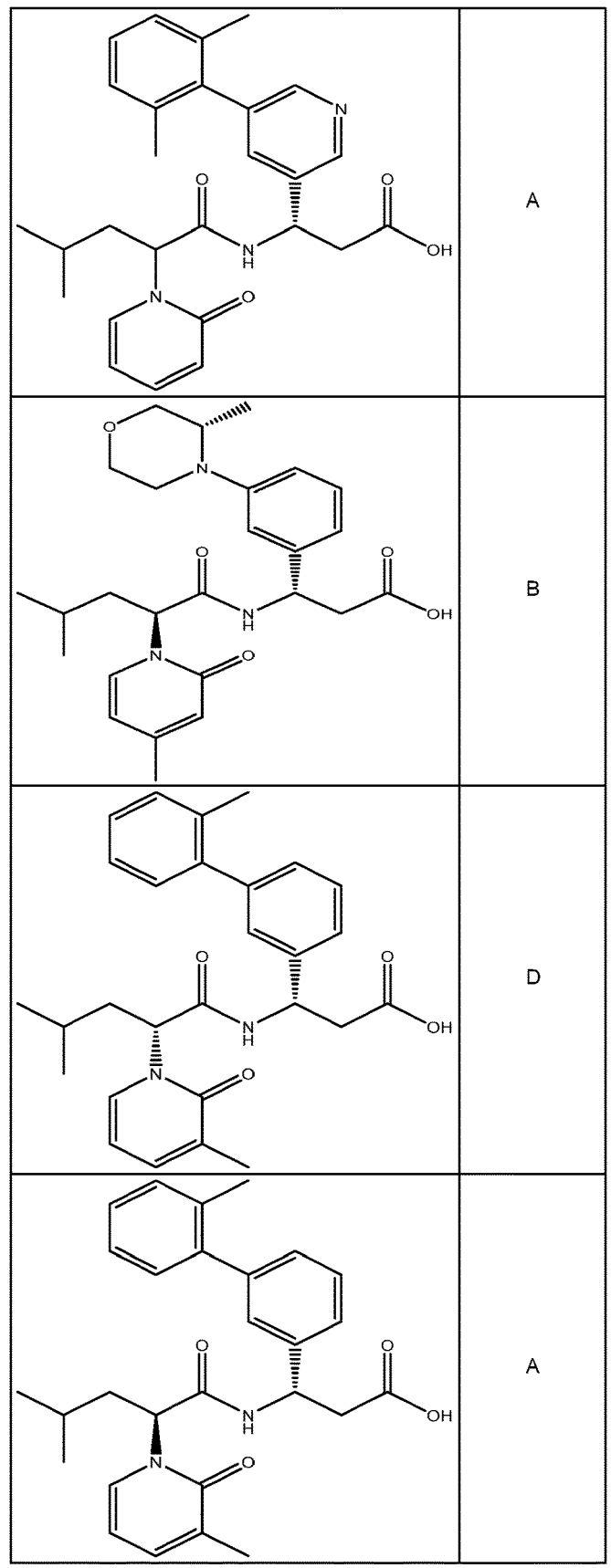

(cont.)
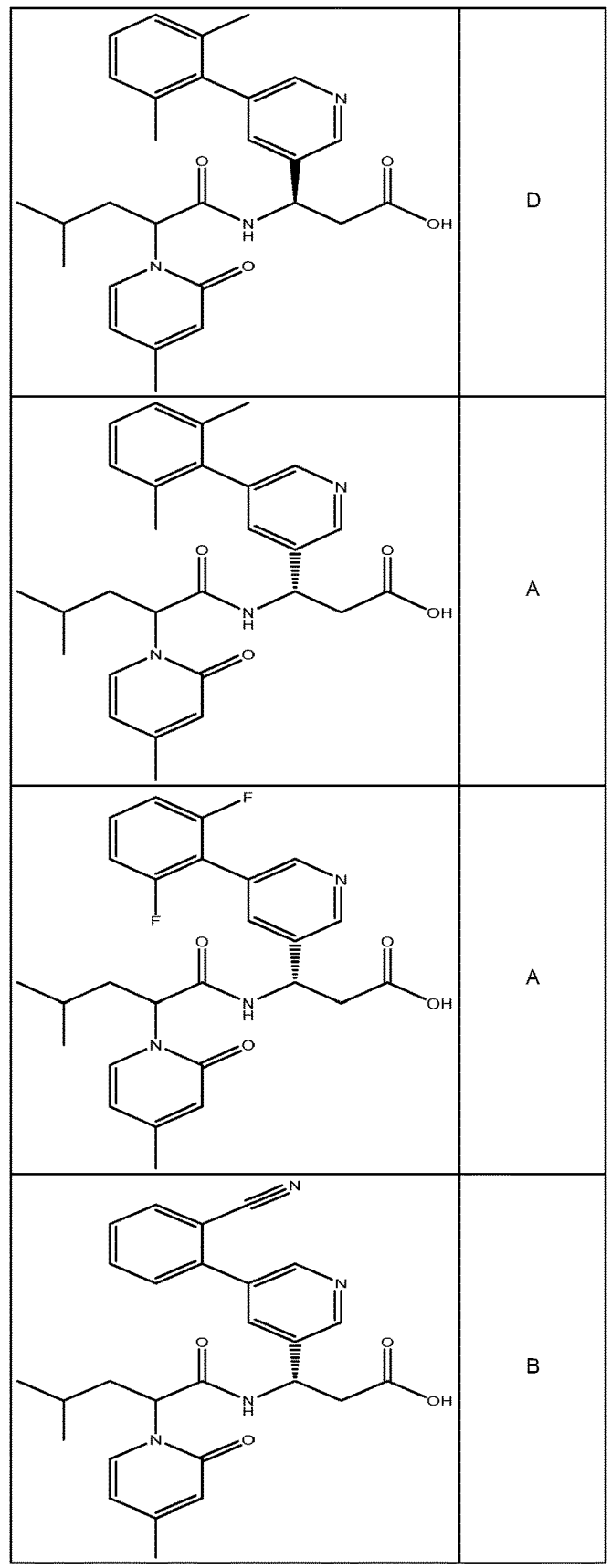

(cont.)
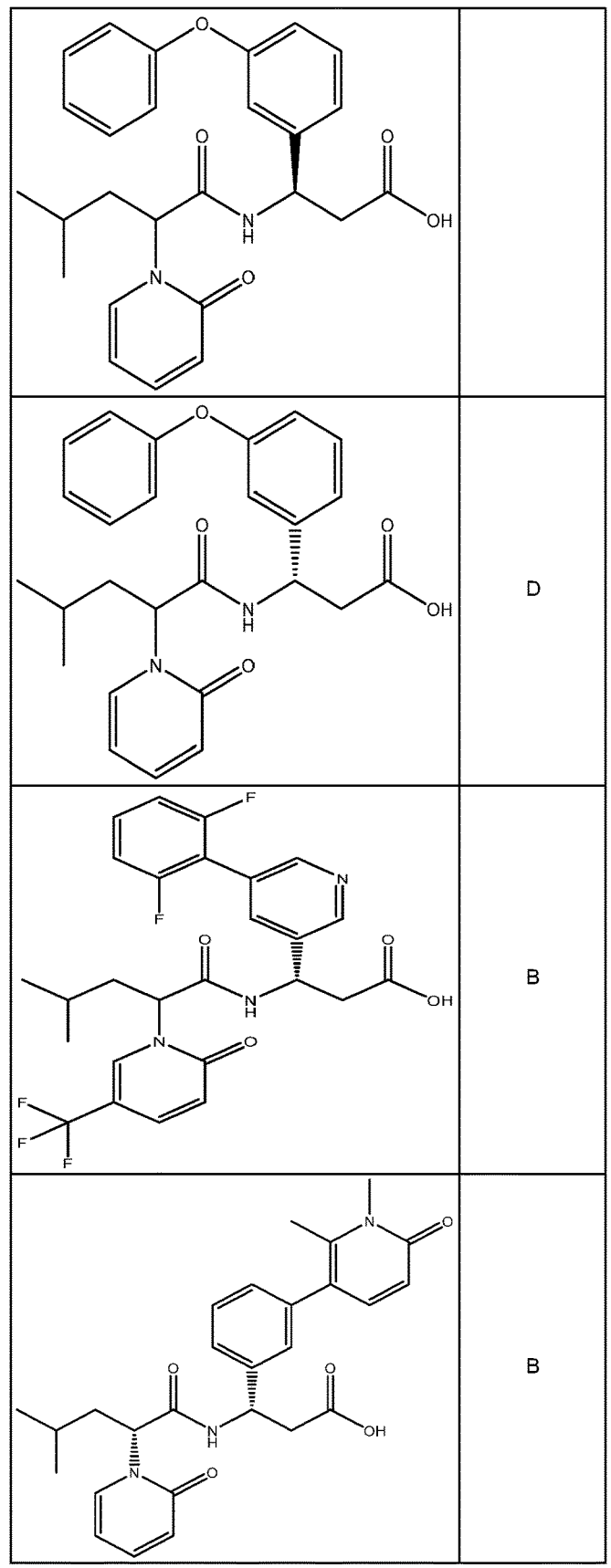

(cont.)
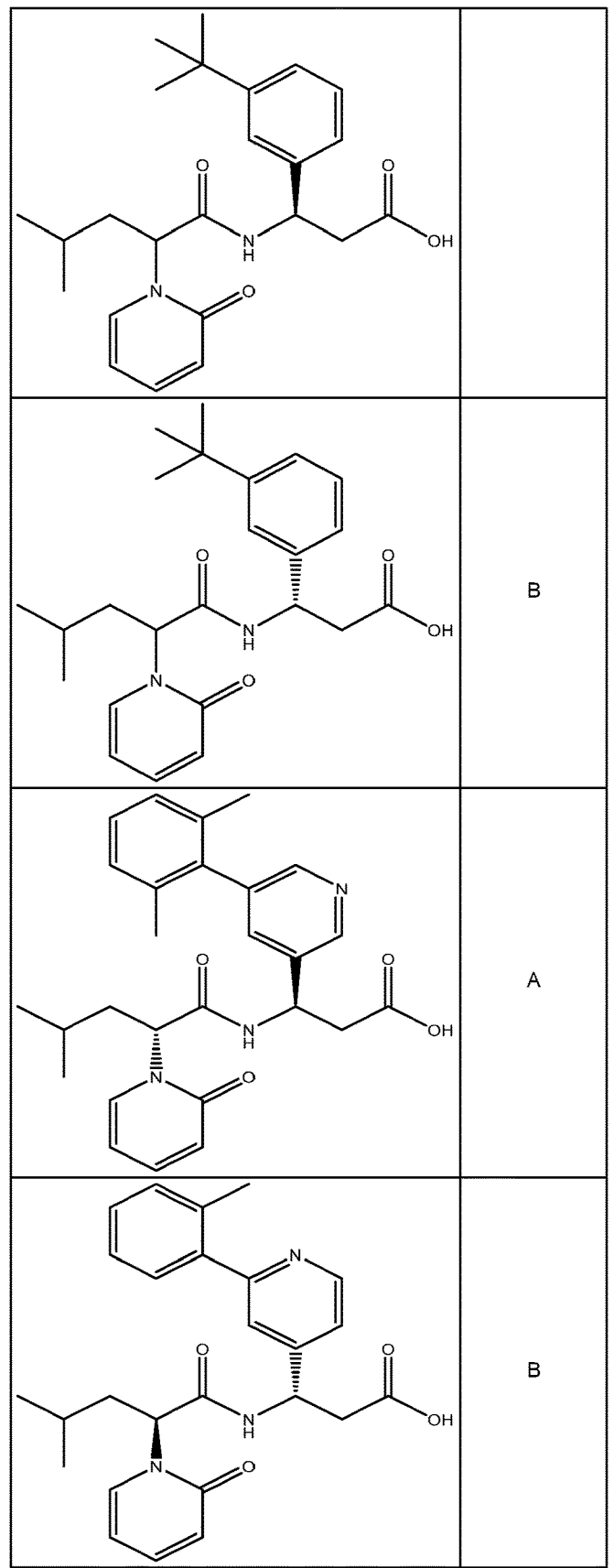

(cont.)
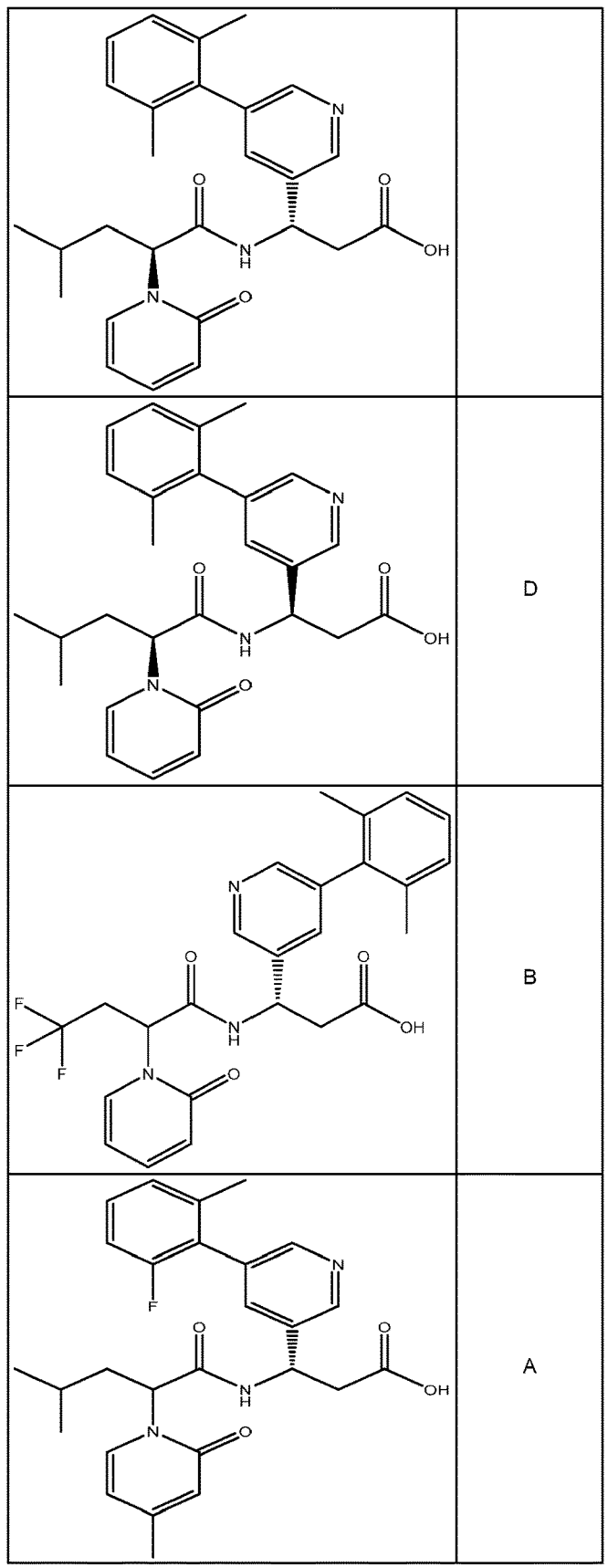

(cont.)
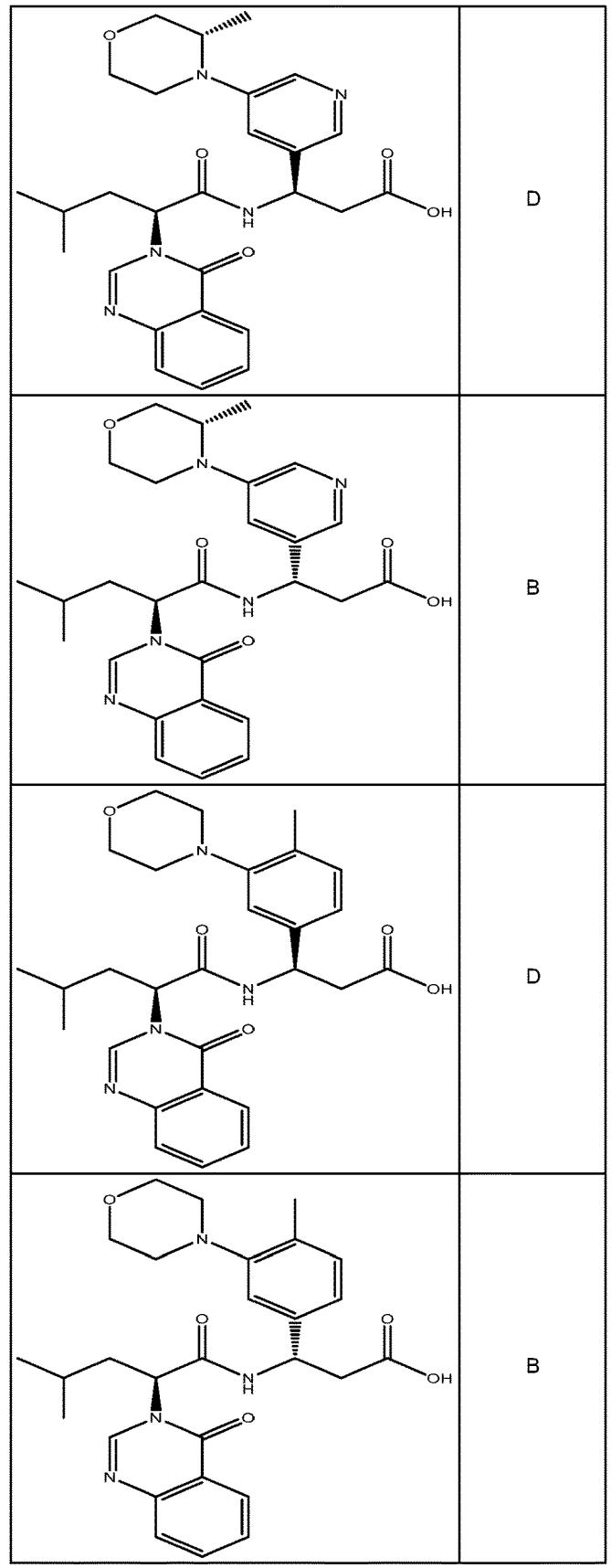

(cont.)
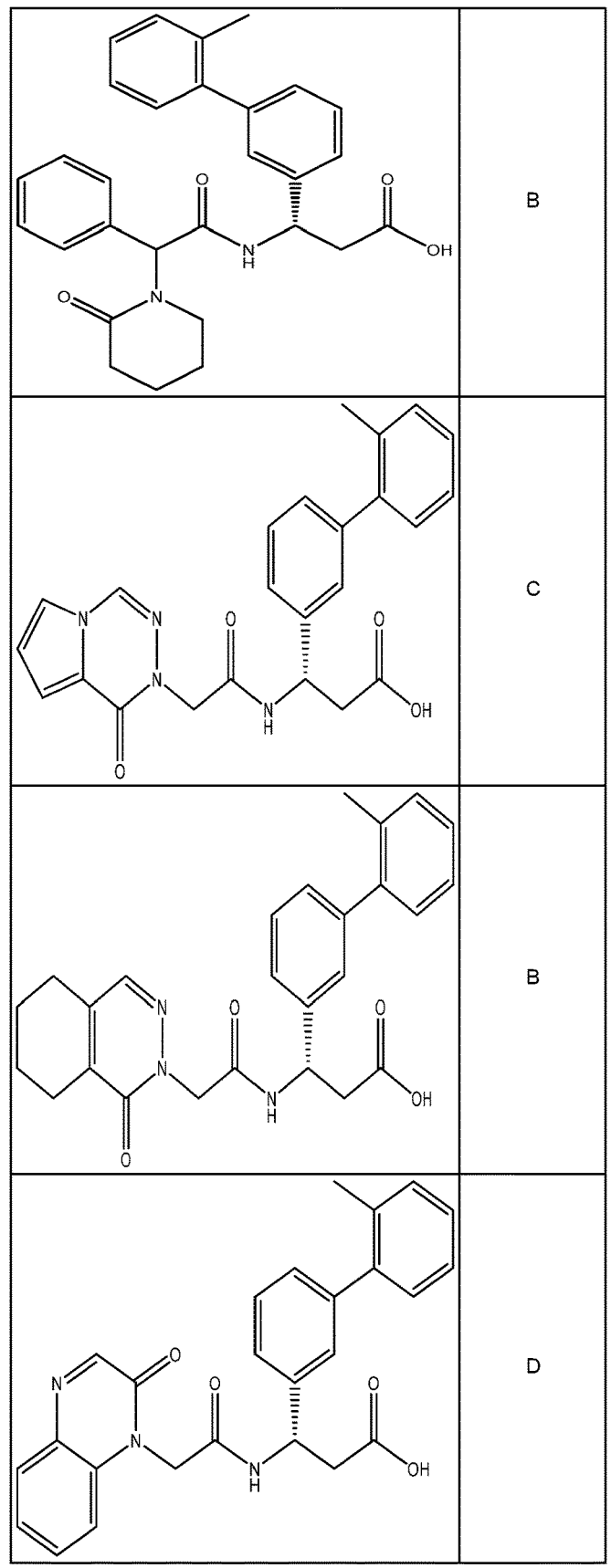

(cont.)
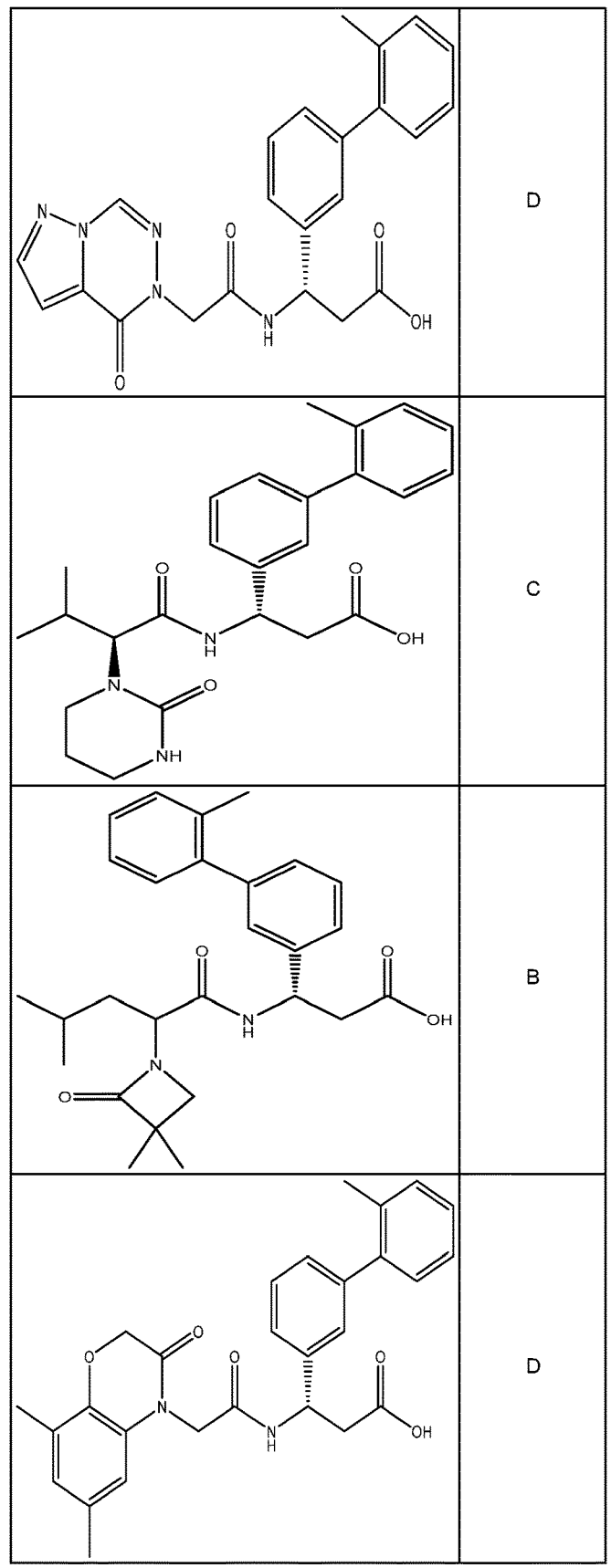

(cont.)
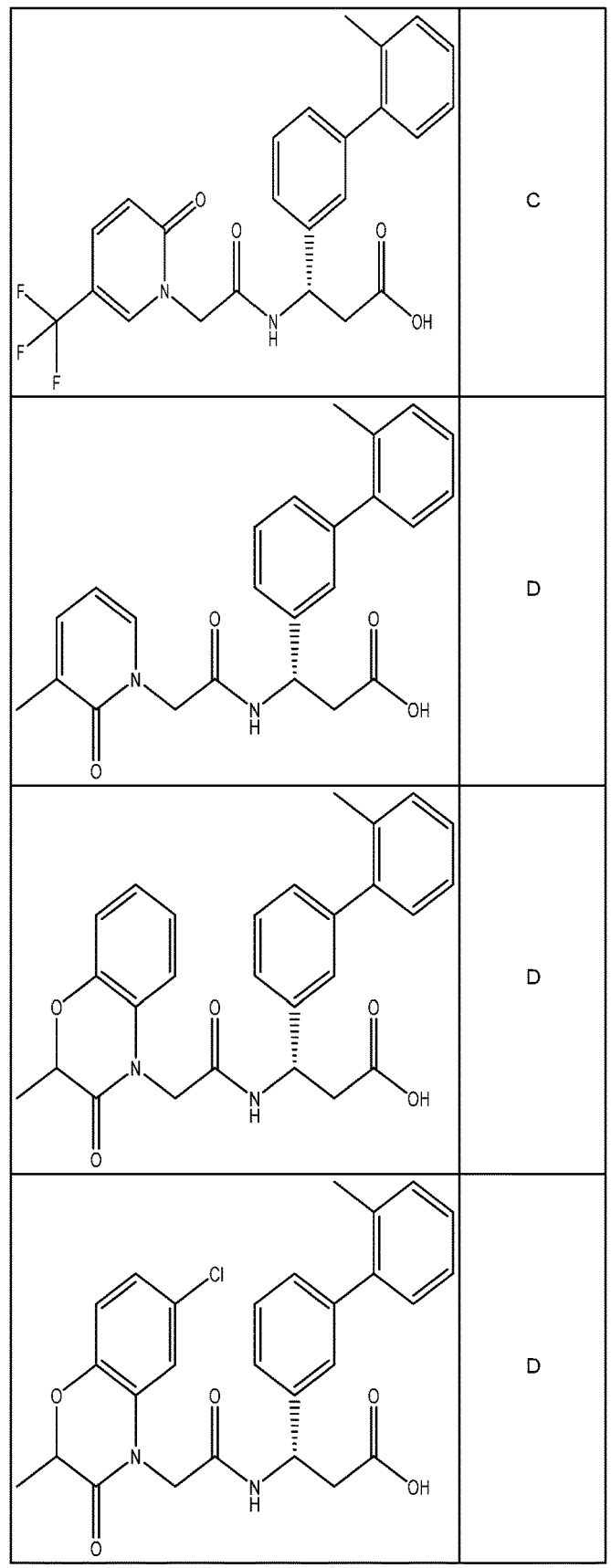

(cont.)
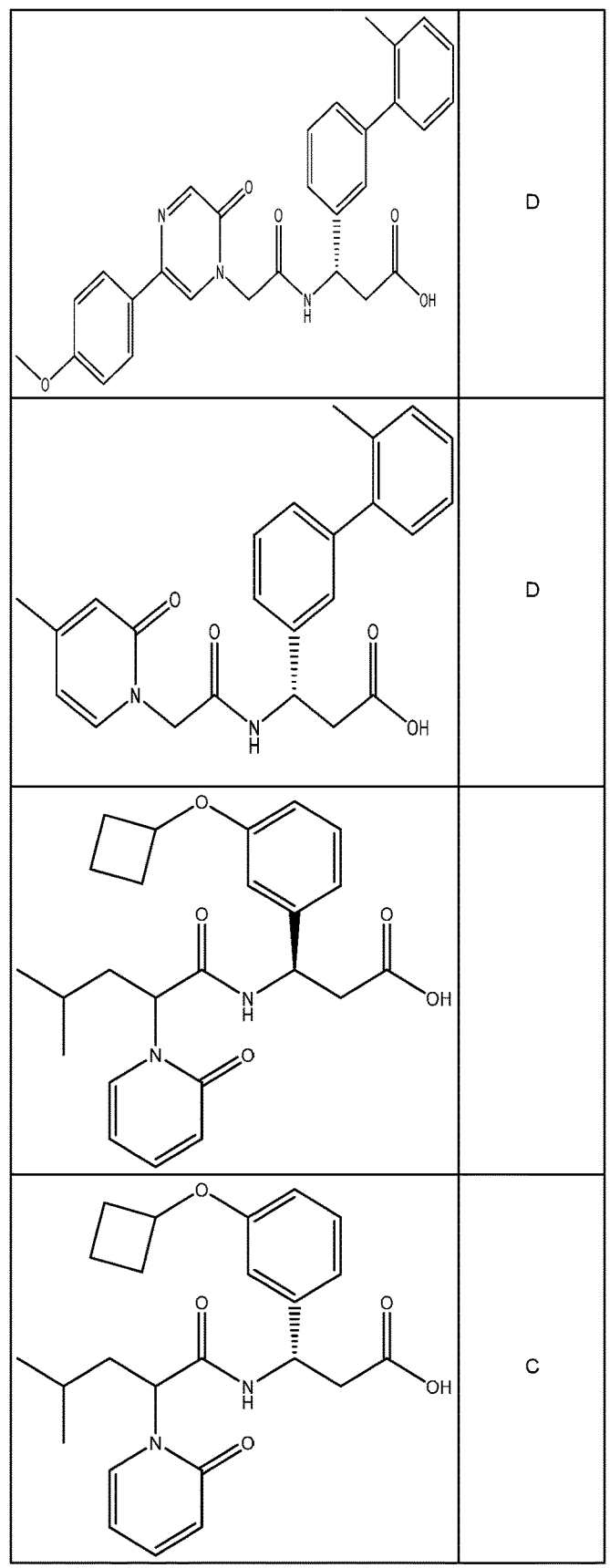

(cont.)
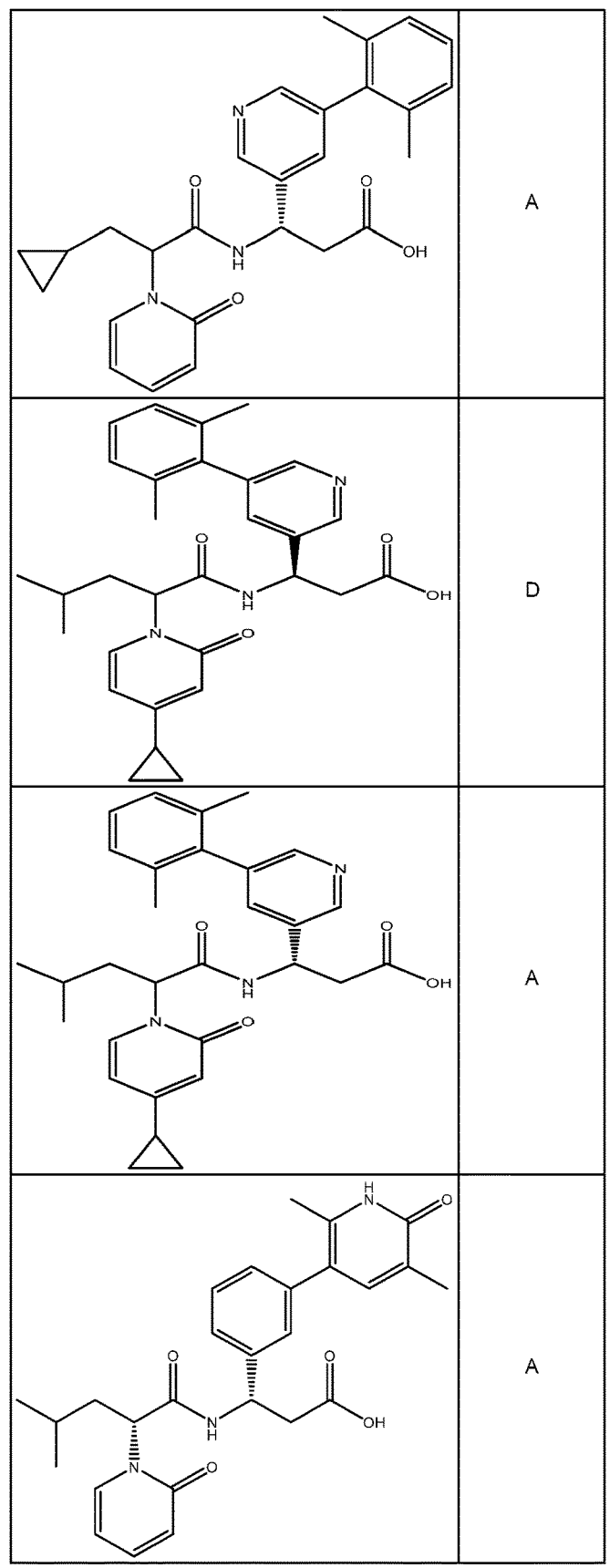

(cont.)
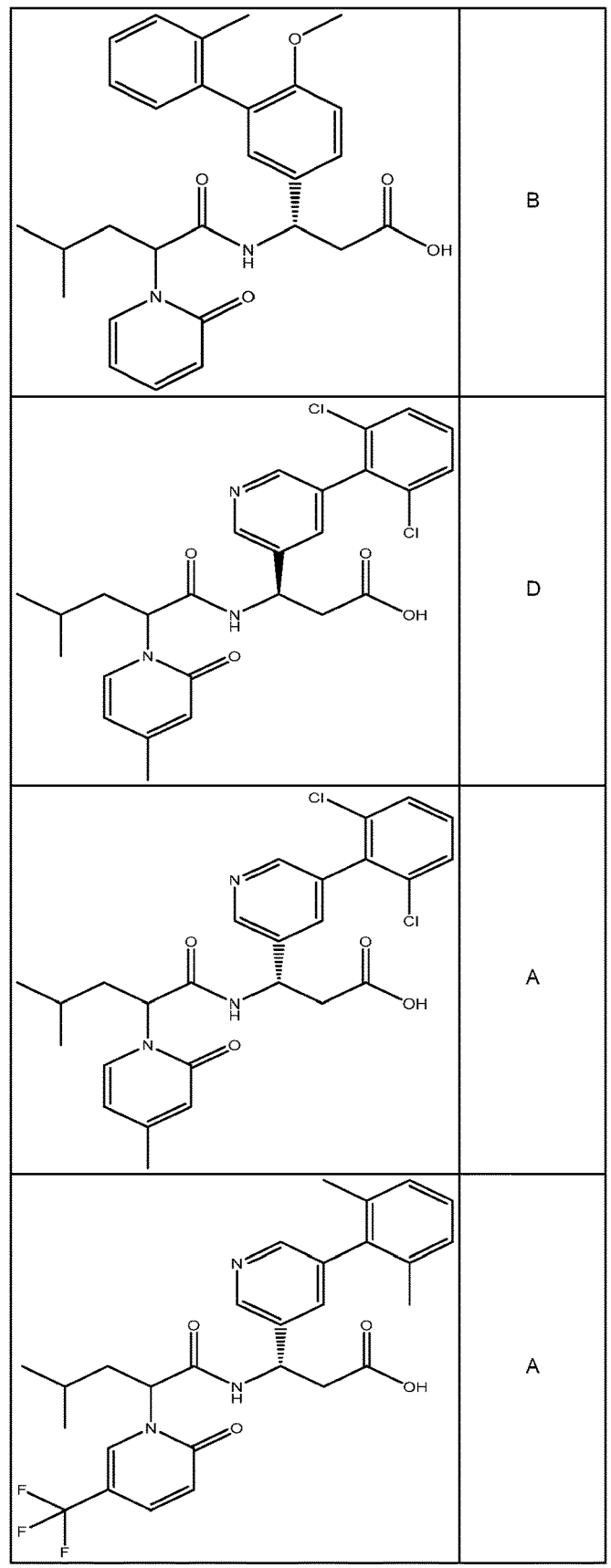

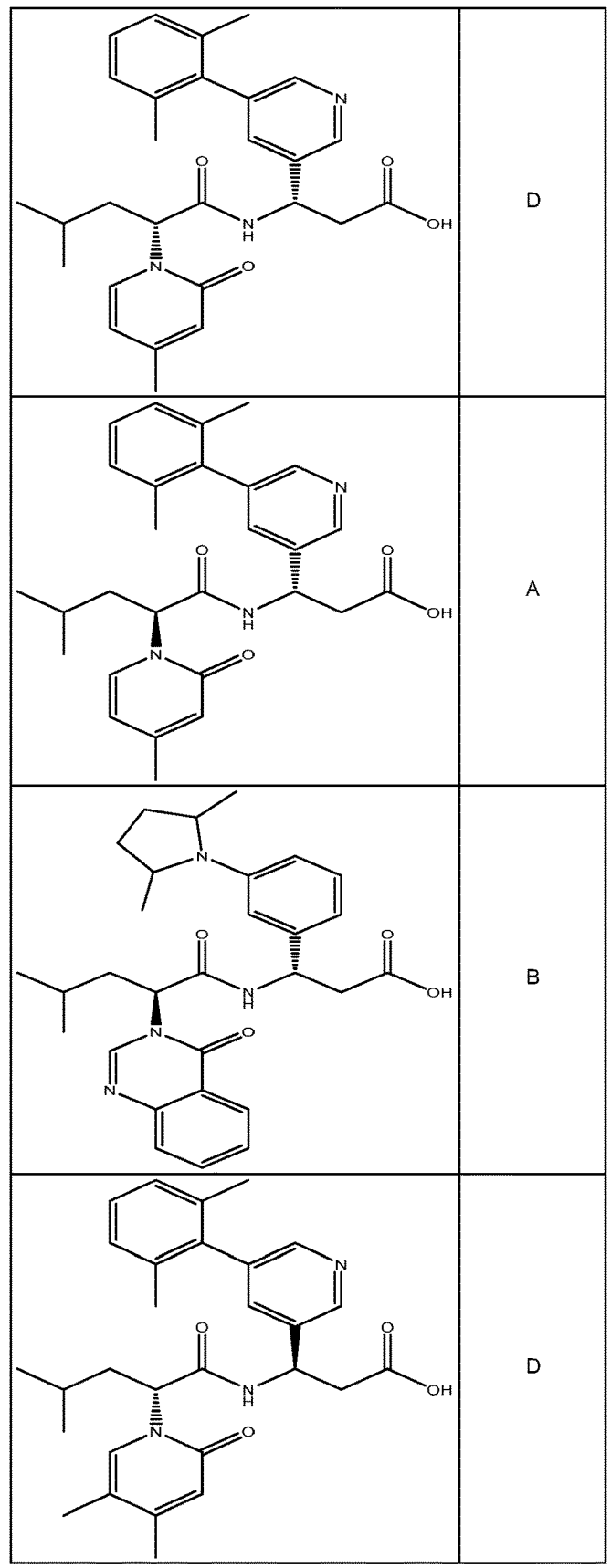

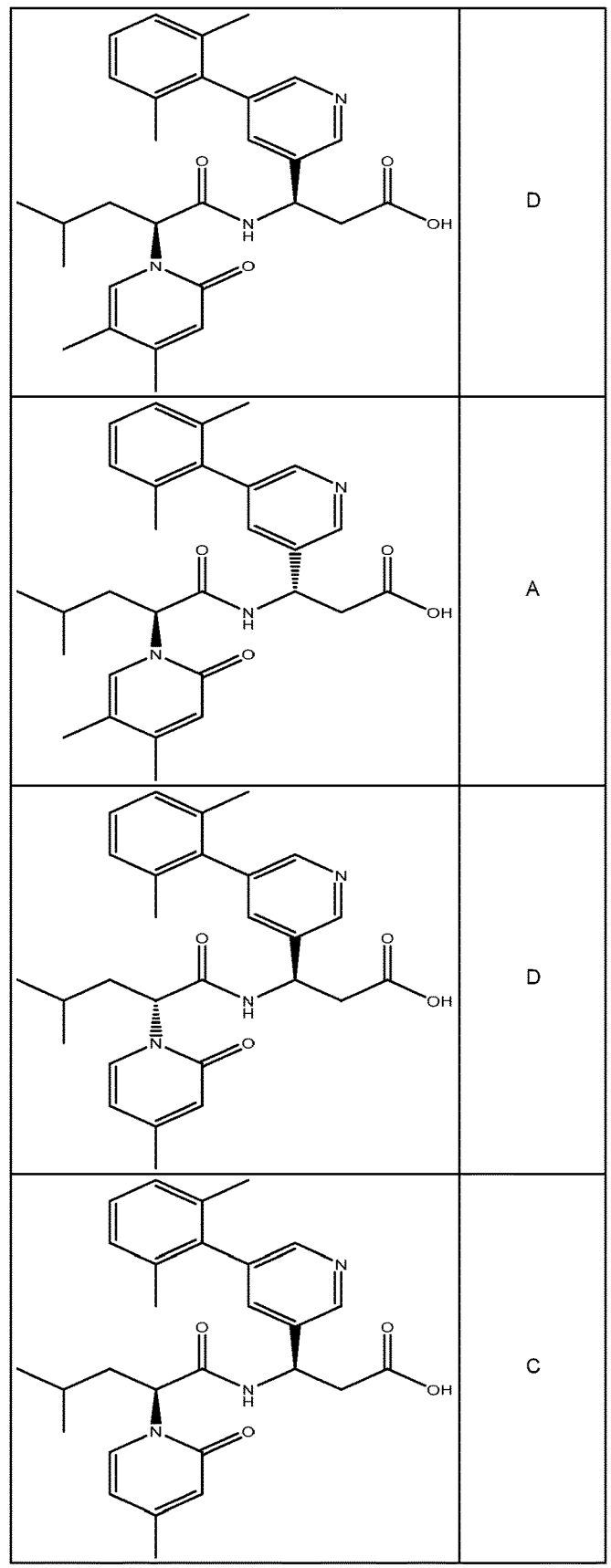

(cont.)
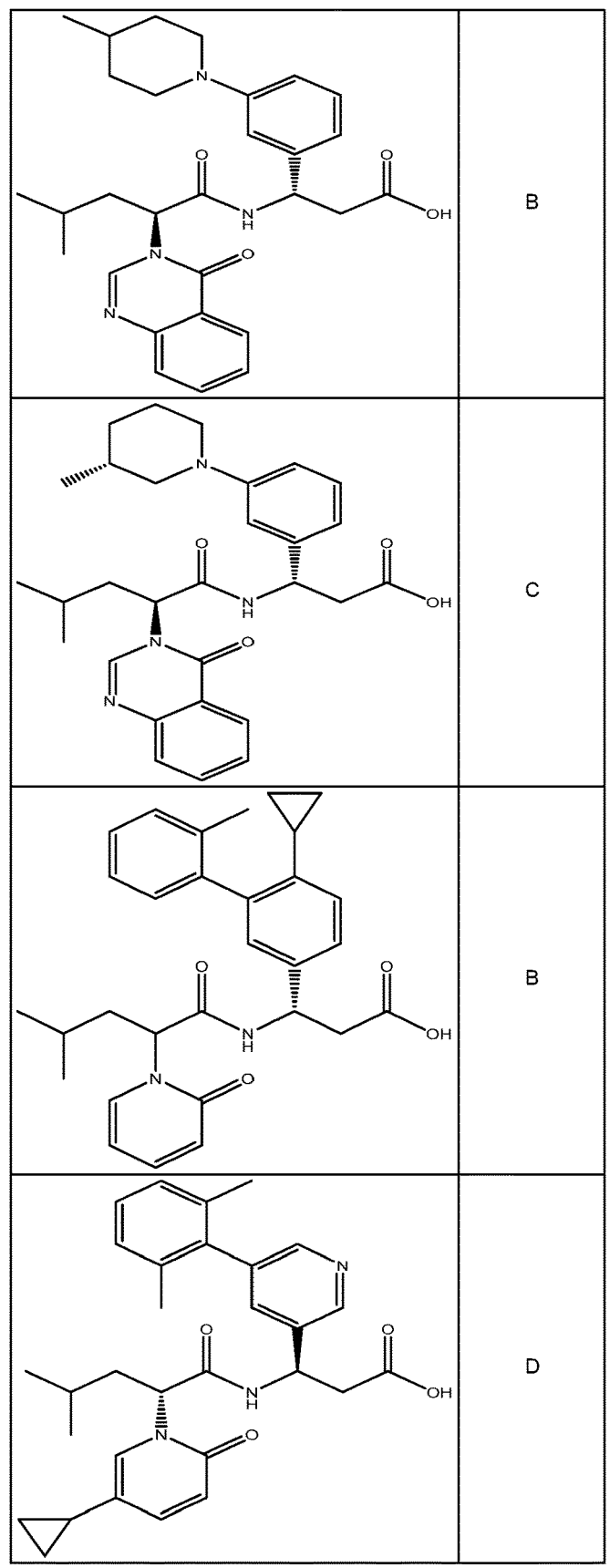

(cont.)
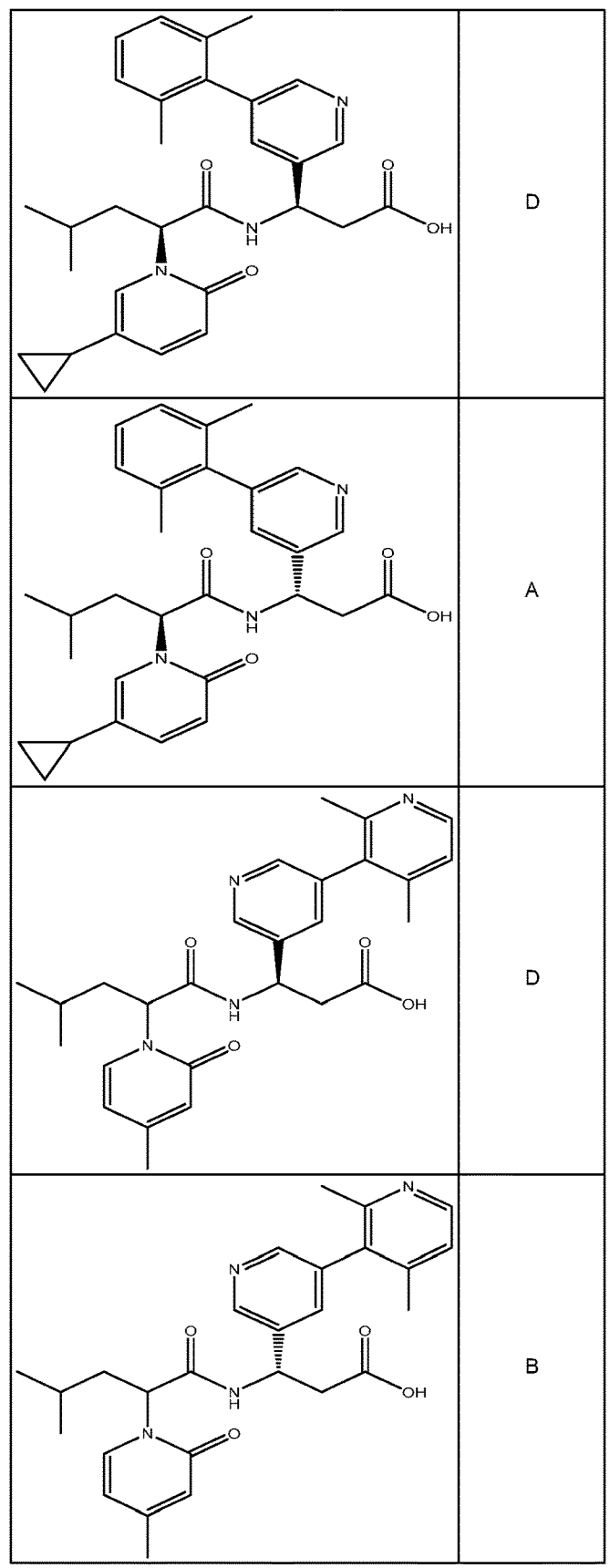

(cont.)
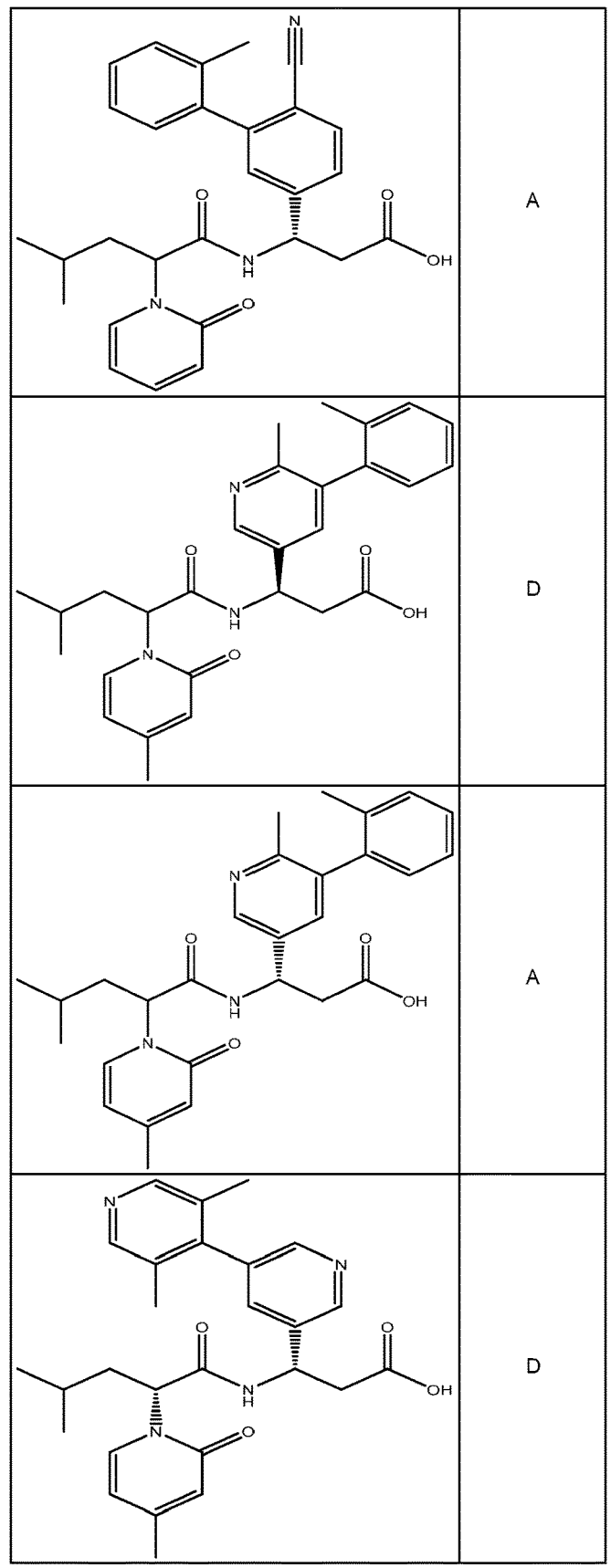

(cont.)
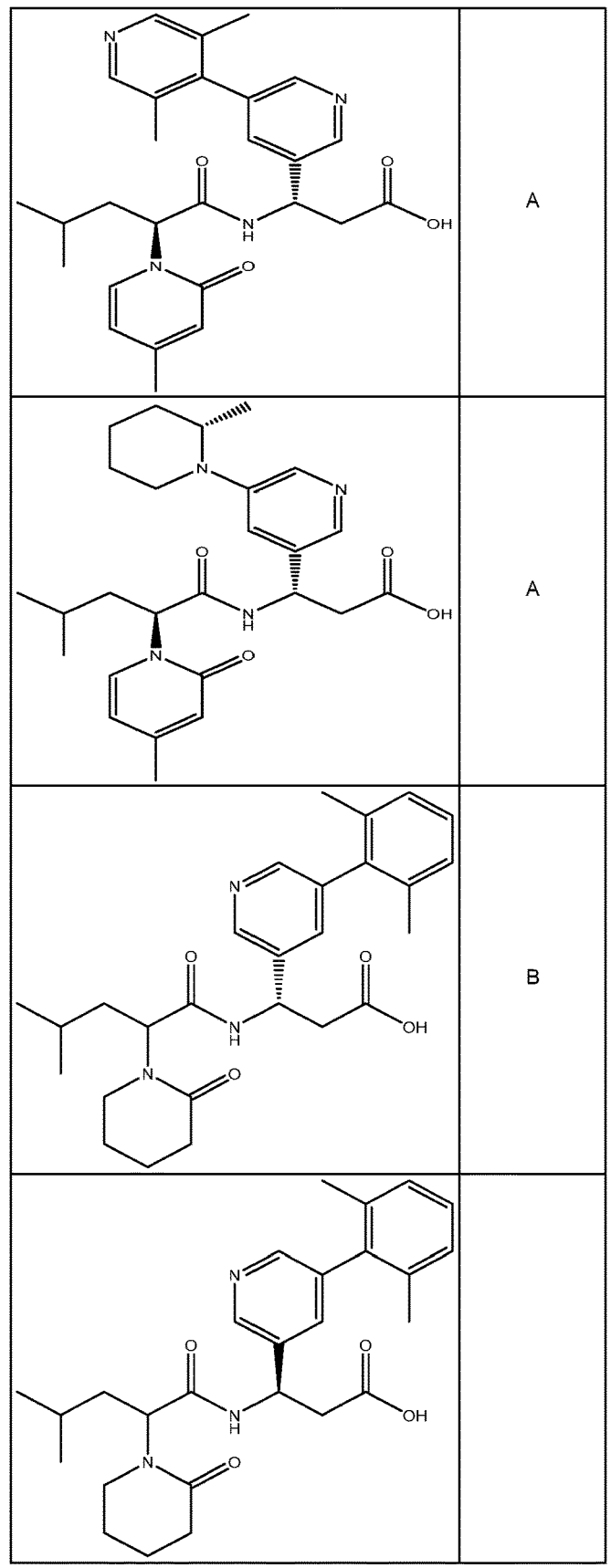

(cont.)
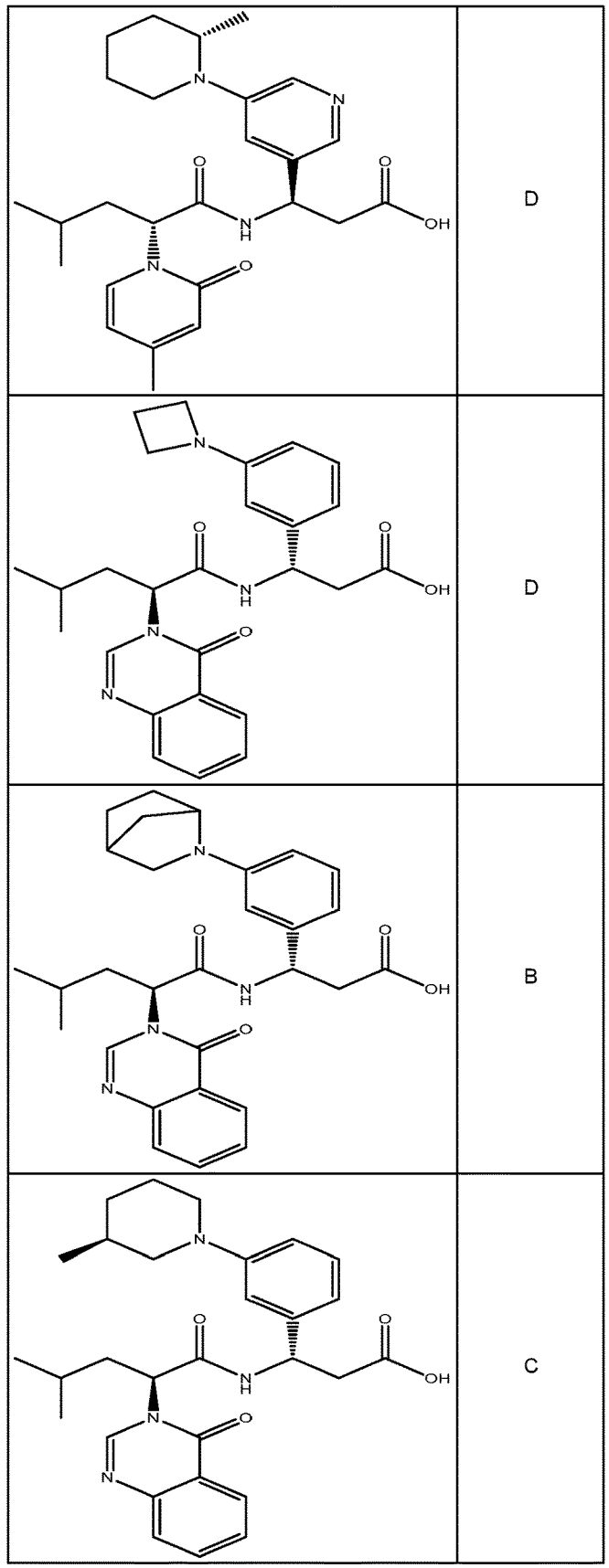

(cont.)
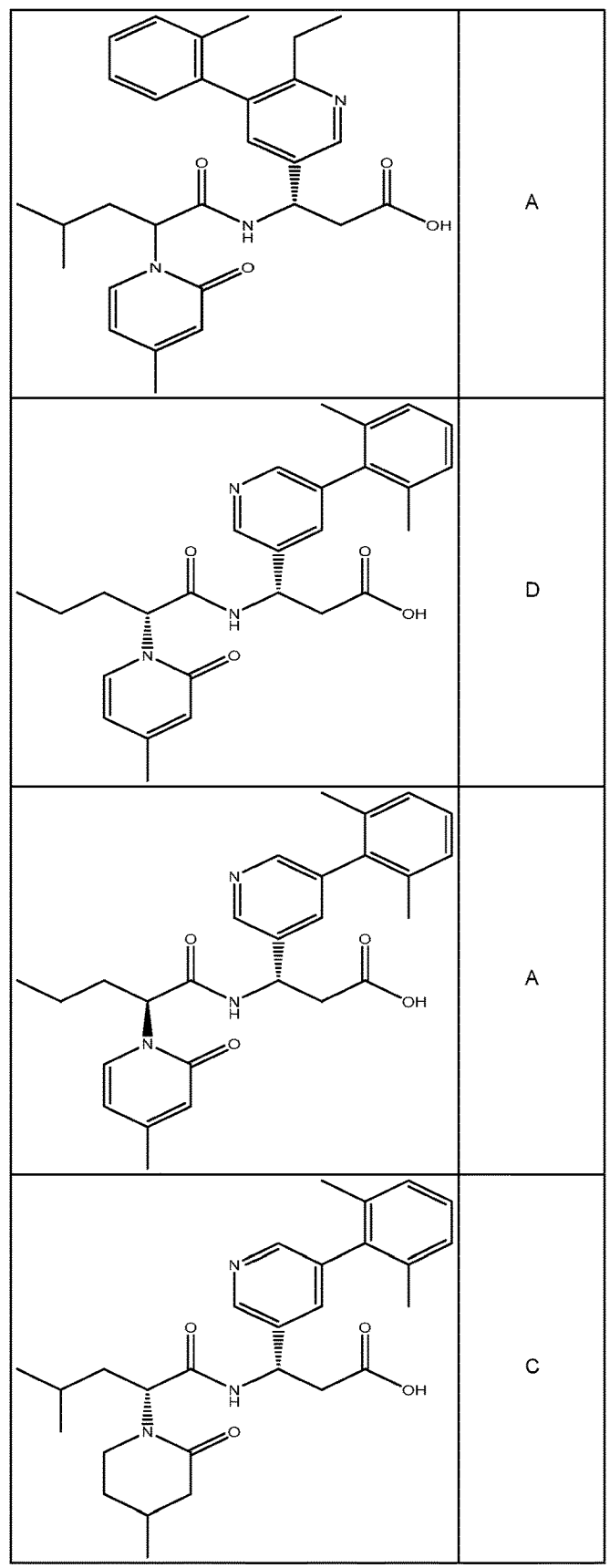

(cont.)
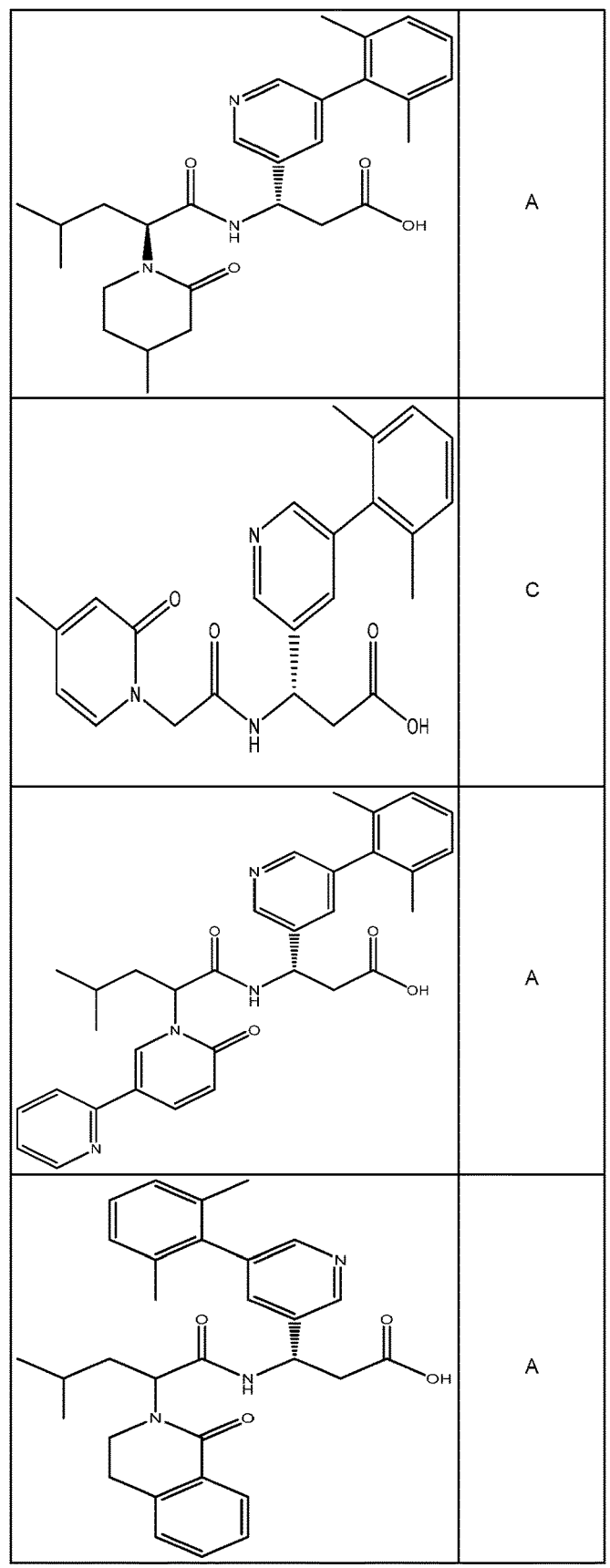

(cont.)
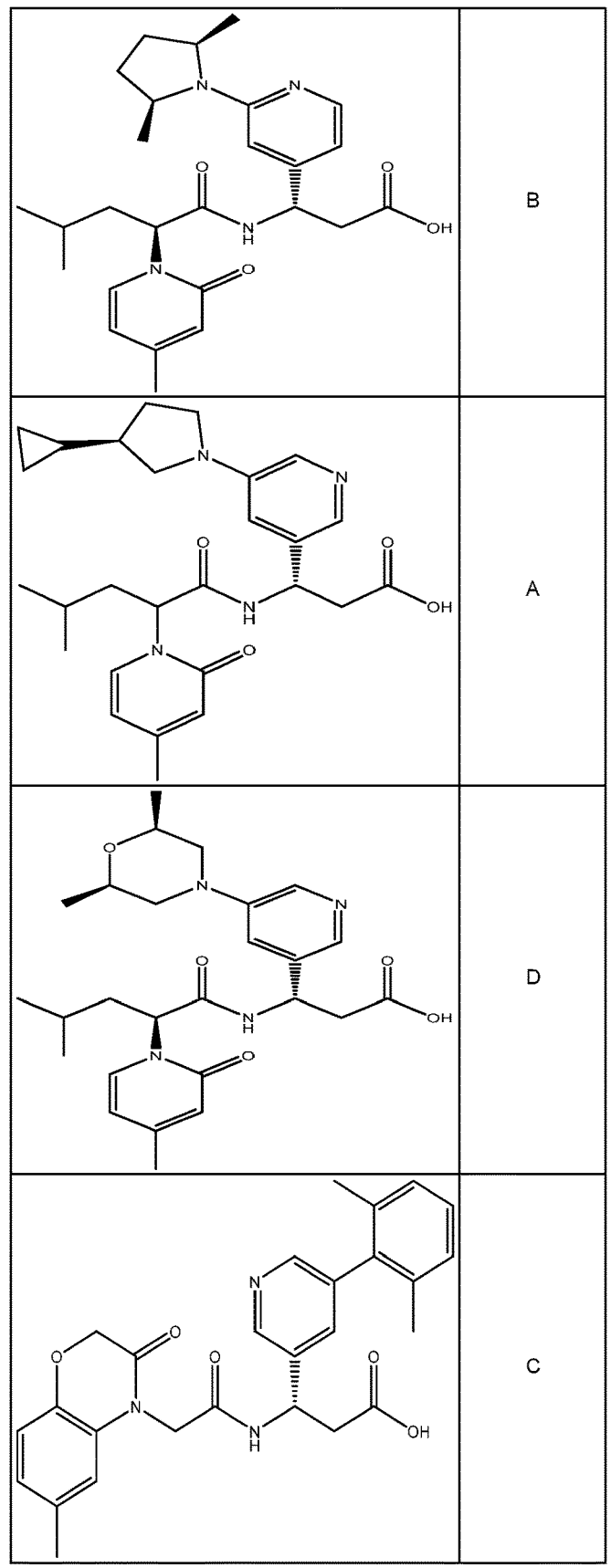

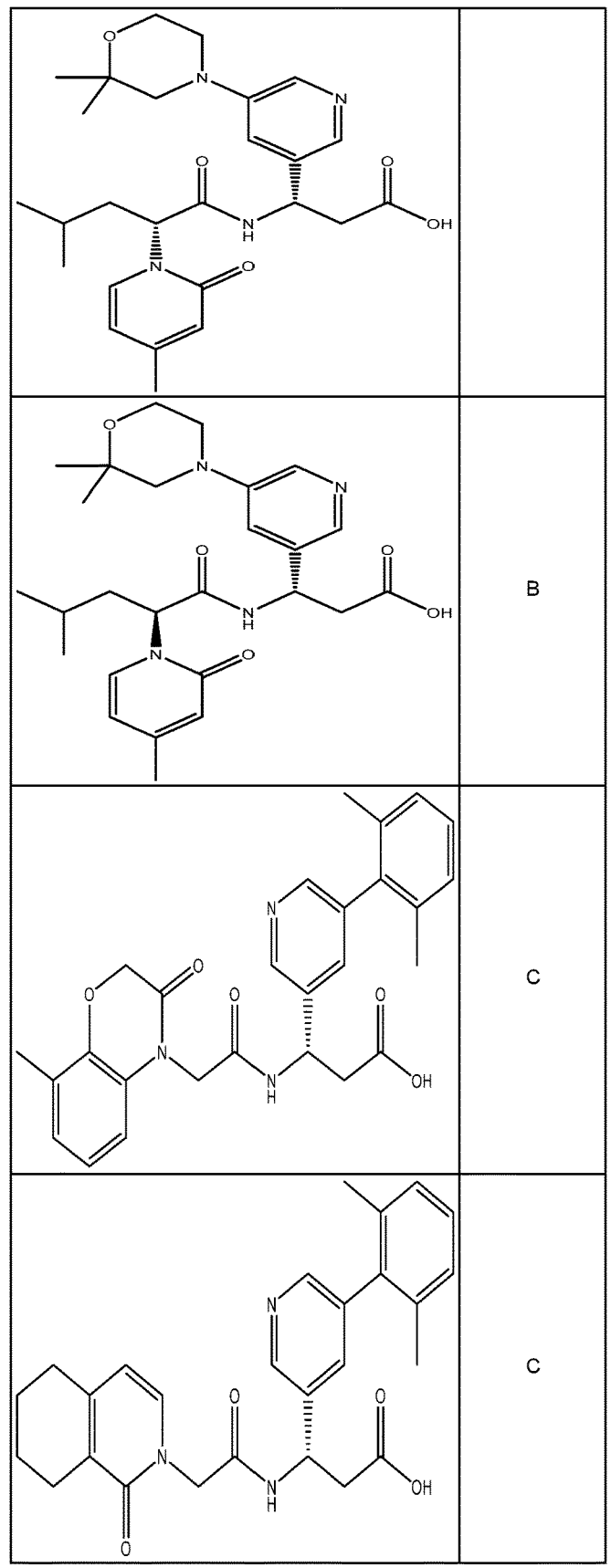

(cont.)
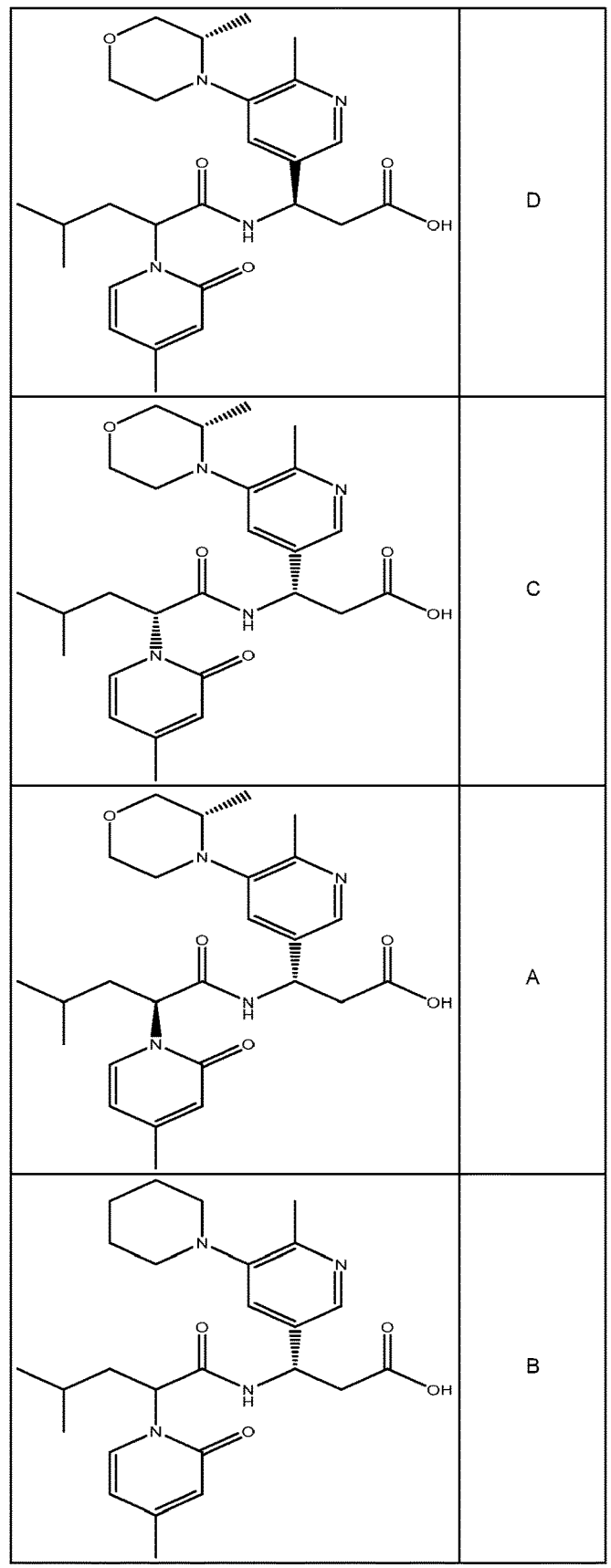

(cont.)
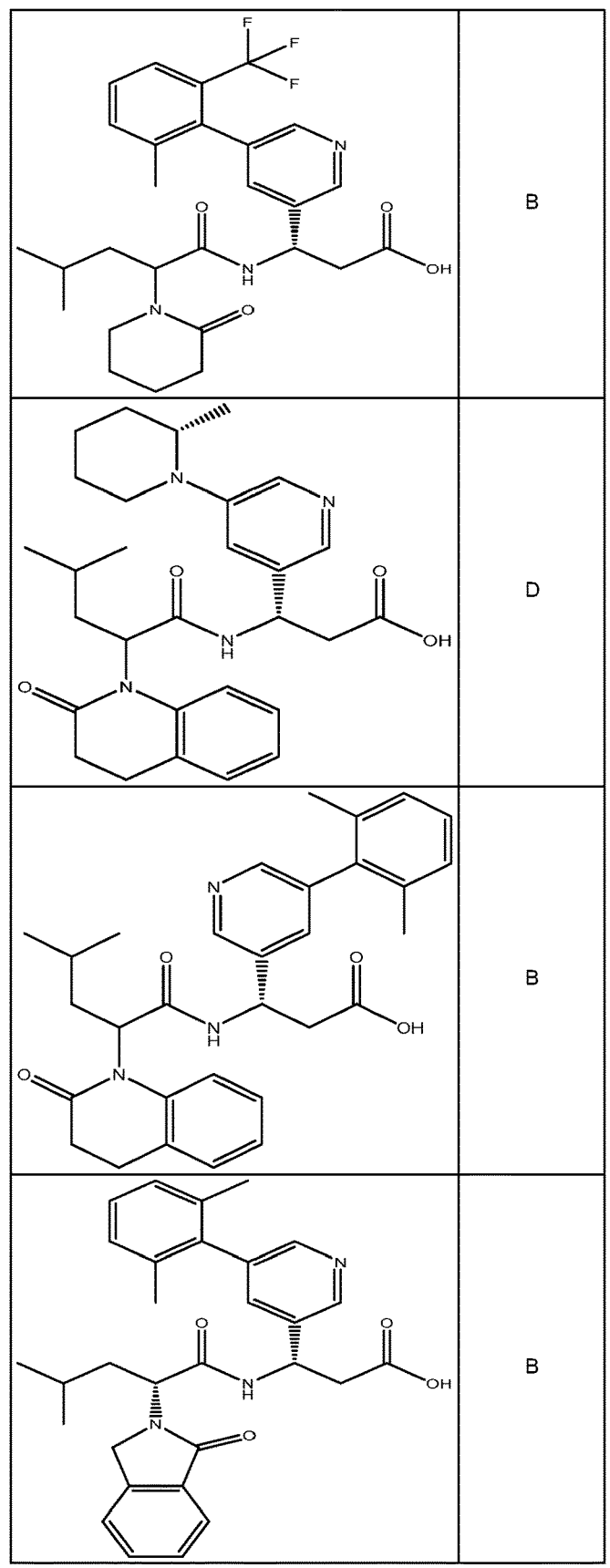

(cont.)
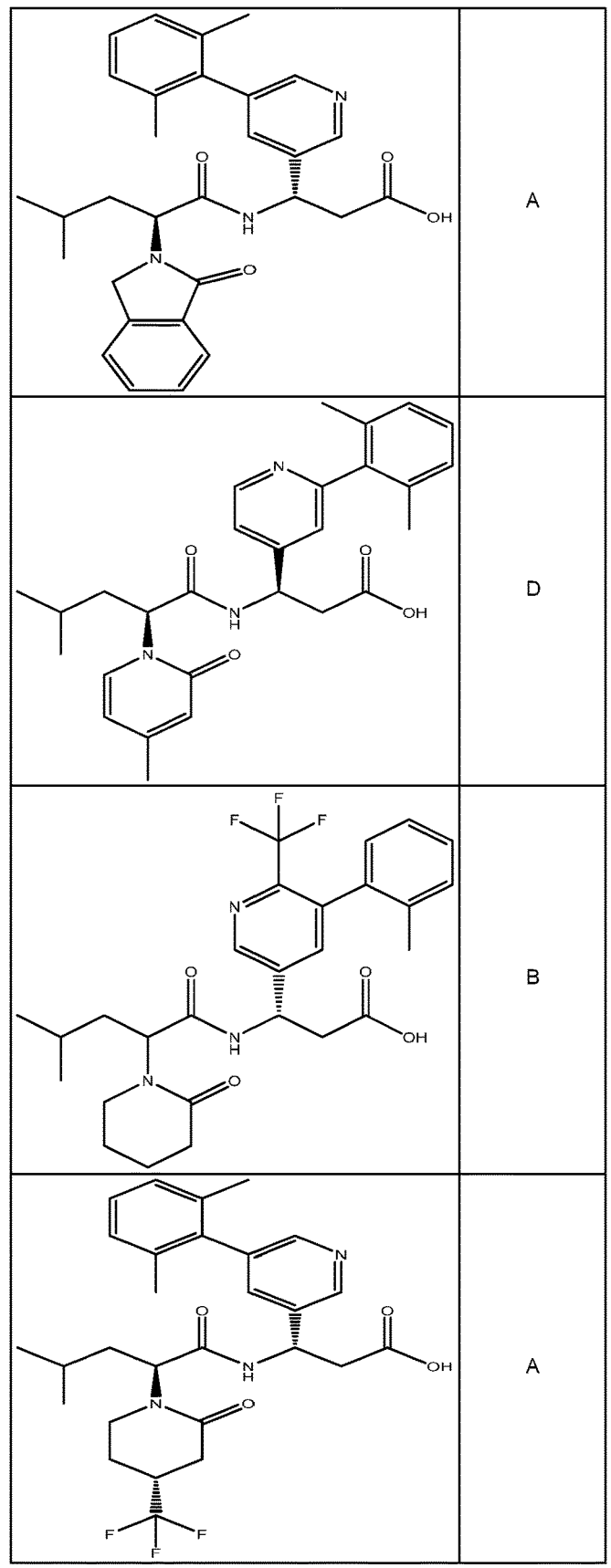

(cont.)
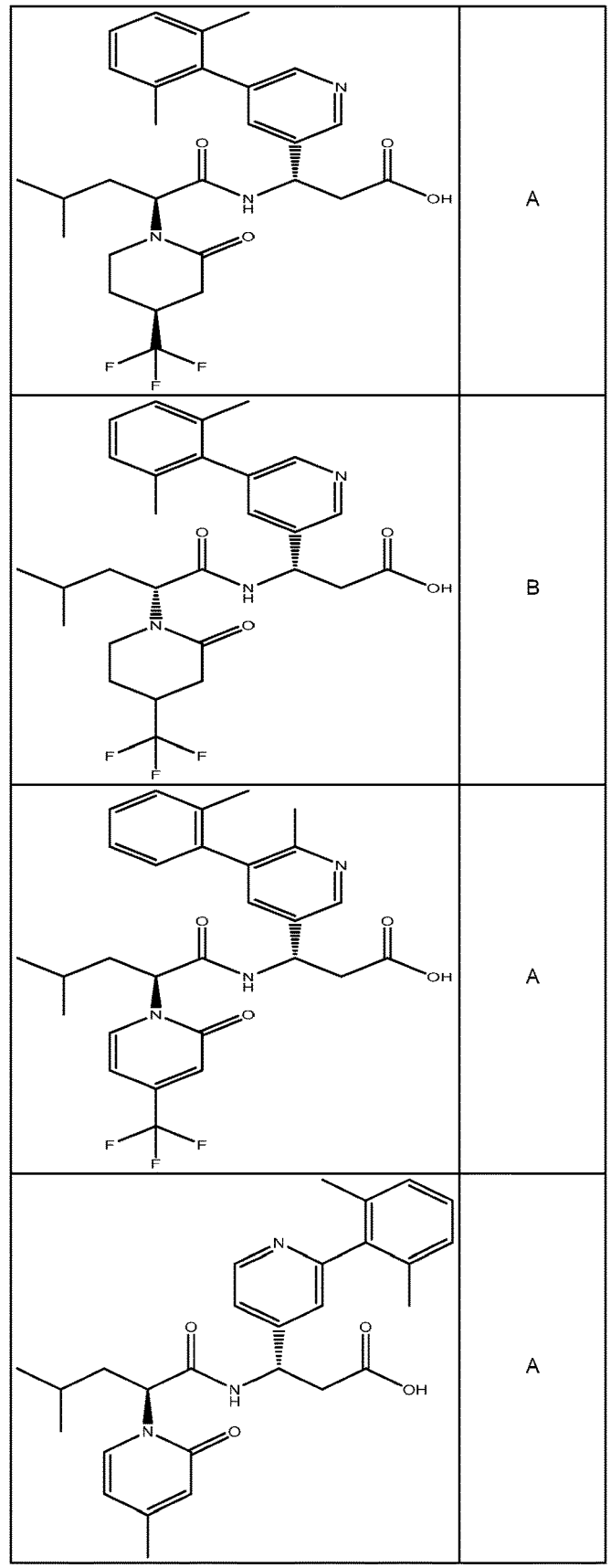

(cont.)
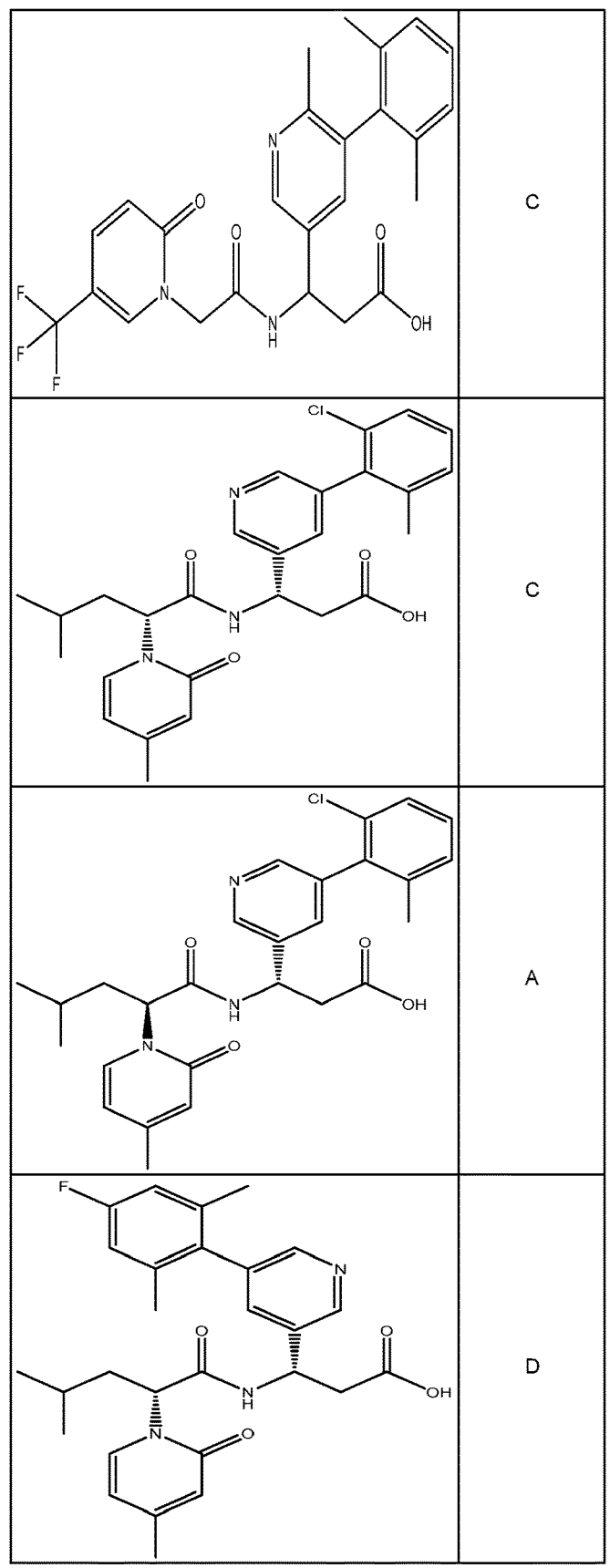

(cont.)
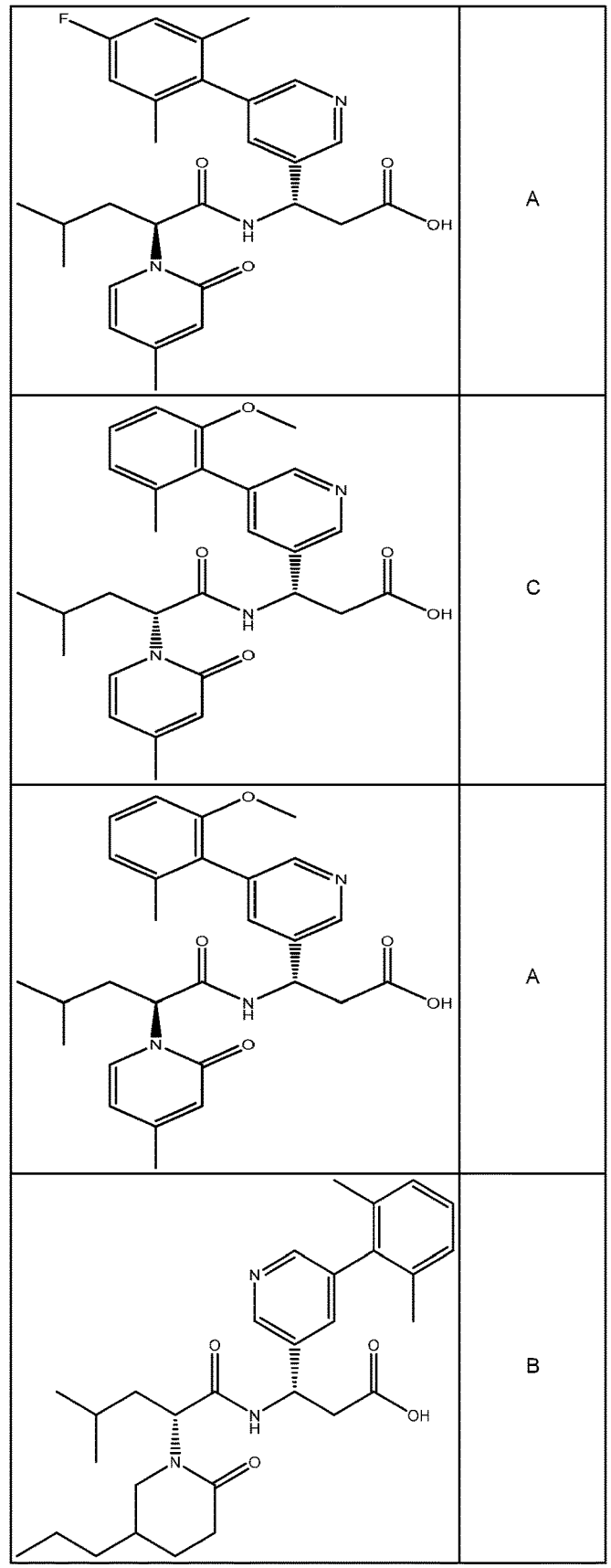

(cont.)
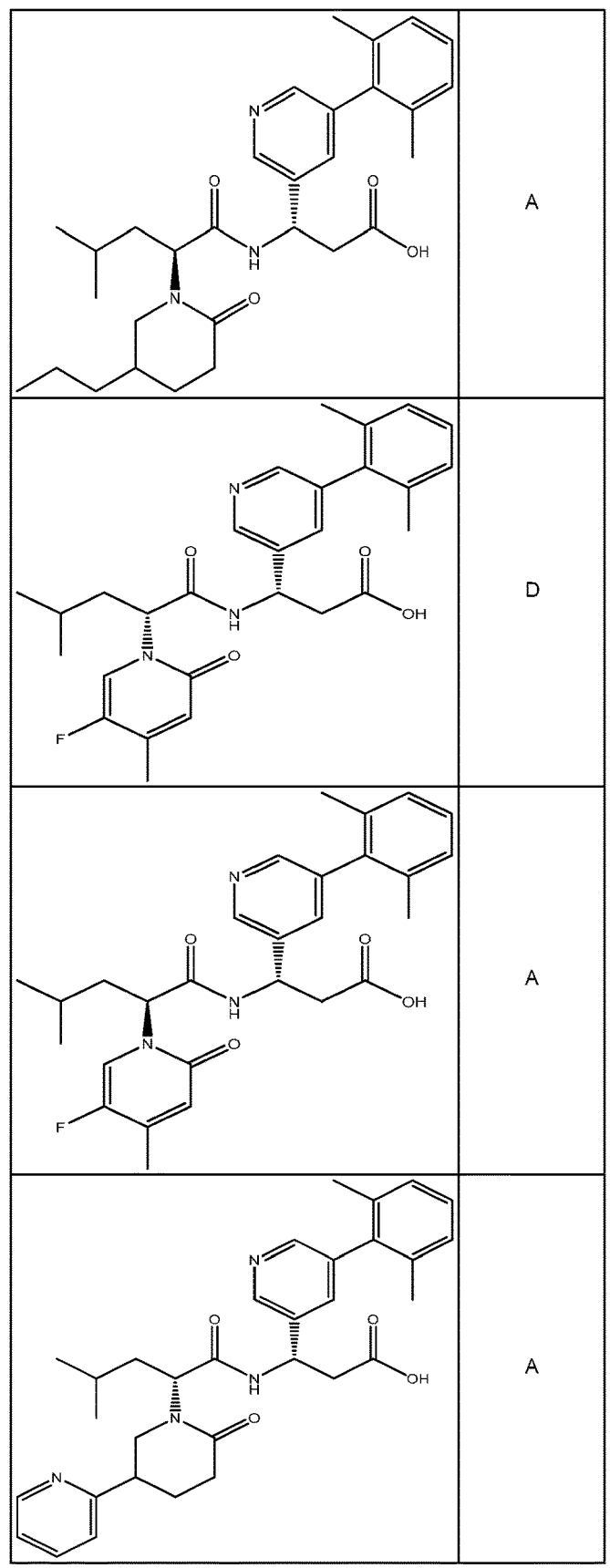

(cont.)
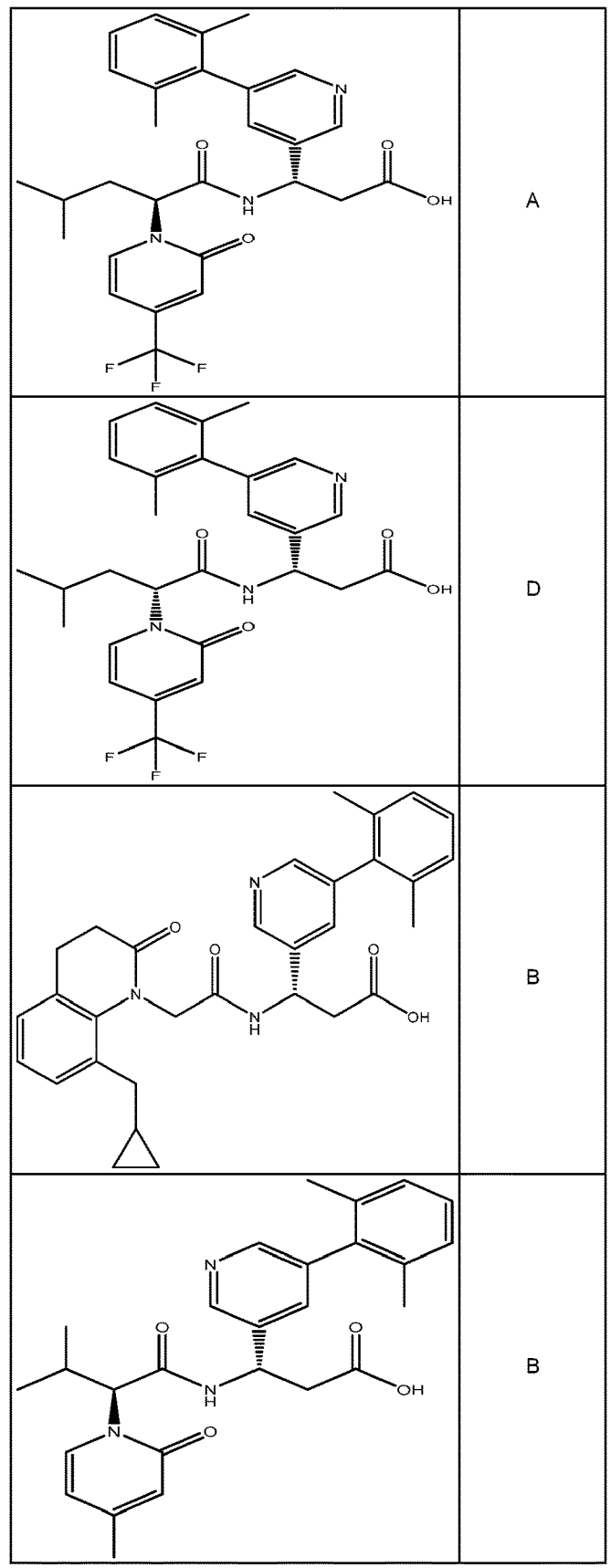

(cont.)
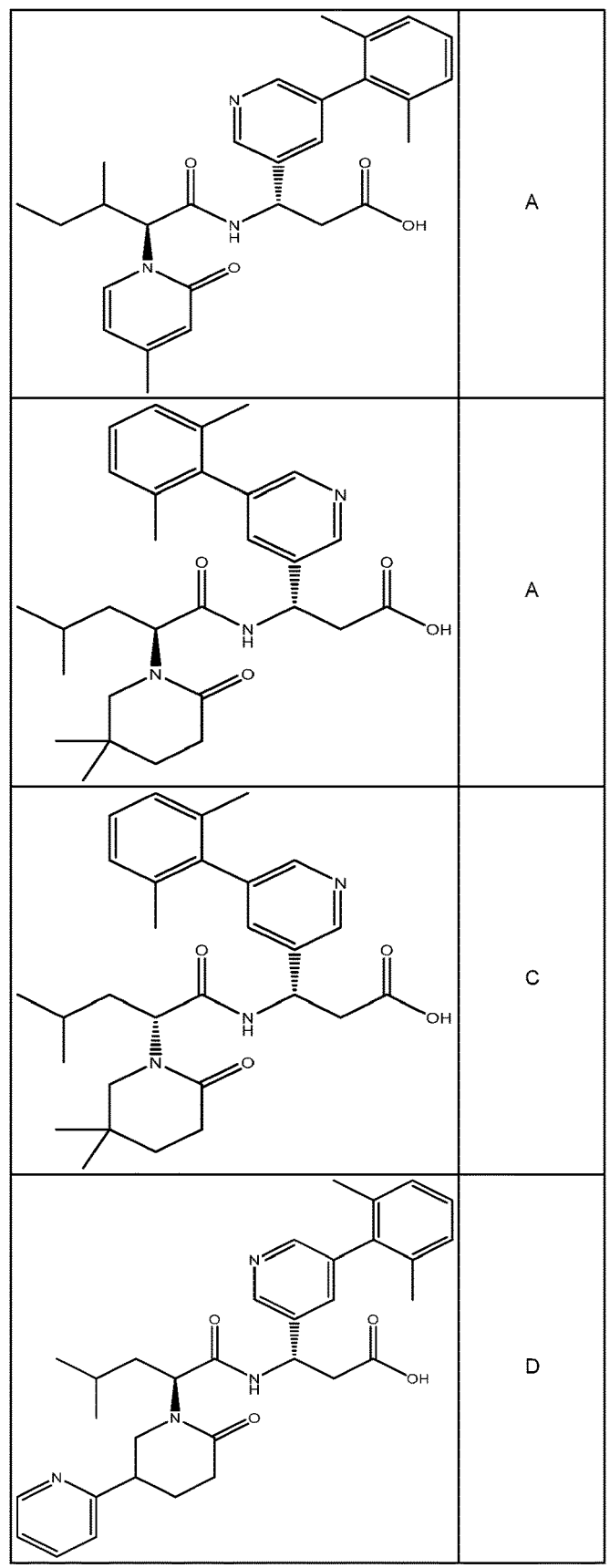

(cont.)
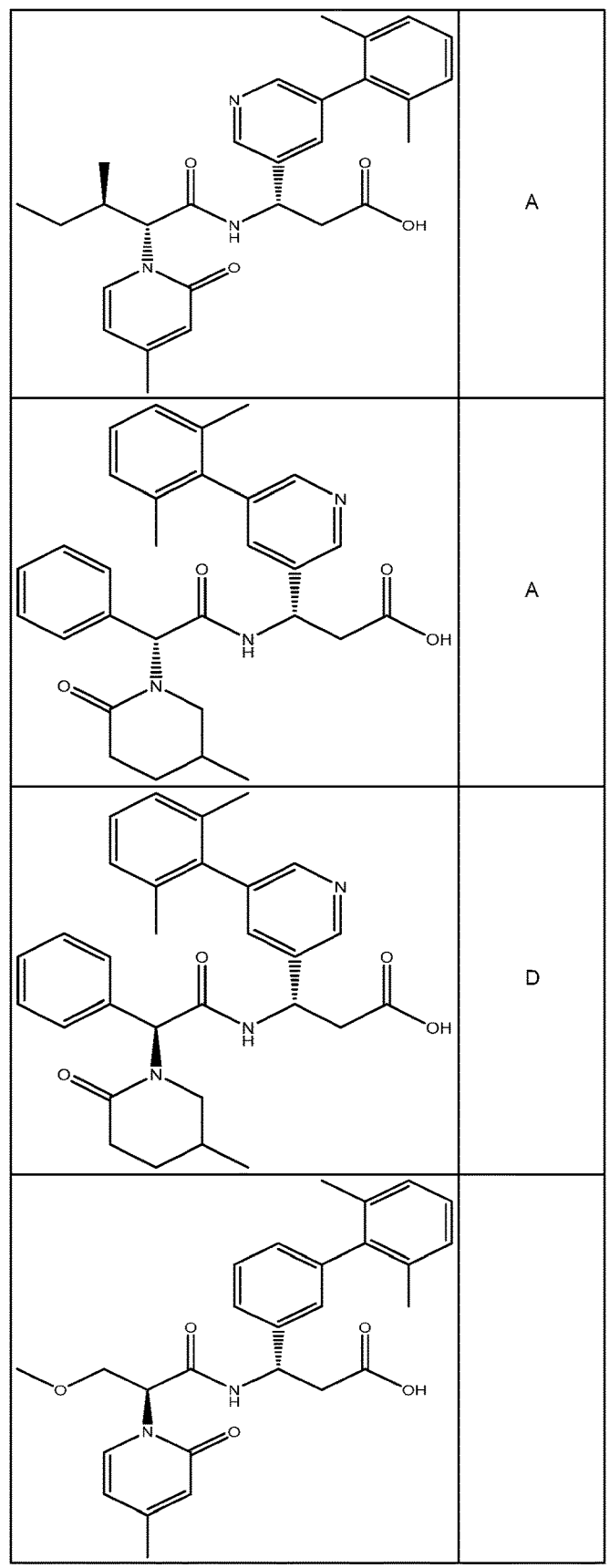

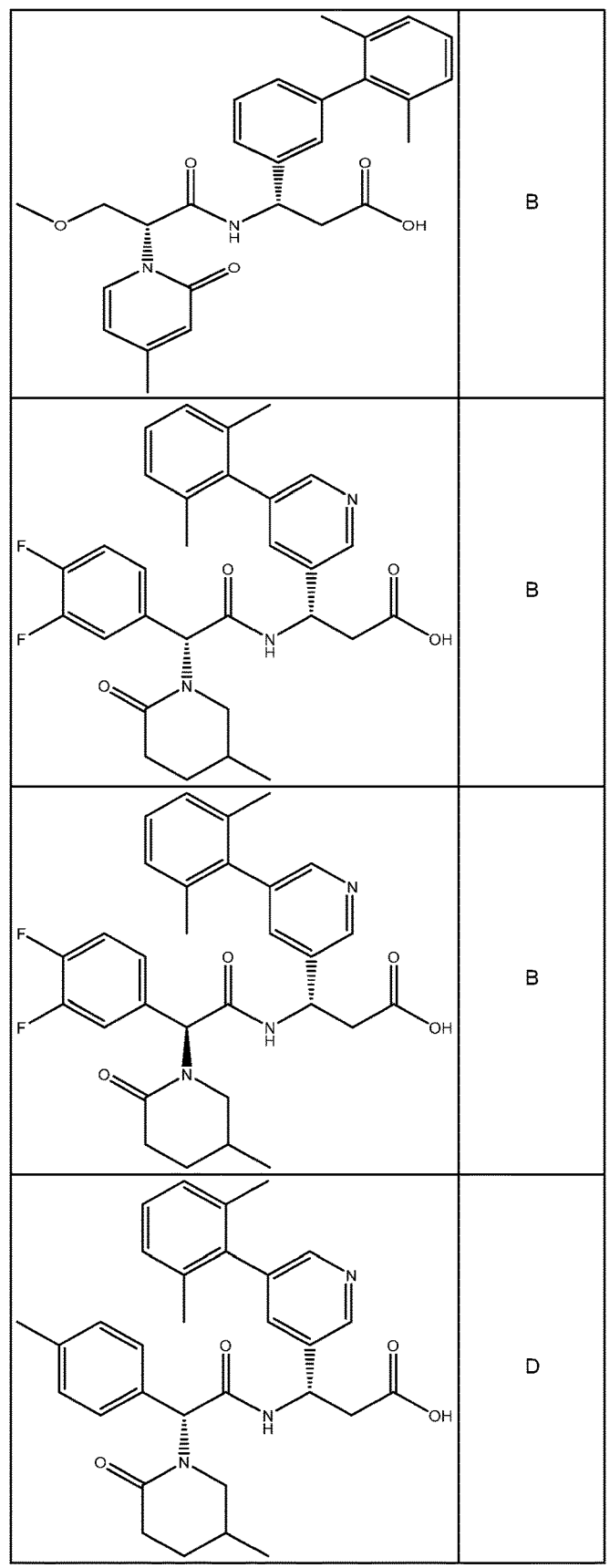

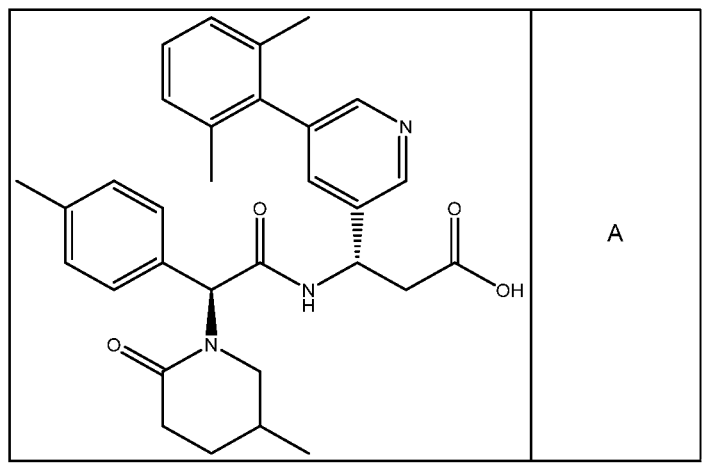
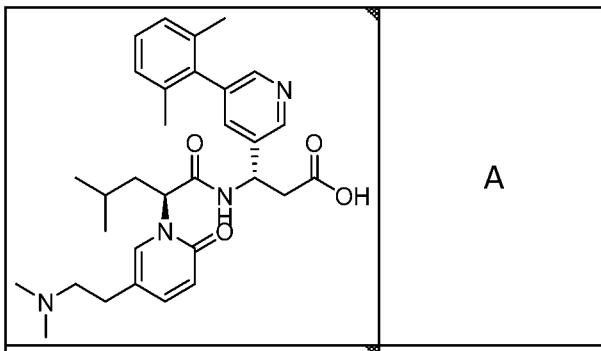
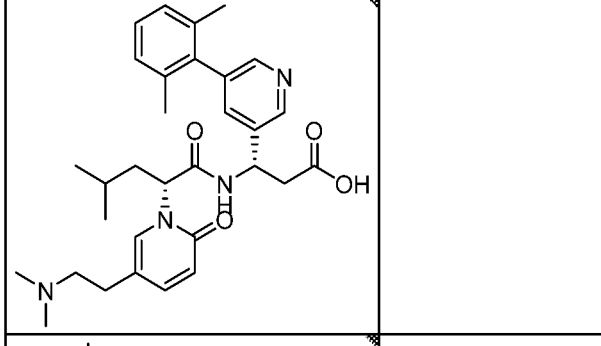
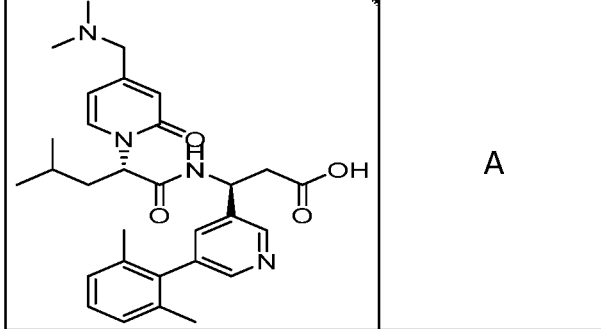

(cont.)
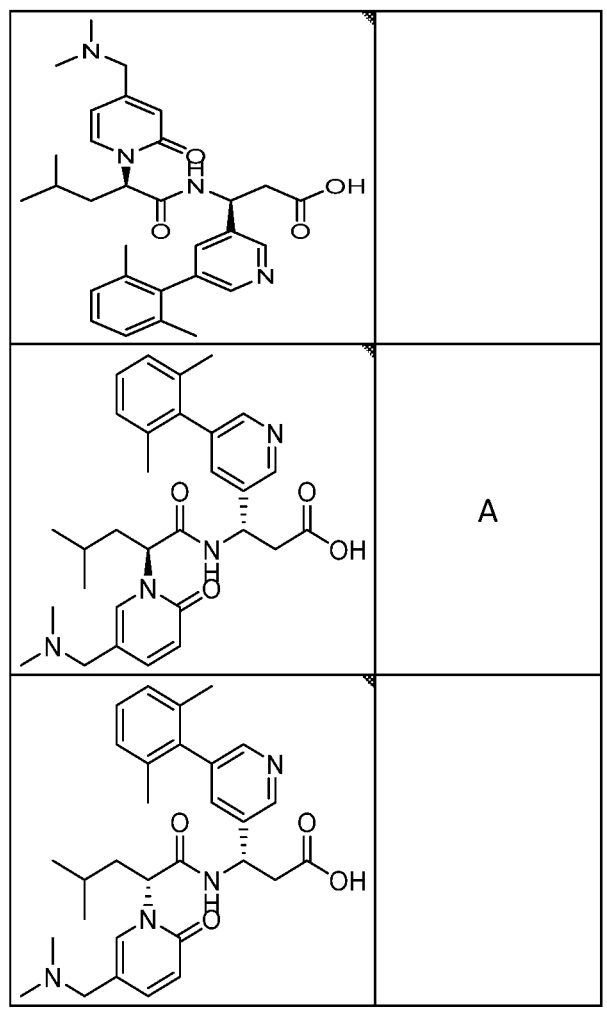
A (cont.)
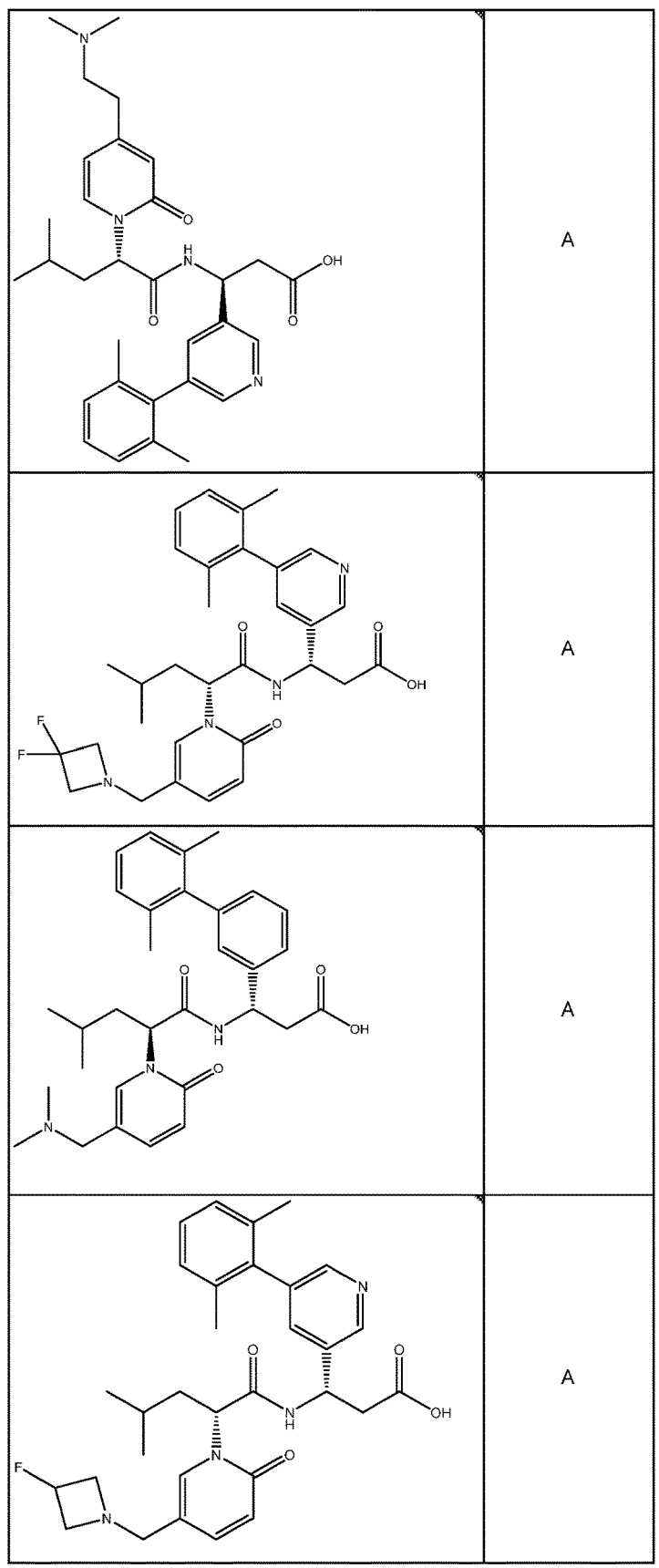

(cont.)
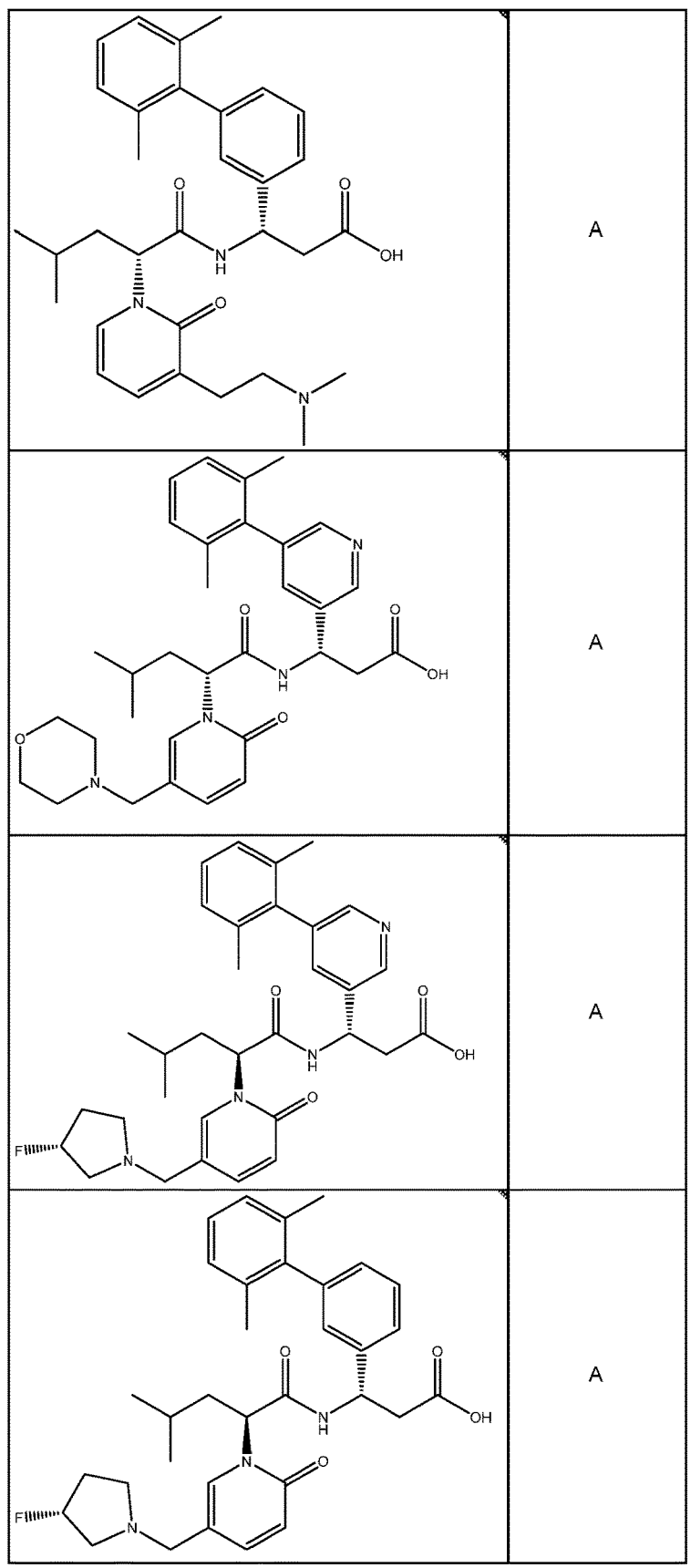

(cont.)
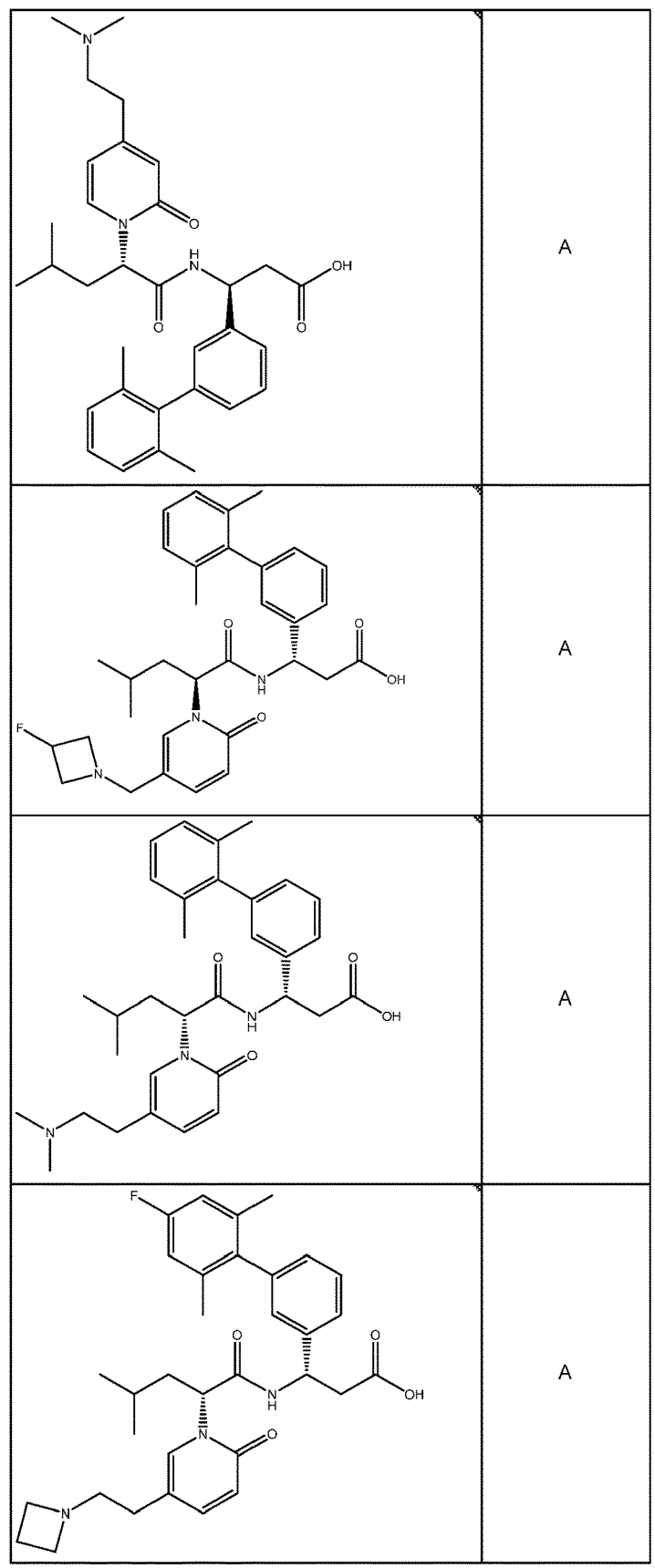

(cont.)
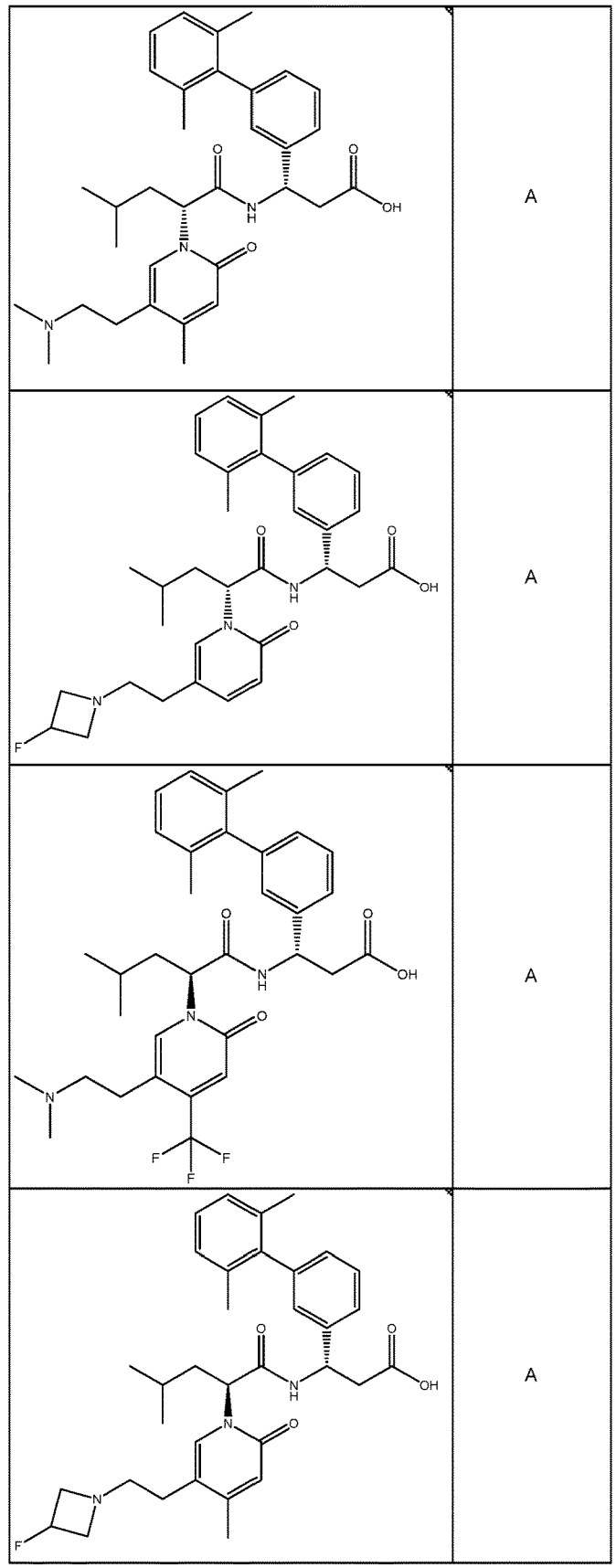

(cont.)
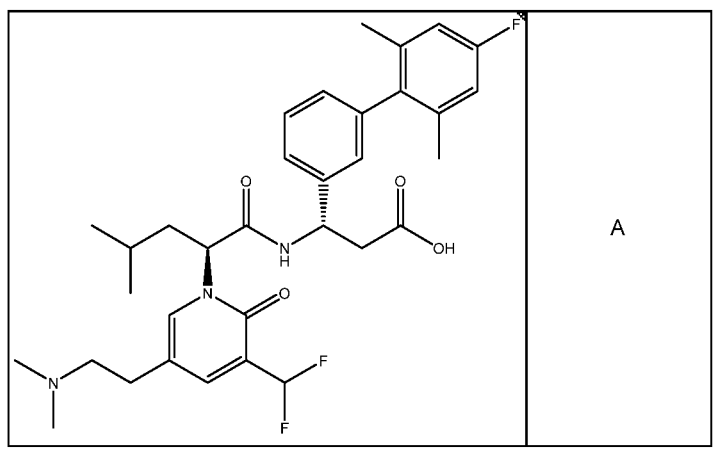
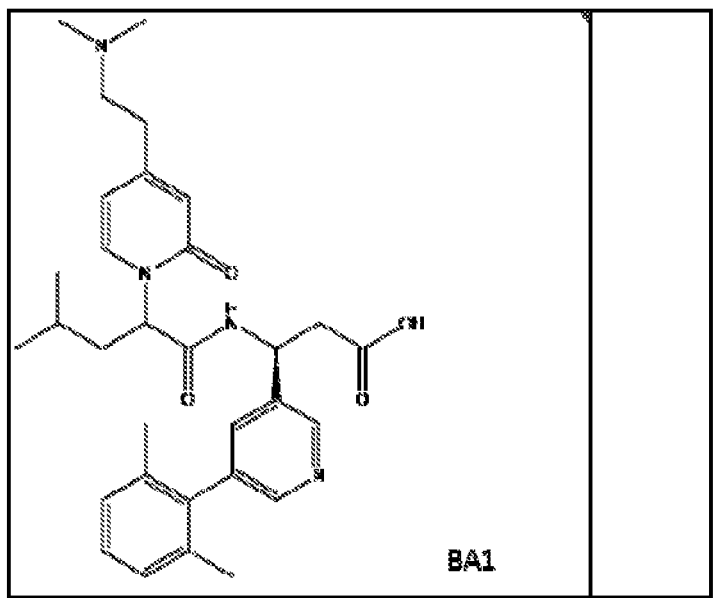
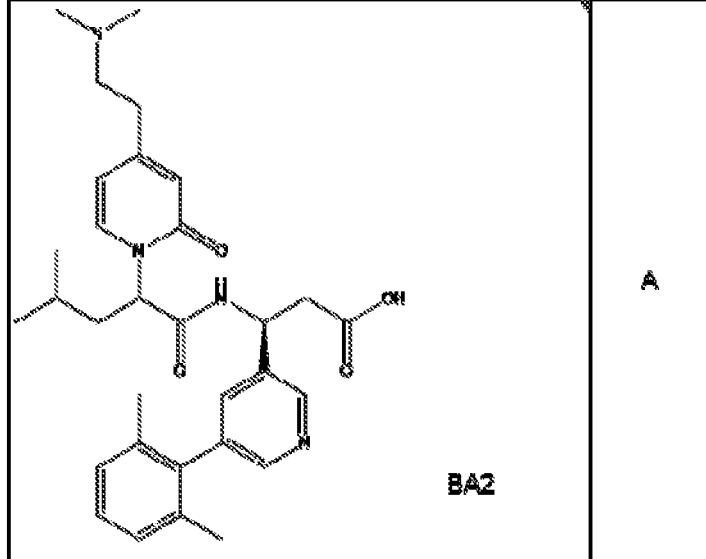

(cont.)
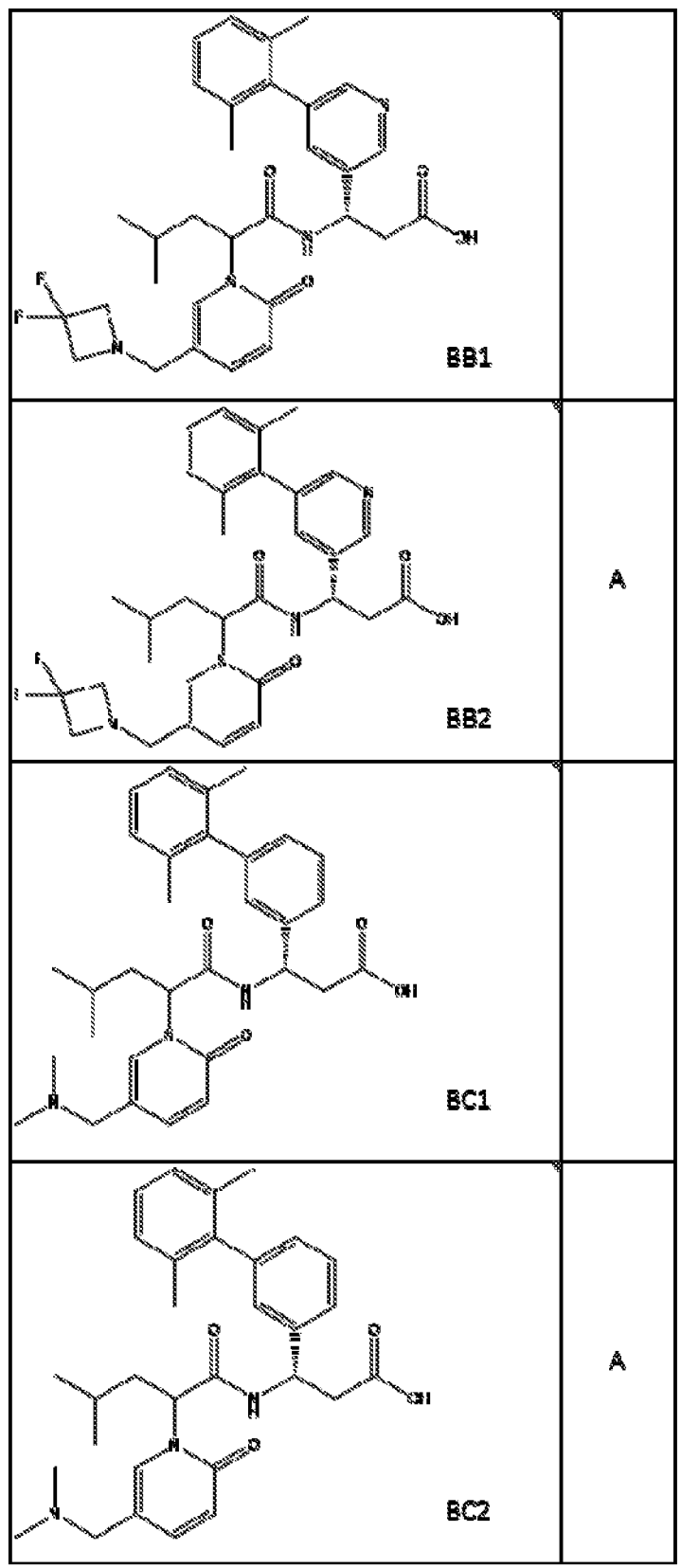

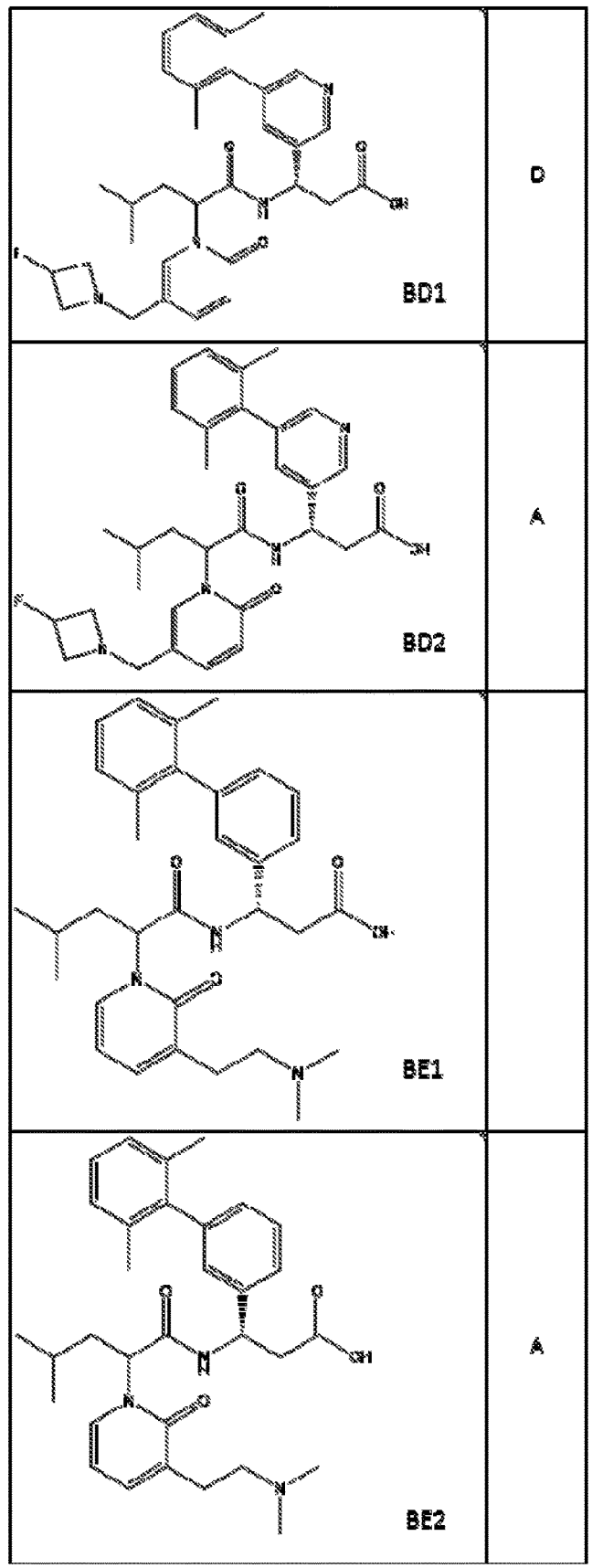

(cont.)
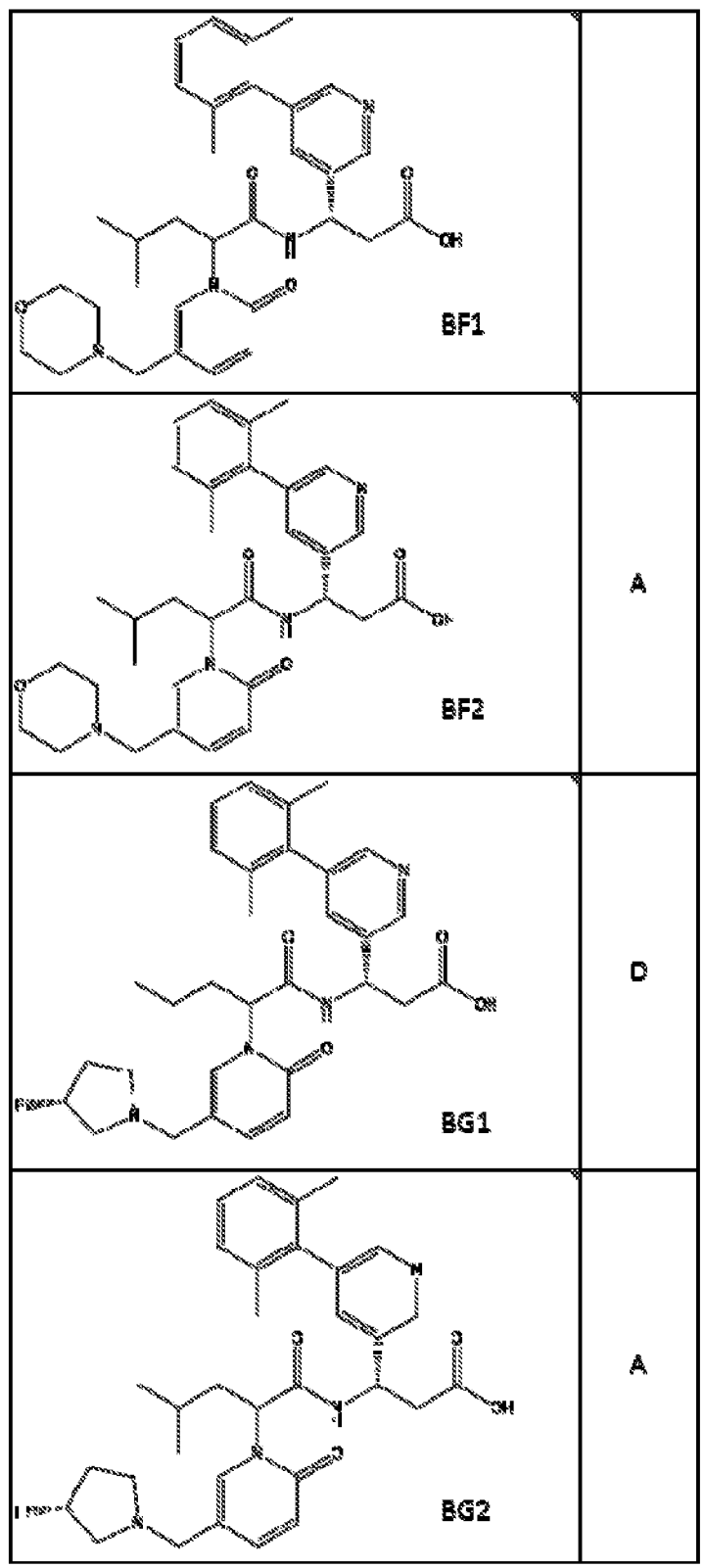

(cont.)
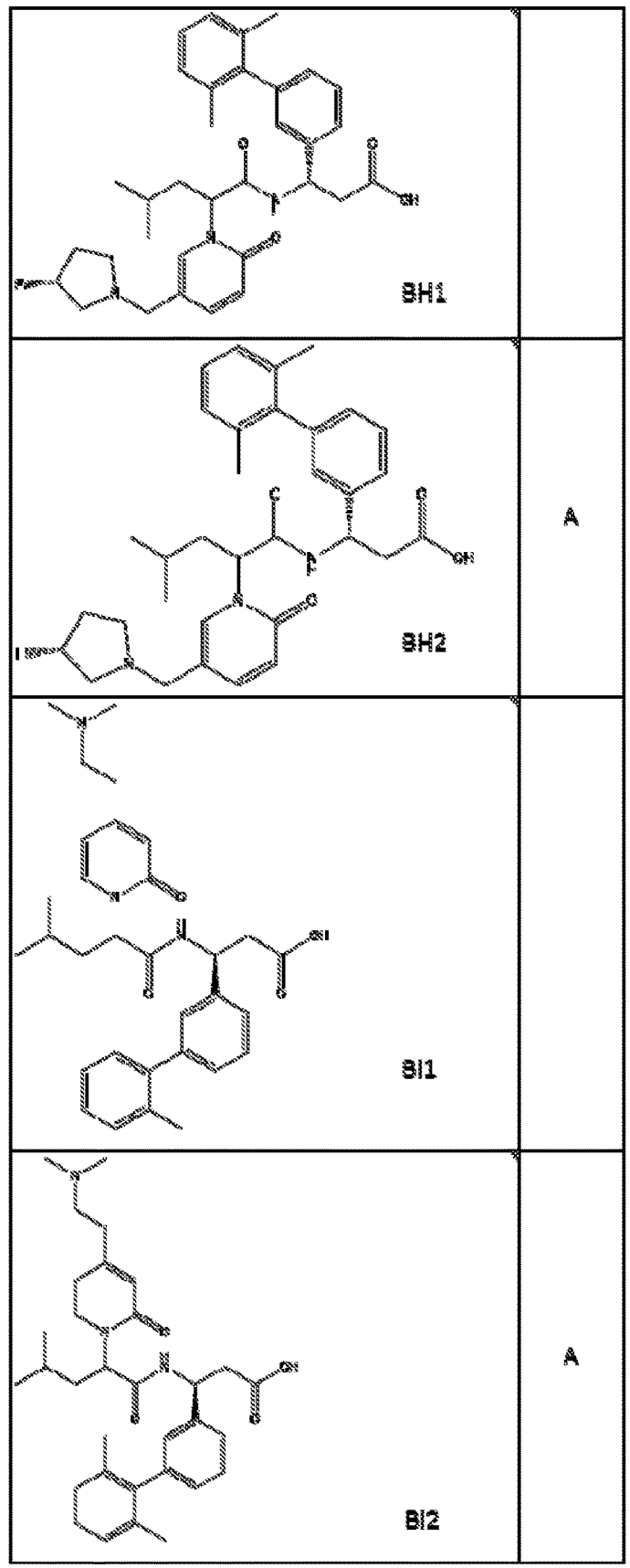

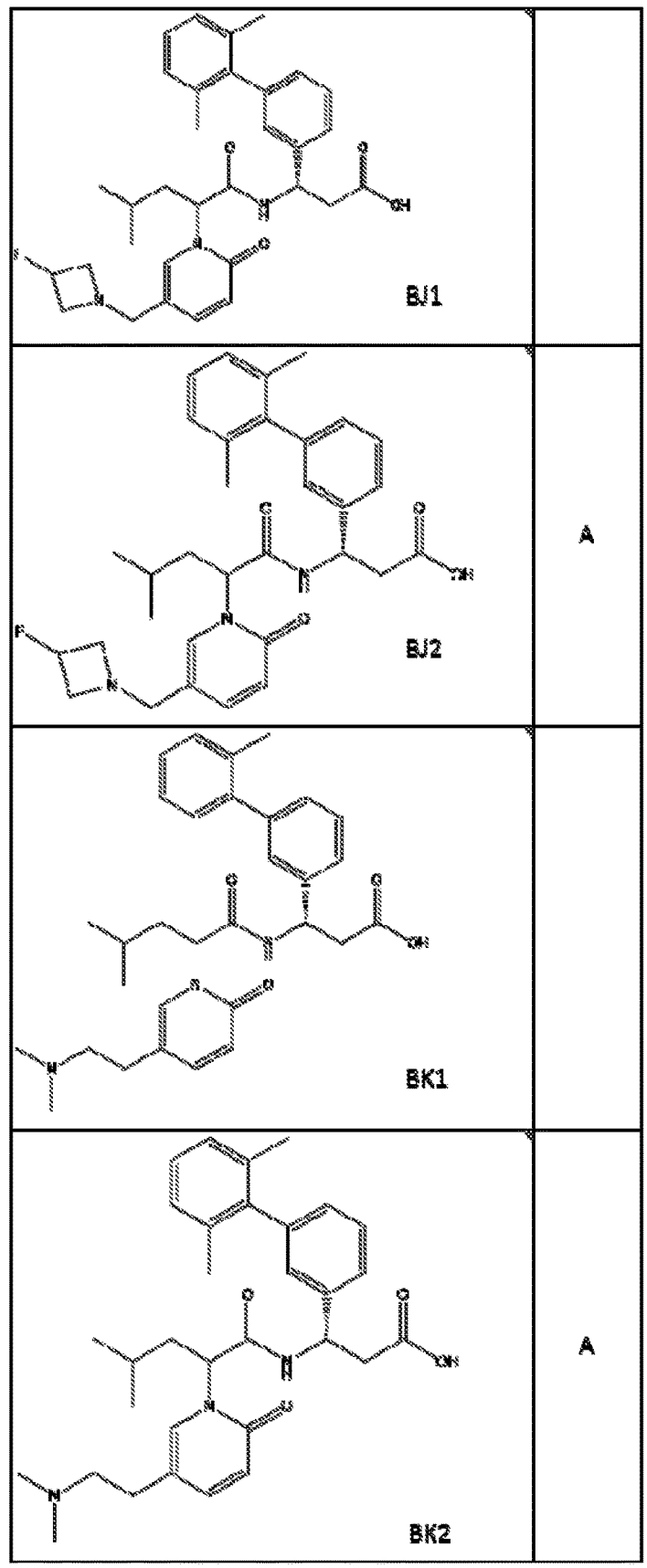

(cont.)
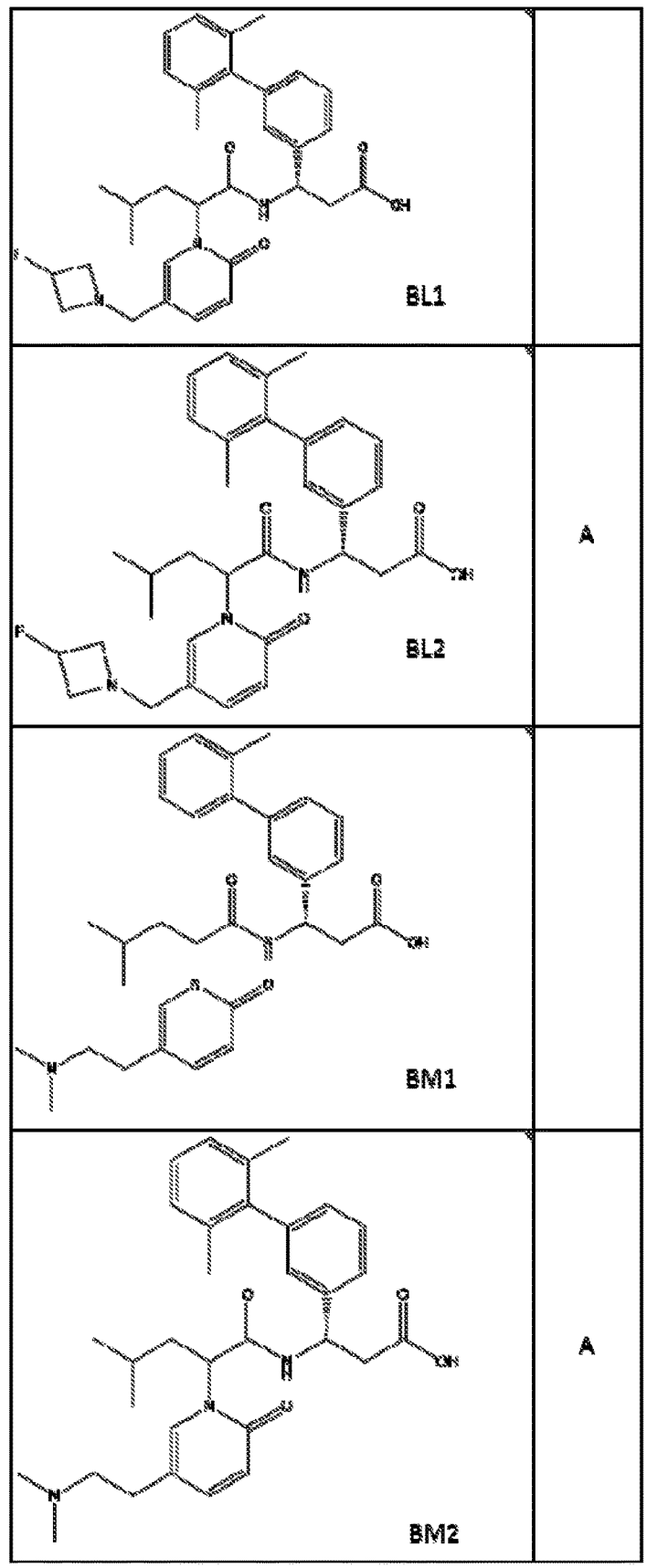

(cont.)
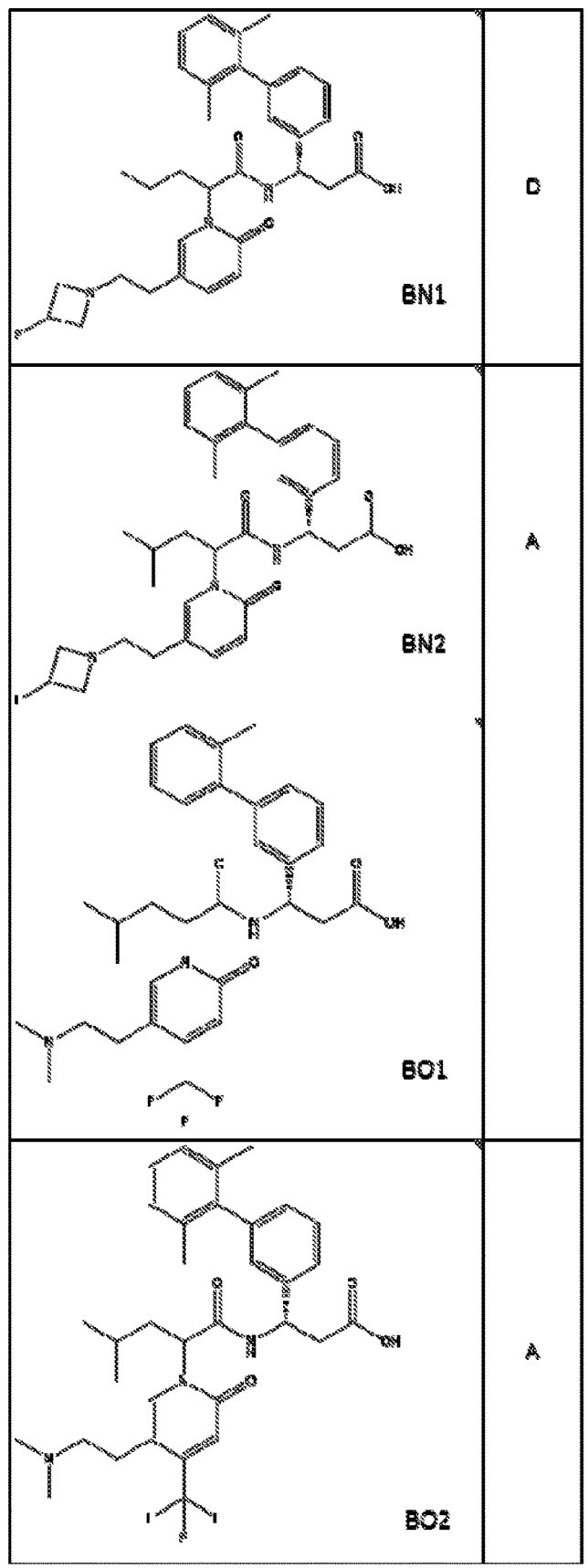

(cont.)
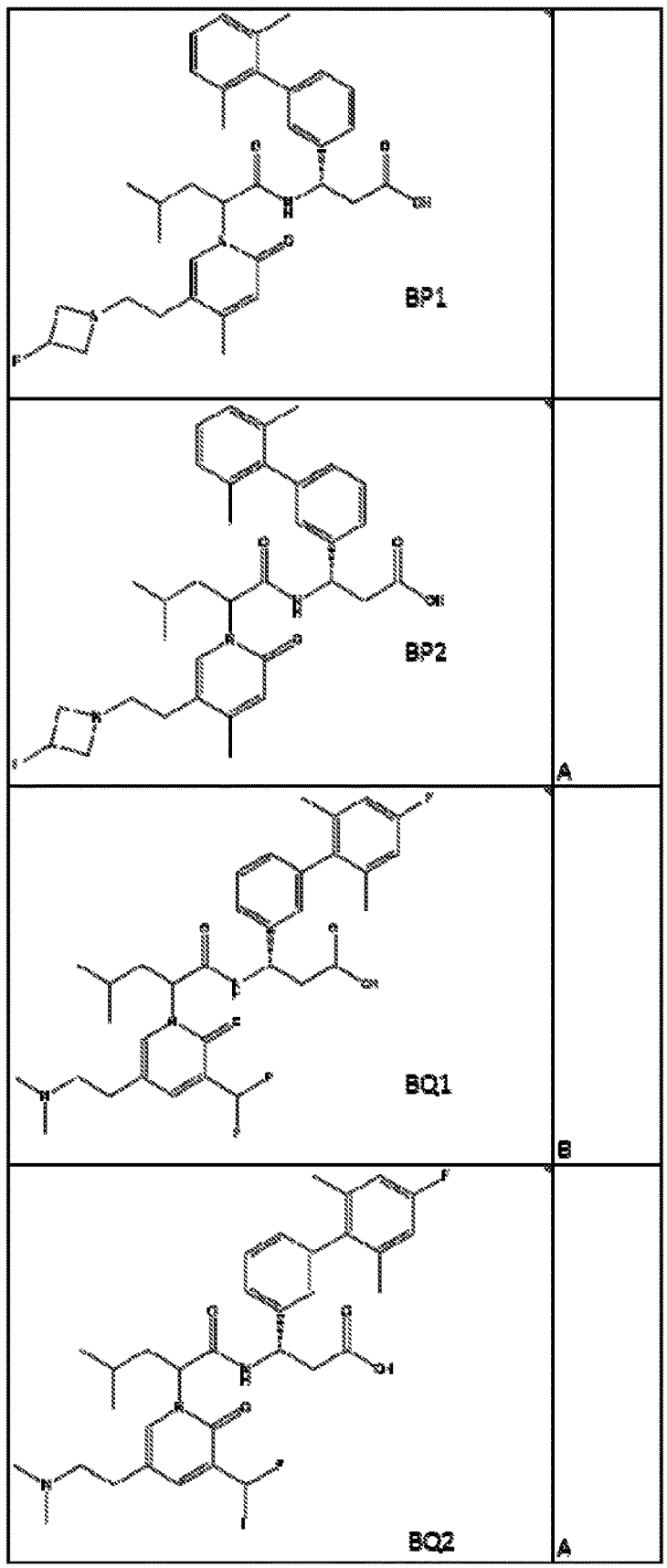

ANTAGONISTS OF HUMAN INTEGRIN (α4)(β7)

RELATED APPLICATIONS

This application is a continuation of U.S. patent application Ser. No. 16/382,512, filed Apr. 12, 2019, which claims the benefit of priority to U.S. Provisional Patent Application No. 62/656,742, filed Apr. 12, 2018.

BACKGROUND OF THE INVENTION

The heterodimeric integrin family of receptors modulate cellular shape and cell adhesion to the extracellular matrix in response to extrinsic and intrinsic cues.

Integrin signaling controls cell survival, cell cycle progression, cell differentiation, and cell migration.

The integrin receptor exclusively can signal a cell bi-directionally, both "inside-out" and "outside-in." Thus, they mediate cell migration by transmitting forces from the extracellular matrix to the cytoskeleton and regulate cytoskeletal organization to achieve shape changes needed during cell migration.

Integrins are expressed on the surface of most of human cells. Their pathology contributes to a diverse set of human diseases, including platelet disorders, atherosclerosis, cancer, osteoporosis, fibrosis, diabetic neuropathy of the kidney, macular degeneration and various autoimmune and chronic inflammation diseases.

Integrins form heterodimers of two different chains: the α (alpha) and β (beta) subunits. The α4β7 integrin is expressed on lymphocytes and is responsible for T-cell homing into gut-associated lymphoid tissues through its binding to mucosal addressin cell adhesion molecule (MAdCAM), which is present on high endothelial venules of mucosal lymphoid organs.

Inhibitors of specific integrin-ligand interactions have been shown effective as antiinflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis.

The role of integrins as drug targets has long been recognized, and a total of six injectable integrin inhibitors have been approved by the Food and Drug Administration for the treatment of various therapeutic indications: inflammatory bowel disease (Entyvio®, Tysabri®), multiple sclerosis (Tysabri®), psoriasis (Raptiva®), and acute coronary syndrome (Reopro®, Aggrastat®, Integrilin®). However, there has been a notable absence of therapeutic success with orally bioavailable integrin inhibitors.

Of the twenty-four known integrin heterodimers, as least half have relevance in inflammation, fibrosis, oncology and vascular disease. Thus, there exists a need for new classes of integrin inhibitors.

SUMMARY OF THE INVENTION

In certain embodiments, the invention relates to a compound of Formula I:

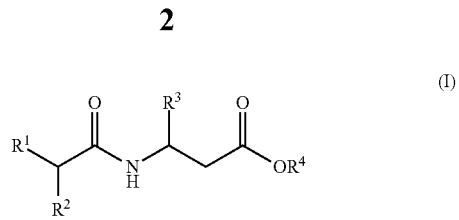

wherein:
$R^1$ is H, alkyl, alkylene-cycloalkyl, heterocyclyl, alkylene-O-alkyl, aryl, heteroaryl, or alkylene-$CF_3$;
$R^2$ is heterocyclyl;
$R^3$ is

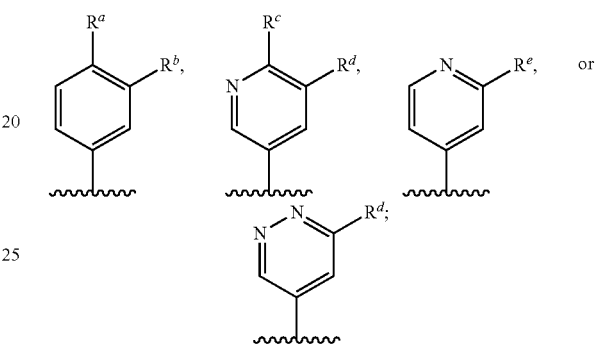

$R^4$ is H, or $(C_1-C_6)$-alkyl;
$R^a$ is H, alkyl, cycloalkyl, CN, or —O-alkyl;
$R^b$ is H, aryl, heterocylcyl, —O-cycloalkyl, —O-aryl, or —O-heterocyclyl;
$R^c$ is H, alkyl, cycloalkyl, hetrocyclyl, or alkylene-$CF_3$;
$R^d$ is aryl, heteroaryl, heterocyclyl, —O-cycloalkyl, —O-aryl, or —O-heterocyclyl;
$R^e$ is aryl, heteroaryl, or heterocyclyl;
or a pharmaceutically acceptable salt thereof.

In certain embodiments, the invention relates to a method of treating a disease or a condition selected from the group consisting of inflammatory bowel disease, ileoanal anastomosis, eosinophilic esophagitis, pancreatitis, insulin-dependent diabetes mellitus, mastitis, cholecystitis, cholangitis, pericholangitis, chronic bronchitis, chronic sinusitis, asthma and graft versus host disease, chronic inflammatory diseases of the lung, HIV, and hematological tumor, comprising the step of: administering to a subject in need thereof a therapeutically effective amount of any one of the compounds described herein.

BRIEF DESCRIPTION OF THE FIGURES

FIG. 1 is a table summarizing in vitro inhibition of α4β7 integrin by exemplary compounds.

DETAILED DESCRIPTION OF THE INVENTION

In certain embodiments, the invention relates to compounds that antagonize α4β7 integrin. The compounds will be useful for the treatment of inflammatory bowel disease, ileoanal anastomosis, eosinophilic esophagitis, pancreatitis, insulin-dependent diabetes mellitus, mastitis, cholecystitis, cholangitis, pericholangitis, chronic bronchitis, chronic sinusitis, asthma, graft versus host disease, chronic inflammatory diseases of the lung, HIV, or hematological tumor.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of" or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", J. Pharm. Sci. 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, preferred cycloalkyls have from 3-10 carbon atoms in their ring structure, and more preferably have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)—$(CH_2)_m$—$R^1$, wherein m and $R^1$ are defined below. Representative alkylthio groups include methylthio, ethylthio, and the like. The terms "alkoxyl" or "alkoxy" as used herein refers to an alkyl group, as defined below, having an oxygen moiety attached thereto. Representative alkoxy groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R_{10}$, where m and $R_{10}$ are described below.

The terms "amine" and "amino" are art-recognized and refer to both unsubstituted and substituted amines, e.g., a moiety that can be represented by the formulae:

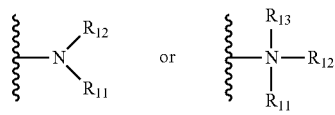

wherein $R_{11}$, $R_{12}$ and $R_{13}$ each independently represent a hydrogen, an alkyl, an alkenyl, —$(CH_2)_m$—$R_{10}$, or $R_{11}$ and $R_{12}$ taken together with the N atom to which they are attached complete a heterocycle having from 4 to 8 atoms in the ring structure; $R_{10}$ represents an alkenyl, aryl, cycloalkyl, a cycloalkenyl, a heterocyclyl, or a polycyclyl; and m is zero or an integer in the range of 1 to 8. In certain embodiments, only one of $R_{11}$ or $R_{12}$ can be a carbonyl, e.g., $R_{11}$, $R_{12}$, and the nitrogen together do not form an imide. In even more certain embodiments, $R_{11}$ and $R_{12}$ (and optionally $R_{13}$) each independently represent a hydrogen, an alkyl, an alkenyl, or —$(CH_2)_m$—$R_{10}$. Thus, the term "alkylamine" as used herein means an amine group, as defined above, having a substituted or unsubstituted alkyl attached thereto, i.e., at least one of $R_{11}$ and $R_{12}$ is an alkyl group. In certain embodiments, an amino group or an alkylamine is basic, meaning it has a conjugate acid with a $pK_a > 7.00$, i.e., the protonated forms of these functional groups have pKas relative to water above about 7.00.

The term "amide", as used herein, refers to a group

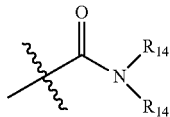

wherein each $R_{14}$ independently represent a hydrogen or hydrocarbyl group, or two $R_{14}$ are taken together with the N atom to which they are attached complete a heterocycle having from 4 to 8 atoms in the ring structure.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

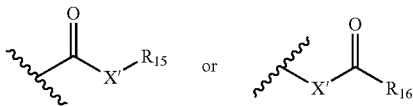

wherein X' is a bond or represents an oxygen or a sulfur, and $R_{15}$ represents a hydrogen, an alkyl, an alkenyl, —$(CH_2)_m$—$R_{10}$ or a pharmaceutically acceptable salt, $R_{16}$ represents a hydrogen, an alkyl, an alkenyl or —$(CH_2)_m$—$R_{10}$, where m and $R_{10}$ are as defined above. Where X' is an oxygen and $R_{15}$ or $R_{16}$ is not hydrogen, the formula represents an "ester." Where X' is an oxygen, and $R_{15}$ is as defined above, the moiety is referred to herein as a carboxyl group, and particularly when $R_{15}$ is a hydrogen, the formula represents a "carboxylic acid". Where X' is an oxygen, and $R_{16}$ is a hydrogen, the formula represents a "formate." In general, where the oxygen atom of the above formula is replaced by a sulfur, the formula represents a "thiocarbonyl" group. Where X' is a sulfur and $R_{15}$ or $R_{16}$ is not hydrogen, the formula represents a "thioester" group. Where X' is a sulfur and $R_{15}$ is a hydrogen, the formula represents a "thiocarboxylic acid" group. Where X' is a sulfur and $R_{16}$ is a hydrogen, the formula represents a "thioformate" group. On the other hand, where X' is a bond, and $R_{15}$ is not hydrogen, the above formula represents a "ketone" group. Where X' is a bond, and $R_{15}$ is a hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —$NO_2$; the term "halogen" designates —F, —Cl, —Br, or —I; the term "sulfhydryl" means —SH; the term "hydroxyl" means —OH; the term "sulfonyl" means —$SO_2$—; the term "azido" means —$N_3$; the term "cyano" means —CN; the term "isocyanato" means —NCO; the term "thiocyanato" means —SCN; the term "isothiocyanato" means —NCS; and the term "cyanato" means —OCN.

The term "sulfamoyl" is art-recognized and includes a moiety that can be represented by the formula:

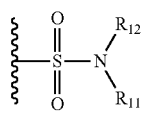

in which $R_{11}$ and $R_{12}$ are as defined above.

The term "sulfate" is art recognized and includes a moiety that can be represented by the formula:

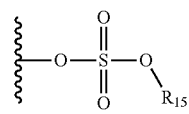

in which $R_{15}$ is as defined above.

The term "sulfonamide" is art recognized and includes a moiety that can be represented by the formula:

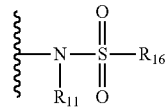

in which $R_{11}$ and $R_{16}$ are as defined above.

The term "sulfonate" is art-recognized and includes a moiety that can be represented by the formula:

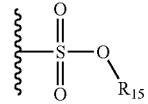

in which $R_{54}$ is an electron pair, hydrogen, alkyl, cycloalkyl, or aryl.

The terms "sulfoxido" or "sulfinyl", as used herein, refers to a moiety that can be represented by the formula:

in which $R_{17}$ is selected from the group consisting of the group consisting of hydrogen, alkyl, alkenyl, alkynyl, cycloalkyl, heterocyclyl, aralkyl, or aryl.

The term "urea" is art-recognized and may be represented by the general formula

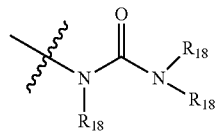

wherein each $R_{18}$ independently represents hydrogen or a hydrocarbyl, such as alkyl, or any occurrence of $R_{18}$ taken together with another and the intervening atom(s) complete a heterocycle having from 4 to 8 atoms in the ring structure.

As used herein, the definition of each expression, e.g., alkyl, m, n, etc., when it occurs more than once in any structure, is intended to be independent of its definition elsewhere in the same structure.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

For purposes of this invention, the chemical elements are identified in accordance with the Periodic Table of the Elements, CAS version, Handbook of Chemistry and Physics, 67th Ed., 1986-87, inside cover.

Exemplary Compounds

In certain embodiments, the invention relates to a compound of Formula I:

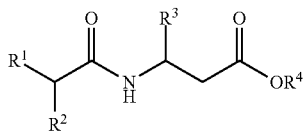 (I)

wherein:

R[1] is H, alkyl, alkylene-cycloalkyl, heterocyclyl, alkylene-O-alkyl, aryl, heteroaryl, or alkylene-CF$_3$;

R[2] is heterocyclyl;

R[3] is

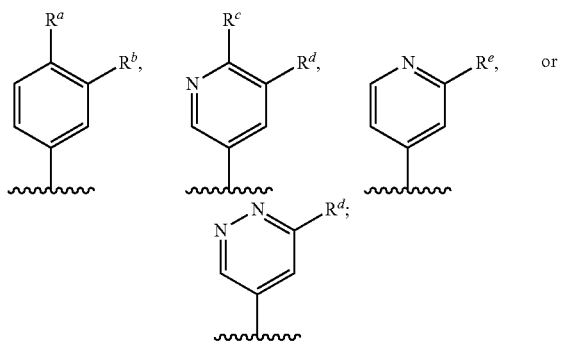

R[4] is H, or (C$_1$-C$_6$)-alkyl;

R[a] is H, alkyl, cycloalkyl, CN, or —O-alkyl;

R[b] is H, alkyl, aryl, heteroaryl, heterocylcyl, —O-cycloalkyl, —O-aryl, or —O— heterocyclyl;

R$_c$ is H, alkyl, cycloalkyl, hetrocyclyl, or alkylene-CF$_3$;

R[d] is aryl, heteroaryl, heterocyclyl, —O-cycloalkyl, —O-aryl, or —O— heterocyclyl; and R[e] is aryl, heteroaryl, or heterocyclyl;

or a pharmaceutically acceptable salt thereof.

In certain embodiments, the invention relates to any one of the aforementioned compounds, wherein R[1] is alkyl. In certain embodiments, R[1] is methyl, ethyl, isopropyl, n-propyl, i-butyl, n-butyl, or t-butyl.

In certain embodiments, the invention relates to any one of the aforementioned compounds, wherein R[1] is alkylene-cycloalkyl. In some embodiments, alkylene-cycloalkyl is methylene-cyclopropyl.

In certain embodiments, the invention relates to any one of the aforementioned compounds, wherein R[1] is heterocyclyl. In some embodiments, R[1] is substituted heterocyclyl. In some embodiments, R[1] is N-containing heterocyclyl. In some embodiments, R[1] is substituted N-containing heterocyclyl.

In certain embodiments, the invention relates to any one of the aforementioned compounds, wherein R[1] is -alkylene-O-alkyl. In some embodiments, R[1] is methylene-O-methyl.

In certain embodiments, the invention relates to any one of the aforementioned compounds, wherein R[1] is aryl. In some embodiments, R[1] is phenyl. In some embodiments, R[1] is unsubstituted phenyl. In some embodiments, R[1] is substituted phenyl. In some embodiments, substituted phenyl is substituted with one or more substituents selected from alkyl and halogen.

In certain embodiments, the invention relates to any one of the aforementioned compounds, wherein R[1] is alkylene-CF$_3$. In some embodiments, R[1] is methylene-CF$_3$.

In certain embodiments, the invention relates to any one of the aforementioned compounds, wherein R[2] is heterocyclyl. In certain embodiments, R[2] is substituted heterocyclyl. In certain embodiments, R[2] is N-containing heterocyclyl. In certain embodiments, the N-containing heterocyclyl is a 6- to 12-membered heterocyclyl. In some embodiments, R[2] is substituted with one or more substituents selected from amino, alkyl and alkoxy, wherein alkyl or alkoxy is substituted with morphilino, a cyclic amino, or an acyclic amino, and wherein said alkyl, alkoxy, morpholino, cyclic amino, or acyclic amino moiety is optionally substituted with one or more alkoxyls or fluorines.

In certain embodiments, R[2] is unsubstituted pyridinonyl. In certain embodiments, R[2] is substituted pyridinonyl. In some embodiments, substituted pyridinonyl is substituted with one or more substituents selected from alkyl, cycloalkyl, heterocycloalkyl, halogen, aryl, heteroaryl, and CF$_3$.

In some embodiments, R[2] is selected from

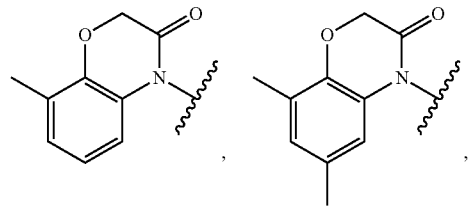

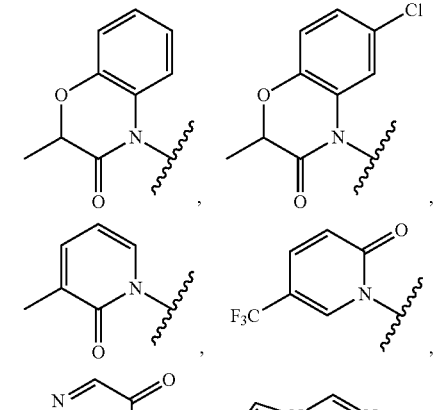

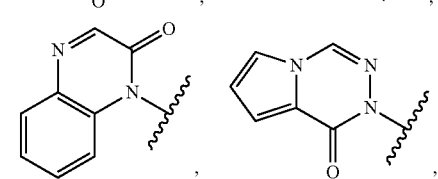

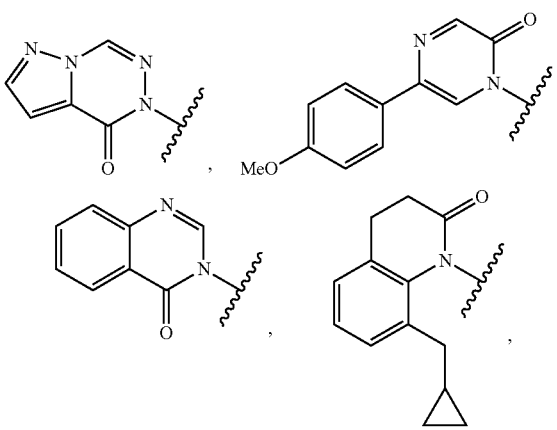

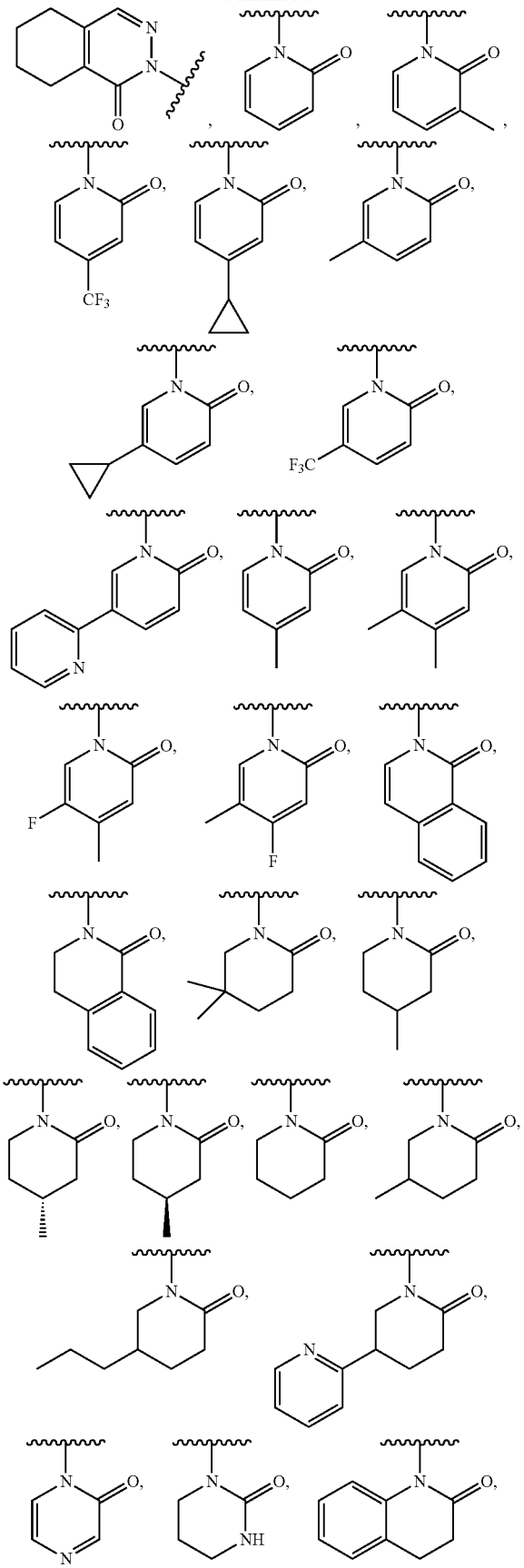
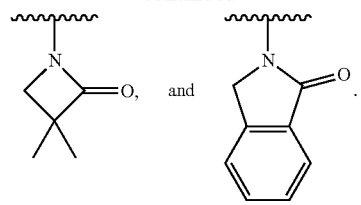
In some embodiments, R² is selected from
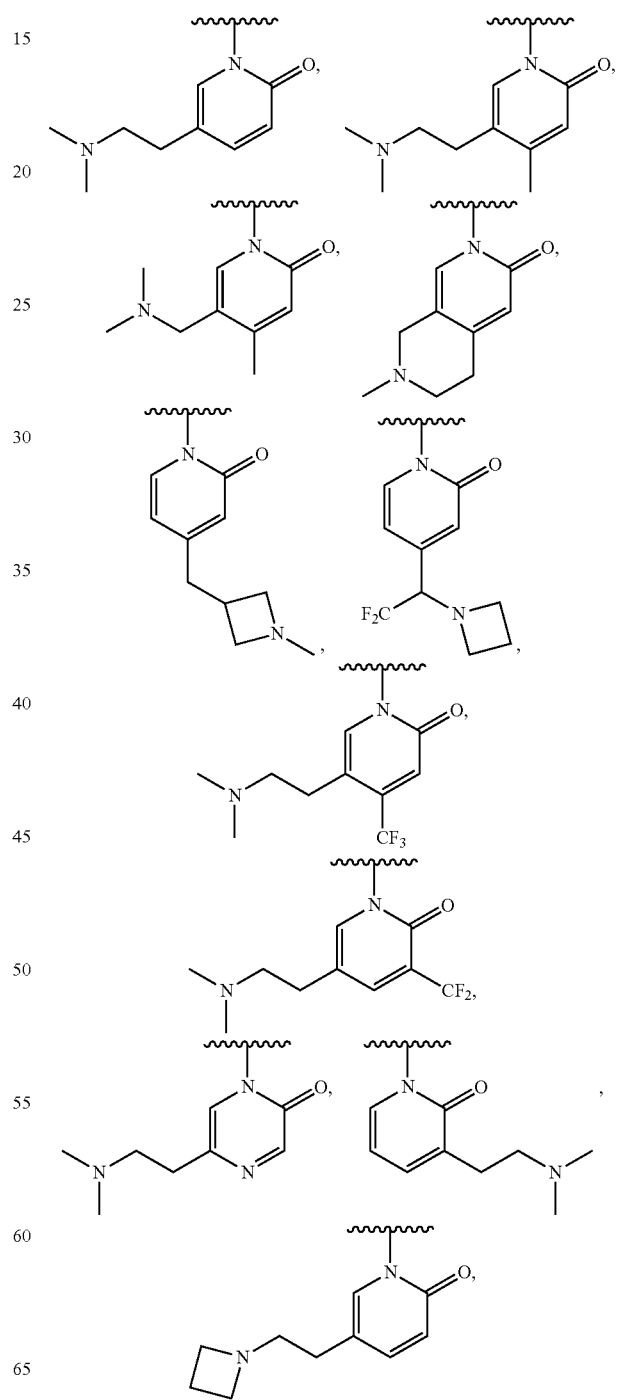

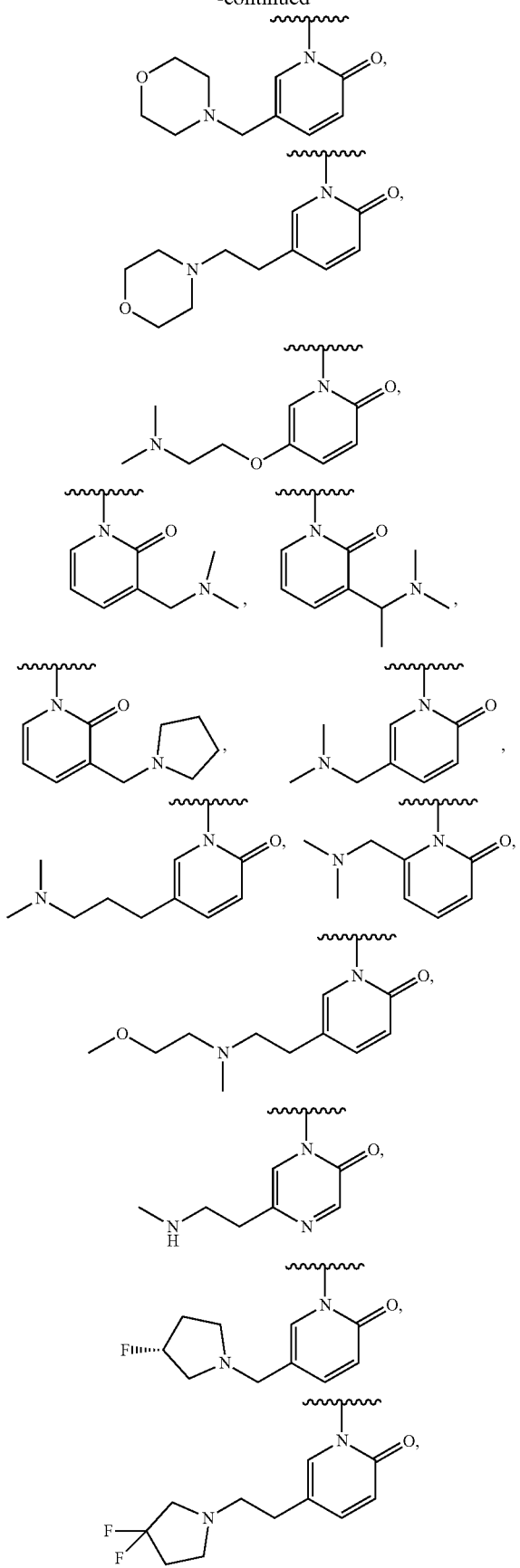
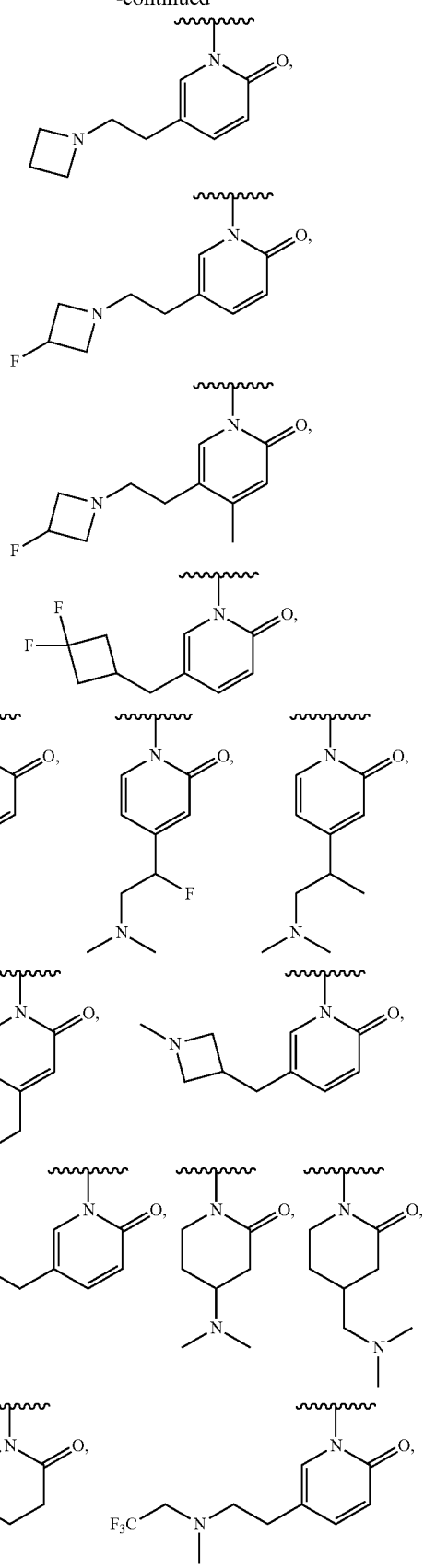

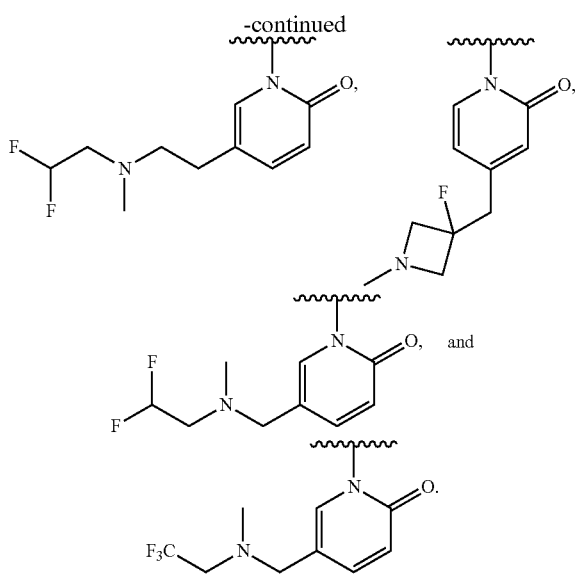

In certain embodiments, the invention relates to any one of the aforementioned compounds, wherein $R^3$ is

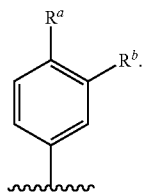

In certain embodiments, the invention relates to any one of the aforementioned compounds, wherein $R^4$ is H.

In certain embodiments, the invention relates to any one of the aforementioned compounds, wherein $R^4$ is $(C_1$-$C_6)$-alkyl. In some embodiments, $R^4$ is methyl, ethyl, isopropyl, n-propyl, iso-butyl, n-butyl, or tert-butyl.

In certain embodiments, the invention relates to any one of the aforementioned compounds, wherein $R^a$ is H.

In certain embodiments, the invention relates to any one of the aforementioned compounds, wherein $R^a$ is alkyl. In some embodiments, $R^a$ is methyl.

In certain embodiments, the invention relates to any one of the aforementioned compounds, wherein $R^a$ is cyclopropyl. In certain embodiments, the invention relates to any one of the aforementioned compounds, wherein $R^a$ is CN.

In certain embodiments, the invention relates to any one of the aforementioned compounds, wherein $R^a$ is —O-alkyl. In some embodiments, $R^a$ is —OMe.

In certain embodiments, the invention relates to any one of the aforementioned compounds, wherein $R^b$ is H.

In certain embodiments, the invention relates to any one of the aforementioned compounds, wherein $R^b$ is alkyl. In some embodiments, $R^b$ is methyl, ethyl, n-propyl, isopropyl, n-butyl, i-butyl, or t-butyl. In some embodiments, $R^b$ is t-butyl.

In certain embodiments, the invention relates to any one of the aforementioned compounds, wherein $R^b$ is aryl. In some embodiments, $R^b$ is substituted aryl.

In certain embodiments, the invention relates to any one of the aforementioned compounds, wherein $R^b$ is heteroaryl. In some embodiments, $R^b$ is substituted heteroaryl. In some embodiments, substituted aryl or substituted heteroaryl is substituted with one or more substituents selected from alkyl, halogen, OH, —O-alkyl, CN, cycloalkyl, or heterocycloalkyl. In some embodiments, $R^b$ is substituted aryl. In some embodiments, $R^b$ is selected from

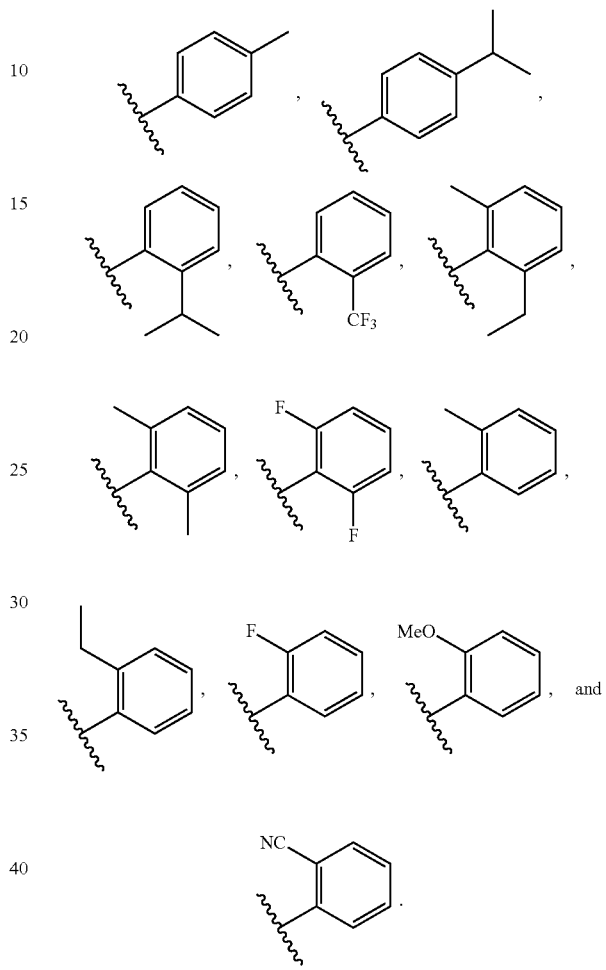

In certain embodiments, the invention relates to any one of the aforementioned compounds, wherein $R^b$ is heterocyclyl. In some embodiments, $R^b$ is substituted heterocyclyl. In some embodiments, substituted heterocyclyl is substituted with one or more substituents selected from alkyl, OH, and —O-alkyl. In some embodiments, $R^b$ is selected from

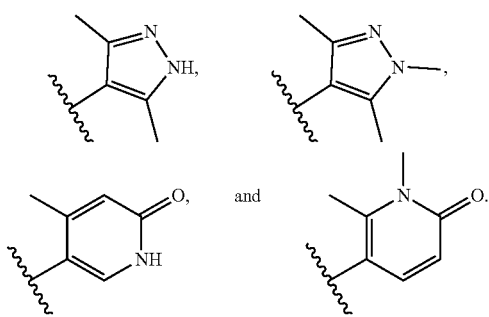

In some embodiments, $R^b$ is selected from

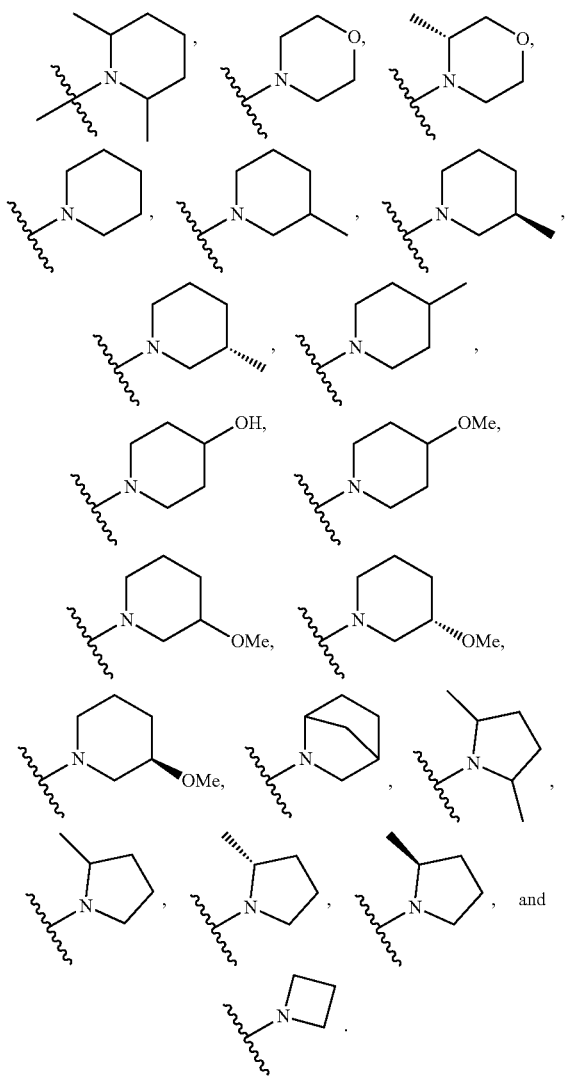

In certain embodiments, the invention relates to any one of the aforementioned compounds, wherein $R^b$ is —O-cycloalkyl. In some embodiments, $R^b$ is —O-cyclobutyl.

In certain embodiments, the invention relates to any one of the aforementioned compounds, wherein $R^b$ is —O-aryl. In some embodiments, $R^b$ is —O-phenyl.

In certain embodiments, the invention relates to any one of the aforementioned compounds, wherein $R^3$ is

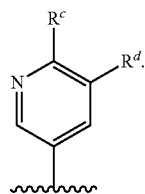

In certain embodiments, the invention relates to any one of the aforementioned compounds, wherein $R^3$ is

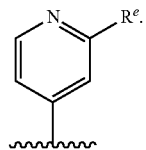

In certain embodiments, the invention relates to any one of the aforementioned compounds, wherein $R^3$ is

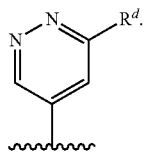

In certain embodiments, the invention relates to any one of the aforementioned compounds, wherein $R^c$ is H.

In certain embodiments, the invention relates to any one of the aforementioned compounds, wherein $R^c$ is alkyl. In some embodiments, $R^c$ is methyl or ethyl.

In certain embodiments, the invention relates to any one of the aforementioned compounds, wherein $R^c$ is cycloalkyl.

In certain embodiments, the invention relates to any one of the aforementioned compounds, wherein $R^c$ is heterocyclylakyl.

In certain embodiments, the invention relates to any one of the aforementioned compounds, wherein $R^c$ is halogen.

In certain embodiments, the invention relates to any one of the aforementioned compounds, wherein $R^c$ is $CF_3$.

In certain embodiments, the invention relates to any one of the aforementioned compounds, wherein $R^d$ is aryl. In some embodiments, $R^d$ is substituted aryl. In some embodiments, substituted aryl is substituted with one or more substituents selected from alkyl, cycloalkyl, heterocyclylakyl, halogen, OH, OMe, $CF_3$, and CN. In some embodiments, $R^d$ is selected from

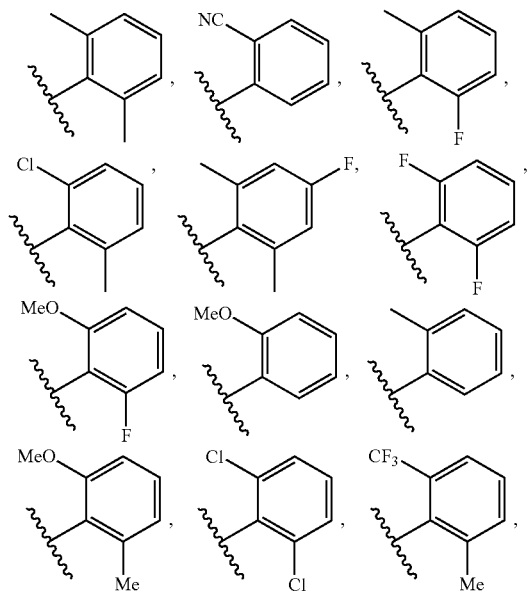

-continued

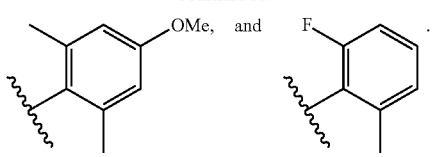 and 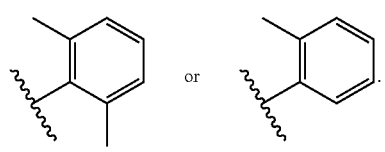 or

In certain embodiments, the invention relates to any one of the aforementioned compounds, wherein $R^d$ is heterocyclyl. In some embodiments, $R^d$ is substituted heterocyclyl.

In certain embodiments, the invention relates to any one of the aforementioned compounds, wherein $R^d$ is heteroaryl. In some embodiments, $R^d$ is substituted heteroaryl. In some embodiments, substituted heterocyclyl or substituted heteroaryl is substituted with one or more substituents selected from alkyl and cycloalkyl.

In certain embodiments, the invention relates to any one of the aforementioned compounds, wherein $R^d$ is

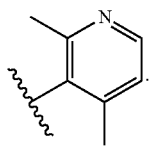 [SMILES: *c1c(C)ccnc1C]

In certain embodiments, the invention relates to any one of the aforementioned compounds, wherein $R^d$ is selected from

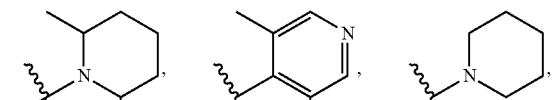

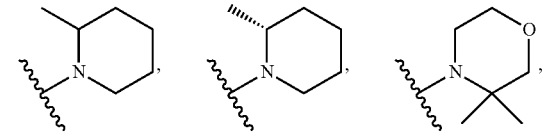

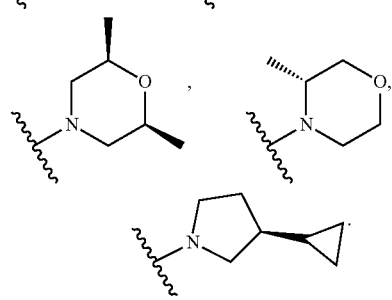

In certain embodiments, the invention relates to any one of the aforementioned compounds, wherein $R^e$ is aryl. In some embodiments, $R^e$ is phenyl. In some embodiments, $R^e$ is substituted phenyl. In some embodiments, substituted phenyl is alkyl-substituted phenyl. In some embodiments, $R^e$ is In certain embodiments, the invention relates to any one of the aforementioned compounds, wherein $R^e$ is heteroaryl.

In certain embodiments, the invention relates to any one of the aforementioned compounds, wherein $R^e$ is heterocyclyl.

In some embodiments, $R^e$ is substituted pyrrolidinyl. In some embodiments, $R^e$ is alkyl substituted pyrrolidinyl. In some embodiments, $R^e$ is

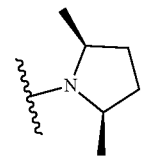

In certain embodiments, the invention relates to any one of the aforementioned compounds, wherein the compound is a pharmaceutically acceptable salt.

In certain embodiments, the invention relates to a compound selected from the group consisting of:

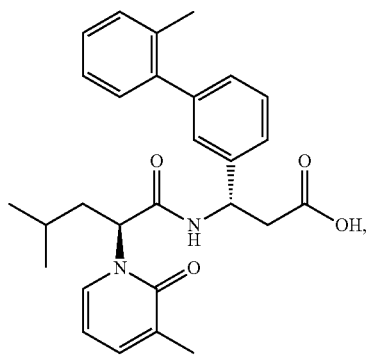

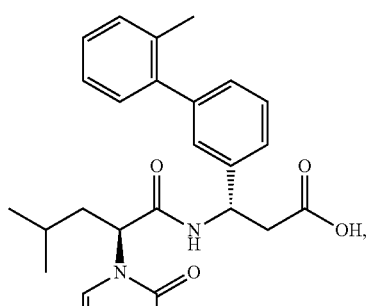

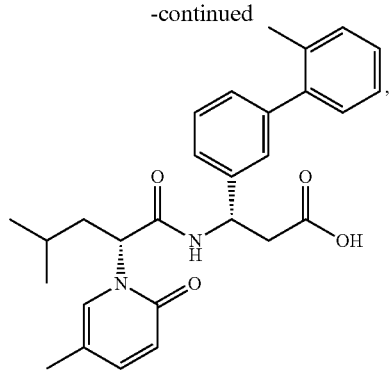
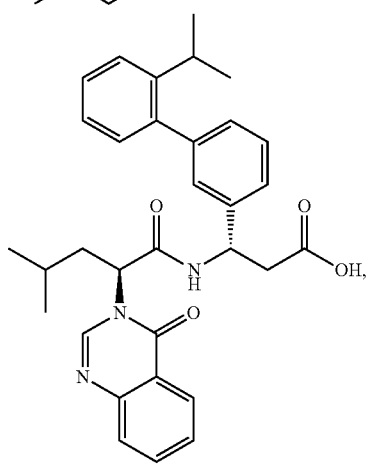
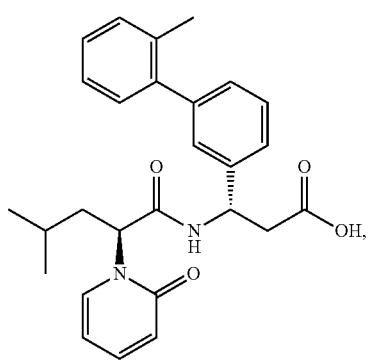
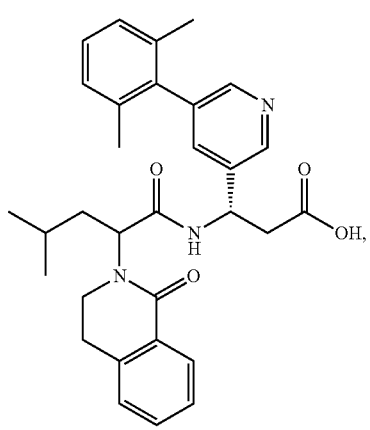
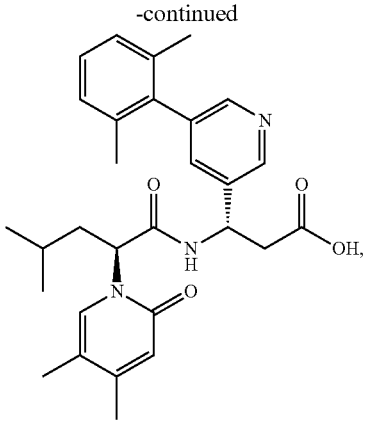
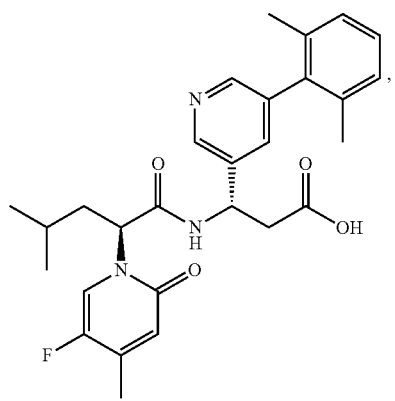
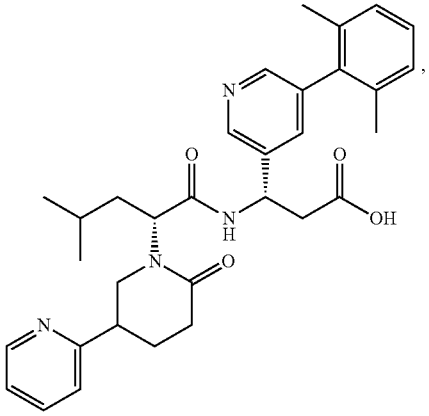
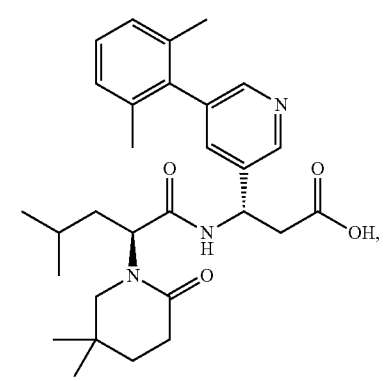

25
-continued
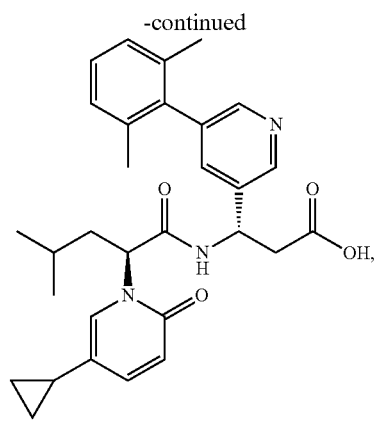
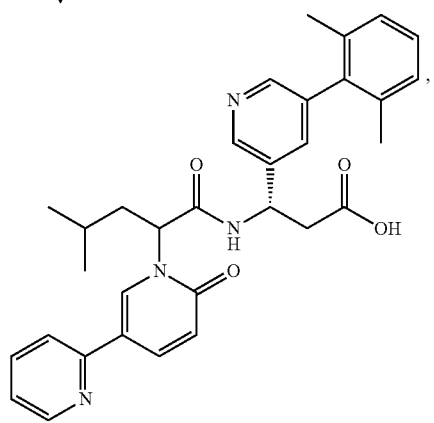
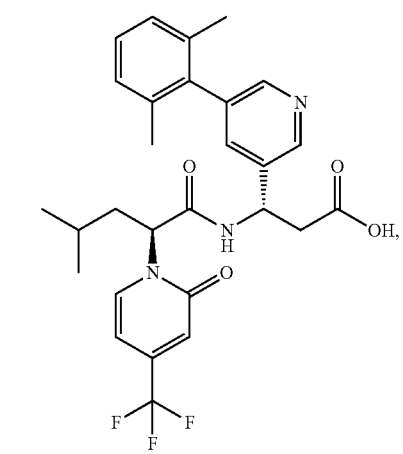
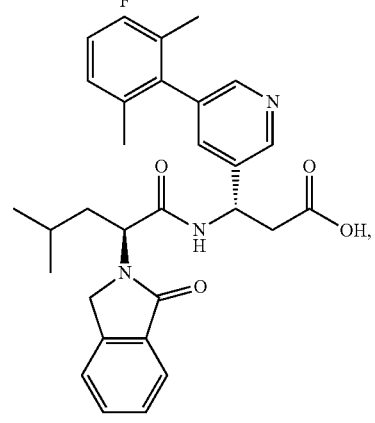
26
-continued
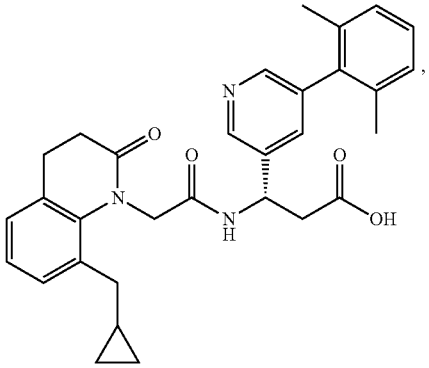
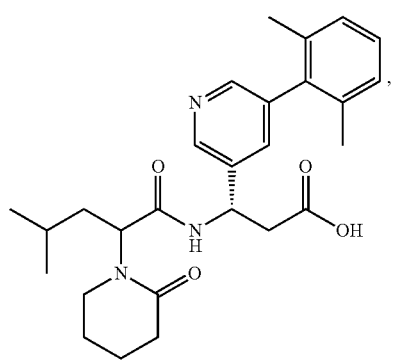
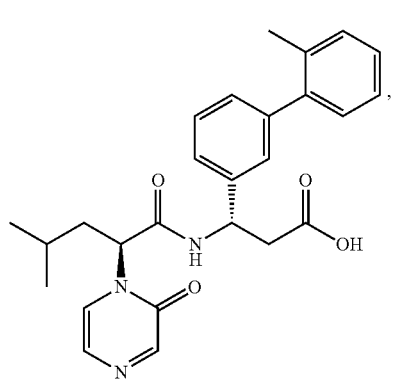
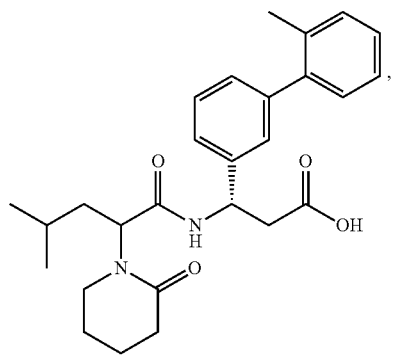

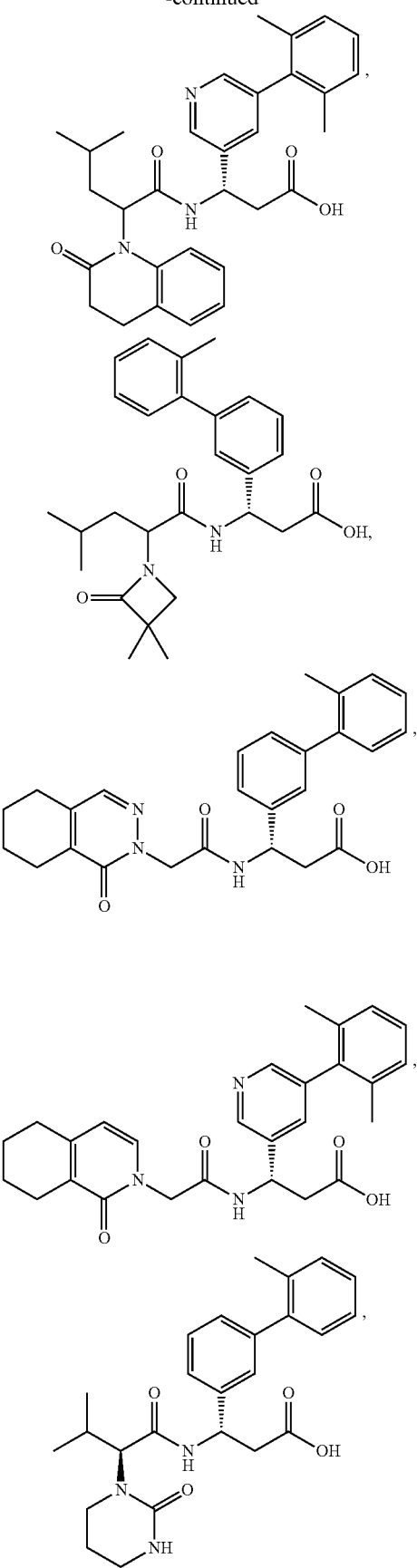
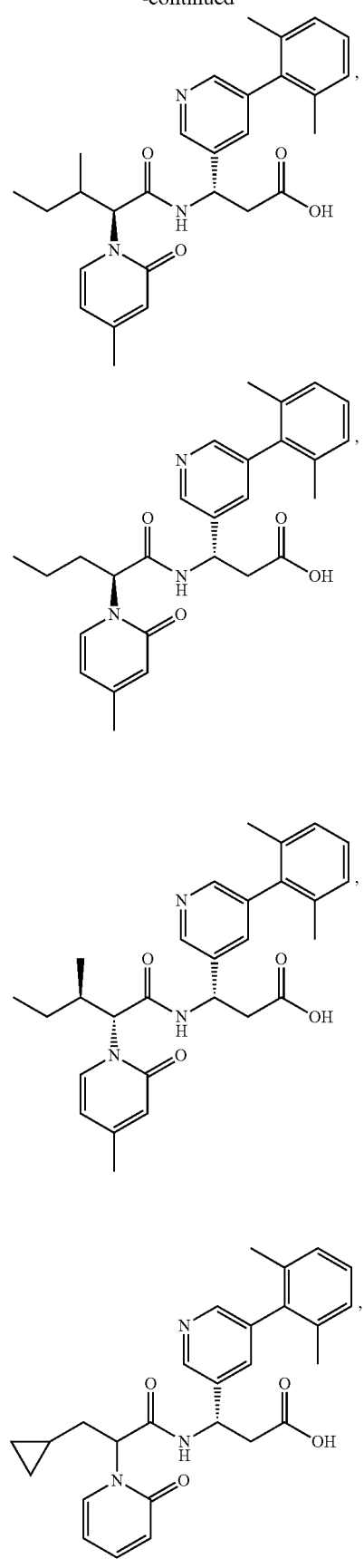

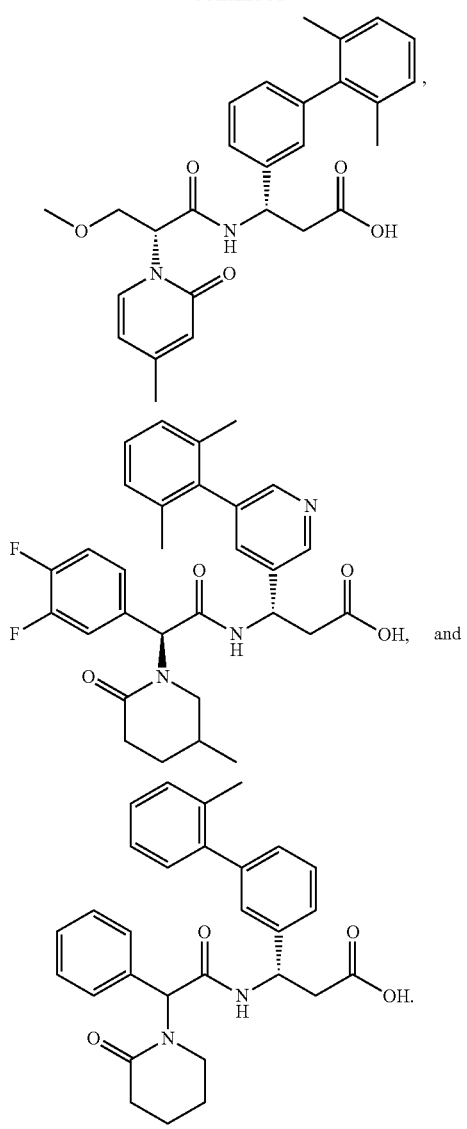
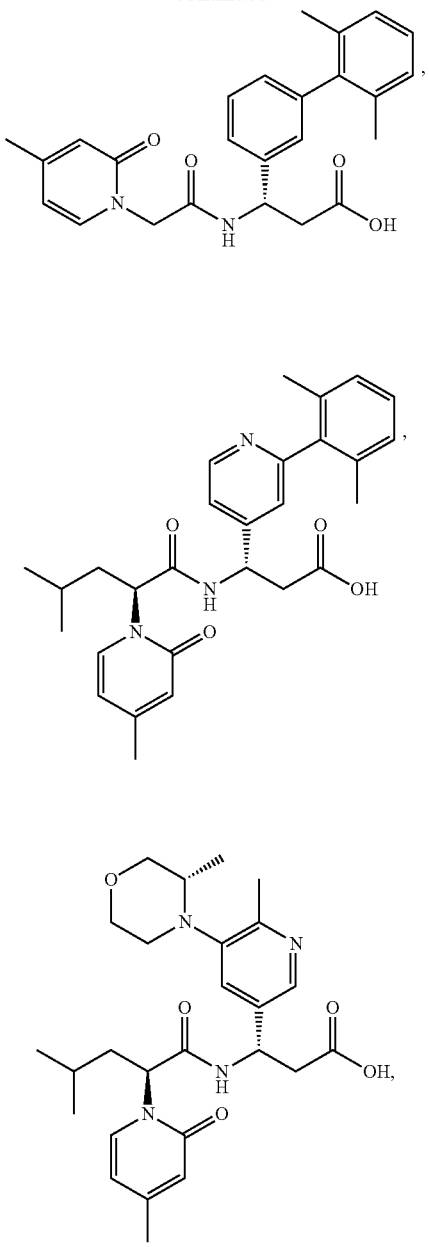
In certain embodiments, the invention relates to a compound selected from the group consisting of:
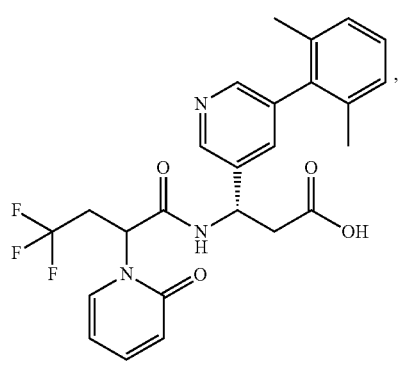
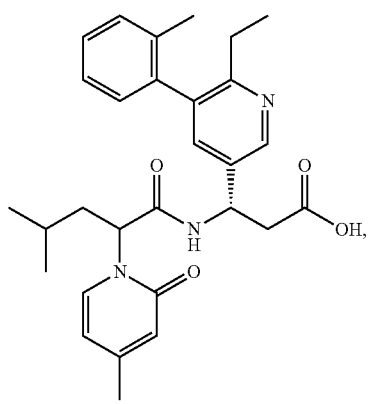

31
-continued
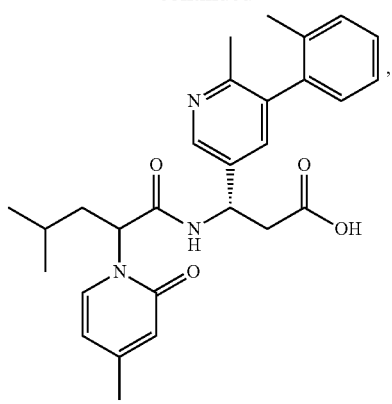
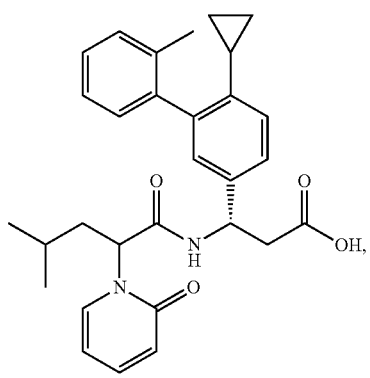
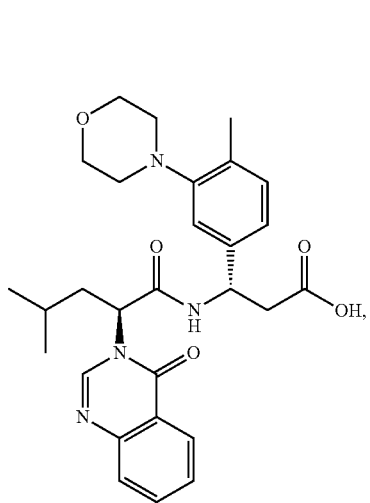
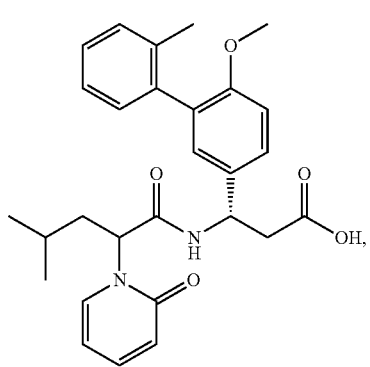
32
-continued
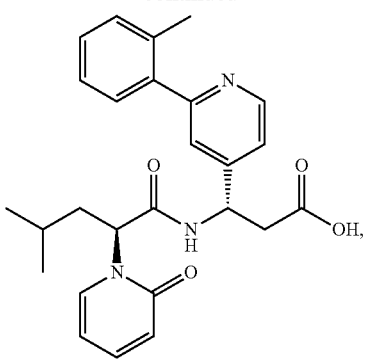
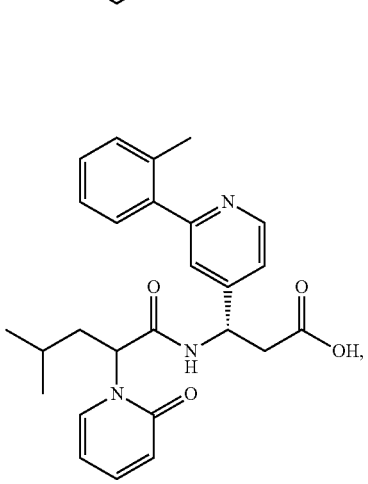
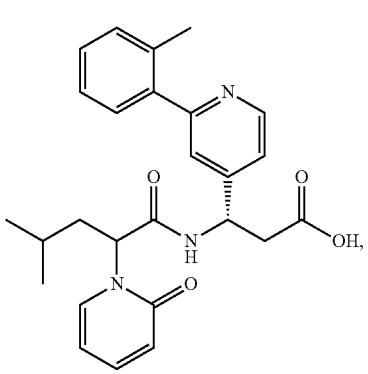
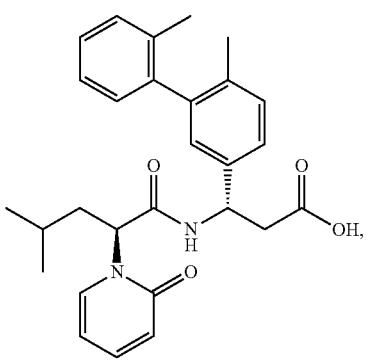

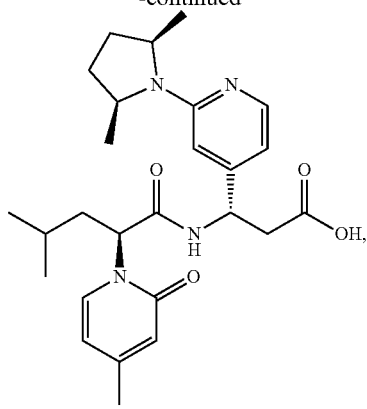
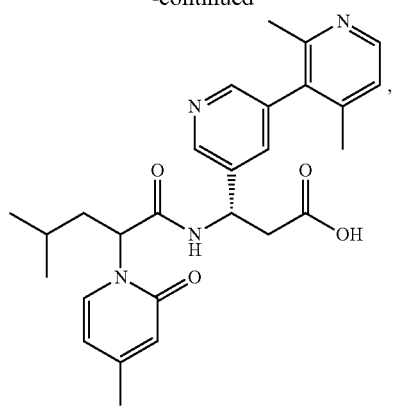

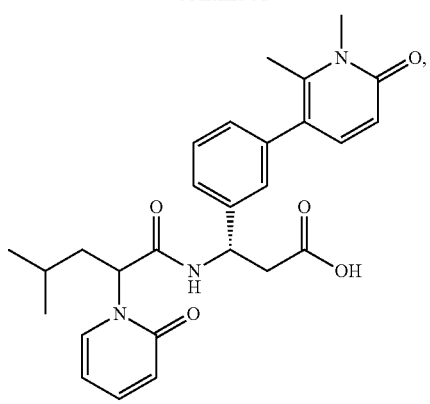
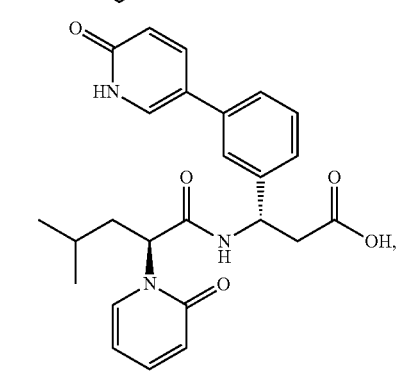
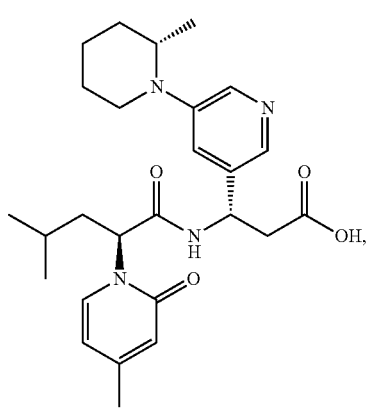
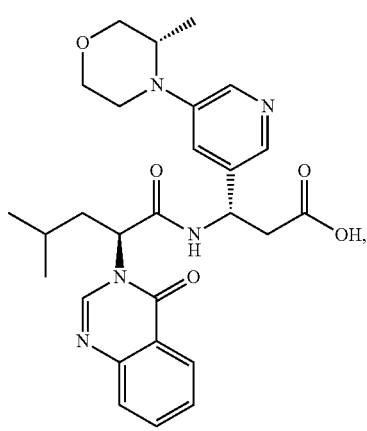
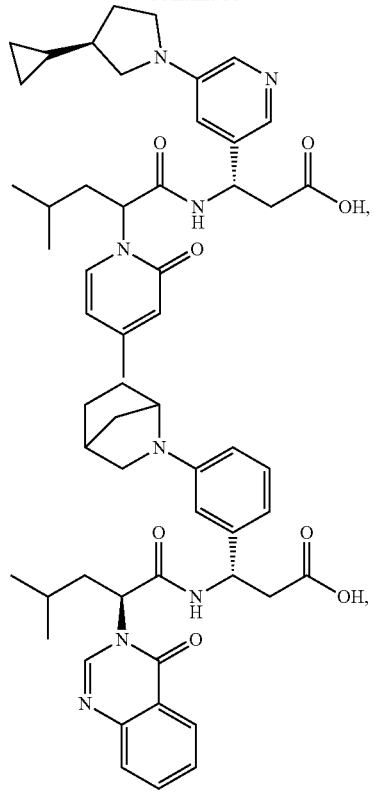
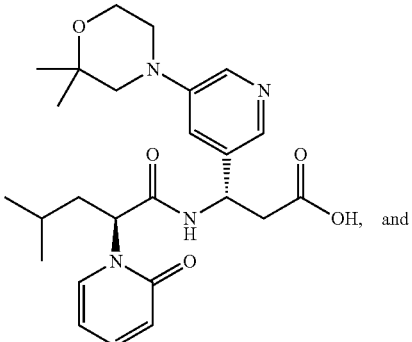
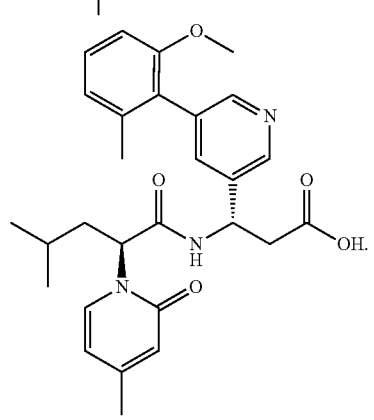
In certain embodiments, the invention relates to a compound selected from the group consisting of:

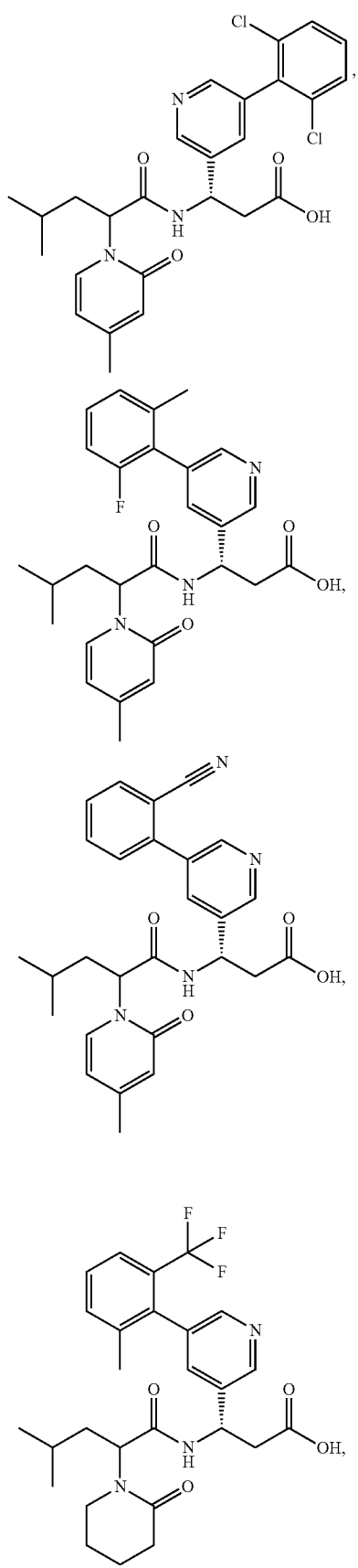
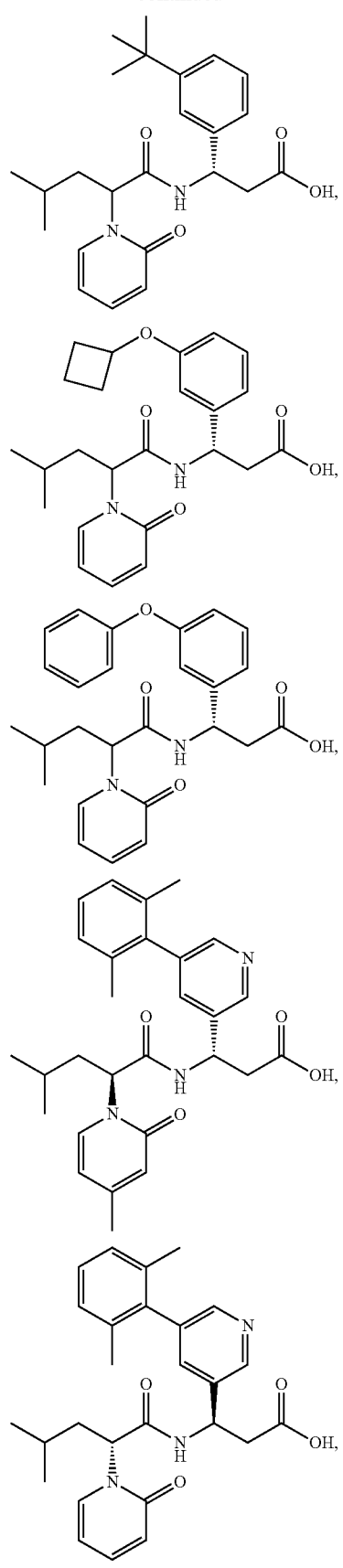

-continued
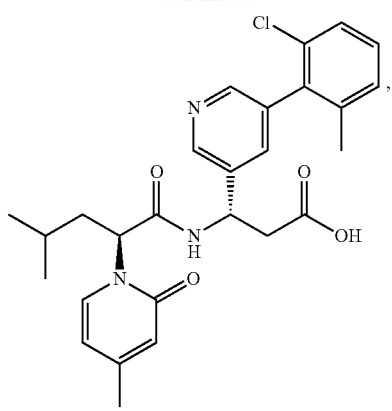
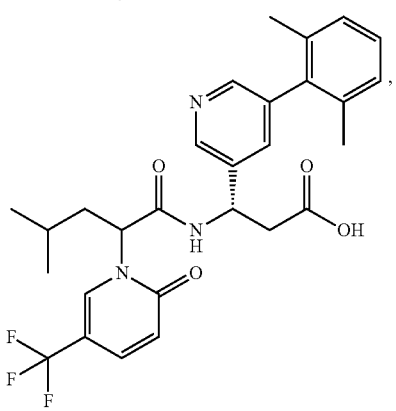
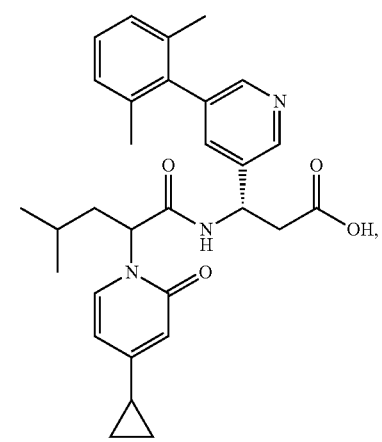
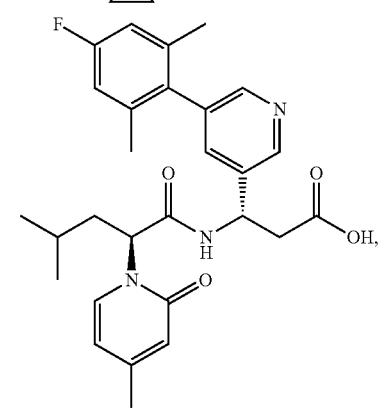
-continued
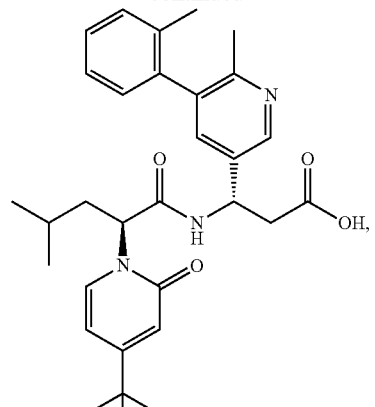
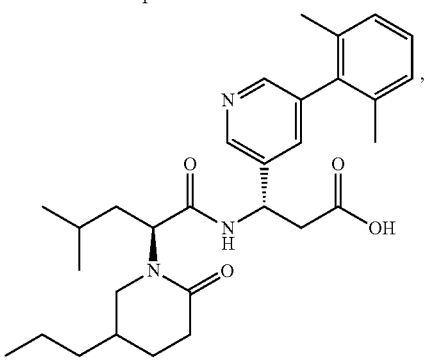
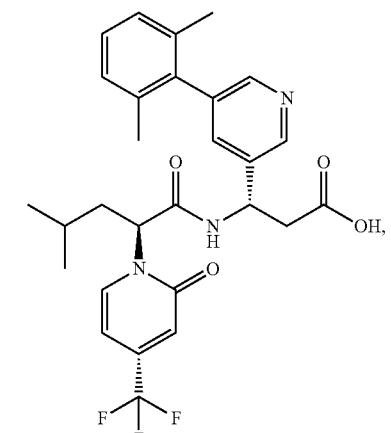
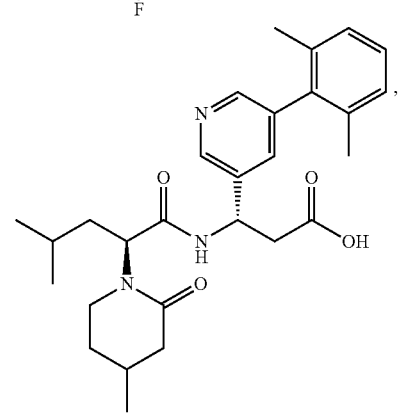

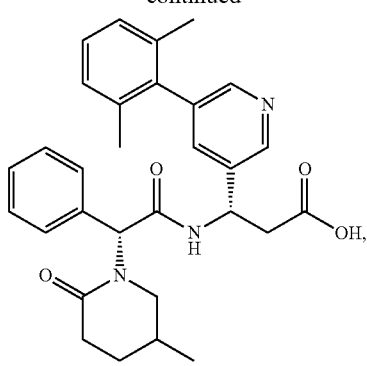
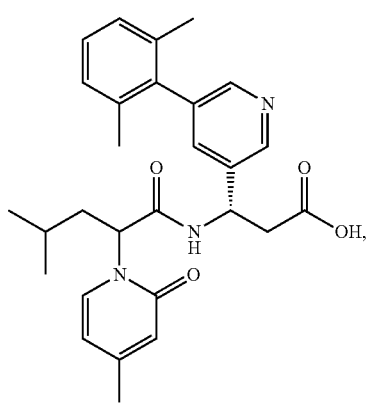
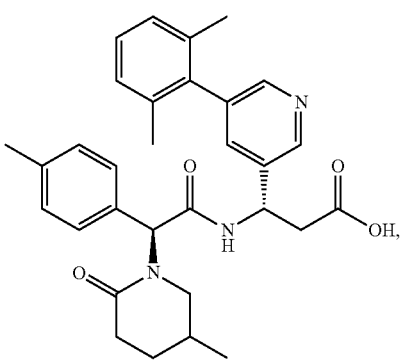
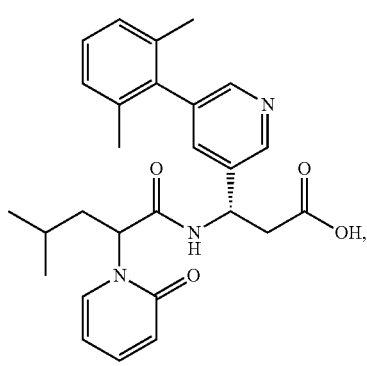
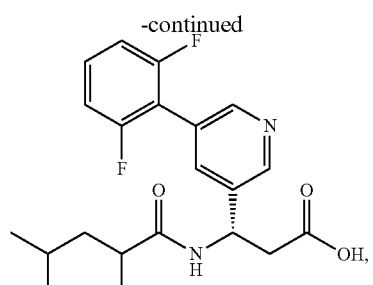
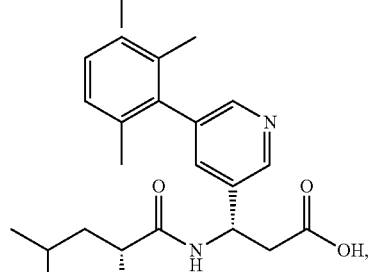
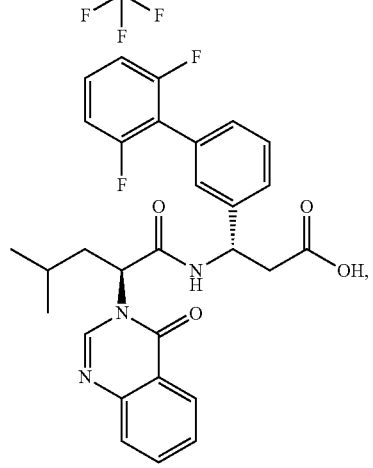
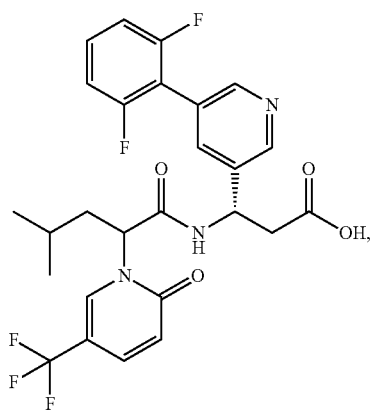

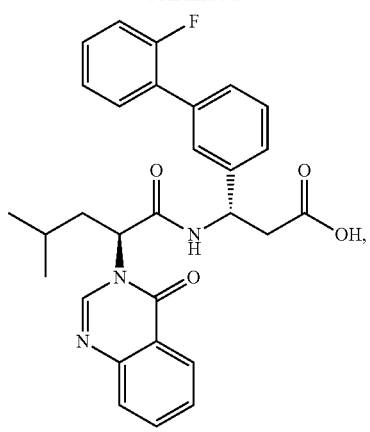
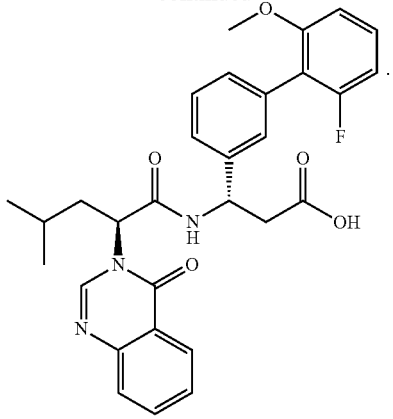
In certain embodiments, the invention relates to a compound selected from the group consisting of:

45
-continued
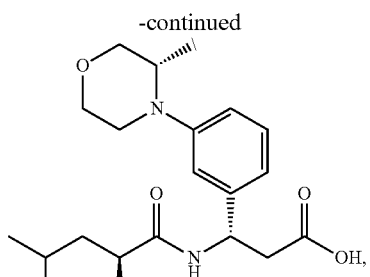
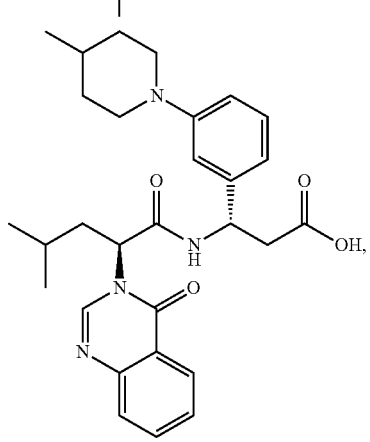
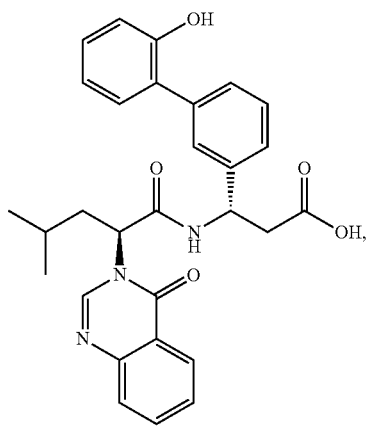
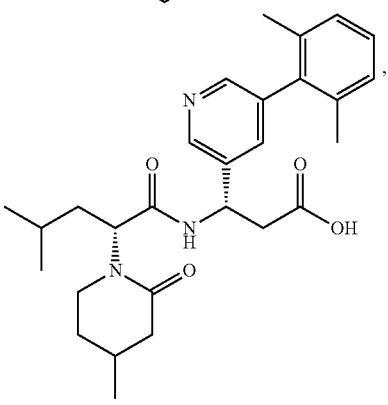
46
-continued
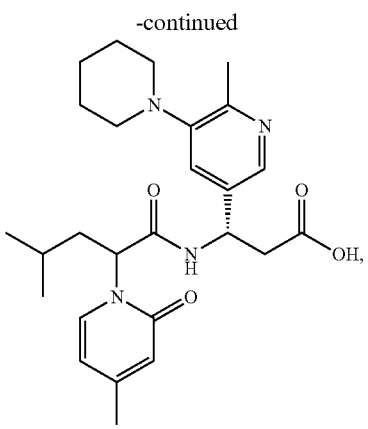
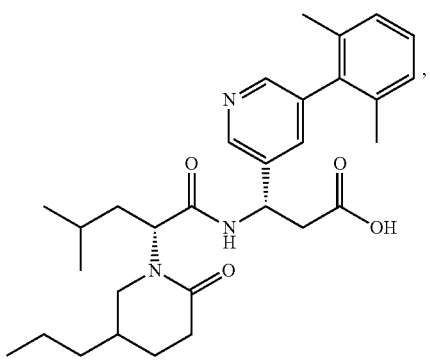
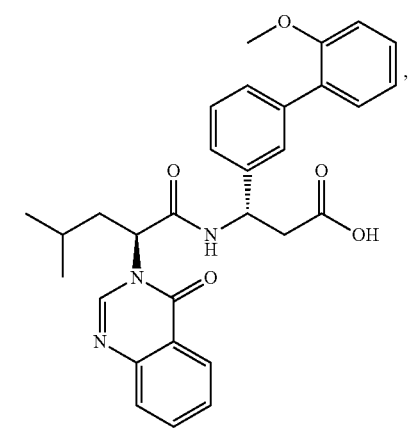
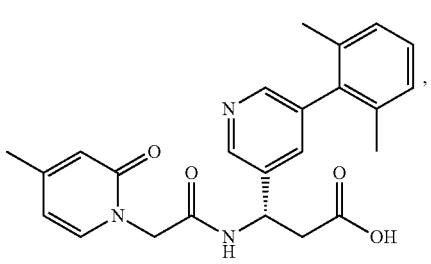

47
-continued
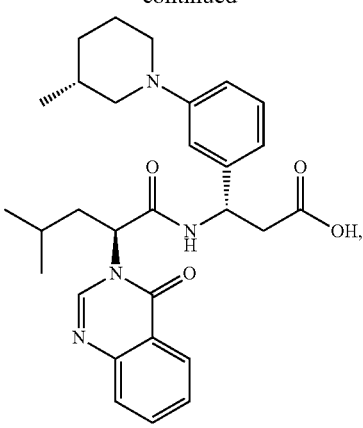
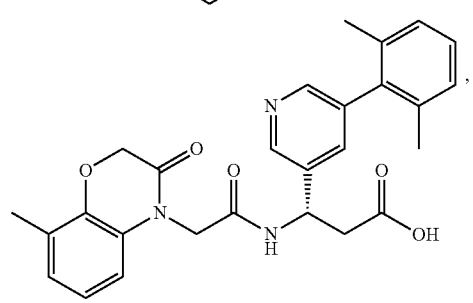
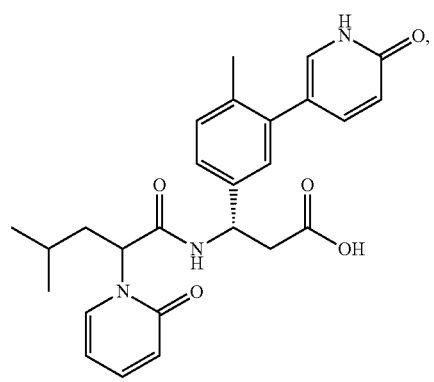
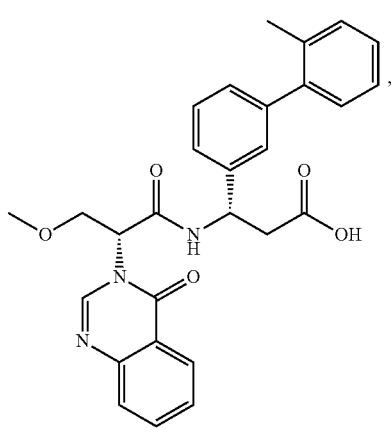
48
-continued
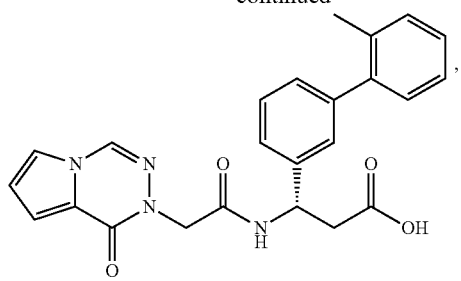
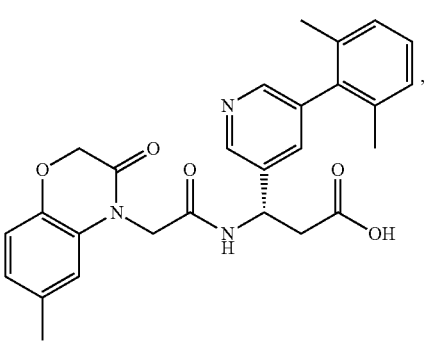
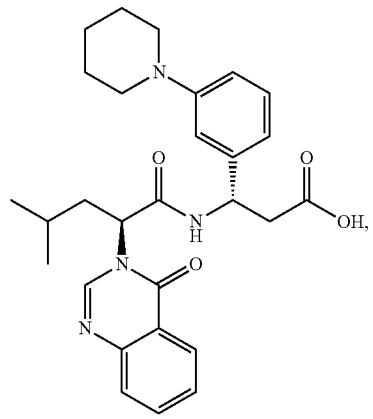
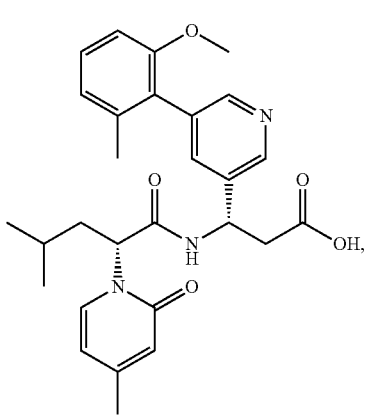

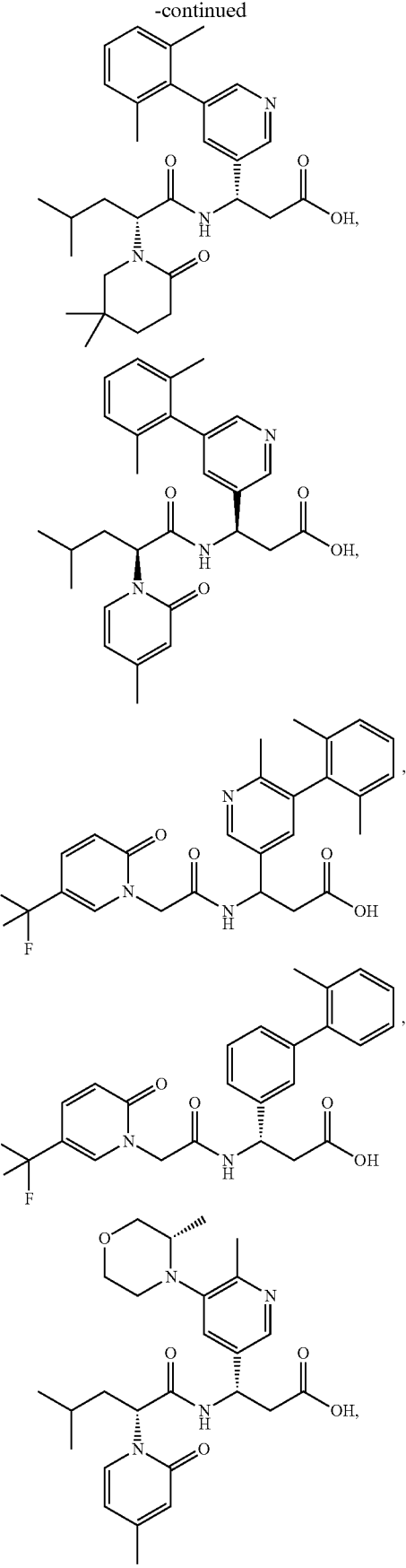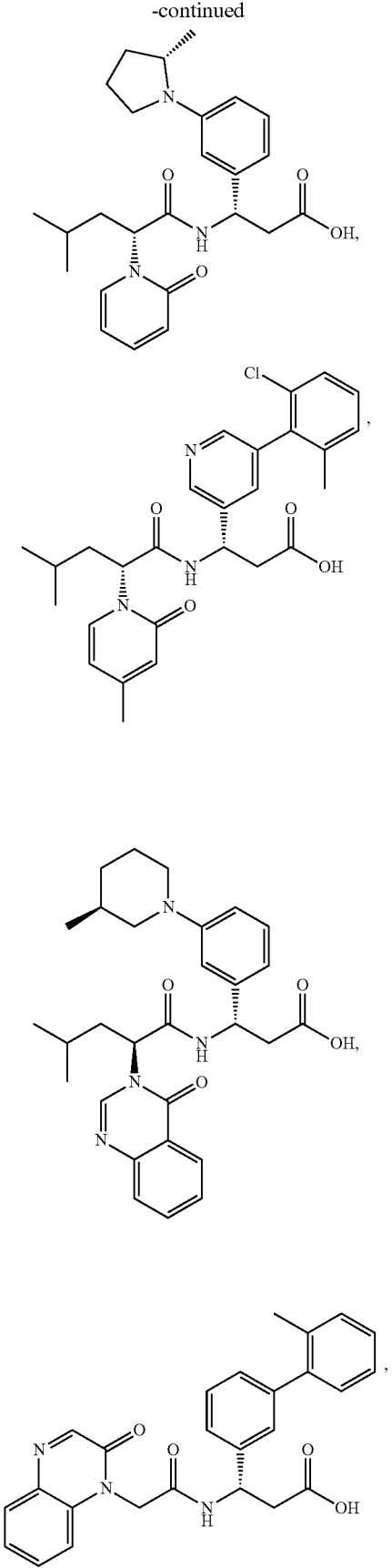

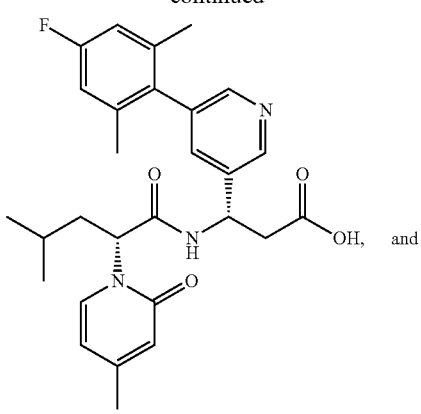
and
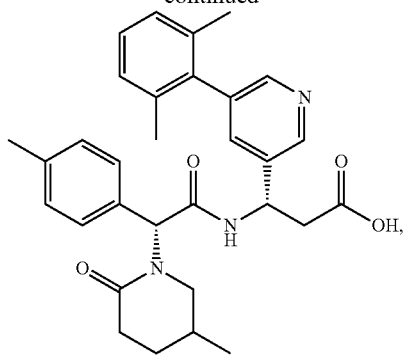
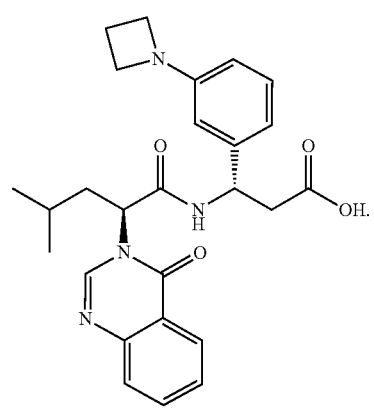
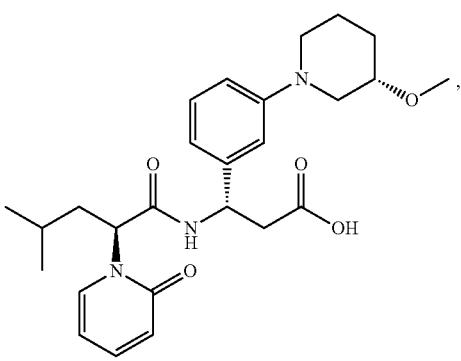
In certain embodiments, the invention relates to a compound selected from the group consisting of:
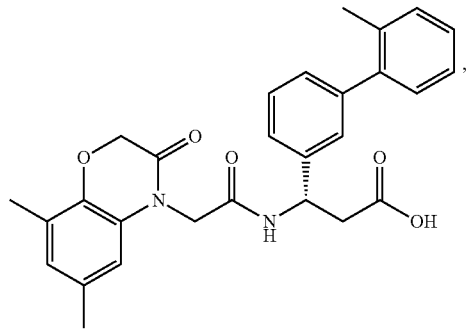
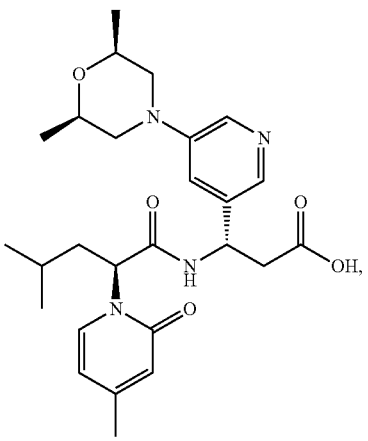
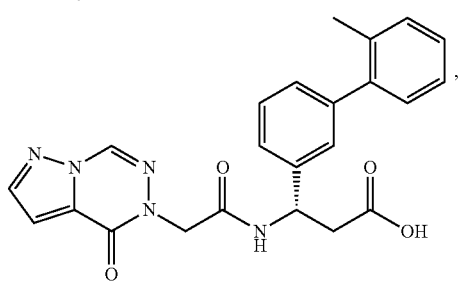
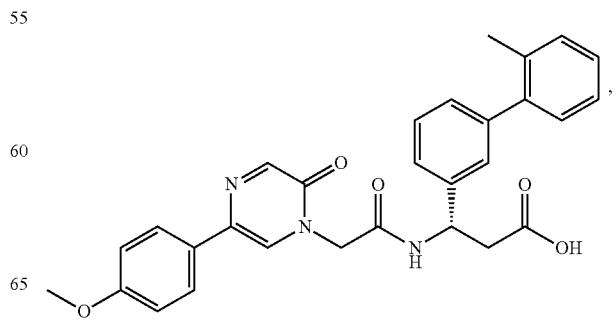

53
-continued
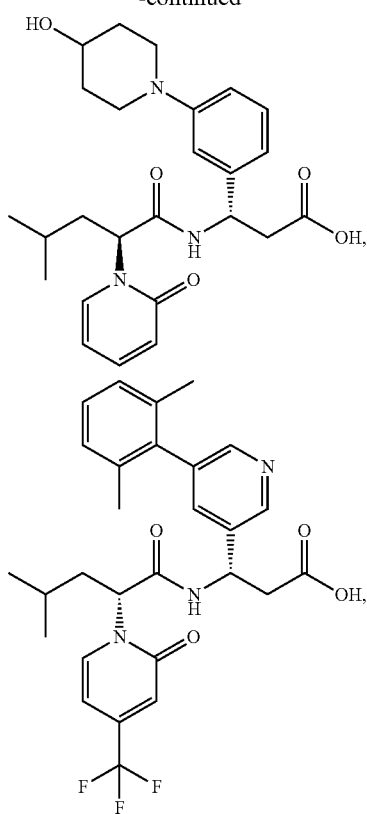
54
-continued
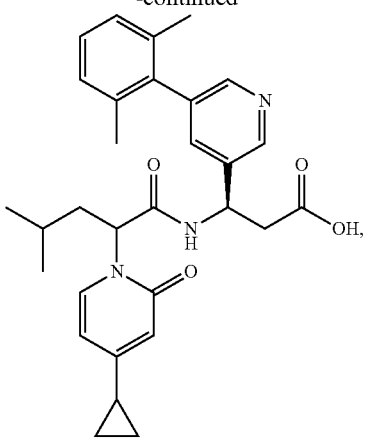
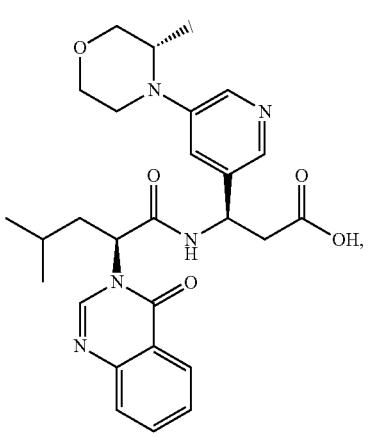
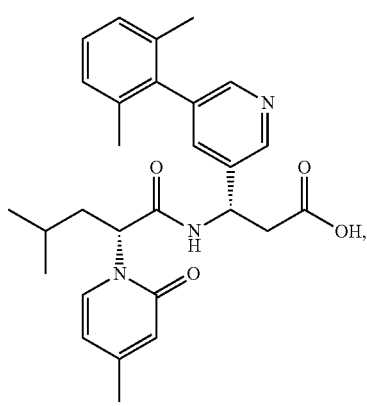
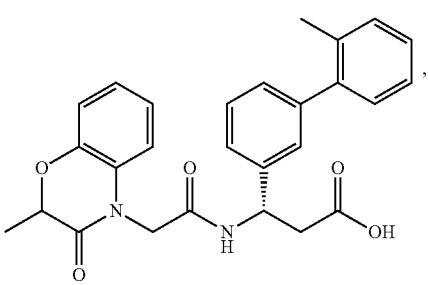
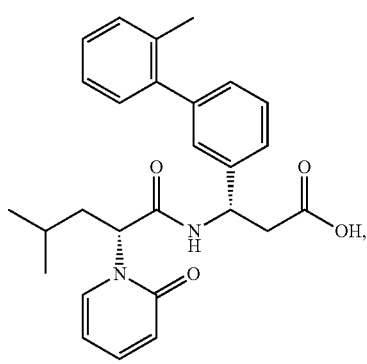 [SMILES: Cc1ccccc1-c1cccc([C@H](CC(=O)O)NC(=O)[C@@H](CC(C)C)n2cccc(C)c2=O)c1]
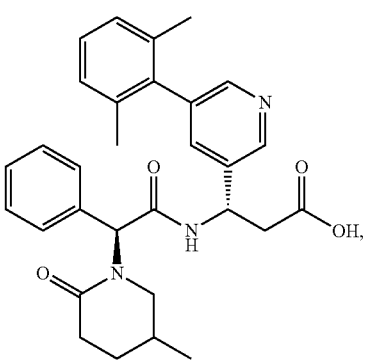

55
-continued
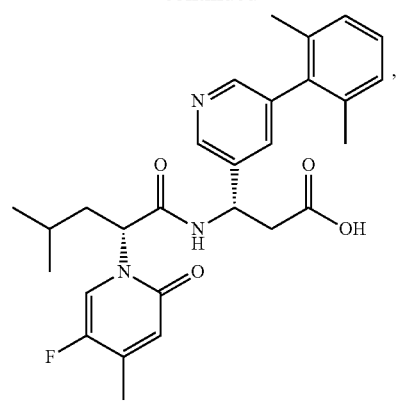
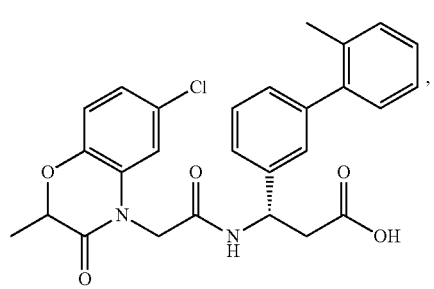
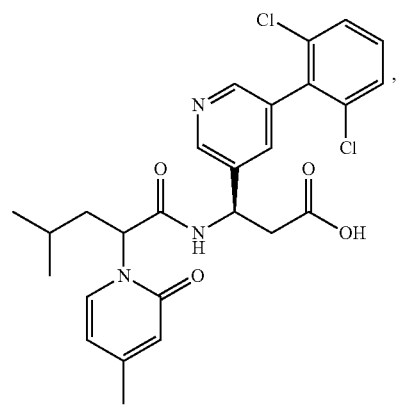
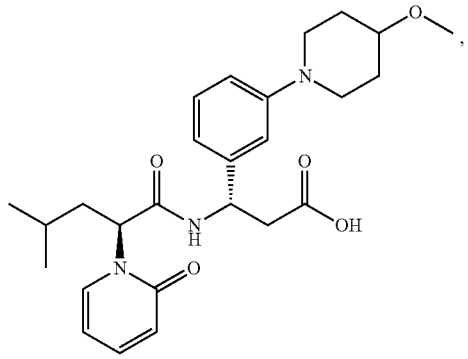
56
-continued
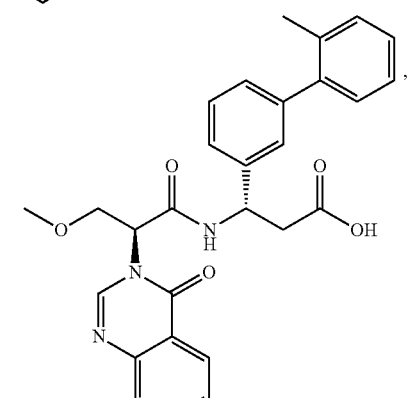
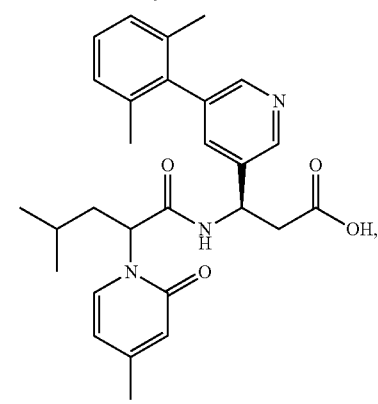
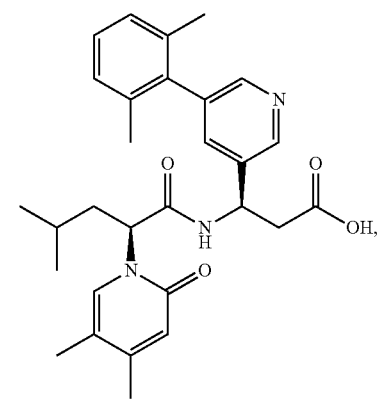

57
-continued
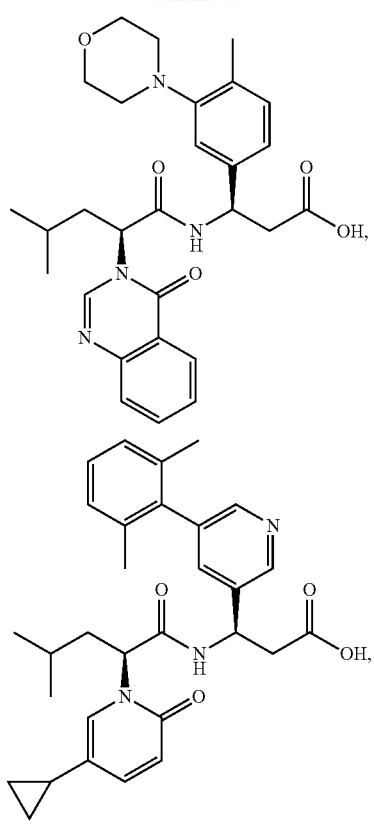
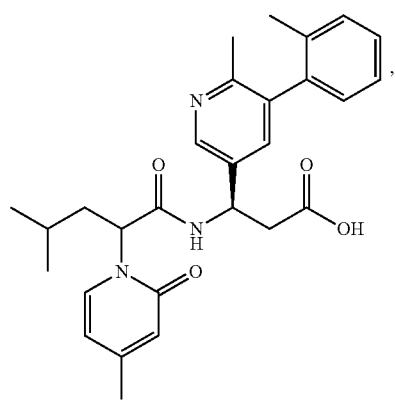
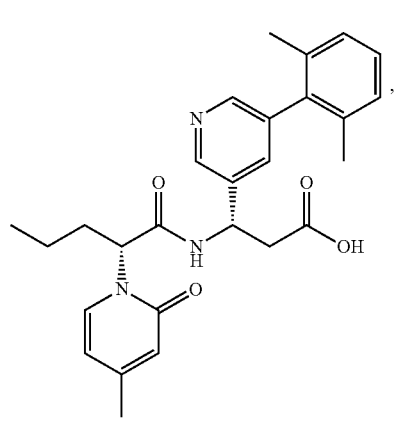
58
-continued
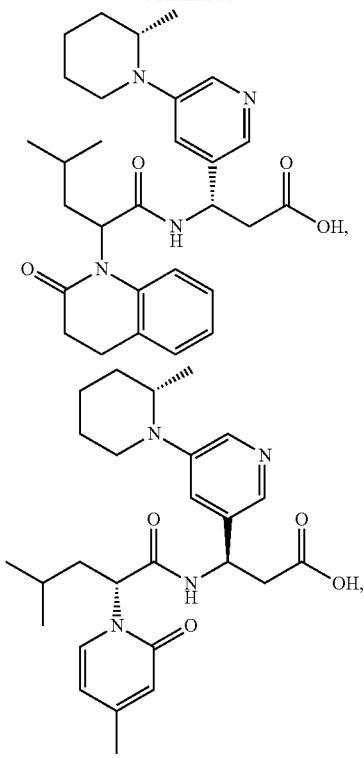
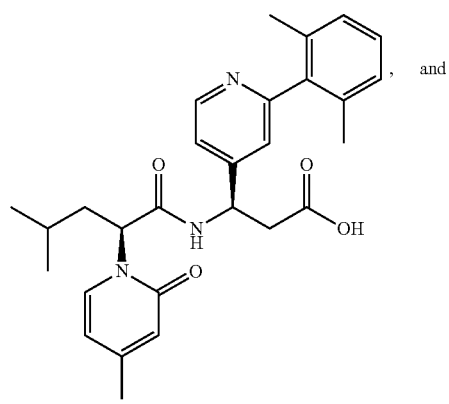
In certain embodiments, the invention relates to a compound selected from the group consisting of:

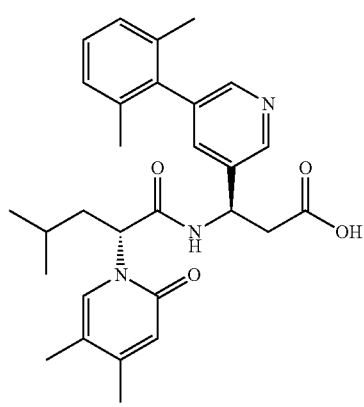
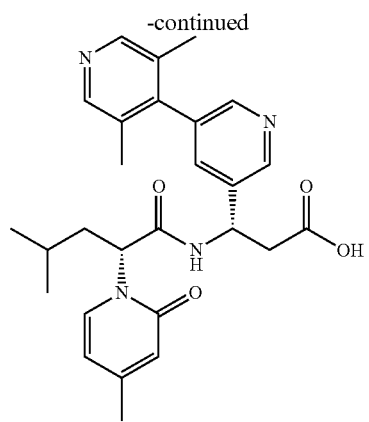
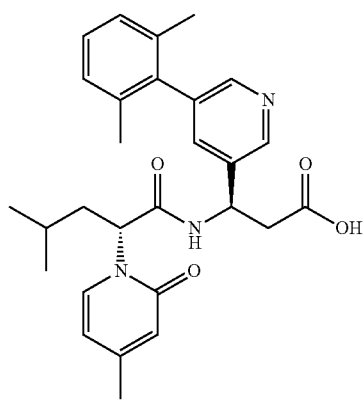
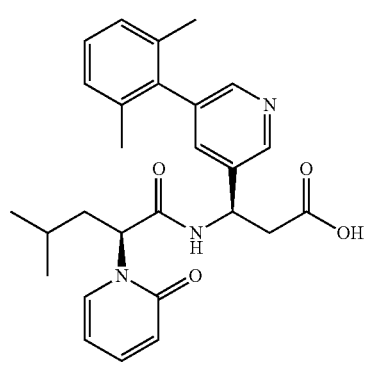
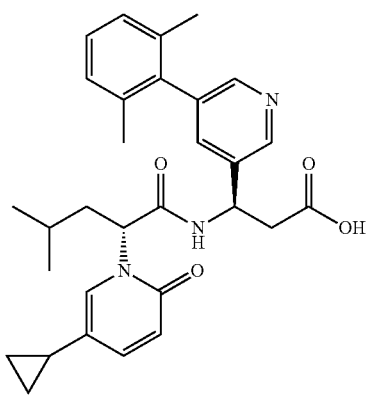
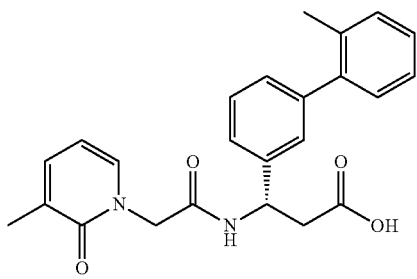
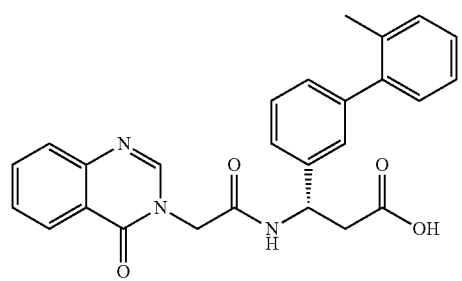
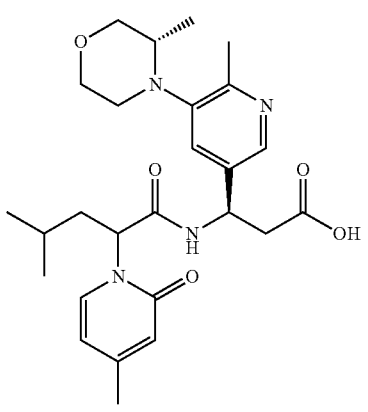
, and -continued
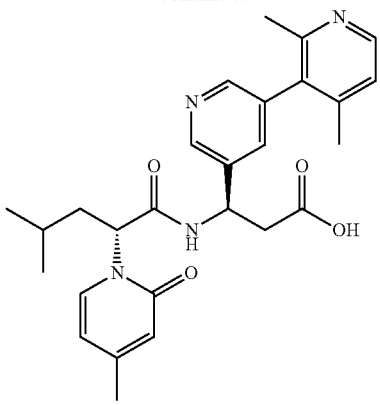
61
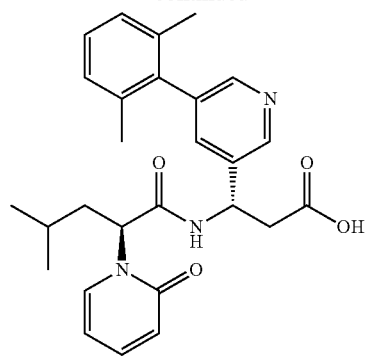
62
-continued
In certain embodiments, the invention relates to a compound selected from the group consisting of:
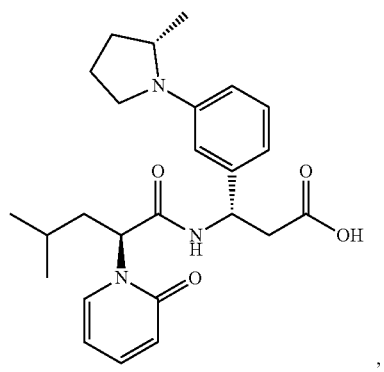
,
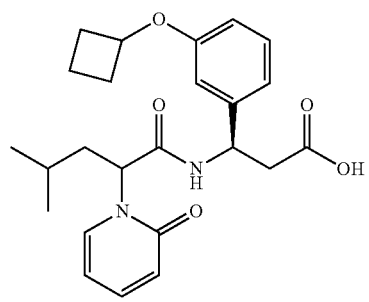
,
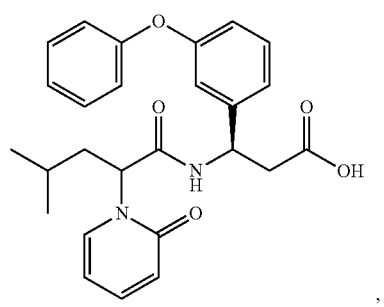
,
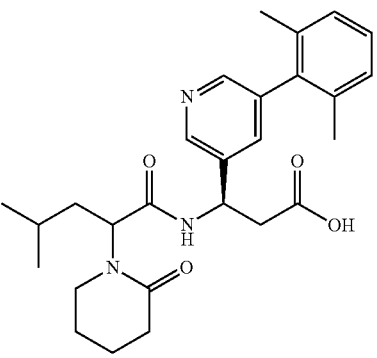
,
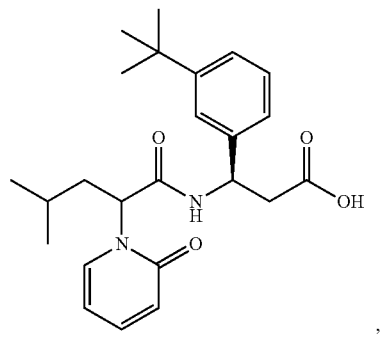
,
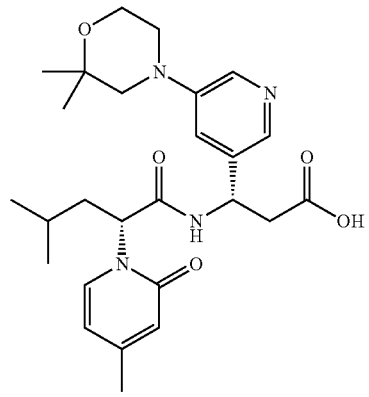
, 63
-continued
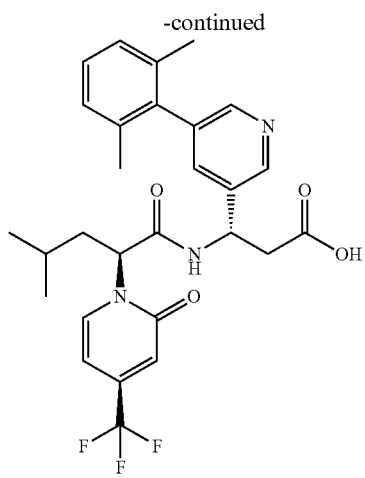
, and
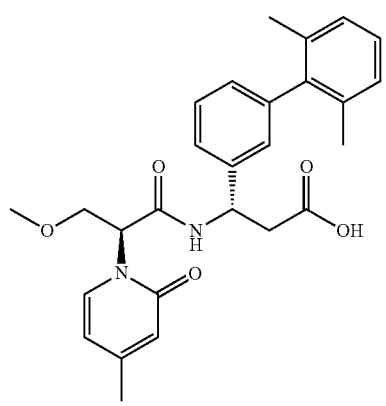
.
In certain embodiments, the invention relates to a compound selected from the group consisting of:
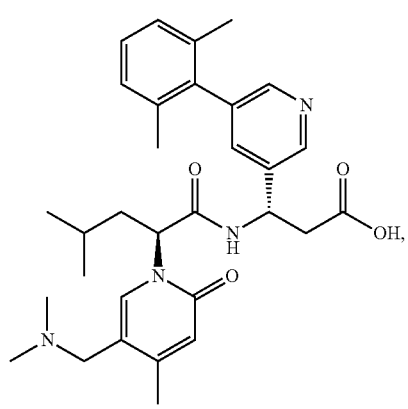
64
-continued
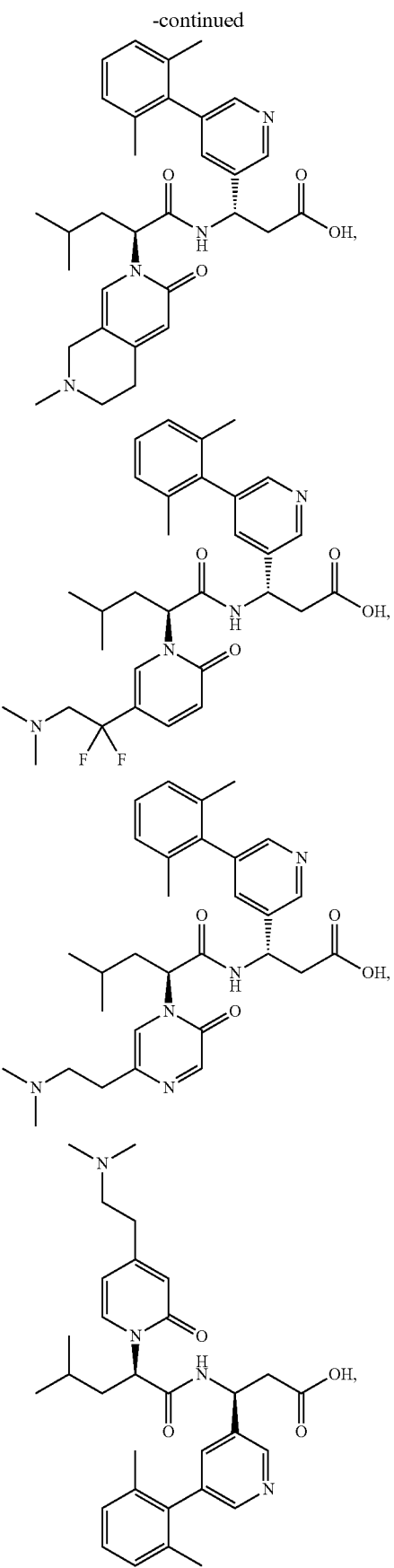

-continued
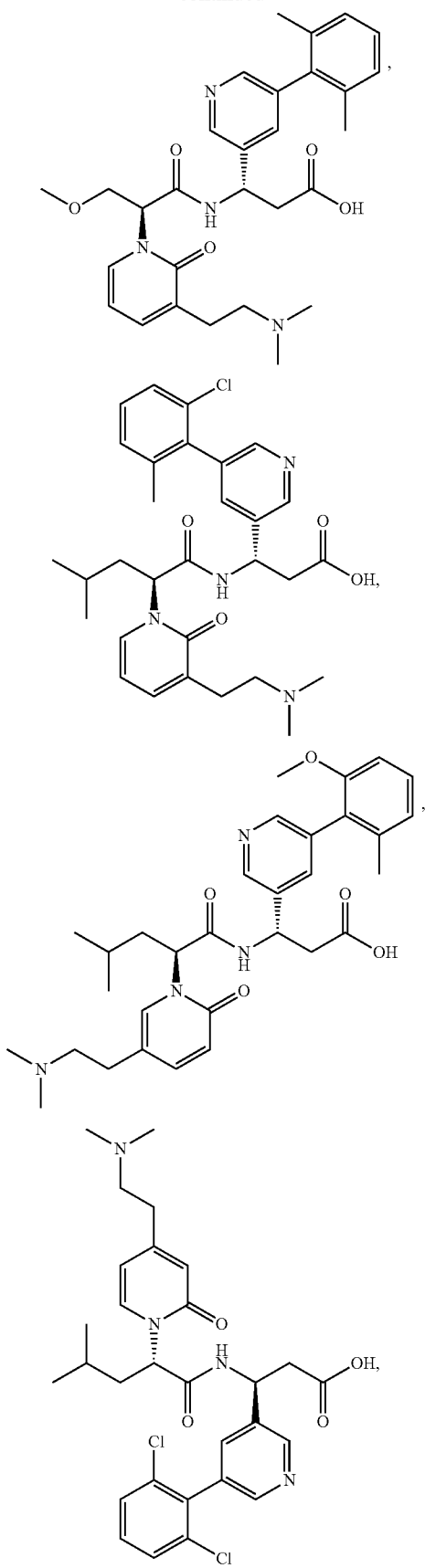
-continued
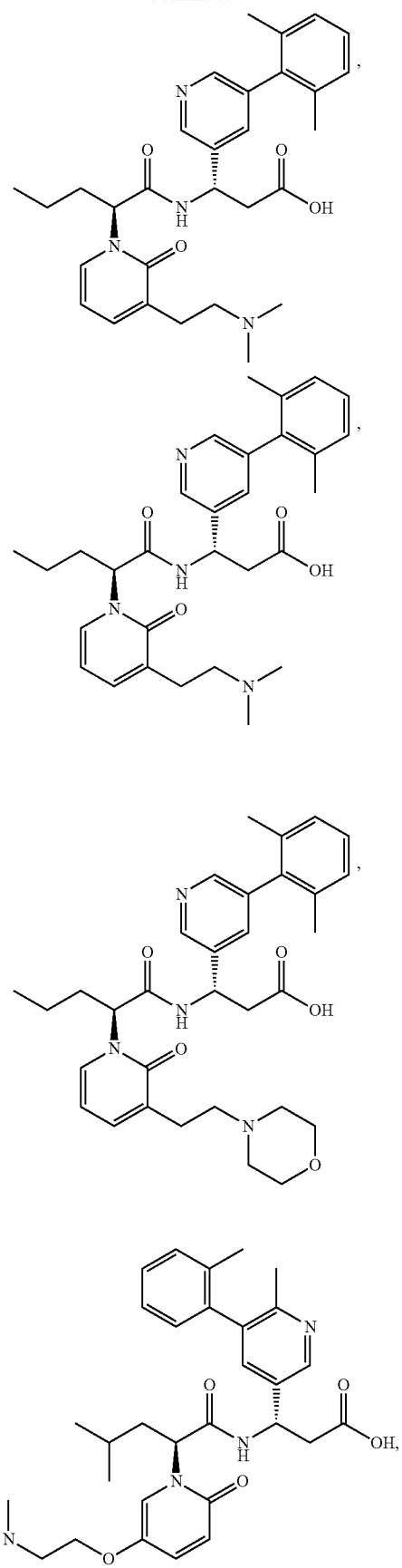

67
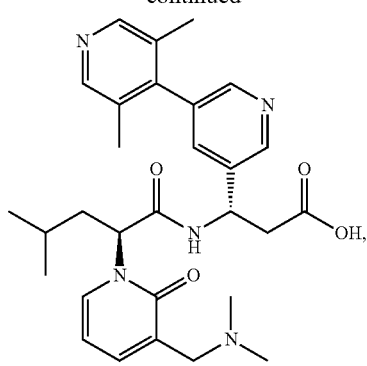
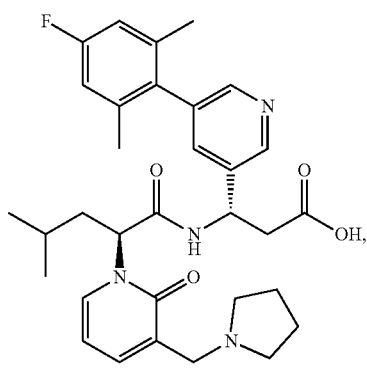
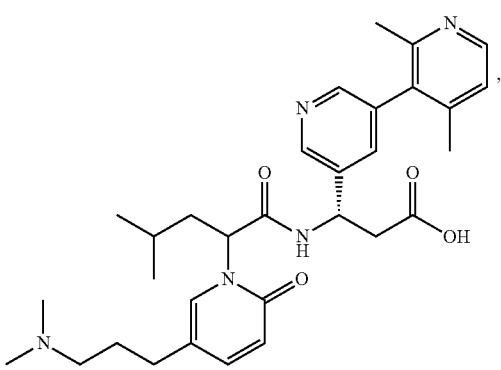
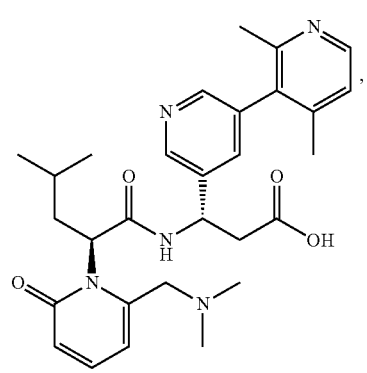
68
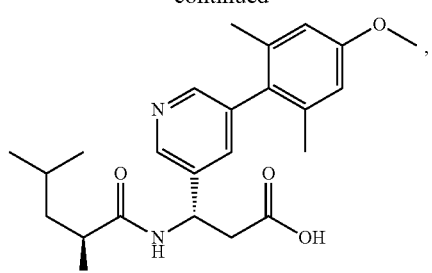
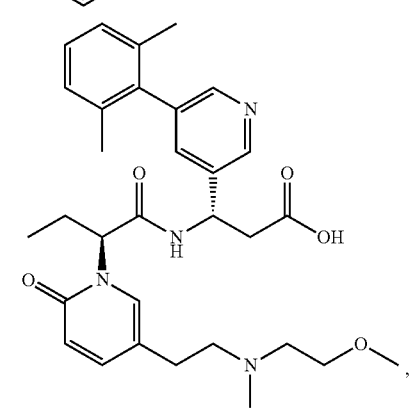
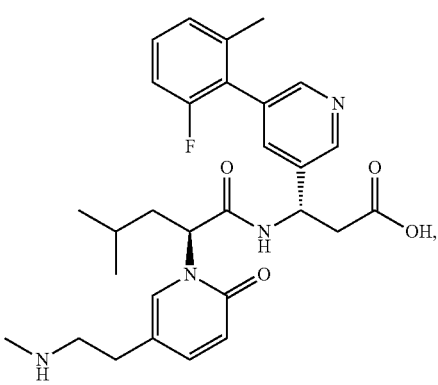
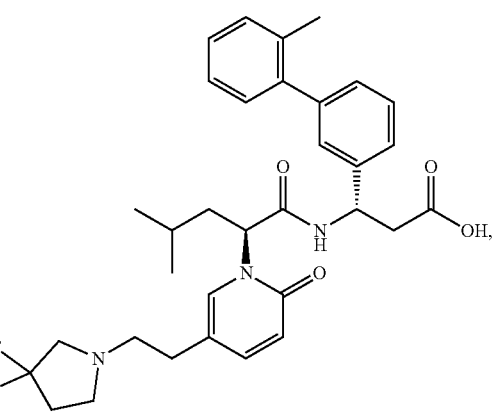

69
-continued
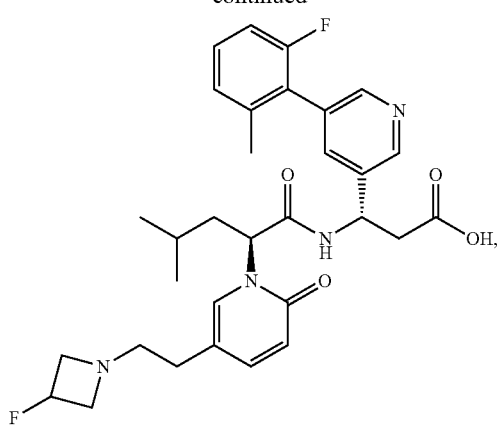
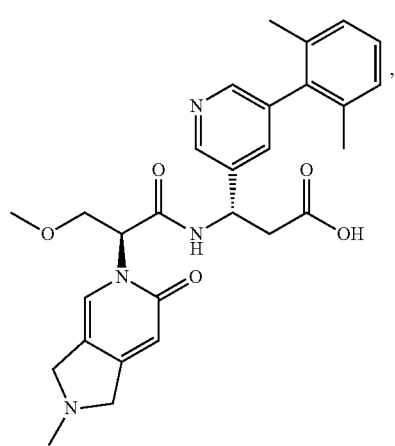
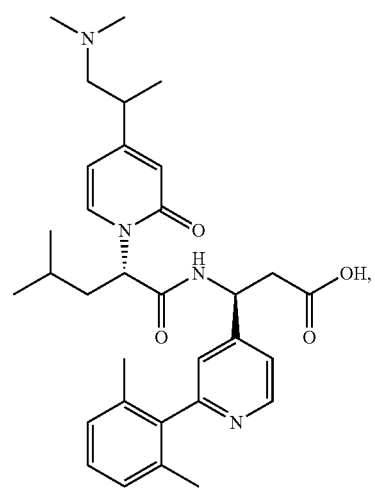
70
-continued
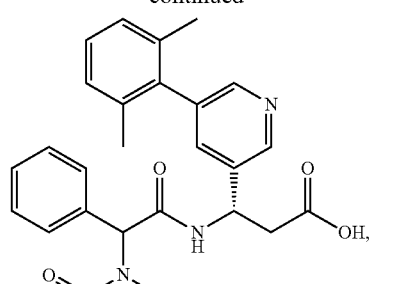
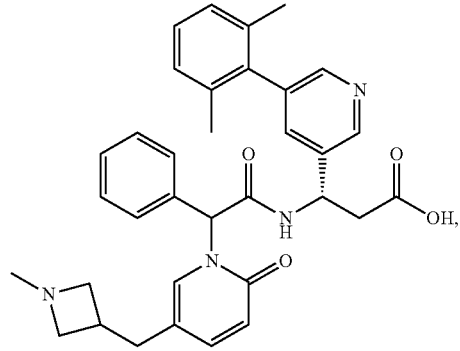
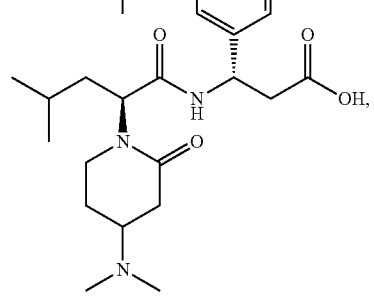
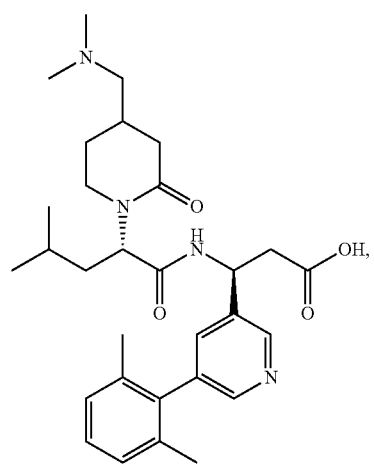

-continued
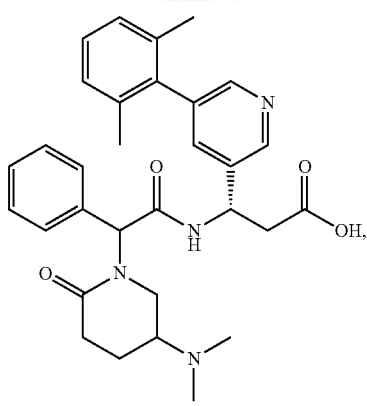
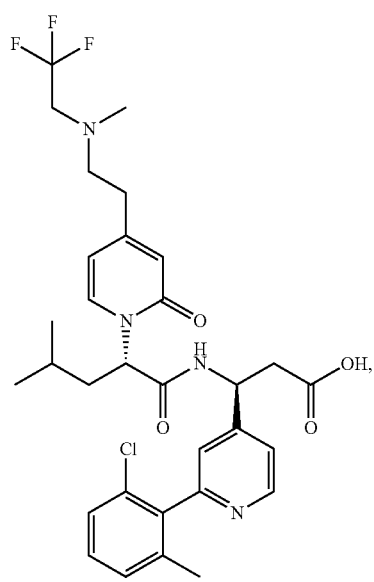
-continued
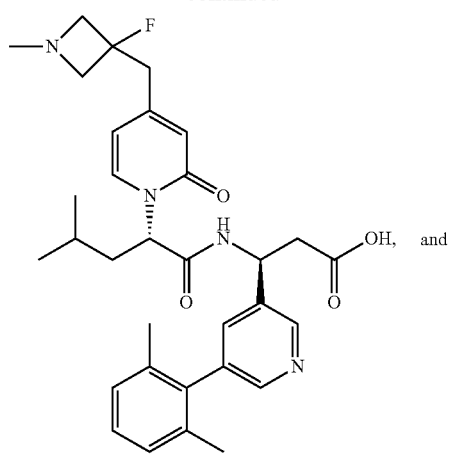
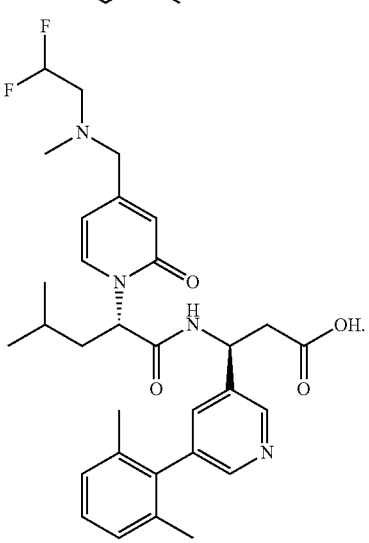
In certain embodiments, the invention relates to a compound selected from the group consisting of:
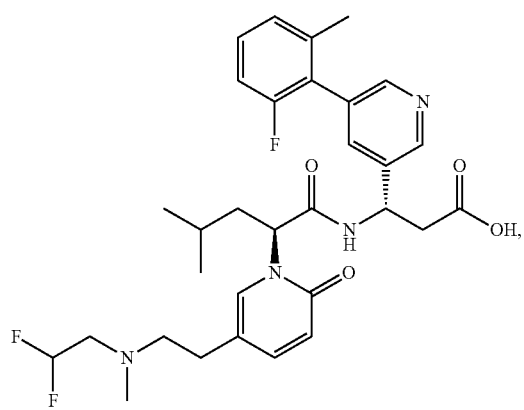
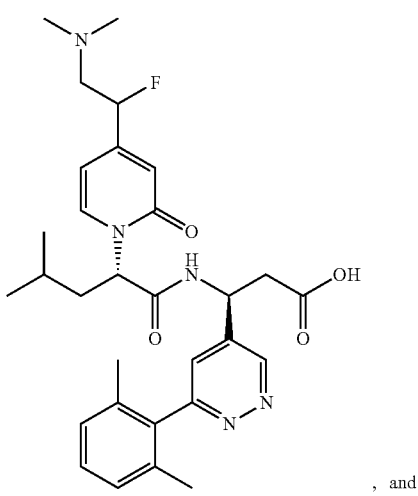
, and -continued
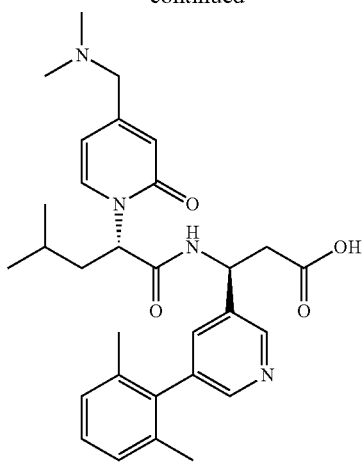
In certain embodiments, the invention relates to a compound selected from the group consisting of:
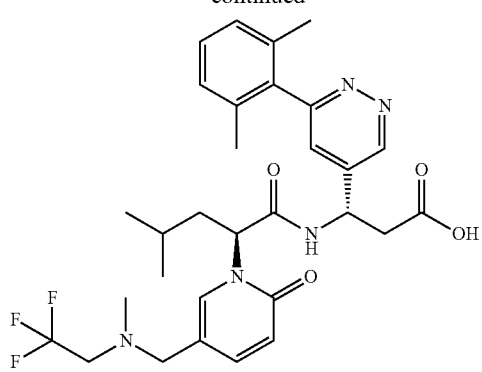
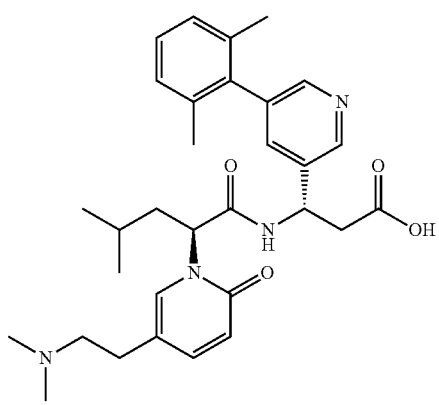
-continued
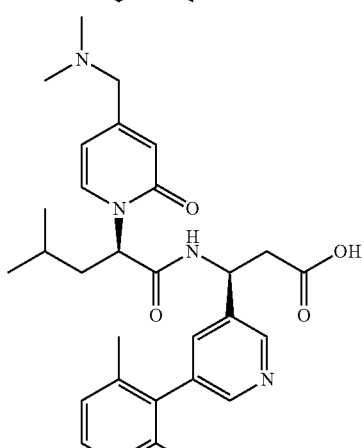
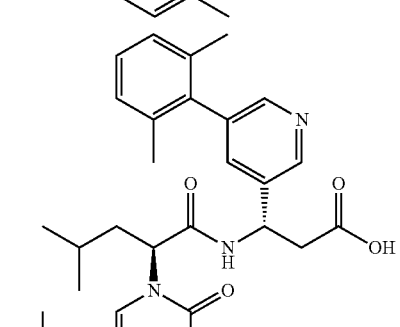
, and
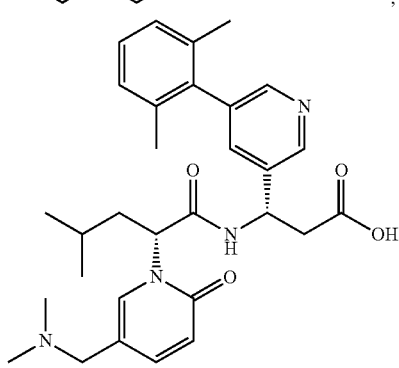
.
In some embodiments, the invention relates to a compound selected from the group consisting of:

75
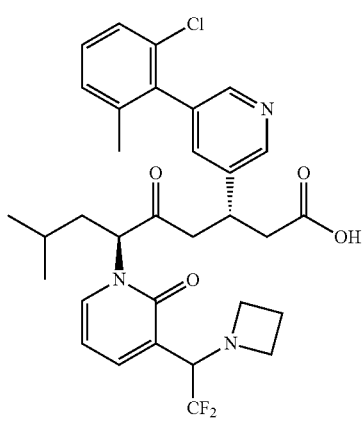
, and
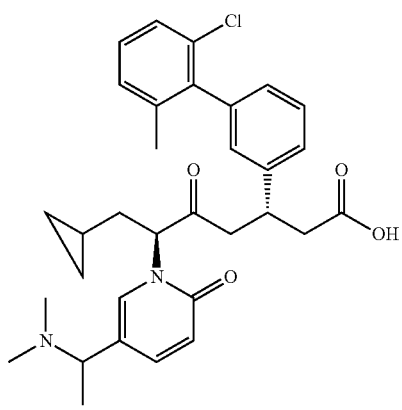
In some embodiments, the invention relates to a compound selected from the group consisting of:
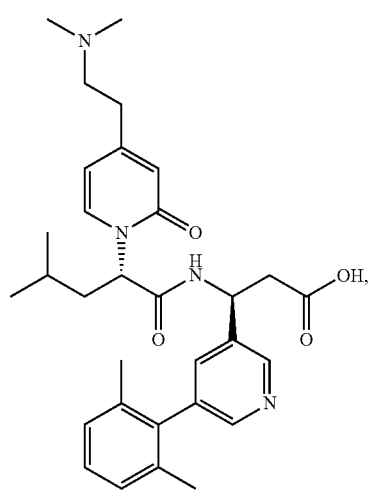
76
-continued
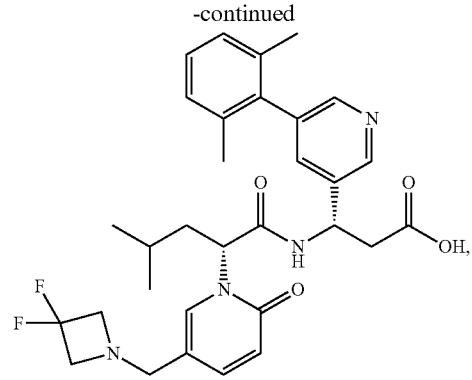
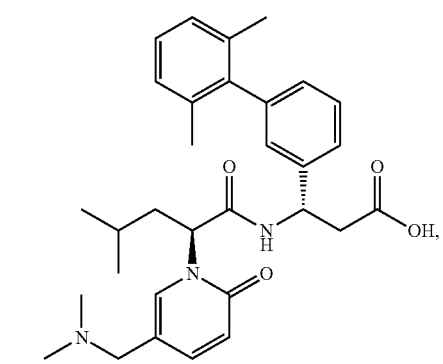
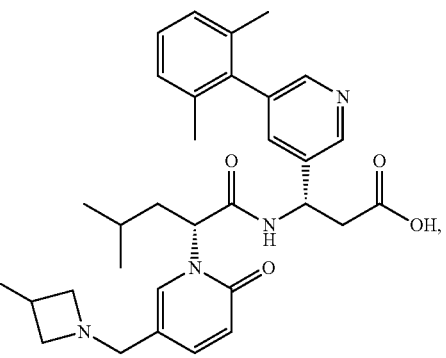
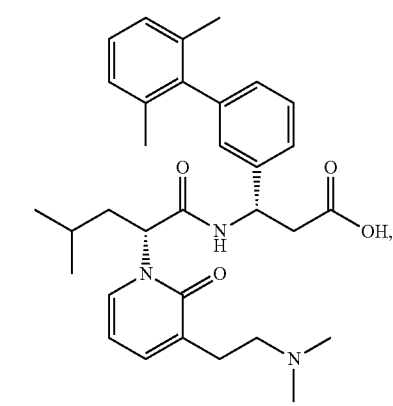

77
-continued
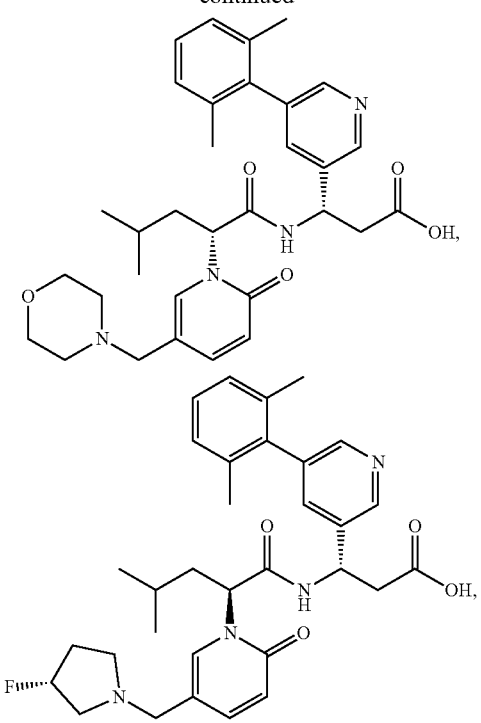
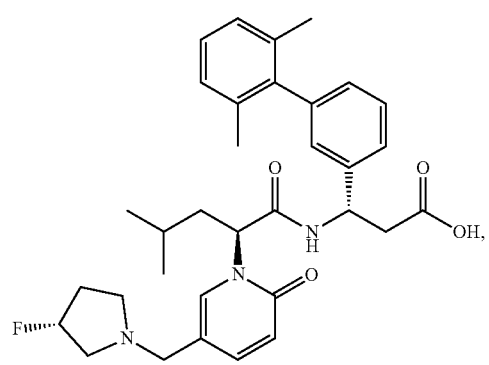
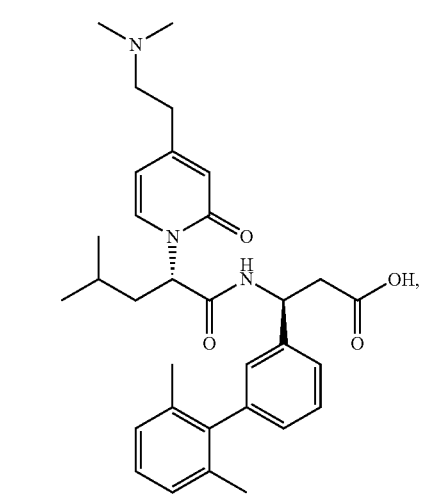
78
-continued
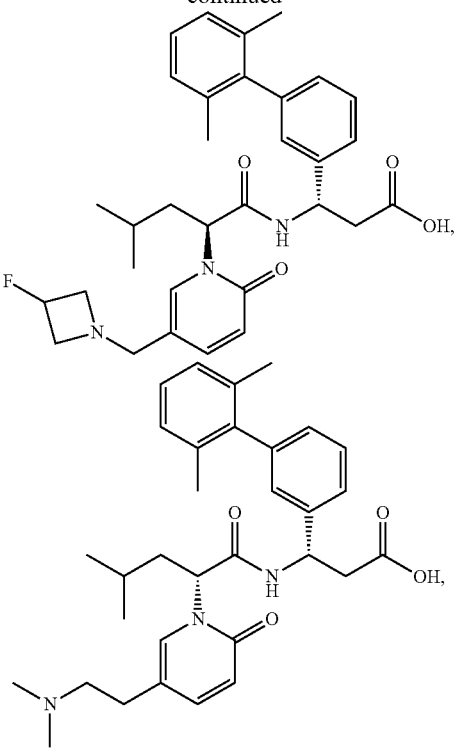
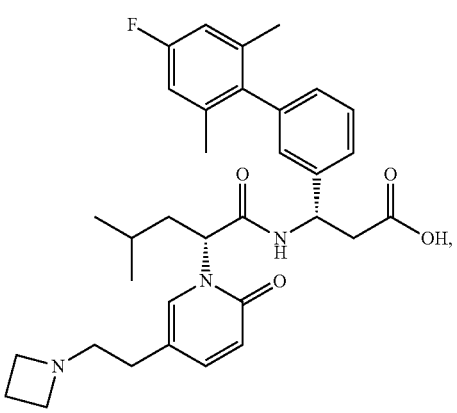
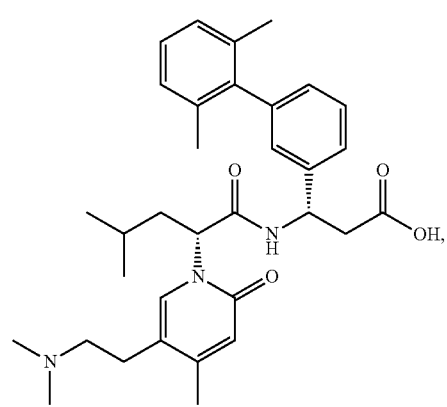

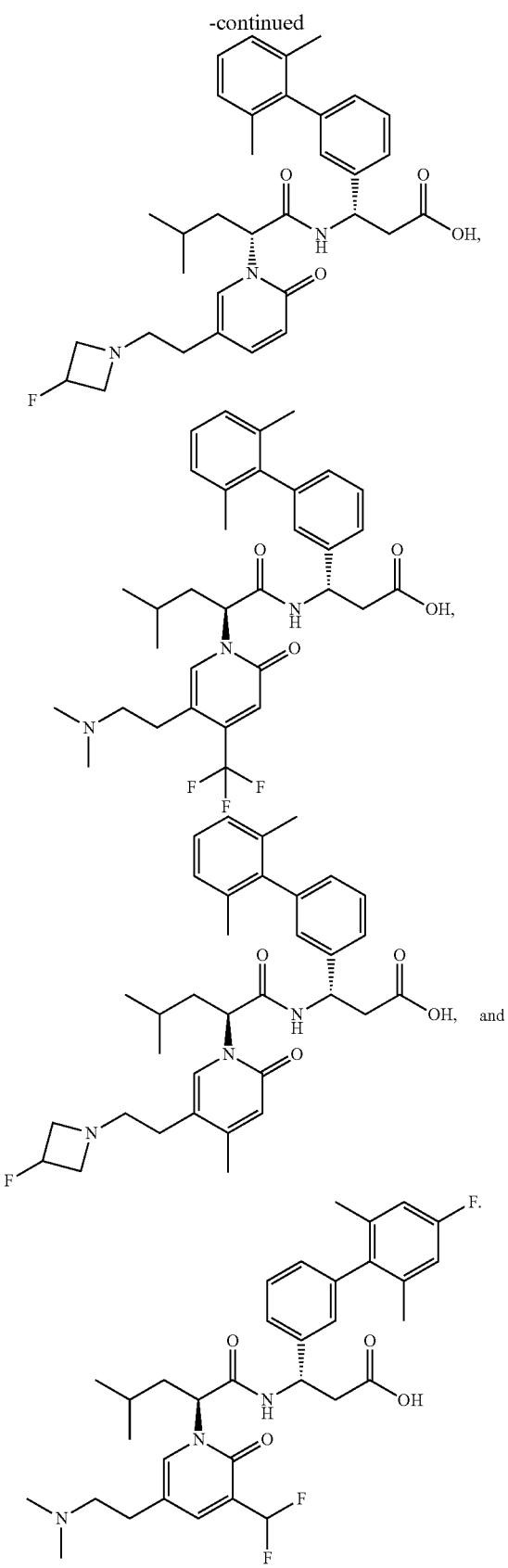
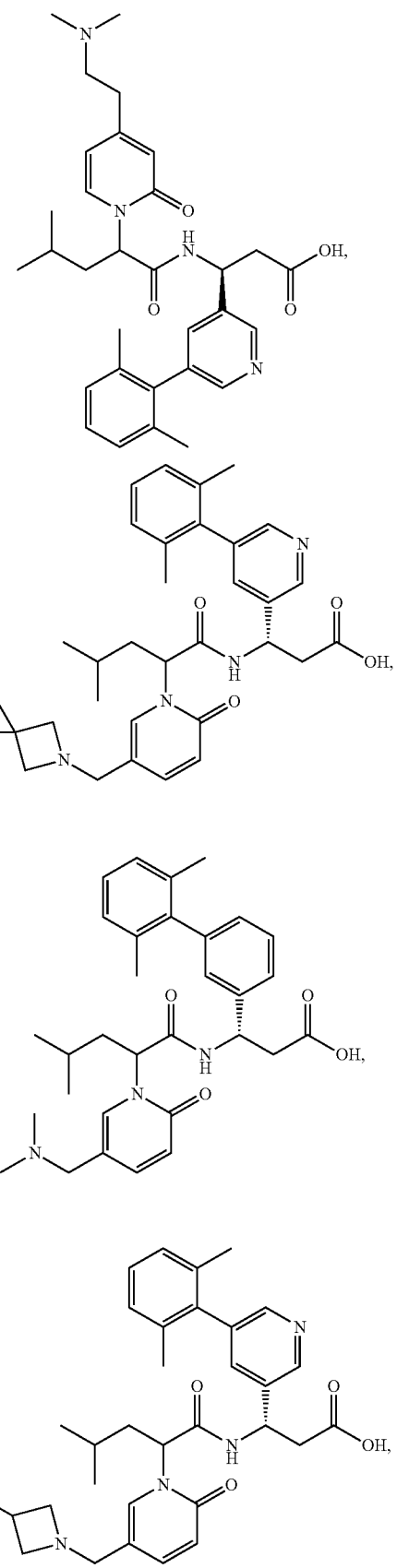
In some embodiments, the invention relates to a compound selected from the group consisting of:

81
-continued
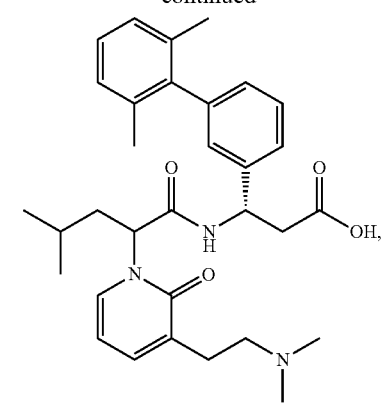
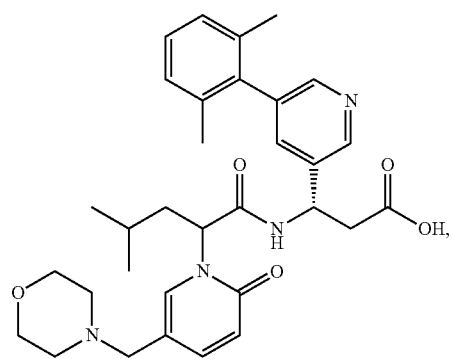
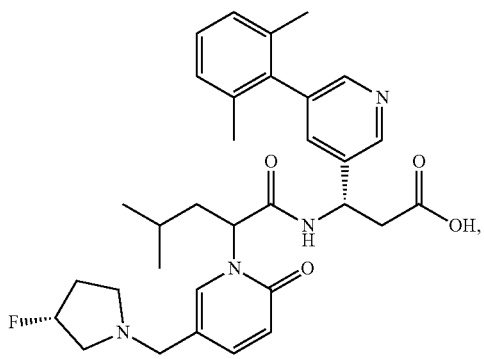
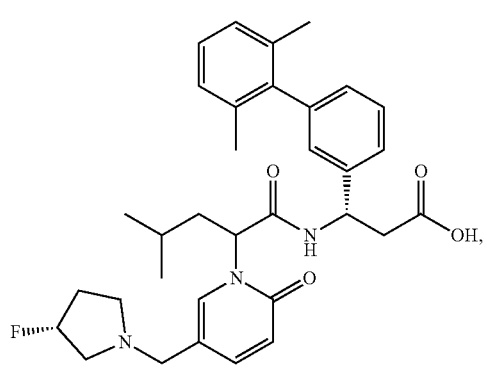
82
-continued
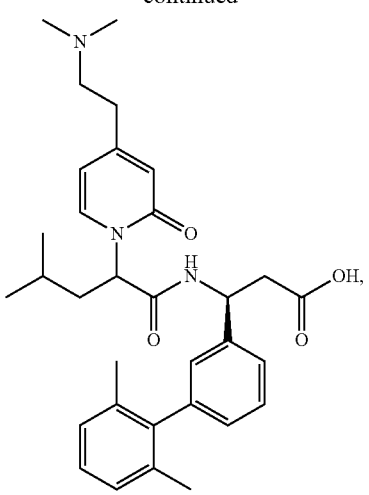
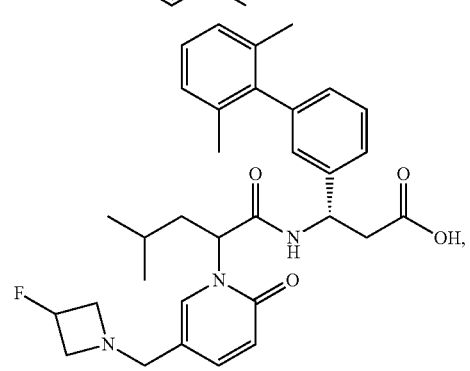
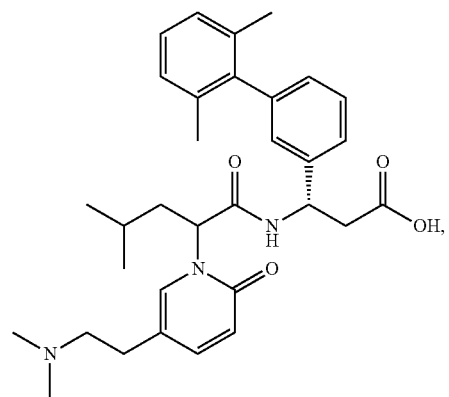
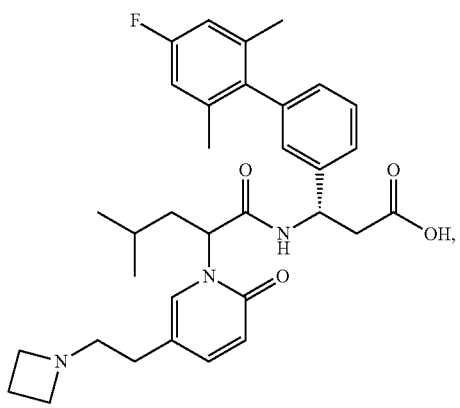

-continued

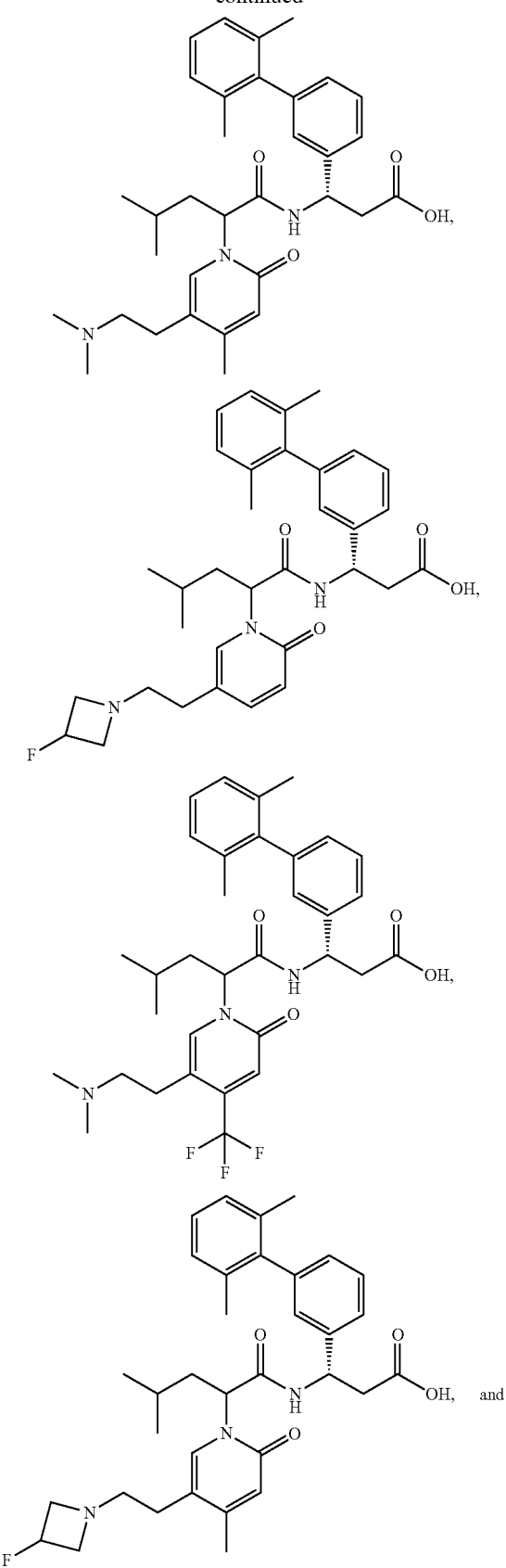

-continued

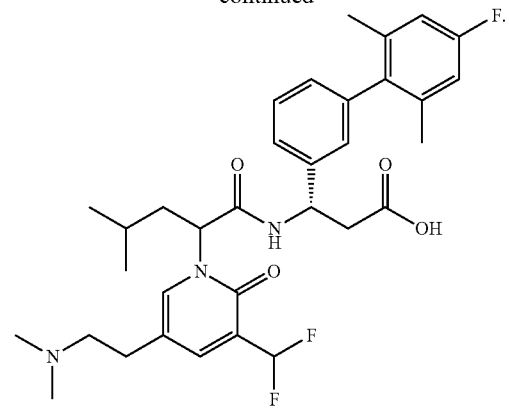

Exemplary Pharmaceutical Compositions

In certain embodiments, the invention relates to a pharmaceutical composition comprising any one of the aforementioned compounds and a pharmaceutically acceptable carrier.

Patients, including but not limited to humans, can be treated by administering to the patient an effective amount of the active compound or a pharmaceutically acceptable salt thereof in the presence of a pharmaceutically acceptable carrier or diluent. The active materials can be administered by any appropriate route, for example, orally, parenterally, intravenously, intradermally, subcutaneously, rectally, or topically, in liquid or solid form.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and certain preservatives, dyes and colorings and flavors.

The compound or a pharmaceutically acceptable salt thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid;

buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, carriers include physiological saline and phosphate buffered saline (PBS).

In certain embodiments, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Methods

In certain embodiments, the invention relates to a method of treating a disease or condition selected from the group consisting of inflammatory bowel disease, ileoanal anastomosis, eosinophilic esophagitis, pancreatitis, insulin-dependent diabetes mellitus, mastitis, cholecystitis, cholangitis, pericholangitis, chronic bronchitis, chronic sinusitis, asthma, graft versus host disease, a chronic inflammatory disease of the lung, HIV, and hematological tumor, comprising the step of: administering to a subject in need thereof a therapeutically effective amount of any one of the aforementioned compounds.

In certain embodiments, the disease or condition is inflammatory bowel disease. In certain embodiments, the inflammatory bowel disease is colitis, Crohn's disease, ileitis, Celiac disease, nontropical Sprue, enteropathy associated with seronegative arthropathies, gastroenteritis, or pouchitis.

In certain embodiments, the disease or condition is colitis; and the colitis is ulcerative colitis, microscopic colitis, or collagenous colitis.

In certain embodiments, the disease or condition is pouchitis; and the pouchitis is the result of proctocolectomy.

In certain embodiments, the disease or condition is gastroenteritis. In certain embodiments, the gastroenteritis is eosinophilic gastroenteritis.

In certain embodiments, the disease or condition is eosinophilic esophagitis.

In certain embodiments, the disease or condition is a chronic inflammatory disease of the lung. In certain embodiments, the chronic inflammatory disease of the lung is interstitial fibrosis. In certain embodiments, the intersititial fibrosis is hypersensitivity pneumonitis, collagen diseases, or sarcoidosis.

In certain embodiments, the disease or condition is a hematological tumor. In certain embodiments, the hematological tumor is selected from the group consisting of acute lymphocytic leukemia, acute myelogenous leukemia, chronic lymphocytic leukemia, chronic myelogenous leukemia, Hodgkin lymphoma, non-Hodgkin lymphoma, and multiple myeloma.

In certain embodiments, the invention relates to any one of the aforementioned methods, wherein the subject is a mammal. In certain embodiments, the invention relates to any one of the aforementioned methods, wherein the subject is human.

EXEMPLIFICATION

The invention now being generally described, it will be more readily understood by reference to the following examples, which are included merely for purposes of illustration of certain aspects and embodiments of the present invention, and are not intended to limit the invention.

Example 1. General Schemes for the Synthesis of α4β7 Inhibitors

General Procedures
Suzuki Coupling

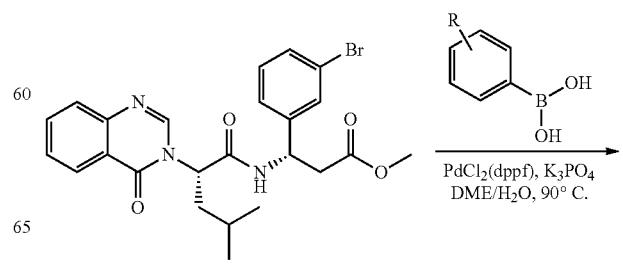

Ester Hydrolysis

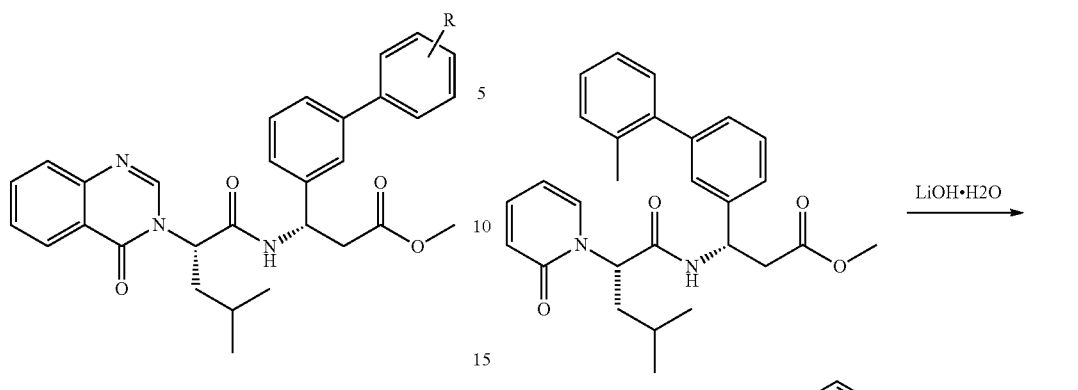

A mixture of Aryl Bromide (1 equiv.), boronic acid (2 equiv.), PdCl₂(dppf) (0.05 equiv.) and K₃PO₄ (2 equiv.) in DME and H₂O (10:1 ratio) was stirred under N₂ atmosphere at 90° C. for 30 mins. The mixture was filtered over Celite, concentrated in vacuo and purified by silica gel column to give the desired product.

Amide Bond Formation

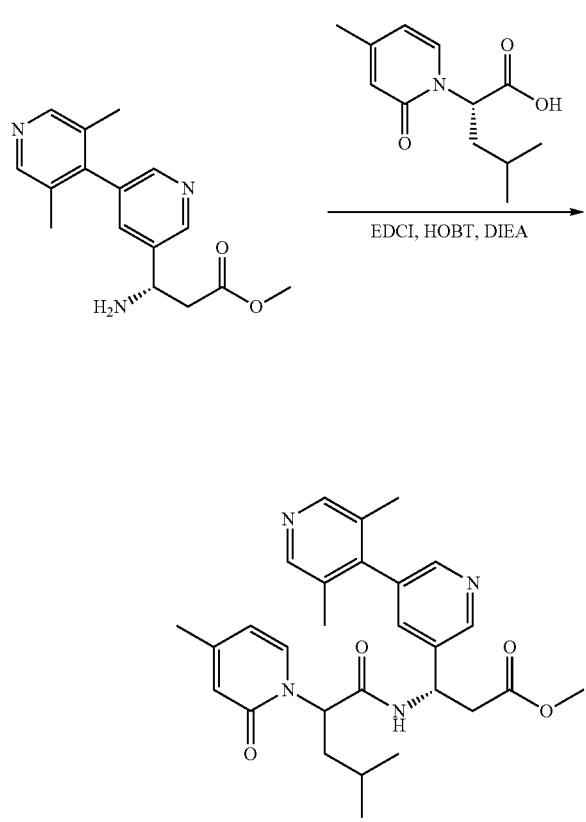

A mixture of amine (1 equiv.), acid (1 equiv.), EDCI (1.5 equiv.), HOBt (1.5 equiv.) and DIEA (3.0 equiv.) in DMF was stirred at room temperature overnight. The solvent was removed in vacuo and the residue was purified by silica gel column to provide the desired product.

The ester was treated with LiOH—H₂O (7 equiv.) in MeOH:H₂O (3:1 ratio) at room temperature for 2 hours. The solution was adjusted with 1 N HCl to pH=5~6. The solvent was removed in vacuo, and the residue purified by preparatory HPLC conditions.

Analytical Methods

LCMS Analytical Methods

Final compounds were analyzed using LC/MS conditions, with UV detector monitoring at 214 nm and 254 nm, and mass spectrometry scanning 110-800 amu in ESI+ ionization mode.

LC/MS A: column: XBridge C18, 4.6×50 mm, 3.5 μm; mobile phase: A water (10 mM ammonium hydrogen carbonate), B CH₃CN; gradient: 5%-95% B in 1.4 min, then 1.6 min hold; flow rate: 1.8 mL/min; oven temperature 50° C.

LC/MS B: column: SunFire C18, 4.6×50 mm, 3.5 μm; mobile phase: A water (0.01% TFA), B CH₃CN; gradient: 5%-95% B in 1.5 min, then 1.5 min hold; flow rate: 2.0 mL/min; oven temperature 50° C.

LC/MS C: column: XBridge C18, 4.6×50 mm, 3.5 μm; mobile phase: A water (10 mM ammonium hydrogen carbonate), B CH₃CN; gradient: 5%-95% B in 1.5 min, then 1.5 min hold; flow rate: 1.8 mL/min; oven temperature 50° C.

LC/MS D: column: Poroshell 120 EC-C138, 4.6×30 mm, 2.7 μm; mobile phase: A water (0.01% TFA), B CH₃CN (0.01% TFA); gradient: 5%-95% B in 1.2 min, then 1.8 min hold; flow rate: 2.2 mL/min; oven temperature 50° C.

Prep-HPLC Methods

Crude samples were dissolved in MeOH and purified by prep HPLC using a Gilson 215 instrument, detection wavelength 214 nm:

Prep HPLC A: column: XBridge C18, 21.2*250 mm, 10 μm; mobile phase: A water (10 mM ammonium hydrogen carbonate), B CH₃CN; gradient elution as in text; flow rate: 20 mL/min.

Prep HPLC B: column: XBridge C18, 21.2*250 mm, 10 μm; mobile phase: A water (10 mM formic acid), B CH₃CN; gradient elution as in text; flow rate: 20 mL/min.

Prep Chiral SFC Methods Racemic and/or diastereomeric products were separated to individual enantiomers by chiral Prep SFC using an SFC-80 (Thar, Waters) instrument, detection wavelength 214 nm:

Prep chiral SFC A: column: (R,R)-Whelk-O1, 20*250 mm, 5 μm (Decial), column temperature: 35° C., mobile phase: CO₂/methanol (0.2% methanol ammonia)=60/40, flow rate: 80 g/min, back pressure: 100 bar.

Prep chiral SFC B: column: AD 20*250 mm, 10 μm (Daicel), column temperature: 35° C., mobile phase: CO₂/methanol (0.2% methanol ammonia)=60/40, flow rate: 80 g/min, back pressure: 100 bar.

Prep chiral SFC C: column: AS 20*250 mm, 10 μm (Daicel), column temperature: 35° C., mobile phase: CO₂/methanol (0.2% methanol ammonia)=60/40, flow rate: 80 g/min, back pressure: 100 bar.

Prep chiral SFC D: column: OD 20*250 mm, 5 μm (Daicel), column temperature: 35° C., mobile phase: CO₂/methanol (0.2% methanol ammonia)=60/40, flow rate: 80 g/min, back pressure: 100 bar.

Prep chiral SFC E: column: (S,S)-Whelk-O1, 20*250 mm, 5 μm (Decial), column temperature: 35° C., mobile phase: CO₂/methanol (0.2% methanol ammonia)=60/40, flow rate: 80 g/min, back pressure: 100 bar.

Prep chiral SFC F: column: OZ 20*250 mm, 5 μm (Daicel), column temperature: 35° C., mobile phase: CO₂/methanol (0.2% methanol ammonia)=60/40, flow rate: 80 g/min, back pressure: 100 bar.

Analytical Prep SFC Methods

Chiral products were analyzed by chiral SFC using an SFC-80 (Thar, Waters) instrument, detection wavelength 214 nm:

Chiral SFC A: column: (R,R)-Whelk-O1, 4.6*100 mm, 5 μm (Decial), column temperature: 40° C., mobile phase: CO₂/methanol (0.2% methanol ammonia), isocratic elution as in text, flow rate: 4 g/min, back pressure: 120 bar.

Chiral SFC B: column: AD 4.6*100 mm, 5 μm (Daicel), column temperature: 40° C., mobile phase: CO₂/methanol (0.2% methanol ammonia), isocratic elution as in text, flow rate: 4 g/min, back pressure: 120 bar.

Chiral SFC C: column: AS 4.6*100 mm, 5 μm (Daicel), column temperature: 40° C., mobile phase: CO₂/methanol (0.2% methanol ammonia), isocratic elution as in text, flow rate: 4 g/min, back pressure: 120 bar.

Example 2. Preparation of Intermediates (R)-2-bromo-4-methylpentanoic acid

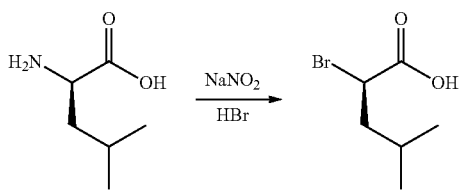

A solution of NaNO₂ (62.7 g, 909 mmol) in H₂O (200 mL) was added to compound D-leucine (75.0 g, 572 mmol) in HBr (6.0 M, 850 mL) at 0° C. The reaction was stirred at 20° C. for 14 hours. Two batches reaction were combined, and then the reaction mixture was extracted with ethyl acetate (1.5 L×2), washed with saturated aqueous NaCl (1.0 L×2), dried over MgSO₄, filtered and concentrated under reduced pressure to give compound (R)-2-bromo-4-methyl-pentanoic acid (230 g, crude) as a red oil. NMR (400 MHz CDCl₃) 11.18 (br, 1H), 4.30 (t, J=7.6 Hz, 1H), 1.94 (t, J=7.2 Hz, 2H), 1.80-1.87 (m, 1H), 0.93-0.99 (m, 6H).

(S)-4-methyl-2-(2-oxopyrazin-1(2H)-yl)pentanoic acid

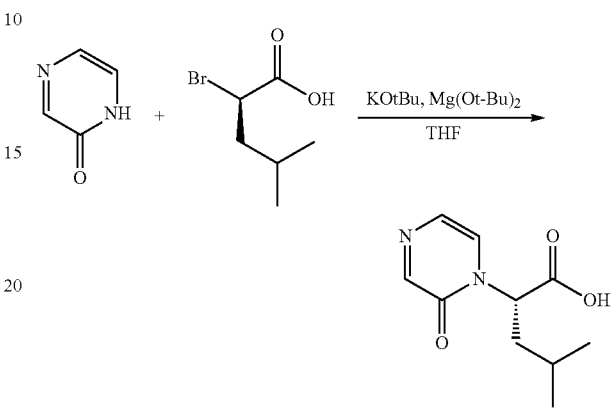

A solution of compound pyrazin-2(1H)-one (11.0 g, 114 mmol), Mg(Ot-Bu)₂ (39.0 g, 229 mmol) and t-BuOK (13.5 g, 120 mmol) in THF (220 mL) was stirred at 25° C. for 20 min under N₂. And then compound (R)-2-bromo-4-methyl-pentanoic acid (33.5 g, 172 mmol) was added drop-wise into the mixture. The reaction was stirred at 25° C. for 20 hrs. HCl (3.0 M, 153 mL) was added dropwise to the mixture. The organic phase was washed with brine (100 mL), and concentrated. The mixture was purified by SFC (Instrument: Thar SFC80 preparative SFC; Column: Chiralpak AD-H 250*30 mm i.d. 5 u; Mobile phase: A for CO₂ and B for IPA (0.1% NH₃H₂O); Gradient: B %=35%; Flow rate: 75 g/min; Wavelength: 220 nm; Column temperature: 40° C.; System back pressure: 100 bar; Cycle time: 13 min; Injection amount: 105 mg per injection) to give (S)-4-methyl-2-(2-oxopyrazin-1(2H)-yl)pentanoic acid (15.0 g, 61.7% Yield, 99.0% purity) as a yellow solid. ¹H NMR (400 MHz, DMSO-d₆) δ 7.96 (d, J=5.6 Hz, 1H), 7.58 (d, J=4.8 Hz, 1H), 7.30 (d, J=4.4 Hz, 1H), 5.14-5.21 (m, 1H), 1.84-1.92 (m, 2H), 1.17-1.26 (m, 1H), 0.82-0.84 (m, 6H).

4-methyl-2-(2-oxopyridin-1(2H)-yl)pentanoic acid

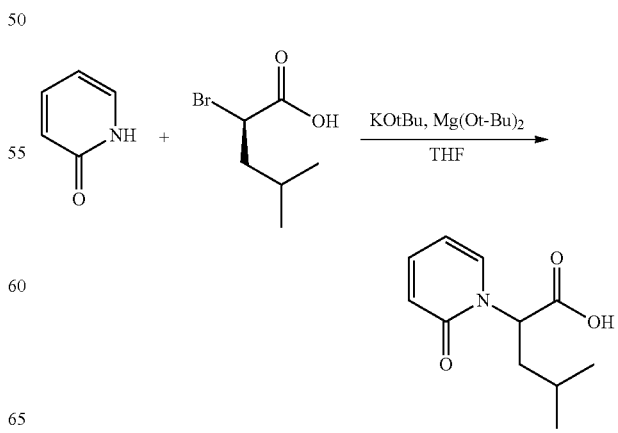

To a mixture of KOtBu (24.8 g, 221 mmol) and Mg(Ot-Bu)₂ (71.7 g, 421 mmol) in THF (300 mL) was added pyridin-2(1H)-one (20.0 g, 210 mmol). The mixture was stirred for 10 min. Compound (R)-2-bromo-4-methylpentanoic acid (61.5 g, 315 mmol) was added to the reaction mixture dropwise under N₂ followed by stirring at 25° C. for 40 h. The reaction was cooled to 0° C. and HCl (3.0 M) was added dropwise to adjust the mixture to pH=3. Then, the mixture was separated and the organic layer was concentrated in vacuo. The white solid product was collected by filtration, washed with EA (100 mL×2) and water (100 mL×2) to give compound 4-methyl-2-(2-oxopyridin-1(2H)-yl)pentanoic acid (27.0 g, 60.7% Yield, 99.0% purity) as an off-white solid. ¹H NMR (400 MHz, DMSO-d6) δ 13.06 (br, 1H), 7.65 (d, J=6.8 Hz, 1H), 7.39-7.43 (m, 1H), 6.38 (d, J=8.8 Hz, 1H), 6.26-6.23 (m, 1H), 5.32-5.36 (m, 1H), 2.06-2.01 (m, 1H), 1.85-1.88 (m, 1H), 1.30-1.20 (m, 1H), 0.86-0.83 (m, 6H).

(S)-4-methyl-2-(4-methyl-2-oxopyridin-1(2H)-yl)pentanoic acid

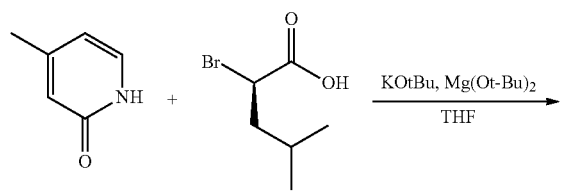

To a solution of KOtBu (21.6 g, 192 mmol) and Mg(Ot-Bu)₂ (62.5 g, 367 mmol) in THF (300 mL) was added compound 4-methylpyridin-2(1H)-one (20.0 g, 183 mmol) under with N₂. The reaction mixture was stirred for 10 min. (R)-2-bromo-4-methylpentanoic acid (53.6 g, 275 mmol) was added to the reaction mixture dropwise. Then, the resulting reaction mixture was stirred at 25° C. for 40 h. The reaction mixture was cooled to 0° C. and HCl (3.0 M) was added to adjust the mixture to pH=3. The organic layer was concentrated using a rotavap and the off-white solid product was collected by filtration. Water (50 mL) was added to the solid and it was stirred for 2 h. The reaction mixture was filtered. The filter cake was collected to give (S)-4-methyl-2-(4-methyl-2-oxopyridin-1(2H)-yl)pentanoic acid (21.0 g, 51.1% Yield, 99.5% purity, 99.0% ee) as an off-white solid. ¹H NMR (400 MHz, DMSO-d₆) δ 13.00 (br, 1H), 7.52 (d, J=6.8 Hz, 1H), 6.19 (s, 1H), 6.10 (d, J=6.8 Hz, 1H), 5.30-5.33 (m, 1H), 2.12 (s, 3H), 1.99-2.03 (m, 1H), 1.82-1.86 (m, 1H), 1.24-1.26 (m, 1H), 0.84 (d, J=6.8 Hz, 6H).

(S)-4-methyl-2-(2-oxo-4-(trifluoromethyl)pyridin-1(2H)-yl)pentanoic acid

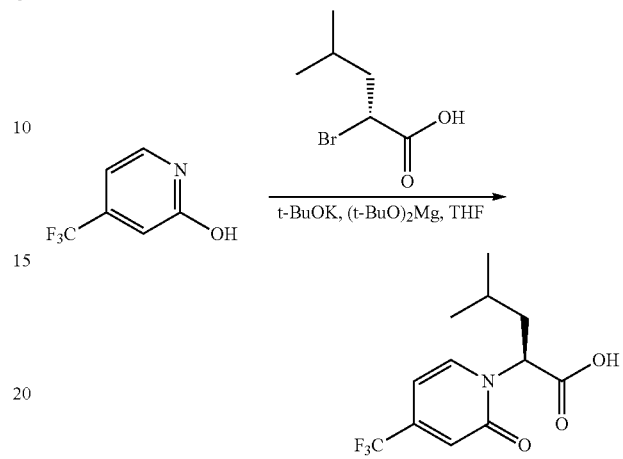

To a solution of (R)-2-bromo-4-methylpentanoic acid (238 mg, 1.2 mmol) in dry THF (10 mL) was added (t-BuO)₂Mg (425 mg, 2.5 mmol) and the solution was stirred at 30° C. under N₂ atmosphere for 1 hour. Then 4-(trifluoromethyl)pyridin-2-ol (200 mg, 1.2 mmol) and t-BuOK (134 mg, 1.2 mmol) was added and the reaction mixture was stirred at 70° C. under N₂ atmosphere for 16 hours. The mixture was cooled to room temperature and acidified to pH=5 with a diluted HCl (4 M) solution. The solvent was removed in vacuo and the residue was purified by preparatory HPLC B (30-60% MeCN) to provide the desired product (S)-4-methyl-2-(2-oxo-4-(trifluoromethyl)pyridin-1(2H)-yl)pentanoic acid as a white solid (150 mg). Yield 44% (98% purity, UV=214 nm, ESI 278 (M+H)⁺).

Step 1: methyl 3-methoxy-2-(4-methyl-2-oxopyridin-1(2H)-yl)propanoate

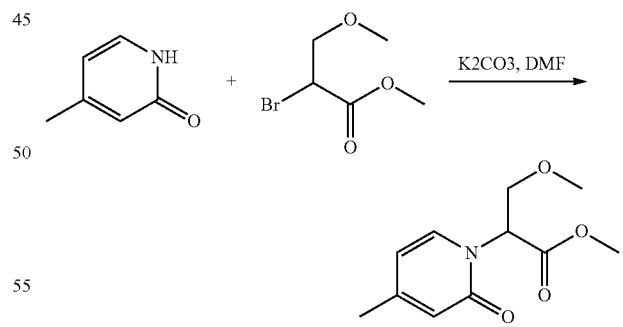

A mixture of 4-methylpyridin-2(1H)-one (350 mg, 3.2 mmol), methyl 2-bromo-3-methoxypropanoate (690 mg, 3.5 mmol) and K₂CO₃ (880 mg, 6.4 mmol) in DMF (10 mL) was stirred at room temperature for 18 hours. The solvent was removed in vacuo and the residue was purified by silica gel column (pet. ether:EtOAc 1:1) to give product methyl 3-methoxy-2-(4-methyl-2-oxopyridin-1(2H)-yl)propanoate as a colorless oil (200 mg). Yield 28% (97% purity, UV=214 nm, ESI 226 (M+H)⁺).

Step 2: 3-methoxy-2-(4-methyl-2-oxopyridin-1(2H)-yl)propanoic acid

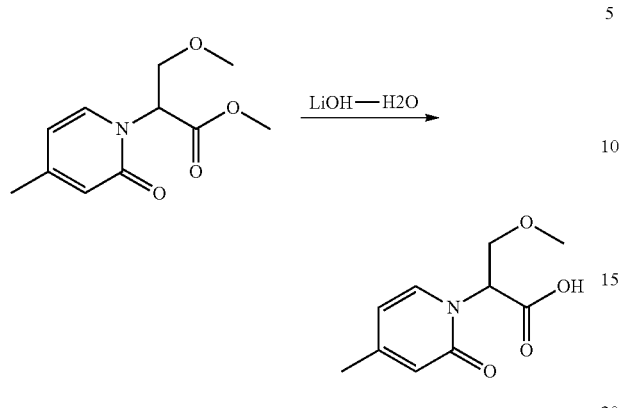

Methyl 3-methoxy-2-(4-methyl-2-oxopyridin-1(2H)-yl)propanoate (200 mg, 0.89 mmol) was treated with LiOH—H$_2$O (180 mg, 4.4 mmol) in THF (8 mL) and H$_2$O (2 mL) at room temperature for 18 hr. The reaction was acidified with 1 N HCl to pH=3. The solvent was removed in vacuo and the residue was purified by preparatory HPLC B to give the desired product 3-methoxy-2-(4-methyl-2-oxopyridin-1(2H)-yl)propanoic acid as a white solid (95 mg). Yield 50% (93% purity, UV=214 nm, ESI 212 (M+H)$^+$).

Synthesis of 2-(5-methyl-2-oxopyridin-1(2H)-yl)-2-phenylacetic acid

Step 1: methyl 2-(5-methyl-2-oxopyridin-1(2H)-yl)-2-phenylacetate

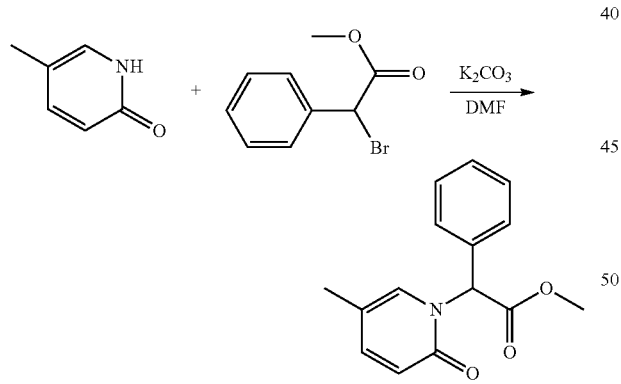

A mixture of 5-methyl-2-pyridone (1.463 g, 13.40 mmol), methyl alpha-bromophenylacetate (2.291 g, 10.00 mmol), and potassium carbonate (1.852 g, 13.40 mmol) in N,N-dimethylformamide (40 mL) was stirred at room temperature overnight. The mixture was concentrated in vacuo and the residue was purified by silica gel column (pet. ether: EtOAc 1:1) to give the desired product methyl 2-(5-methyl-2-oxopyridin-1(2H)-yl)-2-phenylacetate as a light brown oil (2.5 g). Yield 68% (97% purity, UV=214 nm, ESI 258 (M+H)$^+$).

Step 2: 2-(5-methyl-2-oxopyridin-1(2H)-yl)-2-phenylacetic acid

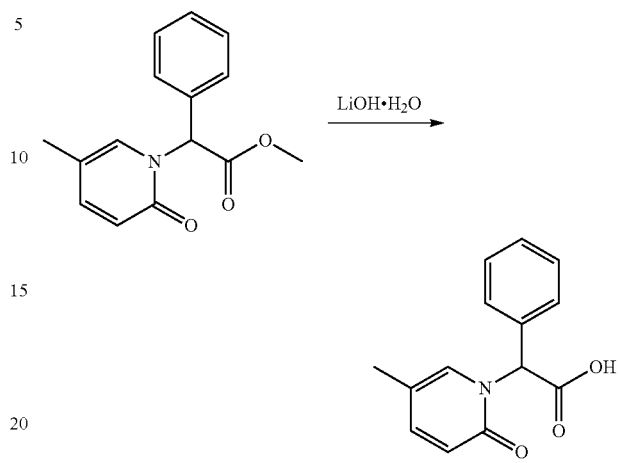

Methyl 2-(5-methyl-2-oxopyridin-1(2H)-yl)-2-phenylacetate (2.5 g, 9.6 mmol) was treated with LiOH—H$_2$O (2.3 g, 54 mmol) in methanol (134 mL) and water (27 mL) at room temperature for 16 hours. The reaction was acidified with 1 N hydrochloric acid to pH=3. The solvent was removed in vacuo and the residue was purified by preparatory HPLC B (30-65% MeCN) to give the desired product 2-(5-methyl-2-oxopyridin-1(2H)-yl)-2-phenylacetic acid as a white solid (2.32 g). Yield 84% (100% purity, UV=254 nm, ESI 244 (M+H)$^+$).

Synthesis of Ethyl (S)-3-(2-bromopyridin-4-yl)-3-((tert-butoxycarbonyl)amino)propanoate

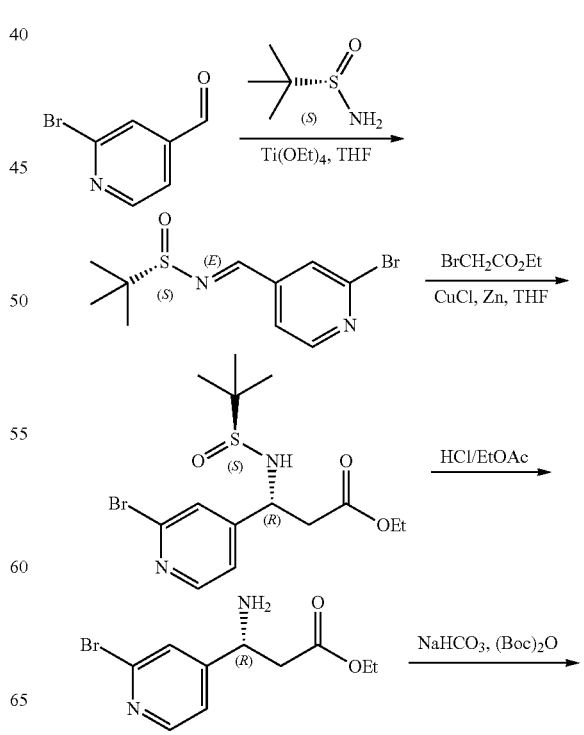

-continued

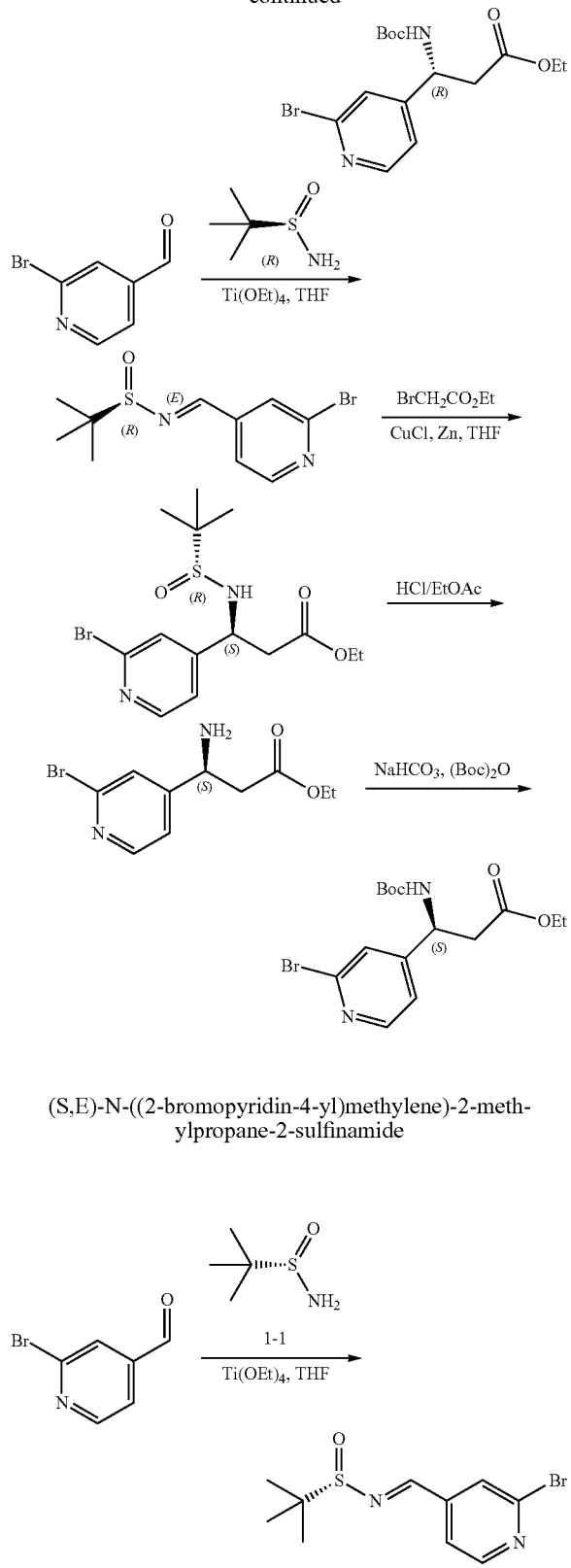

(S,E)-N-((2-bromopyridin-4-yl)methylene)-2-methylpropane-2-sulfinamide

To a mixture of 2-bromoisonicotinaldehyde (68.0 g, 365 mmol) and compound (S)-2-methylpropane-2-sulfinamide (48.7 g, 402 mmol) in THF (400 mL) was added Ti(OEt)$_4$ (125 g, 548 mmol, 113 mL) in one portion at 20° C. under N$_2$. The mixture was stirred at 35° C. for 1 h. Water (200 mL) and EtOAc (200 mL) was added into the mixture, and stirred for 5 min. The mixture was filtered, and the filtered cake was washed with EtOAc (200 mL). The combined organic layers were washed with water (200 mL) and brine (200 mL), dried over anhydrous Na$_2$SO$_4$ and concentrated in vacuo to give compound (S,E)-N-((2-bromopyridin-4-yl)methylene)-2-methylpropane-2-sulfinamide (90.0 g, crude) as a yellow solid.

(R,E)-N-((2-bromopyridin-4-yl)methylene)-2-methylpropane-2-sulfinamide

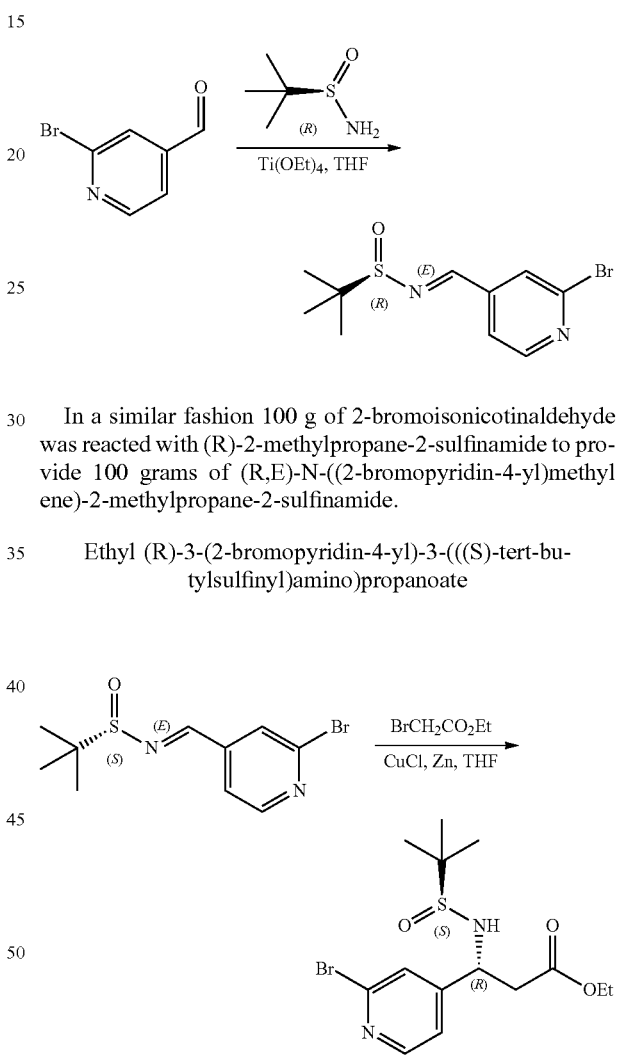

In a similar fashion 100 g of 2-bromoisonicotinaldehyde was reacted with (R)-2-methylpropane-2-sulfinamide to provide 100 grams of (R,E)-N-((2-bromopyridin-4-yl)methylene)-2-methylpropane-2-sulfinamide.

Ethyl (R)-3-(2-bromopyridin-4-yl)-3-(((S)-tert-butylsulfinyl)amino)propanoate

To a mixture of Zn (142 g, 2.18 mol) in THF (900 mL) was added CuCl (46.2 g, 466 mmol) in one portion at 20° C. under N$_2$. The mixture was stirred at 60° C. for 1 h. The reaction mixture was cooled to 20-30° C., and charged ethyl 2-bromoacetate (129 g, 778 mmol) into the mixture at 20-30° C. under N$_2$. The mixture was stirred at 50-60° C. for 1 h. A solution of (S,E)-N-((2-bromopyridin-4-yl)methylene)-2-methylpropane-2-sulfinamide (90 g, 311 mmol) in dry THF (50 mL) was added into the reaction mixture at 0-10° C. under N$_2$. MTBE (500 mL) and a solution of citric acid (10 g) in water (200 mL) were added into the mixture. The aqueous layer was extracted with MTBE (500 mL and

Ethyl (S)-3-(2-bromopyridin-4-yl)-3-(((R)-tert-butylsulfinyl)amino)propanoate

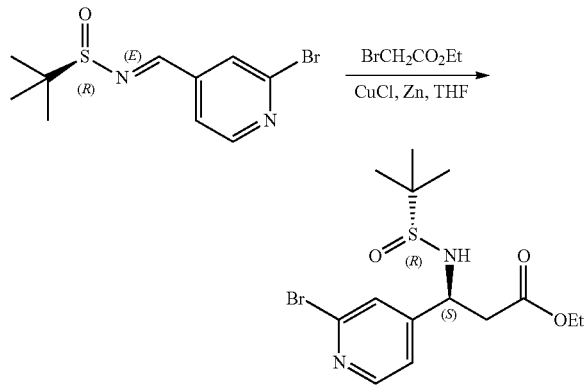

In a similar fashion 45 g×3 of (R,E)-N-((2-bromopyridin-4-yl)methylene)-2-methylpropane-2-sulfinamide was reacted to provide 200 grams of ethyl (S)-3-(2-bromopyridin-4-yl)-3-(((R)-isopropylsulfinyl)amino)propanoate.

Ethyl (R)-3-amino-3-(2-bromopyridin-4-yl)propanoate

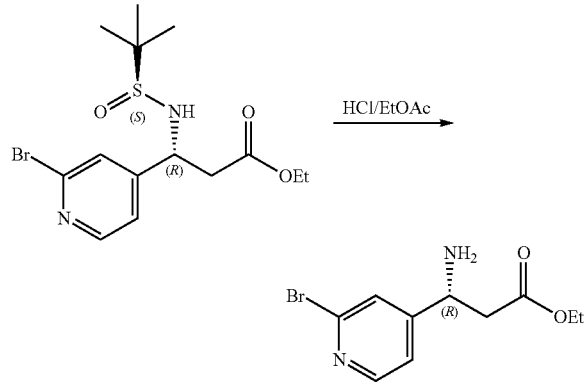

To a mixture of compound ethyl (R)-3-(2-bromopyridin-4-yl)-3-(((S)-tert-butylsulfinyl)amino)propanoate (80.0 g, 212 mmol) in EtOAc (150 mL) was added HCl/EtOAc (4.00 M, 212 mL) in one portion at 20° C. The mixture was stirred at 20° C. for 1 h. Water (400 mL) was added and the aqueous layer was separated. The aqueous layer was adjusted to pH=8~9 with Na$_2$CO$_3$, and extracted with EtOAc (400 mL, 250 mL) for two times. The combined organic phase was washed with brine (200 mL), dried with anhydrous Na$_2$SO$_4$, filtered and concentrated in vacuo to give compound ethyl (R)-3-amino-3-(2-bromopyridin-4-yl)propanoate (55.0 g, crude) as a yellow oil.

Ethyl (S)-3-amino-3-(2-bromopyridin-4-yl)propanoate

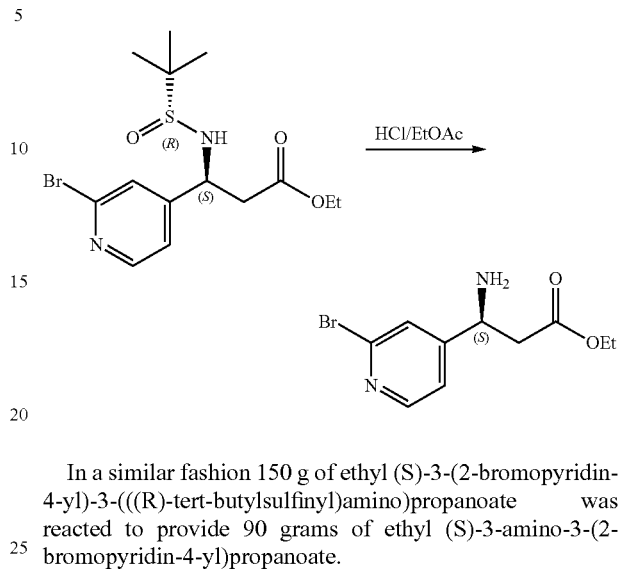

In a similar fashion 150 g of ethyl (S)-3-(2-bromopyridin-4-yl)-3-(((R)-tert-butylsulfinyl)amino)propanoate was reacted to provide 90 grams of ethyl (S)-3-amino-3-(2-bromopyridin-4-yl)propanoate.

Ethyl (R)-3-(2-bromopyridin-4-yl)-3-((tert-butoxycarbonyl)amino)propanoate

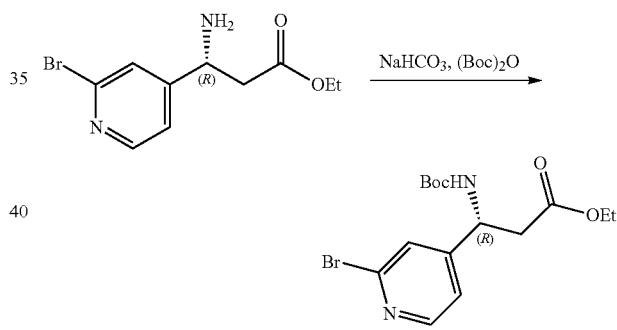

To a mixture of ethyl (R)-3-amino-3-(2-bromopyridin-4-yl)propanoate (55.0 g, 201 mmol) in THF (550 mL) was added a mixture of Na$_2$CO$_3$ (42.6 g, 402 mmol) in H$_2$O (550 mL) in one portion at 25° C. The mixture was stirred at 25° C., then (Boc)$_2$O (48.3 g, 221 mmol, 50.8 mL) was added to the mixture. The mixture was stirred at 25° C. for 1 h. TLC (Petroleum ether/ethyl acetate=3/1, R$_f$=0.5) showed the reaction was completed. Water (400 mL) and CH$_2$Cl$_2$ (400 mL) were added into the mixture. The mixture was separated, and the aqueous was extracted with CH$_2$Cl$_2$ (400 mL×2). The combined organic phase was washed with brine (400 mL), dry over Na$_2$SO$_4$, filtered and concentrated in vacuo. The residue was purified by column chromatography (SiO$_2$, Petroleum ether/Ethyl acetate=20/1 to 3/1) to give a crude ethyl (R)-3-(2-bromopyridin-4-yl)-3-((tert-butoxycarbonyl)amino)propanoate 30 g as a yellow solid, which was further separated by SFC to afford (21 g, 97% purity) as an off-white solid. $^1$H NMR (400 MHz, CDCl$_3$) δ 8.32-8.33 (m, 1H), 7.44 (s, 1H), 7.20 (d, J=5.2 Hz, 1H), 5.75 (s, 1H), 5.05 (s, 1H), 4.03-4.18 (m, 2H), 2.83 (d, J=3.6 Hz, 2H), 1.45 (m, 9H), 3.19-3.21 (m, 3H).

Ethyl (S)-3-(2-bromopyridin-4-yl)-3-((tert-butoxycarbonyl)amino)propanoate

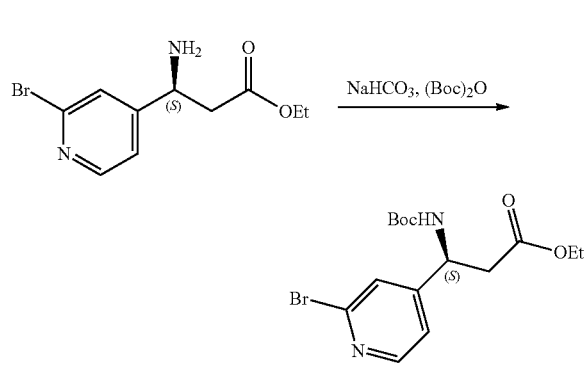

In a similar fashion 90 g of ethyl (S)-3-amino-3-(2-bromopyridin-4-yl)propanoate was reacted to provide 40 grams of ethyl (S)-3-(2-bromopyridin-4-yl)-3-((tert-butoxycarbonyl)amino)propanoate.

Methyl 3-(5-bromopyridin-3-yl)-3-((tert-butoxycarbonyl)amino)propanoate

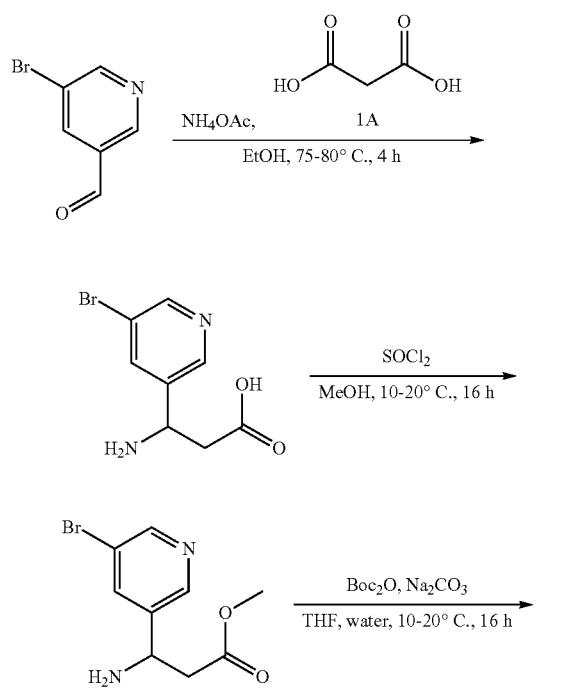

Step 1: 3-amino-3-(5-bromopyridin-3-yl)propanoic acid

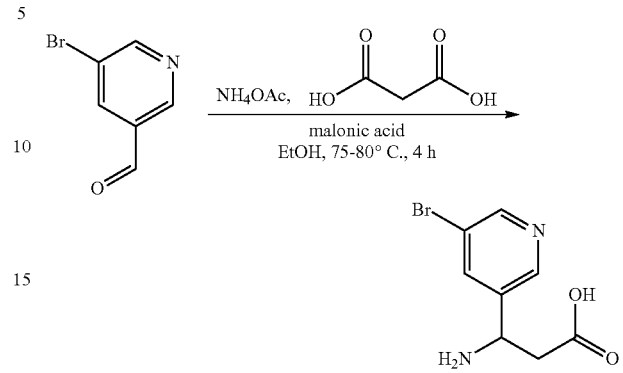

To 5-bromonicotinaldehyde (180 g) in EtOH (414 mL, 2.30× by volume) at 25° C. was added malonic acid (100 g) and NH$_4$OAc (157 g). The mixture was heated to 75-80° C. and stirred for 4 hrs. The mixture was filtered and the resulting solid washed with cold EtOH (180 mL) twice. Concentration of the filtrate provided 3-amino-3-(5-bromopyridin-3-yl)propanoic acid (246 g, crude) as white solid. $^1$H NMR 400 MHz CDCl$_3$ δ 8.62-8.58 (m, 2H), 8.10 (s, 1H), 4.28 (s, 1H), 2.69 (s, 1H), 2.50 (s, 1H).

Synthesis of methyl 3-amino-3-(5-bromopyridin-3-yl)propanoate

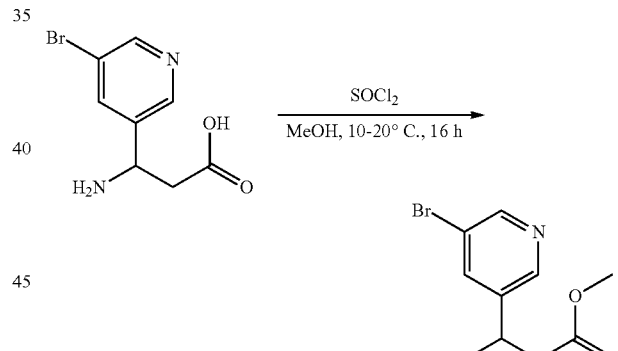

To 3-amino-3-(5-bromopyridin-3-yl)propanoic acid (50.0 g, 1.00× by weigh) in MeOH (800 mL, 16.0× by volume) at 0° C. was added SOCl$_2$ (36.4 g, 0.73× by weight). The mixture was heated to 10-20° C. and stirred at 10-20° C. for 16 hrs. The mixture was concentrated to give the crude product. To the crude material was added water (500 mL) and CH$_2$Cl$_2$ (500 mL, 10.0× by volume). The resulting phases were separated, and the aqueous extracted with CH$_2$Cl$_2$ (250 mL) twice. NaHCO$_3$ was added into the aqueous layer to adjust the pH=8-9 and extracted with CH$_2$Cl$_2$ (500 mL) and CH$_2$Cl$_2$ (250 mL) five times. The organic layers were combined, dry over Na$_2$SO$_4$, and concentrated to give methyl 3-amino-3-(5-bromopyridin-3-yl)propanoate (23.6 g, 40.2% Yield, 89.9% purity) as yellow solid. $^1$H NMR: 400 MHz CDCl$_3$ δ 8.56 (d, J=4.0 Hz, 1H), 8.51 (d, J=4.0 Hz, 1H), 7.91 (t, J=2.0 Hz, 1H), 4.46 (t, J=8.0 Hz, 1H), 3.69 (s, 3H), 2.66 (d, J=8.0 Hz, 1H), 1.81 (s, 2H).

Synthesis of methyl 3-(5-bromopyridin-3-yl)-3-((tert-butoxycarbonyl)amino)propanoate

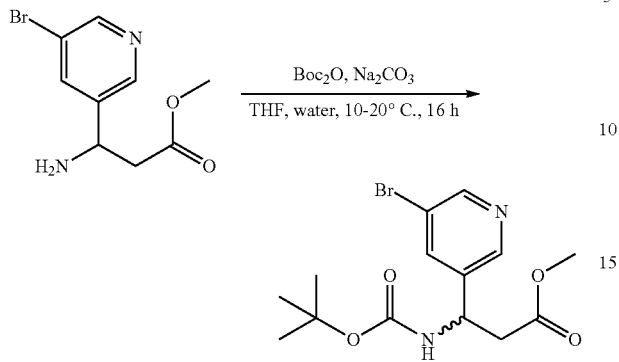

To methyl 3-amino-3-(5-bromopyridin-3-yl)propanoate (23.4 g) in THF (234 mL) at 10-20° C. was added a solution of Na₂CO₃ (19.1 g, 0.82× by weight) in water (234 mL). Boc₂O (21.7 g) was added to the mixture followed by stirring at 10-20° C. for 16 hrs. Water (234 mL) and CH₂Cl₂ (234 mL) was added into the mixture. The phases were separated and the aqueous extracted with CH₂Cl₂ (234 mL) twice. The organics were combined and concentrate to provide the methyl 3-(5-bromopyridin-3-yl)-3-((tert-butoxycarbonyl)amino)propanoate. Purification via SFC provided the two stereoisomers A1 (97.6% purity) and A2 (97.0% purity) both as off-white solids, which are confirmed by ¹H NMR, LCMS.

Compound A1 ¹H NMR δ 8.58 (d, J=4.0 Hz, 1H), 8.49 (d, J=4.0 Hz, 1H), 7.79 (d, J=4.0 Hz, 1H), 5.69 (s, 1H), 5.11 (s, 1H), 3.66 (s, 3H), 2.87 (d, J=8.0 Hz, 2H), 1.43 (s, 9H).

Compound A2 ¹H NMR δ 5.58 (d, J=4.0 Hz, 1H), 8.49 (d, J=4.0 Hz, 1H), 7.79 (d, J=4.0 Hz, 1H), 5.70 (s, 1H), 5.11 (s, 1H), 3.66 (s, 3H), 2.87 (d, J=8.0 Hz, 2H), 1.43 (s, 9H).

Synthesis of (S)-methyl 3-amino-3-(2'-methylbiphenyl-3-yl)propanoate

Step 1: (S)-methyl 3-amino-3-(3-bromophenyl)propanoate

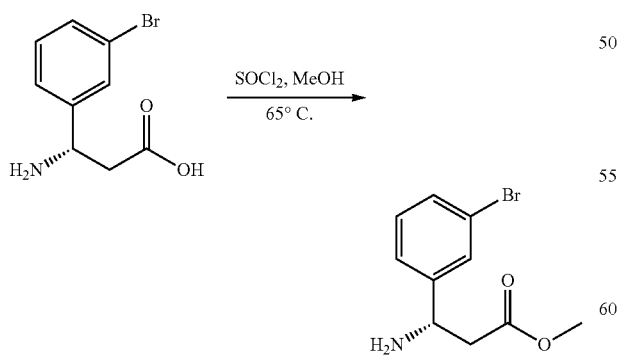

To a solution of (S)-3-amino-3-(3-bromophenyl)propanoic acid (150 mg, 0.62 mmol) in methanol (10 mL) was added SOCl₂ (2 mL) dropwise at 0° C. The solution was heated to 65° C. and stirred for 16 h. The solvent was removed in vacuo, and the residue was dissolved in a solution of NaHCO₃. The solution was extracted with EtOAc (30 mL×2). The combined organic layer were concentrated under reduced pressure to give the crude product (S)-methyl 3-amino-3-(3-bromophenyl)propanoate as a colorless oil (150 mg). Yield 95% (86% purity, UV=214 nm, ESI 258 (M+H)⁺). The crude product was used for the next step directly.

Step 2: (S)-methyl 3-amino-3-(2'-methylbiphenyl-3-yl)propanoate

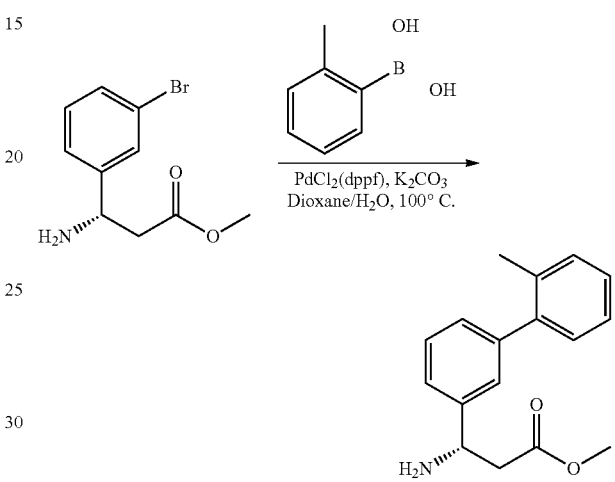

A mixture of (S)-methyl 4-methyl-2-(4-oxoquinazolin-3(4H)-yl)pentanoate (150 mg, 0.58 mmol), o-tolylboronic acid (118 mg, 0.87 mmol), PdCl₂(dppf) (22 mg, 0.029 mmol) and K₂CO₃ (240 mg, 1.74 mmol) in 1,4-Dioxane (3 mL) and H₂O (0.5 mL) under N₂ atmosphere was stirred at 100° C. in a microwave for 1 hour. The mixture was filtered over Celite, and the filtrate was concentrated under reduced pressure. The residue was purified by silica gel column (petroleum ether:EtOAc=3:1) to provide the desired product (S)-methyl 3-amino-3-(2'-methylbiphenyl-3-yl)propanoate (110 mg) as a white solid. Yield 72% (92% purity, UV=254 nm, ESI 270 (M+H)⁺).

Example 3. Preparation of Representative Compounds of the Invention

Preparation of ((3S)-3-(3',5'-dimethyl-[3,4'-bipyridin]-5-yl)-3-(4-methyl-2-(4-methyl-2-oxopyridin-1(2H)-yl)pentanamido)propanoic acid (Compound 1-D1 and 1-D2)

Step 1: (S)-(5-(1-((tert-butoxycarbonyl)amino)-3-methoxy-3-oxopropyl)pyridin-3-yl)boronic acid

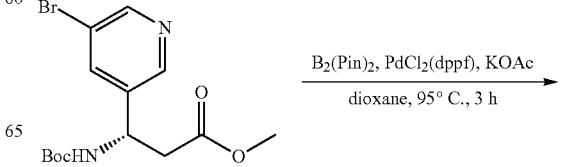

103

-continued

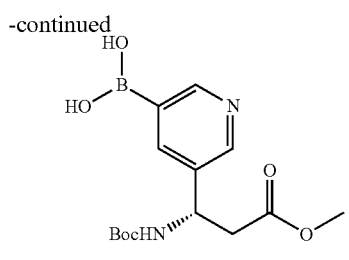

A mixture of methyl methyl (S)-3-(5-bromopyridin-3-yl)-3-((tert-butoxycarbonyl)amino)propanoate (300 mg, 0.83 mmol), $B_2(Pin)_2$ (254 mg, 1.00 mmol), $PdCl_2(dppf)$ (59 mg, 0.08 mmol) and KOAc (325 mg, 3.32 mmol) in dioxane (5 mL) was stirred at 95° C. for 3 hours. The solvent was concentrated in vacuo and the residue was purified by silica gel column (pet. ether:EtOAc 1:2) to give the desired product (S)-(5-(1-((tert-butoxycarbonyl)amino)-3-methoxy-3-oxopropyl)pyridin-3-yl)boronic acid as a yellow oil (200 mg). Yield 74% (75% purity, UV=254 nm, ESI 325 $(M+H)^+$).

Step 2: methyl (S)-3-((tert-butoxycarbonyl)amino)-3-(3',5'-dimethyl-[3,4'-bipyridin]-5-yl)propanoate

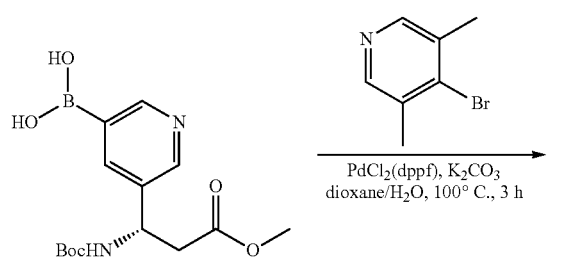

A mixture of (S)-(5-(1-((tert-butoxycarbonyl)amino)-3-methoxy-3-oxopropyl)pyridin-3-yl)boronic acid (200 mg, 0.62 mmol), 4-bromo-3,5-dimethylpyridine (230 mg, 1.23 mmol), $PdCl_2(dppf)$ (88 mg, 0.12 mmol) and $K_2CO_3$ (510 mg, 3.69 mmol) in dioxane (5 mL) and $H_2O$ (1 mL) was stirred at 100° C. for 3 hours. Water (20 mL) was added and the solution was extracted with EtOAc (20 mL×3). The combined organic phases were concentrated in vacuo and the residue was purified by silica gel column (pet. ether: EtOAc 5:4) to give the desired product methyl (S)-3-((tert-butoxycarbonyl)amino)-3-(3',5'-dimethyl-[3,4'-bipyridin]-5-yl)propanoate as a yellow oil (300 mg). Yield 63% (92% purity, UV=254 nm, ESI 386 $(M+H)^+$).

104

Step 3: methyl (S)-3-amino-3-(3',5'-dimethyl-[3,4'-bipyridin]-5-yl)propanoate

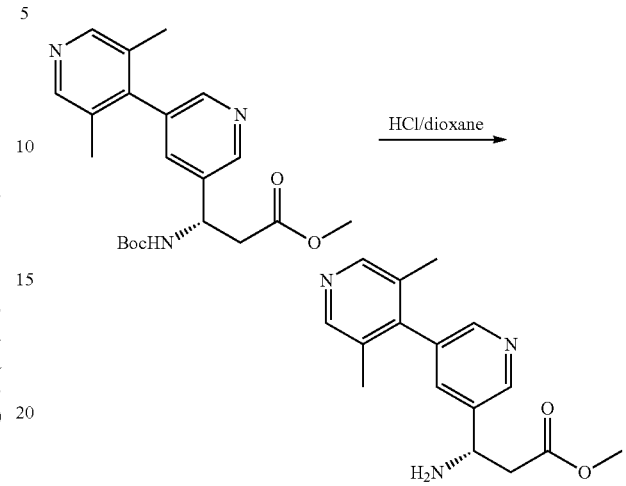

(S)-3-((tert-butoxycarbonyl)amino)-3-(3',5'-dimethyl-[3,4'-bipyridin]-5-yl)propanoate (300 mg, 0.77 mmol) was treated with 4N HCl/dioxane (3 mL) at room temperature for 2 hours. The solvent was removed in vacuo to provide the desired product methyl (S)-3-amino-3-(3',5'-dimethyl-[3,4'-bipyridin]-5-yl)propanoate as a yellow oil (350 mg, crude). (64% purity, UV=254 nm, ESI 286 $(M+H)^+$).

Step 4: methyl (3S)-3-(3',5'-dimethyl-[3,4'-bipyridin]-5-yl)-3-(4-methyl-2-(4-methyl-2-oxopyridin-1(2H)-yl)pentanamido)propanoate

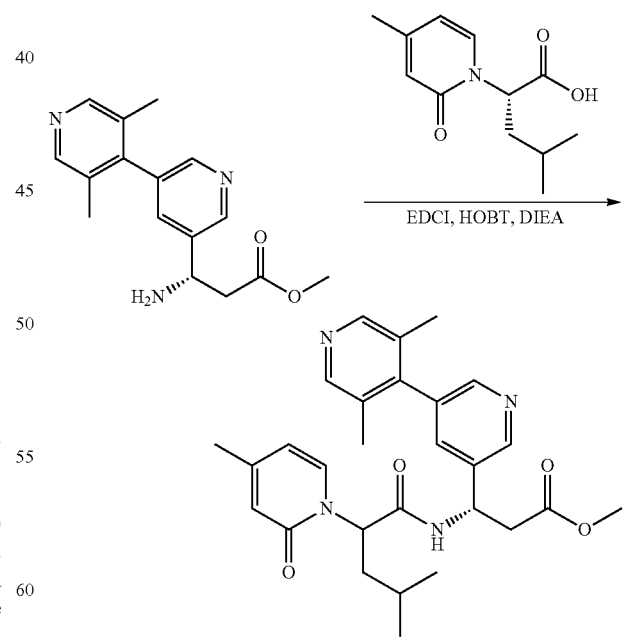

A mixture of methyl (S)-3-amino-3-(3',5'-dimethyl-[3,4'-bipyridin]-5-yl)propanoate (250 mg, 0.87 mmol), (S)-4-methyl-2-(4-methyl-2-oxopyridin-1(2H)-yl)pentanoic acid (196 mg, 0.87 mmol), EDCI (249 mg, 1.3 mmol), HOBt (176 mg, 1.3 mmol) and DIEA (335 mg, 2.6 mmol) in DMF (3 mL) was stirred at room temperature overnight. The solvent was removed in vacuo and the residue was purified by silica gel column (pet. ether:EtOAc 1:1) to provide the desired product methyl (3S)-3-(3',5'-dimethyl-[3,4'-bipyridin]-5-yl)-3-(4-methyl-2-(4-methyl-2-oxopyridin-1(2H)-yl)pentanamido)propanoate as a brown oil (300 mg). Yield 70% (94% purity, UV=254 nm, ESI 491 (M+H)+).

Step 5: ((3S)-3-(3',5'-dimethyl-[3,4'-bipyridin]-5-yl)-3-(4-methyl-2-(4-methyl-2-oxopyridin-1(2H)-yl)pentanamido)propanoic acid

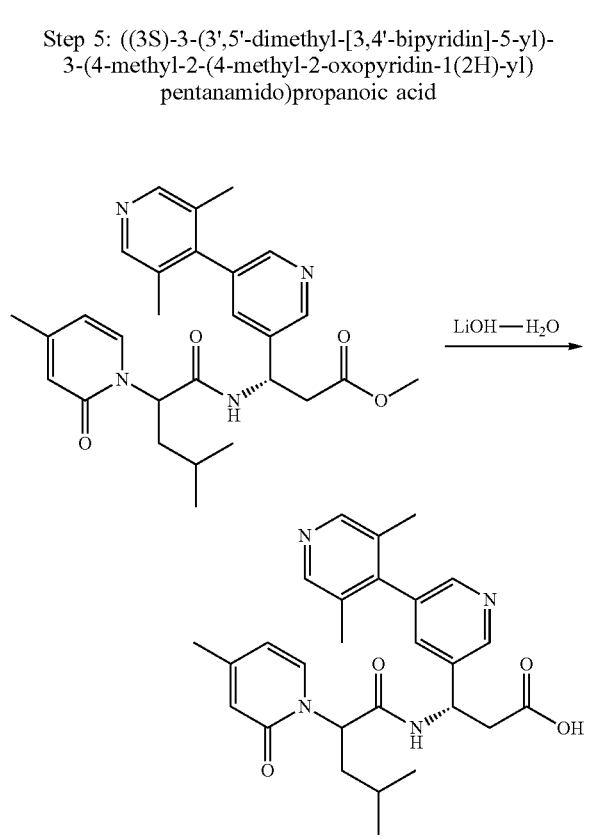

Methyl (3 S)-3-(3',5'-dimethyl-[3,4'-bipyridin]-5-yl)-3-(4-methyl-2-(4-methyl-2-oxopyridin-1(2H)-yl)pentanamido)propanoate (300 mg, 0.61 mmol) was treated with LiOH—H2O (72 mg, 1.83 mmol) in MeOH (3 mL) and H2O (1 mL) at room temperature for 2 hours. The solvent was removed in vacuo and the residue was purified by preparative-HPLC A (30-80% MeCN) to give the compounds B1 (50 mg) and B2 (55 mg) as yellow solids.

Compound B1 LC/MS A: 100% purity, UV=214 nm, Rt=1.40 min, ESI 477 (M+H)+.

1H-NMR (500 MHz, MeOD) δ 8.61 (d, J=2.1 Hz, 1H), 8.34 (d, J=8.3 Hz, 2H), 8.24 (d, J=1.9 Hz, 1H), 7.58 (d, J=7.3 Hz, 2H), 6.25-6.23 (m, 2H), 5.69 (dd, J=9.6, 6.6 Hz, 1H), 5.40 (t, J=7.0 Hz, 1H), 2.83 (d, J=7.1 Hz, 2H), 2.19 (s, 3H), 2.05 (s, 3H), 1.94-1.92 (m, 5H), 1.51-1.40 (m, 1H), 0.98-0.95 (m, 6H).

Compound B2 LC/MS A: 100% purity, UV=214 nm, Rt=1.43 min, ESI 477 (M+H)+.

1H-NMR (500 MHz, MeOD) δ 8.67 (d, J=1.7 Hz, 1H), 8.36 (s, 2H), 8.32 (d, J=1.6 Hz, 1H), 7.73 (d, J=1.9 Hz, 1H), 7.63 (s, 2H), 6.37 (s, 1H), 6.30 (dd, J=7.2, 1.8 Hz, 1H), 5.69 (dd, J=9.3, 6.8 Hz, 1H), 5.36 (t, J=7.1 Hz, 1H), 2.88-2.84 (m, 2H), 2.23 (s, 3H), 2.08 (s, 6H), 1.85-1.81 (m, 2H), 1.32-1.31 (m, 1H), 0.91-0.88 (m, 6H).

Preparation of (3S)-3-(5-(2,6-dimethylphenyl)pyridin-3-yl)-3-(4-methyl-2-(2-oxo-4-(trifluoromethyl)pyridin-1(2H)-yl)pentanamido)propanoic acid Step 1: (3S)-methyl 3-(5-(2,6-dimethylphenyl)pyridin-3-yl)-3-(4-methyl-2-(2-oxo-4-(trifluoromethyl)pyridin-1(2H)-yl)pentanamido)propanoate

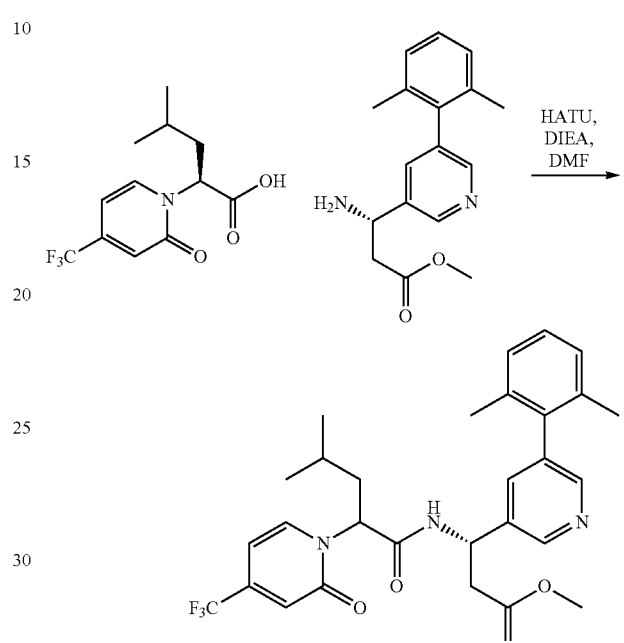

A mixture of (S)-4-methyl-2-(2-oxo-4-(trifluoromethyl)pyridin-1(2H)-yl)pentanoic acid (150 mg, 0.54 mmol), (S)-methyl 3-amino-3-(5-(2,6-dimethylphenyl)pyridin-3-yl)propanoate (169 mg, 0.59 mmol), HATU (246 mg, 0.65 mmol) and DIEA (0.2 mL) in DMF (5 mL) was stirred at room temperature overnight. The mixture was concentrated in vacuo and the residue was purified by silica gel column (pet. ether:EtOAc 1:1) to give the desired product (3 S)-methyl 3-(5-(2,6-dimethylphenyl)pyridin-3-yl)-3-(4-methyl-2-(2-oxo-4-(trifluoromethyl)pyridin-1(2H)-yl)pentanamido)propanoate as a yellow solid (200 mg). Yield 68% (100% purity, UV=214 nm, ESI 544 (M+H)+).

Step 2: (3S)-3-(5-(2,6-dimethylphenyl)pyridin-3-yl)-3-(4-methyl-2-(2-oxo-4-(trifluoromethyl)pyridin-1(2H)-yl)pentanamido)propanoic acid

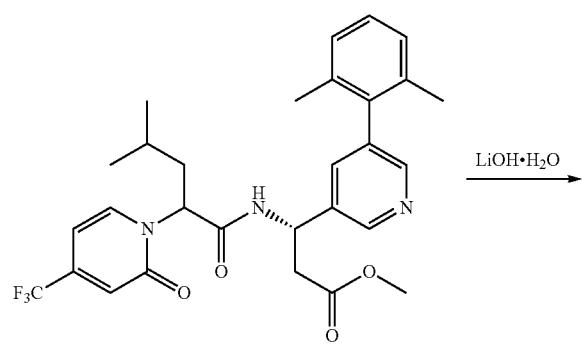

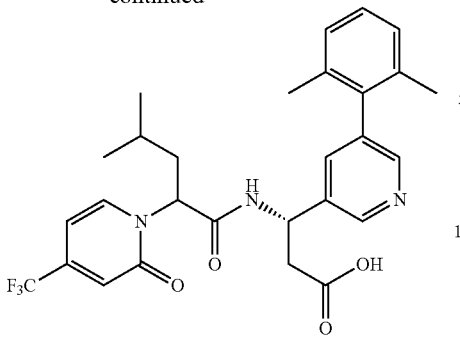

(3S)-methyl 3-(5-(2,6-dimethylphenyl)pyridin-3-yl)-3-(4-methyl-2-(2-oxo-4-(trifluoromethyl)pyridin-1(2H)-yl)pentanamido)propanoate (200 mg, 0.37 mmol) was treated with LiOH—H$_2$O (74 mg, 1.84 mmol) in MeOH (3 mL) and H$_2$O (1 mL) at room temperature for 2 hours. The reaction mixture was acidified to pH 4~5 with 1 N HCl. The solvent was removed in vacuo and the residue was purified by preparatory HPLC A (30-60% MeCN) to give the (3S)-3-(5-(2,6-dimethylphenyl)pyridin-3-yl)-3-(4-methyl-2-(2-oxo-4-(trifluoromethyl)pyridin-1(2H)-yl)pentanamido)propanoic acid as white solid (130 mg, 67% Yield). The diastereomeric mixtures were separated by preparatory chiral SFC A to give the compounds C1 (40 mg) and C2 (20 mg) as white solids.

Compound C1 LC/MS B: 100% purity, UV=214 nm, Rt=2.01 min, ESI 530 (M+H)$^+$.

1H-NMR (500 MHz, MeOD) δ 8.59 (d, J=2.0 Hz, 1H), 8.26 (d, J=1.7 Hz, 1H), 7.99 (d, J=7.3 Hz, 1H), 7.68 (t, J=1.9 Hz, 1H), 7.25-7.19 (m, 1H), 7.16 (d, J=7.6 Hz, 2H), 6.83 (s, 1H), 6.57 (dd, J=7.7, 2.0 Hz, 1H), 5.78-5.68 (m, 1H), 5.39 (t, J=7.4 Hz, 1H), 2.91-2.80 (m, 2H), 2.02 (s, 6H), 1.90-1.80 (m, 2H), 1.38-1.33 (m, 1H), 0.98-0.88 (m, 6H).

Chiral SFC A (15% MeOH): ee 100%, Rt=2.49 min

Compound C2 LC/MS B: 100% purity, UV=214 nm, Rt=1.98 min, ESI 530 (M+H)$^+$. 1H-NMR (500 MHz, MeOD) δ 8.55 (d, J=2.0 Hz, 1H), 8.17 (d, J=1.8 Hz, 1H), 7.95 (d, J=7.3 Hz, 1H), 7.59 (s, 1H), 7.19 (t, J=7.5 Hz, 1H), 7.16-7.12 (m, 2H), 6.71 (s, 1H), 6.53 (dd, J=7.3, 2.0 Hz, 1H), 5.72 (dd, J=9.2, 6.9 Hz, 1H), 5.41 (t, J=7.0 Hz, 1H), 2.85 (t, J=15.6 Hz, 2H), 2.04-1.92 (m, 5H), 1.85 (s, 3H), 1.55-1.42 (m, 1H), 0.98-0.86 (m, 6H). Chiral SFC A (15% MeOH): ee 98%, Rt=3.59 min Preparation of Compounds D1 and D2

Step 1: (3S)-methyl 3-(5-(2,6-dimethylphenyl)pyridin-3-yl)-3-(4-methyl-2-(2-oxo-4-(trifluoromethyl)pyridin-1(2H)-yl)pentanamido)propanoate

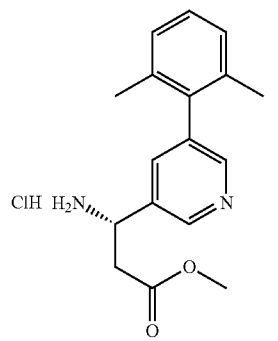

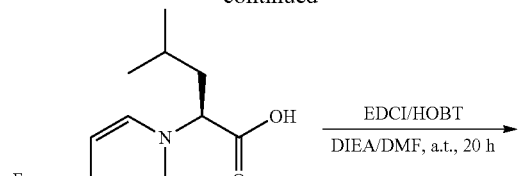

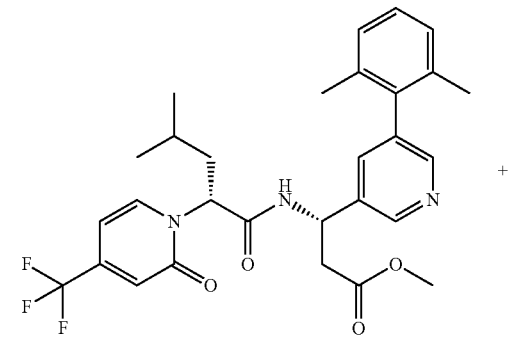

+

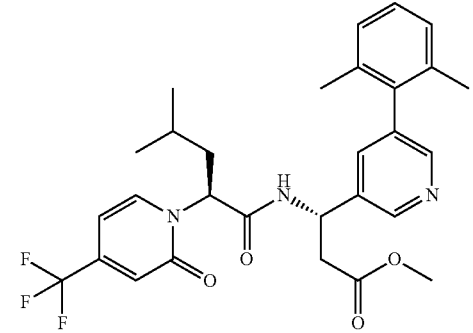

A mixture of (S)-methyl 3-amino-3-(5-(2,6-dimethylphenyl)pyridin-3-yl)propanoate hydrochloride (100 mg, 0.27 mmol), (S)-4-methyl-2-(2-oxo-4-(trifluoromethyl)pyridin-1(2H)-yl)pentanoic acid (97 mg, 0.35 mmol), 1-(3-dimethylaminopropyl)-3-ethylcarbodiimide hydrochloride (77 mg, 0.40 mmol), 1-Hydroxybenzotriazole (40 mg, 0.30 mmol) and N,N-diisopropylethylamine (0.22 mL, 1.35 mmol) in DMF (5 mL) was stirred at room temperature for 16 h. The mixture was concentrated in vacuo and the residue was purified by preparatory TLC (pet. ether:EtOAc 1:2) to give the desired products (S)-methyl 3-(5-(2,6-dimethylphenyl)pyridin-3-yl)-3-((R)-4-methyl-2-(2-oxo-4-(trifluoromethyl)pyridin-1(2H)-yl)pentanamido)propanoate as a colorless oil (54 mg, Yield 23%) (R$_f$=0.75, 76% purity, UV=254 nm, ESI 544 (M+H)$^+$) and (S)-methyl 3-(5-(2,6-dimethylphenyl)pyridin-3-yl)-3-((S)-4-methyl-2-(2-oxo-4-(trifluoromethyl)pyridin-1(2H)-yl)pentanamido)propanoate as a colorless oil (31 mg, Yield 17%) (R$^f$=0.71, 86% purity, UV=254 nm, ESI 544 (M+H)$^+$).

Step 2: (3S)-methyl 3-(5-(2,6-dimethylphenyl)pyridin-3-yl)-3-((2R)-4-methyl-2-(2-oxo-4-(trifluoromethyl)piperidin-1-yl)pentanamido)propanoate

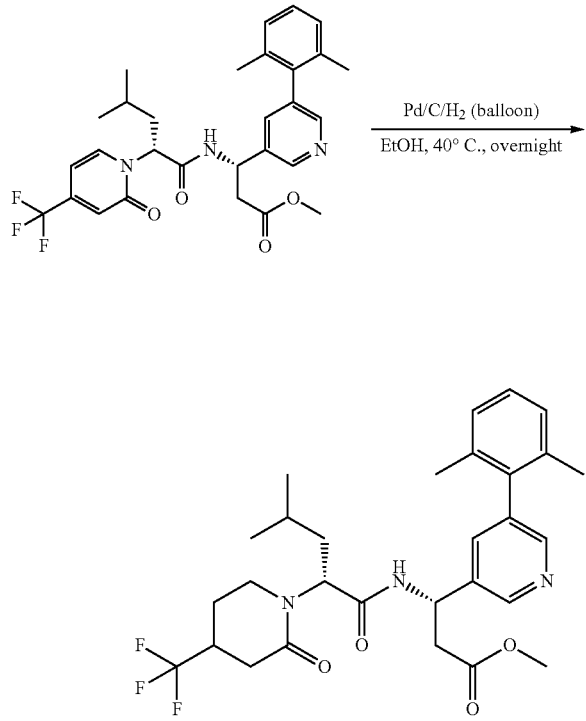 [SMILES: COC(=O)C[C@H](NC(=O)[C@@H](CC(C)C)n1ccc(C(F)(F)F)cc1=O)c1cncc(-c2c(C)cccc2C)c1 ; "EtOH, 40° C., overnight" ; "Pd/C/H2 (balloon)" ; COC(=O)C[C@H](NC(=O)[C@@H](CC(C)C)N1CCC(C(F)(F)F)CC1=O)c1cncc(-c2c(C)cccc2C)c1]

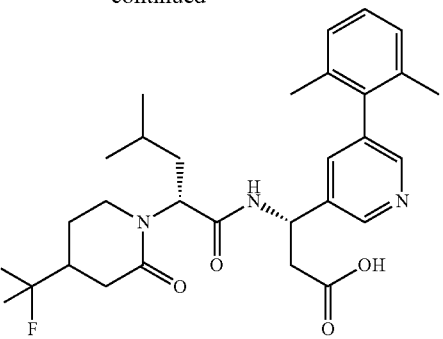

A mixture of (S)-methyl 3-(5-(2,6-dimethylphenyl)pyridin-3-yl)-3-((R)-4-methyl-2-(2-oxo-4-(trifluoromethyl)pyridin-1(2H)-yl)pentanamido)propanoate (54 mg, 0.099 mmol) and palladium on activated carbon (11 mg, 10%, 0.0099 mmol) in anhydrous ethanol (15 mL) was stirred at 40° C. under hydrogen atmosphere overnight. The mixture was filtered and the filtrate was concentrated in vacuo to give the desired product (3S)-methyl 3-(5-(2,6-dimethylphenyl)pyridin-3-yl)-3-((2R)-4-methyl-2-(2-oxo-4-(trifluoromethyl)piperidin-1-yl)pentanamido)propanoate as a colorless oil (63 mg). Yield 95% (92% purity, UV=254 nm, ESI 548 (M+H)$^+$).

Step 3: (3S)-3-(5-(2,6-dimethylphenyl)pyridin-3-yl)-3-((2R)-4-methyl-2-(2-oxo-4-(trifluoromethyl)piperidin-1-yl)pentanamido)propanoic acid

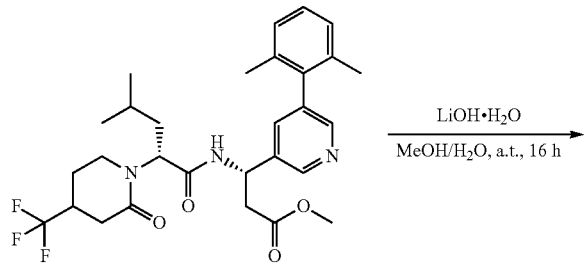

(3S)-methyl 3-(5-(2,6-dimethylphenyl)pyridin-3-yl)-3-((2R)-4-methyl-2-(2-oxo-4-(trifluoromethyl)piperidin-1-yl)pentanamido)propanoate (67 mg, 0.12 mmol) was treated with LiOH—H$_2$O (51 mg, 1.22 mmol) in methanol (9.6 mL) and water (0.61 mL) at room temperature for 2 hours. The reaction was acidified with 1 N hydrochloric acid to pH=3. The solvent was removed in vacuo and the residue was purified by preparatory HPLC B (30-65% MeCN) to give the desired compounds D1 (9 mg) and D2 (4 mg) as white solids.

Compound D1 LC/MS E: 98% purity, UV=214 nm, Rt=1.74 min, ESI 534 (M+H)$^+$, 1H-NMR (500 MHz, MeOD) δ: 8.55 (d, J=1.5 Hz, 1H), 8.23 (d, J=1.5 Hz, 1H), 7.64 (t, J=1.8 Hz, 1H), 7.20 (t, J=7.5 Hz, 1H), 7.14 (d, J=7.5 Hz, 2H), 5.40 (t, J=7.0 Hz, 1H), 5.23 (dd, J=9.0, 6.5 Hz, 1H), 3.59-3.55 (m, 1H), 3.33-3.28 (m, 1H), 2.96-2.87 (m, 2H), 2.84-2.79 (m, 1H), 2.66 (ddd, J=17.5, 6.0, 1.5 Hz, 1H), 2.50 (dd, J=17.3, 10.8 Hz, 1H), 2.14-2.11 (m, 1H), 2.00 (d, J=6.0 Hz, 6H), 1.86 (ddd, J=26.0, 12.0, 5.0 Hz, 1H), 1.74-1.68 (m, 1H), 1.63-1.58 (m, 1H), 1.47-1.41 (m, 1H), 0.92 (d, J=6.5 Hz, 3H), 0.89 (d, J=7.0 Hz, 3H).

Compound D2 LC/MS E: 100% purity, UV=214 nm, Rt=1.76 min, ESI 534 (M+H)$^+$, 1H-NMR (500 MHz, MeOD) δ: 8.55 (d, J=2.0 Hz, 1H), 8.23 (d, J=1.5 Hz, 1H), 7.64 (t, J=1.8 Hz, 1H), 7.20 (t, J=7.5 Hz, 1H), 7.14 (d, J=7.5 Hz, 2H), 5.40 (t, J=7.0 Hz, 1H), 5.23 (dd, J=9.0, 6.5 Hz, 1H), 3.46-3.42 (m, 1H), 3.39-3.34 (m, 1H), 2.90-2.85 (m, 3H), 2.71-2.66 (m, 1H), 2.46 (dd, J=17.0, 10.3 Hz, 1H), 2.19-2.15 (m, 1H), 2.00 (d, J=7.5 Hz, 6H), 1.83-1.76 (m, 1H), 1.72-1.66 (m, 1H), 1.61-1.55 (m, 1H), 1.43-1.37 (m, 1H), 0.91 (d, J=6.5 Hz, 3H), 0.87 (d, J=6.5 Hz, 3H).

Preparation of Compound E

Step 1: (3S)-methyl 3-(5-(2,6-dimethylphenyl)pyridin-3-yl)-3-((2S)-4-methyl-2-(2-oxo-4-(trifluoromethyl)piperidin-1-yl)pentanamido)propanoate

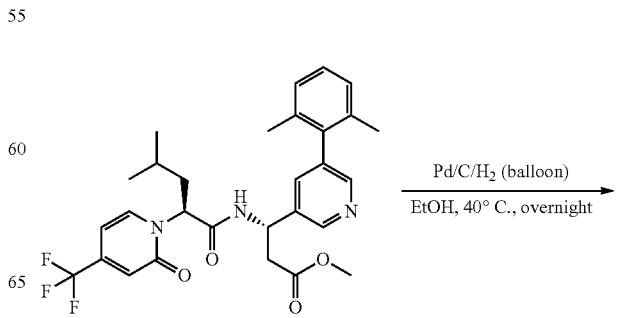

-continued

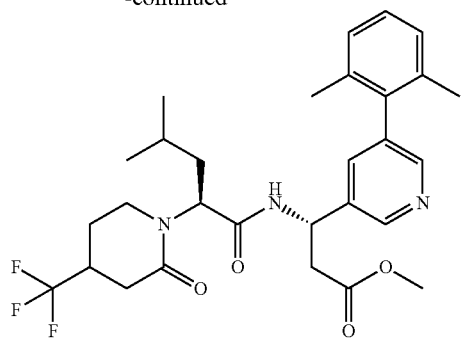

A mixture of (S)-methyl 3-(5-(2,6-dimethylphenyl)pyridin-3-yl)-3-((S)-4-methyl-2-(2-oxo-4-(trifluoromethyl)pyridin-1(2H)-yl)pentanamido)propanoate (31 mg, 0.057 mmol) and palladium on activated carbon (10%, 11 mg, 0.0099 mmol) in anhydrous ethanol (15 mL) was stirred at 40° C. under hydrogen atmosphere overnight. The mixture was filtered and the filtrate was concentrated in vacuo to give the desired product (3S)-methyl 3-(5-(2,6-dimethylphenyl)pyridin-3-yl)-3-((2S)-4-methyl-2-(2-oxo-4-(trifluoromethyl)piperidin-1-yl)pentanamido)propanoate as a colorless oil (23 mg). Yield 74% (92% purity, UV=254 nm, ESI 548 (M+H)⁺).

Step 2: (3S)-3-(5-(2,6-dimethylphenyl)pyridin-3-yl)-3-((2S)-4-methyl-2-(2-oxo-4-(trifluoromethyl)piperidin-1-yl)pentanamido)propanoic acid

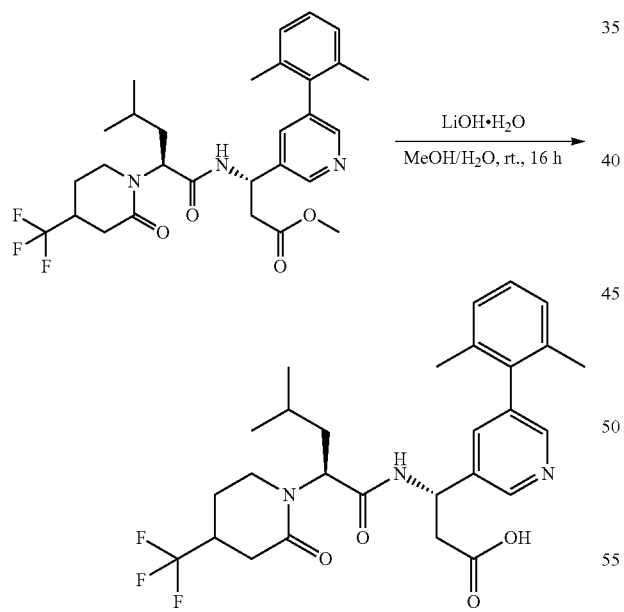

(3 S)-methyl 3-(5-(2,6-dimethylphenyl)pyridin-3-yl)-3-((2R)-4-methyl-2-(2-oxo-4-(trifluoromethyl)piperidin-1-yl)pentanamido)propanoate (23 mg, 0.042 mmol) was treated with LiOH—H₂O (10 mg, 0.25 mmol) in methanol (4 mL) and water (1 mL) at room temperature for 2 hours. The reaction was acidified with 1 N hydrochloric acid to pH=3. The solvent was removed in vacuo and the residue was purified by preparatory HPLC B (30-65% MeCN) to give the desired compound E (2 mg) as a white solid.

Compound E LC/MS E: 98% purity, UV=214 nm, Rt=1.72 min, ESI 534 (M+H)⁺; ¹H

1H-NMR (500 MHz, MeOD) δ: 8.55 (d, J=1.5 Hz, 1H), 8.23 (d, J=1.5 Hz, 1H), 7.64 (t, J=1.8 Hz, 1H), 7.20 (t, J=7.5 Hz, 1H), 7.14 (d, J=7.5 Hz, 2H), 5.40 (t, J=7.0 Hz, 1H), 5.23 (dd, J=9.0, 6.5 Hz, 1H), 3.59-3.55 (m, 1H), 3.33-3.28 (m, 1H), 2.96-2.87 (m, 2H), 2.84-2.79 (m, 1H), 2.66 (ddd, J=17.5, 6.0, 1.5 Hz, 1H), 2.50 (dd, J=17.3, 10.8 Hz, 1H), 2.14-2.11 (m, 1H), 2.00 (d, J=6.0 Hz, 6H), 1.86 (ddd, J₁=26.0, 12.0, 5.0 Hz, 1H), 1.74-1.68 (m, 1H), 1.63-1.58 (m, 1H), 1.47-1.41 (m, 1H), 0.92 (d, J=6.5 Hz, 3H), 0.89 (d, J=7.0 Hz, 3H).

Preparation of Compound F

Step 1: (3S)-methyl 3-(5-(2,6-dimethylphenyl)pyridin-3-yl)-3-(2-(5-methyl-2-oxopyridin-1(2H)-yl)-2-phenylacetamido)propanoate

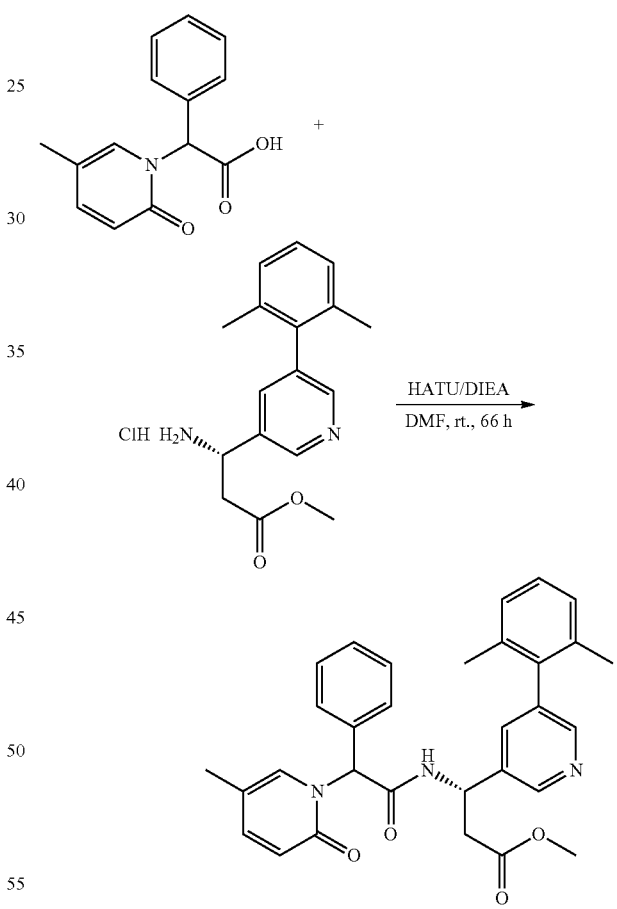

A mixture of 2-(5-methyl-2-oxopyridin-1(2H)-yl)-2-phenylacetic acid (478 mg, 1.96 mmol), (S)-methyl 3-amino-3-(5-(2,6-dimethylphenyl)pyridin-3-yl)propanoate hydrochloride (300 mg, 0.94 mmol), O-(7-Azabenzotriazol-1-yl)-N,N,N',N'-tetramethyluronium hexafluorophosphate (764 mg, 2.01 mmol) and N,N-diisopropylethylamine (0.93 mL, 5.61 mmol) in N,N-dimethylformamide (15 mL) was stirred at room temperature for 66 h. The mixture was concentrated in vacuo and the residue was purified by silica gel column (pet. ether:EtOAc 2:1) to give desired product (3S)-methyl 3-(5-(2,6-dimethylphenyl)pyridin-3-yl)-3-(2-(5-methyl-2-oxopyridin-1 (2H)-yl)-2-phenylacetamido)propanoate as a yellow solid (200 mg). Yield 42% (100% purity, UV=214 nm, ESI 510 (M+H)⁺).

Step 2: (S)-3-(5-(2,6-dimethylphenyl)pyridin-3-yl)-3-((R)-2-(5-methyl-2-oxopyridin-1(2H)-yl)-2-phenylacetamido)propanoic acid & (S)-3-(5-(2,6-dimethylphenyl)pyridin-3-yl)-3-((S)-2-(5-methyl-2-oxopyridin-1(2H)-yl)-2-phenylacetamido)propanoic acid in vacuo and the residue was purified by preparatory HPLC A (30-65% MeCN) to give the desired products (S)-3-(5-(2,6-dimethylphenyl)pyridin-3-yl)-3-((S)-2-(5-methyl-2-oxopyridin-1(2H)-yl)-2-phenylacetamido)propanoic acid (86 mg, 43% Yield) (100% purity, UV=254 nm, ESI 496 (M+H)⁺) and (S)-3-(5-(2,6-dimethylphenyl)pyridin-3-yl)-3-((R)-2-(5-methyl-2-oxopyridin-1(2H)-yl)-2-phenylacetamido)propanoic acid (81 mg, 41% Yield) (100% purity, UV=254 nm, ESI 496 (M+H)⁺) as white solids.

Step 3: (3S)-3-(5-(2,6-dimethylphenyl)pyridin-3-yl)-3-((2R)-2-(5-methyl-2-oxopiperidin-1-yl)-2-phenylacetamido)propanoic acid

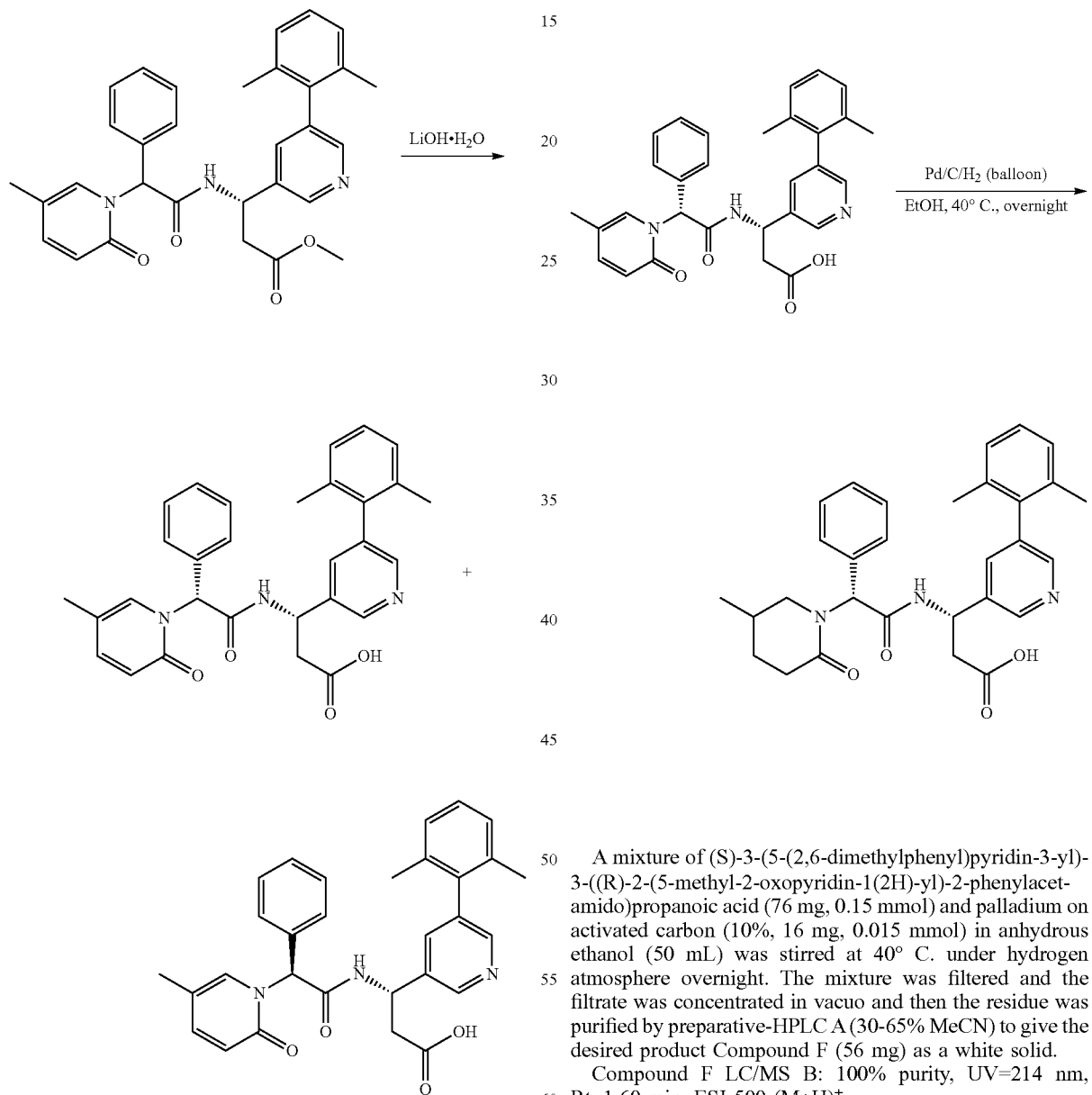

(3 S)-methyl 3-(5-(2,6-dimethylphenyl)pyridin-3-yl)-3-(2-(5-methyl-2-oxopyridin-1 (2H)-yl)-2-phenylacetamido) propanoate (200 mg, 0.39 mmol) was treated with LiOH—H₂O (394 mg, 9.4 mmol) in methanol (10 mL) and water (1 mL) at room temperature for 16 hours. The reaction was acidified with 1 N HCl to pH=3. The solvent was removed A mixture of (S)-3-(5-(2,6-dimethylphenyl)pyridin-3-yl)-3-((R)-2-(5-methyl-2-oxopyridin-1(2H)-yl)-2-phenylacetamido)propanoic acid (76 mg, 0.15 mmol) and palladium on activated carbon (10%, 16 mg, 0.015 mmol) in anhydrous ethanol (50 mL) was stirred at 40° C. under hydrogen atmosphere overnight. The mixture was filtered and the filtrate was concentrated in vacuo and then the residue was purified by preparative-HPLC A (30-65% MeCN) to give the desired product Compound F (56 mg) as a white solid.

Compound F LC/MS B: 100% purity, UV=214 nm, Rt=1.60 min, ESI 500 (M+H)⁺.

1H-NMR (500 MHz, MeOD) δ 8.53 (dd, J=5.0, 2.0 Hz, 1H), 8.22 (t, J=2.3 Hz, 1H), 7.56 (dt, J=11.0, 2.0 Hz, 1H), 7.29-7.23 (m, 3H), 7.19 (t, J=7.5 Hz, 1H), 7.14-7.11 (m, 4H), 6.28 (d, J=30.0 Hz, 1H), 5.50-5.46 (m, 1H), 3.05 (dd, J=12.0, 11.0 Hz, 1H), 2.94-2.78 (m, 3H), 2.54-2.41 (m, 2H), 1.97 (t, J=2.8 Hz, 6H), 1.82-1.70 (m, 2H), 1.57-1.31 (m, 1H), 0.85 (dd, J=21.3, 6.8 Hz, 3H).

115

Preparation of Compound G

Step 1: (3S)-3-(5-(2,6-dimethylphenyl)pyridin-3-yl)-3-(2S)-2-(5-methyl-2-oxopiperidin-1-yl)-2-phenylacetamido)propanoic acid

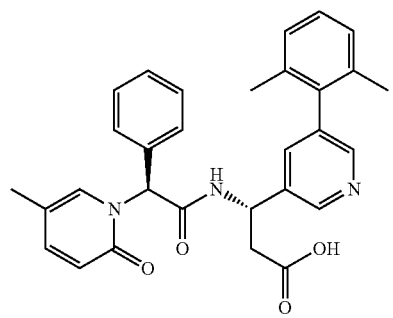

A mixture of (S)-3-(5-(2,6-dimethylphenyl)pyridin-3-yl)-3-((S)-2-(5-methyl-2-oxopyridin-1(2H)-yl)-2-phenylacetamido)propanoic acid (81 mg, 0.16 mmol) and palladium on activated carbon (17 mg, 10%, 0.016 mmol) in anhydrous ethanol (50 mL) was stirred at 40° C. under hydrogen atmosphere for 16 h. The mixture was filtered and the filtrate was concentrated in vacuo and then the residue was purified by preparative-HPLC A (30-65% MeCN) to give the desired compound G (41 mg) as a white solid.

Compound G LC/MS B: 100% purity, UV=214 nm, Rt=1.57 min, ESI 500 (M+H)$^+$.

1H-NMR (500 MHz, MeOD) δ 8.60 (d, J=1.5 Hz, 1H), 8.22 (d, J=1.5 Hz, 1H), 7.67 (t, J=2.3 Hz, 1H), 7.42-7.36 (m, 3H), 7.32 (t, J=7.5 Hz, 2H), 7.19 (dd, J=8.8, 1.5 Hz, 1H), 7.13 (d, J=7.5 Hz, 2H), 6.32 (d, J=14.5 Hz, 1H), 5.52 (t, J=7.3 Hz, 1H), 3.02 (t, J=11.3 Hz, 1H), 2.86-2.83 (m, 3H), 2.41 (q, J=4.5 Hz, 2H), 2.00 (d, J=4.5 Hz, 6H), 1.78-1.69 (m, 2H), 1.48-1.31 (m, 1H), 0.83 (dd, J=16.8, 6.8 Hz, 3H).

116

Preparation of Compounds H1 and H2

Step 1: Methyl 3-(2',6'-dimethylbiphenyl-3-yl)-3-(3-methoxy-2-(4-methyl-2-oxopyridin-1(2H)-yl)propanamido)propanoate

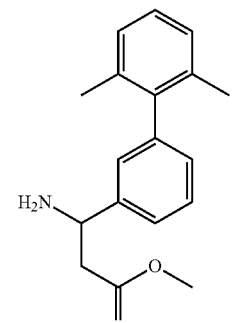

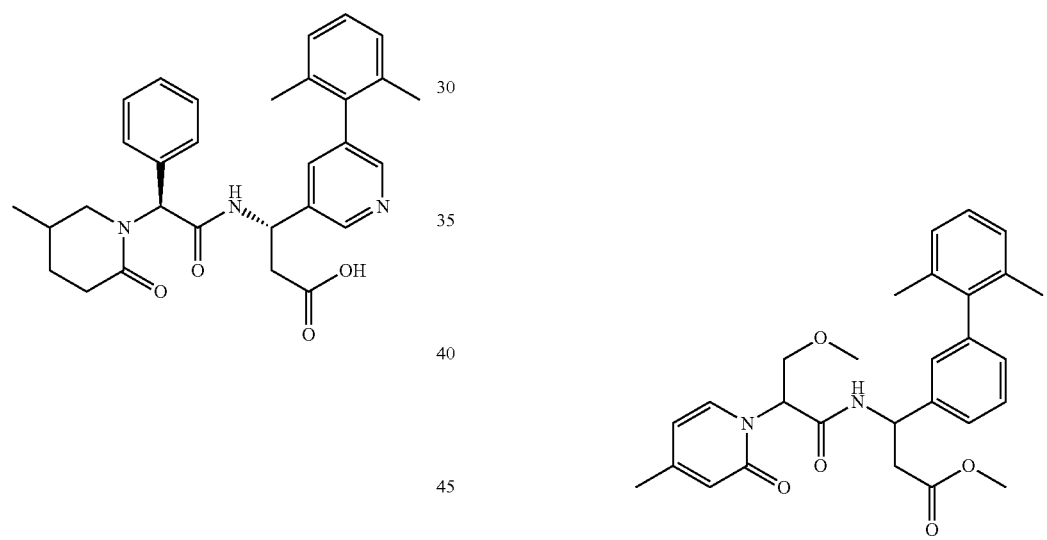

A mixture of methyl 3-methoxy-2-(4-methyl-2-oxopyridin-1(2H)-yl)propanoic acid (95 mg, 0.45 mmol), methyl 3-amino-3-(2',6'-dimethylbiphenyl-3-yl)propanoate (130 mg, 0.45 mmol), HOBT (91 mg, 0.675 mmol), EDCI (130 mg, 0.675 mmol) and DIEA (145 mg, 1.13 mmol) in DMF (5 mL) was stirred at room temperature for 18 hr. The solvent was removed in vacuo and the residue was purified by silica gel column (pet. ether:EtOAc 3:1) to give product Methyl 3-(2',6'-dimethylbiphenyl-3-yl)-3-(3-methoxy-2-(4-methyl-2-oxopyridin-1(2H)-yl)propanamido)propanoate as a yellow solid (150 mg). Yield 70% (78% purity, UV=254 nm, ESI 477 (M+H)$^+$).

117

Step 2: 3-(2',6'-dimethylbiphenyl-3-yl)-3-(3-methoxy-2-(4-methyl-2-oxopyridin-1(2H)-yl)propanamido)propanoic acid

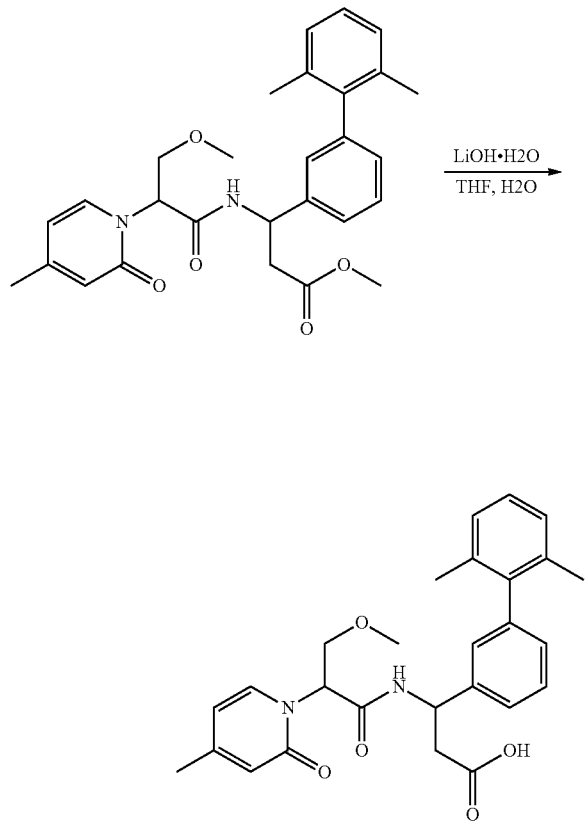

Methyl 3-(2',6'-dimethylbiphenyl-3-yl)-3-(3-methoxy-2-(4-methyl-2-oxopyridin-1(2H)-yl)propanamido)propanoate (150 mg, 0.32 mmol) was treated with LiOH—H$_2$O (66 mg, 1.6 mmol) in THF (8 mL) and H$_2$O (1 mL) at room temperature for 2 hours. Solvent was removed in vacuo and the residue was purified by Prep-HPLC B (30-70% MeCN) to give the compounds H1 (10 mg) and H2 (30 mg) as white solids.

Compound H1 LC/MS A: 100% purity, UV=214 nm, Rt=1.64 min, ESI 463 (M+H)$^+$.

$^1$H NMR (500 MHz, MeOD) δ 7.60 (d, J=7.1 Hz, 1H), 7.39 (t, J=7.6 Hz, 1H), 7.31 (d, J=7.8 Hz, 1H), 7.13-7.09 (m, 1H), 7.05 (d, J=7.8 Hz, 3H), 6.99 (d, J=7.5 Hz, 1H), 6.30 (s, 1H), 6.20 (dd, J=7.2, 1.8 Hz, 1H), 5.71 (dd, J=7.6, 5.1 Hz, 1H), 5.38 (t, J=6.9 Hz, 1H), 3.92 (ddd, J=16.0, 10.8, 6.4 Hz, 2H), 3.34 (s, 3H), 2.86 (d, J=7.1 Hz, 2H), 2.18 (s, 3H), 1.97 (s, 3H), 1.93 (s, 3H).

Compound H2 LC/MS A: 98% purity, UV=214 nm, Rt=1.66 min, ESI 463 (M+H)$^+$. $^1$H NMR (500 MHz, MeOD) δ 7.63 (d, J=7.1 Hz, 1H), 7.41 (t, J=7.6 Hz, 1H), 7.36 (d, J=7.9 Hz, 1H), 7.15 (s, 1H), 7.10 (dt, J=16.6, 6.2 Hz, 3H), 7.01 (d, J=7.4 Hz, 1H), 6.35 (s, 1H), 6.24 (dd, J=7.2, 1.9 Hz, 1H), 5.73 (dd, J=6.7, 4.9 Hz, 1H), 5.37 (t, J=6.8 Hz, 1H), 3.92 (dd, J=10.6, 6.8 Hz, 1H), 3.82-3.79 (m, 1H), 3.20 (s, 3H), 2.83-2.78 (m, 2H), 2.23-2.19 (m, 3H), 1.99 (d, J=3.5 Hz, 6H).

118

Preparation of Compound I

Step 1: (S)-methyl 3-((S)-4-methyl-2-(4-oxoquinazolin-3(4H)-yl)pentanamido)-3-(2'-methylbiphenyl-3-yl)propanoate

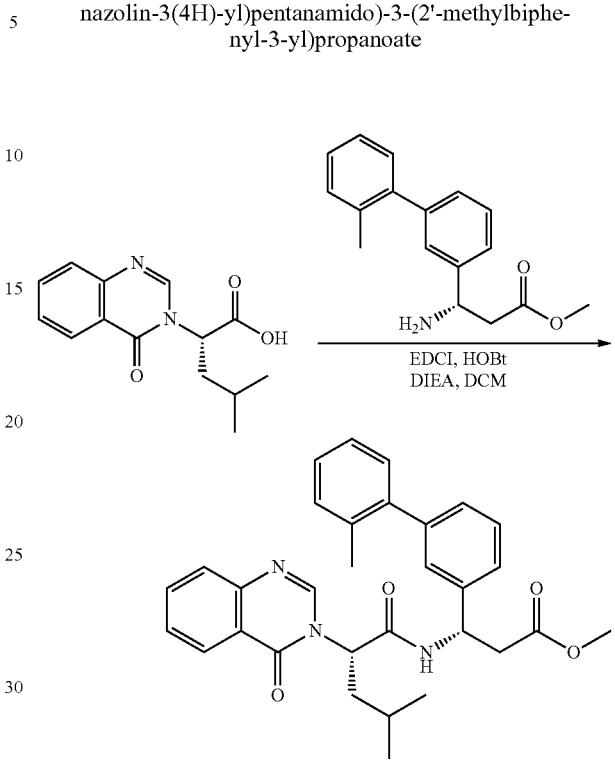

A mixture of (S)-4-methyl-2-(4-oxoquinazolin-3(4H)-yl)pentanoic (100 mg, 0.38 mmol), (S)-methyl 3-amino-3-(2'-methylbiphenyl-3-yl)propanoate (104 mg, 0.38 mmol), EDCI (145 mg, 0.76 mmol), HOBt (103 mg, 0.76 mmol) and DIEA (129 mg, 1.0 mmol) in DCM (5 mL) was stirred at room temperature for 16 hours. The solvent was removed in vacuo and the residue was purified by silica gel column (petroleum ether:EtOAc=1:1) to provide the desired product (S)-methyl 3-((S)-4-methyl-2-(4-oxoquinazolin-3(4H)-yl)pentanamido)-3-(2'-methylbiphenyl-3-yl)propanoate as a brown oil (75 mg). Yield 39% (85% purity, UV=254 nm, ESI 512.1 (M+H)$^+$).

Step 2: (S)-3-((S)-4-methyl-2-(4-oxoquinazolin-3(4H)-yl)pentanamido)-3-(2'-methylbiphenyl-3-yl)propanoic acid

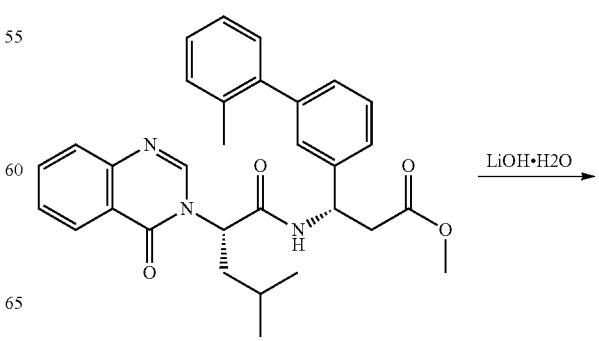

-continued

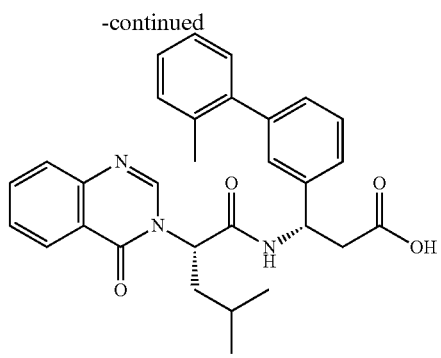

(S)-methyl 3-((S)-4-methyl-2-(4-oxoquinazolin-3(4H)-yl)pentanamido)-3-(2'-methylbiphenyl-3-yl)propanoate (75 mg, 0.15 mmol) was treated with LiOH—H₂O (25.2 mg, 0.6 mmol) in MeOH (3 mL) and H₂O (1 mL) at room temperature for 2 hours. The solution was adjusted with 1 N HCl to pH=5~6. The solvent was removed in vacuo, and the residue was purified by Preparatory HPLC A (30~70% MeCN) to give the desired product (S)-3-((S)-4-methyl-2-(4-oxoquinazolin-3(4H)-yl)pentanamido)-3-(2'-methylbiphenyl-3-yl)propanoic acid as a white solid (30 mg)

Compound I LC/MS A: 100% purity, UV=214 nm, Rt=1.69 min, ESI 498.1 (M+H)⁺.

¹H-NMR (500 MHz, MeOD) δ 8.45 (s, 1H), 8.28-8.26 (m, 1H), 7.88-7.86 (m, 1H), 7.72 (d, J=8.0 Hz, 1H), 7.61-7.57 (m, 1H), 7.43 (t, J=15.5 Hz, 1H), 7.37 (d, J=7.5 Hz, 1H), 7.34 (s, 1H), 5.29-7.19 (m, 5H), 5.74 (m, 1H), 5.77-5.74 (m, 1H), 5.41 (t, J=15 Hz, 1H), 2.93-2.83 (m, 2H), 2.26 (s, 3H), 2.02-1.92 (m, 2H), 1.47-1.41 (m, 1H), 0.95-0.91 (m, 6H)

Preparation of Compound J1

Step 1: (S)-methyl 3-((R)-2-hydroxy-4-methylpentanamido)-3-(2'-methylbiphenyl-3-yl)propanoate

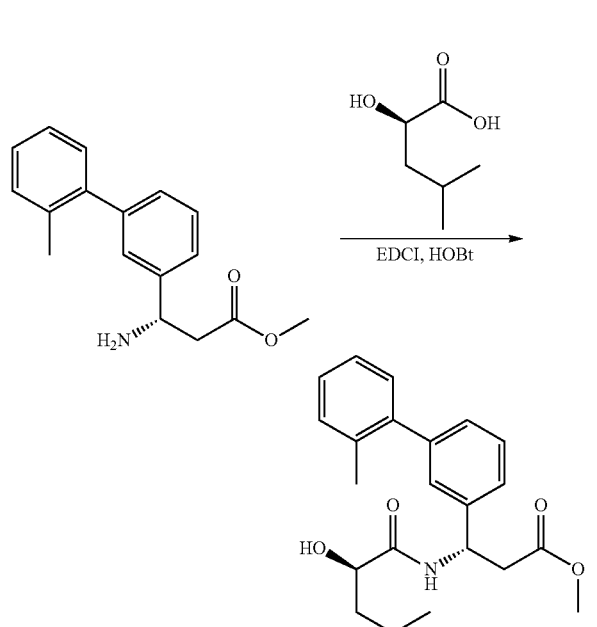

A mixture of (S)-methyl 3-amino-3-(2'-methylbiphenyl-3-yl)propanoate (250 mg, 0.93 mmol), (R)-2-hydroxy-4-methylpentanoic acid (123 mg, 0.93 mmol), EDCI (382 mg, 2.0 mmol), HOBt (270 mg, 2.0 mmol) and DIPEA (258 mg, 2.0 mmol) in DCM (5 mL) was stirred at room temperature for 16 hours. The solvent was removed in vacuo and the residue was purified by silica gel column (petroleum ether: EtOAc=2:1) to provide the desired product (S)-methyl 3-((R)-2-hydroxy-4-methylpentanamido)-3-(2'-methylbiphenyl-3-yl)propanoate as a colorless oil (160 mg). Yield 45% (97% purity, UV=254 nm, ESI 384.1 (M+H)⁺).

Step 2: (S)-methyl 3-((R)-4-methyl-2-(methylsulfonyloxy)pentanamido)-3-(2'-methylbiphenyl-3-yl)propanoate

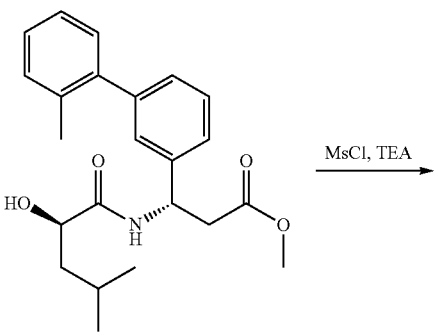

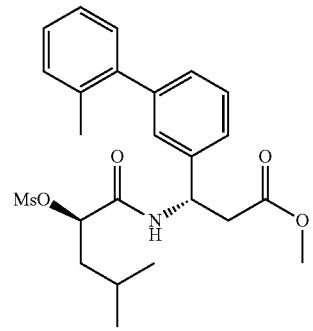

To a solution of (S)-methyl 3-((R)-2-hydroxy-4-methylpentanamido)-3-(2'-methylbiphenyl-3-yl)propanoate (130 mg, 0.34 mmol) in DCM (10 mL) was added TEA (101 mg, 1.0 mmol)) and methanesulfonyl chloride (46 mg, 0.4 mmol) dropwise and stirred at room temperature for 3 h. Water (10 mL) was added, and the solution was extracted with DCM (10 mL×3). The combined organic phases were concentrated under reduced pressure to give the crude product (S)-methyl 3-((R)-4-methyl-2-(methylsulfonyloxy)pentanamido)-3-(2'-methylbiphenyl-3-yl)propanoate as a colorless oil (323 mg). Yield 62% (100% purity, UV=254 nm, ESI 462.1 (M+H)⁺). The crude product was used for the next step directly.

Step 3: methyl (3S)-3-(4-methyl-2-(2-oxopyridin-1 (2H)-yl)pentanamido)-3-(2'-methyl-[1,1'-biphenyl]-3-yl)propanoate

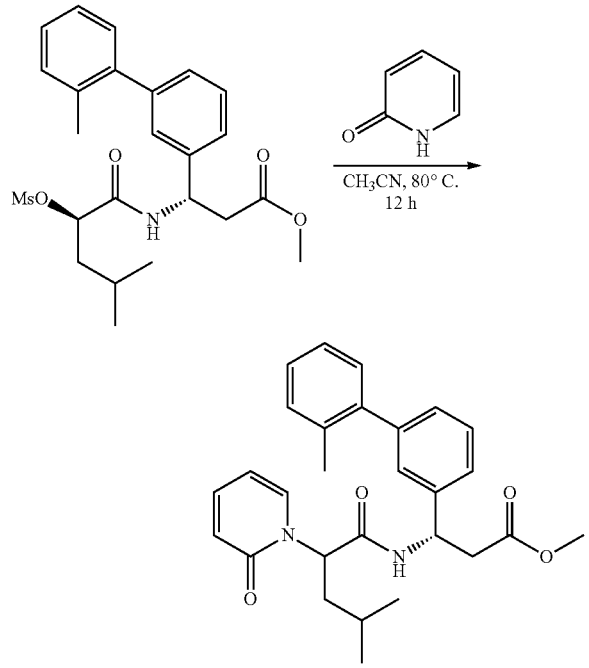

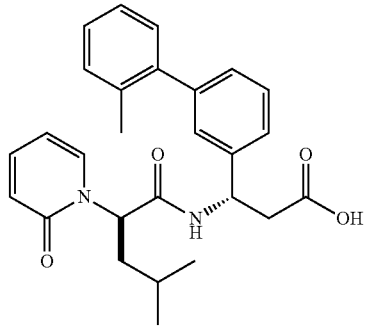

Compound J1a (30 mg, 0.065 mmol) was treated with LiOH—H$_2$O (25.2 mg, 0.6 mmol) in MeOH (3 mL) and H$_2$O (1 mL) at room temperature for 2 hours. The solution was adjusted with 1 N HCl to pH=5~6. The solvent was removed in vacuo, and the residue was purified by preparatory HPLC A (30~70% MeCN) to give the desired product Compound J1 as a white solid (20 mg).

Compound J1 LC/MS A: 100% purity, UV=214 nm, Rt=1.62 min, ESI 447.1 (M+H)$^+$.

$^1$H NMR (500 MHz, MeOD) δ 7.76 (m, J=7.0, 1.7 Hz, 1H), 7.51 (m, 1H), 7.42 (t, J=7.6 Hz, 1H), 7.37 (d, J=7.8 Hz, 1H), 7.32 (s, 1H), 7.24-7.18 (m, 5H), 6.56 (d, J=9.2 Hz, 1H), 6.42 (t, J=6.2 Hz, 1H), 5.78-5.75 (m, 1H), 5.37 (t, J=7.3 Hz, 1H), 2.90-2.79 (m, 2H), 2.26 (s, 3H), 1.92-1.76 (m, 2H), 1.44-1.23 (m, 1H), 0.91-089 (m, 6H).

To a solution of (S)-methyl 3-((R)-4-methyl-2-(methylsulfonyloxy)pentanamido)-3-(2'-methylbiphenyl-3-yl)propanoate (130 mg crude) in MeCN (10 mL) was added K$_2$CO$_3$ (69 m g, 0.5 mmol) and pyridin-2(1H)-one (38 mg, 0.4 mmol). The mixture was stirred at 80° C. for 16 hours and filtered. The filtrate was concentrated under reduced pressure, and the residue was purified by Preparatory HPLC A (40~70% MeCN) to give the compounds J1a (30 mg) and J1b (40 mg) as white solids.

Compound J1a: (100% purity, UV=254 nm, ESI 461.1 (M+H)$^+$).

Compound J1b: (100% purity, UV=254 nm, ESI 461.1 (M+H)$^+$).

Step 4: Compound J1

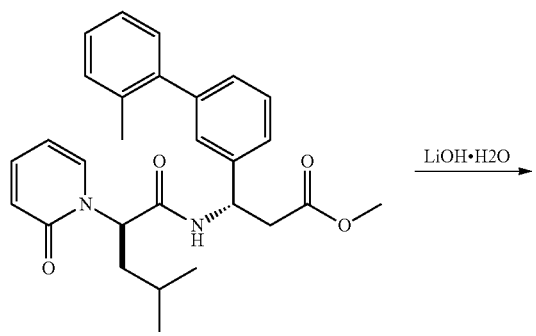

Step 5: Compound J2

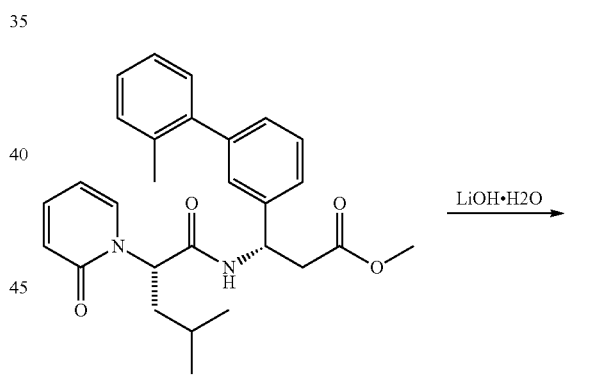

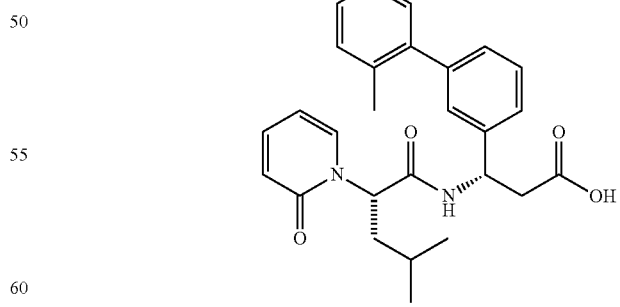

Compound J2a (40 mg, 0.087 mmol) was treated with LiOH—H$_2$O (25.2 mg, 0.6 mmol) in MeOH (3 mL) and H$_2$O (1 mL) at room temperature for 2 hours. The solution was adjusted with 1 N HCl to pH=5~6. The solvent was removed in vacuo, and the residue was purified by preparatory HPLC A (30~70% MeCN) to give the desired product Compound J2 as a white solid (7 mg).

Compound J2 LC/MS A: 100% purity, UV=214 nm, Rt=1.66 min, ESI 447.1 (M+H)+.

$^1$H NMR (500 MHz, MeOD) δ 7.83-7.68 (m, 1H), 7.63-7.55 (m, 1H), 7.38 (s, 1H), 7.31-7.09 (m, 6H), 7.08-6.66 (m, 3H), 5.41 (t, J=6.7 Hz, 1H), 5.33-5.25 (m, 1H), 2.92-2.72 (m, 2H), 2.20 (s, 1H), 2.13 (s, 2H), 1.99-1.82 (m, 2H), 1.73-1.66 (m, 1H), 1.06-0.87 (m, 6H).

Preparation of Compound K

Step 1: (S)-methyl 3-(2',6'-difluorobiphenyl-3-yl)-3-((S)-4-methyl-2-(4-oxoquinazolin-3(4H)-yl)pentanamido)propanoate

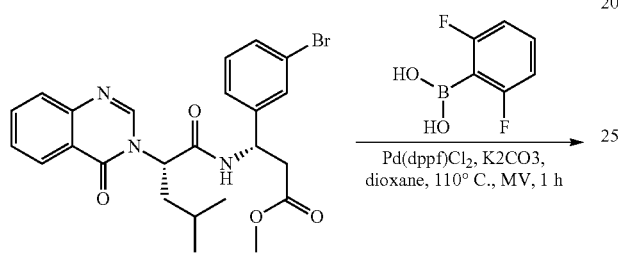

A mixture of (S)-methyl 3-(3-bromophenyl)-3-((S)-4-methyl-2-(4-oxoquinazolin-3(4H)-yl)pentanamido)propanoate (100 mg, 0.2 mmol), 2,6-difluorophenylboronic acid (47 mg, 0.3 mmol), Pd(dppf)Cl$_2$ (15 mg, 0.02 mmol) and K$_2$CO$_3$ (83 mg, 0.6 mmol) in 1,4-dioxane (3 mL) and H$_2$O (0.5 mL) under N$_2$ atmosphere was stirred in a microwave at 110° C. for 1 hour. The reaction was filtered over Celite and the filtrate was concentrated under reduced pressure. The residue was purified by silica gel column (pet. ether:EtOAc 1:3) to give the desired product (S)-methyl (S)-methyl 3-(2',6'-difluorobiphenyl-3-yl)-3-((S)-4-methyl-2-(4-oxoquinazolin-3(4H)-yl)pentanamido)propanoate as a colorless oil (60 mg). Yield 58% (93% purity, UV=214 nm, ESI 534 (M+H)+).

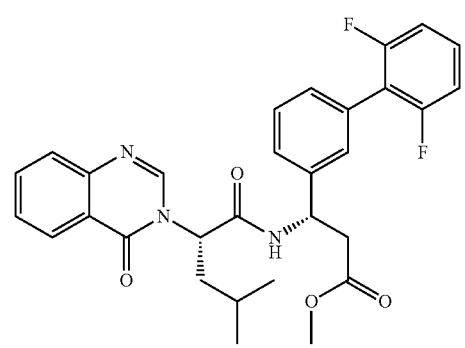

Step 2: (S)-3-(2',6'-difluorobiphenyl-3-yl)-3-((S)-4-methyl-2-(4-oxoquinazolin-3(4H)-yl)pentanamido)propanoic acid

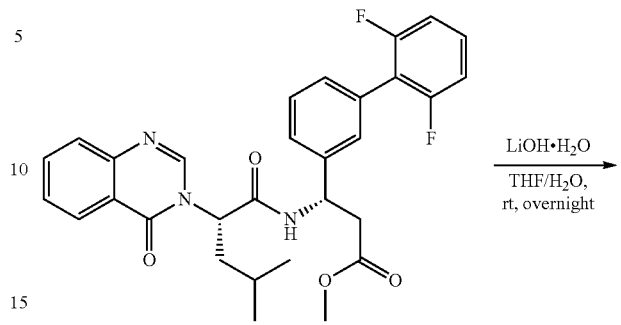

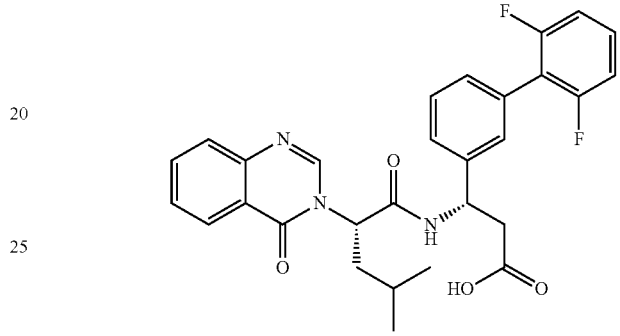

(S)-methyl 3-(2',6'-difluorobiphenyl-3-yl)-3-((S)-4-methyl-2-(4-oxoquinazolin-3 (4H)-yl)pentanamido)propanoate (60 mg, 0.11 mmol) in THF (5 mL) was treated with LiOH—H$_2$O (14 mg, 0.33 mmol) and H$_2$O (0.5 mL) at room temperature for 16 hours. The mixture was acidified with HCl (1 M) until pH=5. The solvent was removed in vacuo and the residue was purified by Preparative-HPLC B (30~70% MeCN) to give the desired product (S)-3-(2',6'-difluorobiphenyl-3-yl)-3-((S)-4-methyl-2-(4-oxoquinazolin-3(4H)-yl)pentanamido)propanoic acid (15 mg) as a white solid.

Compound K LC/MS B: 100% purity, UV=214 nm, Rt=1.87 min, ESI 520 (M+H)+.

$^1$H NMR (500 MHz, MeOD) δ 8.45 (s, 1H), 8.27 (dd, J=8.1, 1.2 Hz, 1H), 7.92-7.82 (m, 1H), 7.72 (d, J=8.1 Hz, 1H), 7.59 (t, J=7.3 Hz, 1H), 7.51-7.33 (m, 5H), 7.17-7.01 (m, 2H), 5.77 (dd, J=10.0, 6.5 Hz, 1H), 5.47-5.39 (m, 1H), 2.92-2.78 (m, 2H), 2.12-1.89 (m, 2H), 1.46-1.41 (m, 1H), 0.95-0.93 (m, 6H).

Preparation of Compound L

Step 1: (S)-methyl 3-(3-bromophenyl)-3-((S)-4-methyl-2-(4-oxoquinazolin-3(4H)-yl)pentanamido)propanoate

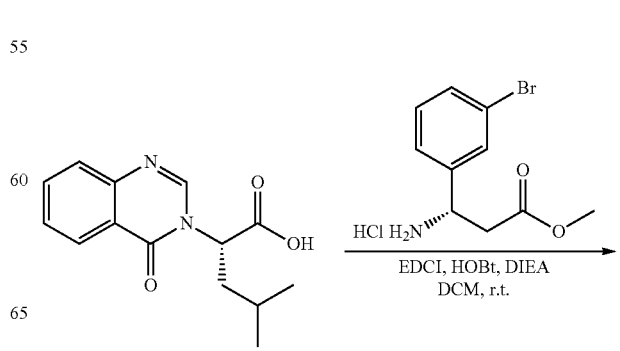

-continued

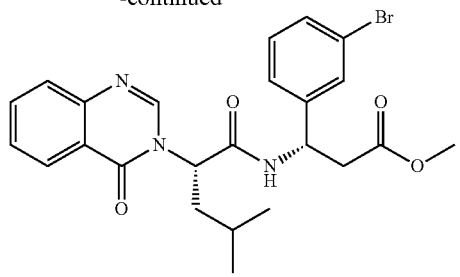

A solution of (S)-4-methyl-2-(4-oxoquinazolin-3(4H)-yl)pentanoic acid (860 mg, 3.3 mmol), (S)-methyl 3-amino-3-(3-bromophenyl)propanoate hydrochloride (980 mg, 3.3 mmol), EDCI (1.15 g, 6 mmol), HOBt (810 mg, 6 mmo) and DIEA (1.29 g, 10 mmol) in DCM (20 mL) was stirred at room temperature for 12 hours. The solution was washed with H$_2$O (10 mL×2) and brine (10 mL). The organic layer was dried over Na$_2$SO$_4$ and filtered. The filtrate was removed in vacuo, and the residue was purified by silica gel column (pet. ether:EtOAc=2:1) to give the desired product (S)-methyl 3-(3-bromophenyl)-3-((S)-4-methyl-2-(4-oxoquinazolin-3(4H)-yl)pentanamido)propanoate as a colorless oil (1.5 g). Yield 62% (97% purity, UV=214 nm, ESI 500.1 (M+H)$^+$).

Step 2: (S)-methyl 3-(2'-cyanobiphenyl-3-yl)-3-((S)-4-methyl-2-(4-oxoquinazolin-3(4H)yl)pentanamido)propanoate

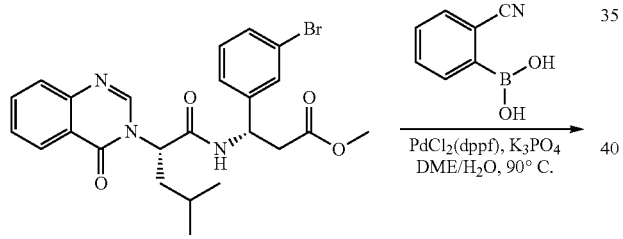

A mixture of (S)-methyl 3-(3-bromophenyl)-3-((S)-4-methyl-2-(4-oxoquinazolin-3(4H)-yl)pentanamido)propanoate (100 mg, 0.2 mmol), 2-cyanophenylboronic acid (59 mg, 0.4 mmol), PdCl$_2$(dppf) (7 mg, 0.01 mmol) and K$_3$PO$_4$ (85 mg, 0.4 mmol) in 5 mL of DME and 0.5 mL of H$_2$O was stirred under N$_2$ atmosphere at 90° C. for 30 mins. The mixture was filtered over Celite. The filtrate was removed in vacuo, and the residue was purified by silica gel column (pet. ether:EtOAc=1:1) to give the desired product (S)-methyl 3-(2'-cyanobiphenyl-3-yl)-3-((S)-4-methyl-2-(4-oxoquinazolin-3(4H)-yl)pentanamido)propanoate as a colorless oil (30 mg), Yield 29% (60% purity, UV=214 nm, ESI 523 (M+H)$^+$).

Step 3: (S)-3-(2'-cyanobiphenyl-3-yl)-3-((S)-4-methyl-2-(4-oxoquinazolin-3(4H)-yl)pentanamido) propanoic acid

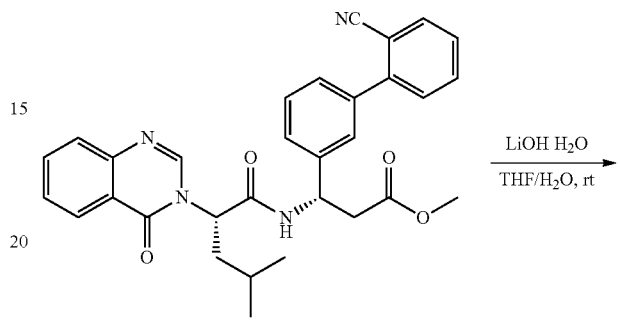

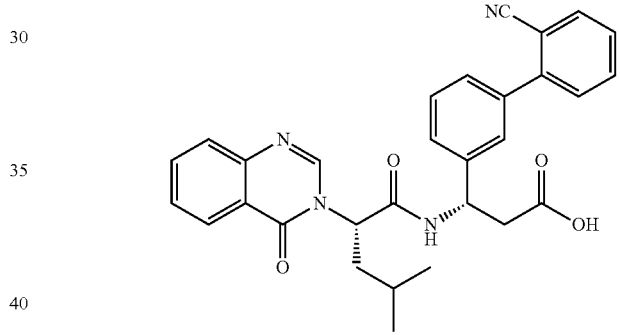

(S)-methyl 3-(2'-cyanobiphenyl-3-yl)-3-((S)-4-methyl-2-(4-oxoquinazolin-3 (4H)-yl)pentanamido)propanoate (30 mg, 0.057 mmol) was treated with LiOH—H$_2$O (7 mg, 0.17 mmol) in 3 mL of THF and 1 mL of H$_2$O at room temperature for 1 h. The solution was adjusted to pH=3~4 with TFA. The solvent was removed in vacuo and the residue was purified by Preparative-HPLC A (33-70% MeCN) to give the desired product (S)-3-(2'-cyanobiphenyl-3-yl)-3-((S)-4-methyl-2-(4-oxoquinazolin-3(4H)-yl)pentanamido)propanoic acid (11 mg) as a white solid.

Compound L LC/MS B: 100% purity, UV=214 nm, Rt=1.81 min, ESI 509.3 (M+H)$^+$.

$^1$H NMR (500 MHz, MeOD) δ 8.44 (s, 1H), 8.26 (d, J=8.0 Hz, 1H), 7.87-7.85 (m, 2H), 7.78-7.75 (m, 1H), 7.72 (d, J=8.1 Hz, 1H), 7.64-7.47 (m, 7H), 5.77 (dd, J=10.4, 6.0 Hz, 1H), 5.47 (t, J=7.1 Hz, 1H), 3.07-2.72 (m, 2H), 2.09-1.88 (m, 2H), 1.53-1.28 (m, 1H), 0.96-0.92 (m, 6H).

Preparation of Compound M

Step 1: (S)-methyl 3-(2'-fluoro-6'-methoxybiphenyl-3-yl)-3-((S)-4-methyl-2-(4-oxoquinazolin-3(4H)-yl)pentanamido)propanoate

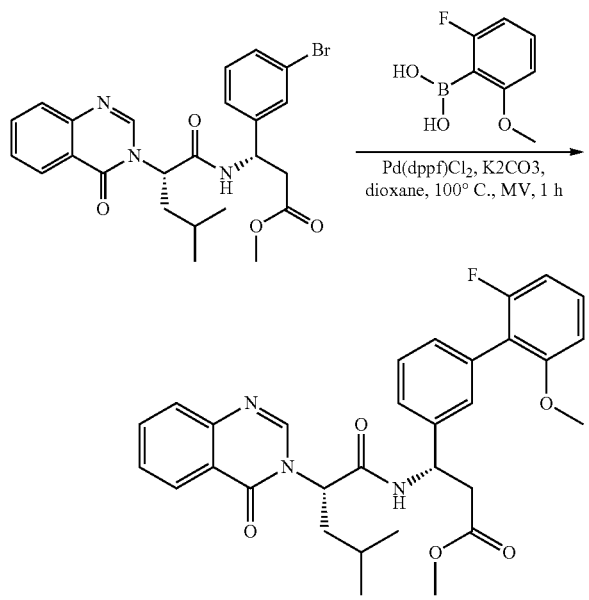

A mixture of (S)-methyl 3-(3-bromophenyl)-3-((S)-4-methyl-2-(4-oxoquinazolin-3(4H)-yl)pentanamido)propanoate (120 mg, 0.24 mmol), 2-fluoro-6-methoxyphenylboronic acid (62 mg, 0.36 mmol), Pd(dppf)Cl$_2$ (18 mg, 0.024 mmol), and K$_2$CO$_3$ (100 mg, 0.72 mmol) in 1,4-dioxane (3 mL) and H$_2$O (0.5 mL) under N$_2$ atmosphere was stirred in a microwave at 100° C. for 1 hour. Water (15 mL) was added, and the solution was extracted with EtOAc (20 mL×3). The combined organic phases were concentrated in vacuo. The resulting residue was purified by silica gel column (pet. ether:EtOAc 1:2) to give the desired product (S)-methyl 3-(2'-fluoro-6'-methoxybiphenyl-3-yl)-3-((S)-4-methyl-2-(4-oxoquinazolin-3(4H)-yl)pentanamido)propanoate as a colorless oil (100 mg). Yield 76% (100% purity, UV=214 nm, ESI 546 (M+H)$^+$).

Step 2: (S)-3-(2'-fluoro-6'-methoxybiphenyl-3-yl)-3-((S)-4-methyl-2-(4-oxoquinazolin-3(4H)-yl)pentanamido)propanoic acid

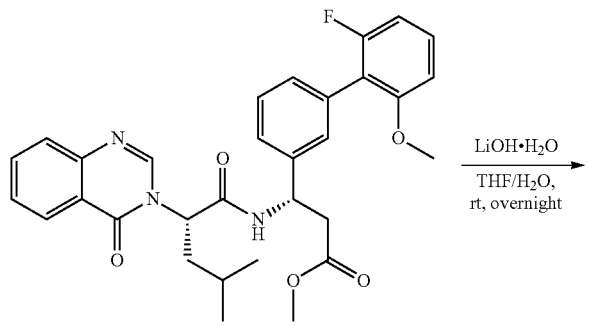

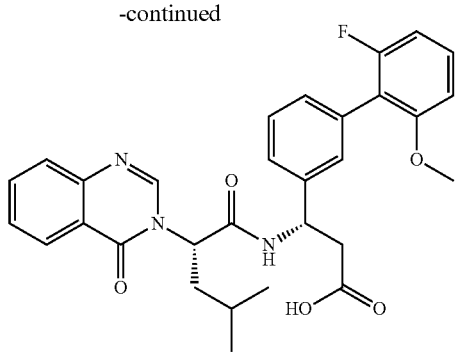

(S)-methyl 3-(2'-fluoro-6'-methoxybiphenyl-3-yl)-3-((S)-4-methyl-2-(4-oxoquinazolin-3(4H)-yl)pentanamido)propanoate (100 mg, 0.18 mmol) was treated with LiOH—H$_2$O (23 mg, 0.54 mmol) in THF (10 mL) and H$_2$O (0.5 mL) at room temperature for 16 hours. The mixture was acidified with HCl (1 M) until pH=5. The solvent was removed in vacuo and the residue was purified by Preparative-HPLC B (30~70% MeCN) to give the products (S)-3-(2'-fluoro-6'-methoxybiphenyl-3-yl)-3-((S)-4-methyl-2-(4-oxoquinazolin-3(4H)-yl)pentanamido)propanoic acid (40 mg) as a white solid Compound M LC/MS B: 100% purity, UV=214 nm, Rt=1.86 min, ESI 532 (M+H)$^+$.

$^1$H NMR (500 MHz, MeOD) δ 8.45 (s, 1H), 8.26 (dd, J=8.1, 1.1 Hz, 1H), 7.93-7.79 (m, 1H), 7.72 (d, J=8.0 Hz, 1H), 7.63-7.55 (m, 1H), 7.44-7.25 (m, 5H), 6.92 (d, J=8.4 Hz, 1H), 6.81 (t, J=8.6 Hz, 1H), 5.77 (dd, J=10.1, 6.4 Hz, 1H), 5.47-5.32 (m, 1H), 3.79 (s, 3H), 2.95-2.71 (m, 2H), 2.13-1.85 (m, 2H), 1.58-1.33 (m, 1H), 0.94-0.92 (m, 6H).

Preparation of Compound M1

Step 1: (S)-methyl 3-(3-bromophenyl)-3-(tert-butoxycarbonylamino)propanoate

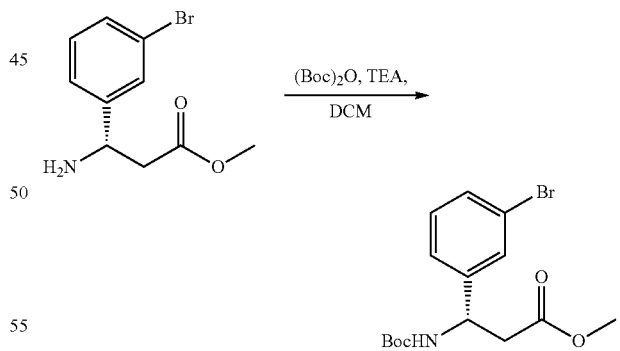

To a solution of (S)-methyl 3-amino-3-(3-bromophenyl)propanoate (6 g, 23 mmol) and triethylamine (9.65 mL, 69 mmol) in DCM (10 mL) was added di-tert-butyl dicarbonate (5 g, 23 mmol) at 0° C. and the reaction was stirred at 20° C. for 16 h. Water was added and the solution was extracted with DCM (70 mL×2). The organic phase was washed with brine, dried over Na$_2$SO$_4$. The mixture was filtered and the filtrate was concentrated in vacuo. The residue was purified by silica gel column (pet. ether:EtOAc=10:1) to give the desired product (S)-methyl 3-(3-bromophenyl)-3-(tert-butoxycarbonylamino)propanoate as a white solid (7 g). Yield 84% (92% purity, UV=214 nm, ESI 258 (MH-Boc)+).

Step 2: (S)-methyl 3-(tert-butoxycarbonylamino)-3-(3-(piperidin-1-yl)phenyl) propanoate

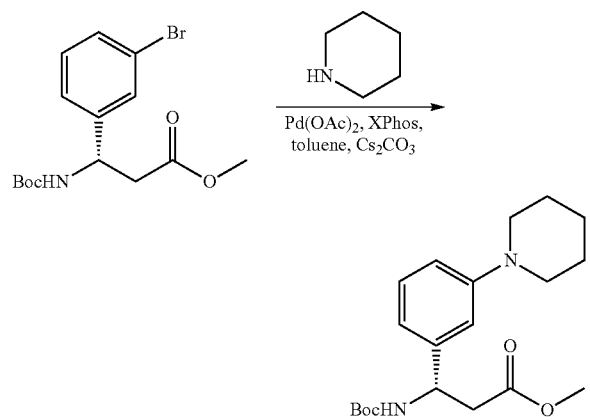

A mixture of (S)-methyl 3-(3-bromophenyl)-3-(tert-butoxycarbonylamino)propanoate (300 mg, 0.84 mmol), piperidine (143 mg, 1.68 mmol), Cs$_2$CO$_3$ (822 mg, 2.52 mmol), Pd(OAC)$_2$ (19 mg, 0.084 mmol) and XPhos (81 mg, 0.17 mmol) in toluene (4 mL) was stirred at 120° C. under N$_2$ for 16 h. The mixture was filtered over Celite and the filtrate was concentrated in vacuo. The residue was purified by silica gel column (pet. ether:EtOAc=2:1) to give (S)-methyl 3-(tert-butoxycarbonylamino)-3-(3-(piperidin-1-yl)phenyl) propanoate (200 mg). Yield 66% (92% purity, UV=214 nm, ESI 263 (MH-Boc)+).

Step 3: (S)-methyl 3-amino-3-(3-(piperidin-1-yl)phenyl)propanoate

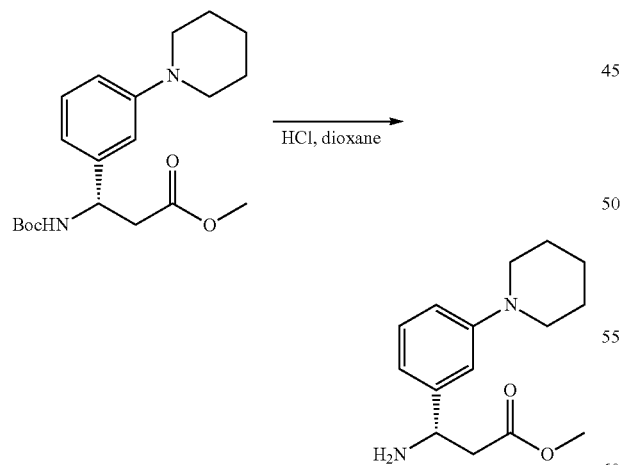

(S)-methyl 3-(tert-butoxycarbonylamino)-3-(3-(piperidin-1-yl)phenyl)propanoate (200 mg, 0.55 mmol) was treated with HCl (1 mL) in dioxane (5 mL) at room temperature for 1 hour. The solvent was removed in vacuo to provide the crude product (S)-methyl 3-amino-3-(3-(piperidin-1-yl)phenyl)propanoate as a yellow oil (145 mg).

Yield 100% (98% purity, UV=254 nm, ESI 263 (M+H)+). The crude product was used for the next step directly.

Step 4: (S)-methyl 3-((S)-4-methyl-2-(4-oxoquinazolin-3(4H)-yl)pentanamido)-3-(3-(piperidin-1-yl)phenyl)propanoate

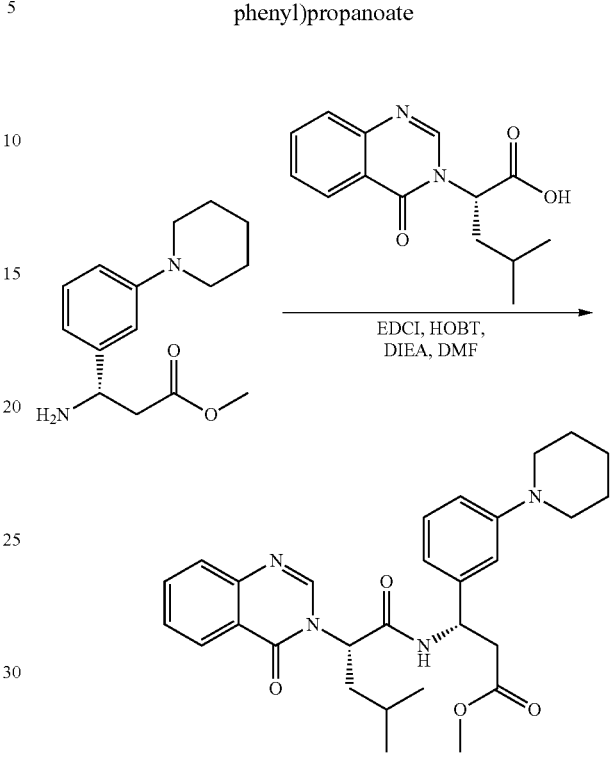

A mixture of (S)-methyl 3-amino-3-(3-(piperidin-1-yl)phenyl)propanoate (145 mg, 0.55 mmol), (S)-4-methyl-2-(4-oxoquinazolin-3(4H)-yl)pentanoic acid (144 mg, 0.55 mmol), EDCI (159 mg, 0.83 mmol), HOBt (112 mg, 0.83 mmol) and DIPEA (214 mg, 1.66 mmol) in DMF (10 mL) was stirred at room temperature for 4 hours. The mixture was poured into 10 mL of water and the solution was extracted with DCM (30 mL×3). The organic layer was washed with brine and dried over Na$_2$SO$_4$, filtered. The filtrate was concentrated in vacuo. The residue was purified by silica gel column (pet. ether:EtOAc=1:1) to provide the desired product (S)-methyl 3-((S)-4-methyl-2-(4-oxoquinazolin-3(4H)-yl)pentanamido)-3-(3-(piperidin-1-yl)phenyl)propanoate as a pale orange oil (224 mg). Yield 80% (95% purity, UV=254 nm, ESI 505 (M+H)+).

Step 5: (S)-3-((S)-4-methyl-2-(4-oxoquinazolin-3(4H)-yl)pentanamido)-3-(3-(piperidin-1-yl)phenyl)propanoic acid

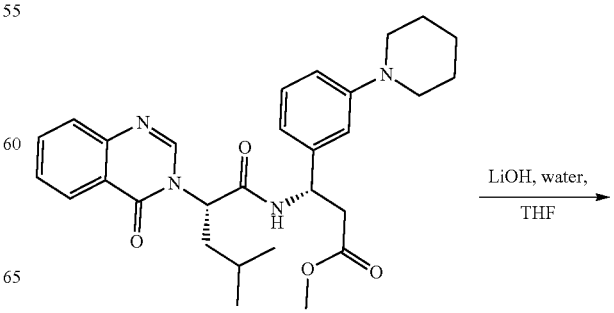

131
-continued

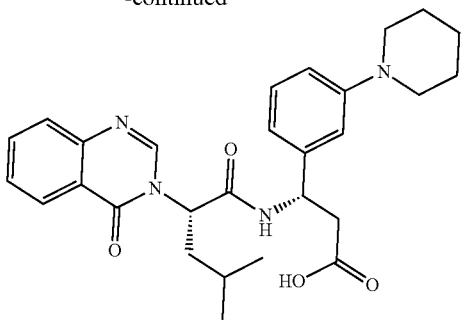

(S)-methyl 3-((S)-4-methyl-2-(4-oxoquinazolin-3(4H)-yl)pentanamido)-3-(3-(piperidin-1-yl)phenyl)propanoate (224 mg, 0.44 mmol) was treated with LiOH (1 M in H$_2$O, 0.6 mL) in THF (2 mL) at room temperature for 2 h. The mixture was adjusted to pH=5~6 with 1 M HCl. The solvent was removed in vacuo and the residue was purified by Preparative-HPLC A (30-70% MeCN) to give the desired product (S)-3-((S)-4-methyl-2-(4-oxoquinazolin-3(4H)-yl)pentanamido)-3-(3-(piperidin-1-yl)phenyl)propanoic acid (44 mg) as a white solid.

Compound M1: LC/MS A: 100% purity, UV=214 nm, Rt=1.62 min, ESI 491 (M+H)$^+$.

$^1$H NMR (500 MHz, MeOD) δ 8.43 (s, 1H), 8.26 (d, J=6.8 Hz, 1H), 7.85 (dd, J=11.2, 4.2 Hz, 1H), 7.71 (d, J=8.1 Hz, 1H), 7.58 (t, J=7.5 Hz, 1H), 7.21 (t, J=7.9 Hz, 1H), 6.99 (s, 1H), 6.92-6.81 (m, 2H), 5.75 (dd, J=10.1, 6.3 Hz, 1H), 5.29 (t, J=7.4 Hz, 1H), 3.20-3.11 (m, 4H), 2.75-2.79 (m, 2H), 1.98-2.03 (m, 2H), 1.78-1.67 (m, 4H), 1.60-1.62 (m, 2H), 1.50-1.37 (m, 1H), 0.99-0.91 (m, 6H).

Preparation of Compounds M2 and M2a

Step 41: methyl 3-(tert-butoxycarbonylamino)-3-(2-o-tolylpyridin-4-yl)propanoate

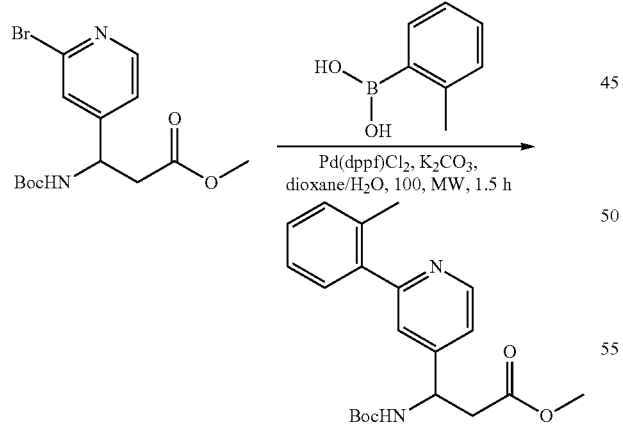

A mixture of methyl 3-(2-bromopyridin-4-yl)-3-(tert-butoxycarbonylamino)propanoate (600 mg, 1.71 mmol), o-tolylboronic acid (267 mg, 1.97 mmol), Pd(dppf)Cl$_2$ (63 mg, 0.086 mmol), and K$_2$CO$_3$ (692 mg, 5.13 mmol) in 1,4-dioxane (4 mL) and H$_2$O (0.5 mL) under N$_2$ atmosphere was stirred in a microwave at 100° C. for 1.5 hours. Filtered over Celite, and the filtrate was concentrated under reduced pressure to give a residue, which was purified by silica gel column (pet. ether:EtOAc 1:3) to give the desired product methyl 3-(tert-butoxycarbonylamino)-3-(2-o-tolylpyridin-4-yl)propanoate as a colorless oil (500 mg). Yield 72% (74% purity, UV=214 nm, ESI 371 (M+H)$^+$).

Step 2: methyl 3-amino-3-(2-o-tolylpyridin-4-yl)propanoate

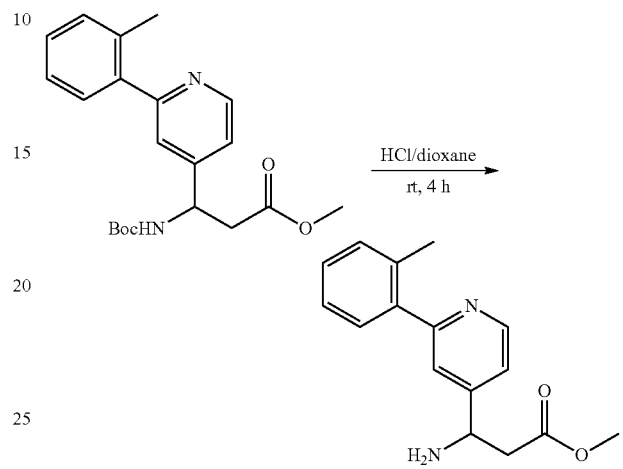

To a solution of methyl 3-(tert-butoxycarbonylamino)-3-(2-o-tolylpyridin-4-yl) propanoate (500 mg, 1.35 mmol) in DCM (6 mL) was added HCl in 1,4-dioxane (4 M, 2 mL), and the solution was stirred at room temperature for 4 hours. The solvent was removed in vacuo to give the crude product methyl 3-amino-3-(2-o-tolylpyridin-4-yl)propanoate hydrochloride as a yellow solid (400 mg). Yield 99% (83% purity, UV=214 nm, ESI 271 (M+H)$^+$). The crude product was used for the next step directly.

Step 3: methyl 3-(4-methyl-2-(2-oxopyridin-1(2H)-yl)pentanamido)-3-(2-o-tolylpyridin-4-yl)propanoate

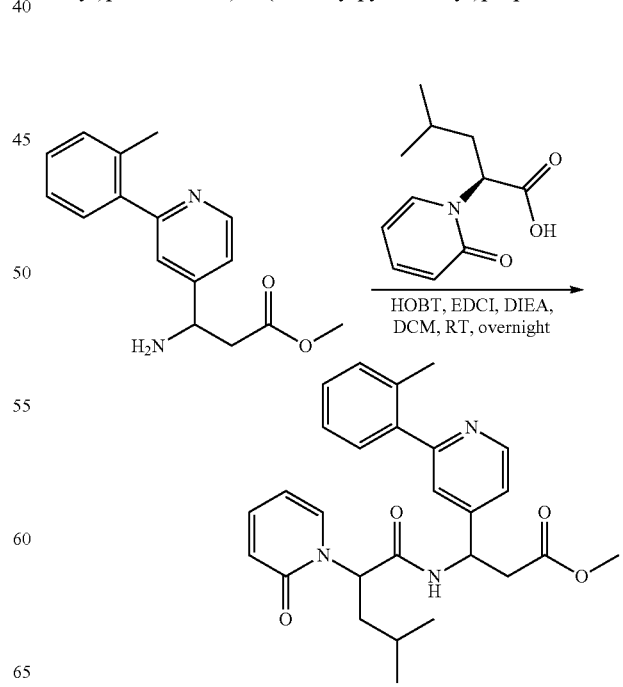

A mixture of (S)-4-methyl-2-(2-oxopyridin-1(2H)-yl)pentanoic acid (110 mg, 0.53 mmol), methyl 3-amino-3-(2-o-tolylpyridin-4-yl)propanoate hydrochloride (173 mg, 0.64 mmol), HOBt (87 mg, 0.64 mmol), EDCI (123 mg, 0.64 mmol) and DIEA (273 mg, 2.12 mmol) in DCM (20 mL) was stirred at room temperature for 16 hours. The mixture was poured into water and the solution was extracted with EtOAc (20 mL×2), the combined organic layers were dried over Na$_2$SO$_4$ and filtered. The filtrate was concentrated under reduced pressure to give a residue, which was purified by flash column chromatography (0%~80% EtOAc in pet ether) to obtain the desired product methyl 3-(4-methyl-2-(2-oxopyridin-1(2H)-yl)pentanamido)-3-(2-o-tolylpyridin-4-yl)propanoate as a colorless oil (200 mg). Yield 82% (91% purity, UV=214 nm, ESI 462 (M+H)$^+$).

Step 4: 3-(4-methyl-2-(2-oxopyridin-1(2H)-yl)pentanamido)-3-(2-o-tolylpyridin-4-yl)propanoic acid

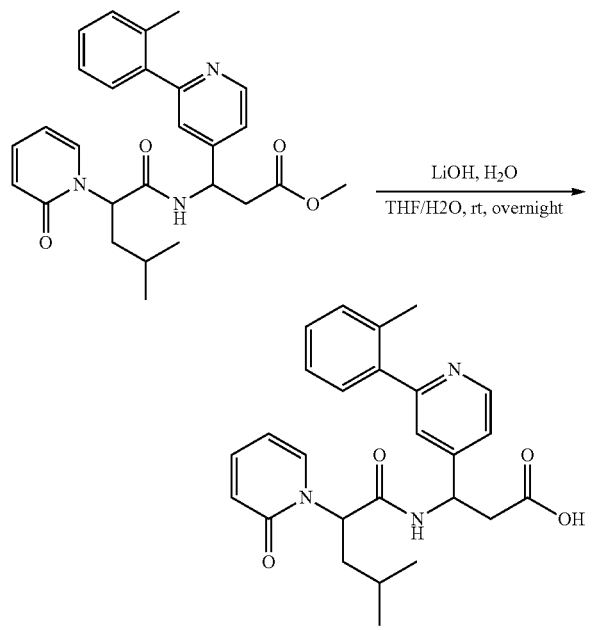

Methyl 3-(4-methyl-2-(2-oxopyridin-1 (2H)-yl)pentanamido)-3-(2-o-tolylpyridin-4-yl)propanoate (200 mg, 0.43 mmol) was treated with LiOH—H$_2$O (54 mg, 1.29 mmol) in THF (10 mL) and H$_2$O (1 mL) at room temperature for 16 hours. The mixture was acidified with HCl (1 M) until pH=5. The solution was concentrated under reduced pressure give a residue, which was purified by Preparative-HPLC A to give the compounds M2 (90 mg) and M2a (50 mg) as white solids.

Compound M2 LC/MS A: 100% purity, UV=214 nm, Rt=1.53 min, ESI 448 (M+H)$^+$.

$^1$H NMR (500 MHz, MeOD) δ 8.57 (d, J=5.2 Hz, 1H), 7.75 (dd, J=6.9, 1.6 Hz, 1H), 7.55-7.27 (m, 7H), 6.57 (d, J=8.8 Hz, 1H), 6.42 (t, J=6.3 Hz, 1H), 5.78 (t, J=8.1 Hz, 1H), 5.35 (t, J=7.0 Hz, 1H), 2.97-2.79 (m, 2H), 2.30 (s, 3H), 1.89 (t, J=7.6 Hz, 2H), 1.37-1.35 (m, 1H), 0.93-0.90 (m, 6H).

Step 5: Compound M2a

Compound M2 (50 mg) was separated into M2a (6 mg) and M2b (12 mg) by Prep chiral SFC E as white solids.

M2a LC/MS A: 100% purity, UV=214 nm, Rt=1.49 min, ESI 448 (M+H)$^+$.

$^1$H NMR (500 MHz, MeOD) δ 8.57 (d, J=5.1 Hz, 1H), 7.75 (dd, J=7.0, 1.8 Hz, 1H), 7.60-7.25 (m, 7H), 6.57 (d, J=9.0 Hz, 1H), 6.42 (m, 1H), 5.78 (t, J=8.1 Hz, 1H), 5.35 (t, J=7.1 Hz, 1H), 3.00-2.75 (m, 2H), 1.89 (t, J=7.6 Hz, 2H), 1.37-1.35 (m, 1H), 0.93-0.90 (m, 6H).

Preparation of Compounds N1 and N2

Step 1: 3-cyclobutoxybenzaldehyde

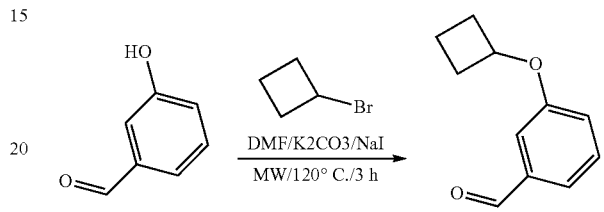

To a solution of 3-hydroxybenzaldehyde (488 mg, 4.0 mmol), bromocyclobutane (1.08 mg, 8.0 mmol) and K$_2$CO$_3$ (1.11 mg, 8.0 mmol), NaI (120 mg, 0.8 mmol) in DMF (20 mL) under N$_2$ atmosphere stirred at 120° C. in a microwave for 3 h. The mixture was diluted with EtOAc (12 mL) and water (6 mL). The organic phase was separated and dried over Na$_2$SO$_4$. The mixture was filtered and the filtrate was concentrated under reduced pressure to a residue, which was purified by silica gel column (5~10% EtOAc in pet ether) to give the desired product 3-cyclobutoxybenzaldehyde as a pale orange oil (550 mg). Yield 61% (90% purity, UV=214 nm, ESI 177 (M+H)$^+$).

Step 2: 3-amino-3-(3-cyclobutoxyphenyl)propanoic acid

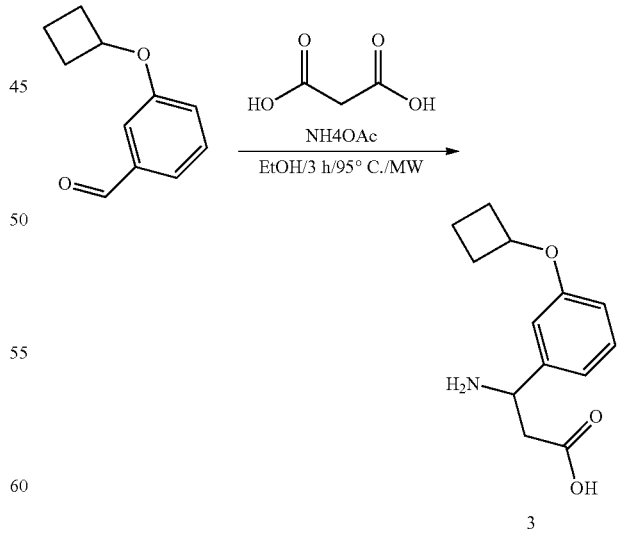

A mixture of 3-cyclobutoxybenzaldehyde (550 mg, 3.12 mmol), malonic acid (487 mg, 4.68 mmol), NH$_4$OAc (481 mg, 6.24 mmol) in EtOH (12 mL) in a sealed tube was stirred at 95° C. for 3 h. The mixture was concentrated in vacuo and purified by silica gel column (10~50% MeOH in DCM) to give the desired product 3-amino-3-(3-cyclobutoxyphenyl)propanoic acid as a colorless oil (257 mg). Yield 35% (100% purity, UV=254 nm, ESI 236 (M+H)+).

Step 3: 3-(tert-butoxycarbonylamino)-3-(3-cyclobutoxyphenyl)propanoic acid

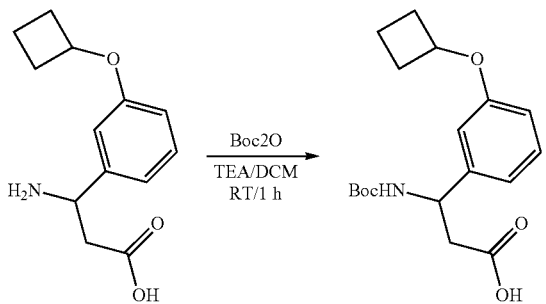 [SMILES: "Boc2O" ; NC(CC(=O)O)c1cccc(OC2CCC2)c1 ; "TEA/DCMRT/1 h" ; CC(C)(C)OC(=O)NC(CC(=O)O)c1cccc(OC2CCC2)c1]

To a solution of 3-amino-3-(3-cyclobutoxyphenyl)propanoic acid (257 mg, 1.09 mmol) and TEA (165 mg, 1.63 mmol) in DCM (12 mL) at room temperature was added di-tert-butyl dicarbonate (250 mg, 1.15 mmol). The solution was stirred at room temperature for 1 h. The solvent was removed in vacuo and the residue was purified by silica gel column (5%~10% EtOAc in pet ether) to provide the desired product 3-(tert-butoxycarbonylamino)-3-(3-cyclobutoxyphenyl)propanoic acid as a colorless oil (361 mg). Yield 98% (91% purity, UV=214 nm, ESI280 (MH-Bu)+).

Step 4: benzyl 3-(tert-butoxycarbonylamino)-3-(3-cyclobutoxyphenyl)propanoate

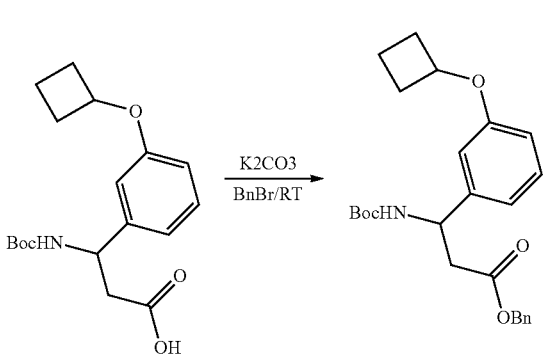

A solution of 3-(tert-butoxycarbonylamino)-3-(3-cyclobutoxyphenyl)propanoic acid (360 mg, 1.07 mmol), BnBr (183 mg, 1.07 mmol) and K$_2$CO$_3$ (298 mg, 2.14 mmol) in DMF (10 mL) was stirred at room temperature overnight. The mixture was diluted with DCM (18 mL) and water (5 mL). The organic phase was separated and dried over Na$_2$SO$_4$. The mixture was filtered and the filtrate was concentrated to give a brown oil, which was purified by silica gel flash (5%~10% EtOAc in pet ether) to provide the desired product benzyl 3-(tert-butoxycarbonylamino)-3-(3-cyclobutoxyphenyl)propanoate as a colorless oil (386 mg). Yield 85% (91% purity, UV=214 nm, ESI 326 (MH-Boc)+).

Step 5: benzyl 3-amino-3-(3-cyclobutoxyphenyl)propanoate

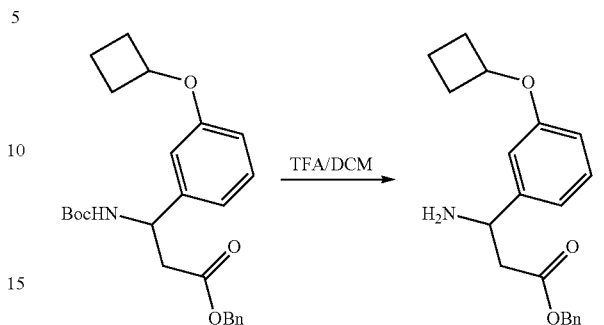

Benzyl 3-amino-3-(3-cyclobutoxyphenyl)propanoate (340 mg, 0.8 mmol) was treated with TFA (1 mL) in DCM (3 mL) at room temperature for 0.5 hours. The solvent was removed in vacuo to provide the crude product benzyl 3-amino-3-(3-cyclobutoxyphenyl)propanoate as a yellow oil (218 mg). Yield 84% (97% purity, UV=254 nm, ESI 326 (M+H)+). The crude product was used for the next step directly.

Step 6: benzyl 3-(3-cyclobutoxyphenyl)-3-((S)-4-methyl-2-(2-oxopyridin-1(2H)-yl)pentanamido)propanoate

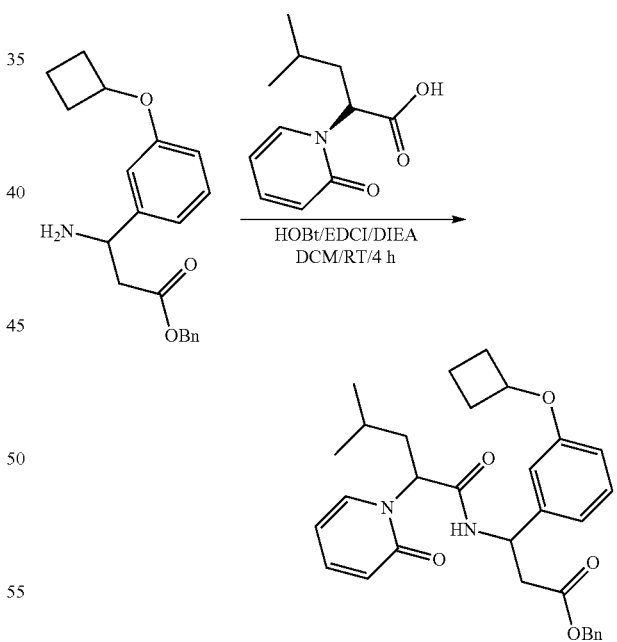

A mixture of benzyl 3-amino-3-(3-cyclobutoxyphenyl) propanoate (109 mg, 0.33 mmol), (S)-4-methyl-2-(2-oxopyridin-1(2H)-yl)pentanoic acid (77 mg, 0.36 mmol), EDCI (96 mg, 0.50 mmol), HOBt (68 mg, 0.50 mmol) and DIEA (86 mg, 0.67 mmol) in DCM (6 mL) was stirred at room temperature for 4 hours. The mixture was diluted with DCM (10 mL) and 5 mL of water. The organic phase was separated and dried over Na$_2$SO$_4$. The mixture was filtered, and the filtrate was concentrated under reduced pressure to give an orange oil, which was purified by silica gel column (5~30% EtOAc in pet ether) to provide the desired product benzyl 3-(3-cyclobutoxyphenyl)-3-(4-methyl-2-(2-oxopyridin-1(2H)-yl)pentanamido)propanoate as a colorless oil (151 mg). Yield 87% (81% purity, UV=254 nm, ESI 517 (M+H)+).

Step 7: Compounds N1 and N2

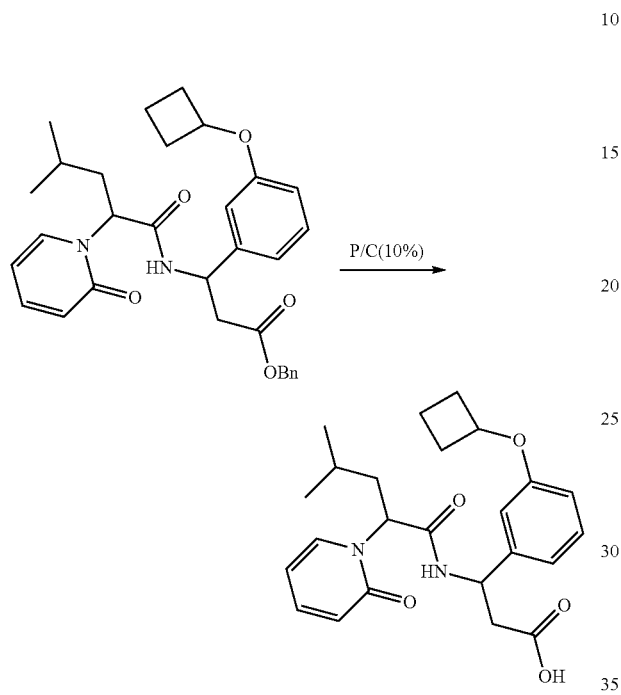

Benzyl 3-(3-cyclobutoxyphenyl)-3-(4-methyl-2-(2-oxopyridin-1 (2H)-yl)pentanamido)propanoate (150 mg, 0.29 mmol) and Pd/C (10%, 30 mg) in EtOAc (18 mL) was stirred under H$_2$ atmosphere at room temperature overnight. The mixture was filtered through a pad of Celite, and the filtrate was concentrated under reduced pressure. The residue was purified by preparatory HPLC B (30-70% MeCN) to provide the desired compounds N1 (15 mg) and N2 (10 mg) as white solids.

Compound N1 LC/MS B: 100% purity, UV=214 nm, Rt=9.01 min, ESI 45127 (M+H)+.

1H-NMR (500 MHz, MeOD) δ 7.74 (dd, J=7.0, 1.5 Hz, 1H), 7.52-7.48 (m, 1H), 7.16 (t, J=7.5 Hz, 1H), 6.84 (d, J=6.0 Hz, 1H), 6.74 (m, 1H), 6.68 (dd, J=7.0, 1.5 Hz, 1H), 6.55 (dd, J=9.5, 0.5 Hz, 1H), 6.41-6.39 (m, 1H), 5.78 (t, J=8.0 Hz, 1H), 5.30 (t, J=7.0 Hz, 1H), 4.62 (t, J=7.5 Hz, 1H), 2.79 (d, J=7.5 Hz, 2H), 2.44-2.40 (m, 2H), 2.09-2.04 (m, 2H), 2.09-2.04 (m, 2H), 1.95-1.92 (m, 2H), 1.82 (m, 1H), 1.70 (m, 1H), 1.48-1.44 (m, 1H), 1.03-0.96 (m, 6H).

Compound N1 LC/MS B: 100% purity, UV=214 nm, Rt=9.26 min, ESI 45127 (M+H)+.

1H-NMR (500 MHz, MeOD) δ 7.74 (dd, J=7.0, 1.5 Hz, 1H), 7.54-7.51 (m, 1H), 7.23 (t, J=7.5 Hz, 1H), 6.91 (s, 1H), 6.83 (s, 1H), 6.74 (dd, J=8.0, 1.5 Hz, 1H), 6.68 (d, J=9.0 Hz, 1H), 6.41-6.39 (m, 1H), 5.76 (m, 1H), 5.28 (t, J=8.0 Hz, 1H), 4.69 (t, J=7.0 Hz, 1H), 2.78 (m, 2H), 2.50-2.45 (m, 2H), 2.15-2.11 (m, 2H), 1.88-1.84 (m, 3H), 1.76-1.74 (m, H), 1.36-1.34 (m, 1H), 1.03-0.96 (m, 6H).

Preparation of Compounds O2 and O4

Step 1: (S)-methyl 3-(tert-butoxycarbonylamino)-3-(3-(4,4,5,5-tetramethyl-1,3,2-dioxaborolan-2-yl)phenyl)propanoate

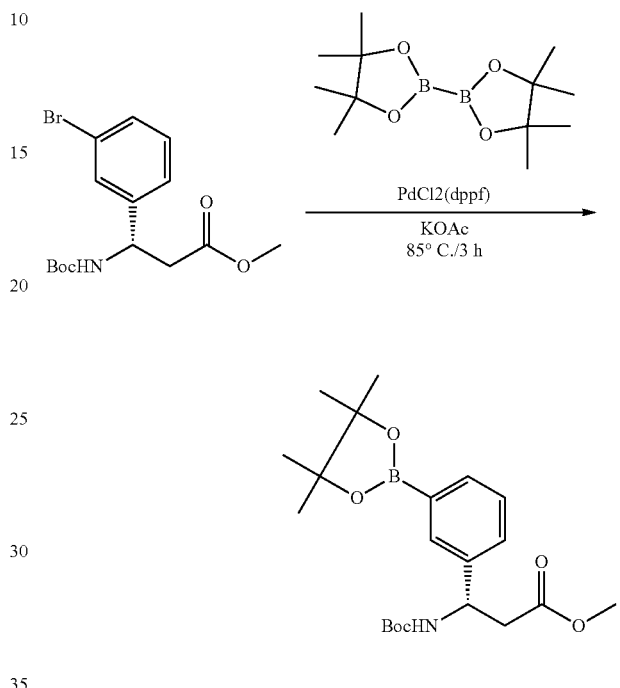

A solution of (S)-methyl 3-(3-bromophenyl)-3-(tert-butoxycarbonylamino)propanoate (537 mg, 1.5 mmol), Bis(pinacoiato)diboron (765 mg, 3.0 mmol) and KOAc (442 mg, 4.5 mmol) in dioxane (20 mL) was degassed with bubbling nitrogen, PdCl$_2$(dppf) (54 mg, 0.037 mmol) was added and the reaction was stirred at 80° C. for 3 h. The mixture was diluted with EtOAc (12 mL) and filtered through a pad of Celite. The filtrate was concentrated under reduced pressure to give a brown oil, which was purified by silica gel column (5~10% EtOAc in pet ether) to give (S)-methyl 3-(tert-butoxycarbonylamino)-3-(3-(4,4,5,5-tetramethyl-1,3,2-dioxaborolan-2-yl)phenyl)propanoate as a white solid (565 mg). Yield 93% (92% purity, UV=214 nm, ESI306 (MH-Boc)+).

Step 2: (S)-methyl 3-(tert-butoxycarbonylamino)-3-(3-(3,5-dimethyl-1H-pyrazol-4-yl)phenyl)propanoate

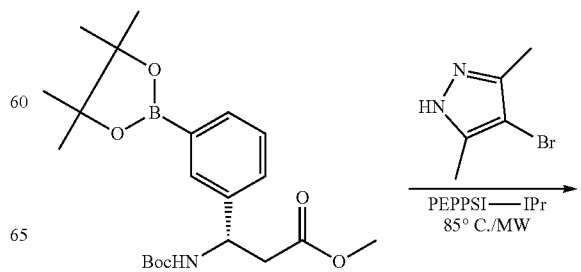

139
-continued

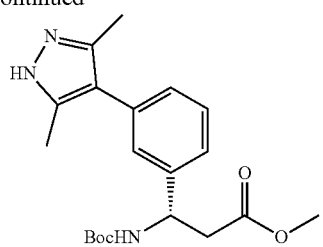

A mixture of (S)-methyl 3-(tert-butoxycarbonylamino)-3-(3-(4,4,5,5-tetramethyl-1,3,2-dioxaborolan-2-yl)phenyl)propanoate (405 mg, 1.0 mmol), 4-bromo-3,5-dimethyl-1H-pyrazole (350 mg, 2.0 mmol), PEPPSI-IPr (34 mg, 0.05 mmol) and $K_2CO_3$ (276 mg, 2.0 mmol) in dioxane (20 mL) and $H_2O$ (4 mL) was stirred under $N_2$ atmosphere in a microwave at 85° C. for 4 hs. Water (8 mL) was added, and the solution was extracted with EtOAc (20 mL×3). The combined organic phases were concentrated in vacuo and the residue was purified by silica gel column (pet. ether:EtOAc=2:3) to give the desired product (S)-methyl 3-(tert-butoxycarbonylamino)-3-(3-(3,5-dimethyl-1H-pyrazol-4-yl)phenyl)propanoate as a pale orange oil (240 mg). Yield 64% (100% purity, UV=254 nm, ESI 374 (M+H)⁺).

Step 3: (S)-methyl 3-amino-3-(3-(3,5-dimethyl-1H-pyrazol-4-yl)phenyl)propanoate

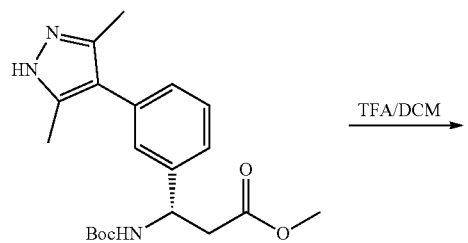

(S)-methyl 3-(tert-butoxycarbonylamino)-3-(3-(3,5-dimethyl-1H-pyrazol-4-yl)phenyl)propanoate (112 mg, 0.3 mmol) was treated with TFA (0.5 mL) in DCM (2 mL) at room temperature for 1 hour. The solvent was removed in vacuo to provide the crude product (S)-methyl 3-amino-3-(3-(3,5-dimethyl-1H-pyrazol-4-yl)phenyl)propanoate as a yellow oil (79 mg). Yield 96% (98% purity, UV=254 nm, ESI 274 (M+H)⁺). The crude product was used for the next step directly.

140

Step 4: (S)-methyl 3-(3-(3,5-dimethyl-1H-pyrazol-4-yl)phenyl)-3-((S)-4-methyl-2-(2-oxopyridin-1(2H)-yl)pentanamido)propanoate

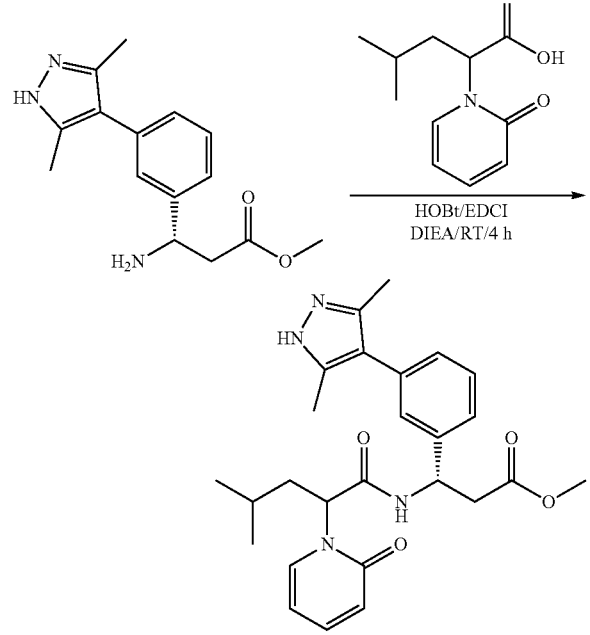

A mixture of (S)-methyl 3-amino-3-(3-(3,5-dimethyl-1H-pyrazol-4-yl)phenyl)propanoate (78 mg, 0.28 mmol), 4-methyl-2-(2-oxopyridin-1(2H)-yl)pentanoic acid (63 mg, 0.30 mmol), EDCI (82 mg, 0.43 mmol), HOBt (58 mg, 0.43 mmol) and DIEA (110 mg, 0.85 mmol) in DCM (6 mL) was stirred at room temperature for 4 hours. The mixture was diluted with DCM (10 mL) and 5 mL of water. The organic phase was dried over $Na_2SO_4$, filtered and the filtrate was concentrated under reduced pressure to give an orange oil, which was purified by silica gel column (pet. etherEtOAc=10:1~4:1) to provide the desired compounds 01 (51 mg) and 02 (70 mg) as pale orange oils. Yield 91% (95% purity, UV=254 nm, ESI 465 (M+H)⁺).

Step 5: Compound O2

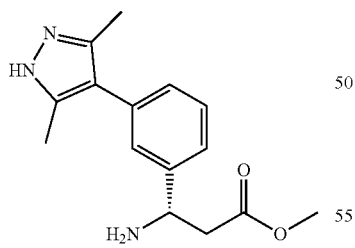

O1

-continued

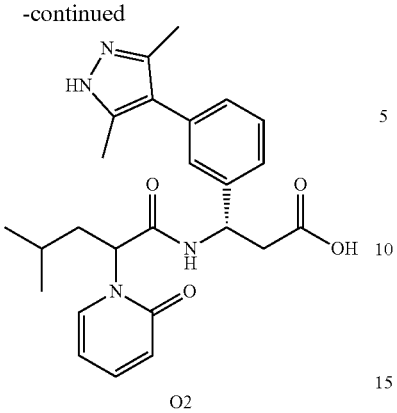

O2

O1 (50 mg, 0.11 mmol) was treated with LiOH (1M in H₂O, 0.6 mL) in THF (2 mL) at room temperature overnight. The mixture was adjusted with 1M HCl to pH=5~6, and the solvent was removed in vacuo. The residue was purified by preparatory HPLC A (30-64% MeCN) to give the compounds 01 (37 mg) and 02 (15 mg) as white solids.

Compound O2 LC/MS A: 100% purity, UV=214 nm, Rt=7.27 min, ESI 451 (M+H)⁺.

1H-NMR (500 MHz, MeOD) δ 7.75 (dd, J=7.0, 1.5 Hz, 1H), 7.50-7.53 (m, 1H), 7.39-7.42 (m, 1H), 7.31-7.30 (m, 2H), 7.20 (d, J=7.0 Hz, 1H), 6.56 (d, J=9.0 Hz, 1H), 6.44-6.41 (m, 1H), 5.75 (dd, J=7.0, 9.5 Hz, 1H), 5.35 (t, J=7.0 Hz, 1H), 2.87-2.77 (m, 2H), 2.27 (s, 6H), 1.88-1.84 (m, 2H), 1.37-1.32 (m, 1H), 0.92-0.89 (m, 6H).

Step 6: Compound O4

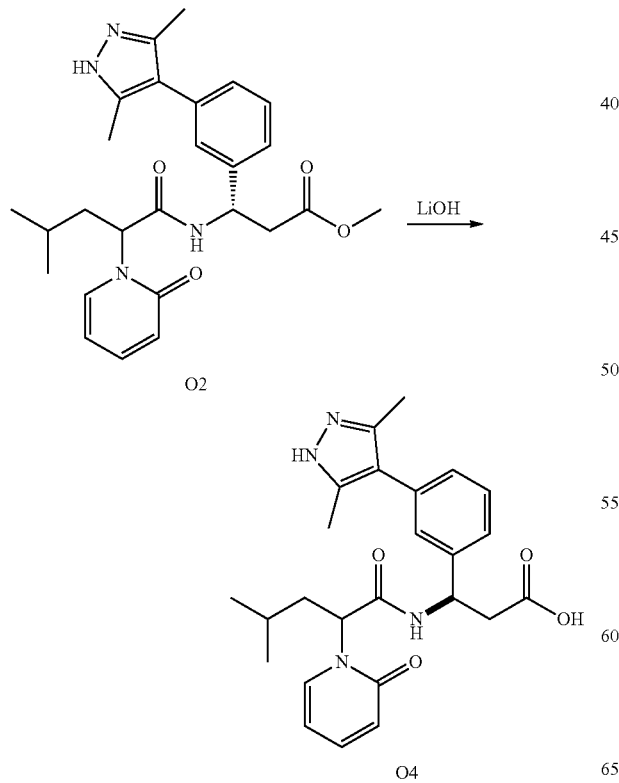

Compound O2 (70 mg, 0.15 mmol) was treated with LiOH (1M in H₂O, 0.6 mL) in THF (2 mL) at room temperature overnight. The mixture was adjusted with 1 M HCl to pH=5~6, and the solvent was removed in vacuo. The residue was purified by preparatory HPLC A (30-64% MeCN) to give the compounds 03 (35 mg) and 04 (26 mg) as white solids.

Compound O4 LC/MS A: 100% purity, UV=214 nm, Rt=7.26 min, ESI 451 (M+H)⁺.

1H-NMR (500 MHz, MeOD) δ 7.75 (dd, J=7.0, 1.5 Hz, 1H), 7.50-7.53 (m, 1H), 7.38-7.42 (m, 1H), 7.31-7.30 (m, 2H), 7.21 (d, J=6.5 Hz, 1H), 6.56 (d, J=9.0 Hz, 1H), 6.44-6.41 (m, 1H), 5.75 (dd, J=7.0, 9.5 Hz, 1H), 5.35 (t, J=7.0 Hz, 1H), 2.88-2.78 (m, 2H), 2.27 (s, 6H), 1.88-1.84 (m, 2H), 1.37-1.32 (m, 1H), 0.92-0.89 (m, 6H).

Preparation of Compound P2

Step 1:
6-hydroxy-2'-methylbiphenyl-3-carbaldehyde

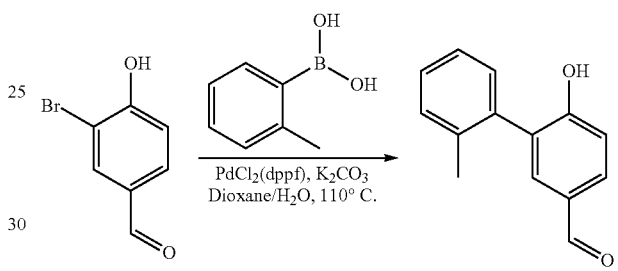

A mixture of 3-bromo-4-hydroxybenzaldehyde (2 g, 9.9 mmol), o-tolylboronic acid (2 g, 15 mmol), PdCl₂(dppf) (364 mmg, 0.5 mmol) and K₂CO₃ (4.1 g, 29.8 mmol) in 9 mL of 1,4-Dioxane and 0.9 mL of H₂O under N₂ atmosphere was stirred at 110° C. in a microwave for 1 h. The mixture was filtered over Celite. The filtrate was removed in vacuo, and the residue was purified by silica gel column (pet. ether:EtOAc=3:1) to give the desired product 6-hydroxy-2'-methylbiphenyl-3-carbaldehyde as a brown solid (1.5 g). Yield 71% (62% purity, UV=214 nm, ESI 213 (M+H)⁺).

Step 2: 5-formyl-2'-methylbiphenyl-2-yl trifluoromethanesulfonate

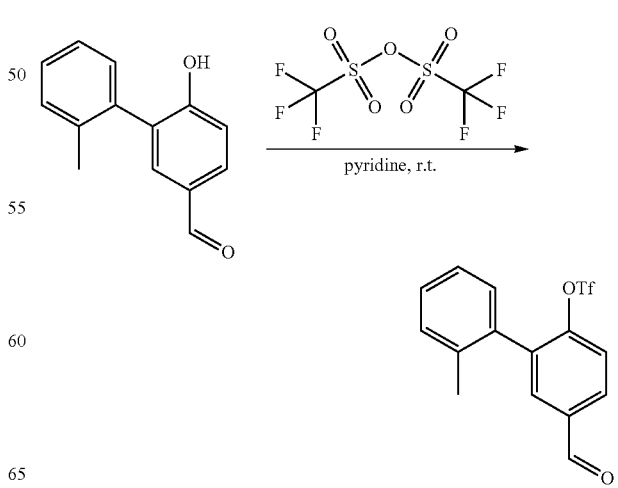

To a solution of 6-hydroxy-2'-methylbiphenyl-3-carbaldehyde (600 mg, 2.83 mmol) in 20 mL of pyridine was added trifluoromethanesulfonic anhydride (957 mg, 3.39 mmol) at 0° C. The solution was warmed up to room temperature and stirred at room temperature for 16 hours. The solvent was removed in vacuo, and the residue was purified by silica gel column (pet. ether:EtOAc=5:1) to give the desired product 5-formyl-2'-methylbiphenyl-2-yl trifluoromethanesulfonate as a colorless oil (650 mg), Yield 67% (89% purity, UV=214 nm, ESI 345 (M+H)+).

Step 3: 6-cyclopropyl-2'-methylbiphenyl-3-carbaldehyde

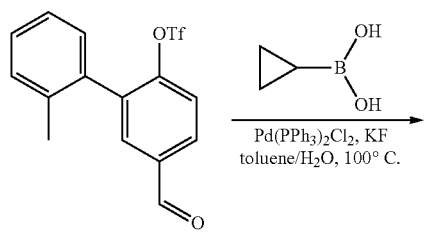

A mixture of 5-formyl-2'-methylbiphenyl-2-yl trifluoromethanesulfonate (650 mg, 1.89 mmol), cyclopropylboronic acid (811 mg, 9.44), Pd(PPh₃)₂Cl₂ (133 mg, 0.19 mmol) and KF (329 mg, 5.66 mmol) in 5 mL of toluene and 0.5 mL of H₂O was stirred at 100° C. for 16 hours. The mixture was filtered over Celite. The filtrate was removed in vacuo and the residue was purified by silica gel column (pet. ether:EtOAc=5:1) to give the desired product 6-cyclopropyl-2'-methylbiphenyl-3-carbaldehyde as a yellow oil (380 mg). Yield 85% (87% purity, UV=214 nm, ESI 237 (M+H)+).

Step 4: 3-amino-3-(6-cyclopropyl-2'-methylbiphenyl-3-yl)propanoic acid

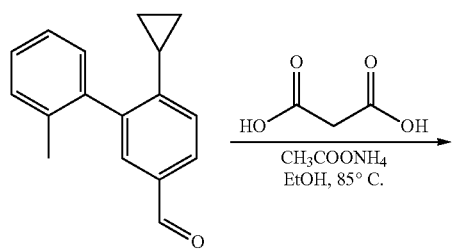

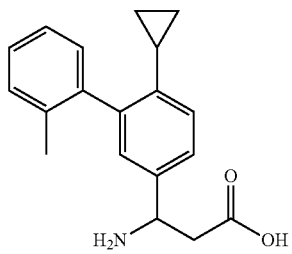

A mixture of 6-cyclopropyl-2'-methylbiphenyl-3-carbaldehyde (350 mg, 1.48 mmol), malonic acid (185 mg, 1.78 mmol) and Ammonium Acetate (571 mg, 7.41 mmol) in EtOH (5 mL) was stirred 85° C. for 16 hours. The mixture was filtered and the filtrated was concentrated under reduced pressure to give the crude product 3-amino-3-(6-cyclopropyl-2'-methylbiphenyl-3-yl)propanoic acid (400 mg). Yield 91% (46% purity, UV=214 nm, ESI 296 (M+H)+). The crude product was used for the next step directly.

Step 5: methyl 3-amino-3-(6-cyclopropyl-2'-methylbiphenyl-3-yl)propanoate

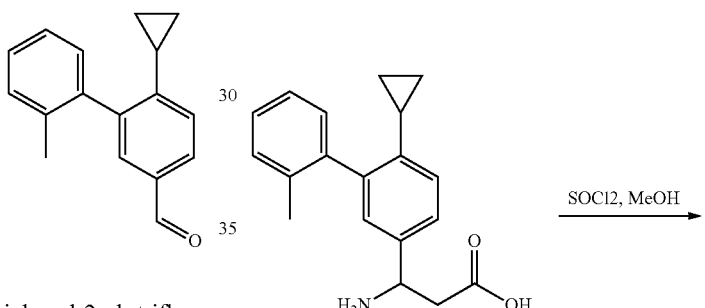

To a solution of 3-amino-3-(6-cyclopropyl-2'-methylbiphenyl-3-yl)propanoic acid (400 mg, 1.74 mmol) in 20 mL of anhydrous methanol was added sulfurous dichloride (25 mL) dropwise at 0° C. The solution was heated to 75° C., and stirred at 75° C. for 2 h. The solvent was removed in vacuo to give crude product methyl 3-amino-3-(6-cyclopropyl-2'-methylbiphenyl-3-yl)propanoate (400 mg). Yield 85% (42% purity, UV=214 nm, ESI 310 (M+H)+). The crude product was used for the next step directly.

Step 6: methyl 3-(6-cyclopropyl-2'-methylbiphenyl-3-yl)-3-((S)-4-methyl-2-(2-oxopyridin-1(2H)-yl)pentanamido)propanoate

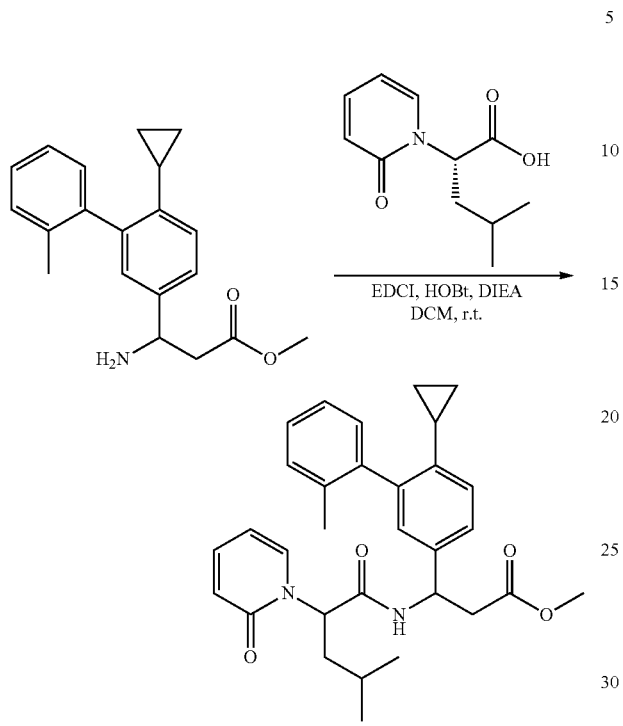

A solution of methyl 3-amino-3-(6-cyclopropyl-2'-methylbiphenyl-3-yl)propanoate (400 mg, 1.15 mmol), (S)-4-methyl-2-(2-oxopyridin-1(2H)-yl)pentanoic acid (290 mg, 1.38 mmol), EDCI (483 mg, 2.31 mmol), HOBt (234 mg, 1.73 mmol) and DIEA (598 mg, 4.62 mmol) in 25 mL of DCM was stirred at room temperature for 16 hours. The solvent was removed in vacuo and the residue was purified by silica gel column (pet. ether:EtOAc=2:1) to give the desired compounds P1 (180 mg) and P2 (140 mg) as brown oils. (ESI 501 (M+H)$^+$).

Step 7: 3-(6-cyclopropyl-2'-methylbiphenyl-3-yl)-3-(4-methyl-2-(2-oxopyridin-1(2H)-yl)pentanamido)propanoic acid

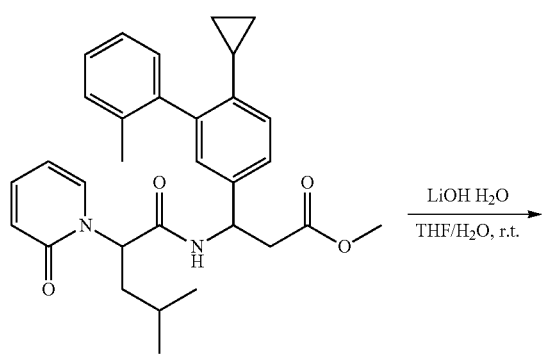

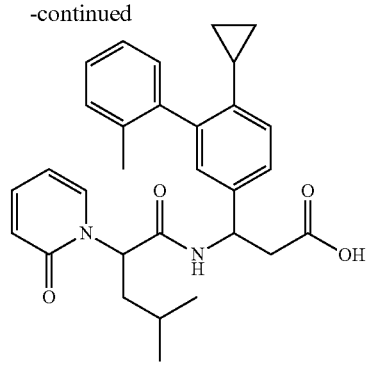

P2 (140 mg, 0.28 mmol) was treated with LiOH—H$_2$O (35 mg, 0.84 mmol) in 6 mL of THF and 2 mL of H$_2$O at room temperature for 3 h. The solution was adjusted to pH=3~4 with TFA. The solvent was removed in vacuo and the residue was purified by Preparative-HPLC A (33-70% MeCN) to give the product 3-(6-cyclopropyl-2'-methylbiphenyl-3-yl)-3-(4-methyl-2-(2-oxopyridin-1(2H)-yl)pentanamido)propanoic acid (47 mg) as a white solid.

Compound P2 LC/MS A: 100% purity, UV=214 nm, Rt=1.69 min, ESI 487.2 (M+H)$^+$.

$^1$H NMR (500 MHz, MeOD) δ 7.76 (dd, J=9.0, 3.7 Hz, 1H), 7.52-7.49 (m, 1H), 7.32-7.19 (m, 4H), 7.15 (dd, J=10.2, 7.0 Hz, 1H), 7.09-7.03 (m, 1H), 6.88 (d, J=8.1 Hz, 1H), 6.55 (d, J=9.1 Hz, 1H), 6.41 (t, J=6.8 Hz, 1H), 5.76-5.72 (m, 1H), 5.30 (t, J=7.2 Hz, 1H), 2.86-2.68 (m, 2H), 2.11 (d, J=6.3 Hz, 3H), 1.94-1.77 (m, 2H), 1.60-1.46 (m, 1H), 1.41-1.24 (m, 1H), 0.92-0.86 (m, 6H), 0.83-0.71 (m, 2H), 0.69-0.59 (m, 2H).

Preparation of Compound Q2

Step 1: 3-amino-3-(3-bromo-4-methylphenyl)propanoic acid

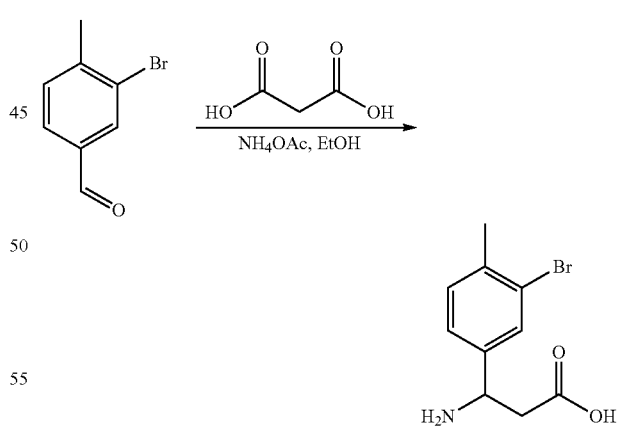

To a solution of 3-bromo-4-methylbenzaldehyde (6.0 g, 30.1 mmol) in EtOH (50 mL) was added malonic acid (3.1 g, 30.1 mmol) and NH$_4$OAc (4.6 g, 60.2 mmol). The mixture was heated to 80° C. and stirred for 16 hours. The mixture was concentrated under reduced pressure to give the crude product 3-amino-3-(3-bromo-4-methylphenyl)propanoic acid as a white solid (7.4 g), which was used in next step without further purification. (11% purity, UV=214 nm, ESI 258 (M+H)$^+$).

Step 2: methyl 3-amino-3-(3-bromo-4-methylphenyl)propanoate

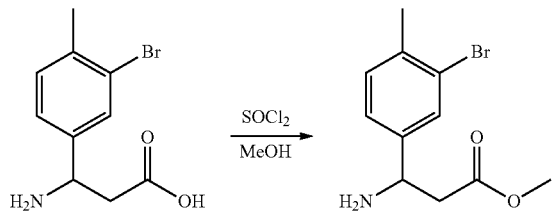

To a solution of 3-amino-3-(3-bromo-4-methylphenyl) propanoic acid (7.4 g, 28.8 mmol) in MeOH (50 mL) at 0° C. was added SOCl$_2$ (5 mL, 20.6 mmol) dropwise and the reaction mixture was stirred at 80° C. for 2 hours. Water (50 mL) was added and the solution was extracted with EtOAc (50 mL×3). The combined organic phase was washed with saturated aqueous NaHCO$_3$(20 mL×2) and brine (20 mL). The organic phase was dried over Na$_2$SO$_4$, filtered and concentrated under reduced pressure to give a residue which was purified by silica gel column (EtOAc) to give the desired product methyl 3-amino-3-(3-bromo-4-methylphenyl)propanoate as a colorless oil (2.5 g). Yield 33% two step (90% purity, UV=214 nm, ESI 272 (M+H)$^+$).

Step 3: methyl 3-amino-3-(2',6-dimethyl-[1,1'-biphenyl]-3-yl)propanoate

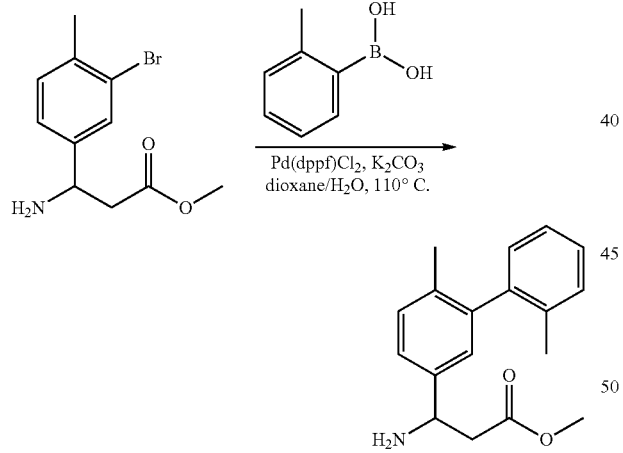

A mixture of methyl 3-amino-3-(3-bromo-4-methylphenyl)propanoate (350 mg, 1.29 mmol) and o-tolylboronic acid (263 mg, 1.94 mmol), PdCl$_2$(dppf) (94 mg, 0.13 mmol) and K$_2$CO$_3$ (535 mg, 3.87 mmol) in dioxane (3 mL) and H$_2$O (0.6 mL) under N$_2$ atmosphere was heated to 110° C. in a microwave for 1 hour. Water (10 mL) was added and the solution was extracted with EtOAc (20 mL×3). The combined organic phases were concentrated under reduced pressure to give a residue, which was purified by silica gel column (pet. ether:EtOAc 1:1) to give the desired product methyl 3-amino-3-(2',6-dimethyl-[1,1'-biphenyl]-3-yl)propanoate as a colorless oil (280 mg). Yield 77% (70% purity, UV=254 nm, ESI 284 (M+H)$^+$).

Step 4: methyl 3-(2',6-dimethyl-[1,1'-biphenyl]-3-yl)-3-(4-methyl-2-(2-oxopyridin-1(2H)-yl)pentanamido)propanoate

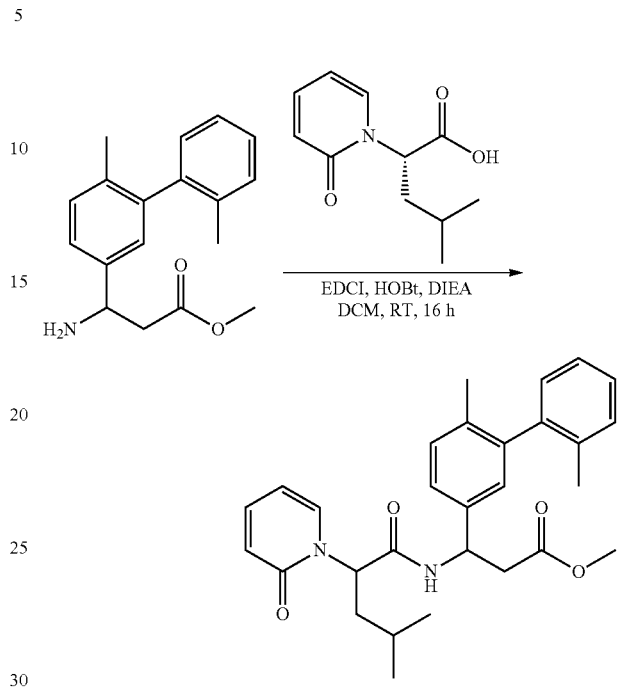

A mixture of methyl 3-amino-3-(2',6-dimethyl-[1,1'-biphenyl]-3-yl)propanoate (130 mg, 0.46 mmol), (S)-4-methyl-2-(2-oxopyridin-1(2H)-yl)pentanoic acid (96 mg, 0.46 mmol), HOBt (74 mg, 0.55 mmol), EDCI (105 mg, 0.55 mmol) and DIEA (178 mg, 1.38 mmol) in DCM (10 mL) was stirred at room temperature for 16 hours. The mixture was concentrated under reduced pressure to give a residue which was purified by preparative-TLC (pet. ether: EtOAc 1:1) to obtain the desired product methyl 3-(2',6-dimethyl-[1,1'-biphenyl]-3-yl)-3-(4-methyl-2-(2-oxopyridin-1(2H)-yl)pentanamido)propanoate as a colorless oil (150 mg). Yield 63% (86.83% purity, UV=214 nm, ESI 475 (M+H)$^+$).

Step 5: 3-(2',6-dimethyl-[1,1'-biphenyl]-3-yl)-3-(4-methyl-2-(2-oxopyridin-1(2H)-yl)pentanamido)propanoic acid

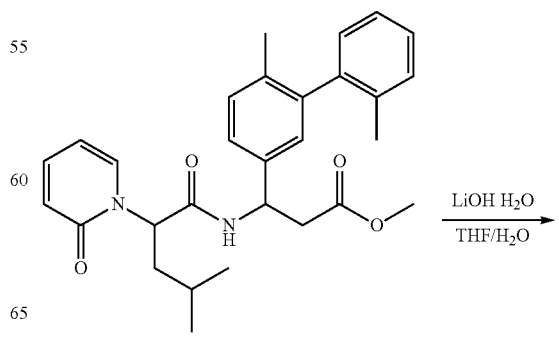

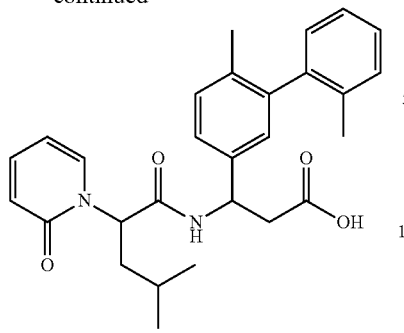

Methyl 3-(2',6-dimethyl-[1,1'-biphenyl]-3-yl)-3-(4-methyl-2-(2-oxopyridin-1(2H)-yl)pentanamido)propanoate (150 mg, 0.32 mmol) was treated with LiOH—H$_2$O (67 mg, 1.60 mmol) in THF (10 mL) and H$_2$O (2 mL) at room temperature for 0.5 hour. The mixture was acidified with HCl (1 M) to pH=5~6. The solvent was removed in vacuo and the residue was purified by preparatory HPLC A (30~70% MeCN) to give the compounds Q1 (24 mg) and Q2 (20 mg) as white solids.

Compound Q2 LC/MS B 100% purity, UV=214 nm, Rt=1.91 min, ESI 461 (M+H)$^+$.

$^1$H NMR (500 MHz, MeOD-d$_4$) δ 7.80-7.72 (m, 1H), 7.52-7.49 (m, 1H), 7.30-7.19 (m, 5H), 7.08-7.04 (m, 2H), 6.55 (d, J=9.1 Hz, 1H), 6.41 (t, J=10.0 Hz, 1H), 5.77-5.72 (m, 1H), 5.31 (t, J=7.2 Hz, 1H), 2.84-2.70 (m, 2H), 2.07-1.98 (m, 6H), 1.88-1.75 (m, 2H), 1.37-1.32 (m, 1H), 0.90-0.88 (m, 6H).

Preparation of Compounds R1 and R2

Step 1: 3-amino-3-(3-tert-butylphenyl)propanoic acid

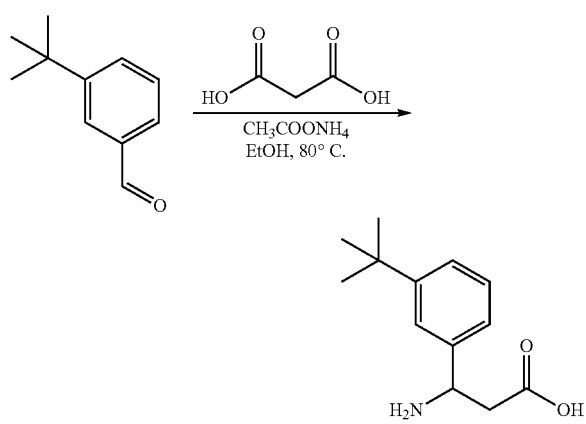

A mixture of 3-tert-butylbenzaldehyde (500 mg, 3.08 mmol), malonic acid (285 mg, 3.7 mmol) and Ammonium Acetate (962 mg, 9.25 mmol) in EtOH (15 mL) was stirred 80° C. for 16 hours. The mixture was filtered, and the filtrate was concentrated under reduced pressure. The residue was purified by Preparative-HPLC (20~50% MeCN) to give the desired product 3-amino-3-(3-tert-butylphenyl)propanoic acid as a white solid (65 mg). Yield 9% (90% purity, UV=214 nm, ESI 222 (M+H)$^+$).

Step 2: 3-(3-tert-butylphenyl)-3-(4-methyl-2-(2-oxopyridin-1(2H)-yl)pentanamido)propanoic acid

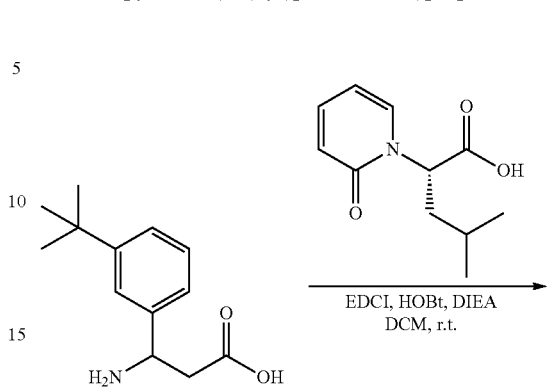

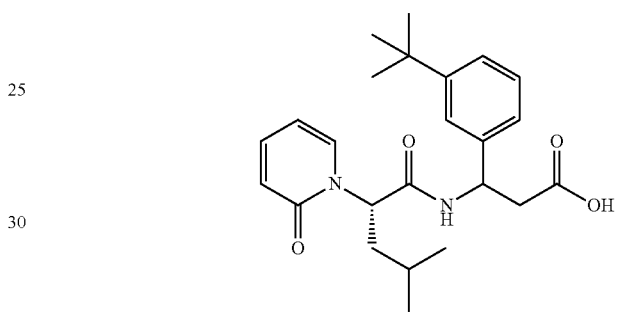

A solution of 3-amino-3-(3-tert-butylphenyl)propanoic acid (59 mg, 0.27 mmol), (S)-4-methyl-2-(2-oxopyridin-1(2H)-yl)pentanoic acid (70 mg, 0.33 mmol), EDCI (128 mg, 0.67 mmol), HOBt (46 mg, 0.34 mmol) and DIEA (103 mg, 0.8 mmol) in DCM (15 mL) was stirred at room temperature for 1 hour. The mixture was poured into 30 mL of water, and the solution was extracted with Ethyl Acetate (30 mL×2). The combined organic layers were washed with brine (10 mL), dried over Na$_2$SO$_4$ and filtered. The filtrate was concentrated under reduced pressure, and the residue was purified by Preparative-HPLC A (30~65% MeCN) to give the desired compounds R1 (19 mg) and R2 (13 mg) as white solids Compound R1 LC/MS A: 100% purity, UV=214 nm, Rt=1.58 min, ESI 413 (M+H)$^+$.

$^1$H NMR (500 MHz, MeOD) δ 7.73 (dd, J=6.9, 1.7 Hz, 1H), 7.50-7.46 (m, 1H), 7.33 (s, 1H), 7.27 (d, J=8.0 Hz, 1H), 7.21 (t, J=7.7 Hz, 1H), 7.10 (d, J=7.5 Hz, 1H), 6.54 (d, J=9.1 Hz, 1H), 6.39-6.36 (m, 1H), 5.79 (dd, J=9.1, 7.0 Hz, 1H), 5.34 (t, J=7.3 Hz, 1H), 2.79 (dd, J=11.8, 5.1 Hz, 2H), 1.99-1.87 (m, 2H), 1.54-1.37 (m, 1H), 1.27 (s, 9H), 1.03-0.89 (m, 6H).

Compound R2 LC/MS A: 100% purity, UV=214 nm, Rt=1.63 min, ESI 413 (M+H)$^+$.

$^1$H NMR (500 MHz, MeOD) δ 7.76 (dd, J=7.0, 1.8 Hz, 1H), 7.52-7.50 (m, 1H), 7.42 (s, 1H), 7.33 (d, J=7.9 Hz, 1H), 7.28 (t, J=7.7 Hz, 1H), 7.17 (d, J=7.5 Hz, 1H), 6.57 (d, J=8.4 Hz, 1H), 6.43-6.41 (m, 1H), 5.77 (dd, J=9.2, 6.9 Hz, 1H), 5.33 (t, J=7.3 Hz, 1H), 2.88-2.69 (m, 2H), 1.91-1.79 (m, 2H), 1.41-1.35 (m, 1H), 1.35 (s, 9H), 0.98-0.91 (m, 6H).

Preparation of Compounds S1 and S2

Step 1: 3-amino-3-(3-phenoxyphenyl)propanoic acid

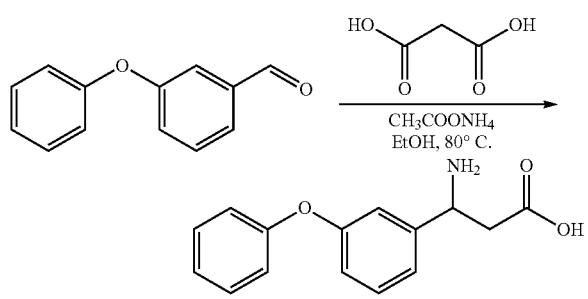

A mixture of 3-phenoxybenzaldehyde (1 g, 5 mmol), malonic acid (467 mg, 6.1 mmol) and Ammonium Acetate (1.6 g, 15.1 mmol) in EtOH (10 mL) was stirred 80° C. for 16 hours. The mixture was filtered and concentrated under reduced pressure. The residue was purified by Preparative-HPLC B (20~50% MeCN) to give the desired product 3-amino-3-(3-phenoxyphenyl)propanoic acid as a white solid (300 mg). Yield 23% (90% purity, UV=214 nm, ESI 258 (M+H)$^+$).

Step 2: 3-(4-methyl-2-(2-oxopyridin-1(2H)-yl)pentanamido)-3-(3-phenoxyphenyl)propanoic acid

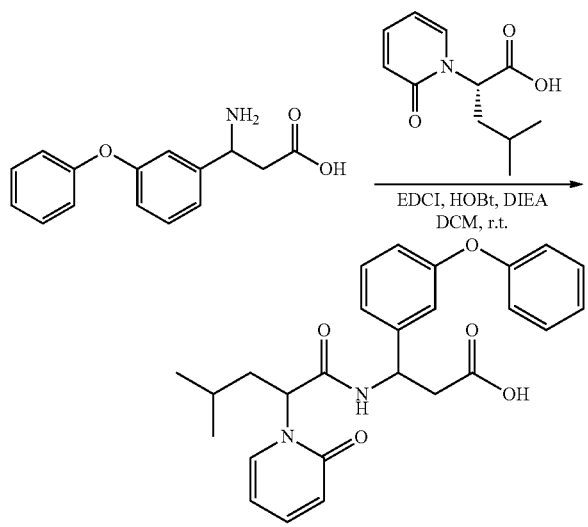

A solution of 3-amino-3-(3-phenoxyphenyl)propanoic acid (49 mg, 0.19 mmol), (S)-4-methyl-2-(2-oxopyridin-1(2H)-yl)pentanoic acid (50 mg, 0.24 mmol), EDCI (92 mg, 0.48 mmol), HOBt (48 mg, 0.36 mmol) and DIEA (93 mg, 0.72 mmol) in DCM (10 mL) was stirred at room temperature for 1 hour. The mixture was poured into 30 mL of water, and the solution was extracted with EtOAc (30 mL×2). The combined organic layers were washed with brine (10 mL), dried over Na$_2$SO$_4$ and filtered. The filtrate was concentrated under reduced pressure, and the residue was purified by Preparative-HPLC A (30~70% MeCN) to give the desired compounds 51 (6.6 mg) and S2 (1 mg) as white solids Compound S1 LC/MS A: 100% purity, UV=214 nm, Rt=1.58 min, ESI 449 (M+H)$^+$.

$^1$H NMR (500 MHz, MeOD) δ 7.69 (dd, J=7.0, 1.6 Hz, 1H), 7.47-7.45 (m, 1H), 7.34 (t, J=8.0 Hz, 2H), 7.27 (t, J=7.9 Hz, 1H), 7.13-7.04 (m, 2H), 6.99-6.91 (m, 3H), 6.82 (dd, J=8.1, 1.7 Hz, 1H), 6.53 (d, J=8.7 Hz, 1H), 6.37 (t, J=6.8 Hz, 1H), 5.76 (t, J=8.1 Hz, 1H), 5.31 (t, J=7.2 Hz, 1H), 2.90-2.65 (m, 2H), 1.93 (t, J=7.6 Hz, 2H), 1.46-1.41 (m, 1H), 0.97-0.93 (m, 6H).

Compound S2 LC/MS A: 100% purity, UV=214 nm, Rt=1.84 min, ESI 449 (M+H)$^+$.

$^1$H NMR (500 MHz, MeOD) δ 7.61 (dd, J=7.0, 1.8 Hz, 1H), 7.41-7.37 (m, 1H), 7.27-7.21 (m, 3H), 7.04-6.98 (m, 2H), 6.94-6.84 (m, 3H), 6.79 (dd, J=8.2, 1.7 Hz, 1H), 6.44 (d, J=9.1 Hz, 1H), 6.30 (t, J=6.9 Hz, 1H), 5.62 (dd, J=9.6, 6.6 Hz, 1H), 5.17 (t, J=7.3 Hz, 1H), 2.74-2.32 (m, 2H), 1.77-1.55 (m, 2H), 1.33-1.03 (m, 1H), 0.80-0.77 (m, 6H).

Preparation of Compound T2

Step 1: 3 3-amino-3-(5-bromopyridin-3-yl)propanoic acid

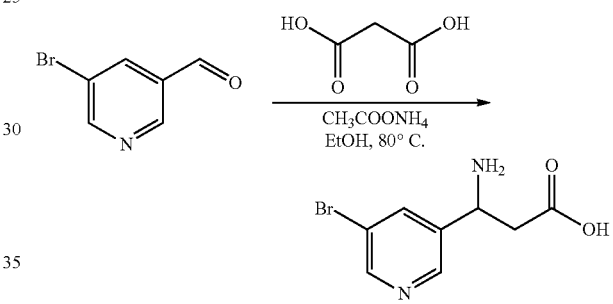

A mixture of 5-bromonicotinaldehyde (3 g, 16.1 mmol), malonic acid (1.7 g, 16.1 mmol) and Ammonium Acetate (2.6 g, 33.9 mmol) in EtOH (10 mL) was stirred 80° C. for 3 hours. The mixture was filtered and the filtrate was concentrated under reduced pressure to give the crude product 3-amino-3-(5-bromopyridin-3-yl)propanoic acid as a white solid (1.7 g). Yield 43% (UV=214 nm, ESI 245 (M+H)$^+$). The crude product was used for the next step directly.

Step 2: methyl 3-amino-3-(5-bromopyridin-3-yl)propanoate

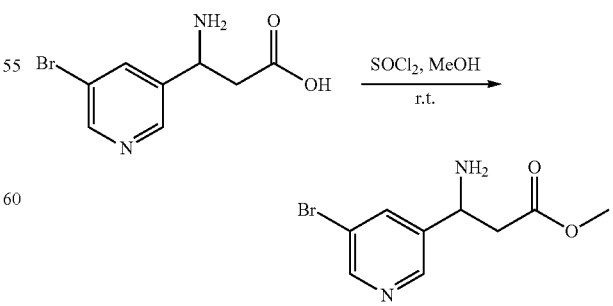

To a solution of 3-amino-3-(5-bromopyridin-3-yl)propanoic acid (1.7 g, 6.9 mmol) in 20 mL of methanol was added SOCl$_2$ (3 mL) at 0° C. The solution was stirred at room temperature for 15 hours. The solvent was removed in vacuo, and the residue was purified by silica gel column (pet. ether:EtOAc=1:2) to give the desired product methyl 3-amino-3-(5-bromopyridin-3-yl)propanoate as a colorless oil (1.2 g), Yield 67% (94% purity, UV=214 nm, ESI 259 (M+H)$^+$).

Step 3: methyl 3-amino-3-(5-(2,6-dimethylphenyl)pyridin-3-yl)propanoate

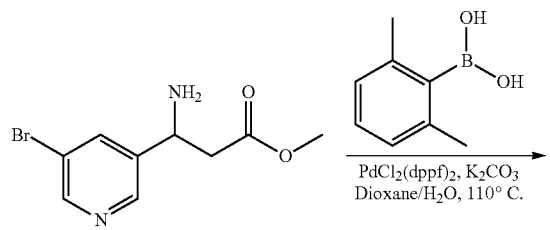

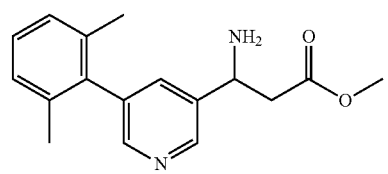

A mixture of methyl 3-amino-3-(5-bromopyridin-3-yl)propanoate (200 mg, 0.77 mmol), 2,6-dimethylphenylboronic acid (174 mg, 1.16 mmol), PdCl$_2$(dppf) (28 mg, 0.039 mmol) and K$_2$CO$_3$ (320 mg, 2.32 mmol) in 2 mL of 1,4-Dioxane and 0.1 mL of H$_2$O under N$_2$ was stirred at 110° C. for 1 h in a microwave. The mixture was filtered over Celite. The filtrate was removed in vacuo, and the residue was purified by silica gel column (pet. ether:EtOAc=1:2) to give the desired product methyl 3-amino-3-(5-(2,6-dimethylphenyl)pyridin-3-yl)propanoate as a colorless oil (200 mg). Yield 91% (90% purity, UV=214 nm, ESI 285 (M+H)$^+$).

Step 4: methyl 3-(5-(2,6-dimethylphenyl)pyridin-3-yl)-3-(4-methyl-2-(2-oxopyridin-1(2H)-yl)pentanamido)propanoate

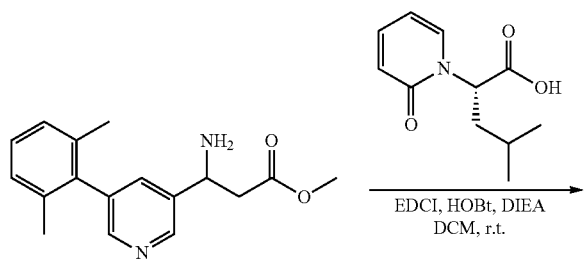

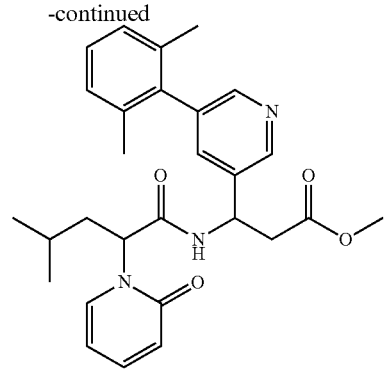

A mixture of methyl 3-amino-3-(5-(2,6-dimethylphenyl)pyridin-3-yl)propanoate (100 mg, 0.35 mmol), (S)-4-methyl-2-(2-oxopyridin-1(2H)-yl)pentanoic acid (88 mg, 0.42 mmol), EDCI (135 mg, 0.7 mmol), HOBt (71 mg, 0.53 mmol) and DIEA (136 mg, 1.06 mmol) in DCM (15 mL) was stirred at room temperature for 1 hour. The solvent was removed under reduced pressure, and the residue was purified by silica gel column (pet. ether:EtOAc=1:1) to give the desired product methyl 3-(5-(2,6-dimethylphenyl)pyridin-3-yl)-3-(4-methyl-2-(2-oxopyridin-1(2H)-yl)pentanamido)propanoate (100 mg) yield 60%. (97% purity, UV=214 nm, ESI 476 (M+H)$^+$).

Step 5: 3-(5-(2,6-dimethylphenyl)pyridin-3-yl)-3-(4-methyl-2-(2-oxopyridin-1(2H)-yl)pentanamido)propanoic acid

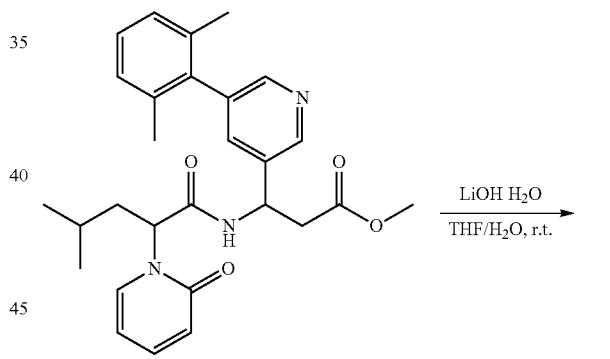

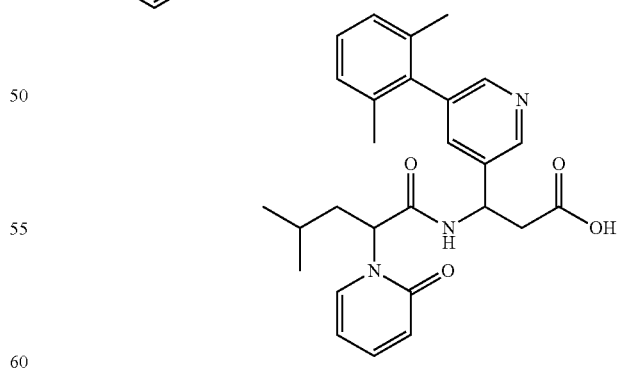

Methyl 3-(5-(2,6-dimethylphenyl)pyridin-3-yl)-3-(4-methyl-2-(2-oxopyridin-1(2H)-yl)pentanamido)propanoate (100 mg, 0.21 mmol) was treated with LiOH—H$_2$O (26 mg, 0.63 mmol) in 6 mL of THF and 2 mL of H$_2$O at room temperature for 1 h. The solution was adjusted to pH=3~4 with TFA. The solvent was removed in vacuo and the residue was purified by Preparative-HPLC A (33-70% MeCN) to give the compounds T1 (43 mg) and T2 (38 mg) as white solids Compound T1 LC/MS A: 100% purity, UV=214 nm, Rt=1.57 min, ESI 462 (M+H)+.

$^1$H NMR (500 MHz, MeOD) δ 8.53 (d, J=2.1 Hz, 1H), 8.18 (d, J=1.9 Hz, 1H), 7.70 (dd, J=7.0, 1.6 Hz, 1H), 7.53 (t, J=1.9 Hz, 1H), 7.43-7.40 (m, 1H), 7.20 (t, J=7.6 Hz, 1H), 7.15-7.10 (m, 2H), 6.44 (d, J=9.1 Hz, 1H), 5.79-5.65 (m, 1H), 5.42 (t, J=7.2 Hz, 1H), 2.88 (d, J=7.2 Hz, 2H), 1.98 (s, 3H), 1.94 (t, J=7.4 Hz, 2H), 1.87 (s, 3H), 1.48-1.42 (m, 1H), 0.98-0.95 (m, 6H)

Compound T2 LC/MS A: 99% purity, UV=214 nm, Rt=1.59 min, ESI 462 (M+H)+.

$^1$H NMR (500 MHz, MeOD) δ 8.59 (d, J=2.1 Hz, 1H), 8.26 (d, J=1.9 Hz, 1H), 7.76 (dd, J=7.0, 1.7 Hz, 1H), 7.68 (t, J=2.0 Hz, 1H), 7.53-7.50 (m, 1H), 7.26-7.19 (m, 1H), 7.23-7.15 (m, 2H), 6.56 (d, J=8.4 Hz, 1H), 6.43-6.40 (m, 1H), 5.80-5.70 (m, 1H), 5.38 (t, J=7.3 Hz, 1H), 2.96-2.85 (m, 2H), 2.02 (s, 6H), 1.91-1.75 (m, 2H), 1.35-1.30 (m, 1H), 0.91-0.88 (m, 6H).

Preparation of Compounds T2a and T2b

The T2 mixture was further separated by Preparative chiral SFC D to give diastereomeric compounds T2a (8 mg) and T2b (7.5 mg) as white solids Compound T2a LC/MS A: 99% purity, UV=214 nm, Rt=1.56 min, ESI 462 (M+H)+.

$^1$H NMR (500 MHz, MeOD) δ 8.59 (d, J=2.0 Hz, 1H), 8.26 (d, J=1.8 Hz, 1H), 7.76 (dd, J=6.9, 1.7 Hz, 1H), 7.68 (t, J=2.0 Hz, 1H), 7.53-7.50 (m 1H), 7.26-7.19 (m, 1H), 7.23-7.15 (m, 2H), 6.56 (d, J=9.1 Hz, 1H), 6.43-6.40 (m, 1H), 5.75 (t, J=8.1 Hz, 1H), 5.38 (t, J=7.3 Hz, 1H), 2.97-2.86 (m, 2H), 2.02 (s, 6H), 1.83 (t, J=7.4 Hz, 2H), 1.36-1.30 (m, 1H), 0.91-0.88 (m, 6H).

Compound T2b LC/MS A: 100% purity, UV=214 nm, Rt=1.49 min, ESI 462 (M+H)+.

$^1$H NMR (500 MHz, MeOD) δ 8.52 (s, 1H), 8.18 (s, 1H), 7.69 (dd, J=7.0, 1.8 Hz, 1H), 7.50 (s, 1H), 7.43-7.39 (m, 1H), 7.20 (t, J=7.6 Hz, 1H), 7.15-7.09 (m, 2H), 6.45 (d, J=9.1 Hz, 1H), 6.36-6.33 (m, 1H), 5.73 (t, J=8.0 Hz, 1H), 5.42 (t, J=7.0 Hz, 1H), 2.91 (d, J=7.1 Hz, 2H), 1.97 (s, 3H), 1.96-1.92 (m, 2H), 1.87 (s, 3H), 1.49-1.43 (m, 1H), 0.98-0.95 (m, 6H).

Preparation of Compound U2

Step 1: 2-bromo-4,4,4-trifluorobutanoic acid

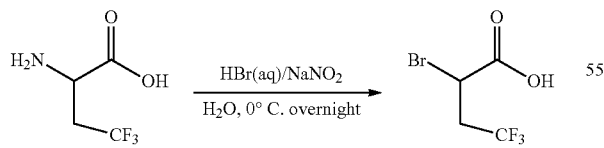

To a solution of 2-amino-4,4,4-trifluorobutanoic acid (1.0 g, 6.4 mmol) in HBr (40% in water, 6 mL) at 0° C. was added a solution of NaNO$_2$ (0.66 g, 9.6 mmol) in H$_2$O (4 mL) dropwise. The reaction mixture was stirred at room temperature for 16 hours. The solution was extracted with EtOAc (20 mL×2). The combined organic layers were dried over Na$_2$SO$_4$, filtered and the filtrate was concentrated under reduced pressure to give the crude product 2-bromo-4,4,4-trifluorobutanoic acid as an orange solid (1 g). The crude product was used for the next step directly.

Step 2: 4,4,4-trifluoro-2-(2-oxopyridin-1(2H)-yl)butanoic acid

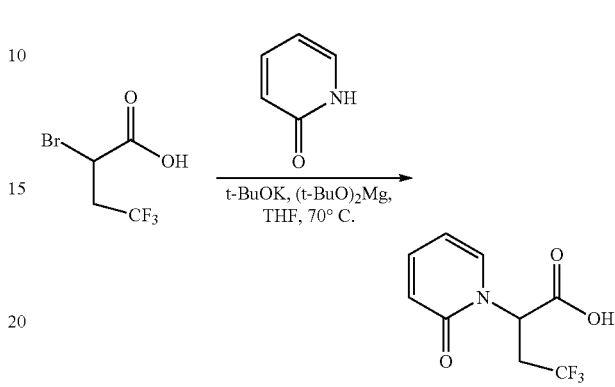

A mixture of 2-bromo-4,4,4-trifluorobutanoic acid (1 g, 4.5 mmol) and (t-BuO)$_2$Mg (1.02 g, 6 mmol) in dry THF (20 mL) was stirred at 30° C. for 3 hours under N$_2$ atmosphere, and then pyridin-2-ol (336 mg, 3 mmol) and t-BuOK (340 mg, 3.06 mmol) was added. The reaction mixture was stirred at 70° C. for 16 hours under N$_2$. The mixture was cooled to room temperature and acidified with HCl (4 M) until pH=5. The solution was concentrated under reduced pressure to give a residue. Purification via reversed phase flash chromatography (0%~60% MeOH in H$_2$O (5% TFA)) to provide the desired product (4,4,4-trifluoro-2-(2-oxopyridin-1(2H)-yl)butanoic acid (130 mg). Yield 23% (96% purity, UV=214 nm, ESI 236 (M+H)+).

Step 3: methyl 3-(5-(2,6-dimethylphenyl)pyridin-3-yl)-3-(4,4,4-trifluoro-2-(2-oxopyridin-1(2H)-yl)butanamido)propanoate

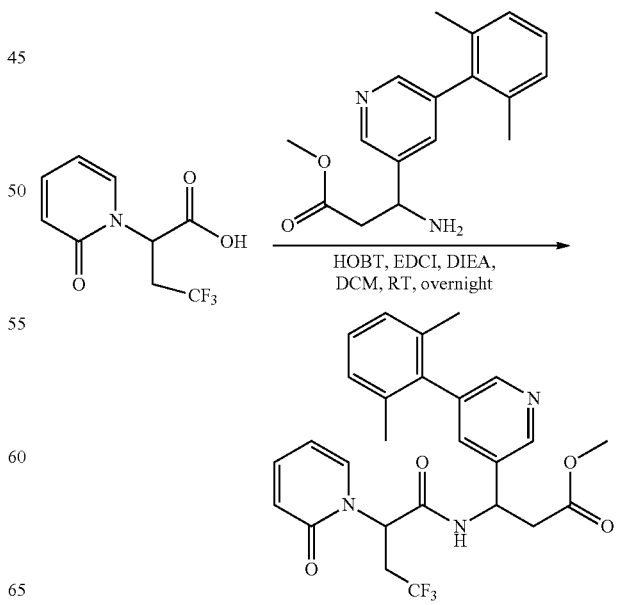

A mixture of (4,4,4-trifluoro-2-(2-oxopyridin-1(2H)-yl) butanoic acid (130 mg, 0.55 mmol), methyl 3-amino-3-(5-(2,6-dimethylphenyl)pyridin-3-yl)propanoate (140 mg, 0.5 mmol), HOBt (81 mg, 0.6 mmol), EDCI (115 mg, 0.6 mmol) and DIEA (258 mg, 2 mmol) in DCM (10 mL) was stirred at room temperature for 16 hours. The mixture was poured into water and the solution was extracted with DCM (30 mL×2). The combined organic layers were dried over Na$_2$SO$_4$, filtered and the filtrate was concentrated under reduced pressure to give a residue, which was purified by flash column chromatography (0%~80% EtOAc in pet ether) to give the desired product methyl 3-(5-(2,6-dimethylphenyl)pyridin-3-yl)-3-(4,4,4-trifluoro-2-(2-oxopyridin-1(2H)-yl)butanamido)propanoate (160 mg). Yield 64% (92% purity, UV=214 nm, ESI 502 (M+H)$^+$).

Step 4: 3-(5-(2,6-dimethylphenyl)pyridin-3-yl)-3-(4,4,4-trifluoro-2-(2-oxopyridin-1(2H)-yl)butanamido)propanoic acid

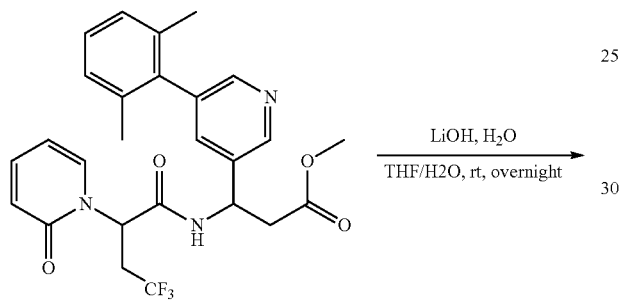

Methyl 3-(5-(2,6-dimethylphenyl)pyridin-3-yl)-3-(4,4,4-trifluoro-2-(2-oxopyridin-1 (2H)-yl)butanamido)propanoate (160 mg, 0.32 mmol) was treated with LiOH—H$_2$O (40 mg, 0.96 mmol) in THF (6 mL) and H$_2$O (1 mL) at room temperature for 16 hours. The mixture was acidified with HCl (1 M) until pH=5. The mixture was concentrated under reduced pressure to give a residue, which was purified by Preparative-HPLC B (30~70% MeCN) to give the compounds U1 (34 mg) and U2 (12 mg) as white solids.

Compound U2 LC/MS B: 100% purity, UV=214 nm, Rt=1.50 min, ESI 488 (M+H)$^+$.

$^1$H NMR (500 MHz, MeOD) δ 8.58 (d, J=1.7 Hz, 1H), 8.25 (d, J=1.6 Hz, 1H), 7.73 (d, J=5.5 Hz, 1H), 7.68 (s, 1H), 7.59-7.51 (m, 1H), 7.23-7.14 (m, 3H), 6.58 (d, J=9.1 Hz, 1H), 6.45 (t, J=6.4 Hz, 1H), 5.71 (d, J=5.3 Hz, 1H), 5.44 (t, J=7.1 Hz, 1H), 3.15 (m, 1H), 3.06-2.93 (m, 1H), 2.88 (d, J=6.8 Hz, 2H), 2.01 (s, 6H).

Preparation of Compound V2

Step 1: 2-bromo-3-cyclopropylpropanoic acid

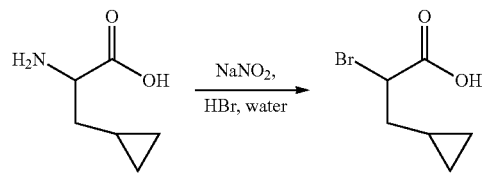 [SMILES: NC(CC1CC1)C(=O)O ; "HBr, water" ; "NaNO2," ; O=C(O)C(Br)CC1CC1]

To a solution of (2-amino-3-cyclopropylpropanoic acid (300 mg, 2.32 mmol) in HBr (40% in water, 4 mL) at 0° C. was added a solution of NaNO$_2$ (321 mg, 4.65 mmol) in H$_2$O (4 mL) dropwise. The reaction mixture was stirred at room temperature for 16 hours. The solution was extracted with EtOAc (30 mL×2), and the combined organic layers were dried over Na$_2$SO$_4$ and filtered. The filtrate was concentrated in vacuo to provide the crude product 2-bromo-3-cyclopropylpropanoic acid (447 mg) as a yellow oil. Yield 100%. The crude product was used for the next step directly.

Step 2: 3-cyclopropyl-2-(2-oxopyridin-1(2H)-yl)propanoic acid

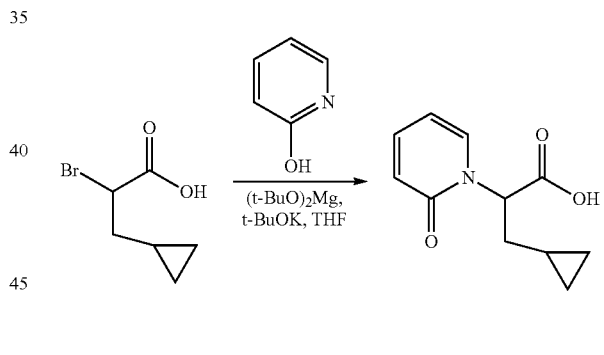

To a solution of (2-bromo-3-cyclopropylpropanoic acid (740 mg, 3.85 mmol) in dry THF (20 mL) was added (t-BuO)$_2$Mg (1.32 g, 7.71 mmol) and the solution was stirred at 30° C. for 1 hour under N$_2$ atmosphere. Then pyridin-2-ol (366 mg, 3.85 mmol) and t-BuOK (431 mg, 3.85 mmol) were added, and the reaction mixture was stirred at 70° C. for 16 hours under N$_2$. The mixture was cooled to room temperature and acidified to pH=5 with a HCl (4 M) solution. The solvent was concentrated under reduced pressure to give a residue, which was purified by reversed phase flash chromatography (0%~80% MeOH in H$_2$O (5% NH$_4$HCO$_3$)) to provide the desired product 3-cyclopropyl-2-(2-oxopyridin-1(2H)-yl)propanoic acid as a white solid (83 mg). Yield 10% (98% purity, UV=214 nm, ESI 208 (M+H)$^+$).

Step 3: methyl 3-(3-cyclopropyl-2-(2-oxopyridin-1(2H)-yl)propanamido)-3-(5-(2,6-dimethylphenyl)pyridin-3-yl)propanoate

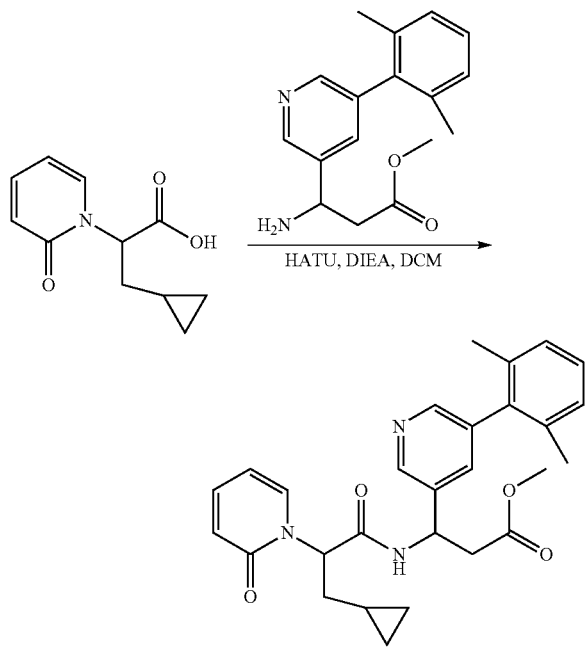

A mixture of 3-cyclopropyl-2-(2-oxopyridin-1(2H)-yl)propanoic acid (83 mg, 0.40 mmol), methyl 3-amino-3-(5-(2,6-dimethylphenyl)pyridin-3-yl)propanoate (114 mg, 0.40 mmol), HATU (228 mg, 0.60 mmol), and DIEA (155 mg, 1.20 mmol) in DCM (10 mL) was stirred at room temperature for 2 hours. The mixture was poured into 10 mL of water and the solution was extracted with DCM (30 mL×3). The organic phase was dried over $Na_2SO_4$, filtered and the filtrate concentrated in vacuo to provide a yellow oil, which was purified by silica gel column (pet. ether:EtOAc=1:1) to provide the desired product methyl 3-(3-cyclopropyl-2-(2-oxopyridin-1(2H)-yl)propanamido)-3-(5-(2,6-dimethylphenyl)pyridin-3-yl)propanoate as a yellow oil (200 mg). Yield 88% (95% purity, UV=254 nm, ESI 474 $(M+H)^+$).

Step 4: 3-((S)-3-cyclopropyl-2-(2-oxopyridin-1(2H)-yl)propanamido)-3-(5-(2,6-dimethylphenyl)pyridin-3-yl)propanoic acid

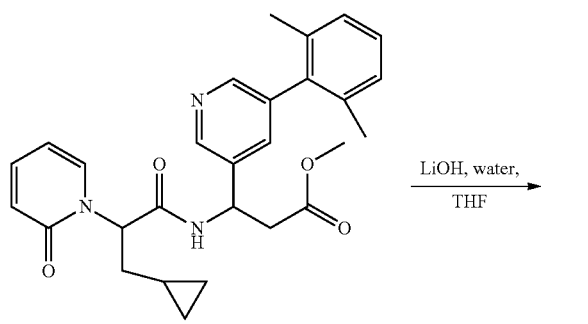

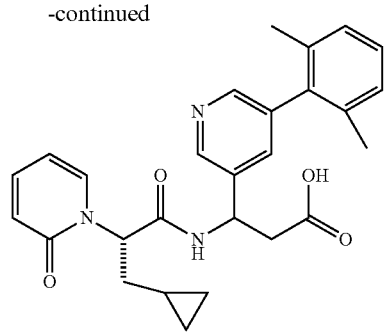

Methyl 3-(3-cyclopropyl-2-(2-oxopyridin-1 (2H)-yl)propanamido)-3-(5-(2,6-dimethylphenyl)pyridin-3-yl)propanoate (200 mg, 0.42 mmol) was treated with LiOH (1 M in $H_2O$, 0.6 mL) in THF (2 mL) at room temperature for 2 h. The mixture was adjusted with 1 M HCl to pH=5-6, and the solvent was removed in vacuo. The residue was purified by preparatory HPLC B (30-70% MeCN) to give the desired compounds V1 (23.6 mg) and V2 (30.4 mg) as white solids.

Compound V2 LC/MS A: 98% purity, UV=214 nm, Rt=1.52 min, ESI 460 $(M+H)^+$.

$^1$H NMR (500 MHz, MeOD) δ 8.59 (s, 1H), 8.24 (s, 1H), 7.77 (dd, J=7.0, 1.7 Hz, 1H), 7.67 (s, 1H), 7.51 (t, J=8.8, 6.7, 1.9 Hz, 1H), 7.24-7.12 (m, 3H), 6.55 (d, J=8.9 Hz, 1H), 6.41 (t, J=6.8 Hz, 1H), 5.62 (t, J=7.8 Hz, 1H), 5.41 (t, J=7.3 Hz, 1H), 3.00-2.83 (m, 2H), 2.00 (s, 3H), 1.99 (s, 3H), 1.88-1.94 (m, 1H), 1.84-1.76 (m, 1H), 0.53 (s, 1H), 0.33-0.35 (m, 1H), 0.23-0.27 (m, 1H), 0.02-0.04 (m, 2H).

Preparation of Compounds W1 and W2

Step 1: methyl 3-(5-(2,6-dimethylphenyl)pyridin-3-yl)-3-(4-methyl-2-(4-methyl-2-oxopyridin-1(2H)-yl)pentanamido)propanoate

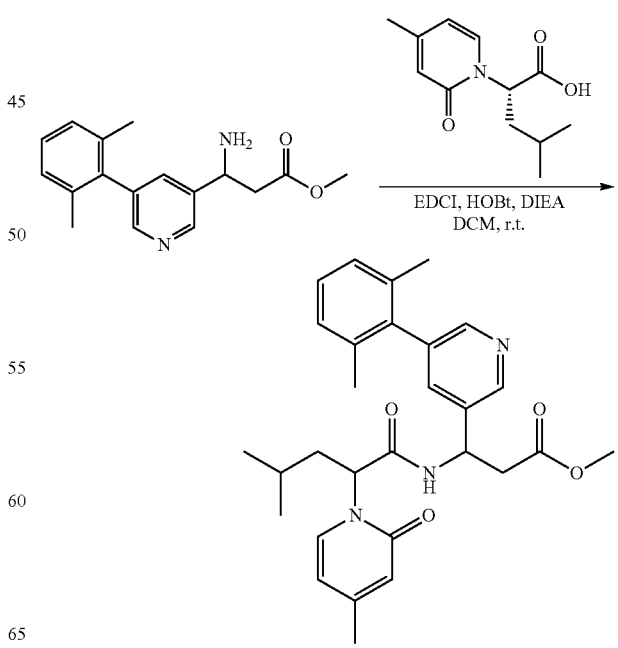

A mixture of methyl 3-amino-3-(5-(2,6-dimethylphenyl)pyridin-3-yl)propanoate (100 mg, 0.35 mmol), (S)-4-methyl-2-(4-methyl-2-oxopyridin-1(2H)-yl)pentanoic acid (94 mg, 0.42 mmol), EDCI (135 mg, 0.7 mmol), HOBt (71 mg, 0.53 mmol) and DIEA (136 mg, 1.06 mmol) in DCM (15 mL) was stirred at room temperature for 1 hour. The solvent was removed under reduced pressure, and the residue was purified by silica gel column (pet. ether:EtOAc=1:1) to give the desired product methyl 3-(5-(2,6-dimethylphenyl)pyridin-3-yl)-3-(4-methyl-2-(4-methyl-2-oxopyridin-1(2H)-yl)pentanamido)propanoate (100 mg) Yield 58%. (96% purity, UV=214 nm, ESI 490 (M+H)$^+$).

Step 2: 3-(5-(2,6-dimethylphenyl)pyridin-3-yl)-3-(4-methyl-2-(4-methyl-2-oxopyridin-1(2H)-yl)pentanamido)propanoic acid

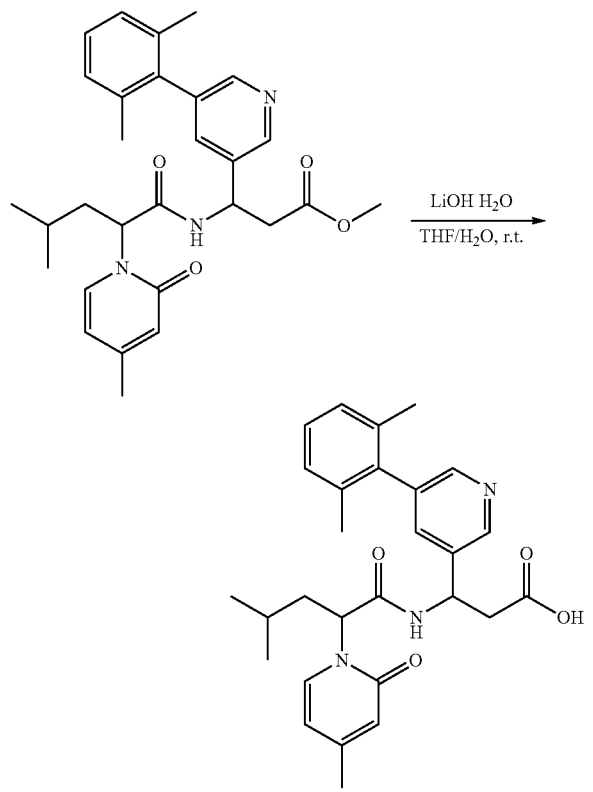

Methyl 3-(5-(2,6-dimethylphenyl)pyridin-3-yl)-3-(4-methyl-2-(4-methyl-2-oxopyridin-1(2H)-yl)pentanamido)propanoate (100 mg, 0.20 mmol) was treated with LiOH—H$_2$O (26 mg, 0.6 mmol) in 6 mL of THF and 2 mL of H$_2$O at room temperature for 1 h. The solution was adjusted to pH=3~4 with TFA. The solvent was removed in vacuo and the residue was purified by Preparative-HPLC A (33-70% MeCN) to give the compounds W1 (28 mg) and W2 (27 mg) as white solids Compound W1 LC/MS A: 100% purity, UV=214 nm, Rt=1.58 min, ESI 475.8 (M+H)$^+$.

$^1$H NMR (500 MHz, MeOD) δ 8.53 (d, J=1.9 Hz, 1H), 8.17 (d, J=1.6 Hz, 1H), 7.57 (d, J=7.1 Hz, 1H), 7.53 (t, J=1.9 Hz, 1H), 7.21-7.11 (m, 3H), 6.27 (s, 1H), 6.23 (dd, J=7.1, 1.8 Hz, 1H), 5.70 (t, J=8.0 Hz, 1H), 5.41 (t, J=7.2 Hz, 1H), 2.87 (d, J=7.2 Hz, 2H), 2.19 (s, 3H), 1.98 (s, 3H), 1.91 (dd, J=18.5, 11.1 Hz, 2H), 1.86 (s, 3H), 1.46-1.43 (m, 1H), 0.98-0.94 (m, 6H).

Compound W2 LC/MS A: 99% purity, UV=214 nm, Rt=1.61 min, ESI 475.8 (M+H)$^+$.

$^1$H NMR (500 MHz, MeOD) δ 8.59 (d, J=1.8 Hz, 1H), 8.24 (d, J=1.6 Hz, 1H), 7.67 (t, J=1.9 Hz, 1H), 7.63 (d, J=7.2 Hz, 1H), 7.25-7.12 (m, 3H), 6.38 (s, 1H), 6.31 (dd, J=7.1, 1.8 Hz, 1H), 5.70 (t, J=8.1 Hz, 1H), 5.37 (t, J=7.2 Hz, 1H), 2.88-2.85 (m, 2H), 2.24 (s, 3H), 2.02 (s, 6H), 1.81 (t, J=7.6 Hz, 2H), 1.33-1.31 (m, 1H), 0.90-0.88 (m, 6H).

Preparation of Compounds W1a and W1b

Step 1: methyl (S)-3-((tert-butoxycarbonyl)amino)-3-(5-(2,6-dimethylphenyl)pyridin-3-yl)propanoate

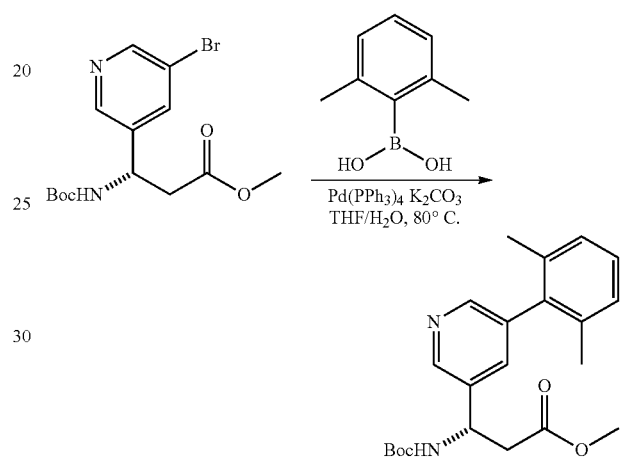

A mixture of methyl (S)-3-(5-bromopyridin-3-yl)-3-((tert-butoxycarbonyl)amino)propanoate (3.0 g, 8.38 mmol), (2,6-dimethylphenyl)boronic acid (2.5 g, 16.78 mmol), Pd(PPh$_3$)$_4$ (969 mg, 0.84 mmol) and K$_2$CO$_3$ (2.3 mg, 16.76 mmol) in THF (20 mL) and H$_2$O (2 mL) under N$_2$ atmosphere was stirred at 80° C. for 16 hours. The mixture was poured into water and the solution was extracted with EtOAc (30 mL×2). The combined organic phase was dried over Na$_2$SO$_4$ and filtered. The filtrate was concentrated under reduced pressure, and the residue was purified by silica gel column (pet. ether:EtOAc=4:1) to give the desired product methyl (S)-3-((tert-butoxycarbonyl)amino)-3-(5-(2,6-dimethylphenyl)pyridin-3-yl)propanoate as a yellow oil (2.7 g). Yield 63% (73% purity, UV=214 nm, ESI 385.1 (M+H)$^+$).

Step 2: methyl (S)-3-amino-3-(5-(2,6-dimethylphenyl)pyridin-3-yl)propanoate

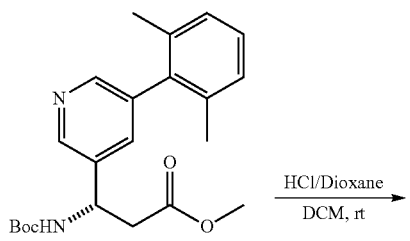

-continued

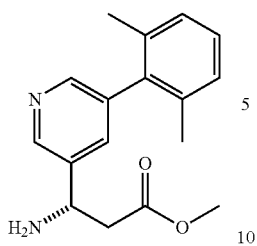

To a solution of methyl (S)-3-((tert-butoxycarbonyl)amino)-3-(5-(2,6-dimethylphenyl)pyridin-3-yl)propanoate (2.7 g, 7.03 mmol) in DCM (10 mL) was added HCl in Dioxane (4 M, 5 mL). The solution was stirred at room temperature for 2 hours. Sat. aqueous NaHCO$_3$ (20 mL) was added, and the solution was extracted with EtOAc (30 mL×2). The combined organic phase was dried over Na$_2$SO$_4$ and filtered. The filtrate was concentrated under reduced pressure to provide the crude product methyl (S)-3-amino-3-(5-(2,6-dimethylphenyl)pyridin-3-yl)propanoate as a yellow oil (1.9 g). Yield 95% (68% purity, UV=214 nm, ESI 285.1 (M+H)$^+$). The crude product was used for the next step directly.

Step 3: methyl (3S)-3-(5-(2,6-dimethylphenyl)pyridin-3-yl)-3-(4-methyl-2-(4-methyl-2-oxopyridin-1(2H)-yl)pentanamido)propanoate

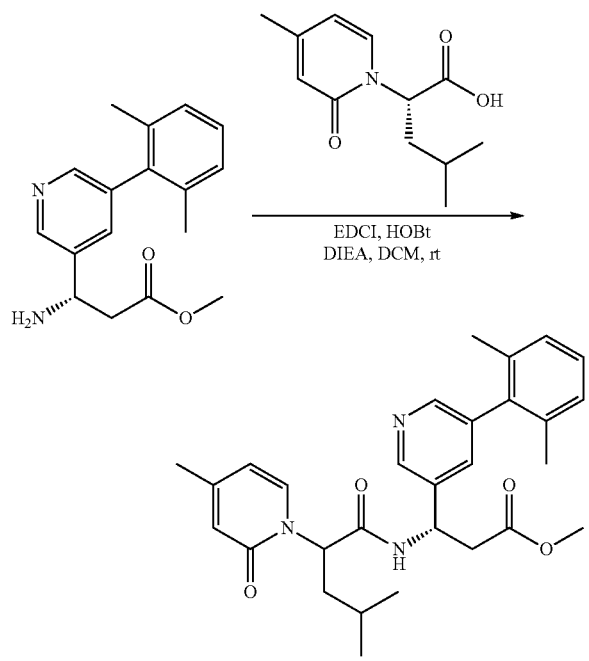

A mixture of methyl (S)-3-amino-3-(5-(2,6-dimethylphenyl)pyridin-3-yl)propanoate (1.5 g, 5.28 mmol), (S)-4-methyl-2-(4-methyl-2-oxopyridin-1(2H)-yl)pentanoic acid (1.4 g, 6.34 mmol), HOBt (1.06 g, 7.92 mmol), EDCI (1.5 g, 7.92 mmol) and DIEA (2.04 g, 15.85 mmol) in DCM (30 mL) was stirred at room temperature for 2 hours. The mixture was poured into water, and the solution was extracted with EtOAc (30 mL×2). The combined organic phase was dried over Na$_2$SO$_4$ and filtered. The filtrate was concentrated under reduced pressure to give the crude product methyl (3S)-3-(5-(2,6-dimethylphenyl)pyridin-3-yl)-3-(4-methyl-2-(4-methyl-2-oxopyridin-1(2H)-yl)pentanamido)propanoate as a yellow oil (3.95 g). Yield 52% (52% purity, UV=214 nm, ESI 490.1 (M+H)$^+$). The crude product was used for the next step directly.

Step 4: (3S)-3-(5-(2,6-dimethylphenyl)pyridin-3-yl)-3-(4-methyl-2-(4-methyl-2-oxopyridin-1(2H)-yl)pentanamido)propanoic acid

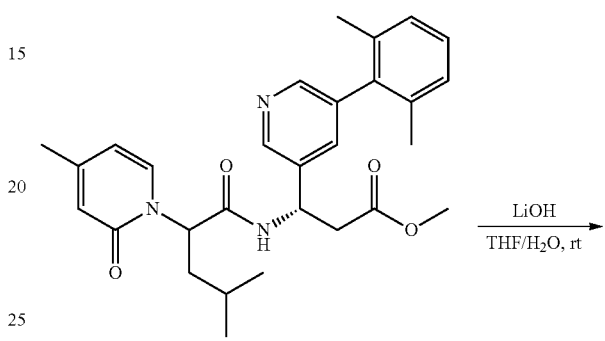

Methyl (3 S)-3-(5-(2,6-dimethylphenyl)pyridin-3-yl)-3-(4-methyl-2-(4-methyl-2-oxopyridin-1 (2H)-yl)pentanamido)propanoate (3.95 g, 8.08 mmol) was treated with LiOH—H$_2$O (1.02 g, 24.23 mmol) in THF (10 mL) and H$_2$O (2 mL) at room temperature for 2 hours. The mixture was acidified with HCl (1 M) until pH=5. The solvent was removed in vacuo and the residue was purified by Preparative-HPLC A (30~70% MeCN) to give the compounds W1a (380 mg) and W1b (453 mg) as white solids.

Compound W1a LC/MS B: 99% purity, UV=214 nm, Rt=1.59 min, ESI 476.2 (M+H)$^+$.

$^1$H NMR (500 MHz, CDCl$_3$) δ 8.53 (s, 1H), 8.20 (s, 1H), 7.58 (d, J=7.1 Hz, 1H), 7.54 (s, 1H), 7.21 (t, J=7.5 Hz, 1H), 7.14 (t, J=6.6 Hz, 2H), 6.32-6.15 (m, 2H), 5.70 (t, J=8.0 Hz, 1H), 5.43 (t, J=7.3 Hz, 1H), 2.94 (d, J=7.3 Hz, 2H), 2.19 (s, 3H), 1.98 (s, 3H), 1.92 (t, J=7.4 Hz, 2H), 1.87 (s, 3H), 1.47 (t, J=6.9 Hz, 1H), 1.40-1.40 (m, 1H), 0.95-0.92 (m, 6H).

Compound W1b LC/MS B: 100% purity, UV=214 nm, Rt=1.62 min, ESI 476.3 (M+H)$^+$.

$^1$H NMR (500 MHz, CDCl$_3$) δ 8.54 (s, 1H), 8.22 (s, 1H), 7.62 (s, 1H), 7.59 (d, J=7.1 Hz, 1H), 7.20-7.12 (m, 3H), 6.34 (s, 1H), 6.26 (dd, J=7.1, 1.5 Hz, 1H), 5.65 (t, J=8.1 Hz, 1H), 5.34 (t, J=7.3 Hz, 1H), 2.89 (dd, J=17.3, 7.4 Hz, 2H), 2.19 (s, 3H), 1.97 (s, 6H), 1.78-1.75 (m, 2H), 1.32-1.25 (m, 1H), 0.87-0.80 (m, 6H).

Preparation of Compounds W2a and W2b

Step 1: (R)-methyl 3-(tert-butoxycarbonylamino)-3-(5-(2,6-dimethylphenyl)pyridin-3-yl)propanoate

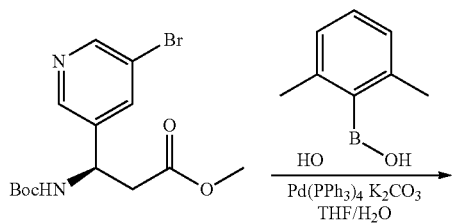

A mixture of (R)-methyl 3-(5-bromopyridin-3-yl)-3-(tert-butoxycarbonylamino)propanoate (3.0 g, 8.38 mmol), 2,6-dimethylphenylboronic acid (2.5 g, 16.78 mmol), Pd(PPh$_3$)$_4$ (969 mg, 0.84 mmol) and K$_2$CO$_3$ (2.3 g, 16.76 mmol) in THF (20 mL) and H$_2$O (2 mL) was stirred at 80° C. for 16 hours under N$_2$ atmosphere. The mixture was cooled to room temperature and poured into water. The solution was extracted with EtOAc (30 mL×2). The combined organic layer was dried over Na$_2$SO$_4$, filtered and the filtrate was concentrated under reduced pressure to give a residue, which was purified by flash column (0%~20% EtOAc in Petroleum) to provide the desired product (R)-methyl 3-(tert-butoxycarbonylamino)-3-(5-(2,6-dimethylphenyl)pyridin-3-yl)propanoate as a yellow oil (2.7 g). Yield 63% (73.57% purity, UV=214 nm, ESI 385 (M+H)$^+$).

Step 2: methyl (R)-3-amino-3-(5-(2,6-dimethylphenyl)pyridin-3-yl)propanoate

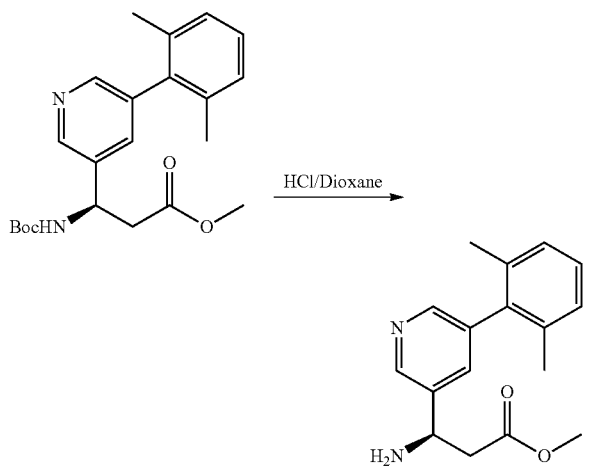

To a solution of (R)-methyl 3-(tert-butoxycarbonylamino)-3-(5-(2,6-dimethylphenyl)pyridin-3-yl)propanoate (2.7 g, 7 mmol) in DCM (10 mL) was added HCl/Dioxane (4M, 5 mL), and the solution was stirred at room temperature for 2 hours. The mixture was poured into Sat. aqueous NaHCO$_3$(20 mL) and the solution was extracted with EtOAc (30 mL×2). The combined organic layers were dried over Na$_2$SO$_4$, filtered, and the filtrate was concentrated under reduced pressure to provide the crude product (R)-methyl 3-amino-3-(5-(2,6-dimethylphenyl)pyridin-3-yl)propanoate as a yellow oil (1.9 g). Yield 95% (68.19% purity, UV=214 nm, ESI 285 (M+H)$^+$). The crude product was used for next step directly without further purification.

Step 3: (3R)-methyl 3-(5-(2,6-dimethylphenyl)pyridin-3-yl)-3-(4-methyl-2-(4-methyl-2-oxopyridin-1(2H)-yl)pentanamido)propanoate

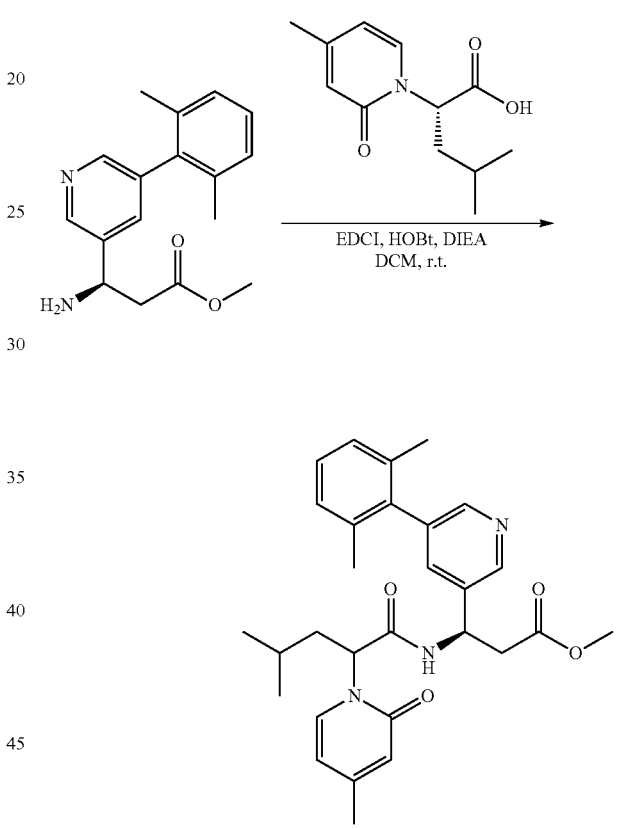

A mixture of (R)-methyl 3-amino-3-(5-(2,6-dimethylphenyl)pyridin-3-yl)propanoate (100 mg, 0.31 mmol), (S)-4-methyl-2-(4-methyl-2-oxopyridin-1(2H)-yl)pentanoic acid (84 mg, 0.37 mmol), EDCI (120 mg, 0.62 mmol), HOBt (63 mg, 0.47 mmol) and DIEA (121 mg, 0.94 mmol) in DCM (15 mL) was stirred at room temperature for 1 hour. The solvent was removed under reduced pressure, and the residue was purified by silica gel column (pet. ether:EtOAc=1:2) to give the desired product (3R)-methyl 3-(5-(2,6-dimethylphenyl)pyridin-3-yl)-3-(4-methyl-2-(4-methyl-2-oxopyridin-1(2H)-yl)pentanamido)propanoate as a colorless oil (100 mg). Yield 66%. (76% purity, UV=214 nm, ESI 490 (M+H)$^+$).

Step 4: (3R)-3-(5-(2,6-dimethylphenyl)pyridin-3-yl)-3-(4-methyl-2-(4-methyl-2-oxopyridin-1(2H)-yl)pentanamido)propanoic acid

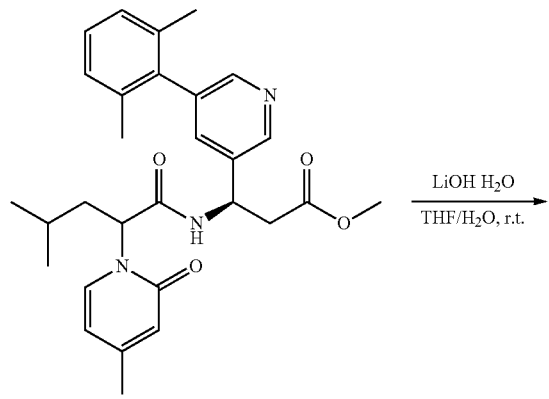

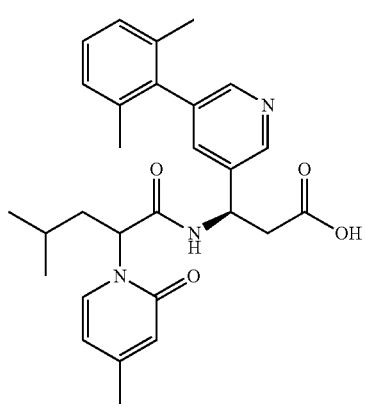

(3R)-methyl 3-(5-(2,6-dimethylphenyl)pyridin-3-yl)-3-(4-methyl-2-(4-methyl-2-oxopyridin-1(2H)-yl)pentanamido)propanoate (100 mg, 0.20 mmol) was treated with LiOH—H$_2$O (26 mg, 0.6 mmol) in 6 mL of THF and 2 mL of H$_2$O at room temperature for 3 h. The solution was adjusted to pH=3~4 with TFA. The solvent was removed in vacuo and the residue was purified by Preparative-HPLC A (33-70% MeCN) to give the compounds W2a (31 mg) and W2b (22 mg) as white solids Compound W2a LC/MS A: 99% purity, UV=214 nm, Rt=1.57 min, ESI 476 (M+H)$^+$.

$^1$H NMR (500 MHz, MeOD) δ 8.52 (d, J=1.9 Hz, 1H), 8.19 (d, J=1.6 Hz, 1H), 7.57 (d, J=7.1 Hz, 1H), 7.53 (t, J=1.9 Hz, 1H), 7.23-7.10 (m, 3H), 6.26 (d, J=10.2 Hz, 1H), 6.23 (dd, J=7.1, 1.9 Hz, 1H), 5.72-5.66 (m, 1H), 5.42 (t, J=7.2 Hz, 1H), 2.93 (d, J=7.2 Hz, 2H), 2.19 (s, 3H), 1.97 (s, 3H), 1.94-1.89 (m, 2H), 1.86 (s, 3H), 1.52-1.37 (m, 1H), 0.98-0.87 (m, 6H).

Compound W2b LC/MS A: 99% purity, UV=214 nm, Rt=1.60 min, ESI 476 (M+H)$^+$.

$^1$H NMR (500 MHz, MeOD) δ 8.58 (s, 1H), 8.26 (s, 1H), 7.67 (t, J=1.9 Hz, 1H), 7.63 (d, J=7.1 Hz, 1H), 7.27-7.10 (m, 3H), 6.38 (s, 1H), 6.31 (dd, J=7.2, 1.9 Hz, 1H), 5.70 (t, J=8.1 Hz, 1H), 5.38 (t, J=7.4 Hz, 1H), 2.99-2.83 (m, 2H), 2.24 (s, 3H), 2.02 (s, 5H), 1.89-1.74 (m, 2H), 1.35-1.30 (m, 1H), 0.90-0.87 (m, 6H).

Preparation of Compounds X1 and X2

Step 1: methyl 3-(5-bromopyridin-3-yl)-3-(tert-butoxycarbonylamino)propanoate

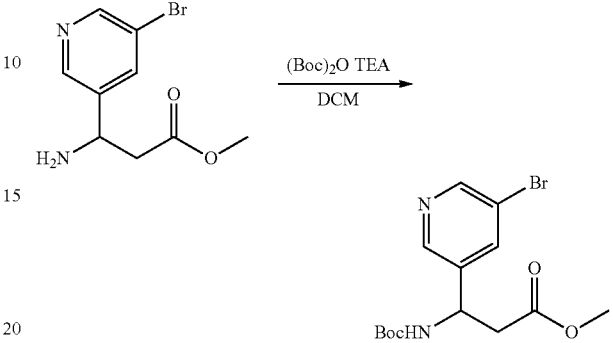

To a solution of methyl 3-amino-3-(5-bromopyridin-3-yl) propanoate (300 mg, 1.16 mmol) and Et$_3$N (351 mg, 3.48 mmol) in DCM (4 mL) at room temperature was added di-tert-butyl dicarbonate (278 mg, 1.27 mmol), and the solution was stirred at room temperature for 16 hours. The mixture was concentrated in vacuo to give crude product, which was purified by Preparative-TLC (EtOAc:pet ether 1:1) to provide desired product methyl 3-(5-bromopyridin-3-yl)-3-(tert-butoxycarbonylamino) propanoate as a colorless oil (301 mg). Yield 72% (100% purity, UV=214 nm, ESI 359 (M+H)$^+$).

Step 2: methyl 3-(tert-butoxycarbonylamino)-3-(5-((S)-3-methylmorpholino) pyridin-3-yl)propanoate

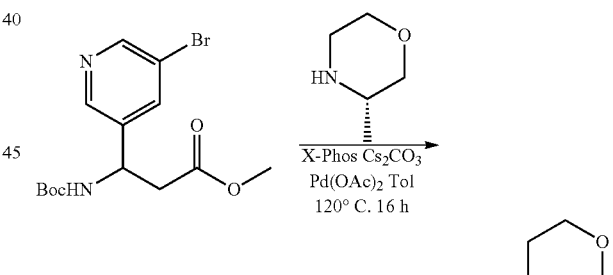

A solution of methyl 3-(5-bromopyridin-3-yl)-3-(tert-butoxycarbonylamino) propanoate (260 mg, 0.73 mmol), (S)-3-methylmorpholine (147 mg, 1.46 mmol), Pd(OAc)$_2$ (17 mg, 0.073 mmol), X-Phos (65 mg, 0.146 mmol) and Cs$_2$CO$_3$ (714 mg, 2.19 mmol) in Toluene (3 mL) was stirred at 120° C. for 16 hours under N$_2$. The mixture was cooled to room temperature and filtered over Celite. The filtrate was concentrated under reduced pressure, and the residue was purified by flash column chromatography (0%~60% EtOAc in Petroleum) to provide the desired product methyl 3-(tert-butoxycarbonylamino)-3-(5-((S)-3-methylmorpholino) pyridin-3-yl)propanoate as a yellow oil (162 mg). Yield 52% (90% purity, UV=214 nm, ESI 280 (M+H)$^+$).

Step 3: methyl 3-amino-3-(5-((S)-3-methylmorpholino)pyridin-3-yl)propanoate hydrochloride

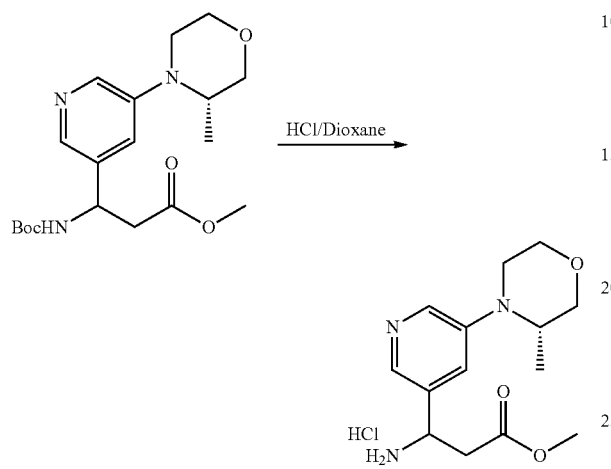

To a solution of methyl 3-(tert-butoxycarbonylamino)-3-(5-((S)-3-methylmorpholino) pyridin-3-yl)propanoate (162 mg, 0.43 mmol) in DCM (4 mL) was added HCl in dioxane (4 M, 2 mL), and the solution was stirred at room temperature for 16 hours. The solvent was removed in vacuo to provide the crude product methyl 3-amino-3-(5-((S)-3-methylmorpholino) pyridin-3-yl)propanoate hydrochloride as a yellow solid (119 mg), Which was used for the next step directly without further purification. Yield 99% (92.24% purity, UV=214 nm, ESI 280 (M+H)$^+$).

Step 4: (S)-methyl 4-methyl-2-(4-oxoquinazolin-3(4H)-yl)pentanoate

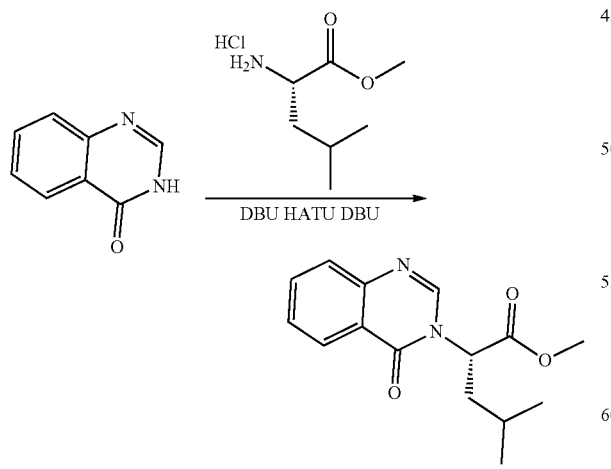

A mixture of quinazolin-4(3H)-one (1.0 g, 6.85 mmol), (S)-methyl 2-amino-4-methylpentanoate hydrochloride (1.49 g, 8.22 mmol), DBU (1.57 g, 10.3 mmol) and HATU (3.38 g, 8.9 mmol) in THF (20 mL) was stirred at 35° C. for 16 hours. The mixture was poured into water and the solution was extracted with EtOAc (30 mL×2). The combined organic layers were dried over Na$_2$SO$_4$ and filtered. The filtrate was concentrated under reduced pressure to give a residue, which was purified by flash column (0~25% EtOAc in Petroleum) to provide the desired product (S)-methyl 4-methyl-2-(4-oxoquinazolin-3(4H)-yl)pentanoate as a colorless oil (612 mg). Yield 33% (88.42% purity, UV=214 nm, ESI 275 (M+H)$^+$).

Step 5: (S)-4-methyl-2-(4-oxoquinazolin-3(4H)-yl) pentanoic acid

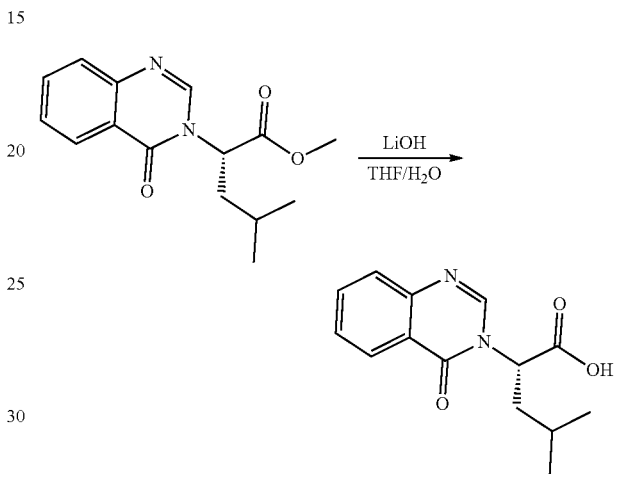

(S)-methyl 4-methyl-2-(4-oxoquinazolin-3(4H)-yl)pentanoate (612 mg, 2.23 mmol) was treated with LiOH—H$_2$O (281 mg, 6.69 mmol) in THF (6 mL) and H$_2$O (1 mL) at room temperature for 3 hours. The mixture was poured into water and the solution was extracted with EtOAc (20 mL×2). The aqueous phase was acidified to pH=3 with HCl (1 M) and then the solution was extracted with EtOAc (20 mL×2). The combined organic layers were dried over Na$_2$SO$_4$ and filtered. The filtrate was concentrated under reduced pressure to give the crude product (S)-4-methyl-2-(4-oxoquinazolin-3(4H)-yl)pentanoic acid as a colorless oil (494 mg). Yield 85% (100% purity, UV=214 nm, ESI 261 (M+H)$^+$). The crude product was used for the next step directly without further purification.

Step 6: methyl 3-((S)-4-methyl-2-(4-oxoquinazolin-3(4H)-yl)pentanamido)-3-(5-((S)-3-methylmorpholino)pyridin-3-yl)propanoate

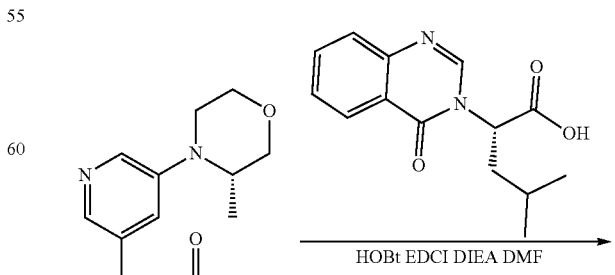

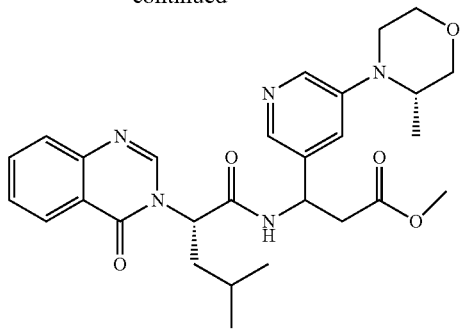

A mixture of methyl 3-amino-3-(5-((S)-3-methylmorpholino) pyridin-3-yl)propanoate hydrochloride (119 mg, 0.43 mmol), (S)-4-methyl-2-(4-oxoquinazolin-3(4H)-yl) pentanoic acid (168 mg, 0.645 mmol), HOBt (87 mg, 0.645 mmol), EDCI (123 mg, 0.645 mmol) and DIEA (166 mg, 1.29 mmol) in DMF (6 mL) was stirred at room temperature for 16 hours. The mixture was poured into water and the solution was extracted with EtOAc (20 mL×2), The combined organic layers were dried over $Na_2SO_4$ and filtered. The filtrate was concentrated under reduced pressure to give a residue, which was purified by Preparative-TLC (EtOAc) to provide the desired product methyl 3-((S)-4-methyl-2-(4-oxoquinazolin-3 (4H)-yl)pentanamido)-3-(5-((S)-3-methylmorpholino)pyridin-3-yl)propanoate as a colorless oil (40 mg). Yield 18% two steps (96% purity, UV=214 nm, ESI 522 (M+H)$^+$).

Step 7: 3-((S)-4-methyl-2-(4-oxoquinazolin-3(4H)-yl)pentanamido)-3-(5-((S)-3-methylmorpholino) pyridin-3-yl)propanoic acid

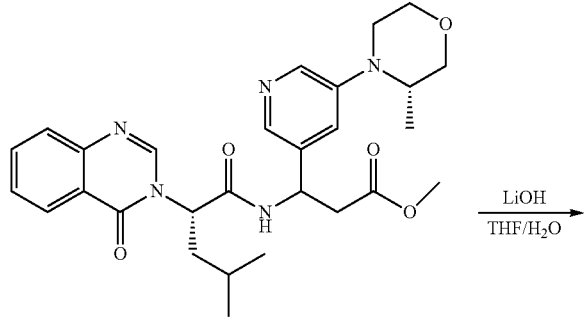

Methyl 3-((S)-4-methyl-2-(4-oxoquinazolin-3(4H)-yl) pentanamido)-3-(5-((S)-3-methylmorpholino)pyridin-3-yl) propanoate (40 mg, 0.077 mmol) was treated with LiOH—$H_2O$ (10 mg, 0.231 mmol) in THF (6 mL) and $H_2O$ (1 mL) at room temperature for 2 hours. The mixture was acidified to pH=5 with HCl (1 M). The solvent was removed in vacuo, and the residue was purified by Preparative-HPLC A (30~70% MeCN) to give the compounds X1 (2.3 mg) and X2 (8.7 mg) as white solids.

Compound X1 LC/MS A: 100% purity, UV=214 nm, Rt=1.40 min, ESI 508 (M+H)$^+$.

$^1$H NMR (500 MHz, MeOD) δ 8.41 (d, J=3.7 Hz, 1H), 8.25 (d, J=6.8 Hz, 1H), 8.03 (s, 1H), 7.97 (s, 1H), 7.86 (dd, J=11.1, 4.2 Hz, 1H), 7.71 (d, J=8.1 Hz, 1H), 7.59 (t, J=7.2 Hz, 1H), 7.27 (s, 1H), 5.69 (dd, J=10.0, 6.4 Hz, 1H), 5.37 (t, J=7.2 Hz, 1H), 3.94-3.60 (m, 5H), 3.09-3.03 (m, 2H), 2.97-2.79 (m, 2H), 2.22-1.96 (m, 2H), 1.68-1.46 (m, 1H), 1.07-0.78 (m, 9H).

Compound X2 LC/MS B: 100% purity, UV=214 nm, Rt=1.36 min, ESI 508 (M+H)$^+$.

$^1$H NMR (500 MHz, MeOD) δ 8.44 (s, 1H), 8.27 (d, J=6.9 Hz, 1H), 8.11 (s, 1H), 8.02 (s, 1H), 7.87 (t, J=7.0 Hz, 1H), 7.73 (d, J=8.0 Hz, 1H), 7.60 (t, J=7.2 Hz, 1H), 7.36 (s, 1H), 5.72 (dd, J=10.4, 5.9 Hz, 1H), 5.36 (t, J=6.8 Hz, 1H), 4.08-3.63 (m, 5H), 3.30-3.09 (m, 2H), 2.81 (s, 2H), 2.17-1.88 (m, 2H), 1.44 (s, 1H), 1.14 (d, J=6.6 Hz, 3H), 1.07-0.78 (m, 9H).

Preparation of Compounds Y1, Y2, and Y4

Step 1: 4,5-dimethylpyridin-2-ol

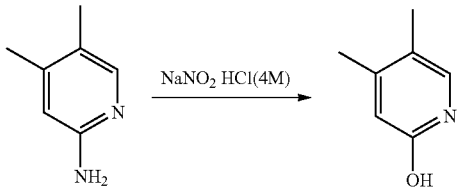

To a solution of 4,5-dimethylpyridin-2-amine (1.0 g, 8.2 mmol) in HCl (4N, 12 mL) at 0° C. was added a solution of NaNO$_2$ (1.13 g, 16.4 mmol) in H$_2$O (4 mL). The reaction mixture was stirred at room temperature for 16 hours and concentrated in vacuo to give crude product, which was purified by reversed phase chromatography (0%~40% MeOH in H$_2$O (5% TFA)) to provide the desired product 4,5-dimethylpyridin-2-ol as a white solid (466 mg). Yield 46% (96.34% purity, UV=214 nm, ESI 124 (M+H)$^+$).

Step 2: (S)-2-(4,5-dimethyl-2-oxopyridin-1(2H)-yl)-4-methylpentanoic acid

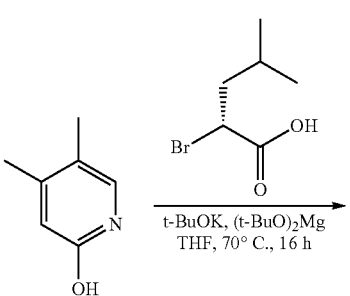

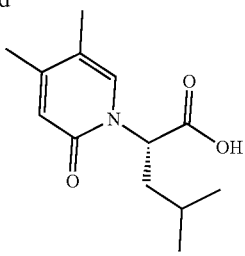

To a solution of (R)-2-bromo-4-methylpentanoic acid (500 mg, 2.56 mmol) in dry THF (20 mL) was added (t-BuO)$_2$Mg (581 mg, 3.42 mmol), and the solution was stirred at 30° C. for 3 hours under N$_2$ atmosphere. Then 4,5-dimethylpyridin-2-ol (210 mg, 1.71 mmol) and t-BuOK (195 mg, 1.74 mmol) was added, and the reaction mixture was stirred at 70° C. for 16 hours under N$_2$. The mixture was cooled to room temperature and acidified to pH=5 with HCl (1 M). The solution was concentrated under reduced pressure to give a residue, which purified by reversed phase flash chromatography (0%~60% MeOH in H$_2$O (5% TFA)) to provide the desired product (S)-2-(4,5-dimethyl-2-oxopyridin-1(2H)-yl)-4-methylpentanoic acid as a white solid (169 mg). Yield 42% (96% purity, UV=214 nm, ESI 238 (M+H)$^+$).

Step 3: (3R)-methyl 3-(2-(4,5-dimethyl-2-oxopyridin-1(2H)-yl)-4-methylpentanamido)-3-(5-(2,6-dimethylphenyl)pyridin-3-yl)propanoate

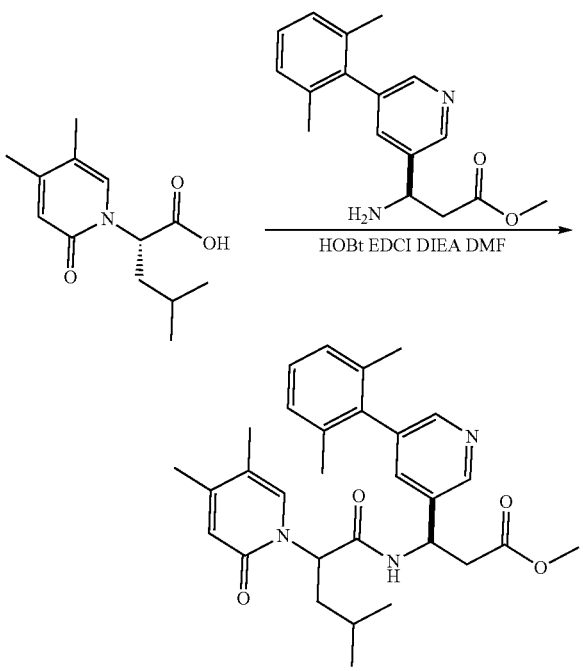

A mixture of (S)-2-(4,5-dimethyl-2-oxopyridin-1(2H)-yl)-4-methylpentanoic acid (89 mg, 0.375 mmol), (R)-methyl 3-amino-3-(5-(2,6-dimethylphenyl)pyridin-3-yl)propanoate (70 mg, 0.25 mmol), HOBt (51 mg, 0.37 mmol), EDCI (72 mg, 0.37 mmol) and DIEA (97 mg, 0.75 mmol) in DMF (4 mL) was stirred at room temperature for 2 hours. The mixture was poured into water and the solution was extracted with EtOAc (30 mL×2). The combined organic layers were dried over Na$_2$SO$_4$ and filtered. The filtrate was concentrated under reduced pressure to give a residue, which was purified by flash column chromatography (0%~80% EtOAc in Petroleum) to provide the desired product (3R)-methyl 3-(2-(4,5-dimethyl-2-oxopyridin-1 (2H)-yl)-4-methylpentanamido)-3-(5-(2,6-dimethylphenyl)pyridin-3-yl)propanoate as a colorless oil (92 mg). Yield 74% (86.01% purity, UV=214 nm, ESI 504 (M+H)$^+$).

Step 4: (3R)-3-(2-(4,5-dimethyl-2-oxopyridin-1(2H)-yl)-4-methylpentanamido)-3-(5-(2,6-dimethylphenyl)pyridin-3-yl)propanoic acid

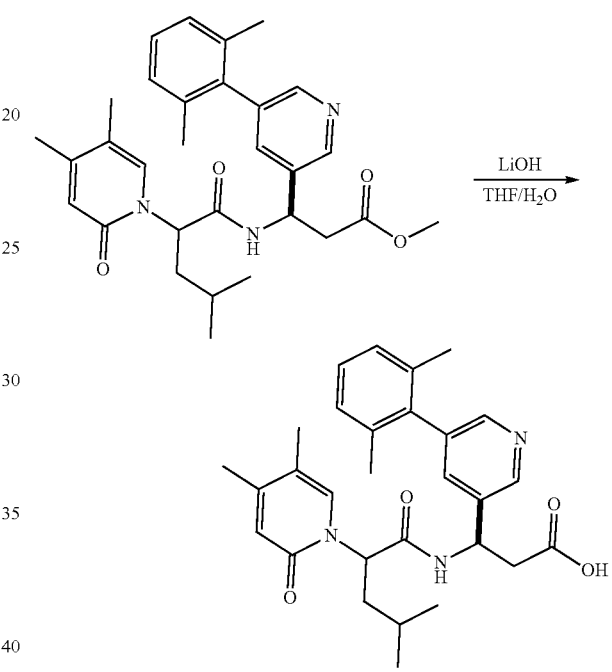

(3R)-methyl 3-(2-(4,5-dimethyl-2-oxopyridin-1(2H)-yl)-methylpentanamido)-3-(5-(2,6-dimethylphenyl)pyridin-3-yl)propanoate (92 mg, 0.18 mmol) was treated with LiOH—H$_2$O (23 mg, 0.54 mmol) in THF (6 mL) and H$_2$O (1 mL) at room temperature for 5 hours. The mixture was acidified to pH=5 with HCl (1 M). The solvent was removed in vacuo and the residue was purified by Preparative-HPLC A (30~70% MeCN) to give the compounds Y1 (24.7 mg) and Y2 (22.1 mg) as white solids.

Compound Y1 LC/MS A: 100% purity, UV=214 nm, Rt=1.58 min, ESI 490 (M+H)$^+$.

$^1$H NMR (500 MHz, MeOD) δ 8.51 (s, 1H), 8.18 (s, 1H), 7.50 (s, 1H), 7.40 (s, 1H), 7.20 (t, J=7.6 Hz, 1H), 7.13 (t, J=7.7 Hz, 2H), 6.30 (s, 1H), 5.68 (dd, J=9.0, 7.0 Hz, 1H), 5.42 (t, J=7.1 Hz, 1H), 2.91 (d, J=7.1 Hz, 2H), 2.15 (s, 3H), 2.02 (s, 3H), 1.96 (d, J=7.9 Hz, 3H), 1.95-1.87 (m, 2H), 1.85 (s, 3H), 1.47-1.40 (m, 1H), 0.97-0.94 (m, 6H).

Compound Y2 LC/MS A: 97% purity, UV=214 nm, Rt=1.60 min, ESI 490 (M+H)$^+$.

$^1$H NMR (500 MHz, MeOD) δ 8.58 (s, 1H), 8.26 (s, 1H), 7.66 (t, J=1.9 Hz, 1H), 7.46 (s, 1H), 7.27-7.18 (m, 1H), 7.16 (d, J=7.6 Hz, 2H), 6.41 (s, 1H), 5.67 (t, J=8.0 Hz, 1H), 5.38 (t, J=7.3 Hz, 1H), 2.97-2.86 (m, 2H), 2.20 (s, 3H), 2.09 (s, 3H), 2.02 (s, 6H), 1.82 (t, J=7.5 Hz, 2H), 1.36-1.28 (m, 1H), 0.90-0.87 (m, 6H).

Step 5: (3S)-methyl 3-(2-(4,5-dimethyl-2-oxopyridin-1(2H)-yl)-4-methylpentanamido)-3-(5-(2,6-dimethylphenyl)pyridin-3-yl)propanoate

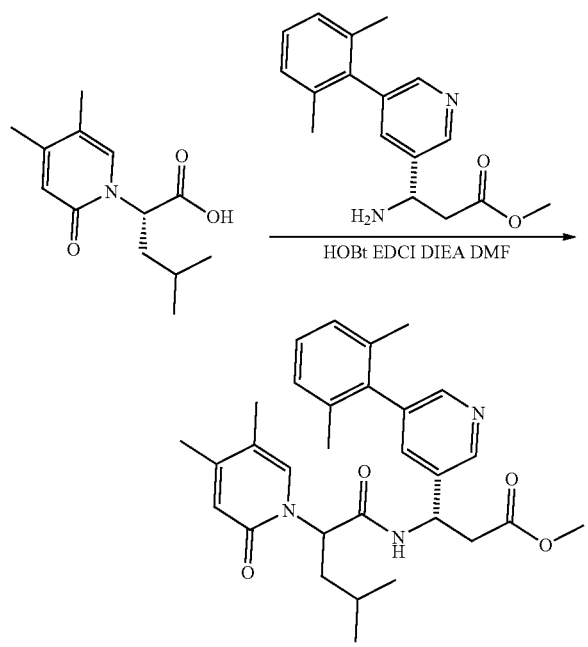

A mixture of (S)-2-(4,5-dimethyl-2-oxopyridin-1(2H)-yl)-4-methylpentanoic acid (89 mg, 0.375 mmol), (S)-methyl 3-amino-3-(5-(2,6-dimethylphenyl)pyridin-3-yl)propanoate (70 mg, 0.25 mmol), HOBt (51 mg, 0.375 mmol), EDCI (72 mg, 0.375 mmol) and DIEA (97 mg, 0.75 mmol) in DMF (4 mL) was stirred at room temperature for 2 hours. The mixture was poured into water and the solution was extracted with EtOAc (30 mL×2). The combined organic layers were dried over $Na_2SO_4$ and filtered. The filtrate was concentrated under reduced pressure to give a residue, which was purified by flash column chromatography (0%~80% EtOAc in Petroleum) to provide the desired product (3S)-methyl 3-(2-(4,5-dimethyl-2-oxopyridin-1 (2H)-yl)-4-methylpentanamido)-3-(5-(2,6-dimethylphenyl)pyridin-3-yl)propanoate as a colorless oil (85 mg). Yield 68% (93.96% purity, UV=214 nm, ESI 504 (M+H)$^+$).

Step 6: (3S)-3-(2-(4,5-dimethyl-2-oxopyridin-1 (2H)-yl)-4-methylpentanamido)-3-(5-(2,6-dimethylphenyl)pyridin-3-yl)propanoic acid

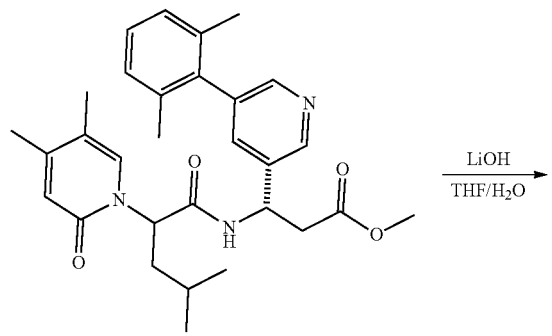

(3 S)-methyl 3-(2-(4,5-dimethyl-2-oxopyridin-1 (2H)-yl)-4-methylpentanamido)-3-(5-(2,6-dimethylphenyl)pyridin-3-yl)propanoate (92 mg, 0.18 mmol) was treated with LiOH—$H_2O$ (23 mg, 0.54 mmol) in THF (6 mL) and $H_2O$ (1 mL) at room temperature for 5 hours. The mixture was acidified to pH=5 with HCl (1 M). The solvent was removed in vacuo, and the residue was purified by Preparative-HPLC A (30-70% MeCN) to give the compounds Y3 (14.9 mg) and Y4 (20.8 mg) as white solids.

Compound Y4 LC/MS A: 100% purity, UV=214 nm, Rt=1.60 min, ESI 490 (M+H)$^+$ $^1$H NMR (500 MHz, MeOD) δ 8.59 (s, 1H), 8.26 (s, 1H), 7.66 (t, J=1.8 Hz, 1H), 7.46 (s, 1H), 7.28-7.11 (m, 3H), 6.41 (s, 1H), 5.67 (t, J=8.0 Hz, 1H), 5.38 (t, J=7.3 Hz, 1H), 2.95-2.71 (m, 2H), 2.20 (s, 3H), 2.09 (s, 3H), 2.02 (s, 6H), 1.84 (t, J=7.5 Hz, 2H), 1.37-1.28 (m, 1H), 0.90-0.87 (m, 6H).

Preparation of Compound Z

Step 1: methyl (S)-methyl 3-(tert-butoxycarbonylamino)-3-(5-(2,6-dimethylphenyl)pyridin-3-yl)propanoate

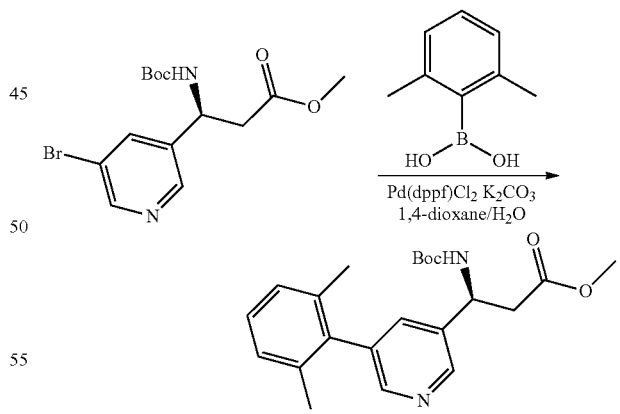

A mixture of (S)-methyl 3-(5-bromopyridin-3-yl)-3-(tert-butoxycarbonylamino)propanoate (1.0 g, 2.79 mmol), 2,6-dimethylphenylboronic acid (628 mg, 4.19 mmol), Pd(dppf)Cl$_2$ (164 mg, 0.22 mmol) and $K_2CO_3$ (963 mg, 7.0 mmol) in 1,4-Dioxane (10 mL) and $H_2O$ (2 mL) under $N_2$ atmosphere was stirred at 110° C. for 4 hours under microwave. The mixture was poured into water and the solution was extracted with EtOAc (30 mL×2). The combined organic layers were dried over $Na_2SO_4$ and filtered. The filtrate was concentrated under reduced pressure to give a residue, which was purified by flash column chromatography (0%~45% EtOAc in Petroleum) to provide the desired product methyl (S)-methyl 3-(tert-butoxycarbonylamino)-3-(5-(2,6-dimethylphenyl)pyridin-3-yl)propanoate as a light yellow oil (987 mg). Yield 82% (88% purity, UV=214 nm, ESI 385 (M+H)+).

Step 2: (S)-methyl 3-amino-3-(5-(2,6-dimethylphenyl)pyridin-3-yl)propanoate hydrochloride

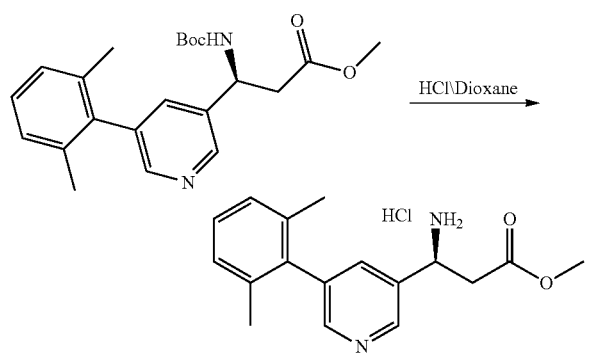

To a solution of methyl (S)-methyl 3-(tert-butoxycarbonylamino)-3-(5-(2,6-dimethylphenyl)pyridin-3-yl)propanoate (410 mg, 1.07 mmol) in DCM (4 mL) was added HCl/Dioxane (4M, 2 mL), and the solution was stirred at room temperature for 2 hours. The mixture was concentrated under reduced pressure to provide the crude product (S)-methyl 3-amino-3-(5-(2,6-dimethylphenyl)pyridin-3-yl)propanoate hydrochloride as a white solid (303 mg) used for next step directly without further purification. Yield 99% (90.38% purity, UV=214 nm, ESI 285 (M+H)+).

Step 3: (S)-methyl 3-(5-(2,6-dimethylphenyl)pyridin-3-yl)-3-((R)-2-hydroxy-4-methylpentanamido)propanoate

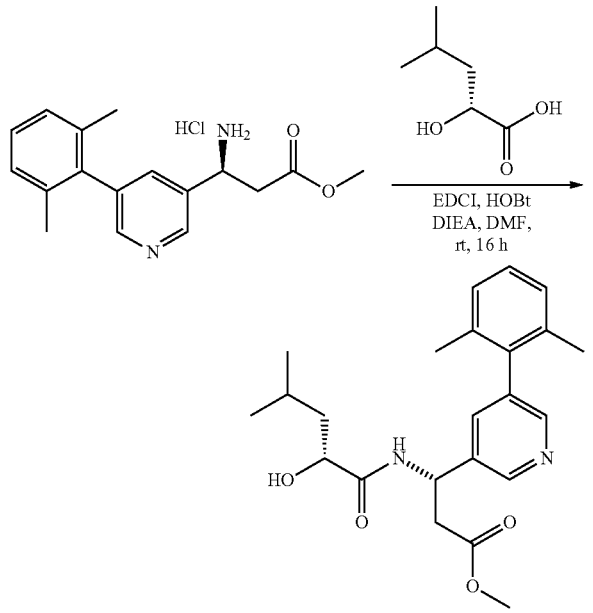

A mixture of (S)-methyl 3-amino-3-(5-(2,6-dimethylphenyl)pyridin-3-yl)propanoate hydrochloride (303 mg, 1.07 mmol), (R)-2-hydroxy-4-methylpentanoic acid (169 mg, 1.28 mmol), HOBt (217 mg, 1.61 mmol), EDCI (308 mg, 1.61 mmol) and DIEA (690 mg, 5.35 mmol) in DMF (6 mL) was stirred at room temperature for 16 hours. The mixture was poured into water and the solution was extracted with EtOAc (20 mL×2). The combined organic layers were dried over Na$_2$SO$_4$ and filtered. The filtrate was concentrated under reduced pressure to give a residue, which was purified by flash column chromatography (0%~85% EtOAc in Petroleum) to provide the desired product (S)-methyl 3-(5-(2,6-dimethylphenyl)pyridin-3-yl)-3-((R)-2-hydroxy-4-methylpentanamido)propanoate as a colorless oil (340 mg). Yield 80% (90% purity, UV=214 nm, ESI 399 (M+H)+).

Step 4: (S)-methyl 3-(5-(2,6-dimethylphenyl)pyridin-3-yl)-3-((R)-4-methyl-2-(methylsulfonyloxy)pentanamido)propanoate

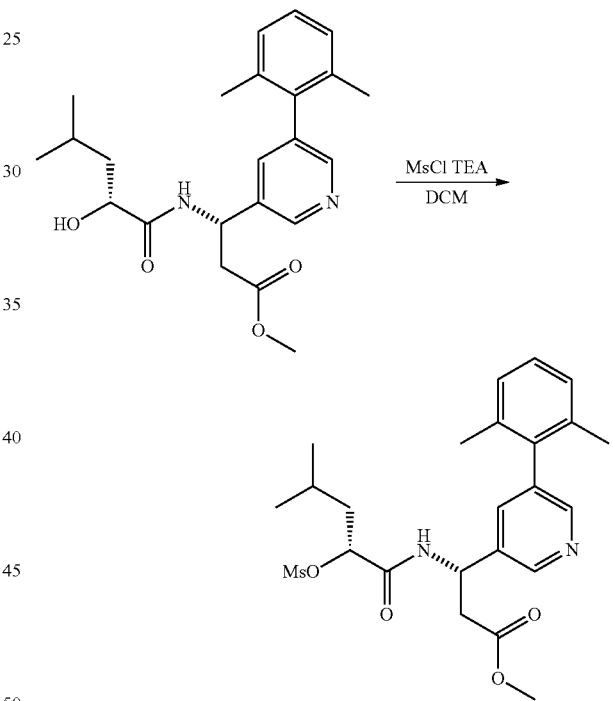

To a solution of (S)-methyl 3-(5-(2,6-dimethylphenyl)pyridin-3-yl)-3-((R)-2-hydroxy-4-methylpentanamido)propanoate (340 mg, 0.85 mmol) and Et$_3$N (258 mg, 2.55 mmol) in DCM (4 mL) at 0° C. was added MsCl (116 mg, 1.02 mmol). The solution was stirred at room temperature for 16 hours. The mixture was poured into water and the solution was extracted with DCM (20 mL×2). The combined organic layers were dried over Na$_2$SO$_4$ and filtered. The filtrate was concentrated under reduced pressure to give a residue, which was purified by flash column chromatography (0%~60% EtOAc in Petroleum) to provide the desired product (S)-methyl 3-(5-(2,6-dimethylphenyl)pyridin-3-yl)-3-((R)-4-methyl-2-(methylsulfonyloxy)pentanamido)propanoate as a light yellow oil (337 mg). Yield 83% (95% purity, UV=214 nm, ESI 477 (M+H)+).

Step 5: (3S)-methyl 3-(5-(2,6-dimethylphenyl)pyridin-3-yl)-3-(2-iodo-4-methylpentanamido)propanoate

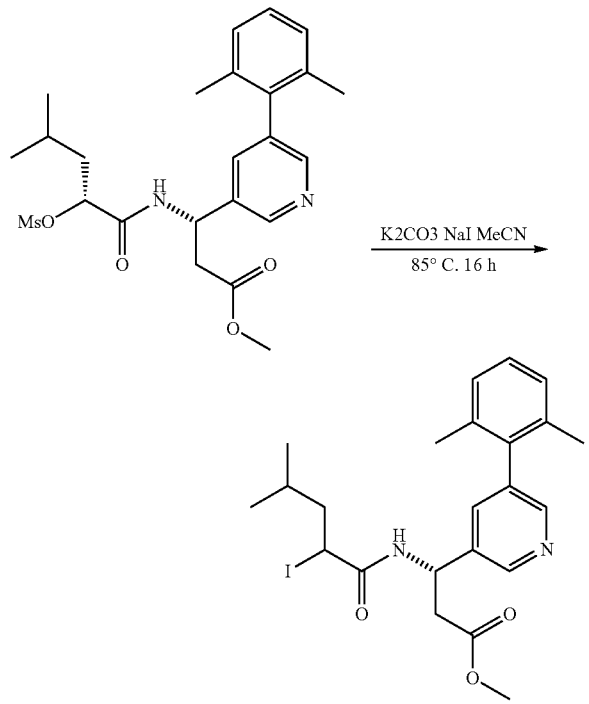

A mixture of (S)-methyl 3-(5-(2,6-dimethylphenyl)pyridin-3-yl)-3-((R)-4-methyl-2-(methylsulfonyloxy)pentanamido)propanoate (337 mg, 0.71 mmol), NaI (319 mg, 2.13 mmol) and K$_2$CO$_3$ (490 mg, 3.55 mmol) in MeCN (20 mL) was stirred at 85° C. for 20 hours. The mixture was cooled to room temperature and filtered. The filtrate was concentrated under reduced pressure to give a residue, which was purified by flash column chromatography (0%~40% EtOAc in Petroleum) to provide the desired product (3S)-methyl 3-(5-(2,6-dimethylphenyl)pyridin-3-yl)-3-(2-iodo-4-methylpentanamido)propanoate as a light yellow oil (233 mg). Yield 64% (96% purity, UV=214 nm, ESI 509 (M+H)$^+$).

Step 6: (3S)-3-(5-(2,6-dimethylphenyl)pyridin-3-yl)-3-(4-methyl-2-(1-oxo-3,4-dihydroisoquinolin-2(1H)-yl)pentanamido)propanoic acid

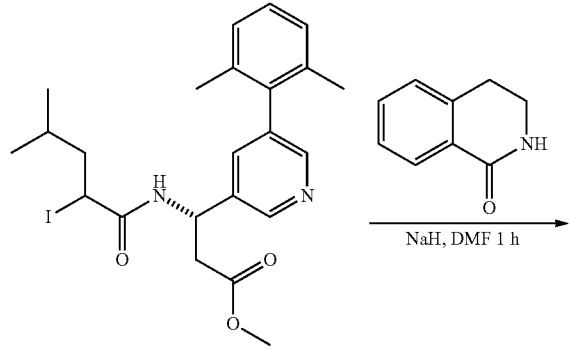

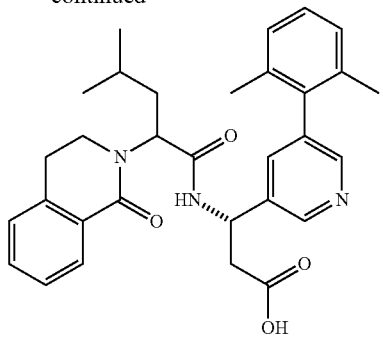

To a solution of 3,4-dihydroisoquinolin-1(2H)-one (135 mg, 0.92 mmol) in DMF (10 mL) was added NaH (60% in oil, 37 mg, 0.92 mmol) and the solution was stirred at room temperature for 0.5 hours under N$_2$ atmosphere. Then a solution of (3S)-methyl 3-(5-(2,6-dimethylphenyl)pyridin-3-yl)-3-(2-iodo-4-methylpentanamido) propanoate (233 mg, 0.46 mmol) in DMF (2 mL) was added dropwise at room temperature and the reaction mixture was stirred at room temperature for another 1 hour. The reaction mixture was quenched with a HCl (1 M) solution. The solvent was removed in vacuo and the residue was purified by Preparative-HPLC A (30~70% MeCN) to give the product (3S)-3-(5-(2,6-dimethylphenyl)pyridin-3-yl)-3-(4-methyl-2-(1-oxo-3,4-dihydroisoquinolin-2(1H)-yl)pentanamido) propanoic acid (52.7 mg) as a white solid.

Compound Z LC/MS A: 100% purity, UV=214 nm, Rt=1.67 min, ESI 514 (M+H)$^+$ $^1$H NMR (500 MHz, MeOD) δ 8.59-8.56 (m, 1H), 8.25-8.18 (m, 1H), 7.97-7.84 (m, 1H), 7.73-7.58 (m, 1H), 7.49 (q, J=7.7 Hz, 1H), 7.40-7.00 (m, 5H), 5.49-5.32 (m, 2H), 3.76-3.42 (m, 2H), 3.17-2.78 (m, 4H), 2.01-1.95 (m, 5H), 1.87-1.66 (m, 3H), 1.65-1.43 (m, 1H), 1.07-0.89 (m, 6H).

Preparation of Compounds AA1 and AA2

Step 1: ethyl 4-methyl-2-(1-oxoisoindolin-2-yl)pentanoate

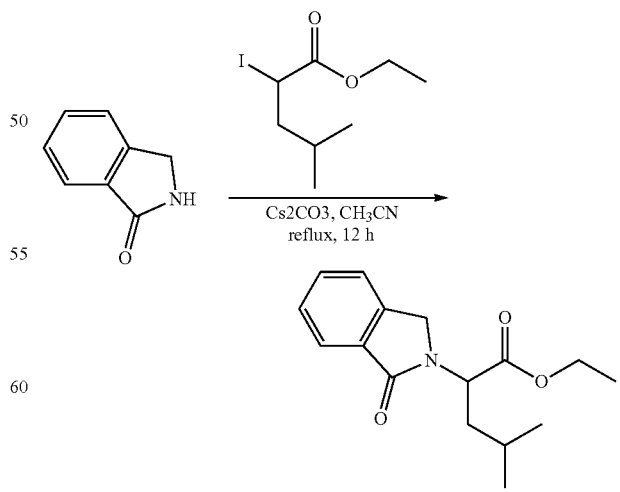

To a solution of isoindolin-1-one (120 mg 0.90 mmol) in MeCN (10 mL) was added Cs$_2$CO$_3$ (652 mg, 2.0 mmol) and ethyl 2-iodo-4-methylpentanoate (540 mg, 2.0 mmol). The mixture was stirred at 85° C. for 12 hours and filtered. The filtrate was concentrated under pressure, and the residue was purified by silica gel column (petroleum etherEtOAc=3:1) to give the desired product ethyl 4-methyl-2-(1-oxoisoindolin-2-yl)pentanoate as a colorless oil (120 mg). Yield 50% (95% purity, UV=254 nm, ESI 276.1 (M+H)$^+$).

Step 2: 4-methyl-2-(1-oxoisoindolin-2-yl)pentanoic acid

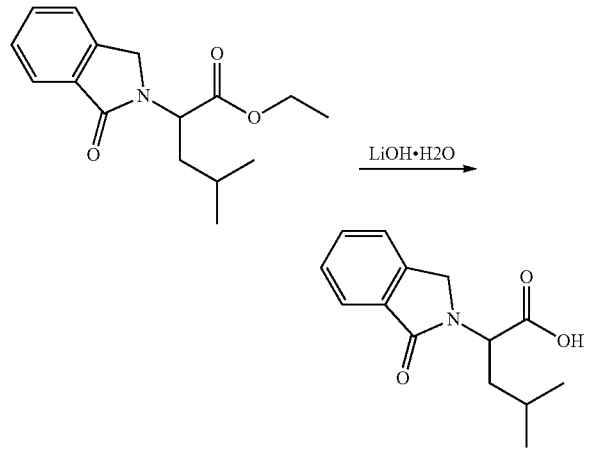

Ethyl 4-methyl-2-(1-oxoisoindolin-2-yl)pentanoate (120 mg, 0.44 mmol) was treated with LiOH—H$_2$O (82 mg, 2.0 mmol) in MeOH (4 mL) and H$_2$O (1 mL) at room temperature for 2 hours. The solvent was removed in vacuo, and the residue was diluted with H$_2$O (10 mL). The solution was adjusted to pH=6 with 1 N HCl. The solid were collected by filtration to provide the title compound 4-methyl-2-(1-oxoisoindolin-2-yl)pentanoic acid as a white solid (95 mg). Yield 81% (100% purity, UV=254 nm, ESI 248.1 (M+H)$^+$).

Step 3: (3S)-methyl 3-(5-(2,6-dimethylphenyl)pyridin-3-yl)-3-(4-methyl-2-(1-oxoisoindolin-2-yl)pentanamido)propanoate

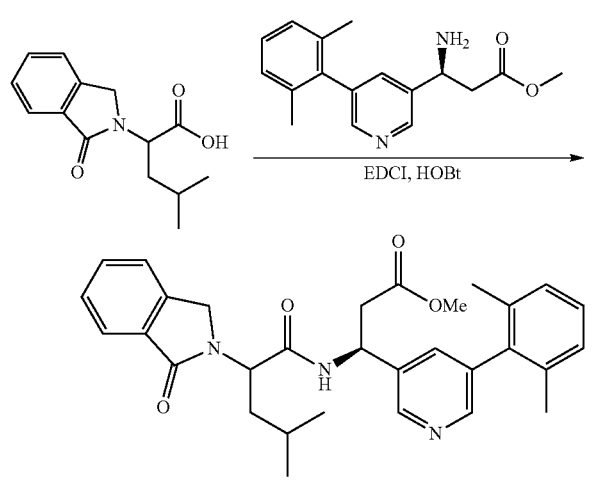

A mixture of 4-methyl-2-(1-oxoisoindolin-2-yl)pentanoic acid (95 mg, 0.38 mmol), (S)-methyl 3-amino-3-(5-(2,6-dimethylphenyl)pyridin-3-yl)propanoate (114 mg, 0.4 mmol), EDCI (153 mg, 0.8 mmol), HOBt (108 mg, 0.8 mmol) and DIEA (129 mg, 1.0 mmol) in DCM (5 mL) was stirred at room temperature for 16 hours. The solvent was removed in vacuo, and the residue was purified by silica gel column (petroleum:EtOAc=2:1) to provide the desired product (3S)-methyl 3-(5-(2,6-dimethylphenyl)pyridin-3-yl)-3-(4-methyl-2-(1-oxoisoindolin-2-yl)pentanamido)propanoate as a colorless oil (65 mg). Yield 35% (97% purity, UV=254 nm, ESI 514.1 (M+H)$^+$).

Step 4: Compounds AA1 and AA2

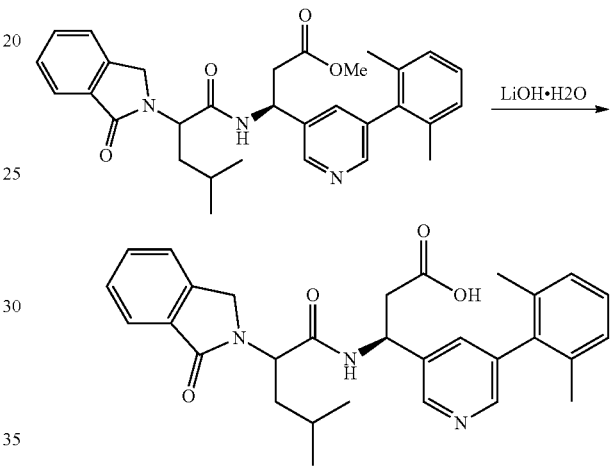

(3S)-methyl 3-(5-(2,6-dimethylphenyl)pyridin-3-yl)-3-(4-methyl-2-(1-oxoisoindolin-2-yl)pentanamido)propanoate (65 mg, 0.13 mmol) was treated with LiOH—H$_2$O (25.2 mg, 0.6 mmol) in MeOH (3 mL) and H$_2$O (1 mL) at room temperature for 2 hours. The solution was adjusted with 1 N HCl to pH=5~6. The solvent was removed in vacuo, and the residue was purified by preparatory HPLC A (30~70% MeCN) to give the compounds AA1 (13 mg) and AA2 (12 mg) as white solids.

Compound AA1 LC/MS A: 100% purity, UV=214 nm, Rt=1.61 min, ESI 500.3 (M+H)$^+$.

$^1$H NMR (500 MHz, MeOD) δ 8.55 (s, 1H), 8.14 (s, 1H), 7.69 (d, J=7.6 Hz, 1H), 7.62 (t, J=7.4 Hz, 1H), 7.59-7.45 (m, 3H), 7.16 (t, J=7.6 Hz, 1H), 7.09 (d, J=7.6 Hz, 1H), 7.00 (d, J=7.5 Hz, 1H), 5.42 (t, J=7.3 Hz, 1H), 5.05 (t, J=7.9 Hz, 1H), 4.64 (d, J=17.7 Hz, 1H), 4.51 (d, J=17.7 Hz, 1H), 2.92 (t, J=8.0 Hz, 2H), 1.93 (s, 3H), 1.89-1.85 (m, 2H), 1.67 (s, 3H), 1.54-1.49 (m, 1H), 1.03-0.97 (m, 6H).

Compound AA2 LC/MS A: 100% purity, UV=214 nm, Rt=1.63 min, ESI 500.3 (M+H)$^+$.

$^1$H NMR (500 MHz, MeOD) δ 8.59 (s, 1H), 8.26 (s, 1H), 7.80 (d, J=7.6 Hz, 1H), 7.71-7.56 (m, 3H), 7.52 (t, J=7.3 Hz, 1H), 7.26-7.19 (m, 1H), 7.16 (d, J=7.5 Hz, 2H), 5.42 (t, J=7.4 Hz, 1H), 5.06 (t, J=7.9 Hz, 1H), 4.77 (d, J=17.8 Hz, 1H), 4.52 (d, J=17.7 Hz, 1H), 2.97-2.87 (m, 2H), 2.02 (s, 6H), 1.78 (t, J=7.5 Hz, 2H), 1.39-1.34 (m, 1H), 0.95-0.93 (m, 6H).

Preparation of Compound AB2

Step 1: 2-bromo-4-formylbenzonitrile

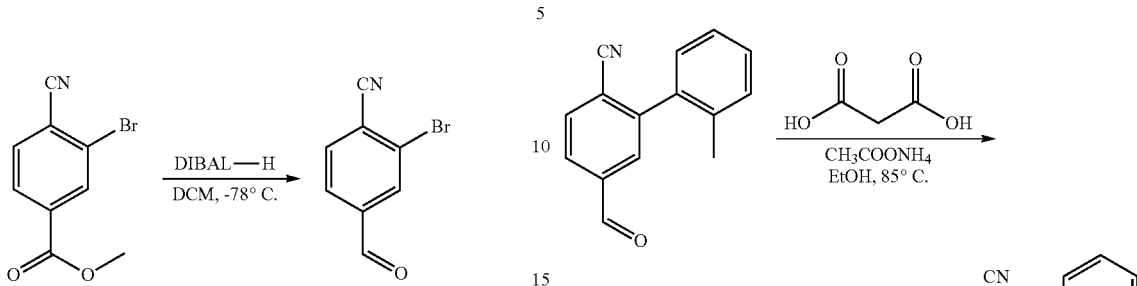

To a solution of methyl 3-bromo-4-cyanobenzoate (500 mg, 1.97 mmol) in 25 mL was added DIBAL-H (1 M in toluene, 2.56 mL, 2.56 mmol) dropwise at −78° C. The mixture was stirred at −78° C. for 4 hours. The solution was quenched with MeOH (10 mL). The mixture was stirred at room temperature for 10 min, and treated with Sat. aqueous Potassium Sodium tartrate. The mixture was extracted with DCM (30 mL×2). The organic layer was dried over $Na_2SO_4$ and filtered. The filtrate was concentrated under reduced pressure, and the residue was purified by silica gel column (pet. ether:EtOAc=5:1) to give the desired product 2-bromo-4-formylbenzonitrile as a brown solid (240 mg). Yield 58% (97% purity, UV=214 nm, ESI 210 (M+H)$^+$).

Step 2: 5-formyl-2'-methylbiphenyl-2-carbonitrile

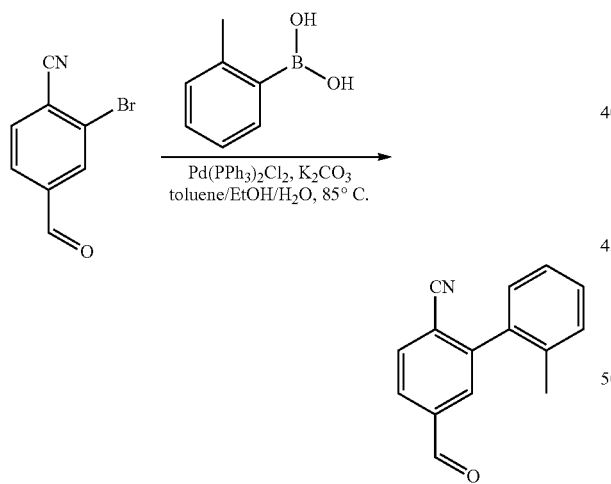

A mixture of 2-bromo-4-formylbenzonitrile (210 mg, 1 mmol), o-tolylboronic acid (272 mg, 2 mmol), $Pd(PPh_3)_2Cl_2$ (70 mg, 0.1 mmol) and $K_2CO_3$ (415 mg, 3 mmol) in toluene (5 mL), Ethanol (1 mL) and $H_2O$ (1 mL) was stirred under $N_2$ atmosphere at 85° C. overnight. Water was added and the solution was extracted with DCM (30 mL×2). The combined organic layers were concentrated under reduced pressure, and the residue was purified by silica gel column (pet. ether:EtOAc=5:1) to give the desired product 5-formyl-2'-methylbiphenyl-2-carbonitrile as a brown solid (250 mg), Yield 99% (100% purity, UV=214 nm, ESI 222 (M+H)$^+$).

Step 3: 3-amino-3-(6-cyano-2'-methylbiphenyl-3-yl)propanoic acid

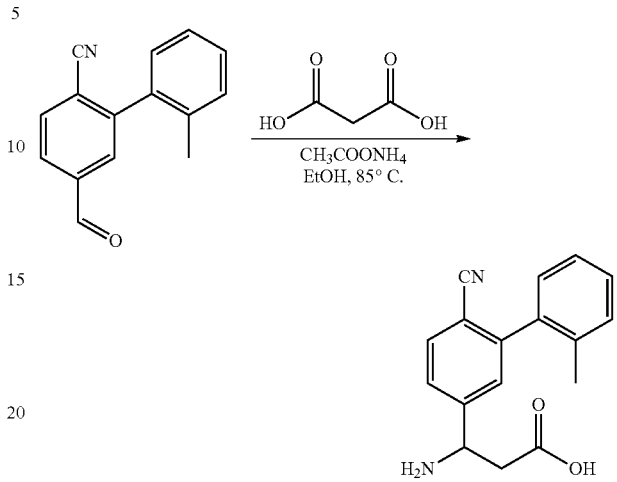

A mixture of 5-formyl-2'-methylbiphenyl-2-carbonitrile (250 mg, 1.1 mmol), malonic acid (141 mg, 1.4 mmol) and Ammonium Acetate (435 mg, 5.6 mmol) in EtOH (5 mL) was stirred 85° C. for 16 hours. The mixture was filtered, and the filtrate was concentrated under reduced pressure to give the crude product 3-amino-3-(6-cyano-2'-methylbiphenyl-3-yl)propanoic acid as a brown oil (120 mg). Yield 38% (19% purity, UV=214 nm, ESI 281 (M+H)$^+$). The crude product was used for the next step directly.

Step 4: methyl 3-amino-3-(6-cyano-2'-methylbiphenyl-3-yl)propanoate

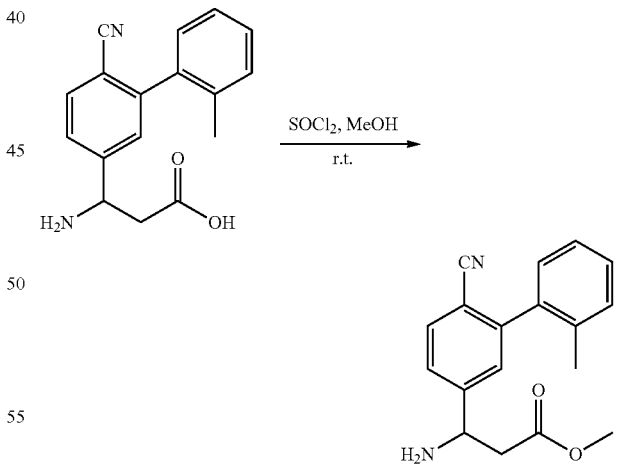

To a solution of 3-amino-3-(6-cyano-2'-methylbiphenyl-3-yl)propanoic acid (120 mg, 0.43 mmol) in 15 mL of methanol was added $SOCl_2$ (2 mL) dropwise at 0° C. The solution was warmed up to room temperature and stirred for 2 hours. The solvent was removed in vacuo to give the crude product methyl 3-amino-3-(6-cyano-2'-methylbiphenyl-3-yl)propanoate as a brown oil (100 mg). Yield 70% (28% purity, UV=214 nm, ESI 295 (M+H)$^+$). The crude product was used for the next step directly Step 5: methyl 3-(6-cyano-2'-methylbiphenyl-3-yl)-3-(4-methyl-2-(2-oxopyridin-1(2H)-yl)pentanamido)propanoate

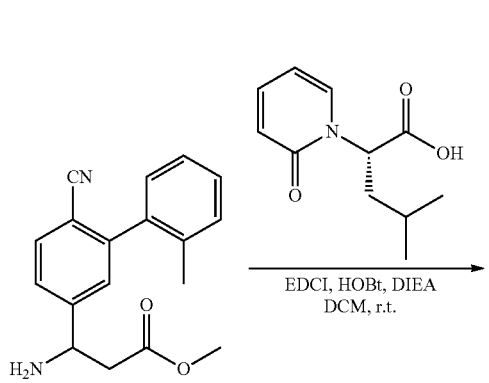

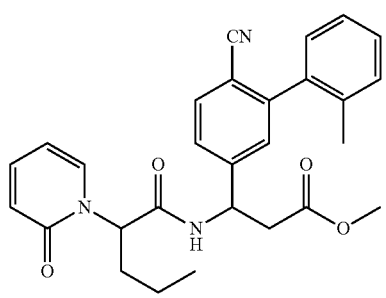

A mixture of methyl 3-amino-3-(6-cyano-2'-methylbiphenyl-3-yl)propanoate (100 mg, 0.3 mmol), (S)-4-methyl-2-(2-oxopyridin-1(2H)-yl)pentanoic acid (76 mg, 0.36 mmol), EDCI (116 mg, 0.6 mmol), HOBt (61 mg, 0.45 mmol) and DIEA (156 mg, 1.21 mmol) in 15 mL of DCM was stirred at room temperature for 16 hours. The solvent was removed in vacuo, and the residue was purified by silica gel column (Ethyl acetate) to give the desired product methyl 3-(6-cyano-2'-methyl biphenyl-3-yl)-3-(4-methyl-2-(2-oxopyridin-1 (2H)-yl)pentanamido)propanoate as a brown oil (70 mg) Yield 48% (50% purity, UV=214 nm, ESI 486 (M+H)+).

Step 6: 3-(6-cyano-2'-methylbiphenyl-3-yl)-3-(4-methyl-2-(2-oxopyridin-1(2H)-yl)pentanamido)propanoic acid

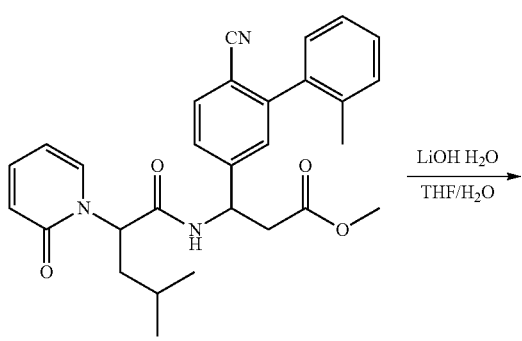

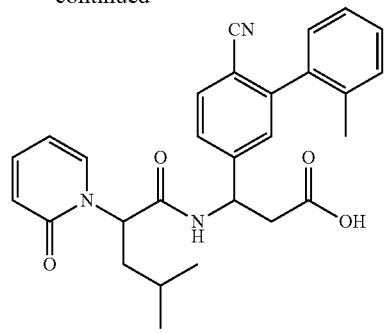

Methyl 3-(6-cyano-2'-methyl biphenyl-3-yl)-3-(4-methyl-2-(2-oxopyridin-1 (2H)-yl)pentanamido)propanoate (70 mg, 0.14 mmol) was treated with LiOH—H$_2$O (18 mg, 0.43 mmol) in 3 mL of THF and 1 mL of H$_2$O at room temperature for 1 h. The solution was adjusted to pH=3~4 with TFA. The solvent was removed in vacuo and the residue was purified by Preparative-HPLC A (33-70% MeCN) to give the compounds AB1 (8.8 mg) and AB2 (8.4 mg) as white solids Compound AB2 LC/MS A: 100% purity, UV=214 nm, Rt=1.59 min, ESI 472 (M+H)+.

$^1$H NMR (500 MHz, MeOD) δ 7.82 (d, J=8.1 Hz, 1H), 7.74 (d, J=5.6 Hz, 1H), 7.57-7.55 (m, 1H), 7.53-7.50 (m, 1H), 7.42 (d, J=1.6 Hz, 1H), 7.41-7.34 (m, 2H), 7.31 (dd, J=10.7, 5.3 Hz, 1H), 7.21 (d, J=6.8 Hz, 1H), 6.56 (d, J=8.4 Hz, 1H), 6.43-6.40 (m, 1H), 5.75 (t, J=8.1 Hz, 1H), 5.36 (t, J=7.2 Hz, 1H), 2.93-2.73 (m, 2H), 2.18 (s, 3H), 1.85 (t, J=7.5 Hz, 2H), 1.36-1.31 (m, 1H), 0.91-0.89 (m, 6H).

Preparation of Compound AC2

Step 1: 6-methoxy-2'-methylbiphenyl-3-carbaldehyde

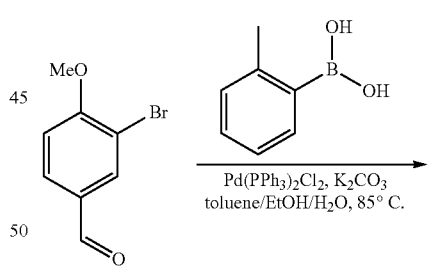

A mixture of 3-bromo-4-methoxybenzaldehyde (200 mg, 0.93 mmol), o-tolylboronic acid (190 mg, 1.4 mmol), PdCl$_2$(dppf) (34 mg, 0.05 mmol) and K$_2$CO$_3$ (386 mg, 2.79 mmol) in 1,4-Dioxane (2 mL) and H$_2$O (0.2 mL) was stirred in a microwave at 110° C. for 1 hour. Water added and the solution was extracted with EtOAc (30 mL×2). The combined organic layers were concentrated under reduced pressure, and the residue was purified by silica gel column (pet. ether:EtOAc=5:1) to give the desired product 6-methoxy-2'-methylbiphenyl-3-carbaldehyde as a colorless oil (245 mg), Yield 99% (96% purity, UV=214 nm, ESI 227 (M+H)⁺).

Step 2: 3-amino-3-(6-methoxy-2'-methylbiphenyl-3-yl)propanoic acid

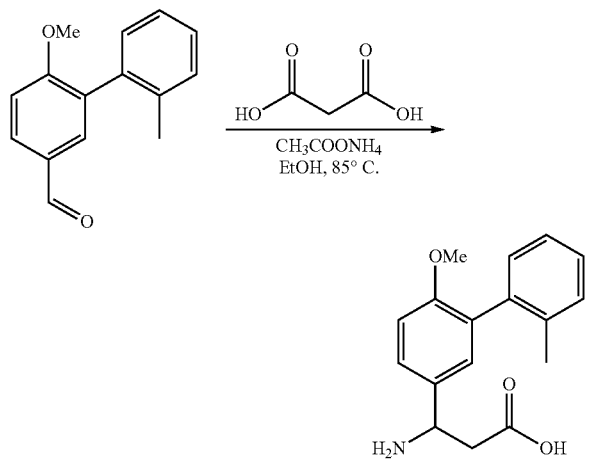

A mixture of 6-methoxy-2'-methylbiphenyl-3-carbaldehyde (245 mg, 1.08 mmol), malonic acid (100 mg, 1.3 mmol) and Ammonium Acetate (563 mg, 5.41 mmol) in EtOH (10 mL) was stirred 85° C. for 20 hours. The mixture was filtered, and the filtrate was concentrated under reduced pressure to give the crude product 3-amino-3-(6-methoxy-2'-methylbiphenyl-3-yl)propanoic acid as a brown oil (70 mg). Yield 23% (22% purity, UV=214 nm, ESI 269 (M+H)⁺). The crude product was used for the next step directly.

Step 3: methyl 3-amino-3-(6-methoxy-2'-methylbiphenyl-3-yl)propanoate

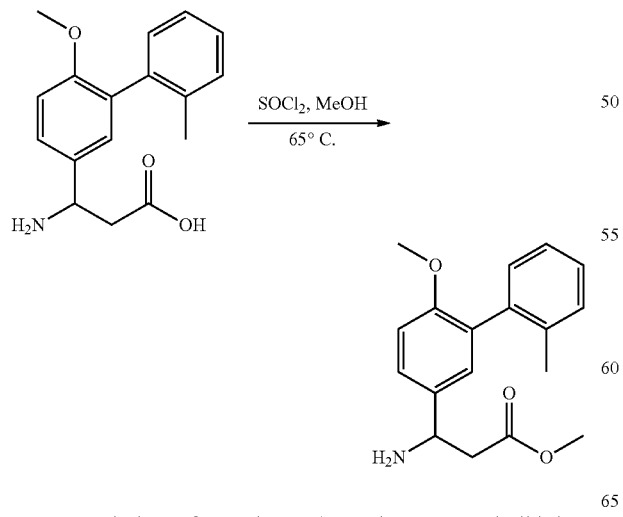

To a solution of 3-amino-3-(6-methoxy-2'-methylbiphenyl-3-yl)propanoic acid (70 mg, 0.25 mmol) in 10 mL of methanol was added SOCl₂ (2 mL) dropwise at 0° C. The solution was stirred at 65° C. for 3 hours. The solvent was removed in vacuo to give the crude product methyl 3-amino-3-(6-methoxy-2'-methylbiphenyl-3-yl)propanoate as a brown oil (80 mg). Yield 97% (27% purity, UV=214 nm, ESI 283 (M+H)⁺). The crude product was used for the next step directly Step 4: methyl 3-(6-methoxy-2'-methylbiphenyl-3-yl)-3-(4-methyl-2-(2-oxopyridin-1(2H)-yl)pentanamido)propanoate

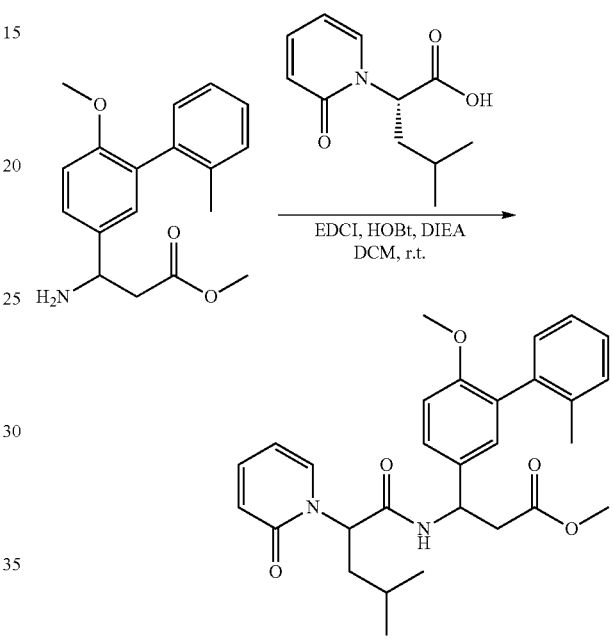

A mixture of methyl 3-amino-3-(6-methoxy-2'-methylbiphenyl-3-yl)propanoate (80 mg, 0.27 mmol), (S)-4-methyl-2-(2-oxopyridin-1(2H)-yl)pentanoic acid (67 mg, 0.32 mmol), EDCI (102 mg, 0.53 mmol), HOBt (54 mg, 0.4 mmol) and DIEA (104 mg, 0.8 mmol) in 10 mL of DCM was stirred at room temperature for 16 hours. The solvent was removed in vacuo, and the residue was purified by silica gel column (pet. ether:EtOAc=1:1) to give the desired compounds AC1 (40 mg) and AC2 (30 mg) as colorless oils (70 mg) Yield 60% (90% purity, UV=214 nm, ESI 491 (M+H)⁺).

Step 5: Compound AC2

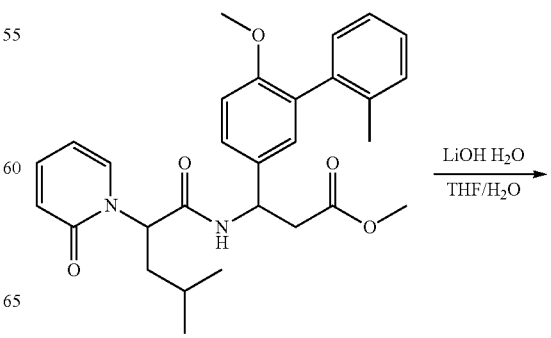

-continued

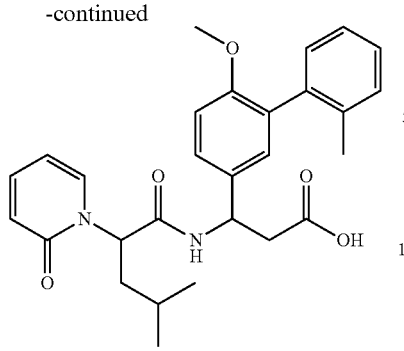

AC1 (30 mg, 0.06 mmol) was treated with LiOH—H$_2$O (8 mg, 0.18 mmol) in 3 mL of THF and 1 mL of H$_2$O at room temperature for 1 h. The solution was adjusted to pH=3~4 with TFA. The solvent was removed in vacuo, and the residue was purified by Preparative-HPLC A (33-70% MeCN) to give the desired product AC2 (10 mg) as a white solid Compound AC2 LC/MS A: 100% purity, UV=214 nm, Rt=1.60 min, ESI 477 (M+H)$^+$.

$^1$H NMR (500 MHz, MeOD) δ 7.64 (dd, J=6.9, 1.6 Hz, 1H), 7.39-7.35 (m, 1H), 7.26 (dd, J=8.5, 2.3 Hz, 1H), 7.12-7.03 (m, 3H), 7.00-6.99 (m, 2H), 6.87 (d, J=8.5 Hz, 1H), 6.42 (d, J=8.6 Hz, 1H), 6.27 (dd, J=6.8, 5.7 Hz, 1H), 5.62 (dd, J=9.4, 6.8 Hz, 1H), 5.15 (t, J=6.8 Hz, 1H), 3.61 (s, 3H), 2.54 (d, J=6.8 Hz, 2H), 1.97 (s, 3H), 1.72 (d, J=32.4 Hz, 2H), 1.22 (br, 1H), 0.78-0.76 (m, 6H).

Preparation of Compounds AD1 and AD2

Step 1: methyl 3-(3-bromo-4-methylphenyl)-3-((tert-butoxycarbonyl)amino)propanoate

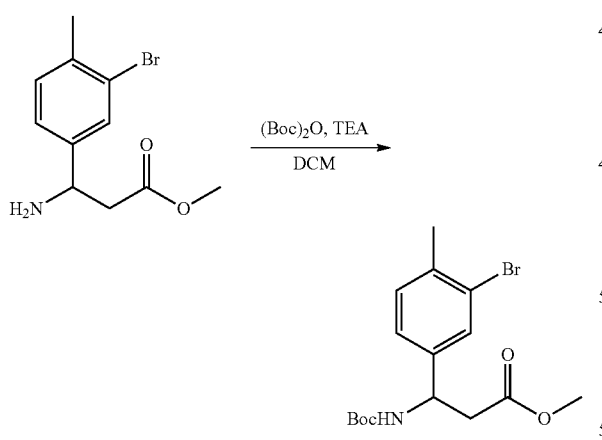

To a solution of methyl 3-amino-3-(3-bromo-4-methylphenyl)propanoate (1.8 g, 6.6 mmol) and Et$_3$N (2.0 g, 19.8 mmol) in DCM (20 mL) was added di-tert-butyl dicarbonate (1.2 g, 5.28 mmol). The reaction mixture was stirred at room temperature for 16 hours. The mixture was concentrated under reduced pressure to give crude the product, which was purified by silica gel column (20% EtOAc in pet. ether) to provide the desired product methyl 3-(3-bromo-4-methylphenyl)-3-((tert-butoxycarbonyl)amino)propanoate as a white solid (2.0 g). Yield 81% (96% purity, UV=214 nm, ESI 272 (MH-Boc)$^+$).

Step 2: methyl 3-((tert-butoxycarbonyl)amino)-3-(4-methyl-3-morpholinophenyl)propanoate

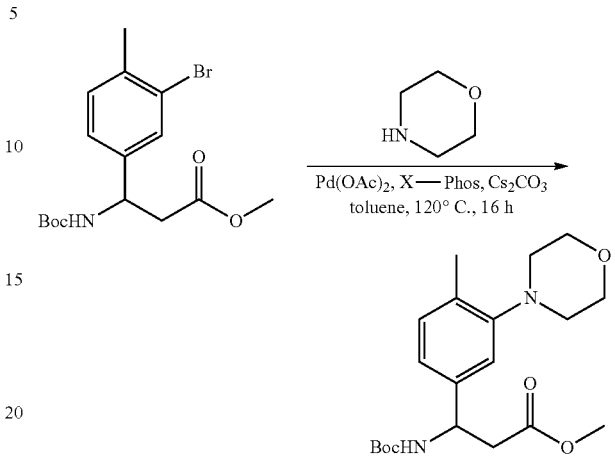

A mixture of methyl 3-(3-bromo-4-methylphenyl)-3-((tert-butoxycarbonyl)amino)propanoate (550 mg, 1.5 mmol), morpholine (261 mg, 3.0 mmol), Pd(OAc)$_2$ (34 mg, 0.15 mmol), X-Phos (143 mg, 0.30 mmol) and Cs$_2$CO$_3$ (1.5 g, 4.5 mmol) in toluene (10 mL) under N$_2$ was heated to 120° C. and stirred for 16 hours. The mixture was filtered though a pad of Celite and the filtrate was concentrated under reduced pressure to give crude product, which was purified by silica gel column (15% EtOAc in pet ether) to provide desired product methyl 3-((tert-butoxycarbonyl)amino)-3-(4-methyl-3-morpholinophenyl)propanoate as a white solid (200 mg). Yield 34% (89% purity, UV=254 nm, ESI 379 (M+H)$^+$).

Step 3: methyl 3-amino-3-(4-methyl-3-morpholinophenyl)propanoate hydrochloride

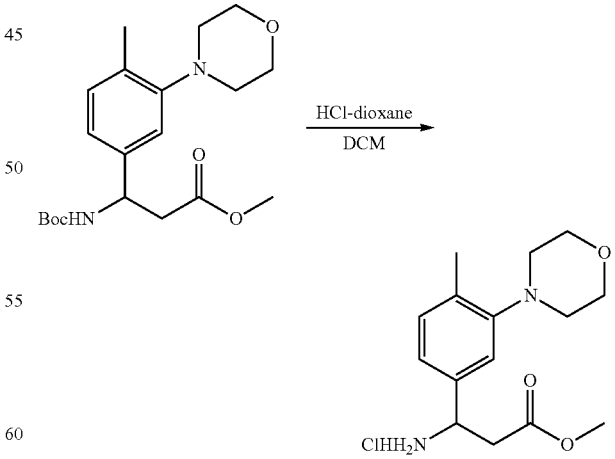

To a solution of methyl 3-((tert-butoxycarbonyl)amino)-3-(4-methyl-3-morpholinophenyl)propanoate (130 mg, 0.34 mmol) in DCM (5 mL) was added HCl in dixane (4M) (1 mL) and the solution was stirred at room temperature for 1 hour. The mixture was concentrated under reduced pressure to provide the crude product methyl 3-amino-3-(4-methyl-3-morpholinophenyl)propanoate hydrochloride as a white solid (95 mg) which was used in next step without further purification. Yield 99% (80% purity, UV=254 nm, ESI 279 (M+H)+).

Step 4: 4-methyl-2-(4-oxoquinazolin-3(4H)-yl)pentanamido)-3-(4-methyl-3-morpholinophenyl)propanoate

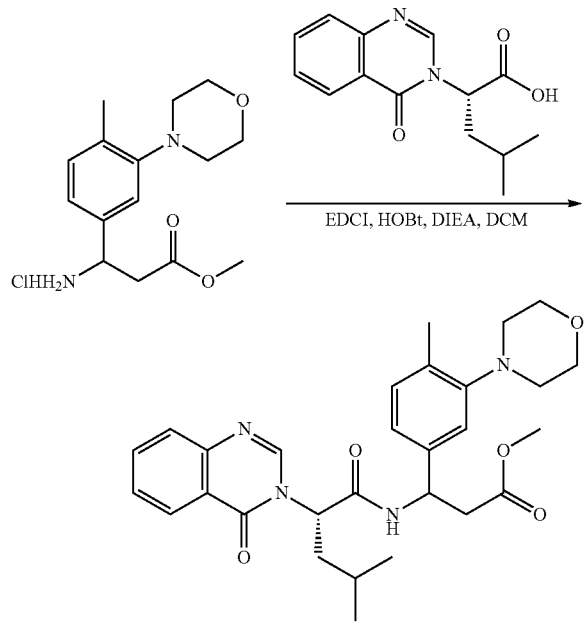

A mixture of methyl 3-amino-3-(4-methyl-3-morpholinophenyl)propanoate hydrochloride (95 mg, 0.30 mmol), (S)-4-methyl-2-(4-oxoquinazolin-3(4H)-yl)pentanoic acid (79 mg, 0.30 mmol), HOBt (53 mg, 0.39 mmol), EDCI (69 mg, 0.39 mmol) and DIEA (116 mg, 0.90 mmol) in DCM (10 mL) was stirred at room temperature for 16 hours. The mixture was concentrated under reduced pressure to give the residue which was purified by preparative-TLC (pet. ether: EtOAc 1:1) to obtain the desired product methyl 3-((S)-4-methyl-2-(4-oxoquinazolin-3(4H)-yl)pentanamido)-3-(4-methyl-3-morpholinophenyl)propanoate as a colorless oil (100 mg). Yield 73% (98% purity, UV=254 nm, ESI 521 (M+H)+).

Step 5: 3-((S)-4-methyl-2-(4-oxoquinazolin-3(4H)-yl)pentanamido)-3-(4-methyl-3-morpholinophenyl)propanoic acid

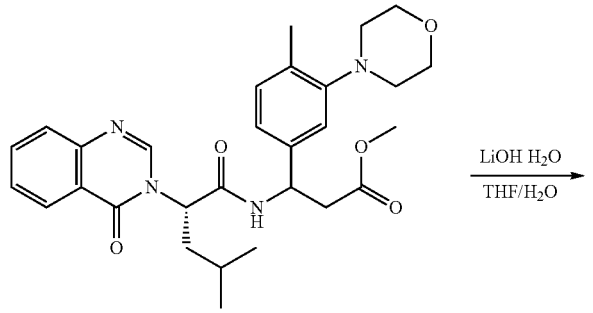

Methyl 3-((S)-4-methyl-2-(4-oxoquinazolin-3 (4H)-yl)pentanamido)-3-(4-methyl-3-morpholinophenyl)propanoate (100 mg, 0.19 mmol) was treated with LiOH—H$_2$O (24 mg, 0.57 mmol) in THF (5 mL) and H$_2$O (2 mL) at room temperature for 1 hour. The mixture was acidified with HCl (1 M) to pH=5~6 and the solvent was removed under reduced pressure. The residue was purified by preparatory HPLC A (30~70% MeCN) to give the desired compounds AD1 (29 mg) and AD2 (13 mg) as white solids.

Compound AD1 LC/MS C 100% purity, UV=214 nm, Rt=1.54 min, ESI 507 (M+H)+

$^1$H NMR (500 MHz, MeOD) δ 8.41 (s, 1H), 8.28 (dd, J=8.0, 1.2 Hz, 1H), 7.88-7.82 (m, 1H), 7.70 (d, J=5.0 Hz, 1H), 7.58 (t, J=7.6 Hz, 1H), 7.07 (d, J=7.8 Hz, 1H), 6.97 (s, 1H), 6.94 (d, J=7.7 Hz, 1H), 5.75 (dd, J=9.4, 6.9 Hz, 1H), 5.32 (t, J=7.3 Hz, 1H), 3.76-3.69 (m, 4H), 2.77 (dd, J=10.5, 6.0 Hz, 6H), 2.22 (s, 3H), 2.11-2.02 (m, 2H), 1.60-1.52 (m, 1H), 1.05-0.98 (m, 6H).

Compound AD2 LC/MS B 100% purity, UV=214 nm, Rt=1.76 min, ESI 507 (M+H)+.

$^1$H NMR (500 MHz, MeOD) δ 8.45 (s, 1H), 8.28 (d, J=7.1 Hz, 1H), 7.89-7.83 (m, 1H), 7.72 (d, J=8.1 Hz, 1H), 7.59 (t, J=7.6 Hz, 1H), 7.16 (d, J=7.8 Hz, 1H), 7.08 (s, 1H), 7.01 (d, J=7.7 Hz, 1H), 5.75 (dd, J=10.0, 6.4 Hz, 1H), 5.31 (t, J=7.1 Hz, 1H), 3.88-3.81 (m, 4H), 2.95-2.89 (m, 4H), 2.79-2.74 (m, 2H), 2.30 (s, 3H), 2.07-1.92 (m, 2H), 1.48-1.43 (m, 1H), 0.98-0.95 (m, 6H).

Preparation of Compounds AE1 and AE2

Step 1: methyl 6-methyl-5-o-tolylnicotinate

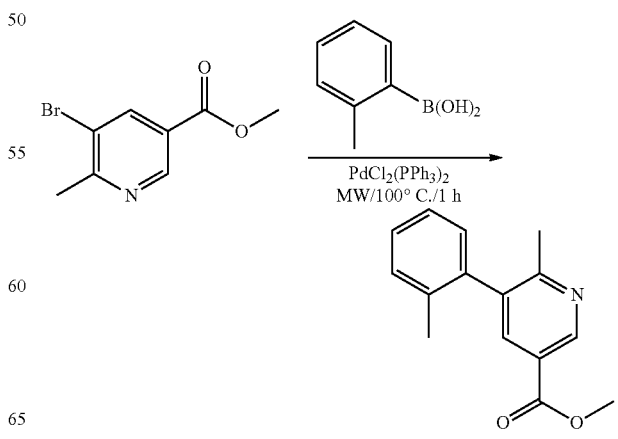

A solution of methyl 5-bromo-6-methylnicotinate (460 mg, 2.0 mmol), o-tolylboronic acid (544 mg, 4.0 mmol) and K$_2$CO$_3$ (553 mg, 4.0 mmol) in dioxane (12 mL) and water (3 mL) was degassed with bubbling nitrogen, PdCl$_2$(PPh$_3$)$_2$ (70 mg, 0.1 mmol) was added and then the reaction was stirred at 100° C. for 1 h. The mixture was diluted with EtOAc (18 mL) and water (5 mL). The organic phase was dried over Na$_2$SO$_4$, filtered and the filtrate was concentrated under reduced pressure to give a brown oil, which was purified by silica gel column (pet ether/EtOAc=10:15:1) to provide the desired product methyl 6-methyl-5-o-tolylnicotinate as a yellow solid (410 mg). Yield 85% (98% purity, UV=214 nm, ESI 242 (M+H)$^+$).

Step 2: (6-methyl-5-o-tolylpyridin-3-yl)methanol

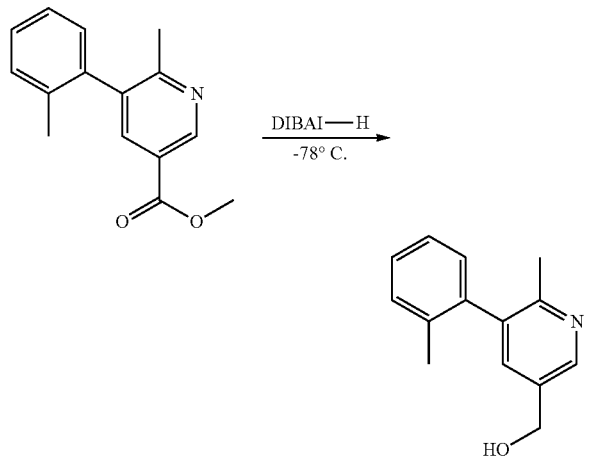

To a solution of methyl 6-methyl-5-o-tolylnicotinate (591 mg, 2.45 mmol) in toluene (16 mL) was added DIBL-H (1M in toluene, 7.35 ml, 7.35 mmol) dropwise at −78° C. The mixture was stirred at −78° C. for 1 h. The mixture was quenched with Na$_2$SO$_4$-10H$_2$O at −10° C. and the solution was stirred at room temperature for 0.5 h, The mixture was filtered off salt and washed with MeCN. The filtrate was concentrated under reduced pressure to give the crude product (6-methyl-5-o-tolylpyridin-3-yl)methanol as yellow solid (490 mg). Yield 90% (85% purity, UV=214 nm, ESI 214 (M+H)$^+$). The crude product was used for the next step directly.

Step 3: 6-methyl-5-o-tolylnicotinaldehyde

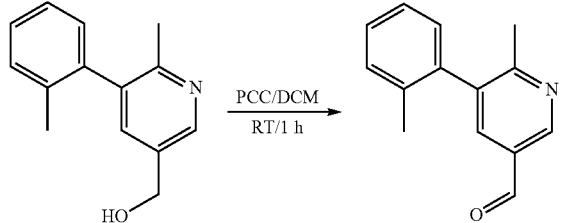 [SMILES: Cc1ccccc1-c1cc(CO)cnc1C ; "PCC/DCM" ; "RT/1 h" ; Cc1ccccc1-c1cc(C=O)cnc1C]

To a solution of (6-methyl-5-o-tolylpyridin-3-yl)methanol (490 mg, 2.32 mmol) in DCM (20 mL) was added PCC (750 mg, 3.48 mmol), and the solution was stirred at room temperature for 1 h. The mixture was diluted with EtOAc (12 mL) and water (6 mL). The organic layer was dried over Na$_2$SO$_4$ and filtered. The filtrate was concentrated under reduced pressure to give a brown oil, which was purified by silica gel column (DCM/MeOH=20:1~2:1) to provide the desired product 6-methyl-5-o-tolylnicotinaldehyde as an orange solid (448 mg). Yield 91% (99% purity, UV=214 nm, ESI212 (M+H)$^+$).

Step 4: 3-amino-3-(6-methyl-5-o-tolylpyridin-3-yl)propanoic acid

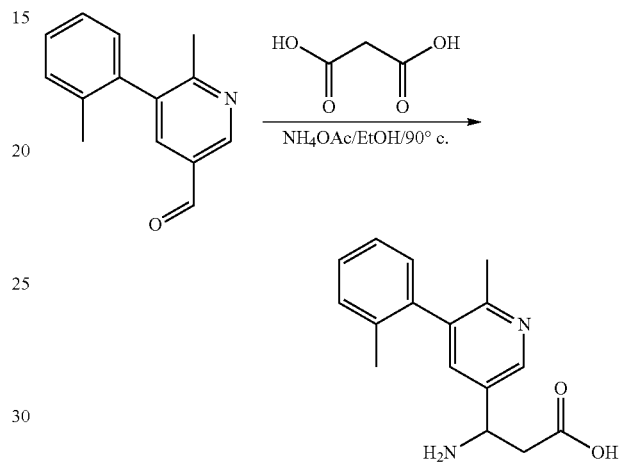

A mixture of 6-methyl-5-o-tolylnicotinaldehyde (254 mg, 1.2 mmol), malonic acid (187 mg, 1.8 mmol), NH$_4$OAc (185 mg, 2.4 mmol) in EtOH (16 mL) was heated to reflux overnight. The solvent was removed in vacuo, and the residue was purified by silica gel column (DCM:MeOH=8:1-1:1) to provide the crude product 3-amino-3-(6-methyl-5-o-tolylpyridin-3-yl)propanoic acid as a brown solid (155 mg). Yield 31% (91% purity, UV=254 nm, ESI 271 (M+H)$^+$).

Step 5: methyl 3-amino-3-(6-methyl-5-o-tolylpyridin-3-yl)propanoate

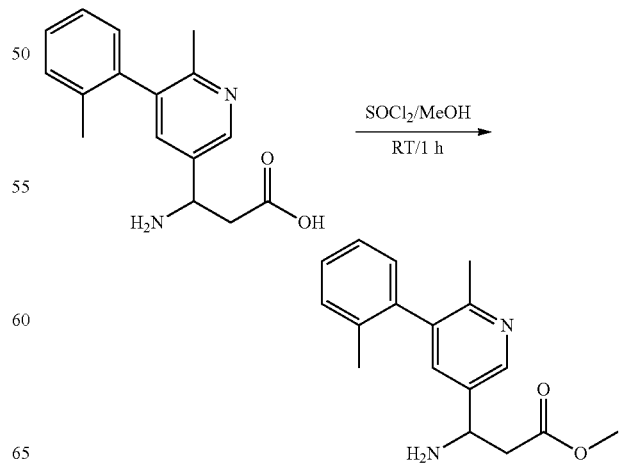

A mixture of 3-amino-3-(6-methyl-5-o-tolylpyridin-3-yl)propanoic acid (128 mg. 0.31 mmol) in MeOH (5 mL) was added SOCl$_2$ (184 mg, 1.55 mmol) at room temperature. The mixture was stirred at room temperature for 1 h. The solution was adjusted with sat. NaHCO$_3$ solution to pH=7~8, and the solution was extracted with EtOAc (30 mL×2). The organic layer was concentrated under reduced pressure to give an oil, which was purified by silica gel column (DCM:MeOH=20:1-2:1) to provide the desired product methyl 3-amino-3-(6-methyl-5-o-tolylpyridin-3-yl)propanoate as a green oil (41 mg). Yield 47% (99% purity, UV=254 nm, ESI 284 (M+H)$^+$).

Step 6: methyl 3-(4-methyl-2-(4-methyl-2-oxopyridin-1(2H)-yl)pentanamido)-3-(6-methyl-5-o-tolylpyridin-3-yl)propanoate A mixture of methyl 3-amino-3-(6-methyl-5-o-tolylpyridin-3-yl)propanoate (41 mg, 0.14 mmol), (S)-4-methyl-2-(4-methyl-2-oxopyridin-1(2H)-yl)pentanoic acid (34 mg, 0.15 mmol), EDCI (41 mg, 0.21 mmol), HOBt (29 mg, 0.21 mmol) and DIEA (56 mg, 0.43 mmol) in DCM (5 mL) was stirred at room temperature for 0.5 hours. The mixture was diluted with DCM (10 mL) and 5 mL of water. The organic phase was dried over Na$_2$SO$_4$ and filtered. The filtrate was concentrated under reduced pressure to give a brown oil, which was purified by silica gel column (pet. ether:EtOAc 1:10) to provide the desired product methyl 3-(4-methyl-2-(4-methyl-2-oxopyridin-1(2H)-yl)pentanamido)-3-(6-methyl-5-o-tolylpyridin-3-yl)propanoate (53 mg) as colorless oil. Yield 75% (99% purity, UV=254 nm, ESI 490 (M+H)$^+$).

Step 5: Compounds AE1 and AE2

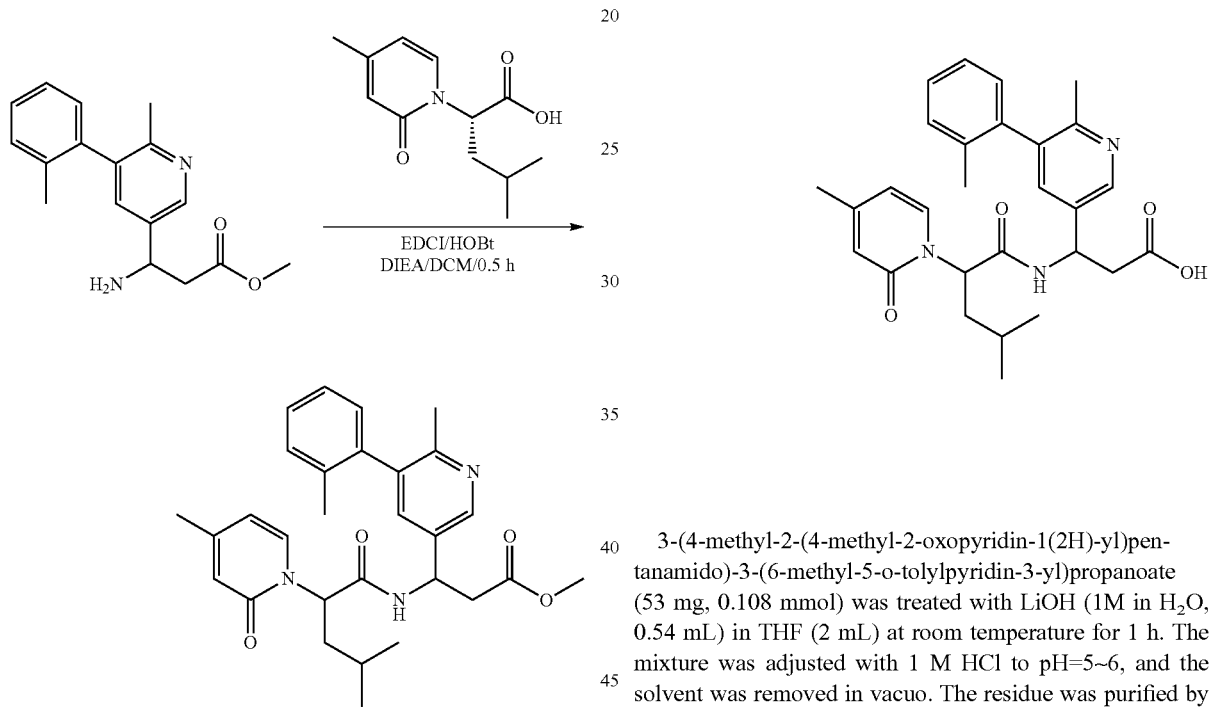

3-(4-methyl-2-(4-methyl-2-oxopyridin-1(2H)-yl)pentanamido)-3-(6-methyl-5-o-tolylpyridin-3-yl)propanoate (53 mg, 0.108 mmol) was treated with LiOH (1M in H$_2$O, 0.54 mL) in THF (2 mL) at room temperature for 1 h. The mixture was adjusted with 1 M HCl to pH=5~6, and the solvent was removed in vacuo. The residue was purified by preparatory HPLC A (30-64% MeCN) to give the compounds AE1 (14 mg) and AE2 (11 mg) as white solids.

Compound AE1 LC/MS A: 100% purity, UV=214 nm, Rt=8.25 min, ESI 476 (M+H)$^+$.

$^1$H NMR (500 MHz, MeOD) δ 8.40 (s, 1H), 7.57 (t, J=6.9 Hz, 1H), 7.45 (dd, J=8.6, 2.2 Hz, 1H), 7.38-7.24 (m, 3H), 7.05 (dd, J=26.6, 7.4 Hz, 1H), 6.29 (d, J=8.8 Hz, 1H), 6.25 (dd, J=7.1, 1.9 Hz, 1H), 5.70-5.65 (m, 1H), 5.38 (dd, J=15.1, 7.7 Hz, 1H), 2.99-2.78 (m, 2H), 2.21 (dd, J=13.4, 2.6 Hz, 6H), 2.10-1.89 (m, 5H), 1.45-1.42 (m, 1H), 0.97-0.94 (m, 6H).

Compound AE2-P2 LC/MS A: 100% purity, UV=214 nm, Rt=8.44 min, ESI 476 (M+H)$^+$.

$^1$H NMR (500 MHz, MeOD) δ 8.46 (d, J=1.7 Hz, 1H), 7.63 (dd, J=7.0, 5.5 Hz, 1H), 7.58-7.53 (m, 1H), 7.42-7.23 (m, 3H), 7.12 (dd, J=10.8, 7.3 Hz, 1H), 6.38 (s, 1H), 6.31 (d, J=7.1 Hz, 1H), 5.69 (q, J=7.7 Hz, 1H), 5.34-5.32 (m, 1H), 3.02-2.76 (m, 2H), 2.27 (s, 3H), 2.23 (s, 3H), 2.05 (s, 3H), 1.91-1.71 (m, 2H), 1.43-1.22 (m, 1H), 0.98-0.75 (m, 6H).

Preparation of Compounds AF1 and AF2

Step 1: methyl 5-bromo-6-iodonicotinate

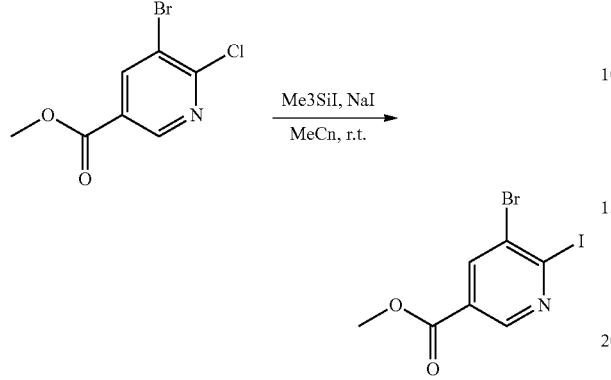

A mixture of methyl 5-bromo-6-chloronicotinate (3.2 g, 0.013 mol), iodotrimethylsilane (2.57 g, 0.013 mol) and NaI (5.8 g, 0.039 mol) in MeCN (50 mL) was stirred at room temperature for 16 hours. The mixture was adjusted to pH=8 with 2N NaOH solution and the solution was extracted with EtOAc (50 mL×2). The combined organic layer was concentrated under reduced pressure to give crude product methyl 5-bromo-6-iodonicotinate as a white solid (290 mg). Yield 100% (43% purity, UV=254 nm, ESI 341.9 (M+H)$^+$).

Step 2: methyl 5-bromo-6-methylnicotinate

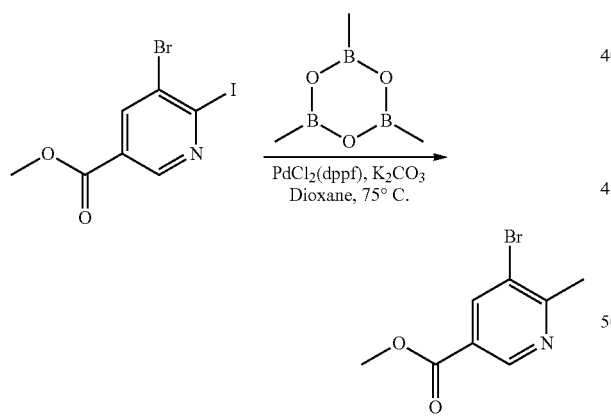

A mixture of methyl 5-bromo-6-iodonicotinate (5.2 g, 0.015 mol), 2,4,6-trimethyl-1,3,5,2,4,6-trioxatriborinane (50% in THF, 6.4 mL, 0.045 mol), PdCl$_2$(dppf) (1.11 g, 1.52 mmol) and K$_2$CO$_3$ (6.3 g, 0.046 mol) in 1,4-Dioxane (80 mL) was stirred at 75° C. for 16 hours. Water (50 mL) was added, and the solution was extracted with EtOAc (60 mL×2). The combined organic layers were concentrated under reduced pressure, and the residue was purified by flash column chromatography (20% EtOAc in per ether) to provide the desired product methyl 5-bromo-6-methylnicotinate as a white solid (1.67 g). Yield 48% (92% purity, UV=254 nm, ESI 230 (M+H)$^+$).

Step 3: methyl (S)-6-methyl-5-(3-methylmorpholino)nicotinate

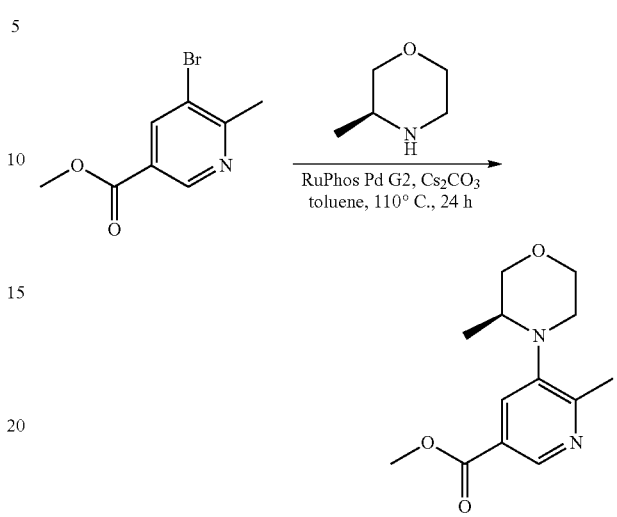

A mixture of methyl 5-bromo-6-methylnicotinate (1.6 g, 6.95 mmol), (S)-3-methylmorpholine (2.1 g, 20.85 mmol), RuPhos-Pd-G2 (270 mg, 0.35 mmol) and Cs$_2$CO$_3$ (6.8 g, 20.85 mmol) in toluene (10 mL) under N$_2$ atmosphere was heated to 110° C. and stirred for 24 hours. The mixture was filtered though a pad of Celite and the filtrate was concentrated under reduced pressure to give crude product, which was purified by silica gel column (20% EtOAc in pet ether) to provide the desired product methyl (S)-6-methyl-5-(3-methylmorpholino)nicotinate as a white solid (290 mg). Yield 17% (43% purity, UV=254 nm, ESI 251 (M+H)$^+$).

Step 4: (S)-(6-methyl-5-(3-methylmorpholino)pyridin-3-yl)methanol

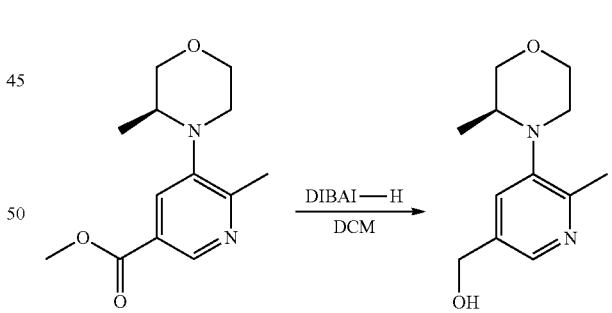

To a solution of methyl (S)-6-methyl-5-(3-methylmorpholino)nicotinate (290 mg, 1.16 mmol) in DCM (10 mL) was added dropwise DIBAL-H (1M in hexane, 3.5 mL, 3.5 mmol) at −78° C. and the reaction solution was stirred at room temperature for 16 hours. Water (5 mL) was added slowly and the mixture was stirred for 10 mins. The mixture was filtered though a pad of Celite and the filtrate was concentrated under reduced pressure to provide the crude product (S)-(6-methyl-5-(3-methylmorpholino)pyridin-3-yl)methanol as a colorless oil (220 mg), which was used in next step without further purification. Yield 86% (60% purity, UV=254 nm, ESI 223 (M+H)$^+$).

Step 5: (S)-6-methyl-5-(3-methylmorpholino)nicotinaldehyde

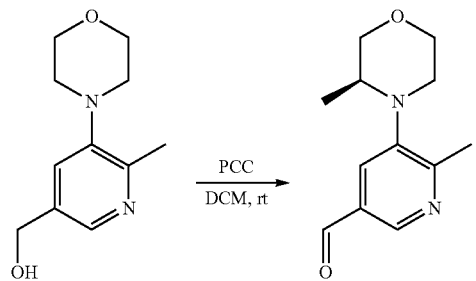

To a solution of (S)-(6-methyl-5-(3-methylmorpholino)pyridin-3-yl)methanol (220 mg, 0.99 mmol) in DCM (10 mL) was added PCC (320 mg, 1.49 mmol) and the solution was stirred at room temperature for 2 hours. The mixture was filtered though a pad of Celite and the filtrate was concentrated under reduced pressure to provide the crude product which was purified by preparative-TLC (pet. ether: EtOAc 1:1) to provide desired product (S)-6-methyl-5-(3-methylmorpholino)nicotinaldehyde as a colorless oil (150 mg). Yield 69% (44% purity, UV=254 nm, ESI 221 (M+H)$^+$).

Step 6: 3-amino-3-(6-methyl-5-((S)-3-methylmorpholino)pyridin-3-yl)propanoic acid

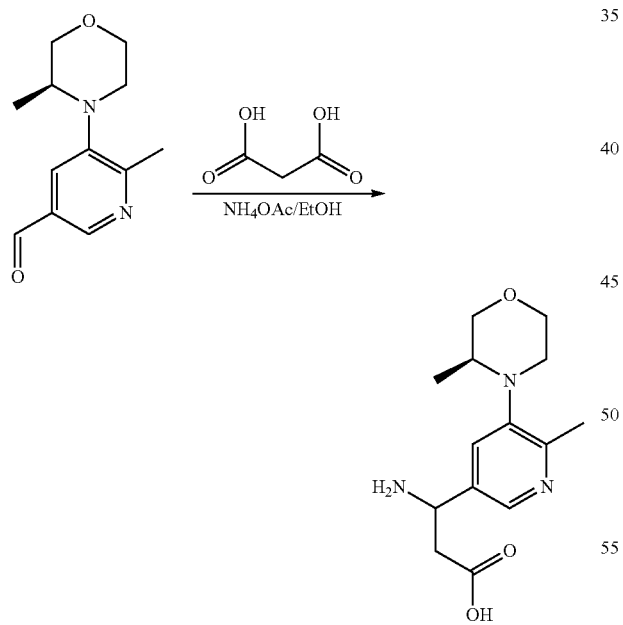

To a solution of (S)-6-methyl-5-(3-methylmorpholino)nicotinaldehyde (130 mg, 0.59 mmol) in EtOH (10 mL) was added malonic acid (92 mg, 0.89 mmol) and NH$_4$OAc (136 mg, 1.77 mmol). The mixture was heated to 60° C. and stirred for 16 hours. The mixture was concentrated under reduced pressure to give the crude product 3-amino-3-(6-methyl-5-((S)-3-methylmorpholino)pyridin-3-yl)propanoic acid as a white solid (164 mg), which was used in next step without further purification. Yield 100% (21% purity, UV=214 nm, ESI 280 (M+H)$^+$).

Step 7: methyl 3-amino-3-(6-methyl-5-((S)-3-methylmorpholino)pyridin-3-yl)propanoate

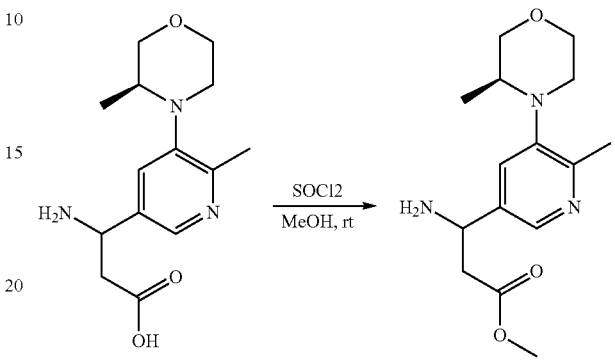

To a solution of 3-amino-3-(6-methyl-5-((S)-3-methylmorpholino)pyridin-3-yl)propanoic acid (164 mg, 0.59 mmol) in MeOH (10 mL) at 0° C. was added SOCl$_2$ (1 mL) dropwise and the solution was stirred at at room temperature for 2 hours. Water (20 mL) was added and the solution was extracted with EtOAc (20 mL×3). The organic layer was washed with saturated aqueous NaHCO$_3$ (10 mL×2) and brine (20 mL), dried over Na$_2$SO$_4$, filtered and the filtrate was concentrated under reduced pressure to give a residue which was purified by preparative-TLC (pet. ether:EtOAc 1:1) to give the desired product methyl 3-(2',6-dimethyl 3-amino-3-(3-bromo-4-methylphenyl)propanoate as a white solid (50 mg). Yield 29% two step (76% purity, UV=254 nm, ESI 294 (M+H)$^+$).

Step 8: methyl 3-(4-methyl-2-(4-methyl-2-oxopyridin-1(2H)-yl)pentanamido)-3-(6-methyl-5-((S)-3-methylmorpholino)pyridin-3-yl)propanoate

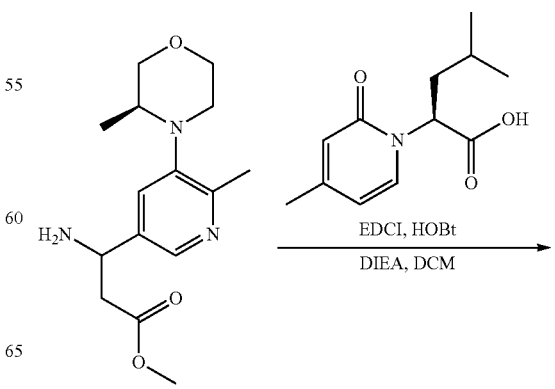

-continued

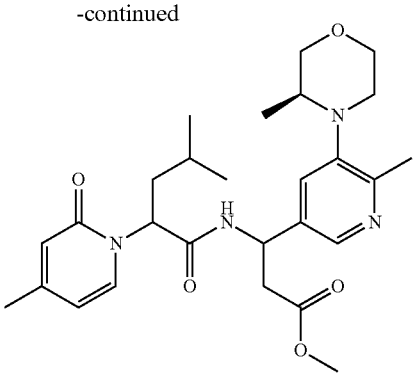

A mixture of methyl 3-amino-3-(6-methyl-5-((S)-3-methylmorpholino)pyridin-3-yl)propanoate (50 mg, 0.17 mmol), (S)-4-methyl-2-(4-methyl-2-oxopyridin-1(2H)-yl)pentanoic acid (49 mg, 0.22 mmol), HOBt (34 mg, 0.26 mmol), EDCI (49 mg, 0.26 mmol) and DIEA (66 mg, 0.51 mmol) in DCM (10 mL) was stirred at room temperature for 16 hours. The mixture was concentrated under reduced pressure to give a residue which was purified by preparative-TLC (pet. ether: EtOAc 1:1) to obtain the desired product methyl 3-(4-methyl-2-(4-methyl-2-oxopyridin-1 (2H)-yl)pentanamido)-3-(6-methyl-5-((S)-3-methylmorpholino)pyridin-3-yl)propanoate as a colorless oil (60 mg). Yield 71% (58% purity, UV=254 nm, ESI 499 (M+H)$^+$).

Step 9: Compounds AF1, AF2 and AF3

Methyl 3-((S)-methyl 3-((S)-4-methyl-2-(4-methyl-2-oxopyridin-1(2H)-yl)pentanamido)-3-(6-methyl-5-((S)-3-methylmorpholino)pyridin-3-yl)propanoate (60 mg, 0.12 mmol) was treated with LiOH—H$_2$O (15 mg, 0.36 mmol) in THF (5 mL) and H$_2$O (2 mL) at room temperature for 1 hour. The mixture was acidified with HCl (1 M) to pH=5~6. The solvent was removed under reduced pressure, and the residue was purified by preparatory HPLC B (30~70% MeCN) to give the compounds AF1 (4 mg), AF2 (2 mg) and AF3 (2 mg) as white solids.

Compound AF1 LC/MS A 97% purity, UV=214 nm, Rt=1.26 min, ESI 485 (M+H)$^+$.

$^1$H NMR (500 MHz, MeOD) δ 8.14 (s, 1H), 7.60 (t, J=7.8 Hz, 1H), 7.48 (d, J=4.6 Hz, 1H), 6.43 (d, J=12.6 Hz, 1H), 6.31 (d, J=7.0 Hz, 1H), 5.68-5.66 (m, 1H), 5.32 (s, 1H), 3.92-3.71 (m, 3H), 3.42-3.35 (m, 1H), 3.20-3.15 (m, 1H), 2.89-2.73 (m, 3H), 2.69-2.66 (m, 0.5H), 2.58-2.55 (m, 0.5H), 2.47 (s, 3H), 2.24 (d, J=4.1 Hz, 3H), 2.01-1.86 (m, 2H), 1.48-1.43 (m, 1H), 0.99-0.96 (m, 6H), 0.72 (d, J=6.1 Hz, 1.5H), 0.63 (d, J=6.1 Hz, 1.5H).

Compound AF2 LC/MS A 100% purity, UV=214 nm, Rt=1.27 min, ESI 485 (M+H)$^+$.

$^1$H NMR (500 MHz, MeOD) δ 8.21 (d, J=1.7 Hz, 1H), 7.63 (d, J=7.3 Hz, 2H), 6.41 (s, 1H), 6.32 (d, J=5.6 Hz, 1H), 5.70-5.65 (m, 1H), 5.30 (t, J=7.1 Hz, 1H), 3.94-3.77 (m, 3H), 3.43 (m, 1H), 3.30 (m, 1H), 2.97-2.71 (m, 4H), 2.53 (s, 3H), 2.25 (s, 3H), 1.87-1.82 (m, 2H), 1.39-1.33 (m, 1H), 0.95-0.91 (m, 6H), 0.80 (d, J=6.2 Hz, 3H).

Compound AF3 LC/MS A: 96% purity, UV=214 nm, Rt=1.28 min, ESI 485 (M+H)$^+$.

$^1$H NMR (500 MHz, MeOD) δ 8.21 (s, 1H), 7.66-7.59 (m, 2H), 6.40 (s, 1H), 6.32 (d, J=7.2 Hz, 1H), 5.72-5.69 (m, 1H), 5.29 (t, J=7.1 Hz, 1H), 3.94-3.76 (m, 3H), 3.40 (m, 1H), 3.30 (m, 1H), 2.97-2.73 (m, 4H), 2.53 (s, 3H), 2.25 (s, 3H), 1.87-1.80 (m, 2H), 1.38-1.32 (m, 1H), 0.94-0.91 (m, 6H), 0.79 (d, J=6.1 Hz, 3H).

Preparation of Compound AG1b

Step 1: (S)-methyl 3-(5-bromopyridin-3-yl)-3-(tert-butoxycarbonylamino)propanoate

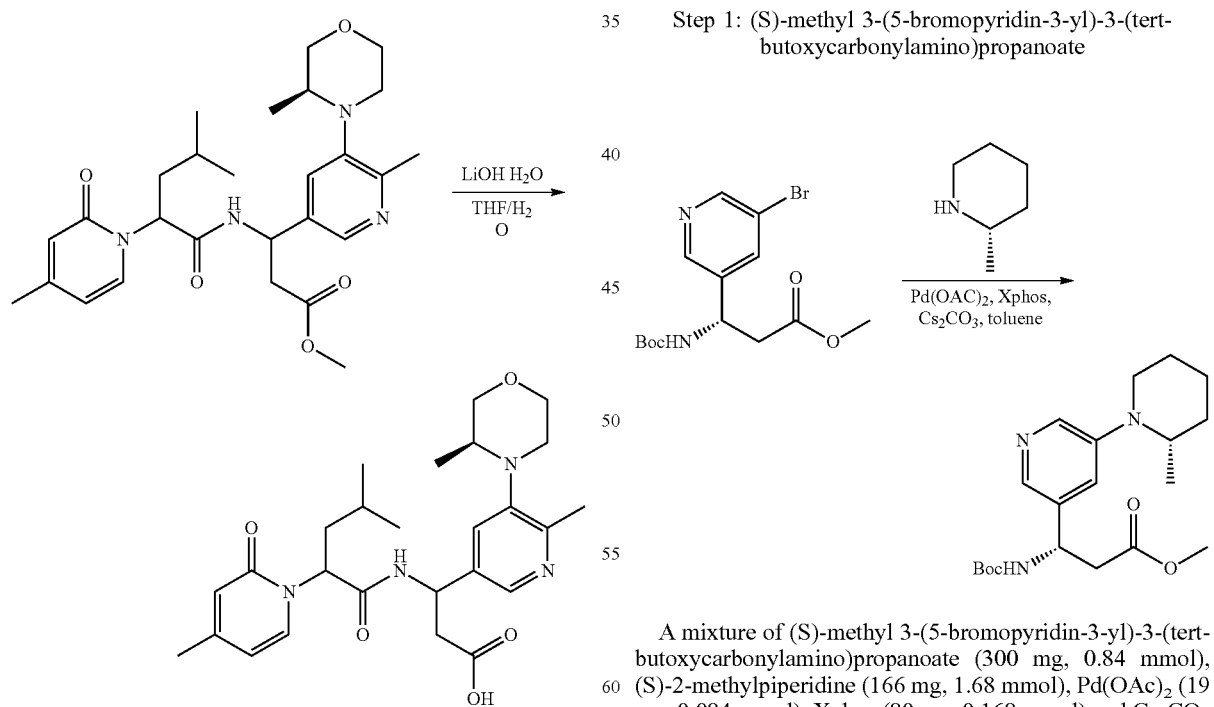

A mixture of (S)-methyl 3-(5-bromopyridin-3-yl)-3-(tert-butoxycarbonylamino)propanoate (300 mg, 0.84 mmol), (S)-2-methylpiperidine (166 mg, 1.68 mmol), Pd(OAc)$_2$ (19 mg, 0.084 mmol), Xphos (80 mg, 0.168 mmol) and Cs$_2$CO$_3$ (822 mg, 2.52 mmol) in toluene (2 mL) was stirred at 120° C. under N$_2$ for 16 h. The mixture was filtered over Celite and the filtrate was concentrated in vacuo. The residue was purified by silica gel column (pet. ether:EtOAc=1:1) to give the desired product (S)-methyl 3-(tert-butoxycarbonylamino)-3-(5-((S)-2-methylpiperidin-1-yl)pyridin-3-yl)

propanoate (30 mg) as a yellow oil. Yield 10% (98% purity, UV=214 nm, ESI 378 (M+H)+).

Step 2: (S)-methyl 3-amino-3-(5-((S)-2-methylpiperidin-1-yl)pyridin-3-yl)propanoate

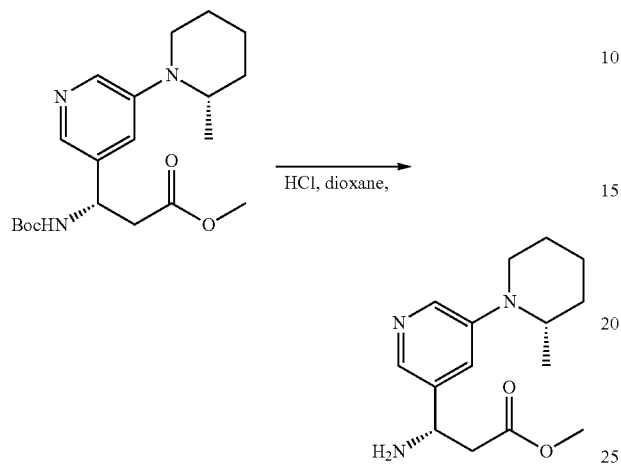

(S)-methyl 3-(tert-butoxycarbonylamino)-3-(5-((S)-2-methylpiperidin-1-yl)pyridin-3-yl)propanoate (50 mg, 0.13 mmol) was treated with HCl (1 mL) in dioxane (5 mL) at room temperature for 1 hour. The solvent was removed in vacuo to provide the crude product (S)-methyl 3-amino-3-(5-((S)-2-methylpiperidin-1-yl)pyridin-3-yl)propanoate as a yellow oil (37 mg). Yield 100% (98% purity, UV=214 nm, ESI 278 (M+H)+). The crude product was used for the next step directly.

Step 3: (3S)-methyl 3-(4-methyl-2-(4-methyl-2-oxopyridin-1(2H)-yl)pentanamido)-3-(5-((S)-2-methylpiperidin-1-yl)pyridin-3-yl)propanoate

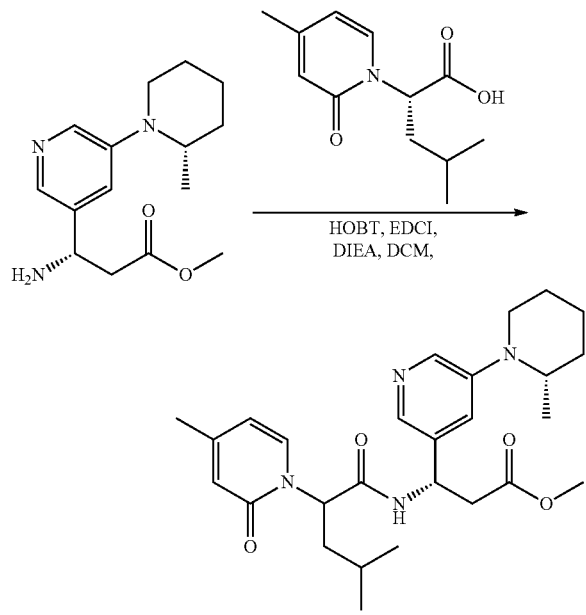

A mixture of (S)-methyl 3-amino-3-(5-((S)-2-methylpiperidin-1-yl)pyridin-3-yl)propanoate (37 mg, 0.13 mmol), (S)-4-methyl-2-(4-methyl-2-oxopyridin-1(2H)-yl)pentanoic acid (29 mg, 0.13 mmol), HOBt (27 mg, 0.20 mmol), EDCI (38 mg, 0.20 mmol) and DIEA (52 mg, 0.40 mmol) in DCM (5 mL) was stirred at room temperature for 2 hours. The mixture was poured into 10 mL of water and the solution was extracted with DCM (30 mL×3). The organic phase was dried over Na2SO4, filtered and the filtrate was concentrated in vacuo. The residue was purified by silica gel column (pet. ether:EtOAc=1:1) to provide the desired product (3S)-methyl 3-(4-methyl-2-(4-methyl-2-oxopyridin-1(2H)-yl)pentanamido)-3-(5-((S)-2-methylpiperidin-1-yl)pyridin-3-yl)propanoate as a yellow oil (40 mg). Yield 63% (95% purity, UV=254 nm, ESI 483 (M+H)+).

Step 4: (S)-3-((S)-4-methyl-2-(4-methyl-2-oxopyridin-1(2H)-yl)pentanamido)-3-(5-((S)-2-methylpiperidin-1-yl)pyridin-3-yl)propanoic acid

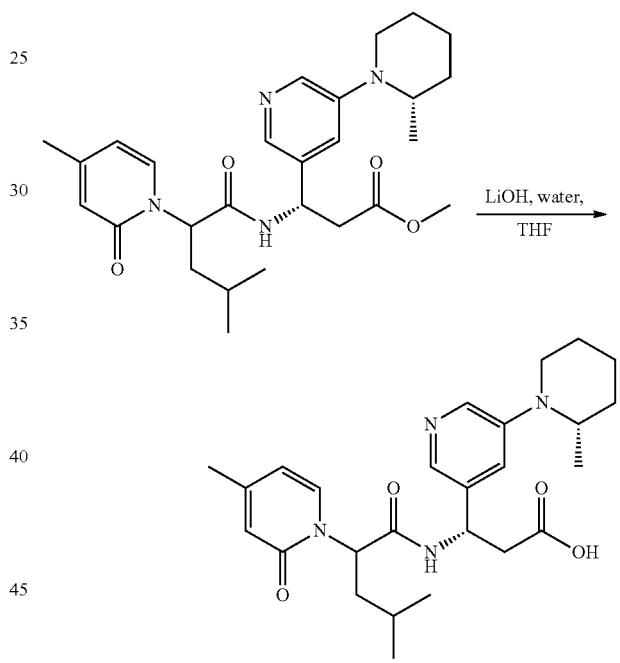

(3 S)-methyl 3-(4-methyl-2-(4-methyl-2-oxopyridin-1 (2H)-yl)pentanamido)-3-(5-((S)-2-methylpiperidin-1-yl) pyridin-3-yl)propanoate (40 mg, 0.08 mmol) was treated with LiOH (1M in H2O, 0.6 mL) in THF (2 mL) at room temperature for 2 h. The mixture was adjusted with 1M HCl to pH=5~6 and the solvent was removed in vacuo. The residue was purified by preparatory HPLC A (30-70% MeCN) to give the desired compounds AG1a (7.4 mg) as a white solid and AG1b (10.0 mg) as white solids.

Compound AG1b LC/MS A: 98% purity, UV=214 nm, Rt=1.57 min, ESI 469 (M+H)+.

$^1$H NMR (500 MHz, MeOD) δ 8.09 (d, J=2.7 Hz, 1H), 7.93 (d, J=1.4 Hz, 1H), 7.61 (d, J=7.1 Hz, 1H), 7.35 (s, 1H), 6.38 (s, 1H), 6.30 (dd, J=7.2, 1.8 Hz, 1H), 5.70 (dd, J=9.3, 6.8 Hz, 1H), 5.26 (t, J=7.3 Hz, 1H), 4.10 (s, 1H), 3.39 (d, J=12.3 Hz, 1H), 3.00-3.04 (m, 1H), 2.76-2.89 (m, 2H), 2.23 (s, 3H), 1.95-1.57 (m, 9H), 1.42-1.28 (m, 1H), 1.07 (d, J=6.7 Hz, 3H), 0.90-0.93 (m, 6H).

Preparation of Compound AG2b

Step 1: (R)-methyl 3-(5-bromopyridin-3-yl)-3-(tert-butoxycarbonylamino)propanoate

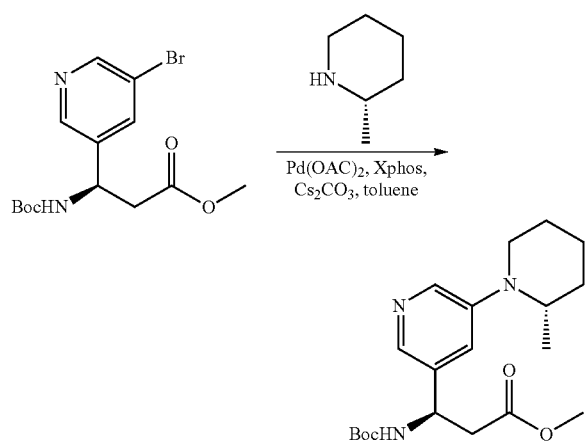

A mixture of (R)-methyl 3-(5-bromopyridin-3-yl)-3-(tert-butoxycarbonylamino)propanoate (300 mg, 0.84 mmol), (S)-2-methylpiperidine (166 mg, 1.68 mmol), Pd(OAc)$_2$ (19 mg, 0.084 mmol), Xphos (80 mg, 0.168 mmol) and Cs$_2$CO$_3$ (822 mg, 2.52 mmol) in toluene (2 mL) was stirred at 120° C. under N$_2$ for 16 h. The mixture was filtered over Celite and the filtrate was concentrated in vacuo. The residue was purified by silica gel column (pet. ether:EtOAc=1:1) to give (R)-methyl 3-(tert-butoxycarbonylamino)-3-(5-4S)-2-methylpiperidin-1-yl)pyridin-3-yl)propanoate (30 mg). Yield 10% (98% purity, UV=214 nm, ESI 378 (M+H)$^+$).

Step 2: (R)-methyl 3-amino-3-(5-((S)-2-methylpiperidin-1-yl)pyridin-3-yl)propanoate

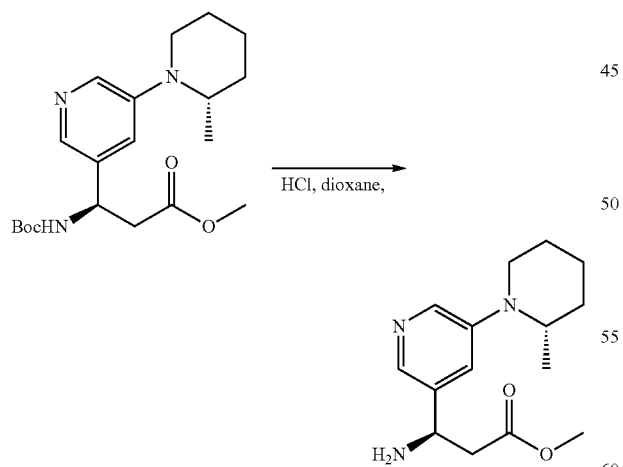

(R)-methyl 3-(tert-butoxycarbonylamino)-3-(5-((S)-2-methylpiperidin-1-yl)pyridin-3-yl)propanoate (50 mg, 0.13 mmol) was treated with HCl (1 mL) in dioxane (5 mL) at room temperature for 1 hour. The solvent was removed in vacuo to provide the crude product (R)-methyl 3-amino-3-(5-((S)-2-methylpiperidin-1-yl)pyridin-3-yl)propanoate as a yellow oil (37 mg). Yield 100% (98% purity, UV=214 nm, ESI 278 (M+H)$^+$). The crude product was used for the next step directly.

Step 3: methyl (3R)-3-(4-methyl-2-(4-methyl-2-oxopyridin-1(2H)-yl)pentanamido)-3-(5-((S)-2-methylpiperidin-1-yl)pyridin-3-yl)propanoate

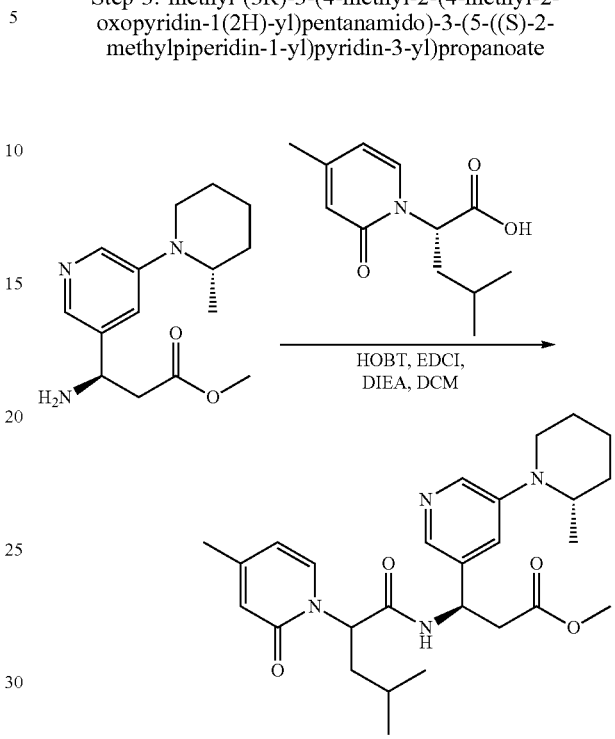

A mixture of (R)-methyl 3-amino-3-(5-((S)-2-methylpiperidin-1-yl)pyridin-3-yl)propanoate (37 mg, 0.13 mmol), (S)-4-methyl-2-(4-methyl-2-oxopyridin-1(2H)-yl)pentanoic acid (29 mg, 0.13 mmol), HOBt (27 mg, 0.20 mmol), EDCI (38 mg, 0.20 mmol) and DIEA (52 mg, 0.40 mmol) in DCM (5 mL) was stirred at room temperature for 2 hours. The mixture was poured into 10 mL of water and the solution was extracted with DCM (30×3). The organic phase was dried over Na$_2$SO$_4$, filtered and the filtrate was concentrated in vacuo. The residue was purified by silica gel column (pet. ether:EtOAc=1:1) to provide the desired product methyl (3R)-3-(4-methyl-2-(4-methyl-2-oxopyridin-1(2H)-yl)pentanamido)-3-(5-((S)-2-methylpiperidin-1-yl)pyridin-3-yl)propanoate as a yellow oil (40 mg). Yield 63% (95% purity, UV=254 nm, ESI 483 (M+H)$^+$).

Step 4: (3R)-3-(4-methyl-2-(4-methyl-2-oxopyridin-1(2H)-yl)pentanamido)-3-(5-((S)-2-methylpiperidin-1-yl)pyridin-3-yl)propanoic acid

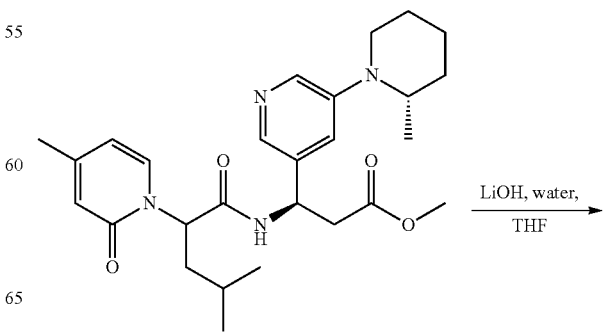

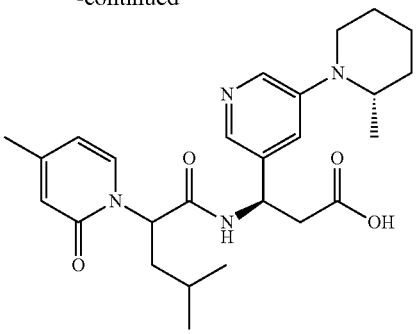

Methyl (3R)-3-(4-methyl-2-(4-methyl-2-oxopyridin-1(2H)-yl)pentanamido)-3-(5-((S)-2-methylpiperidin-1-yl)pyridin-3-yl)propanoate (40 mg, 0.08 mmol) was treated with LiOH (1M in H$_2$O, 0.6 mL) in THF (2 mL) at room temperature for 2 h. The mixture was adjusted with 1M HCl to pH=5~6 and the solvent was removed in vacuo. The resulting residue was purified by preparatory HPLC A (30-70% MeCN) to give the desired compounds AG2a (1.3 mg) and AG2b (5.6 mg) as white solids.

Compound AG2b LC/MS A: 98% purity, UV=214 nm, Rt=1.58 min, ESI 469 (M+H)$^+$.

$^1$H NMR (500 MHz, MeOD) δ 8.11 (d, J=2.7 Hz, 1H), 7.95 (s, 1H), 7.64 (d, J=7.1 Hz, 1H), 7.38 (s, 1H), 6.43-6.25 (m, 2H), 5.70 (t, J=8.0 Hz, 1H), 5.29 (t, J=7.3 Hz, 1H), 4.11 (s, 1H), 3.42 (d, J=12.4 Hz, 1H), 3.04 (t, J=11.7 Hz, 1H), 2.82-2.86 (m, 2H), 2.25 (s, 3H), 1.98-1.58 (m, 8H), 1.41-1.31 (m, 1H), 1.09 (d, J=6.7 Hz, 3H), 0.95-0.91 (m, 6H).

Preparation of Compound AH1

Step 1: (R)-benzyl 3-amino-3-(5-(2,6-dimethylphenyl)pyridin-3-yl)propanoate hydrochloride

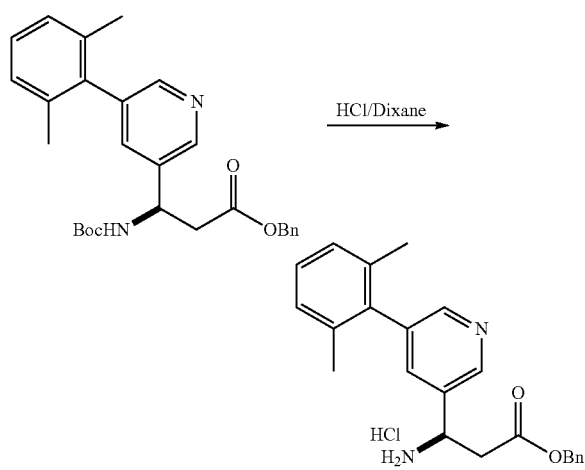

To a solution of (R)-benzyl 3-(tert-butoxycarbonylamino)-3-(5-(2,6-dimethylphenyl)pyridin-3-yl)propanoate (150 mg, 0.33 mmol) in DCM (4 mL) was added HCl/Dioxane (4M, 2 mL) and the solution was stirred at room temperature for 1 hour. The mixture was concentrated under reduced pressure to provide the crude product (R)-benzyl 3-amino-3-(5-(2,6-dimethylphenyl)pyridin-3-yl)propanoate hydrochloride as a light yellow oil (117 mg), which was used for next step directly without further purification. Yield 99% (97% purity, UV=214 nm, ESI 361 (M+H)$^+$).

Step 2: (3R)-benzyl 3-(5-(2,6-dimethylphenyl)pyridin-3-yl)-3-(4-methyl-2-(2-oxopyridin-1(2H)-yl)pentanamido)propanoate

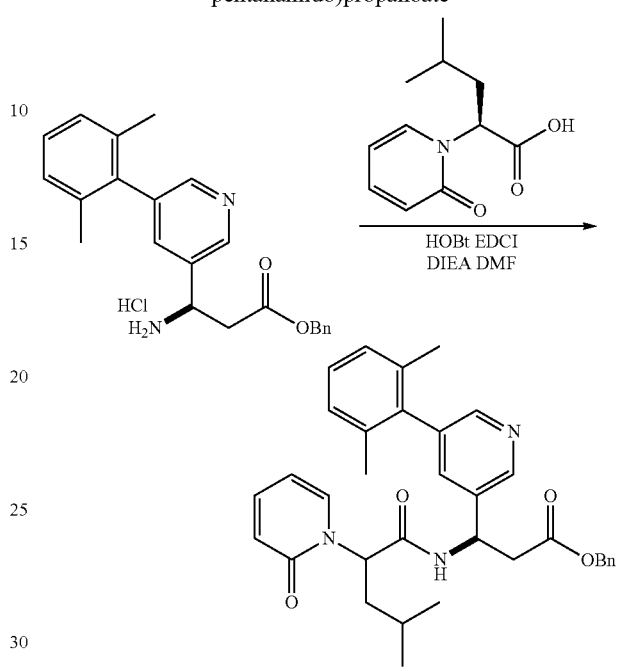

A mixture of (R)-benzyl 3-amino-3-(5-(2,6-dimethylphenyl)pyridin-3-yl)propanoate hydrochloride (117 mg, 0.325 mmol), (S)-4-methyl-2-(2-oxopyridin-1(2H)-yl)pentanoic acid (71 mg, 0.34 mmol), HOBt (66 mg, 0.49 mmol), EDCI (94 mg, 0.49 mmol) and DIEA (126 mg, 0.98 mmol) in DMF (4 mL) was stirred at room temperature for 3 hours. The mixture was poured into water and the solution was extracted with EtOAc (20 mL×2). The combined organic layers were dried over Na$_2$SO$_4$ and filtered. The filtrate was concentrated under reduced pressure to give a residue, which was purified by Preparative-TLC (EtOAc:Petroleum ether=1:1) to obtain the desired product (3R)-benzyl 3-(5-(2,6-dimethylphenyl)pyridin-3-yl)-3-(4-methyl-2-(2-oxopyridin-1 (2H)-yl)pentanamido)propanoate as a colorless oil (80 mg). Yield 44% (70% purity, UV=214 nm, ESI 552 (M+H)$^+$).

Step 3: (3R)-3-(5-(2,6-dimethylphenyl)pyridin-3-yl)-3-(4-methyl-2-(2-oxopiperidin-1-yl)pentanamido)propanoic acid

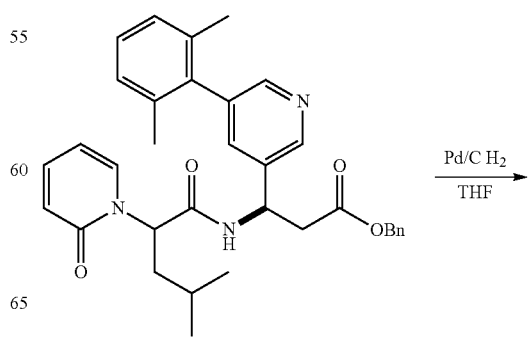

-continued

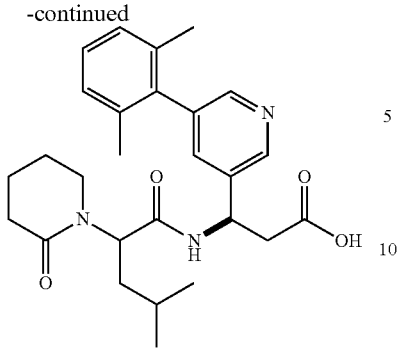

To a solution of (3R)-benzyl 3-(5-(2,6-dimethylphenyl)pyridin-3-yl)-3-(4-methyl-2-(2-oxopyridin-1(2H)-yl)pentanamido)propanoate (80 mg, 0.145 mmol) in THF (6 mL) was added Pd/C (10%, 40 mg), and the solution was stirred at room temperature for 16 hours under H₂ atmosphere. The mixture was filtered over Celite, and the filtrate was concentrated under reduced pressure to give a residue, which was purified by Preparative-HPLC A (30~70% MeCN) to provide the desired product (3R)-3-(5-(2,6-dimethylphenyl)pyridin-3-yl)-3-(4-methyl-2-(2-oxopiperidin-1-yl)pentanamido)propanoic acid as a white solid (26.2 mg).

Compound AH1 LC/MS A: 100% purity, UV=214 nm, Rt=1.58 min, ESI 466 (M+H)$^+$.

$^1$H NMR (500 MHz, MeOD) δ 8.57 (d, J=5.6 Hz, 1H), 8.25 (s, 1H), 7.67-7.59 (m, 1H), 7.27-7.07 (m, 3H), 5.42 (t, J=7.0 Hz, 1H), 5.31-5.19 (m, 1H), 3.32-3.09 (m, 2H), 2.98-2.86 (m, 2H), 2.56-2.21 (m, 2H), 2.06-1.95 (m, 6H), 1.91-1.36 (m, 7H), 1.09-0.83 (m, 6H).

Preparation of Compound AH2

Step 1: 3-amino-3-(5-bromopyridin-3-yl)propanoic acid

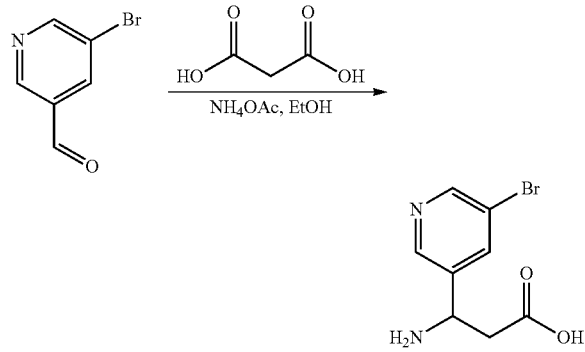

To a solution of 5-bromonicotinaldehyde (20.0 g, 107.5 mmol) in EtOH (100 mL) was added malonic acid (11.2 g, 107.5 mmol) and NH₄OAc (16.6 g, 215.0 mmol). The mixture was heated to 80° C. and stirred for 16 hours. The mixture was concentrated under reduced pressure to give the crude product 3-amino-3-(5-bromopyridin-3-yl)propanoic acid as a white solid (26.3 g), which was used in next step without further purification. (ESI 245 (M+H)$^+$).

Step 2: methyl 3-amino-3-(5-bromopyridin-3-yl)propanoate

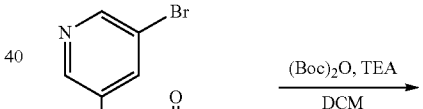

To a solution of 3-amino-3-(5-bromopyridin-3-yl)propanoic acid (26.3 g, 107.3 mmol) in MeOH (50 mL) at 0° C. was added SOCl₂ (8 mL) dropwise, and the reaction mixture was stirred at 80° C. for 2 hours. Water (50 mL) was added and the solution was extracted with EtOAc (50 mL×3). The combined organic phase was washed with saturated aqueous NaHCO₃ (20 mL×2) and brine (20 mL). The organic phase was dried over Na₂SO₄, filtered and the filtrate was concentrated under reduced pressure to give a residue, which was purified by silica gel column (5% MeOH in EtOAc) to give the desired product methyl 3-amino-3-(5-bromopyridin-3-yl)propanoate as a colorless oil (10 g). Yield 36%, two steps (73% purity, UV=214 nm, ESI 260 (M+H)$^+$).

Step 3: methyl 3-(5-bromopyridin-3-yl)-3-((tert-butoxycarbonyl)amino)propanoate

To a solution of methyl 3-amino-3-(5-bromopyridin-3-yl)propanoate (5.0 g, 19.3 mmol) and Et₃N (5.8 g, 57.9 mmol) in DCM (20 mL) was added di-tert-butyl dicarbonate (4.3 g, 19.3 mmol). The reaction mixture was stirred at room temperature for 16 hours. The mixture was concentrated under reduced pressure to give a residue, which was purified by silica gel column (35% EtOAc in pet ether) to provide the desired product methyl 3-(5-bromopyridin-3-yl)-3-((tert-butoxycarbonyl)amino)propanoate as a colorless oil (5.1 g). Yield 74% (86% purity, UV=214 nm, ESI 361 (M+H)$^+$).

Step 4: 3-(5-bromopyridin-3-yl)-3-((tert-butoxycarbonyl)amino)propanoic acid

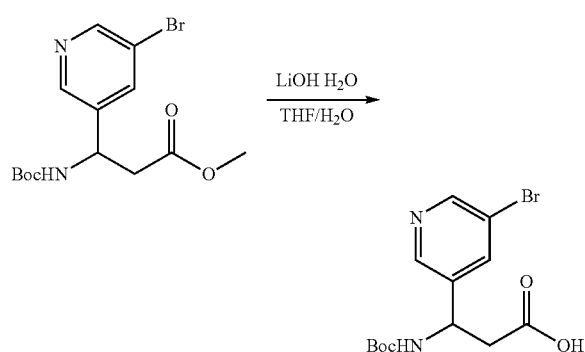

To a solution of methyl 3-(5-bromopyridin-3-yl)-3-((tert-butoxycarbonyl)amino)propanoate (5.1 g, 14.2 mmol) in THF (20 mL) was added LiOH—H$_2$O (1.2 g, 28.4 mmol) in water (5 mL). The mixture was stirred at room temperature for 1 hour. The mixture was acidified with HCl (1 M) to pH=6~7. The mixture was extracted with EtOAc (20 mL×5). The combined organic phase was dried over Na$_2$SO$_4$, filtered and concentrated under reduced pressure to give the crude product 3-(5-bromopyridin-3-yl)-3-((tert-butoxycarbonyl)amino)propanoic acid as a colorless oil (4.2 g), which was used in next step without further purification. Yield 86% (98% purity, UV=214 nm, ESI 347 (M+H)$^+$).

Step 5: benzyl 3-(5-bromopyridin-3-yl)-3-((tert-butoxycarbonyl)amino)propanoate

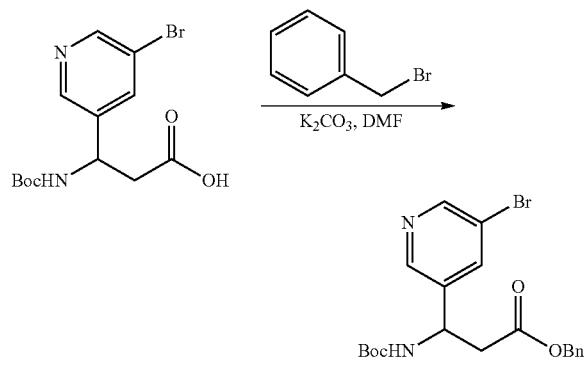

To a solution of 3-(5-bromopyridin-3-yl)-3-((tert-butoxycarbonyl)amino)propanoic acid (4.2 g, 12.2 mmol) in DMF (20 mL) was added K$_2$CO$_3$ (3.4 g, 24.4 mmol) and (bromomethyl)benzene (2.5 g, 14.6 mmol). The mixture was stirred at room temperature for 16 hours. Water (100 mL) was added and the solution was extracted with EtOAc (30 mL×3). The combined organic phase was washed with brine (20 mL) and dried over Na$_2$SO$_4$. The mixture was filtered and the filtrate was concentrated under reduced pressure to give a residue which was purified by silica gel column (35% EtOAc in pet ether) to give the product benzyl 3-(5-bromopyridin-3-yl)-3-((tert-butoxycarbonyl)amino)propanoate as a colorless oil (4.2 g). Yield 79% (83% purity, UV=214 nm, ESI 436 (M+H)$^+$).

Step 6: benzyl 3-((tert-butoxycarbonyl)amino)-3-(5-(2,6-dimethylphenyl)pyridin-3-yl)propanoate

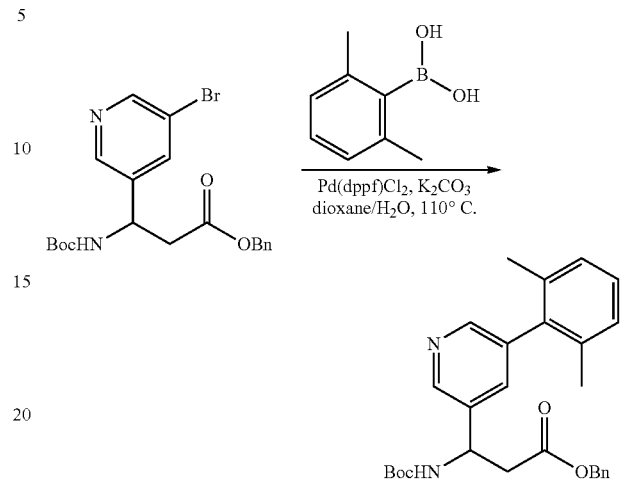

A mixture of benzyl 3-(5-bromopyridin-3-yl)-3-((tert-butoxycarbonyl)amino)propanoate (4.3 g, 9.9 mmol), (2,6-dimethylphenyl)boronic acid (1.78 g, 11.9 mmol), PdCl$_2$ (dppf) (724 mg, 0.99 mmol) and K$_2$CO$_3$ (2.7 g, 19.8 mmol) in dioxane (10 mL) and H$_2$O (2 mL) under N$_2$ atmosphere was heated to 110° C. in a microwave for 1 hour. Water (20 mL) was added and the solution was extracted with EtOAc (20 mL×3). The combined organic phases were concentrated under reduced pressure to give a residue, which was purified by silica gel column (35% EtOAc in pet ether) to give the desired product benzyl 3-((tert-butoxycarbonyl)amino)-3-(5-(2,6-dimethylphenyl)pyridin-3-yl)propanoate as a brown oil (3.1 g). Yield 70% (94% purity, UV=214 nm, ESI 461 (M+H)$^+$). The racemic product was separated by Preparative chiral HPLC into benzyl (S)-3-((tert-butoxycarbonyl)amino)-3-(5-(2,6-dimethylphenyl)pyridin-3-yl)propanoate (1.3 g) and benzyl (R)-3-((tert-butoxycarbonyl)amino)-3-(5-(2,6-dimethylphenyl)pyridin-3-yl)propanoate (1.3 g) as white solids.

Step 7: (S)-benzyl 3-amino-3-(5-(2,6-dimethylphenyl)pyridin-3-yl)propanoate hydrochloride

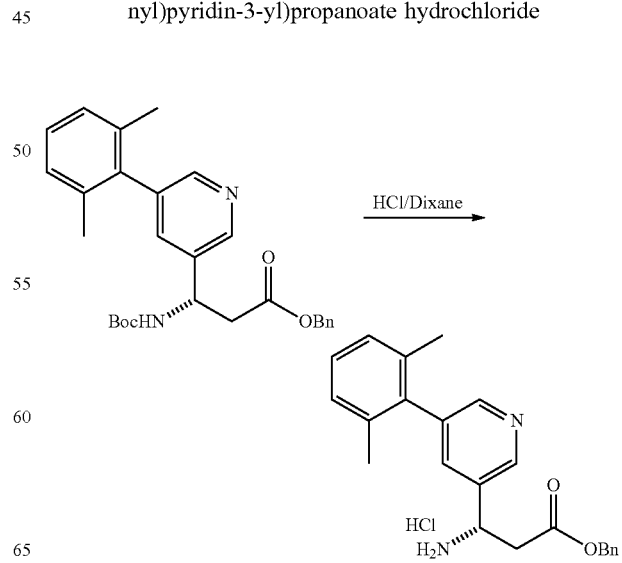

To a solution of (S)-benzyl 3-(tert-butoxycarbonylamino)-3-(5-(2,6-dimethylphenyl)pyridin-3-yl)propanoate (150 mg, 0.33 mmol) in DCM (4 mL) was added HCl/Dioxane (4M, 2 mL) and the solution was stirred at room temperature for 1 hour. The mixture was concentrated under reduced pressure to provide the crude product (S)-benzyl 3-amino-3-(5-(2,6-dimethylphenyl)pyridin-3-yl)propanoate hydrochloride as a light yellow oil (117 mg), which was used for next step directly without further purification. Expect yield 99% (97.70% purity, UV=214 nm, ESI 361 (M+H)$^+$).

Step 8: (3S)-benzyl 3-(5-(2,6-dimethylphenyl)pyridin-3-yl)-3-(4-methyl-2-(2-oxopyridin-1(2H)-yl)pentanamido)propanoate

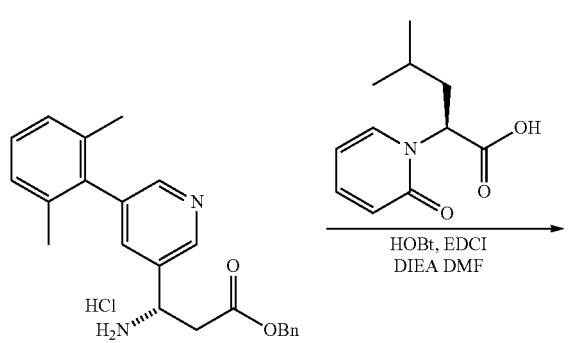

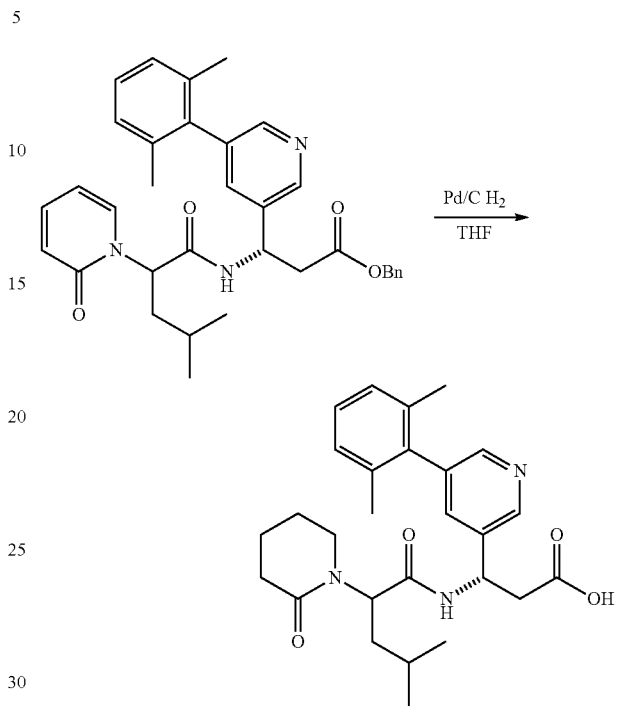

A mixture of (S)-benzyl 3-amino-3-(5-(2,6-dimethylphenyl)pyridin-3-yl)propanoate hydrochloride (117 mg, 0.325 mmol), (S)-4-methyl-2-(2-oxopyridin-1(2H)-yl)pentanoic acid (71 mg, 0.34 mmol), HOBt (66 mg, 0.49 mmol), EDCI (94 mg, 0.49 mmol) and DIEA (126 mg, 0.98 mmol) in DMF (4 mL) was stirred at room temperature for 3 hours. The mixture was poured into water and the solution was extracted with EtOAc (20 mL×2). The combined organic layers were dried over Na$_2$SO$_4$ and filtered. The filtrate was concentrated under reduced pressure to give a residue, which was purified by Preparative-TLC (EtOAc:Petroleum=1:1) to obtain the desired product (3S)-benzyl 3-(5-(2,6-dimethylphenyl)pyridin-3-yl)-3-(4-methyl-2-(2-oxopyridin-1(2H)-yl)pentanamido)propanoate as a colorless oil (103 mg). Yield 57% (83% purity, UV=214 nm, ESI 552 (M+H)$^+$).

Step 9: (3S)-3-(5-(2,6-dimethylphenyl)pyridin-3-yl)-3-(4-methyl-2-(2-oxopiperidin-1-yl)pentanamido)propanoic acid To a solution of (3S)-benzyl 3-(5-(2,6-dimethylphenyl)pyridin-3-yl)-3-(4-methyl-2-(2-oxopyridin-1(2H)-yl)pentanamido)propanoate (103 mg, 0.19 mmol) in THF (6 mL) was added Pd/C (10%, 50 mg) and the mixture was stirred at room temperature for 24 hours under H$_2$ atmosphere. The mixture was filtered over Celite, and the filtrate was concentrated under reduced pressure to give a residue, which was purified by Preparative-HPLC A (30~70 MeCN) to provide the desired product (3S)-3-(5-(2,6-dimethylphenyl)pyridin-3-yl)-3-(4-methyl-2-(2-oxopiperidin-1-yl)pentanamido)propanoic acid as a white solid (38.8 mg).

Compound AH2 LC/MS A: 100% purity, UV=214 nm, Rt=1.58 min, ESI 466 (M+H)$^+$.

$^1$H NMR (500 MHz, MeOD) δ 8.57 (dd, J=6.2, 2.1 Hz, 1H), 8.24 (d, J=1.9 Hz, 1H), 7.67-7.59 (m, 1H), 7.24-7.18 (m, 1H), 7.15 (d, J=7.4 Hz, 2H), 5.41 (t, J=6.9 Hz, 1H), 5.32-5.20 (m, 1H), 3.30-3.20 (m, 2H), 2.91 (dd, J=7.0, 4.9 Hz, 2H), 2.52-2.23 (m, 2H), 2.02 (s, 3H), 2.01 (d, J=3.0 Hz, 3H), 1.92-1.56 (m, 6H), 1.55-1.41 (m, 1H), 0.99-0.90 (m, 6H).

Preparation of Compound AI

Step 1: (R)-2-bromopentanoic acid

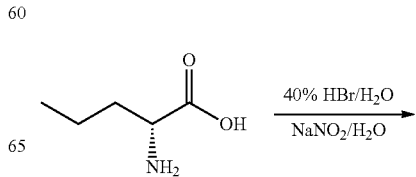

-continued

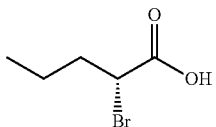

To a solution of (R)-2-aminopentanoic acid (2.0 g, 17.1 mmol) in 40% HBr in H₂O (10 mL) at 0° C. under N₂ atmosphere was added dropwise a solution of NaNO₂ (1.89 g, 27.4 mmol) in H₂O (8 mL). The reaction mixture was stirred at room temperature for 16 hours. The mixture was extracted with EtOAc (20 mL×2). The combined organic layers were washed with brine (20 mL) and dried over Na₂SO₄. The mixture was filtered and the filtrate was concentrated under reduced pressure to give the crude product (R)-2-bromopentanoic acid as a brown oil (2.5 g), which was used in next step without further purification. Yield 81%

Step 2: (S)-2-(4-methyl-2-oxopyridin-1(2H)-yl)pentanoic acid

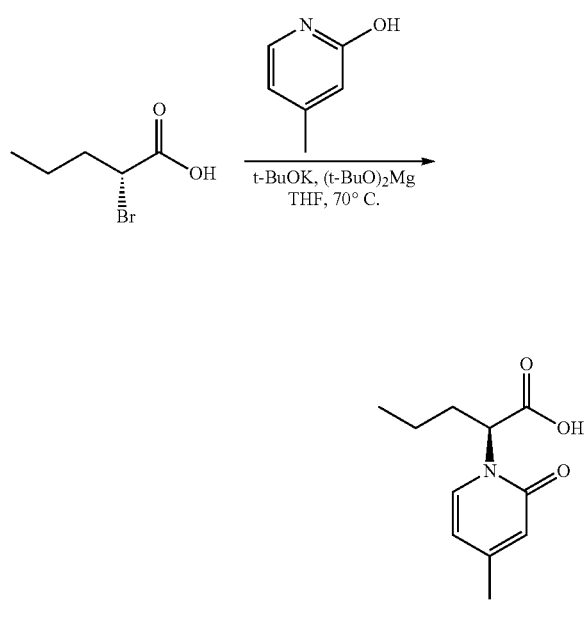

To a solution of (R)-2-bromopentanoic acid (1.45 g, 8.02 mmol) in anhydrous THF (15 mL) was added (t-BuO)₂Mg (1.56 g, 9.16 mmol). The mixture was stirred at 30° C. for 3 hours under N₂ atmosphere. Then, 4-methylpyridin-2-ol (500 mg, 4.58 mmol) and t-BuOK (524 mg, 34.67 mmol) was added to the reaction mixture. Then, the mixture was stirred at 70° C. for 16 hours under N₂ atmosphere. The mixture was cooled to room temperature and acidified with HCl (1 M) to pH=3~4. The mixture was extracted with EtOAc (20 mL×5) and the combined organic layer was dried over Na₂SO₄. The mixture was filtered and the filtrate was concentrated under reduced pressure and purified by reversed phase flash chromatography (0%~60% MeOH in H₂O (5% TFA)) to provide the desired product (S)-2-(4-methyl-2-oxopyridin-1(2H)-yl)pentanoic acid (110 mg). Yield 11% (94% purity, UV=214 nm, ESI 210 (M+H)⁺).

Step 3: methyl (3S)-3-(5-(2,6-dimethylphenyl)pyridin-3-yl)-3-(2-(4-methyl-2-oxopyridin-1(2H)-yl)pentanamido)propanoate

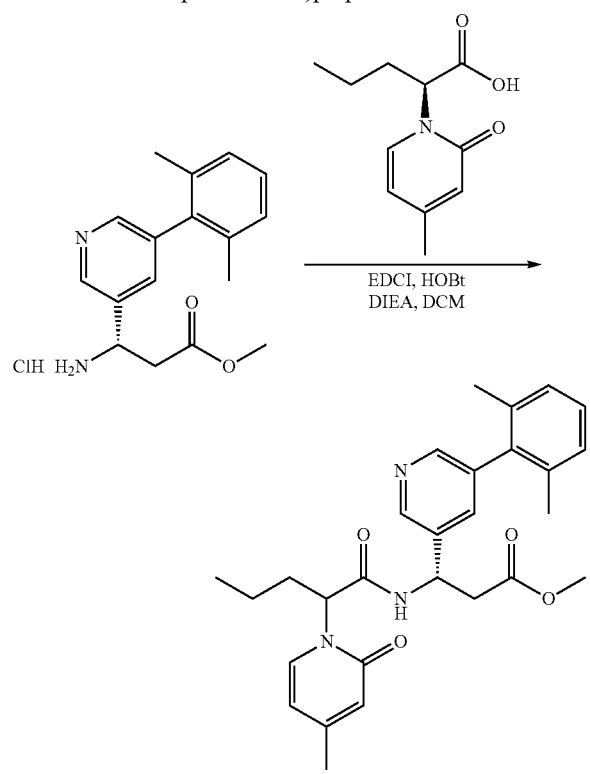

A mixture of (S)-2-(4-methyl-2-oxopyridin-1(2H)-yl) pentanoic acid (65 mg, 0.31 mmol), methyl (S)-3-amino-3-(5-(2,6-dimethylphenyl)pyridin-3-yl)propanoate hydrochloride (83 mg, 0.26 mmol), HOBt (42 mg, 0.31 mmol), EDCI (59 mg, 0.31 mmol) and DIEA (101 mg, 0.78 mmol) in DCM (10 mL) was stirred at room temperature for 16 hours. The mixture was concentrated under reduced pressure to give a residue which was purified by preparative-TLC (pet. ether:EtOAc 1:1) to obtain the desired product methyl (3S)-3-(5-(2,6-dimethylphenyl)pyridin-3-yl)-3-(2-(4-methyl-2-oxopyridin-1 (2H)-yl)pentanamido)propanoate as a colorless oil (70 mg). Yield 57% (100% purity, UV=214 nm, ESI 476 (M+H)⁺).

Step 4: (3S)-3-(5-(2,6-dimethylphenyl)pyridin-3-yl)-3-(2-(4-methyl-2-oxopyridin-1(2H)-yl)pentanamido) propanoic acid

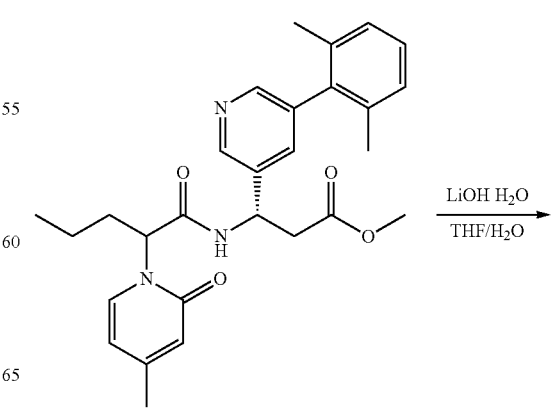

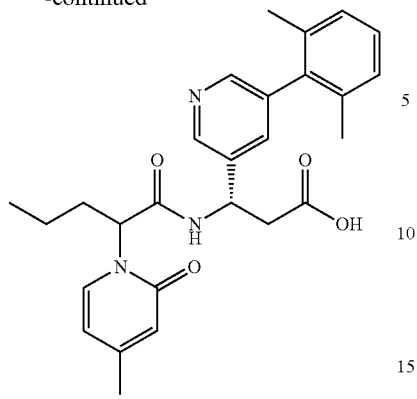

Methyl (3S)-3-(5-(2,6-dimethylphenyl)pyridin-3-yl)-3-(2-(4-methyl-2-oxopyridin-1(2H)-yl)pentanamido)propanoate (70 mg, 0.15 mmol) was treated with LiOH—H₂O (19 mg, 0.45 mmol) in THF (4 mL) and H₂O (2 mL) at room temperature for 1 hour. The mixture was acidified with HCl (1 M) to pH=5~6. The solvent was removed under reduced pressure, and the residue was purified by preparatory HPLC A (30~70% MeCN) to give the compounds AI1 (16.7 mg) and AI2 (16.8 mg) as white solids.

Compound AI1 LC/MS A 100% purity, UV=214 nm, Rt=1.54 min, ESI 462 (M+H)⁺.

¹H NMR (500 MHz, MeOD) δ 8.53 (d, J=1.7 Hz, 1H), 8.19 (d, J=1.4 Hz, 1H), 7.57 (d, J=7.1 Hz, 1H), 7.54 (s, 1H), 7.21 (t, J=7.5 Hz, 1H), 7.13 (t, J=6.6 Hz, 2H), 6.26 (s, 1H), 6.23 (dd, J=7.1, 1.8 Hz, 1H), 5.57 (dd, J=8.8, 7.1 Hz, 1H), 5.42 (t, J=7.2 Hz, 1H), 2.93 (d, J=7.2 Hz, 2H), 2.19 (s, 3H), 2.14-2.04 (m, 1H), 1.97 (s, 3H), 1.96-1.88 (m, 1H), 1.87 (s, 3H), 1.37-1.27 (m, 2H), 0.98 (t, J=7.4 Hz, 3H).

Compound AI2 LC/MS A 100% purity, UV=214 nm, Rt=1.57 min, ESI 462 (M+H)⁺.

¹H NMR (500 MHz, MeOD) δ 8.59 (d, J=1.9 Hz, 1H), 8.26 (d, J=1.7 Hz, 1H), 7.68 (t, J=1.9 Hz, 1H), 7.63 (d, J=7.1 Hz, 1H), 7.26-7.19 (m, 1H), 7.16 (d, J=7.5 Hz, 2H), 6.38 (s, 1H), 6.31 (dd, J=7.2, 1.8 Hz, 1H), 5.56 (dd, J=8.9, 6.9 Hz, 1H), 5.39 (t, J=7.3 Hz, 1H), 2.96-2.87 (m, 2H), 2.24 (s, 3H), 2.05-1.93 (m, 7H), 1.90-1.79 (m, 1H), 1.31-1.12 (m, 2H), 0.90 (t, J=7.4 Hz, 3H).

Preparation of Compounds AJ1a and AJ1b

Step 1: (3S)-3-(5-(2,6-dimethylphenyl)pyridin-3-yl)-3-((2R)-4-methyl-2-(4-methyl-2-oxopiperidin-1-yl)pentanamido)propanoic acid

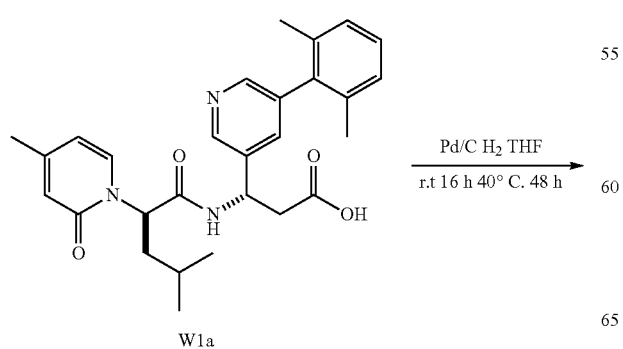

W1a

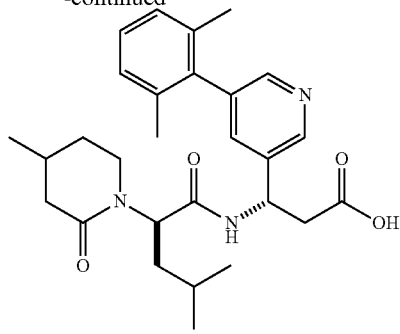

To a solution of W1a (60 mg, 0.13 mmol) in THF (10 mL) was added Pd/C (10%, 50 mg) and the mixture was stirred at 40° C. for 48 hours under H₂ atmosphere. The mixture was filtered over Celite, and the filtrate was concentrated under reduced pressure to give a residue, which was purified by Preparative-HPLC A (30~70% MeCN) to provide the desired product AJ1a (23.6 mg) as a white solid.

Compound AJ1a LC/MS A: 100% purity, UV=214 nm, Rt=1.64 min, ESI 480 (M+H)⁺.

¹H NMR (500 MHz, MeOD) δ 8.57 (s, 1H), 8.25 (s, 1H), 7.57 (dd, J=3.9, 2.1 Hz, 1H), 7.22 (t, J=7.5 Hz, 1H), 7.19-7.13 (m, 2H), 5.42 (t, J=7.0 Hz, 1H), 5.26 (t, J=7.9 Hz, 1H), 3.42-3.34 (m, 1H), 3.16 (m, 1H), 2.94 (dd, J=6.8, 1.9 Hz, 2H), 2.49-2.29 (m, 1H), 2.02 (s, 3H), 2.00 (d, J=2.8 Hz, 3H), 1.98-1.61 (m, 5H), 1.56-1.13 (m, 2H), 0.96-0.91 (m, 9H).

Step 2: (3S)-3-(5-(2,6-dimethylphenyl)pyridin-3-yl)-3-((2S)-4-methyl-2-(4-methyl-2-oxopiperidin-1-yl)pentanamido)propanoic acid

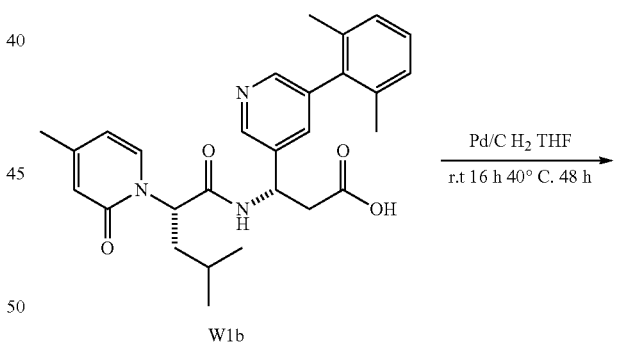

W1b

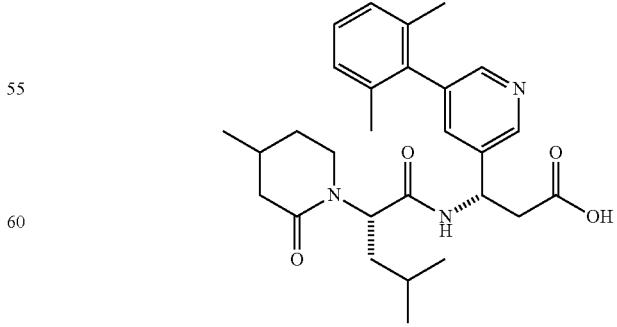

To a solution of W1b (30 mg, 0.06 mmol) in THF (10 mL) was added Pd/C (10%, 50 mg) and stirred at 40° C. for 20 hours under H₂ atmosphere. The mixture was filtered over Celite, and the filtrate was concentrated under reduced pressure to give a residue, which was purified by Preparative-HPLC A (30~70% MeCN) to provide the desired product AJ1b (9.1 mg) as a white solid.

Compound AJ1b LC/MS A: 100% purity, UV=214 nm, Rt=1.62 min, ESI 480 (M+H)⁺.

¹H NMR (500 MHz, MeOD) δ 8.58 (s, 1H), 8.25 (s, 1H), 7.66 (s, 1H), 7.25-7.19 (m, 1H), 7.16 (d, J=7.5 Hz, 2H), 5.42 (t, J=6.9 Hz, 1H), 5.27-5.23 (m, 1H), 3.50-3.36 (m, 1H), 3.31-3.20 (m, 1H), 2.98-2.88 (m, 2H), 2.14-2.04 (m, 1H), 2.01 (d, J=6.9 Hz, 6H), 1.94-1.88 (m, 2H), 1.74-1.34 (m, 4H), 1.08-1.00 (m, 3H), 0.96-0.83 (m, 6H).

Preparation of Compounds AK1 and AK2

Step 1: (S)-methyl 3-(tert-butoxycarbonylamino)-3-(5-(2,2-dimethylmorpholino)pyridin-3-yl)propanoate

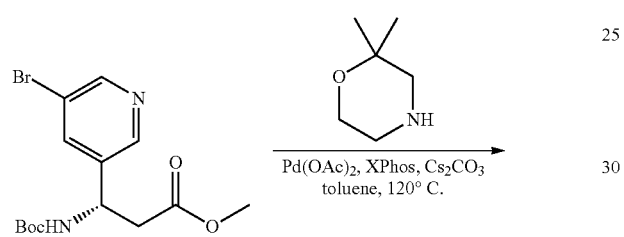

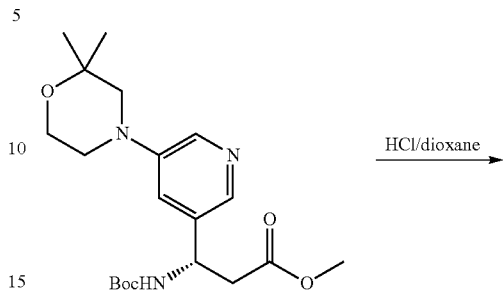

A mixture of (S)-methyl 3-(5-bromopyridin-3-yl)-3-(tert-butoxycarbonylamino)propanoate (150 mg, 0.42 mmol), 2,2-dimethylmorpholine (96 mg, 0.84 mmol), Pd(OAc)₂ (9 mg, 0.04 mmol), X-Phos (40 mg, 0.08 mmol) and Cs₂CO₃ (408 mg, 1.25 mmol) in toluene (2 mL) was stirred at 120° C. for 16 hours under N₂ atmosphere. The mixture was cooled to room temperature and filtered. The filtrate was concentrated under reduced pressure to give a residue, which was purified by Preparative-TLC (EtOAc:Petroleum ether=1:2) to obtain the desired product (S)-methyl 3-(tert-butoxycarbonylamino)-3-(5-(2,2-dimethylmorpholino)pyridin-3-yl)propanoate as a colorless oil (88 mg). Yield 54% (21% purity, UV=214 nm, ESI 394 (M+H)⁺).

Step 2: (S)-methyl 3-amino-3-(5-(2,2-dimethylmorpholino)pyridin-3-yl)propanoate hydrochloride

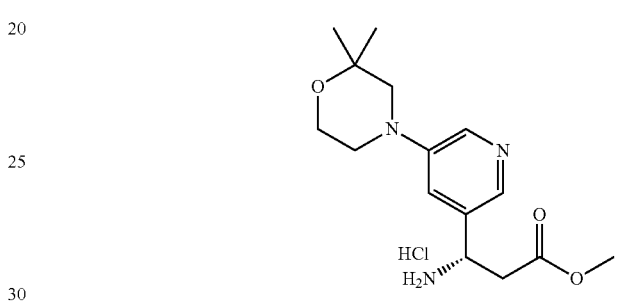

To a solution of methyl (S)-methyl 3-(tert-butoxycarbonylamino)-3-(5-(2,2-dimethylmorpholino)pyridin-3-yl)propanoate (88 mg, 0.22 mmol) in DCM (3 mL) was added HCl/Dioxane (4M, 10 mL), and the solution was stirred at room temperature for 3 hours. The mixture was concentrated under reduced pressure to provide the crude product (S)-methyl 3-amino-3-(5-(2,2-dimethylmorpholino)pyridin-3-yl)propanoate hydrochloride as a light yellow solid (80 mg), which was used for next step directly without further purification. Yield 100% (79% purity, UV=214 nm, ESI 294 (M+H)⁺).

Step 3: (3S)-methyl 3-(5-(2,2-dimethylmorphohno)pyridin-3-yl)-3-(4-methyl-2-(4-methyl-2-oxopyridin-1(2H)-yl)pentanamido)propanoate

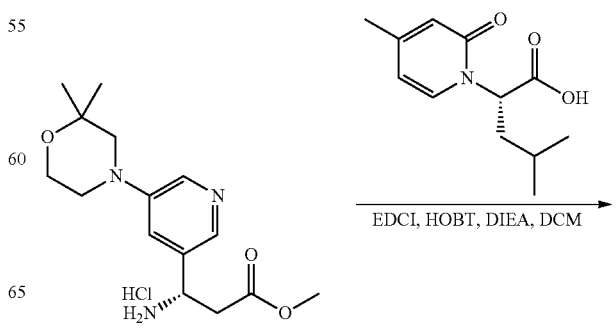

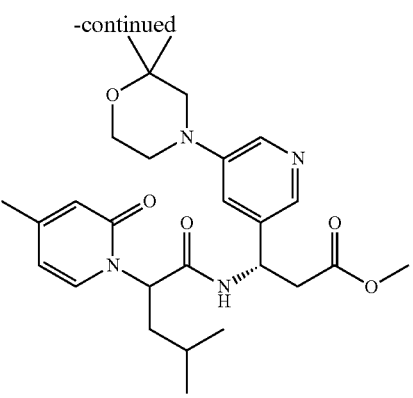

A mixture of (S)-methyl 3-amino-3-(5-(2,2-dimethylmorpholino)pyridin-3-yl)propanoate hydrochloride (80 mg, 0.24 mmol), (S)-4-methyl-2-(4-methyl-2-oxopyridin-1(2H)-yl)pentanoic acid (65 mg, 0.29 mmol), HOBt (49 mg, 0.36 mmol), EDCI (93 mg, 0.49 mmol) and DIEA (125 mg, 0.97 mmol) in DCM (15 mL) was stirred at room temperature for 16 hours. The mixture was concentrated under reduced pressure to give a crude product, which was purified by Preparative-TLC (EtOAc) to give the desired product (3S)-methyl 3-(5-(2,2-dimethylmorpholino)pyridin-3-yl)-3-(4-methyl-2-(4-methyl-2-oxopyridin-1(2H)-yl)pentanamido)propanoate as a colorless oil (68 mg). Yield 56% (69% purity, UV=214 nm, ESI 499 (M+H)$^+$).

Step 4: (3S)-3-(5-(2,2-dimethylmorpholino)pyridin-3-yl)-3-(4-methyl-2-(4-methyl-2-oxopyridin-1(2H)-yl)pentanamido)propanoic acid

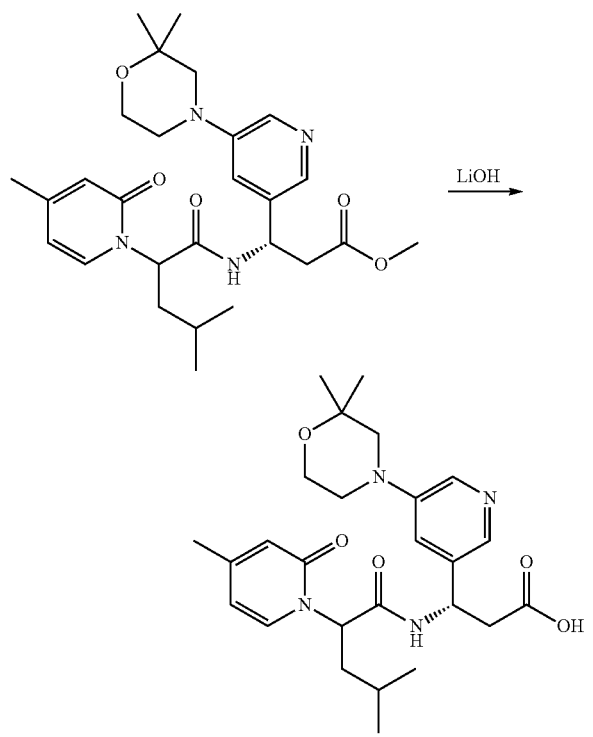

(3S)-methyl 3-(5-(2,2-dimethylmorpholino)pyridin-3-yl)-3-(4-methyl-2-(4-methyl-2-oxopyridin-1(2H)-yl)pentanamido)propanoate (68 mg, 0.14 mmol) was treated with LiOH—H$_2$O (18 mg, 0.42 mmol) in THF (6 mL) and H$_2$O (1 mL) at room temperature for 2 hours. The mixture was acidified to pH=5 with HCl (1 M). The solvent was removed in vacuo, and the residue was purified by Preparative-HPLC A (30~70% MeCN) to give the desired compounds AK1 (20.9 mg) and AK2 (13.6 mg) as white solids.

Compound AK1 LC/MS A: 100% purity, UV=214 nm, Rt=1.49 min, ESI 485 (M+H)$^+$.

$^1$H NMR (500 MHz, MeOD) δ 8.08 (d, J=2.3 Hz, 1H), 7.94 (s, 1H), 7.60 (d, J=7.2 Hz, 1H), 7.28 (s, 1H), 6.36 (s, 1H), 6.28 (dd, J=7.1, 1.8 Hz, 1H), 5.69 (dd, J=9.3, 6.8 Hz, 1H), 5.33 (t, J=7.2 Hz, 1H), 3.95-3.82 (m, 2H), 3.18-3.11 (m, 2H), 3.06-2.99 (m, 2H), 2.83 (d, J=7.3 Hz, 2H), 2.22 (s, 3H), 1.98-1.83 (m, 2H), 1.49-1.43 (dtm, 1H), 1.32 (s, 6H), 0.99-0.96 (m, 6H).

Compound AK2 LC/MS A: 100% purity, UV=214 nm, Rt=1.52 min, ESI 485 (M+H)$^+$.

$^1$H NMR (500 MHz, MeOD) δ 8.14 (d, J=2.5 Hz, 1H), 8.01 (s, 1H), 7.63 (d, J=7.1 Hz, 1H), 7.37 (s, 1H), 6.40 (s, 1H), 6.31 (dd, J=7.1, 1.8 Hz, 1H), 5.69 (dd, J=9.1, 7.0 Hz, 1H), 5.28 (t, J=7.3 Hz, 1H), 3.98-3.79 (m, 2H), 3.24-3.17 (m, 2H), 3.08 (s, 2H), 2.91-2.79 (m, 2H), 2.25 (s, 3H), 1.93-1.75 (m, 2H), 1.40-1.35 (m, 1H), 1.34 (s, 6H), 0.94-0.90 (m, 6H).

Preparation of Compounds AL1 and AL2

Step 1: 2-(5,5-dimethyl-2-oxopiperidin-1-yl)-4-methylpentanoic acid

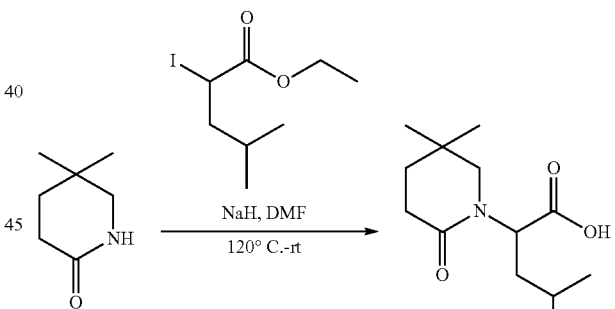

To a solution of 5,5-dimethylpiperidin-2-one (100 mg, 0.79 mmol) in DMF (3 mL) at was added NaH (60% in oil, 158 mg, 3.95 mmol) and stirred at 120° C. for 2 hours. Then, ethyl 2-iodo-4-methylpentanoate (320 mg, 1.19 mmol) was added and the solution was stirred at room temperature for 2 hours. The reaction was quenched with MeOH and concentrated under reduced pressure. The residue was purified by preparative-HPLC B (20~50% MeCN) to give the desired product 2-(5,5-dimethyl-2-oxopiperidin-1-yl)-4-methylpentanoic acid as a white solid (38 mg). Yield 20% (100% purity, UV=254 nm, ESI 242 (M+H)$^+$).

Step 2: methyl (3S)-3-(2-(5,5-dimethyl-2-oxopiperidin-1-yl)-4-methylpentanamido)-3-(5-(2,6-dimethylphenyl)pyridin-3-yl)propanoate

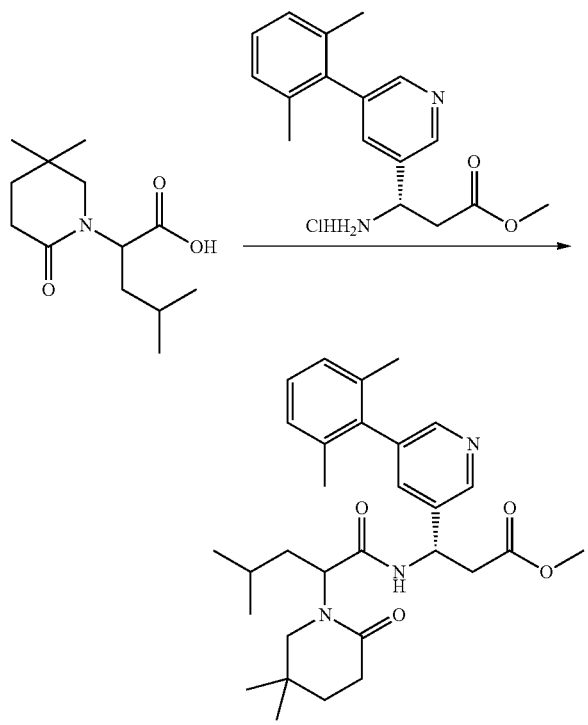

A mixture of 2-(5,5-dimethyl-2-oxopiperidin-1-yl)-4-methylpentanoic acid (38 mg, 0.16 mmol), methyl (S)-3-amino-3-(5-(2,6-dimethylphenyl)pyridin-3-yl)propanoate hydrochloride (56 mg, 0.18 mmol), HOBt (26 mg, 0.19 mmol), EDCI (36 mg, 0.19 mmol) and DIEA (62 mg, 0.48 mmol) in DCM (5 mL) was stirred at at room temperature for 16 hours. The mixture was concentrated under reduced pressure to give a residue, which was purified by preparative-TLC (pet. ether:EtOAc 1:1) to obtain the desired product methyl (3S)-3-(2-(5,5-dimethyl-2-oxopiperidin-1-yl)-4-methylpentanamido)-3-(5-(2,6-dimethylphenyl)pyridin-3-yl)propanoate as a colorless oil (50 mg). Yield 63% (94% purity, UV=254 nm, ESI 508 (M+H)⁺).

Step 3: (3S)-3-(2-(5,5-dimethyl-2-oxopiperidin-1-yl)-4-methylpentanamido)-3-(5-(2,6-dimethylphenyl)pyridin-3-yl)propanoic acid

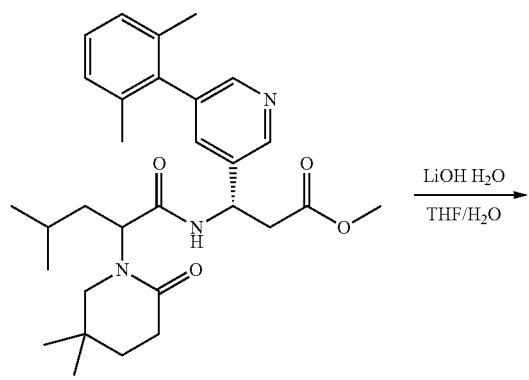

LiOH H₂O
THF/H₂O
→

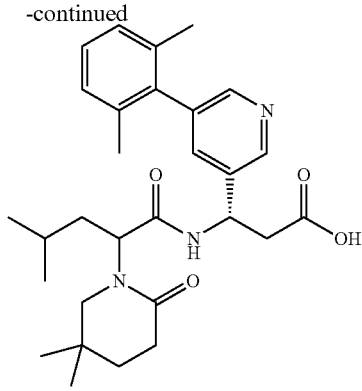

Methyl (3S)-3-(2-(5,5-dimethyl-2-oxopiperidin-1-yl)-4-methylpentanamido)-3-(542, 6-dimethylphenyl)pyridin-3-yl)propanoate (50 mg, 0.1 mmol) was treated with LiOH—H₂O (21 mg, 0.5 mmol) in THF (5 mL) and H₂O (1 mL) at room temperature for 1 hour. The mixture was acidified with HCl (1 M) to pH=5~6, and the solvent was removed under reduced pressure. The residue was purified by preparative-HPLC A (30~70% MeCN) to give the product (3S)-3-(2-(5,5-dimethyl-2-oxopiperidin-1-yl)-4-methylpentanamido)-3-(5-(2,6-dimethylphenyl)pyridin-3-yl)propanoic acid as a white solid (35 mg). Yield 72% (100% purity, UV=254 nm, ESI 494 (M+H)⁺). The diastereomic (3S)-3-(2-(5,5-dimethyl-2-oxopiperidin-1-yl)-4-methylpentanamido)-3-(5-(2,6-dimethylphenyl)pyridin-3-yl)propanoic acid was separated by Prep chiral SFC F into two compounds AL1 (10 mg) and AL2 (11 mg) as white solids.

Compound AL1 LC/MS B 99% purity, UV=214 nm, Rt=1.66 min, ESI 494 (M+H)⁺.

¹H NMR (500 MHz, MeOD) δ 8.46 (s, 1H), 8.12 (s, 1H), 7.55 (s, 1H), 7.13-6.98 (m, 3H), 5.27 (t, J=6.9 Hz, 1H), 5.18-5.08 (m, 1H), 3.02 (d, J=12.2 Hz, 1H), 2.91 (dd, J=25.8, 9.8 Hz, 1H), 2.84-2.70 (m, 2H), 2.46-2.25 (m, 2H), 1.90 (s, 3H), 1.89 (s, 3H), 1.62-1.45 (m, 3H), 1.45-1.34 (m, 1H), 1.35-1.27 (m, 1H), 0.91 (d, J=1.2 Hz, 6H), 0.83-0.71 (m, 6H).

Compound AL2 LC/MS B 99% purity, UV=214 nm, Rt=1.66 min, ESI 494 (M+H)⁺.

¹H NMR (500 MHz, MeOD) δ 8.57 (s, 1H), 8.24 (s, 1H), 7.62 (s, 1H), 7.23-7.14 (m, 3H), 5.43 (t, J=6.9 Hz, 1H), 5.25 (dd, J=8.4, 7.1 Hz, 1H), 3.06 (dd, J=19.3, 9.8 Hz, 1H), 2.97 (d, J=12.2 Hz, 1H), 2.92 (d, J=6.8 Hz, 2H), 2.42-2.25 (m, 2H), 2.02 (s, 3H), 2.01 (s, 3H), 1.76-1.66 (m, 1H), 1.64-1.58 (m, 1H), 1.58-1.47 (m, 2H), 1.46-1.41 (m, 1H), 1.05-0.86 (m, 9H), 0.77 (s, 3H).

Preparation of Compound AM

Step 1: 4-methyl-2-(methylsulfonyloxy)pentanoate

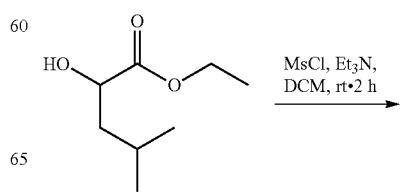

MsCl, Et₃N,
DCM, rt•2 h
→

225
-continued

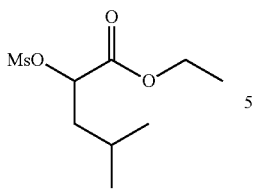

To a solution of ethyl 2-hydroxy-4-methylpentanoate (5.0 g, 31.2 mmol) and Et₃N (6.3 g, 62.4 mmol) in DCM (20 mL) was added MsCl (4.3 g, 37.4 mmol) dropwise at 0° C. The reaction mixture was stirred at room temperature for 2 hours. The mixture was poured into water and the solution was extracted with EtOAc (20 mL×2). The combined organic layers were dried over Na₂SO₄, filtered and the filtrate was concentrated under reduced pressure to give crude product ethyl 4-methyl-2-(methylsulfonyloxy)pentanoate as a brown oil (7.2 g). Yield 95% (68% purity, UV=214 nm, ESI 239 (M+H)⁺). The crude product was used for the next step directly.

Step 2: ethyl 2-iodo-4-methylpentanoate

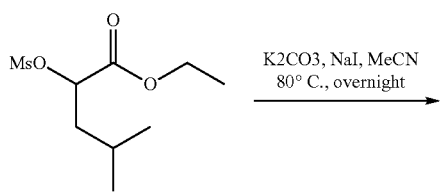

To a solution of ethyl 4-methyl-2-(methylsulfonyloxy) pentanoate (2.0 g, 8.4 mmol) in MeCN (80 mL) was added K₂CO₃ (3.5 g, 25.2 mmol) and NaI (2.5 g, 16.8 mmol). The reaction mixture was stirred at 80° C. for 16 hours. The mixture was poured into water and the solution was extracted with EtOAc (20 mL×2). The combined organic layers were dried over Na₂SO₄, filtered and the filtrate was concentrated under reduced pressure to give crude product ethyl 2-iodo-4-methylpentanoate as a yellow oil (1.8 g). Yield 79%. The crude product was used for the next step directly.

Step 3: ethyl 4-methyl-2-(2-oxo-3,4-dihydroquinolin-1(2H)-yl)pentanoate

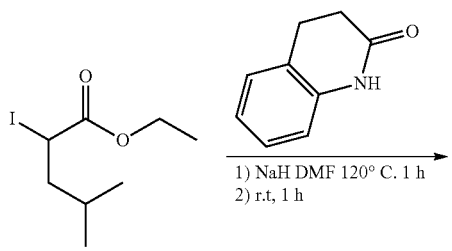

226
-continued

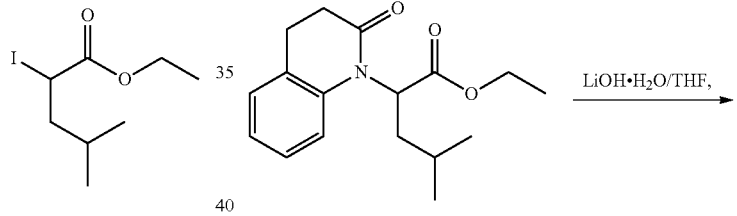

To a solution of 3,4-Dihydro-2(1H)-quinolinone (500 mg, 3.4 mmol) in DMF (10 mL) was added 60% NaH (163 mg, 6.8 mmol) and stirred at 120° C. for 1 hour, then cooled to room temperature and ethyl 2-iodo-4-methylpentanoate (1.0 g, 3.4 mmol) was added. The reaction mixture was stirred at room temperature for 1 hours. The mixture was poured into water and the solution was extracted with EtOAc (20 mL×2). The combined organic layers were dried over Na₂SO₄ and filtered. The filtrate was concentrated under reduced pressure to give a residue, which was purified by flash column chromatography (0%~10% EtOAc in pet ether) to obtain the desired product 4-methyl-2-(2-oxo-3,4-dihydroquinolin-1(2H)-yl) pentanoate as a white solid (370 mg). Yield 38% (89% purity, UV=214 nm, ESI 290 (M+H)⁺).

Step 4: 4-methyl-2-(2-oxo-3,4-dihydroquinolin-1(2H)-yl)pentanoic acid 4-methyl-2-(2-oxo-3,4-dihydroquinolin-1(2H)-yl)pentanoate (170 mg, 0.59 mmol) was treated with LiOH—H₂O (74 mg, 1.77 mmol) in THF (6 mL) and H₂O (1 mL) at room temperature for 16 hours. The mixture was acidified with HCl (1 M) until pH=3. The aqueous solution was extracted with EtOAc (20 mL×2), and the combined organic layers were dried over Na₂SO₄, filtered and the filtrate was concentrated under reduced pressure to give the crude product 4-methyl-2-(2-oxo-3,4-dihydroquinolin-1(2H)-yl)pentanoic acid as a colorless oil (150 mg). Yield 95% (97% purity, UV=214 nm, ESI 262 (M+H)⁺). The crude product was used for the next step directly.

Step 5: (S)-methyl 3-amino-3-(5-(2,6-dimethylphenyl)pyridin-3-yl)propanoate

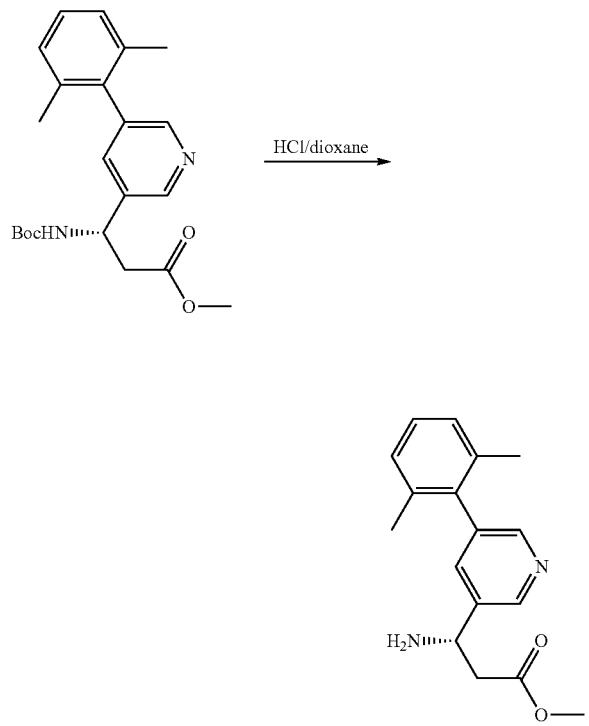 [SMILES: COC(=O)C[C@H](NC(=O)OC(C)(C)C)c1cncc(-c2c(C)cccc2C)c1 ; "HCl/dioxane" ; COC(=O)C[C@H](N)c1cncc(-c2c(C)cccc2C)c1]

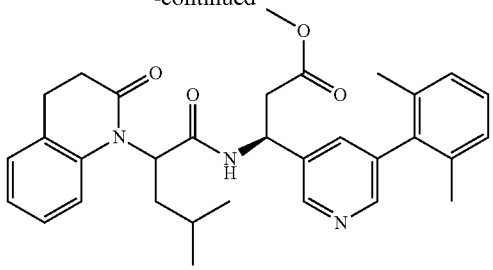

To a solution of methyl (S)-methyl 3-(tert-butoxycarbonylamino)-3-(5-(2,6-dimethylphenyl)pyridin-3-yl)propanoate (70 mg, 0.18 mmol) in DCM (4 mL) was added HCl/Dioxane (4M, 2 mL) and the solution was stirred at room temperature for 2 hours. The solvent was removed in vacuo to provide the crude product (S)-methyl 3-amino-3-(5-(2,6-dimethylphenyl)pyridin-3-yl)propanoate hydrochloride as a white solid (50 mg). Yield 99% (88% purity, UV=214 nm, ESI 285 (M+H)$^+$). The crude product was used for the next step directly.

Step 6: 3-(5-(2,6-dimethylphenyl)pyridin-3-yl)-3-(4-methyl-2-(2-oxo-3,4-dihydroquinolin-1(2H)-yl)pentanamido) propanoate

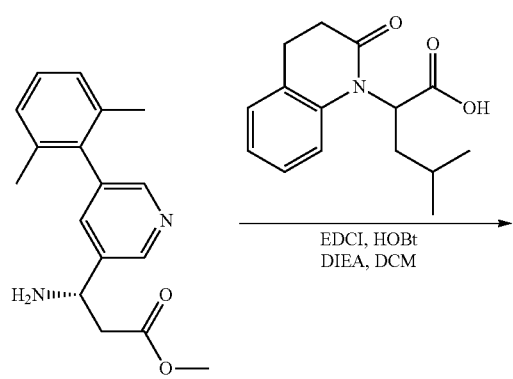

A mixture of (S)-methyl 3-amino-3-(5-(2,6-dimethylphenyl)pyridin-3-yl)propanoate hydrochloride (50 mg, 0.18 mmol), 4-methyl-2-(2-oxo-3,4-dihydroquinolin-1(2H)-yl) pentanoic acid (56 mg, 0.22 mmol), HOBt (30 mg, 0.22 mmol), EDCI (60 mg, 0.22 mmol) and DIEA (93 mg, 0.72 mmol) in DCM (10 mL) was stirred at room temperature for 3 hours. The mixture was poured into water and the solution was extracted with DCM (20 mL×2). The combined organic layers were dried over Na$_2$SO$_4$, filtered and the filtrate was concentrated under reduced pressure to give a residue, which was purified by flash column chromatography (0%~70% EtOAc in pet ether) to give the desired product (3S)-methyl 3-(5-(2,6-dimethylphenyl)pyridin-3-yl)-3-(4-methyl-2-(2-oxo-3,4-dihydroquinolin-1(2H)-yl)pentanamido) propanoate as a colorless oil (70 mg). Yield 75% (93% purity, UV=214 nm, ESI 528 (M+H)$^+$).

Step 7: (3S)-3-(5-(2,6-dimethylphenyl)pyridin-3-yl)-3-(4-methyl-2-(2-oxo-3,4-dihydroquinolin-1(2H)-yl) pentanamido)propanoic acid

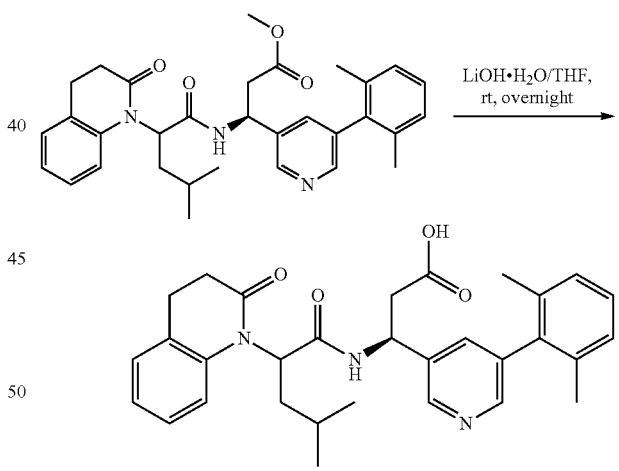

(3 S)-methyl 3-(5-(2,6-dimethylphenyl)pyridin-3-yl)-3-(4-methyl-2-(2-oxo-3,4-dihydroquinolin-1(2H)-yl)pentanamido) propanoate (70 mg, 0.13 mmol) was treated with LiOH—H$_2$O (16 mg, 0.39 mmol) in THF (6 mL) and H$_2$O (1 mL) at room temperature for 4 hours. The mixture was acidified with HCl (1 M) until pH=5. The solvent was removed in vacuo and the residue was purified by Preparative-HPLC A (30~70% MeCN) to give the desired product (3S)-3-(5-(2,6-dimethylphenyl)pyridin-3-yl)-3-(4-methyl-2-(2-oxo-3,4-dihydroquinolin-1(2H)-yl)pentanamido)propanoic acid (16 mg) as a white solid.

Compound AM LC/MS A: 100% purity, UV=214 nm, Rt=1.67 min, ESI 514 (M+H)$^+$.

$^1$H NMR (500 MHz, MeOD) δ 8.58 (s, 0.5H), 8.48 (s, 0.5H), 8.25 (s, 0.5H), 8.19 (s, 0.5H), 7.67 (s, 0.5H), 7.45 (s, 0.5H), 7.31-6.77 (m, 7H), 5.67-5.52 (m, 2H), 3.00-2.77 (m, 4H), 2.77-2.58 (m, 2H), 2.05-1.87 (m, 8H), 1.35 (s, 1H), 0.96-0.75 (m, 6H).

Preparation of Compounds AN1 and AN2

Step 1: (S)-5-(1-(tert-butoxycarbonylamino)-3-methoxy-3-oxopropyl)pyridin-3-ylboronic acid

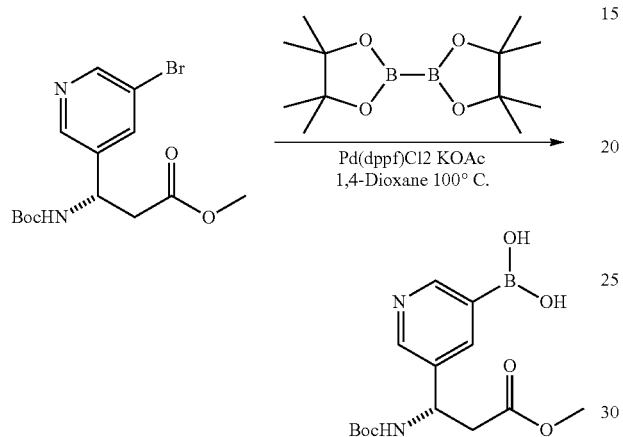

A mixture of (S)-methyl 3-(5-bromopyridin-3-yl)-3-(tert-butoxycarbonylamino)propanoate (600 mg, 1.68 mmol), 4,4,4',4',5,5,5',5'-octamethyl-2,2'-bi(1,3,2-dioxaborolane) (850 mg, 3.36 mmol), Pd(dppf)Cl$_2$ (61 mg, 0.084 mmol) and KOAc (3300 mg, 3.36 mmol) in 1,4-dioxane (10 mL) was stirred at 105° C. for 16 hours under N$_2$ atmosphere. The mixture was cooled to room temperature and filtered over Celite. The filtrate was concentrated under reduced pressure to give a residue, which was purified by reverse phase column (0%~50% MeOH in H$_2$O (TFA 5%)) to give desired product (S)-5-(1-(tert-butoxycarbonylamino)-3-methoxy-3-oxopropyl)pyridin-3-ylboronic acid as a colorless oil (350 mg). Yield 64% (82.10% purity, UV=214 nm, ESI 325 (M+H)$^+$).

Step 2: (S)-methyl 3-(tert-butoxycarbonylamino)-3-(5-(2-chloro-6-methylphenyl)pyridin-3-yl)propanoate

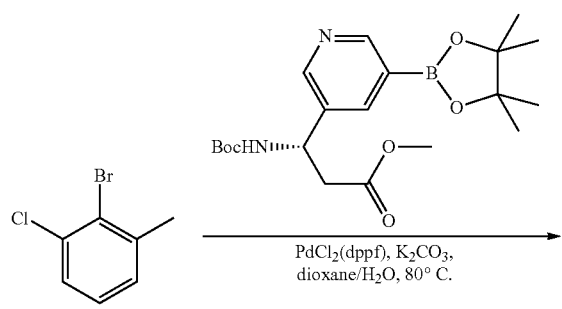

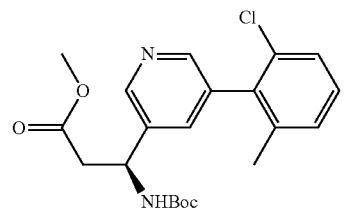

A mixture of methyl 2-bromo-1-chloro-3-methylbenzene (100 mg, 0.49 mmol), (S)-methyl 3-(tert-butoxycarbonylamino)-3-(5-(4,4,5,5-tetramethyl-1,3,2-dioxaborolan-2-yl)pyridin-3-yl)propanoate (199 mg, 0.49 mmol), PdCl$_2$(dppf) (30 mg, 0.04 mmol) and K$_2$CO$_3$ (138 mg, 1.0 mmol) in dioxane (3 mL) and H$_2$O (0.4 mL) was stirred under N$_2$ atmosphere in a microwave at 80° C. for 50 mins. Water (20 mL) was added, and the solution was extracted with EtOAc (10 mL×3). The combined organic phases were concentrated in vacuo and purified by silica gel column (petroleum ether:EtOAc 2:1) to give the desired product (S)-methyl 3-(tert-butoxycarbonylamino)-3-(5-(2-chloro-6-methylphenyl)pyridin-3-yl)propanoate as a colorless oil (120 mg). Yield 51% (85% purity, UV=214 nm, ESI 405.1 (M+H)$^+$).

Step 3: (S)-methyl 3-amino-3-(5-(2-chloro-6-methylphenyl)pyridin-3-yl)propanoate

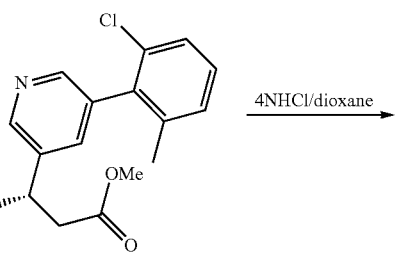

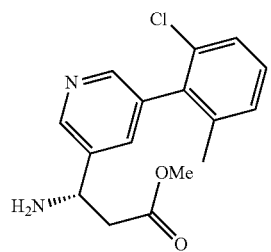

To a solution of (S)-methyl 3-(tert-butoxycarbonylamino)-3-(5-(2-chloro-6-methylphenyl)pyridin-3-yl)propanoate (120 mg, 0.30 mmol) in DCM (4 mL) was added HCl in dioxane (4M, 2 mL) and stirred at room temperature for 2 hours. The solvent was removed in vacuo to provide the crude (S)-methyl 3-amino-3-(5-(2-chloro-6-methylphenyl)pyridin-3-yl)propanoate as a white solid (110 mg). (82% purity, UV=214 nm, ESI 305.1 (M+H)$^+$). The crude product was used for the next step directly.

Step 4: (3S)-methyl 3-(5-(2-chloro-6-methylphenyl)pyridin-3-yl)-3-(4-methyl-2-(4-methyl-2-oxopyridin-1(2H)-yl)pentanamido)propanoate

Step 5: (3S)-3-(5-(2-chloro-6-methylphenyl)pyridin-3-yl)-3-(4-methyl-2-(4-methyl-2-oxopyridin-1(2H)-yl)pentanamido)propanoic acid

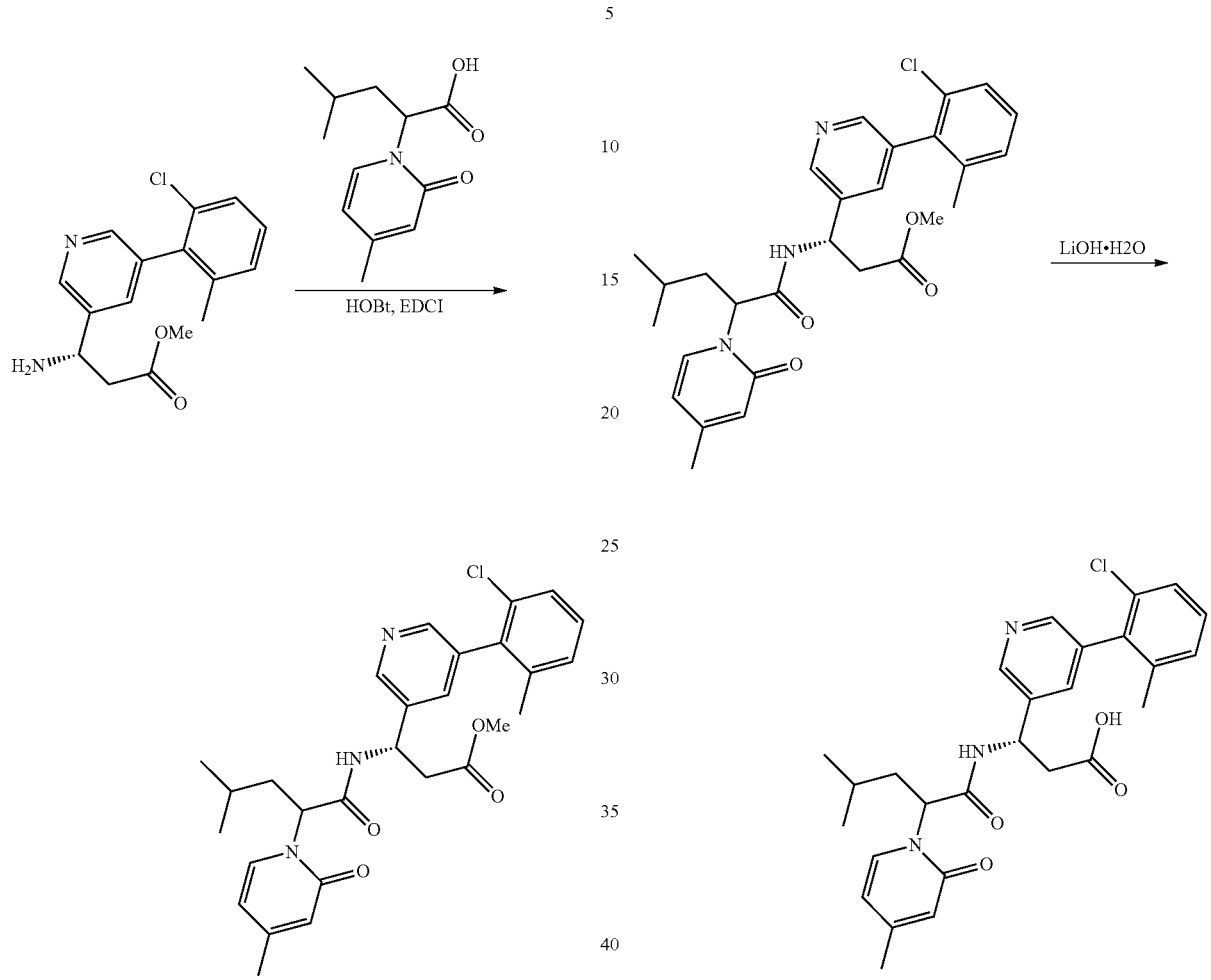

A mixture of (S)-methyl 3-amino-3-(5-(2-chloro-6-methylphenyl)pyridin-3-yl)propanoate (110 mg, 0.36 mmol), (S)-4-methyl-2-(4-methyl-2-oxopyridin-1(2H)-yl)pentanoic acid (81 mg, 0.36 mmol), HOBt (81 mg, 0.6 mmol), EDCI (115 mg, 0.6 mmol) and DIEA (93 mg, 0.72 mmol) in DCM (10 mL) was stirred at room temperature for 5 hours. Water was added, and the solution was extracted with DCM (20 mL×2). The combined organic layers were dried over Na$_2$SO$_4$, filtered and the filtrate was concentrated under reduced pressure to give a residue, which was purified by flash column (10%~90% EtOAc in Petroleum) to give the desired product (3S)-methyl 3-(5-(2-chloro-6-methylphenyl)pyridin-3-yl)-3-(4-methyl-2-(4-methyl-2-oxopyridin-1(2H)-yl)pentanamido)propanoate as a colorless oil (105 mg). yield 49% (83% purity, UV=214 nm, ESI 510.2 (M+H)$^+$).

(3 S)-methyl 3-(5-(2-chloro-6-methylphenyl)pyridin-3-yl)-3-(4-methyl-2-(4-methyl-2-oxopyridin-1(2H)-yl)pentanamido)propanoate (105 mg, 0.21 mmol) was treated with LiOH—H$_2$O (42 mg, 1.0 mmol) in THF (6 mL) and H$_2$O (1 mL) at room temperature for 4 hours. The solution was acidified with HCl (1 M) until pH=5, and the solvent was removed in vacuo, and the residue was purified by Preparative-HPLC A (30~70% MeCN) to give the compounds AN1 (22 mg) and AN2 (23 mg) as white solids.

Compound AN1 LC/MS 100% purity, UV=214 nm, Rt=1.77 min, ESI 496.3 (M+H)$^+$.

$^1$H NMR (500 MHz, MeOD) δ 8.56 (s, 1H), 8.24 (s, 1H), 7.65-7.47 (m, 2H), 7.42-7.21 (m, 3H), 6.28 (s, 1H), 6.25-6.19 (m, 1H), 5.74-5.64 (m, 1H), 5.45-5.41 (m, 1H), 2.91 (d, J=7.0 Hz, 2H), 2.19 (d, J=7.1 Hz, 3H), 1.94-1.86 (m, 4H), 1.48-1.42 (m, 1H), 0.978-0.88 (m, 6H).

Compound AN2 LC/MS 100% purity, UV=214 nm, Rt=1.82 min, ESI 496.3 (M+H)$^+$.

$^1$H NMR (500 MHz, MeOD) δ 8.65-8.56 (m, 1H), 8.34-8.25 (m, 1H), 7.80-7.70 (m, 1H), 7.64-7.62 (m, 1H), 7.41-7.38 (m, 1H), 7.30 (t, J=19.1 Hz, 2H), 6.39 (s, 1H), 6.32-6.30 (m, 1H), 5.72-5.68 (m, 1H), 5.42-5.37 (m, 1H), 3.01-2.74 (m, 2H), 2.21 (d, J=30.5 Hz, 3H), 2.10 (s, 3H), 1.88-1.72 (m, 2H), 1.35-1.30 (m, 1H), 0.91-0.88 (m, 6H).

Preparation of Compounds AO1 and AO2

Step 1: (4-fluoro-2,6-dimethylphenyl)boronic acid

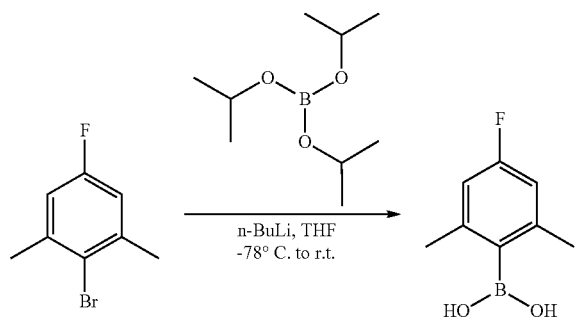

To a solution of 2-bromo-5-fluoro-1,3-dimethylbenzene (2 g, 9.9 mmol) in THF (20 mL) under $N_2$ atmosphere was added n-BuLi (2.5 M in hexane, 6 mL, 14.8 mmol) dropwise at −78° C. The reaction mixture was stirred at −78° C. for 30 min. Triisopropyl borate (5.58 g, 29.7 mmol) was added. The mixture was warmed to room temperature and stirred for 1 hour. HCl (5 M, 20 mL) was added and the mixture was stirred at room temperature for 10 min. The mixture was extracted with EtOAc (30 mL×2). The aqueous phase was acidified with HCl (5 M) until pH=1 and the solution was extracted with EtOAc (30 mL×2). The combined organic phase was dried over $Na_2SO_4$ and filtered. The filtrate was concentrated under reduced pressure to give the crude product (4-fluoro-2,6-dimethylphenyl)boronic acid (500 mg). Yield 30% (86% purity, UV=214 nm, ESI 167.2 $(M+H)^+$). The crude product was used for the next step directly.

Step 2: methyl (S)-3-((tert-butoxycarbonyl)amino)-3-(5-(4-fluoro-2,6-dimethylphenyl)pyridin-3-yl)propanoate

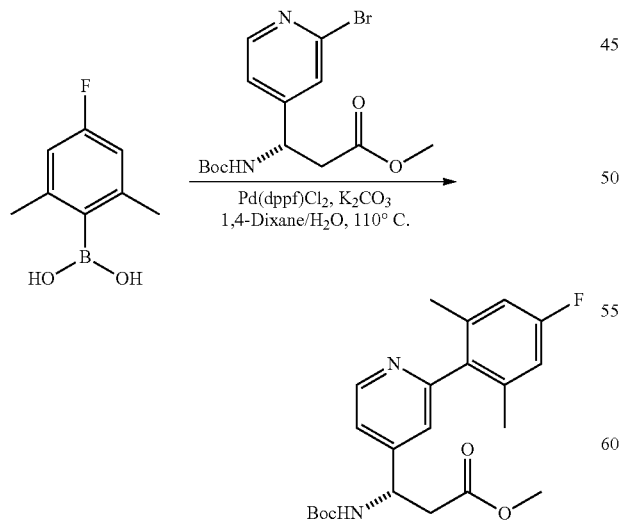

A mixture of (4-fluoro-2,6-dimethylphenyl)boronic acid (171 mg, 1.02 mmol), methyl (S)-3-(5-bromopyridin-3-yl)-3-((tert-butoxycarbonyl)amino)propanoate (120 mg, 0.34 mmol), Pd(dppf)Cl$_2$ (20 mg, 0.027 mmol) and $K_2CO_3$ (117 mg, 0.85 mmol) in 1,4-Dioxane (3 mL) and $H_2O$ (0.5 mL) under $N_2$ atmosphere was stirred at 110° C. for 3 hours under microwave. The mixture was poured into water and the solution was extracted with EtOAc (30 mL×2). The combined organic phase was dried over $Na_2SO_4$ and filtered. The filtrate was concentrated under reduced pressure and the residue was purified by silica gel column (pet. ether:EtOAc 2:1) to give the desired product methyl (S)-3-((tert-butoxycarbonyl)amino)-3-(5-(4-fluoro-2,6-dimethylphenyl)pyridin-3-yl)propanoate as a colorless oil (150 mg). Yield 76% (68% purity, UV=214 nm, ESI 403.2 $(M+H)^+$).

Step 3: methyl (S)-3-amino-3-(5-(4-fluoro-2,6-dimethylphenyl)pyridin-3-yl)propanoate

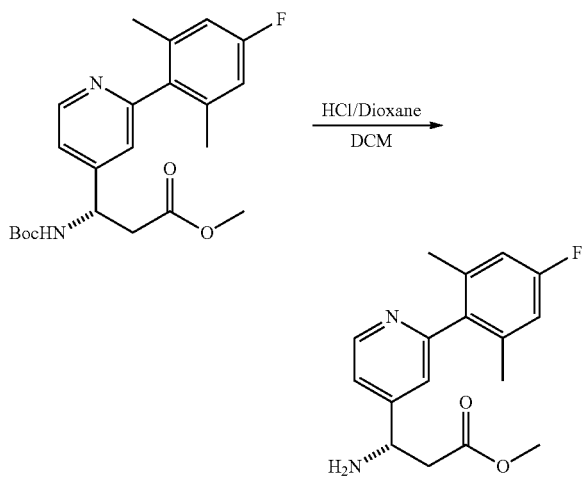

To a solution of methyl (S)-3-((tert-butoxycarbonyl)amino)-3-(5-(4-fluoro-2,6-dimethylphenyl)pyridin-3-yl)propanoate (150 mg, 0.37 mmol) in DCM (2 mL) was added HCl in Dioxane (4M, 1 mL). The solution was stirred at room temperature for 1 hour. Sat. aqueous NaHCO$_3$(20 mL) was added and the solution was extracted with EtOAc (30 mL×2). The combined organic phase was dried over NaSO$_4$ and filtered. The filtrate was concentrated under reduced pressure to provide the crude product methyl (S)-3-amino-3-(5-(4-fluoro-2,6-dimethylphenyl)pyridin-3-yl)propanoate as a colorless oil (110 mg). Yield 99% (81% purity, UV=214 nm, ESI 303.2 $(M+H)^+$). The crude product was used for the next step directly.

Step 4: methyl (3S)-3-(5-(4-fluoro-2,6-dimethylphenyl)pyridin-3-yl)-3-(4-methyl-2-(4-methyl-2-oxopyridin-1(2H)-yl)pentanamido)propanoate

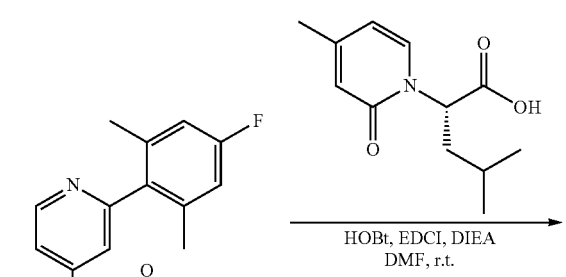

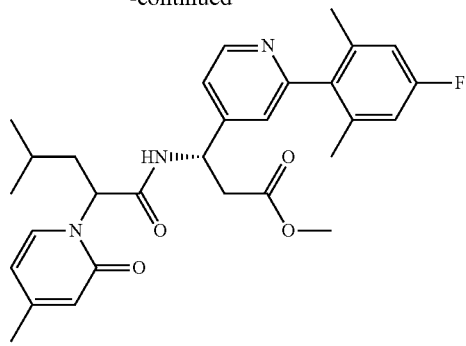

A mixture of methyl (S)-3-amino-3-(5-(4-fluoro-2,6-dimethylphenyl)pyridin-3-yl)propanoate (110 mg, 0.36 mmol), (S)-4-methyl-2-(4-methyl-2-oxopyridin-1(2H)-yl)pentanoic acid (81 mg, 0.36 mmol), HOBt (59 mg, 0.43 mmol), EDCI (83 mg, 0.43 mmol) and DIEA (94 mg, 0.72 mmol) in DMF (6 mL) was stirred at room temperature for 2 hours. The mixture was poured into water and the solution was extracted with EtOAc (30 mL×2). The combined organic phase was dried over $Na_2SO_4$ and filtered. The filtrate was concentrated under reduced pressure to give the crude product methyl (3S)-3-(5-(4-fluoro-2,6-dimethylphenyl)pyridin-3-yl)-3-(4-methyl-2-(4-methyl-2-oxopyridin-1(2H)-yl)pentanamido)propanoate as a yellow oil (117 mg). Yield 63% (26% purity, UV=214 nm, ESI 508.3 (M+H)$^+$). The crude product was used for the next step directly.

Step 5: (S)-3-(5-(4-fluoro-2,6-dimethylphenyl)pyridin-3-yl)-3-((R)-4-methyl-2-(4-methyl-2-oxopyridin-1(2H)-yl)pentanamido)propanoic acid

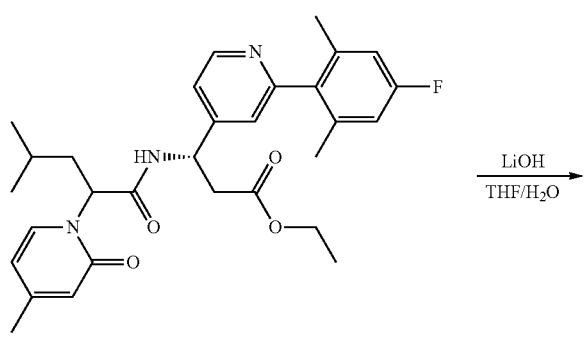

Methyl (3S)-3-(5-(4-fluoro-2,6-dimethylphenyl)pyridin-3-yl)-3-(4-methyl-2-(4-methyl-2-oxopyridin-1(2H)-yl)pentanamido)propanoate (117 mg, 0.23 mmol) was treated with LiOH—$H_2O$ (29 mg, 0.69 mmol) in THF (6 mL) and $H_2O$ (1 mL) at room temperature for 1.5 hours. The mixture was acidified with HCl (1 M) until pH=5. The solvent was removed in vacuo and the residue was purified by Preparative-HPLC A (30~70% MeCN) to give the compounds AO1 (4 mg) and AO2 (5 mg) as white solids.

Compound AO1 LC/MS C: 99% purity, UV=214 nm, Rt=1.58 min, ESI 494.0 (M+H)$^+$.

$^1$H NMR (500 MHz, MeOD) δ 8.53 (s, 1H), 8.17 (s, 1H), 7.57 (d, J=7.1 Hz, 1H), 7.49 (s, 1H), 6.96-6.84 (m, 2H), 6.29 (s, 1H), 6.25 (d, J=7.1 Hz, 1H), 5.68 (t, J=8.1 Hz, 1H), 5.40 (t, J=7.0 Hz, 1H), 2.89 (s, 2H), 2.19 (s, 3H), 1.98 (s, 3H), 1.93 (t, J=7.5 Hz, 2H), 1.86 (s, 3H), 1.47-1.42 (m, 1H), 1.03-0.85 (m, 6H).

Compound AO2 LC/MS C: 100% purity, UV=214 nm, Rt=1.61 min, ESI 494.0 (M+H)$^+$.

$^1$H NMR (500 MHz, MeOD) δ 8.60 (s, 1H), 8.25 (s, 1H), 7.72-7.57 (m, 2H), 6.93 (d, J=9.6 Hz, 2H), 6.41 (s, 1H), 6.34 (d, J=7.0 Hz, 1H), 5.71-5.61 (m, 1H), 5.37 (t, J=6.9 Hz, 1H), 2.85 (s, 2H), 2.25 (s, 3H), 2.02 (s, 5H), 1.92-1.75 (m, 2H), 1.46-1.26 (m, 1H), 0.97-0.87 (m, 6H).

Preparation of Compounds AP1 and AP2

Step 1: 2-bromo-1-methoxy-3-methylbenzene

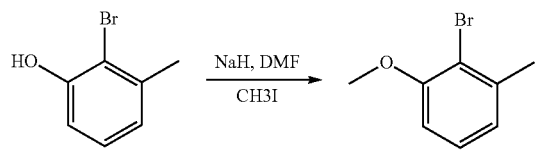

To a solution of 2-bromo-3-methylphenol (500 mg, 2.7 mmol) in DMF (10 mL) was added NaH (60% in oil, 82 mg, 3.4 mmol) at 0° C. The mixture was stirred at 0° C. for 30 min. Then iodomethane (761 mg, 5.4 mmol) was added. The reaction mixture was warmed up to room temperature and stirred for 12 hours. The mixture was poured into water and the solution was extracted with EtOAc (20 mL×2). The combined organic layers were dried over $Na_2SO_4$, filtered and the filtrate was concentrated under reduced pressure give a residue, which was purified by flash column (0%~10% EtOAc in Petroleum) to provide the desired product 2-bromo-1-methoxy-3-methylbenzene as a colorless oil (420 mg).

Step 2: (S)-methyl 3-(tert-butoxycarbonylamino)-3-(5-(2-methoxy-6-methylphenyl)pyridin-3-yl)propanoate

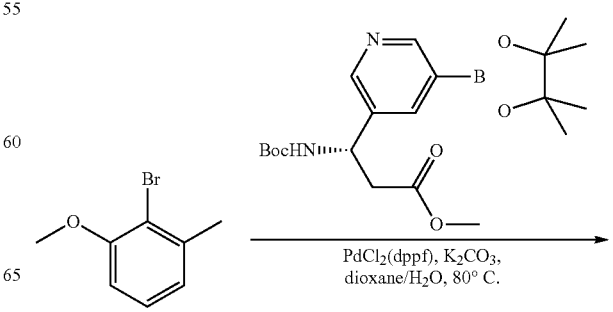

-continued

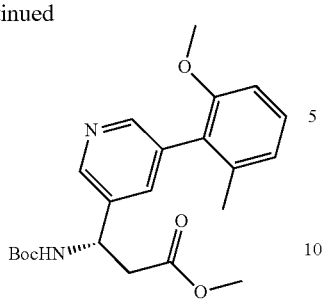

A mixture of 2-bromo-1-methoxy-3-methylbenzene (85 mg), (S)-methyl 3-(tert-butoxycarbonylamino)-3-(5-(4,4,5,5-tetramethyl-1,3,2-dioxaborolan-2-yl)pyridin-3-yl)propanoate (199 mg, 0.49 mmol), PdCl$_2$(dppf) (30 mg, 0.04 mmol) and K$_2$CO$_3$ (138 mg, 1.0 mmol) in dioxane (3 mL) and H$_2$O (0.4 mL) under N$_2$ atmosphere was stirred in a microwave at 80° C. for 50 mins. Water (20 mL) was added, and the solution was extracted with EtOAc (10 mL×3). The combined organic phases were concentrated under reduced pressure, and the residue was purified by silica gel column (petroleum ether:EtOAc 2:1) to give the desired product (S)-methyl 3-(tert-butoxycarbonylamino)-3-(5-(2-methoxy-6-methylphenyl)pyridin-3-yl)propanoate as a colorless oil (110 mg). Yield 44% (61% purity, UV=214 nm, ESI 401.1 (M+H)$^+$).

Step 3: (S)-methyl 3-amino-3-(5-(2-methoxy-6-methylphenyl)pyridin-3-yl)propanoate

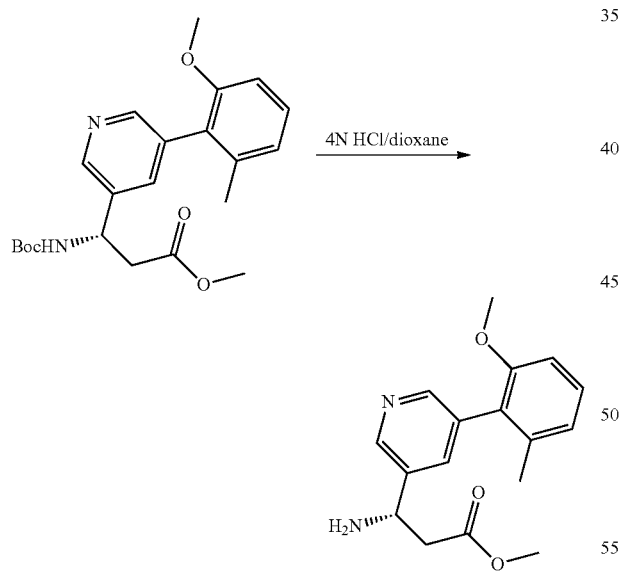

To a solution of (S)-methyl 3-(tert-butoxycarbonylamino)-3-(5-(2-methoxy-6-methylphenyl)pyridin-3-yl)propanoate (110 mg, 0.27 mmol) in DCM (3 mL) was added HCl in dioxane (4M, 2 mL), and the solution was stirred at room temperature for 2 hours. The solvent was removed in vacuo to provide the crude product (S)-methyl 3-amino-3-(5-(2-methoxy-6-methylphenyl)pyridin-3-yl)propanoate as a white solid (90 mg). (74% purity, UV=214 nm, ESI 301.1 (M+H)$^+$). The crude product was used for the next step directly.

Step 4: (3S)-methyl 3-(5-(2-methoxy-6-methylphenyl)pyridin-3-yl)-3-(4-methyl-2-(4-methyl-2-oxopyridin-1(2H)-yl)pentanamido)propanoate

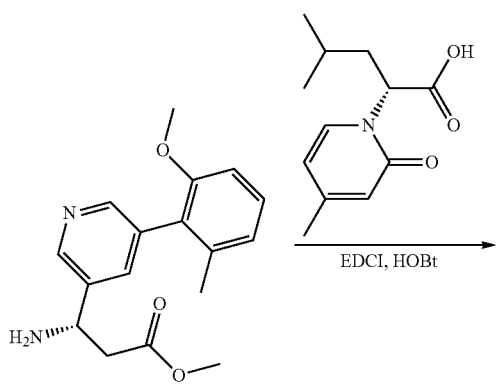

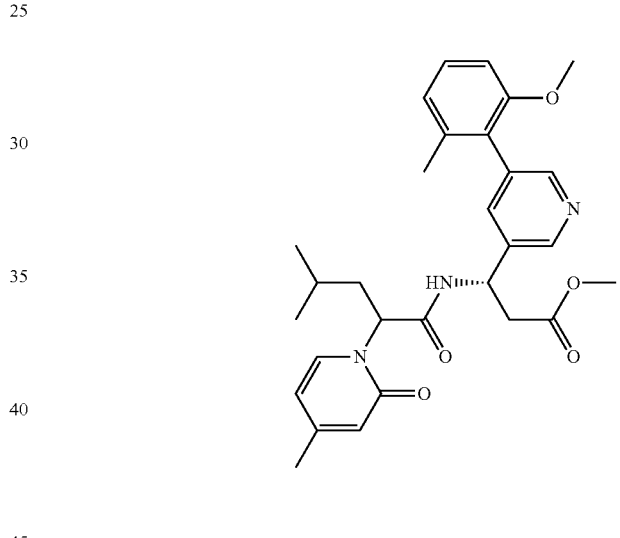

A mixture of (S)-methyl 3-amino-3-(5-(2-methoxy-6-methylphenyl)pyridin-3-yl)propanoate (90 mg, 0.36 mmol), (S)-4-methyl-2-(4-methyl-2-oxopyridin-1(2H)-yl)pentanoic acid (81 mg, 0.36 mmol), HOBt (81 mg, 0.6 mmol), EDCI (115 mg, 0.6 mmol) and DIEA (93 mg, 0.72 mmol) in DCM (10 mL) was stirred at room temperature for 5 hours. The mixture was poured into water, and the solution was extracted with DCM (20 mL×2). The combined organic layers were dried over Na$_2$SO$_4$, filtered and the filtrate was concentrated under reduced pressure to give a residue, which was purified by flash column (10%~50% EtOAc in Petroleum) to give the desired product (3S)-methyl 3-(5-(2-methoxy-6-methylphenyl)pyridin-3-yl)-3-(4-methyl-2-(4-methyl-2-oxopyridin-1 (2H)-yl)pentanamido)propanoate as a colorless oil (72 mg). Yield 52% (67% purity, UV=214 nm, ESI 506.2 (M+H)$^+$).

Step 5: (3S)-3-(5-(2-methoxy-6-methylphenyl)pyridin-3-yl)-3-(4-methyl-2-(4-methyl-2-oxopyridin-1(2H)-yl)pentanamido)propanoic acid

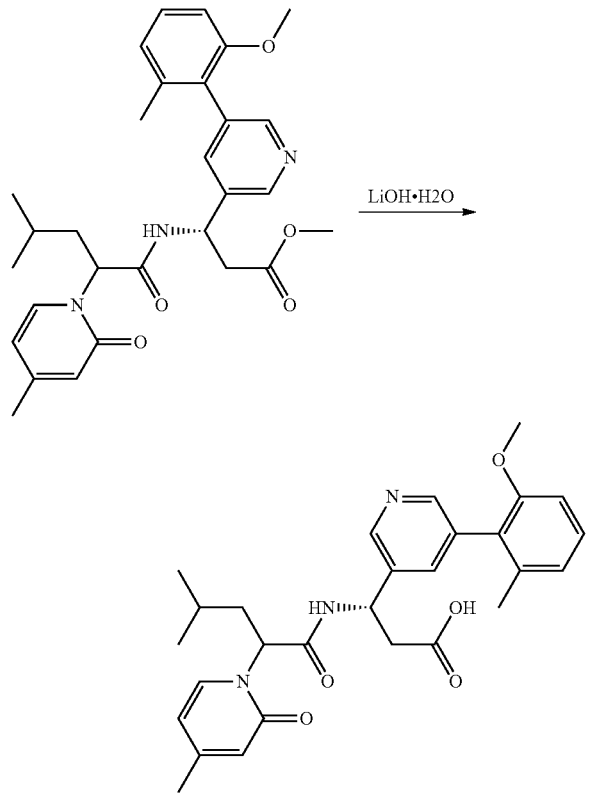

(3S)-methyl 3-(5-(2-methoxy-6-methylphenyl)pyridin-3-yl)-3-(4-methyl-2-(4-methyl-2-oxopyridin-1(2H)-yl)pentanamido)propanoate (72 mg, 0.14 mmol) was treated with LiOH—H₂O (42 mg, 1.0 mmol) in THF (6 mL) and H₂O (1 mL) at room temperature for 4 hours. The mixture was acidified with HCl (1 M) until pH=5 and concentrated under reduced pressure. The residue was purified by Preparative-HPLC A (30~70% MecN) to give the compounds AP1 (17 mg) and AP2 (36 mg) as white solids.

Compound AP1: LC/MS 100% purity, UV=214 nm, Rt=1.73 min ESI 492.3 (M+H)⁺.

¹H NMR (500 MHz, MeOD) δ 8.46 (d, J=2.0 Hz, 1H), 8.21 (d, J=1.7 Hz, 1H), 7.64-7.48 (m, 2H), 7.29 (t, J=8.0 Hz, 1H), 6.92 (d, J=8.1 Hz, 2H), 6.29 (s, 1H), 6.25-6.21 (m, 1H), 5.71 (t, J=8.1 Hz, 1H), 5.42 (t, J=7.3 Hz, 1H), 3.68 (s, 3H), 2.92 (d, J=7.3 Hz, 2H), 2.18 (s, 3H), 2.03-1.73 (m, 5H), 1.47-1.42 (m, 1H), 1.01-0.83 (m, 6H).

Compound AP2: LC/MS 100% purity, UV=214 nm, Rt=1.59 min, ESI 492.3 (M+H)⁺.

¹H NMR (500 MHz, MeOD) δ 8.52 (d, J=1.9 Hz, 1H), 8.27 (d, J=1.7 Hz, 1H), 7.70 (t, J=1.9 Hz, 1H), 7.63 (d, J=7.2 Hz, 1H), 7.30 (t, J=8.0 Hz, 1H), 6.95 (d, J=8.5 Hz, 2H), 6.38 (s, 1H), 6.32-6.30 (m, 1H), 5.72-5.69 (m, 1H), 5.39 (t, J=7.3 Hz, 1H), 3.72 (s, 3H), 2.98-2.73 (m, 2H), 2.24 (s, 3H), 2.08 (s, 3H), 1.88-1.67 (m, 2H), 1.40-1.21 (m, 1H), 1.01-0.83 (m, 6H).

Preparation of Compound AQ1b

Step 1: (R)-ethyl 3-(tert-butoxycarbonylamino)-3-(2-(2,6-dimethylphenyl)pyridin-4-yl)propanoate

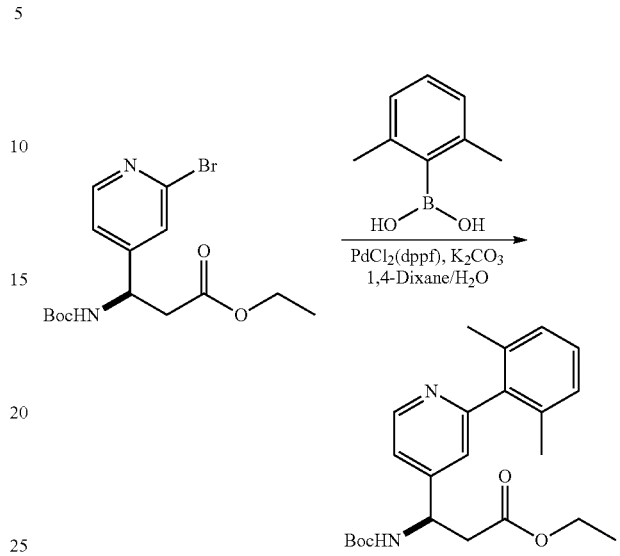

A mixture of (R)-ethyl 3-(2-bromopyridin-4-yl)-3-(tert-butoxycarbonylamino)propanoate (250 mg, 0.67 mmol), 2,6-dimethylphenylboronic acid (201 mg, 1.34 mmol), Pd(dppf)Cl₂ (40 mg, 0.054 mmol) and K₂CO₃ (232 mg, 1.68 mmol) in 1,4-Dioxane (3 mL) and H₂O (0.5 mL) under N₂ atmosphere was stirred at 110° C. for 2 hours under microwave. The mixture was poured into water and the solution was extracted with EtOAc (20 mL×2). The combined organic layers were dried over Na₂SO₄ and filtered. The filtrate was concentrated under reduced pressure to give a residue, which was purified by flash column chromatography (0%~40% EtOAc in Petroleum) to obtain the desired product (R)-ethyl 3-(tert-butoxycarbonylamino)-3-(2-(2,6-dimethylphenyl)pyridin-4-yl)propanoate as a yellow oil (270 mg). Yield 52% (51% purity, UV=214 nm, ESI 399 (M+H)⁺).

Step 2: (R)-ethyl 3-amino-3-(2-(2,6-dimethylphenyl)pyridin-4-yl)propanoate hydrochloride

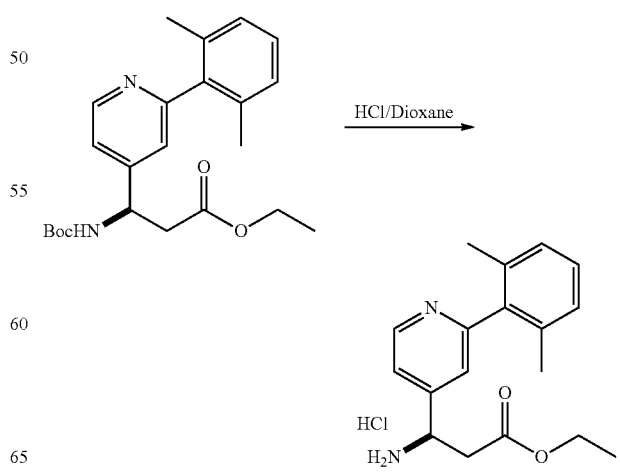

To a solution of (R)-ethyl 3-(tert-butoxycarbonylamino)-3-(2-(2,6-dimethylphenyl)pyridin-4-yl)propanoate (270 mg, 0.346 mmol) in DCM (2 mL) was added HCl/Dioxane (4M, 2 mL) and the solution was stirred at room temperature for 1 hour. The mixture was concentrated in vacuo to provide the crude product (S)-methyl 3-amino-3-(5-(2,6-dimethylphenyl)pyridin-3-yl)propanoate hydrochloride as a yellow oil (200 mg), which was used for next step directly without further purification. Expect yield 99% (31% purity, UV=214 nm, ESI 299 (M+H)+).

Step 3: (3R)-ethyl 3-(2-(2,6-dimethylphenyl)pyridin-4-yl)-3-(4-methyl-2-(4-methyl-2-oxopyridin-1(2H)-yl)pentanamido)propanoate

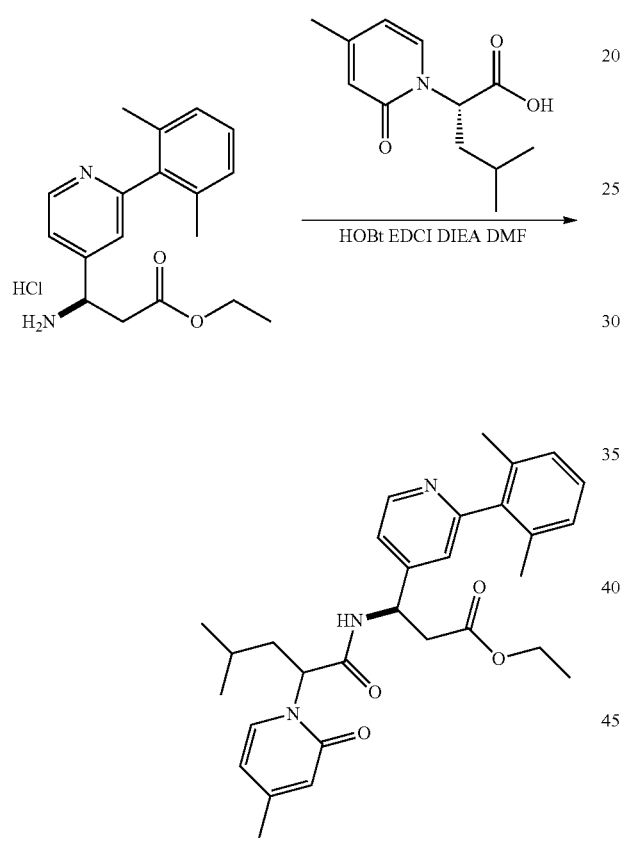

A mixture of (R)-ethyl 3-amino-3-(2-(2,6-dimethylphenyl)pyridin-4-yl)propanoate hydrochloride (200 mg, 0.67 mmol), (S)-4-methyl-2-(4-methyl-2-oxopyridin-1(2H)-yl)pentanoic acid (181 mg, 0.81 mmol), HOBt (135 mg, 1.0 mmol), EDCI (191 mg, 1.0 mmol) and DIEA (258 mg, 2.0 mmol) in DMF (5 mL) was stirred at room temperature for 2 hours. The mixture was poured into water and the solution was extracted with EtOAc (20 mL×2). The combined organic layers were dried over $Na_2SO_4$ and filtered. The filtrate was concentrated under reduced pressure to give a residue, which was purified by flash column chromatography (0%~50% EtOAc in Petroleum) to provide the desired product (3R)-ethyl 3-(2-(2,6-dimethylphenyl)pyridin-4-yl)-3-(4-methyl-2-(4-methyl-2-oxopyridin-1 (2H)-yl)pentanamido)propanoate as a light yellow oil (183 mg). Yield 54%, three steps (93% purity, UV=214 nm, ESI 504 (M+H)+).

Step 4: (3R)-3-(2-(2,6-dimethylphenyl)pyridin-4-yl)-3-(4-methyl-2-(4-methyl-2-oxopyridin-1(2H)-yl)pentanamido)propanoic acid

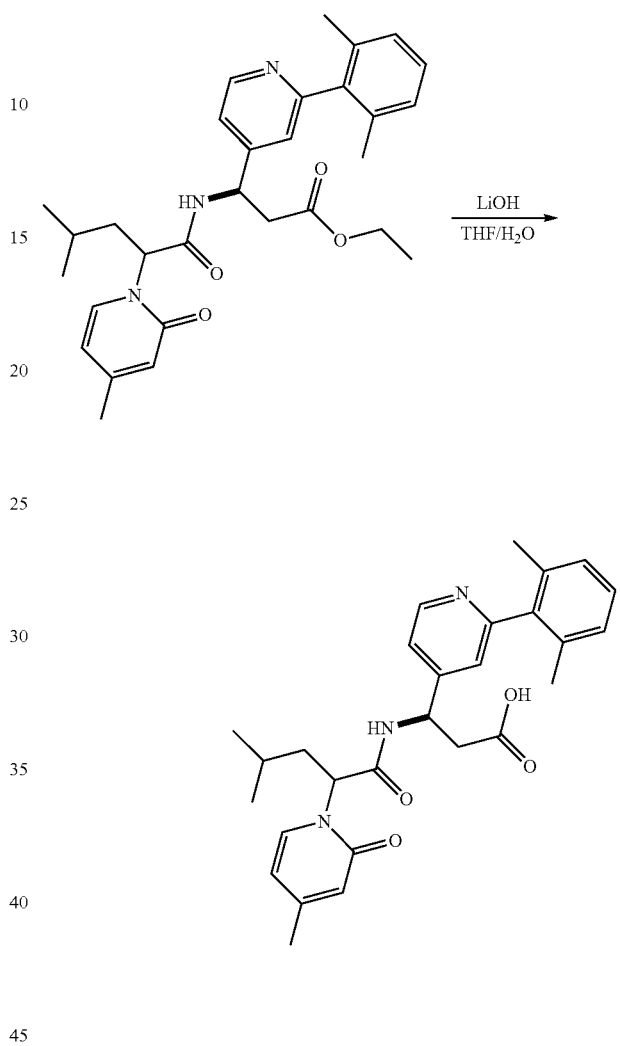

(3R)-ethyl 3-(2-(2,6-dimethylphenyl)pyridin-4-yl)-3-(4-methyl-2-(4-methyl-2-oxopyridin-1(2H)-yl)pentanamido)propanoate (183 mg, 0.36 mmol) was treated with LiOH—$H_2O$ (46 mg, 1.09 mmol) in THF (6 mL) and $H_2O$ (1 mL) at room temperature for 1.5 hours. The mixture was acidified to pH=5 with HCl (1 M). The solvent was removed in vacuo and the residue was purified by Preparative-HPLC A (30~70% MeCN) to give the compounds AQ1a (40.2 mg) and AQ1b (48.4 mg) as white solids.

Compound AQ1b LC/MS A: 100% purity, UV=214 nm, Rt=1.56 min, ESI 476 (M+H)+.

$^1$H NMR (500 MHz, MeOD) δ 8.60 (d, J=5.2 Hz, 1H), 7.62 (d, J=7.1 Hz, 1H), 7.44 (dd, J=5.3, 1.6 Hz, 1H), 7.33 (s, 1H), 7.29-7.20 (m, 1H), 7.15 (d, J=7.6 Hz, 2H), 6.38 (s, 1H), 6.31 (dd, J=7.1, 1.7 Hz, 1H), 5.71 (t, J=8.1 Hz, 1H), 5.34 (t, J=7.1 Hz, 1H), 2.99-2.80 (m, 2H), 2.24 (s, 3H), 2.01 (s, 6H), 1.84 (t, J=7.6 Hz, 2H), 1.38-1.32 (m, 1H), 0.98-0.84 (m, 6H).

Preparation of Compound AQ2b

Step 1: ethyl (S)-3-((tert-butoxycarbonyl)amino)-3-(2-(2,6-dimethylphenyl)pyridin-4-yl)propanoate

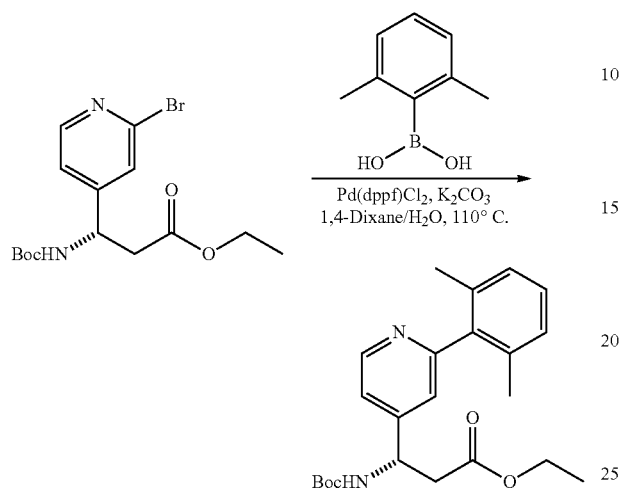

A mixture of ethyl (S)-3-(2-bromopyridin-4-yl)-3-((tert-butoxycarbonyl)amino)propanoate (300 mg, 0.81 mmol), (2,6-dimethylphenyl)boronic acid (181 mg, 1.22 mmol), Pd(dppf)Cl₂ (47 mg, 0.07 mmol) and K₂CO₃ (278 mg, 2.03 mmol) in 1,4-Dioxane (3 mL) and H₂O (0.5 mL) under N₂ atmosphere was stirred at 110° C. for 2 hours under microwave. The mixture was poured into water and the solution was extracted with EtOAc (30 mL×2). The combined organic phase was dried over Na₂SO₄ and filtered. The filtrate was concentrated under reduced pressure and the residue was purified by silica gel column (pet. ether:EtOAc 3:1) to give the desired product ethyl (S)-3-((tert-butoxycarbonyl)amino)-3-(2-(2,6-dimethylphenyl)pyridin-4-yl)propanoate as a yellow oil (265 mg). Yield 82% (83% purity, UV=214 nm, ESI 399.1 (M+H)⁺).

Step 2: ethyl (S)-3-amino-3-(2-(2,6-dimethylphenyl)pyridin-4-yl)propanoate

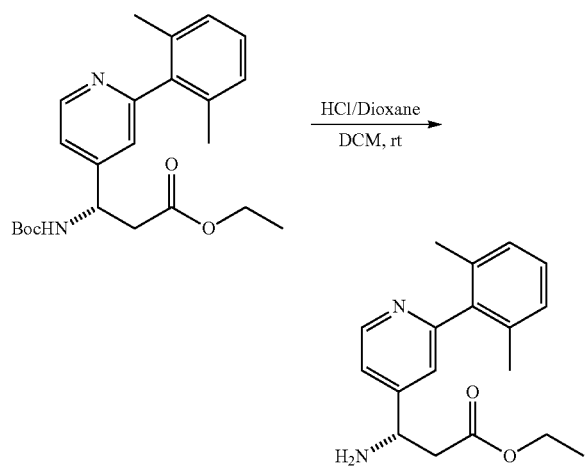

To a solution of ethyl (S)-3-((tert-butoxycarbonyl)amino)-3-(2-(2,6-dimethylphenyl)pyridin-4-yl)propanoate (265 mg, 0.67 mmol) in DCM (2 mL) was added HCl/Dioxane (4M, 1 mL). The solution was stirred at room temperature for 1 hour. Sat. aqueous NaHCO₃ (20 mL) was added and the solution was extracted with EtOAc (30 mL×2). The combined organic phase was dried over Na₂SO₄ and filtered. The filtrate was concentrated under reduced pressure to provide the crude product ethyl (S)-3-amino-3-(2-(2,6-dimethylphenyl)pyridin-4-yl)propanoate as a yellow oil (240 mg). Yield 99% (72% purity, UV=214 nm, ESI 299.0 (M+H)⁺). The crude product was used for the next step directly.

Step 3: ethyl (3S)-3-(2-(2,6-dimethylphenyl)pyridin-4-yl)-3-(4-methyl-2-(4-methyl-2-oxopyridin-1(2H)-yl)pentanamido)propanoate

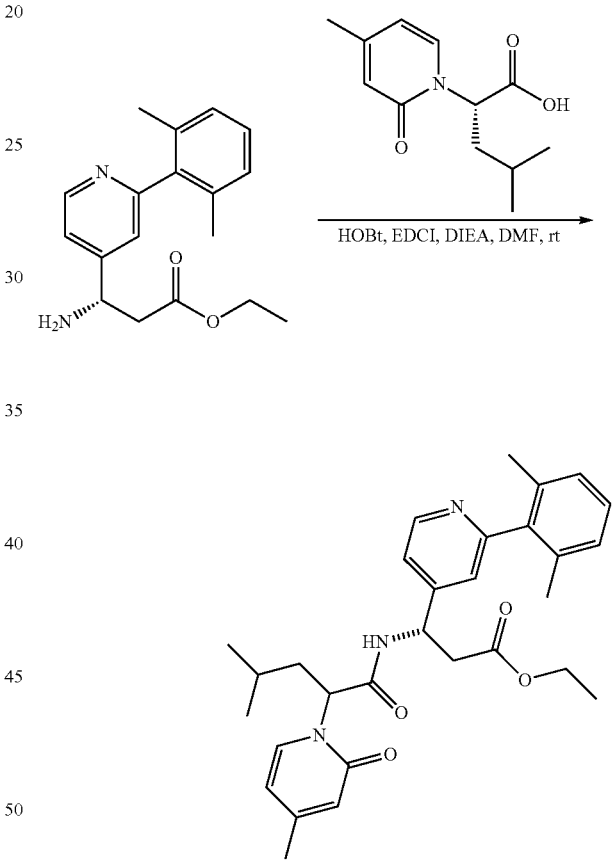

A mixture of ethyl (S)-3-amino-3-(2-(2,6-dimethylphenyl)pyridin-4-yl)propanoate (240 mg, 0.81 mmol), (S)-4-methyl-2-(4-methyl-2-oxopyridin-1(2H)-yl)pentanoic acid (180 mg, 0.81 mmol), HOBt (130 mg, 0.96 mmol), EDCI (185 mg, 0.96 mmol) and DIEA (208 mg, 1.61 mmol) in DMF (8 mL) was stirred at room temperature for 2 hours. Water (20 mL) was added and the solution was extracted with EtOAc (30 mL×2). The combined organic phase was concentrated under reduced pressure and the residue was purified by silica gel column (pet. ether:EtOAc 2:1) to give the desired product ethyl (3S)-3-(2-(2,6-dimethylphenyl)pyridin-4-yl)-3-(4-methyl-2-(4-methyl-2-oxopyridin-1(2H)-yl)pentanamido)propanoate as a yellow oil (233 mg). Yield 57% (11% purity, UV=214 nm, ESI 504.1 (M+H)⁺).

Step 4: (3S)-3-(2-(2,6-dimethylphenyl)pyridin-4-yl)-3-(4-methyl-2-(4-methyl-2-oxopyridin-1(2H)-yl)pentanamido)propanoic acid

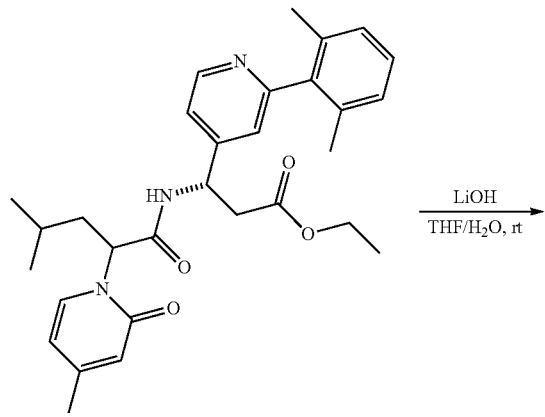

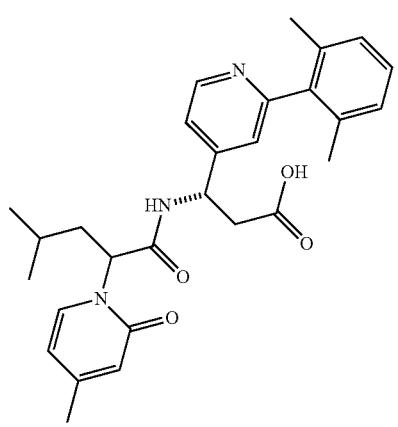

Ethyl (3S)-3-(2-(2,6-dimethylphenyl)pyridin-4-yl)-3-(4-methyl-2-(4-methyl-2-oxopyridin-1(2H)-yl)pentanamido)propanoate (233 mg, 0.46 mmol) was treated with LiOH—H$_2$O (58 mg, 1.39 mmol) in THF (6 mL) and H$_2$O (1 mL) at room temperature for 1.5 hours. The mixture was acidified with HCl (1 M) until pH=5. The solvent was removed in vacuo and the residue was purified by Preparative-HPLC A (30~70% MeCN) to give the compounds AQ2a (26 mg) and AQ2b (15 mg) as white solids.

Compound AQ2b LC/MS A: 98% purity, UV=214 nm, Rt=1.55 min, ESI 476.2 (M+H)$^+$.

$^1$H NMR (500 MHz, MeOD) δ 8.59 (d, J=5.2 Hz, 1H), 7.62 (d, J=7.2 Hz, 1H), 7.44 (dd, J=5.3, 1.5 Hz, 1H), 7.33 (s, 1H), 7.27-7.07 (m, 3H), 6.38 (s, 1H), 6.31 (dd, J=7.1, 1.7 Hz, 1H), 5.70 (t, J=8.0 Hz, 1H), 5.34 (t, J=7.1 Hz, 1H), 3.00-2.74 (m, 2H), 2.24 (s, 3H), 2.01 (s, 6H), 1.84 (t, J=7.5 Hz, 2H), 1.38-1.32 (m, 1H), 0.98-0.83 (m, 6H).

Preparation of Compounds AR1 and AR2

Step 1: ethyl 2-(4-bromo-5-fluoro-2-oxopyridin-1(2H)-yl)-4-methylpentanoate

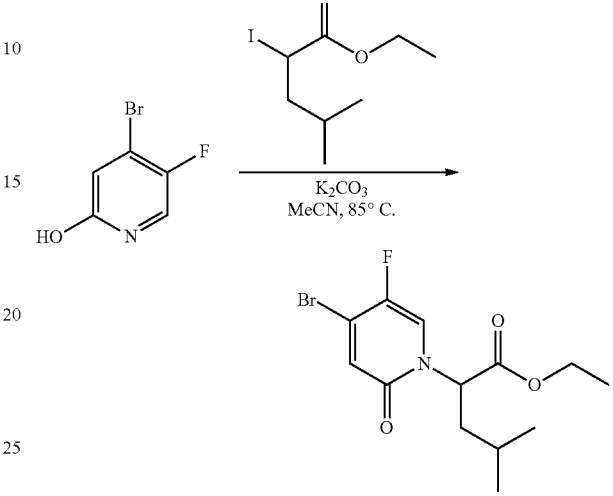

A mixture of 4-bromo-5-fluoropyridin-2-ol (442 mg, 2.31 mmol), ethyl 2-iodo-4-methylpentanoate (937 mg, 3.47 mmol) and K$_2$CO$_3$ (958 mg, 6.94 mmol) in MeCN (10 mL) was stirred at 85° C. overnight and filtered. The filtrate was concentrated in vacuo, and the residue was purified by silica gel column (pet. ether:EtOAc=4:1) to give the desired product ethyl 2-(4-bromo-5-fluoro-2-oxopyridin-1(2H)-yl)-4-methylpentanoate as a colorless oil (402 mg). Yield 52% (97% purity, UV=214 nm, ESI 334.0 (M+H)$^+$).

Step 2: ethyl 2-(5-fluoro-4-methyl-2-oxopyridin-1(2H)-yl)-4-methylpentanoate

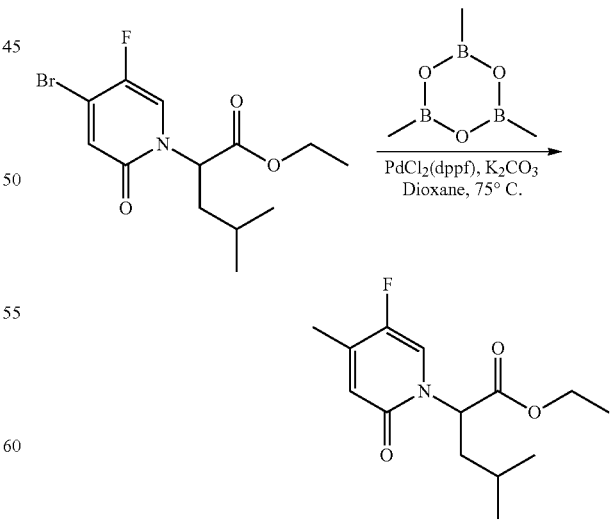

A mixture of ethyl 2-(4-bromo-5-fluoro-2-oxopyridin-1(2H)-yl)-4-methylpentanoate (402 mg, 1.21 mmol), 2,4,6-trimethyl-1,3,5,2,4,6-trioxatriborinane (913 mg, 3.62 mmol), PdCl₂(dppf) (88 mg, 0.12 mmol) and K₂CO₃ (500 mg, 3.62 mmol) in 6 mL of 1,4-dioxane was stirred under N₂ atmosphere at 75° C. overnight. Filtered. The filtrate was concentrated in vacuo, and the residue was purified by silica gel column (pet. ether:EtOAc=3:1) to give the desired product ethyl 2-(5-fluoro-4-methyl-2-oxopyridin-1(2H)-yl)-4-methylpentanoate as a colorless oil (299 mg), Yield 92% (90% purity, UV=214 nm, ESI 270.1 (M+H)⁺).

Step 3: 2-(5-fluoro-4-methyl-2-oxopyridin-1(2H)-yl)-4-methylpentanoic acid

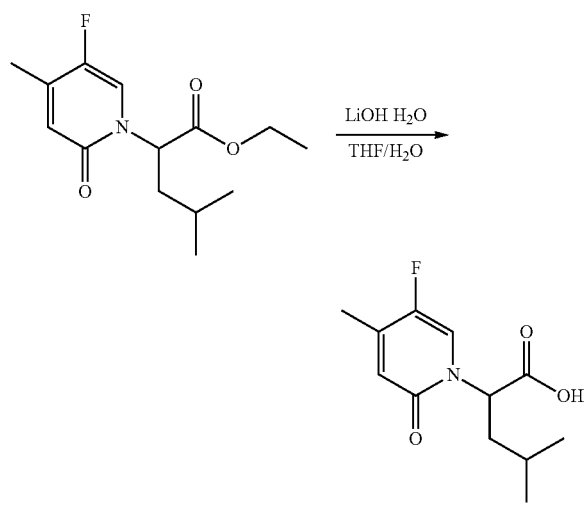

Ethyl 2-(5-fluoro-4-methyl-2-oxopyridin-1(2H)-yl)-4-methylpentanoate (299 mg, 1.11 mmol) was treated with LiOH—H₂O (61 mg, 1.44 mmol) in 3 mL of THF and 0.5 mL of H₂O at room temperature for 2 h. The solution was adjusted to pH=5~6 with TFA. The solvent was removed in vacuo to give the crude product 2-(5-fluoro-4-methyl-2-oxopyridin-1(2H)-yl)-4-methylpentanoic acid as a yellow oil (300 mg). Yield 100% (75% purity, UV=214 nm, ESI 242.2 (M+H)⁺). The crude product was used for the next step directly.

Step 4: (3S)-methyl 3-(5-(2,6-dimethylphenyl)pyridin-3-yl)-3-(2-(5-fluoro-4-methyl-2-oxopyridin-1(2H)-yl)-4-methylpentanamido)propanoate

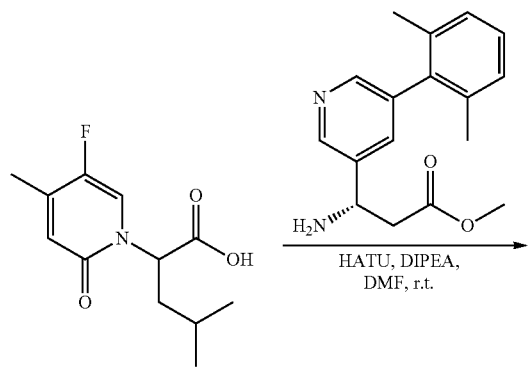

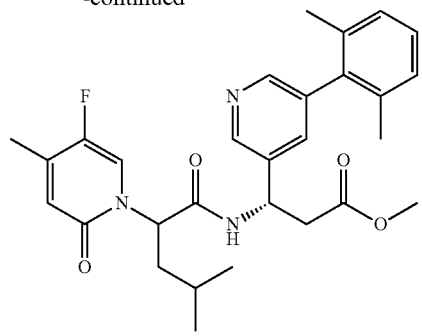

A mixture of 2-(5-fluoro-4-methyl-2-oxopyridin-1(2H)-yl)-4-methylpentanoic acid (100 mg, 0.41 mmol), (S)-methyl 3-amino-3-(5-(2,6-dimethylphenyl)pyridin-3-yl)propanoate (118 mg, 0.41 mmol), HATU (189 mg, 0.5 mmol) and DIEA (107 mg, 0.83 mmol) in DMF (3 mL) was stirred at room temperature for 1 hour. The mixture was poured into 30 mL of water, and the solution was extracted with EtOAc (30 mL×2). The combined organic layers were washed with brine (10 mL), dried over Na₂SO₄. Filtered. The filtrate was concentrated under reduced pressure to give the crude product (3S)-methyl 3-(5-(2,6-dimethylphenyl)pyridin-3-yl)-3-(2-(5-fluoro-4-methyl-2-oxopyridin-1(2H)-yl)-4-methylpentanamido)propanoate (220 mg). Yield 100%. (85% purity, UV=214 nm, ESI 508.3 (M+H)⁺).

Step 5: (3S)-3-(5-(2,6-dimethylphenyl)pyridin-3-yl)-3-(2-(5-fluoro-4-methyl-2-oxopyridin-1(2H)-yl)-4-methylpentanamido)propanoic acid

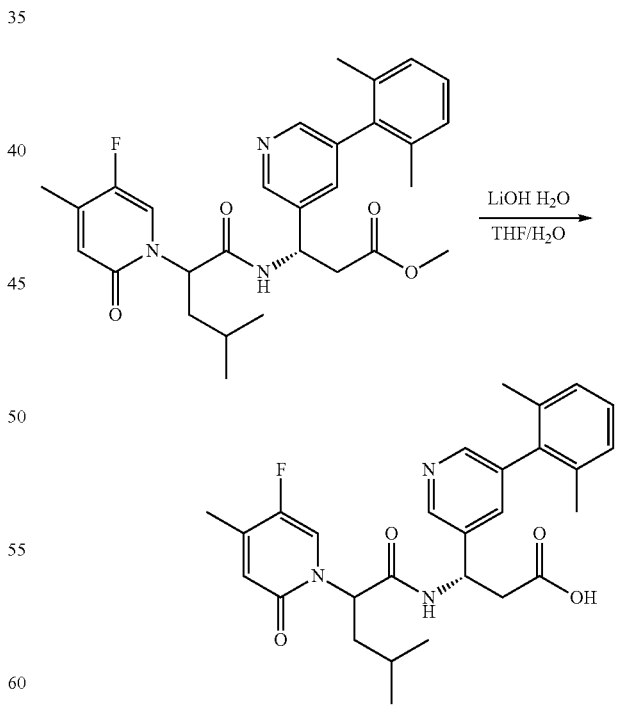

(3S)-methyl 3-(5-(2,6-dimethylphenyl)pyridin-3-yl)-3-(2-(5-fluoro-4-methyl-2-oxopyridin-1(2H)-yl)-4-methylpentanamido)propanoate (220 mg, 0.43 mmol) was treated with LiOH—H₂O (27 mg, 0.65 mmol) in 3 mL of THF and 0.5 mL of H₂O at room temperature for 1 h. The solution was adjusted to pH=3~4 with TFA. The solvent was removed in vacuo, and the residue was purified by Preparative-HPLC A (33-70% MeCN) to give the compounds AR1 (41 mg) and AR2 (47 mg) as white solids.

Compound AR1 LC/MS A: 100% purity, UV=214 nm, Rt=1.65 min, ESI 494.2 (M+H)+.

$^1$H NMR (500 MHz, MeOD) δ 8.54 (s, 1H), 8.18 (s, 1H), 7.68 (d, J=5.7 Hz, 1H), 7.55 (s, 1H), 7.20-7.18 (m, 1H), 7.14-7.11 (m, 2H), 6.32 (d, J=7.2 Hz, 1H), 5.67 (t, J=7.9 Hz, 1H), 5.41 (t, J=7.2 Hz, 1H), 2.89 (d, J=7.2 Hz, 2H), 2.19 (s, 3H), 1.98 (s, 3H), 1.94-1.89 (m, 2H), 1.88 (s, 3H), 1.47-1.44 (m, 1H), 0.99-095 (m, 6H).

Compound AR2 LC/MS A: 100% purity, UV=214 nm, Rt=1.68 min, ESI 494.2 (M+H)+.

$^1$H NMR (500 MHz, MeOD) δ 8.59 (s, 1H), 8.25 (s, 1H), 7.74 (d, J=5.8 Hz, 1H), 7.67 (s, 1H), 7.28-7.19 (m, 1H), 7.16-7.15 (m, 2H), 6.43 (d, J=7.1 Hz, 1H), 5.74-5.58 (m, 1H), 5.38 (t, J=7.3 Hz, 1H), 2.90-2.86 (m, 2H), 2.24 (s, 3H), 2.02 (s, 6H), 1.86-1.72 (m, 2H), 1.41-1.20 (m, 1H), 0.91-0.88 (m, 6H).

Preparation of Compound AS2

Step 1: ethyl 3-methyl-2-(4-methyl-2-oxopyridin-1 (2H)-yl)butanoate

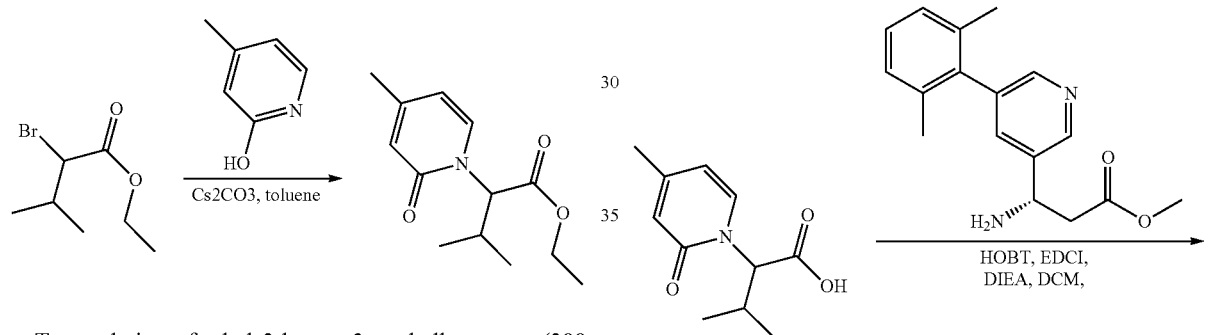

To a solution of ethyl 2-bromo-3-methylbutanoate (200 mg, 0.96 mmol) and 4-methylpyridin-2-ol (105 mg, 0.96 mmol) in toluene (2 mL) was added Cs$_2$CO$_3$ (626 mg, 1.92 mmol) and the reaction was stirred at 110° C. for 16 h. To the mixture was added a saturated sodium carbonate aqueous solution (30 mL) and the solution was extracted with EtOAc (20 mL×2). The organic phase was washed with brine, dried over Na$_2$SO$_4$ and filtered. The filtrate was concentrated in vacuo. The residue was purified by silica gel column (pet. ether:EtOAc=2:1) to provide the desired product ethyl 3-methyl-2-(4-methyl-2-oxopyridin-1(2H)-yl)butanoate (200 mg) as a yellow oil. Yield 46% (98% purity, UV=214 nm, ESI 238 (M+H)+).

Step 2: 3-methyl-2-(4-methyl-2-oxopyridin-1(2H)-yl)butanoic acid

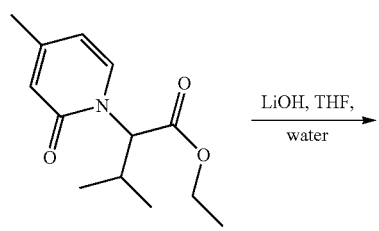

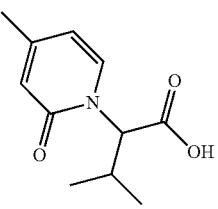

Ethyl 3-methyl-2-(4-methyl-2-oxopyridin-1(2H)-yl)butanoate (200 mg, 0.93 mmol) was treated with LiOH (1M in H$_2$O, 0.6 mL) in THF (5 mL) at room temperature for 2 h. The mixture was adjusted with 1 M HCl to pH=5~6. The solvent was removed in vacuo to provide the crude product 3-methyl-2-(4-methyl-2-oxopyridin-1(2H)-yl)butanoic acid (194 mg) as a white solid. Yield 100% (98% purity, UV=214 nm, ESI 210 (M+H)+). The crude product was used for the next step directly.

Step 3: (3S)-methyl 3-(5-(2,6-dimethylphenyl)pyridin-3-yl)-3-(3-methyl-2-(4-methyl-2-oxopyridin-1 (2H)-yl)butanamido)propanoate

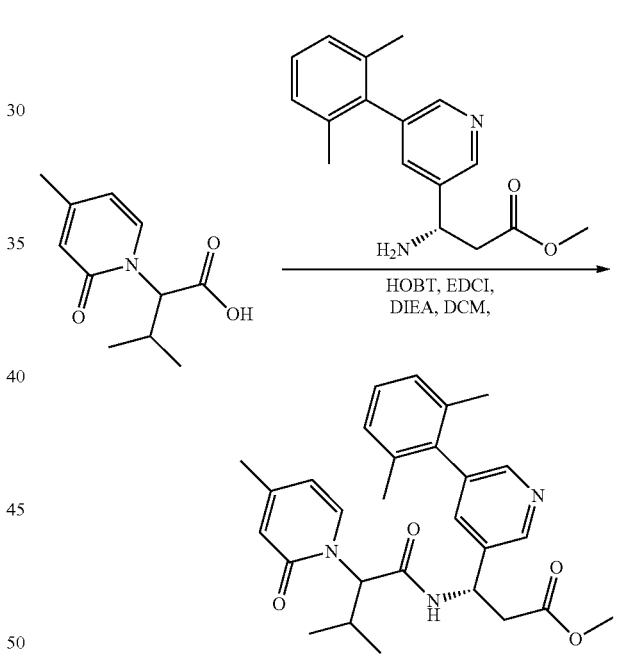

A mixture of 3-methyl-2-(4-methyl-2-oxopyridin-1(2H)-yl)butanoic acid (100 mg, 0.48 mmol), (S)-methyl 3-amino-3-(5-(2,6-dimethylphenyl)pyridin-3-yl)propanoate (136 mg, 0.48 mmol), HOBT (97 mg, 0.72 mmol), EDCI (138 mg, 0.72 mmol) and DIEA (186 mg, 1.44 mmol) in DCM (5 mL) was stirred at room temperature for 2 hours. The mixture was poured into 10 mL of water and the solution was extracted with DCM (30 mL×3). The organic phase was dried over Na$_2$SO$_4$, filtered and the filtrate was concentrated in vacuo. The residue was purified by silica gel column (pet. ether:EtOAc=1:1) to provide the desired product (3 S)-methyl 3-(5-(2,6-dimethylphenyl)pyridin-3-yl)-3-(3-methyl-2-(4-methyl-2-oxopyridin-1(2H)-yl)butanamido) propanoate as a yellow oil (100 mg). Yield 44% (95% purity, UV=254 nm, ESI 476 (M+H)+).

Step 4: (S)-3-(5-(2,6-dimethylphenyl)pyridin-3-yl)-3-((S)-3-methyl-2-(4-methyl-2-oxopyridin-1(2H)-yl)butanamido)propanoic acid

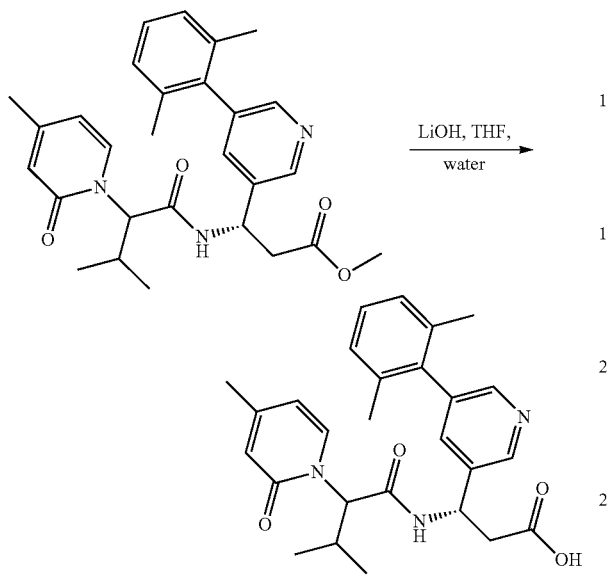

(3 S)-methyl 3-(5-(2,6-dimethylphenyl)pyridin-3-yl)-3-(3-methyl-2-(4-methyl-2-oxopyridin-1(2H)-yl)butanamido)propanoate (100 mg, 0.21 mmol) was treated with LiOH (1M in H$_2$O, 0.6 mL) in THF (5 mL) at room temperature for 2 h. The mixture was adjusted with 1M HCl to pH=5~6, the solvent was removed in vacuo, and the residue was purified by preparatory HPLC B (30-70% MeCN) to give the desired compounds AS1 (17 mg) and AS2 (20 mg) as white solids.

Compound AS2 LC/MS A: 98% purity, UV=214 nm, Rt=1.55 min, ESI 462 (M+H)$^+$.

$^1$H NMR (500 MHz, MeOD) δ 8.63 (d, J=2.0 Hz, 1H), 8.27 (d, J=1.9 Hz, 1H), 7.80 (d, J=7.2 Hz, 1H), 7.71 (t, J=2.0 Hz, 1H), 7.28-7.12 (m, 3H), 6.44-6.30 (m, 2H), 5.38 (t, J=7.4 Hz, 1H), 5.23 (d, J=11.1 Hz, 1H), 2.88-2.95 (m, 2H), 2.42-2.22 (m, 4H), 1.99 (s, 3H), 1.97 (s, 3H), 0.86 (d, J=6.5 Hz, 3H), 0.74 (d, J=6.6 Hz, 3H).

Preparation of Compound AT1b

Step 1: (2R,3S)-2-bromo-3-methylpentanoic acid

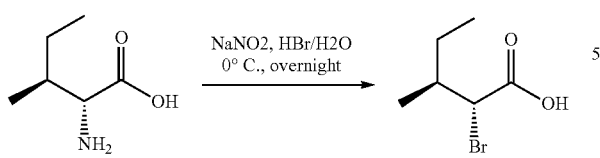

To a solution of (2R,3S)-2-amino-3-methylpentanoic acid (1.0 g, 7.6 mmol) in HBr (40% in water, 8 mL) at 0° C. was added a solution of NaNO$_2$ (0.78 g, 11.4 mmol) in H$_2$O (4 mL) dropwise. The reaction mixture was stirred at room temperature for 16 hours. The solution was extracted with EtOAc (20 mL×2). The combined organic layers were dried over Na$_2$SO$_4$, filtered and the filtrate was concentrated under reduced pressure to give the crude product (2R,3S)-2-bromo-3-methylpentanoic acid as an orange oil (1.1 g). The crude product was used for the next step directly.

Step 2: (2S,3S)-3-methyl-2-(4-methyl-2-oxopyridin-1(2H)-yl)pentanoic acid

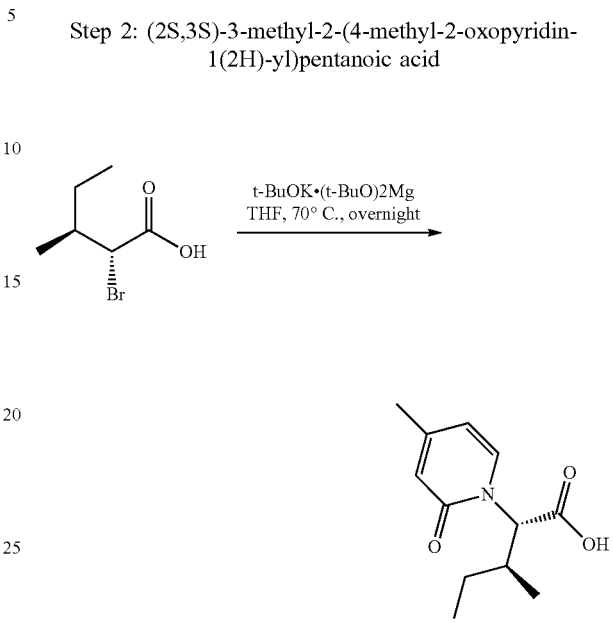

A mixture of (2R,3S)-2-bromo-3-methylpentanoic acid (1.1 g, 5.7 mmol) and (t-BuO)$_2$Mg (1.29 g, 7.6 mmol) in dry THF (20 mL) was stirred at 30° C. for 3 hours under N$_2$ atmosphere, and then 4-methylpyridin-2-ol (420 mg, 3.8 mmol) and t-BuOK (430 mg, 3.88 mmol) were added. The reaction mixture was stirred at 70° C. for 16 hours under N$_2$. The mixture was cooled to room temperature and acidified with HCl (4 M) until pH=5. The solution was concentrated under reduced pressure to give a residue, which was purified by reversed phase flash column chromatography (0%~60% MeOH in H$_2$O (5% TFA)) to provide the desired product (2S,3S)-3-methyl-2-(4-methyl-2-oxopyridin-1(2H)-yl)pentanoic acid as an orange oil (100 mg). Yield 20% (97% purity, UV=214 nm, ESI 224 (M+H)$^+$).

Step 3: (3S)-methyl 3-(5-(2,6-dimethylphenyl)pyridin-3-yl)-3-(3-methyl-2-(4-methyl-2-oxopyridin-1(2H)-yl)pentanamido)propanoate

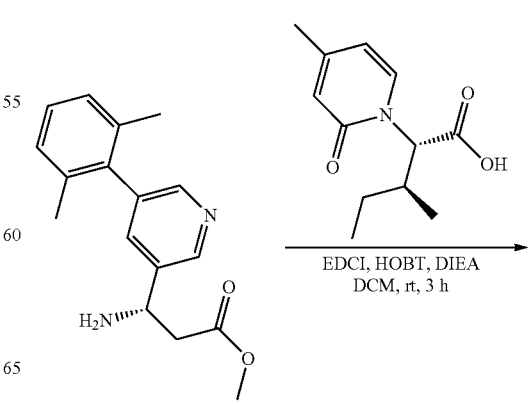

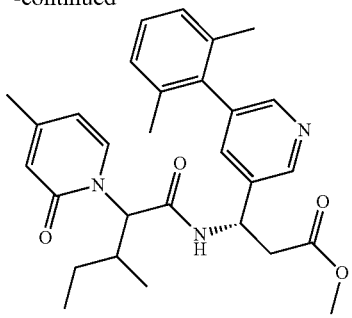

A mixture of (2S,3S)-3-methyl-2-(4-methyl-2-oxopyridin-1(2H)-yl)pentanoic acid (100 mg, 0.45 mmol), (S)-methyl 3-amino-3-(5-(2,6-dimethylphenyl)pyridin-3-yl)propanoate (140 mg, 0.5 mmol), HOBt (73 mg, 0.54 mmol), EDCI (100 mg, 0.54 mmol) and DIEA (230 mg, 1.8 mmol) in DCM (10 mL) was stirred at room temperature for 3 hours. The mixture was poured into water and the solution was extracted with DCM (30 mL×2). The combined organic layers were dried over $Na_2SO_4$ and filtered. The filtrate was concentrated under reduced pressure to give a residue, which was purified by flash column chromatography (0%~80% EtOAc in pet ether) to provide the desired product (3S)-methyl 3-(5-(2,6-dimethylphenyl)pyridin-3-yl)-3-(3-methyl-2-(4-methyl-2-oxopyridin-1 (2H)-yl)pentanamido)propanoate as a colorless oil (150 mg). Yield 68% (93% purity, UV=214 nm, ESI 490 (M+H)$^+$).

Step 4: (3S)-3-(5-(2,6-dimethylphenyl)pyridin-3-yl)-3-(3-methyl-2-(4-methyl-2-oxopyridin-1(2H)-yl)pentanamido)propanoic acid

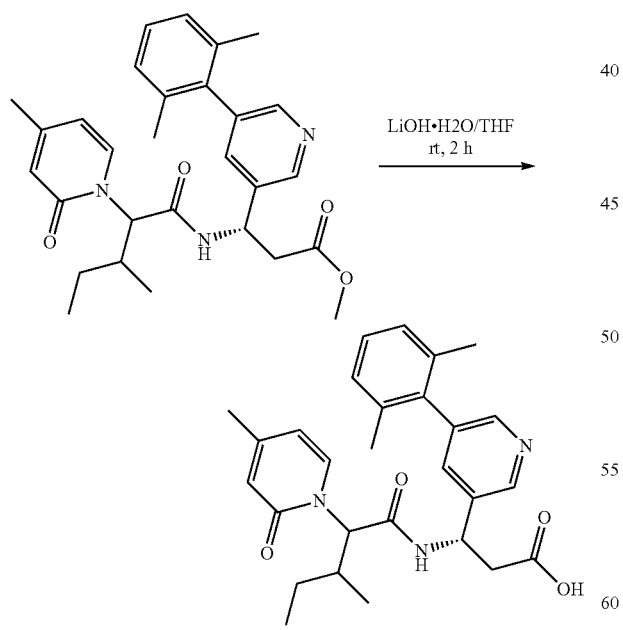

(3 S)-methyl 3-(5-(2,6-dimethylphenyl)pyridin-3-yl)-3-(3-methyl-2-(4-methyl-2-oxopyridin-1(2H)-yl)pentanamido)propanoate (150 mg, 0.31 mmol) was treated with LiOH—$H_2O$ (39 mg, 0.93 mmol) in THF (6 mL) and $H_2O$ (1 mL) at room temperature for 2 hours. The mixture was acidified with HCl (1 M) until pH=5. The solution was concentrated under reduced pressure give a residue, which was purified by Preparative-HPLC A (30~70% MeCN) to give the compounds AT1a (17 mg) and AT1b (17 mg) as white solids.

Compound AT1b LC/MS A: 100% purity, UV=214 nm, Rt=1.69 min, ESI 476 (M+H)$^+$.

$^1$H NMR (500 MHz, MeOD) δ 8.62 (s, 0.5H), 8.59 (s, 0.6H), 8.26 (s, 4H), 7.78 (d, J=7.2 Hz, 0.6H), 7.70 (s, 0.6H), 7.67 (s, 0.4H), 7.63 (d, J=7.2 Hz, 0.4H), 7.27-7.10 (m, 3H), 6.39 (s, 1H), 6.32 (d, J=7.1 Hz, 1H), 5.72-5.29 (m, 2H), 3.02-2.74 (m, 2H), 2.24 (s, 3H), 2.18-1.85 (m, 1H), 2.01 (s, H), 1.99 (s, 3H), 1.43-1.07 (m, 1H), 1.02-0.95 (m, 1H), 0.91-0.57 (m, 6H).

Preparation of Compound AT2b

Step 1: (2R,3R)-2-bromo-3-methylpentanoic acid

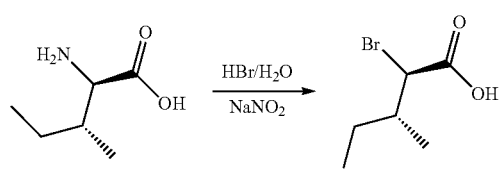

To a solution of (2R,3R)-2-amino-3-methylpentanoic acid (1.0 g, 7.6 mmol) in HBr (40% in water, 8 mL) at 0° C. was added a solution of $NaNO_2$ (0.78 g, 11.4 mmol) in $H_2O$ (4 mL) dropwise. The reaction mixture was stirred at room temperature for 16 hours. The solution was extracted with EtOAc (30 mL×2), and the combined organic layers were dried over $Na_2SO_4$ and filtered. The filtrate was concentrated under reduced pressure to give the crude product (2R,3R)-2-bromo-3-methylpentanoic acid as a red oil (1.41 g) used for next step directly without further purification. Yield 95%.

Step 2: (2S,3R)-3-methyl-2-(4-methyl-2-oxopyridin-1(2H)-yl)pentanoic acid

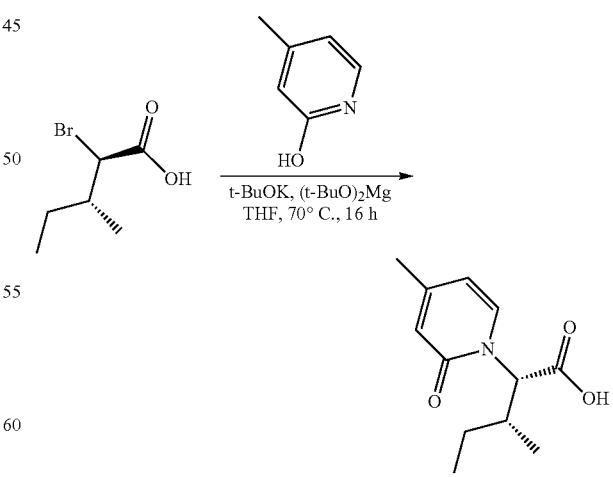

To a solution of (2R,3R)-2-bromo-3-methylpentanoic acid (1.37 g, 5.81 mmol) in dry THF (20 mL) was added (t-BuO)$_2$Mg (1.97 g, 11.62 mmol) and the solution was stirred at 30° C. for 3 hours under $N_2$ atmosphere. Then 4-methylpyridin-2-ol (546 mg, 5.0 mmol) and t-BuOK (664 mg, 5.93 mmol) was added, and the reaction mixture was stirred at 70° C. for 16 hours under N₂. The mixture was cooled to room temperature and acidified to pH=5 with a diluted HCl (4 M) solution. The solvent was concentrated under reduced pressure to give a residue, which was purified by reversed phase column chromatography (0%~80% MeOH in H₂O (5% NH₄HCO₃)) to provide the desired product (2S,3R)-3-methyl-2-(4-methyl-2-oxopyridin-1(2H)-yl)pentanoic acid as a yellow oil (68 mg). Yield 4% (94% purity, UV=214 nm, ESI 224 (M+H)⁺).

Step 3: (3S)-methyl 3-(5-(2,6-dimethylphenyl)pyridin-3-yl)-3-((3R)-3-methyl-2-(4-methyl-2-oxopyridin-1(2H)-yl)pentanamido)propanoate

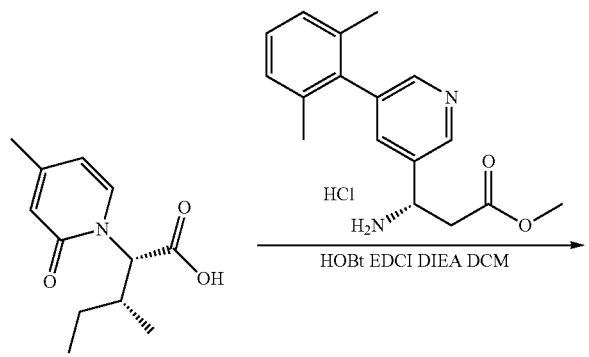

A mixture of (2S,3R)-3-methyl-2-(4-methyl-2-oxopyridin-1(2H)-yl)pentanoic acid (68 mg, 0.30 mmol), (S)-methyl 3-amino-3-(5-(2,6-dimethylphenyl)pyridin-3-yl)propanoate hydrochloride (102 mg, 0.36 mmol), HOBt (61 mg, 0.45 mmol), EDCI (86 mg, 0.45 mmol) and DIEA (116 mg, 0.9 mmol) in DCM (8 mL) was stirred at room temperature for 2 hours. The mixture was poured into water, and the solution was extracted with DCM (20 mL×2). The combined organic layers were dried over Na₂SO₄, and filtered. The filtrate was concentrated under reduced pressure to give the crude product (3S)-methyl 3-(5-(2,6-dimethylphenyl)pyridin-3-yl)-3-((3R)-3-methyl-2-(4-methyl-2-oxopyridin-1(2H)-yl)pentanamido)propanoate as a yellow oil (90 mg), which was used for next step directly without further purification. Yield 68% (68% purity, UV=214 nm, ESI 490 (M+H)⁺).

Step 4: (3S)-3-(5-(2,6-dimethylphenyl)pyridin-3-yl)-3-((3R)-3-methyl-2-(4-methyl-2-oxopyridin-1(2H)-yl)pentanamido)propanoic acid

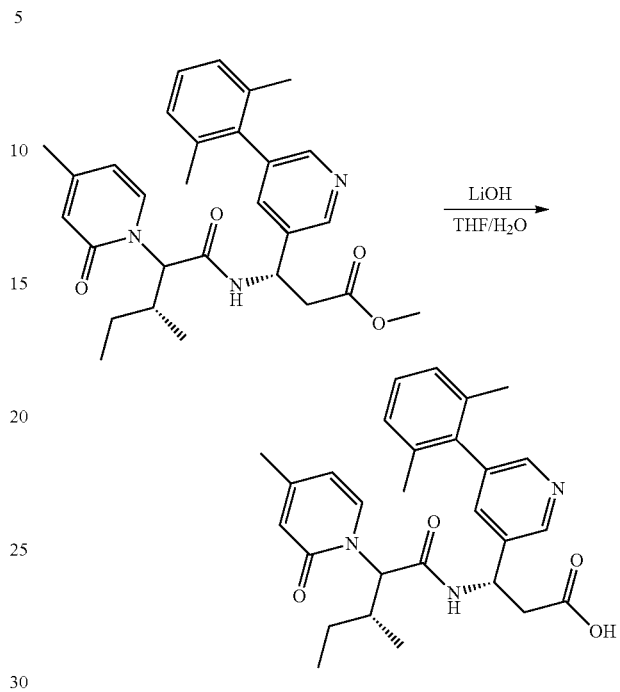

(3S)-methyl 3-(5-(2,6-dimethylphenyl)pyridin-3-yl)-3-((3R)-3-methyl-2-(4-methyl-2-oxopyridin-1(2H)-yl)pentanamido)propanoate (90 mg, 0.18 mmol) was treated with LiOH—H₂O (23 mg, 0.54 mmol) in THF (6 mL) and H₂O (1 mL) at room temperature for 1.5 hours. The mixture was acidified to pH=5 with HCl (1 M). The solvent was removed in vacuo and the residue was purified by Preparative-HPLC A (30~70% MeCN) to give the compounds AT2a (30.9 mg) and AT2b (25.6 mg) as white solids.

AT2b LC/MS A: 100% purity, UV=214 nm, Rt=1.72 min, ESI 476 (M+H)⁺.

¹H NMR (500 MHz, MeOD) δ 8.62 (d, J=1.8 Hz, 1H), 8.25 (d, J=1.7 Hz, 1H), 7.78 (d, J=7.2 Hz, 1H), 7.70 (t, J=1.9 Hz, 1H), 7.25-7.19 (m, 1H), 7.16 (d, J=7.6 Hz, 2H), 6.38 (s, 1H), 6.31 (dd, J=7.2, 1.8 Hz, 1H), 5.41-5.28 (m, 2H), 2.96-2.85 (m, 2H), 2.23 (s, 3H), 2.20-2.13 (m, 1H), 1.99 (s, 3H), 1.97 (s, 3H), 1.20-1.15 (m, 1H), 1.02-0.96 (m, 1H), 0.88-0.76 (m, 6H).

Preparation of Compounds AU1 and AU2

Step 1: 5-((dimethylamino)methyl)pyridin-2(1H)-one

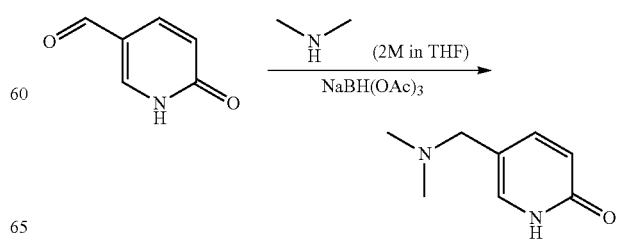

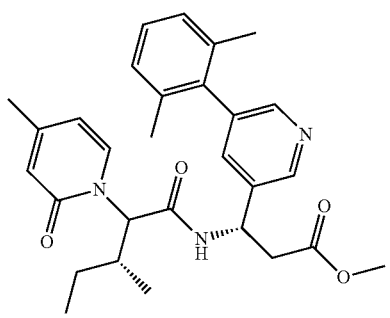

A mixture of 6-oxo-1,6-dihydropyridine-3-carbaldehyde (2 g, 16.2 mmol), dimethylamine (2 M in THF, 4 mL) in DCM (10 mL) was stirred at room temperature for 30 min. Then NaBH(OAc)$_3$ (5.2 g, 24.39 mmol) was added portionwise and stirred at room temperature overnight. The solvent was concentrated in vacuo and the residue was purified by combiflash (Eluent A: water 10 mM NH$_4$HCO$_3$, Eluent B: MeOH, gradient A→B 0~100%) to give the desired product 5-((dimethylamino)methyl)pyridin-2(1H)-one as a yellow oil (1 g). Yield 41% (ESI 153 (M+H)$^+$).

Step 2: ethyl 2-(5-((dimethylamino)methyl)-2-oxopyridin-1(2H)-yl)-4-methylpentanoate

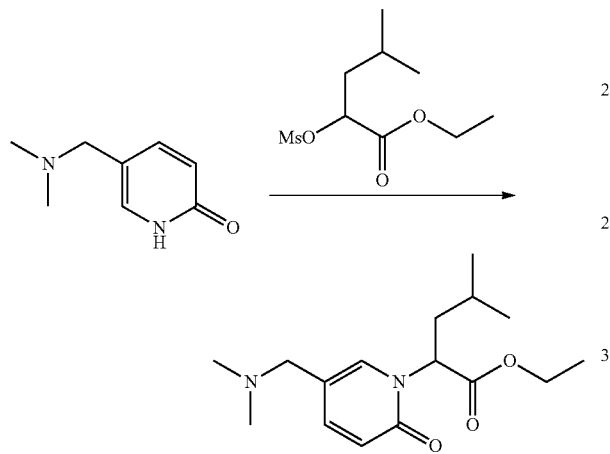

A mixture of 5-((dimethylamino)methyl)pyridin-2(1H)-one (500 mg, 3.28 mmol), K$_2$CO$_3$ (1.36 g, 9.86 mmol) and ethyl 4-methyl-2-(methylsulfonyloxy)pentanoate (1.17 g, 4.93 mmol) in CH$_3$CN (20 ml) was stirred at 70° C. overnight. The solvent was concentrated in vacuo and the residue was purified by silica gel column (pet ether:EtOAc 1:2) to give the desired product ethyl 2-(5-((dimethylamino)methyl)-2-oxopyridin-1(2H)-yl)-4-methylpentanoate as a yellow oil (300 mg). Yield 31% (ESI 295 (M+H)$^+$).

Step 3: 2-(5-((dimethylamino)methyl)-2-oxopyridin-1(2H)-yl)-4-methylpentanoic acid

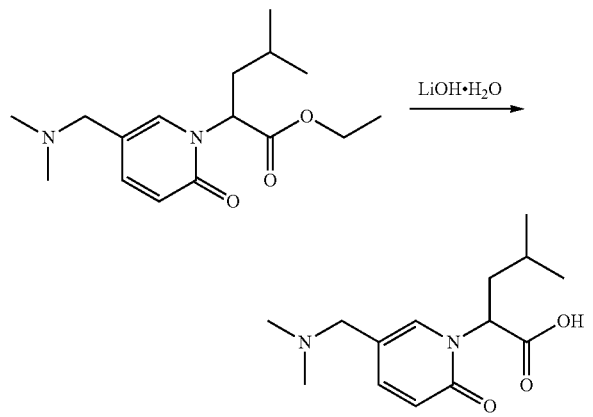

Ethyl 2-(5-((dimethylamino)methyl)-2-oxopyridin-1(2H)-yl)-4-methylpentanoate (300 mg, 1.02 mmol) was treated with LiOH—H$_2$O (120 mg, 3.02 mmol) in methanol (2 mL) and water (1 mL) at room temperature for 2 hours. The reaction was acidified with 1 N hydrochloric acid to pH=3. The solvent was removed in vacuo and the residue was purified by preparatory-HPLC A (30-80% MeCN) to give the desired product 2-(5-((dimethylamino)methyl)-2-oxopyridin-1(2H)-yl)-4-methylpentanoic acid as a white solid (100 mg). Yield 37% (ESI 267 (M+H)$^+$).

Step 4: (3S)-methyl 3-(2-(5-((dimethylamino)methyl)-2-oxopyridin-1(2H)-yl)-4-methylpentanamido)-3-(5-(2,6-dimethylphenyl)pyridin-3-yl)propanoate

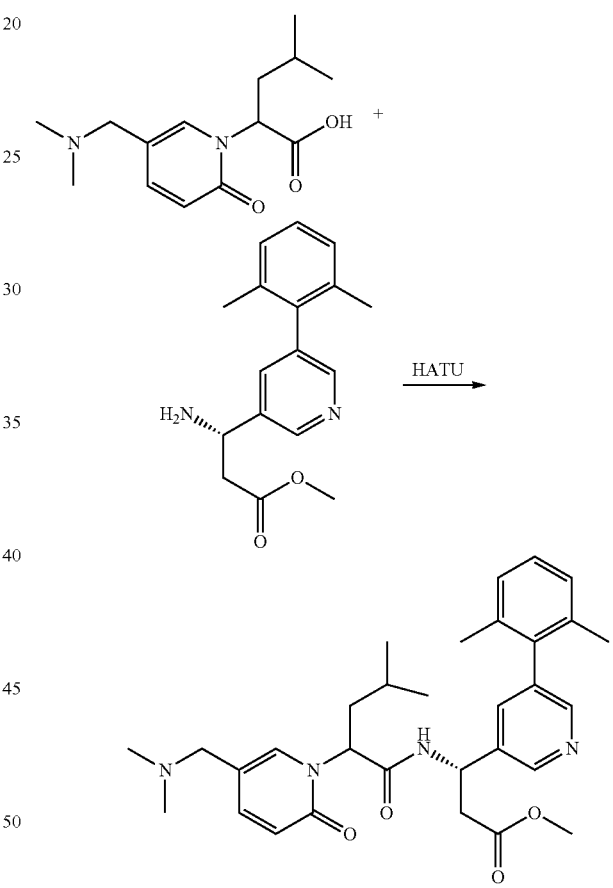

A mixture of (2-(5-((dimethylamino)methyl)-2-oxopyridin-1(2H)-yl)-4-methylpentanoic acid (100 mg, 0.375 mmol), (S)-methyl 3-amino-3-(5-(2,6-dimethylphenyl)pyridin-3-yl)propanoate (117 mg, 0.413 mmol), HATU (142.5 mg, 0.375 mmol) and DIEA (0.5 mL) in DMF (3 mL) was stirred at room temperature overnight. The solvent was removed in vacuo and the residue was purified by combiflash (Eluent A: water 10 mM NH$_4$HCO$_3$, Eluent B: MeOH, gradient A→B 0~100%) to give the desired product (3S)-methyl 3-(2-(5-((dimethylamino)methyl)-2-oxopyridin-1(2H)-yl)-4-methylpentanamido)-3-(5-(2,6-dimethylphenyl)pyridin-3-yl)propanoate as a yellow solid (80 mg). Yield 41% (ESI 533 (M+H)$^+$).

Step 5: (S)-3-((S)-2-(5-((dimethylamino)methyl)-2-oxopyridin-1(2H)-yl)-4-methylpentanamido)-3-(5-(2,6-dimethylphenyl)pyridin-3-yl)propanoic acid

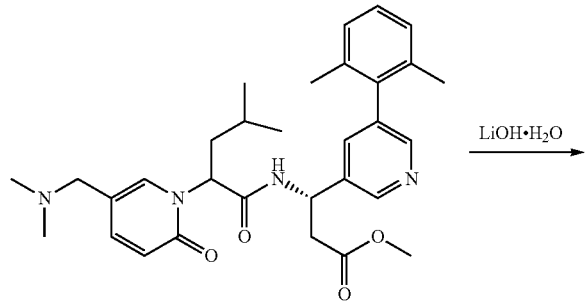

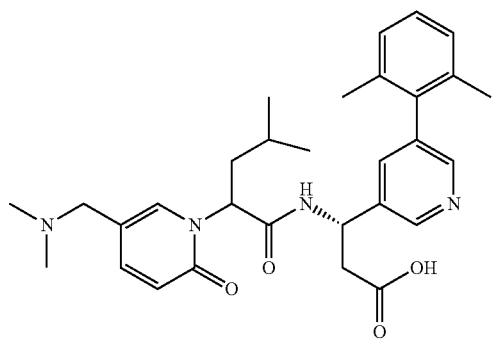

3-(2-(5-((dimethylamino)methyl)-2-oxopyridin-1 (2H)-yl)-4-methylpentanamido)-3-(5-(2,6-dimethylphenyl)pyridin-3-yl)propanoate (80 mg, 0.15 mmol) was treated with LiOH—H₂O (18 mg, 0.45 mmol) in methanol (2 mL) and water (1 mL) at room temperature for 3 hours. The reaction mixture was acidified to pH 4~5 with 1 N HCl. The solvent was removed in vacuo and the residue was purified by preparatory HPLC A (30-60% MeCN) to give the diastereomeric products AU1 (18.3 mg) and AU2 (22.3 mg) as white solids.

Compound AU1 ESI 519 (M+H)⁺

1H NMR (500 MHz, MeOD) δ 8.57 (t, J=13.2 Hz, 1H), 8.21 (t, J=8.7 Hz, 1H), 7.91 (d, J=2.3 Hz, 1H), 7.88-7.86 (m, 1H), 7.65 (t, J=1.9 Hz, 1H), 7.53 (dd, J=9.4, 2.5 Hz, 1H), 7.26-7.18 (m, 1H), 7.14 (d, J=8.4 Hz, 2H), 6.55 (d, J=9.3 Hz, 1H), 5.76 (t, J=8.0 Hz, 1H), 5.34 (dd, J=8.4, 5.9 Hz, 1H), 4.01 (d, J=13.2 Hz, 1H), 3.86 (d, J=13.3 Hz, 1H), 2.87 (dd, J=14.9, 8.6 Hz, 1H), 2.77 (dd, J=14.9, 5.8 Hz, 1H), 2.70 (s, 6H), 2.05-1.88 (m, 8H), 1.48-1.38 (m, 1H), 0.99-0.91 (m, 6H).

Compound AU2 ESI 519 (M+H)⁺

1H NMR (500 MHz, MeOD) δ 8.58 (d, J=2.1 Hz, 1H), 8.24 (dd, J=14.9, 1.9 Hz, 1H), 7.80 (d, J=2.4 Hz, 1H), 7.64 (t, J=1.9 Hz, 1H), 7.57 (dd, J=9.3, 2.5 Hz, 1H), 7.22 (dd, J=8.4, 6.6 Hz, 1H), 7.16 (d, J=7.6 Hz, 2H), 6.60 (d, J=9.3 Hz, 1H), 5.57 (ddd, J=18.8, 9.4, 5.5 Hz, 2H), 4.23 (d, J=13.3 Hz, 1H), 3.84 (d, J=13.3 Hz, 1H), 2.81 (s, 6H), 2.73 (dd, J=15.3, 4.4 Hz, 1H), 2.60 (dd, J=15.3, 11.0 Hz, 1H), 2.07-2.00 (m, 7H), 1.58 (dt, J=13.5, 6.8 Hz, 1H), 1.48 (td, J=13.3, 6.6 Hz, 1H), 0.93-0.84 (m, 6H).

Preparation of Compounds AV1 and AV2

Step 1: 2-oxo-2,3-dihydropyridine-4-carbaldehyde

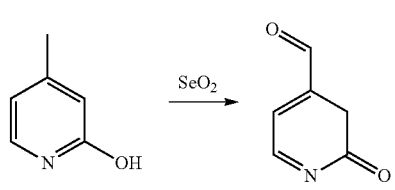

A mixture of 4-methylpyridin-2-ol (3 g, 27.5 mmol) and SeO₂ (4 g, 35.8 mmol) in dioxane (40 ml) was refluxed under N₂ atmosphere overnight and filtered. The filtrate was removed in vacuo and the residue was purified by silica gel column (DCM:MeOH=1:10) to give the desired product as a yellow oil (300 mg). Yield 9% (ESI 124 (M+H)⁺)

Step 2: 4-((dimethylamino)methyl)pyridin-2(1H)-one

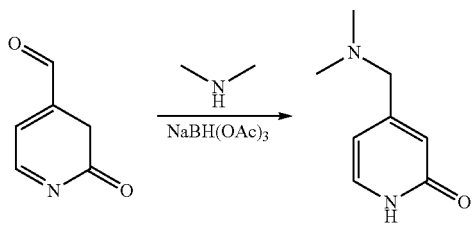

A mixture of 2-oxo-2,3-dihydropyridine-4-carbaldehyde (300 mg, 2.4 mmol), dimethylamine (2 M in THF, 6 mL) in DCM (5 ml) was stirred at room temperature for 30 minutes. Then NaBH(OAc)₃ (775.6 mg, 3.65 mmol) was added portion-wise and stirred at room temperature overnight. The solvent was concentrated in vacuo and the residue was purified by combiflash (Eluent A: water 10 mM NH₄HCO₃, Eluent B: MeOH, gradient A→B 0~100%) to give the desired product 4-((dimethylamino)methyl)pyridin-2(1H)-one as a yellow oil (150 mg). Yield 41% (ESI 153 (M+H)⁺).

Step 3: ethyl 2-(4-((dimethylamino)methyl)-2-oxopyridin-1(2H)-yl)-4-methylpentanoate

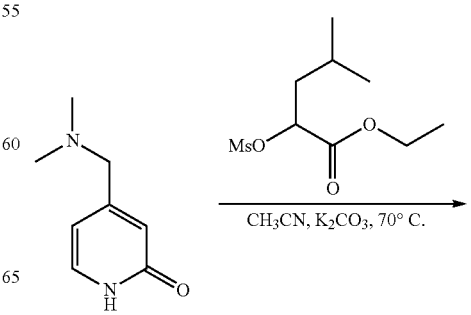

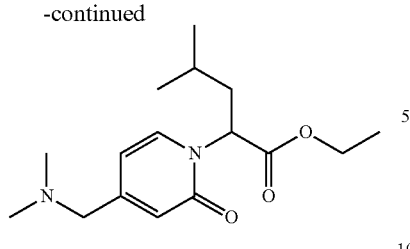

A mixture of 4-((dimethylamino)methyl)pyridin-2(1H)-one (150 mg, 0.98 mmol), K$_2$CO$_3$ (408.5 mg, 2.96 mmol) and ethyl 4-methyl-2-(methylsulfonyloxy)pentanoate (350 mg, 1.47 mmol) in CH$_3$CN (5 mL) was stirred at 70° C. overnight. The solvent was concentrated in vacuo and the residue was purified by silica gel column (pet ether:EtOAc 1:2) to give the desired product ethyl 2-(4-((dimethylamino)methyl)-2-oxopyridin-1(2H)-yl)-4-methylpentanoate as a yellow oil (100 mg). Yield 35% (ESI 295 (M+H)$^+$).

Step 4: 2-(4-((dimethylamino)methyl)-2-oxopyridin-1(2H)-yl)-4-methylpentanoic acid

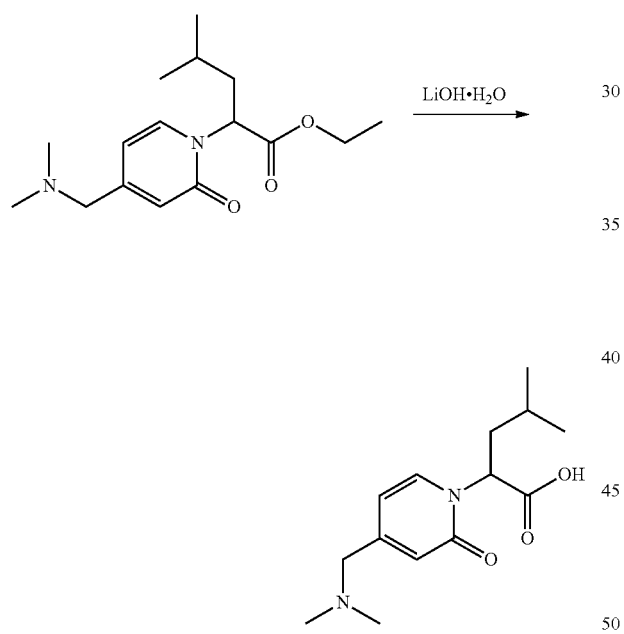

Ethyl 2-(4-((dimethylamino)methyl)-2-oxopyridin-1(2H)-yl)-4-methylpentanoate (100 mg, 0.33 mmol) was treated with LiOH—H$_2$O (40 mg, 1.01 mmol) in methanol (2 mL) and water (1 mL) at room temperature for 2 hours. The solvent was removed in vacuo and the residue was purified by preparatory-HPLC A (30-80% MeCN) to give the desired products 2-(4-((dimethylamino)methyl)-2-oxopyridin-1(2H)-yl)-4-methylpentanoic acid as a white solid (80 mg). Yield 90% (ESI 267 (M+H)$^+$).

Step 5: (S)-methyl 3-((S)-2-(4-((dimethylamino)methyl)-2-oxopyridin-1(2H)-yl)-4-methylpentanamido)-3-(5-(2,6-dimethylphenyl)pyridin-3-yl)propanoate

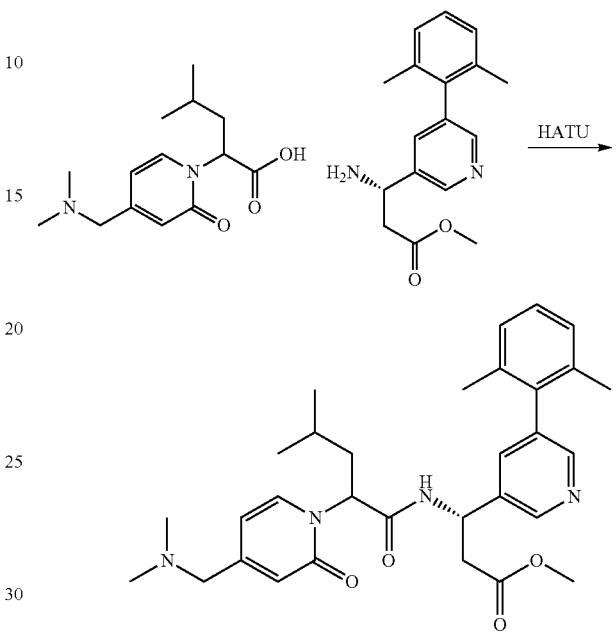

A mixture of (2-(4-((dimethylamino)methyl)-2-oxopyridin-1(2H)-yl)-4-methylpentanoic acid (80 mg, 0.30 mmol), (S)-methyl 3-amino-3-(5-(2,6-dimethylphenyl)pyridin-3-yl)propanoate (85 mg, 0.3 mmol), HATU (125.4 mg, 0.33 mmol) and DIEA (0.3 mL) in DMF (3 mL) was stirred at room temperature overnight. The solvent was removed in vacuo and the residue was purified by combiflash (Eluent A: water 10 mM NH$_4$HCO$_3$, Eluent B: MeOH, gradient A→B 0~100%) to give the desired product (S)-methyl 3-((S)-2-(4-((dimethylamino)methyl)-2-oxopyridin-1(2H)-yl)-4-methylpentanamido)-3-(5-(2,6-dimethylphenyl)pyridin-3-yl)propanoate as a yellow solid (80 mg). Yield 50% (ESI 533 (M+H)$^+$).

Step 6: (S)-3-((S)-2-(4-((dimethylamino)methyl)-2-oxopyridin-1(2H)-yl)-4-methylpentanamido)-3-(5-(2,6-dimethylphenyl)pyridin-3-yl)propanoic acid

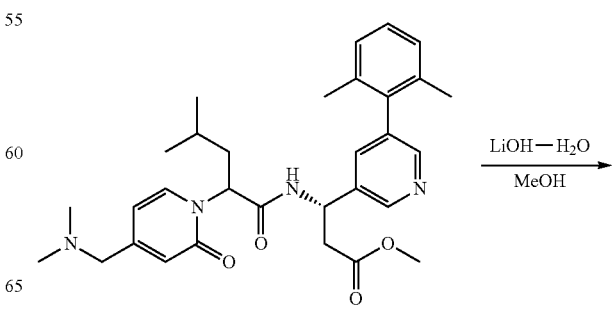

-continued

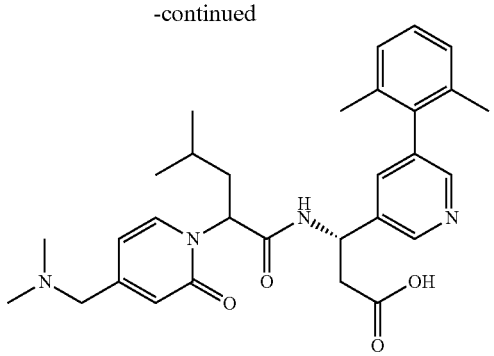

(S)-methyl 3-((S)-2-(4-((dimethylamino)methyl)-2-oxopyridin-1(2H)-yl)-4-methylpentanamido)-3-(5-(2,6-dimethylphenyl)pyridin-3-yl)propanoate (80 mg, 0.15 mmol) was treated with LiOH—H$_2$O (18 mg, 0.45 mmol) in methanol (2 mL) and water (1 mL) at room temperature for 3 hours. The reaction mixture was acidified to pH 4~5 with 1 N HCl. The solvent was removed in vacuo and the residue was purified by preparatory HPLC A (30-60% MeCN) to give the diastereomeric products AV1 (14 mg) and AV2 (17 mg) as white solids.

Compound AV1 ESI 519 (M+H)$^+$
1H NMR (500 MHz, MeOD) δ 8.68 (s, 1H), 8.41 (s, 1H), 7.96 (s, 1H), 7.88 (d, J=7.2 Hz, 1H), 7.26 (t, J=7.6 Hz, 1H), 7.18 (dd, J=7.2, 3.8 Hz, 2H), 6.60 (s, 1H), 6.53-6.38 (m, 1H), 5.70 (dd, J=10.1, 6.0 Hz, 1H), 5.46 (t, J=7.2 Hz, 1H), 4.24-4.12 (m, 2H), 3.02 (t, J=15.9 Hz, 2H), 2.92 (s, 6H), 2.10-1.81 (m, 8H), 1.56-1.43 (m, 1H), 0.99 (dd, J=14.8, 6.6 Hz, 6H).

Compound AV2 ESI 519 (M+H)$^+$
1H NMR (500 MHz, MeOD) δ 8.72 (s, 1H), 8.46 (s, 1H), 7.97 (s, 1H), 7.88 (d, J=7.2 Hz, 1H), 7.31-7.24 (m, 1H), 7.20 (d, J=7.6 Hz, 2H), 6.68 (d, J=1.6 Hz, 1H), 6.49 (dd, J=7.2, 2.0 Hz, 1H), 5.73 (dd, J=10.1, 6.1 Hz, 1H), 5.39 (t, J=7.3 Hz, 1H), 4.26-4.10 (m, 2H), 3.10-2.88 (m, 8H), 2.04 (s, 6H), 1.97-1.80 (m, 2H), 1.39-1.30 (m, 1H), 0.97-0.80 (m, 6H).

Preparation of Compounds AW1 and AW2

Step 1: 5-(2-methoxyvinyl)pyridin-2(1H)-one

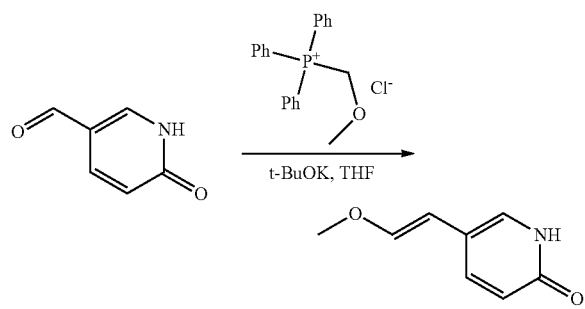

A mixture of (methoxymethyl)triphenylphosphonium chloride (12.5 g, 36.6 mmol), t-BuOK (6.83 g, 61 mmol) in dioxane (60 mL) was stirred at room temperature for 15 minutes. Then 6-oxo-1,6-dihydropyridine-3-carbaldehyde (3 g, 24.4 mmol) in 20 mL THF was added. The mixture was stirred for 16 h at room temperature. To the reaction mixture was added 80 mL water. The mixture was extracted with EtOAc (80 mL×2) and the aqueous phase concentrated in vacuo. The residue was purified by combiflash (Eluent A: water 10 mM NH$_4$HCO$_3$, Eluent B: MeOH, gradient A→B 0~100%) to give the desired product 5-(2-methoxyvinyl)pyridin-2(1H)-one as a red oil (1.3 g). Yield 35% (ESI 152.2 (M+H)$^+$).

Step 2: 2-(6-oxo-1,6-dihydropyridin-3-yl)acetaldehyde

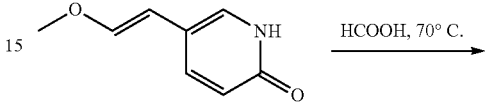

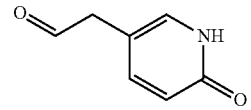

5-(2-methoxyvinyl)pyridin-2(1H)-one (1.2 g, 7.95 mmol) was treated with HCOOH (20 mL) at 70° C. for 2 hours. The solvent was removed in vacuo to provide the crude product 2-(6-oxo-1,6-dihydropyridin-3-yl)acetaldehyde as a red oil (0.8 g, crude). (ESI 138.3 (M+H)$^+$).

Step 3: 5-(2-(dimethylamino)ethyl)pyridin-2(1H)-one

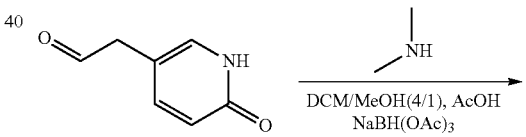

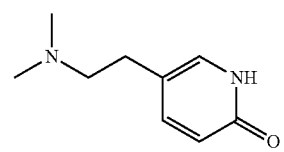

A mixture of methyl 2-(6-oxo-1,6-dihydropyridin-3-yl)acetaldehyde (750 mg, 5.47 mmol), AcOH (394 mg, 6.56 mmol) and dimethylamine (40% in water) (1.23 g, 10.94 mmol) in DCM (10 mL) and MeOH (2.5 mL) was stirred at room temperature for 30 minutes and NaBH(OAc)$_3$ (2.32 g, 10.94 mmol) was added. The mixture was stirred at room temperature overnight. The solvent was removed in vacuo and the residue was purified by silica gel column (DCM: MeOH 2:1) to provide the desired product 5-(2-(dimethylamino)ethyl)pyridin-2(1H)-one as yellow oil (500 mg). Yield 55% (ESI 167.2 (M+H)$^+$).

Step 4: ethyl 2-(5-(2-(dimethylamino)ethyl)-2-oxopyridin-1(2H)-yl)-4-methylpentanoate

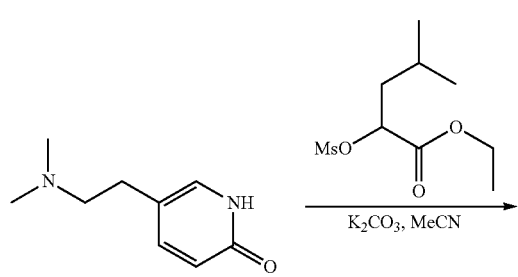

A mixture of methyl 5-(2-(dimethylamino)ethyl)pyridin-2(1H)-one (500 mg, 3 mmol), ethyl 4-methyl-2-(methylsulfonyloxy)pentanoate (1.07 g, 4.5 mmol) and K$_2$CO$_3$ (828 mg, 6 mmol) in MeCN (15 mL) was stirred 70° C. overnight. The solvent was removed in vacuo and the residue was purified by silica gel column (DCM:MeOH 1:2) to provide the desired product methyl ethyl 2-(5-(2-(dimethylamino)ethyl)-2-oxopyridin-1(2H)-yl)-4-methylpentanoate as a white solid (100 mg). Yield 11% (ESI 309.2 (M+H)$^+$).

Step 5: 2-(5-(2-(dimethylamino)ethyl)-2-oxopyridin-1(2H)-yl)-4-methylpentanoic acid

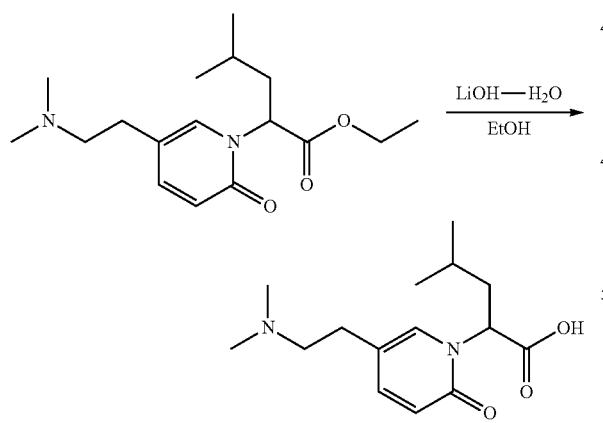

Ethyl 2-(5-(2-(dimethylamino)ethyl)-2-oxopyridin-1(2H)-yl)-4-methylpentanoate (100 mg, 0.32 mmol) was treated with LiOH—H$_2$O (54 mg, 1.28 mmol) in EtOH (3 mL) and H$_2$O (1 mL) at room temperature for 2 hours. The reaction mixture was acidified to pH 4~5 with 1 N HCl. The solvent was removed in vacuo and the residue was purified by combiflash (Eluent A: water 10 mM NH$_4$HCO$_3$, Eluent B: MeOH, gradient A→B 0~100%) to give the product 2-(5-(2-(dimethylamino)ethyl)-2-oxopyridin-1(2H)-yl)-4-methylpentanoic acid as white solids (70 mg). Yield 78% (ESI 281.2 (M+H)$^+$).

Step 6: (S)-methyl 3-((S)-2-(5-(2-(dimethylamino)ethyl)-2-oxopyridin-1(2H)-yl)-4-methylpentanamido)-3-(5-(2,6-dimethylphenyl)pyridin-3-yl)propanoate

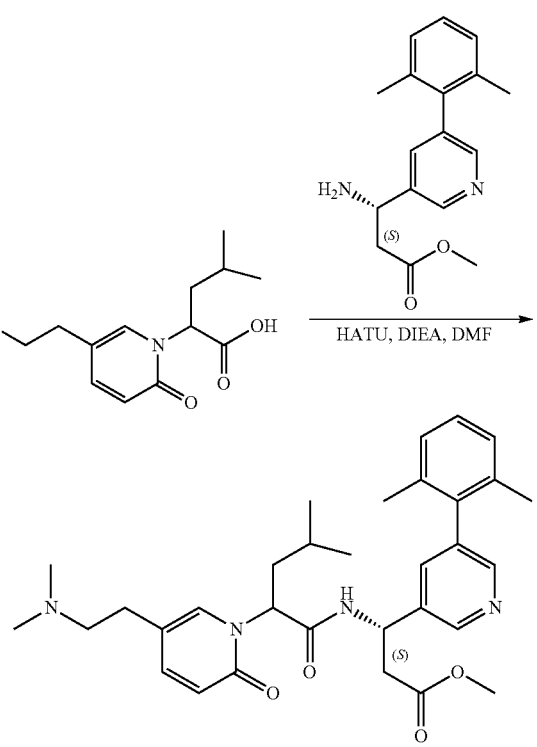

A mixture of 2-(5-(2-(dimethylamino)ethyl)-2-oxopyridin-1(2H)-yl)-4-methylpentanoic acid (70 mg, 0.25 mmol), (S)-methyl 3-amino-3-(5-(2,6-dimethylphenyl)pyridin-3-yl)propanoate (107 mg, 0.375 mmol), HATU (143 mg, 0.375 mmol) and DIEA (129 mg, 1 mmol) in DMF (3 mL) was stirred at room temperature overnight. The solvent was removed in vacuo and the residue was purified by combiflash (Eluent A: water 10 mM NH$_4$HCO$_3$, Eluent B: MeOH, gradient A→B 0~100%) to give the desired product (S)-methyl 3-((S)-2-(5-(2-(dimethylamino)ethyl)-2-oxopyridin-1(2H)-yl)-4-methylpentanamido)-3-(5-(2,6-dimethylphenyl)pyridin-3-yl)propanoate as a oily solid (50 mg). Yield 37% (ESI 548.3 (M+H)$^+$).

Step 7: (S)-3-((S)-2-(5-(2-(dimethylamino)ethyl)-2-oxopyridin-1(2H)-yl)-4-methylpentanamido)-3-(5-(2,6-dimethylphenyl)pyridin-3-yl)propanoic acid

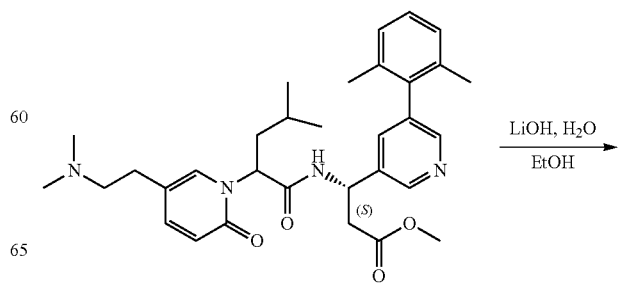

267
-continued

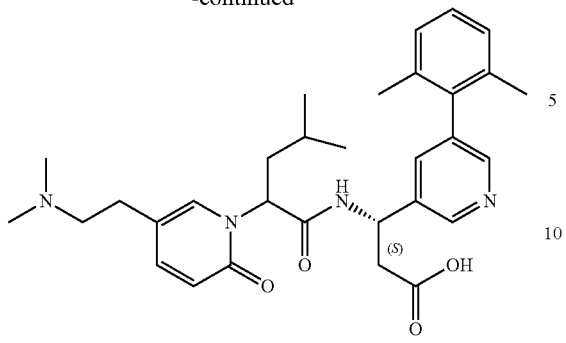

(S)-methyl 3-((S)-2-(5-(2-(dimethylamino)ethyl)-2-oxopyridin-1(2H)-yl)-4-methylpentanamido)-3-(5-(2,6-dimethylphenyl)pyridin-3-yl)propanoate (50 mg, 0.09 mmol) was treated with LiOH—H$_2$O (15 mg, 0.36 mmol) in EtOH (2 mL) and H$_2$O (0.5 mL) at room temperature for 2 hours. The reaction mixture was acidified to pH 4~5 with 1 N HCl. The solvent was removed in vacuo and the residue was purified by preparatory HPLC A (30-60% MeCN) to give the products AW1 (7.4 mg) and AW2 (20 mg) as white solids.

Compound AW1 ESI 533.3 (M+H)$^+$.

$^1$H NMR (500 MHz, MeOD) δ 8.50 (d, J=1.7 Hz, 1H), 8.21 (d, J=1.6 Hz, 1H), 7.76 (d, J=2.1 Hz, 1H), 7.62-7.52 (m, 2H), 7.21 (dd, J=8.2, 6.8 Hz, 1H), 7.15 (d, J=7.6 Hz, 2H), 6.59 (d, J=9.3 Hz, 1H), 5.64 (dd, J=10.7, 5.2 Hz, 1H), 5.25 (t, J=5.8 Hz, 1H), 3.43-3.36 (m, 1H), 3.31-3.25 (m, 1H), 2.99-2.85 (m, 2H), 2.86-2.77 (m, 6H), 2.70 (ddd, J=35.4, 15.0, 5.8 Hz, 2H), 2.14-2.05 (m, 1H), 2.05-1.86 (m, 7H), 1.51-1.40 (m, 1H), 0.96 (dd, J=19.2, 6.6 Hz, 6H).

Compound AW2 ESI 533.3 (M+H)$^+$. $^1$H NMR (500 MHz, MeOD) δ 8.54 (d, J=2.1 Hz, 1H), 8.23 (d, J=1.9 Hz, 1H), 7.67 (d, J=2.1 Hz, 1H), 7.61 (t, J=2.0 Hz, 1H), 7.55 (dd, J=9.3, 2.5 Hz, 1H), 7.26-7.18 (m, 1H), 7.16 (d, J=7.6 Hz, 2H), 6.60 (d, J=9.3 Hz, 1H), 5.64 (dd, J=9.4, 6.3 Hz, 1H), 5.37 (dd, J=8.8, 4.7 Hz, 1H), 3.44-3.36 (m, 1H), 3.31-3.26 (m, 1H), 2.94 (ddd, J=14.5, 9.5, 5.1 Hz, 1H), 2.89-2.77 (m, 7H), 2.70-2.62 (m, 1H), 2.54 (dd, J=15.0, 8.9 Hz, 1H), 2.09-1.94 (m, 7H), 1.94-1.85 (m, 1H), 1.49-1.32 (m, 1H), 0.93 (dd, J=11.1, 6.6 Hz, 6H).

Preparation of Compounds BA1 and BA2 ((3S)-3-(2-(4-(2-(dimethylamino)ethyl)-2-oxopyridin-1(2H)-yl)-4-methylpentanamido)-3-(5-(2,6-dimethylphenyl)pyridin-3-yl)propanoic acid))

Step 1: ethyl 2-(4-bromo-2-oxopyridin-1(2H)-yl)-4-methylpentanoate

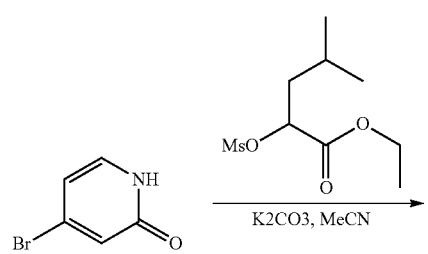

268
-continued

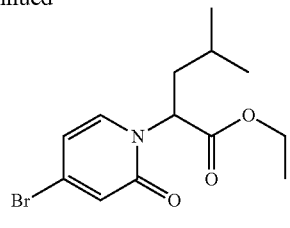

A mixture of 4-bromopyridin-2(1H)-one (1.2 g, 6.94 mmol), K$_2$CO$_3$ (1.92 g, 13.88 mmol) and ethyl 4-methyl-2-(methylsulfonyloxy)pentanoate (1.98 g, 8.33 mmol) in CH$_3$CN (20 ml) was stirred at 80° C. overnight. The solvent was concentrated in vacuo and the residue was purified by silica gel column (pet ether:EtOAc 1:1) to give ethyl 2-(4-bromo-2-oxopyridin-1(2H)-yl)-4-methylpentanoate as a yellow oil (1.6 g). Yield 73% (ESI 316.1 (M+H)$^+$).

Step 2: ethyl 2-(4-(2-(benzyloxycarbonylamino)ethyl)-2-oxopyridin-1(2H)-yl)-4-methylpentanoate

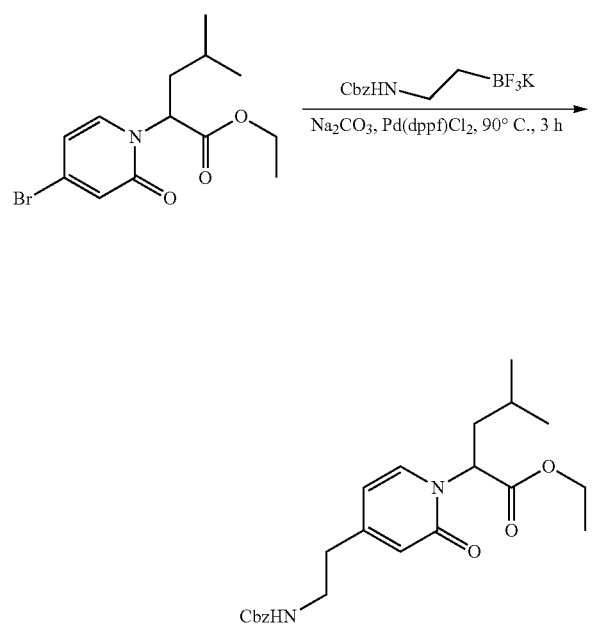

A mixture of ethyl 2-(4-bromo-2-oxopyridin-1(2H)-yl)-4-methylpentanoate (1.6 g, 5.0 mmol), Potassium benzyl N-[2-(trifluoroboraly)ethyl]carbamate (1.71 g, 6 mmol), Pd(dppf)Cl$_2$ (366 mg, 0.5 mmol) and Na$_2$CO$_3$ (1.06 g, 10 mmol) in 1,4-dioxane (20 mL) and H$_2$O (10 mL) was stirred at 90° C. under N$_2$ atmosphere for 4 hours. After completion, the reaction was concentrated and purified by reverse phase HPLC on a C18/40 g column (A: water/0.01% TFA, B: MeOH, 0~100%) to give ethyl 24442-(benzyloxycarbonylamino)ethyl)-2-oxopyridin-1(2H)-yl)-4-methylpentanoate as a yellow oil (700 mg). Yield 35% (ESI 415.1 (M+H)$^+$).

Step 3: ethyl 2-(4-(2-aminoethyl)-2-oxopyridin-1(2H)-yl)-4-methylpentanoate

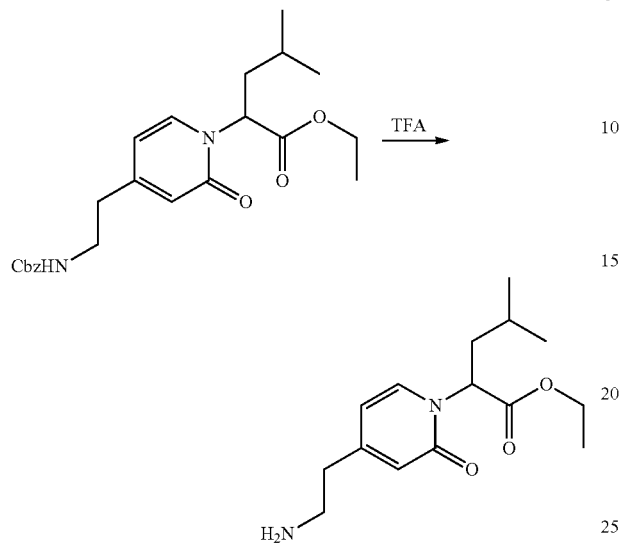

Ethyl 2-(4-(2-(benzyloxycarbonylamino)ethyl)-2-oxopyridin-1(2H)-yl)-4-methylpentanoate (0.7 g, 1.7 mmol) was treated with TFA (10 mL) at 50° C. for 4 hours. The solvent was removed in vacuo and the residue was purified by reverse phase HPLC on a C18/40 g column (A: water 10 mM NH$_4$HCO$_3$, B: MeOH, 0~100%) to provide ethyl 2-(4-(2-aminoethyl)-2-oxopyridin-1(2H)-yl)-4-methylpentanoate as a red oil (0.4 g). Yield 84%. (ESI 281.2 (M+H)$^+$).

Step 4: ethyl 2-(4-(2-(dimethylamino)ethyl)-2-oxopyridin-1(2H)-yl)-4-methylpentanoate

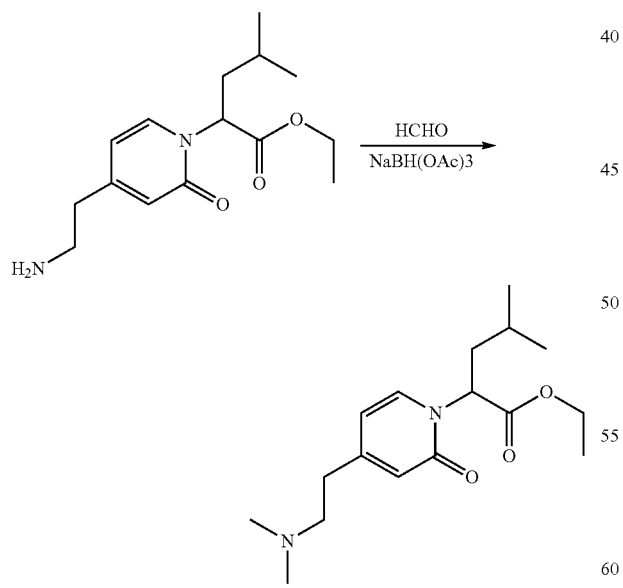

To a mixture of ethyl 2-(4-(2-aminoethyl)-2-oxopyridin-1(2H)-yl)-4-methylpentanoate (400 mg, 1.43 mmol) in MeOH (10 mL) was added HCHO (37% in H$_2$O, 1 mL) and stirred at room temperature for 5 mins. NaBH(OAc)$_3$ (1.21 g, 5.72 mmol) was added and stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl 2-(4-(2-(dimethylamino)ethyl)-2-oxopyridin-1(2H)-yl)-4-methylpentanoate as yellow oil (400 mg). Yield 91% (ESI 309.2 (M+H)$^+$).

Step 5: 2-(4-(2-(dimethylamino)ethyl)-2-oxopyridin-1(2H)-yl)-4-methylpentanoic acid

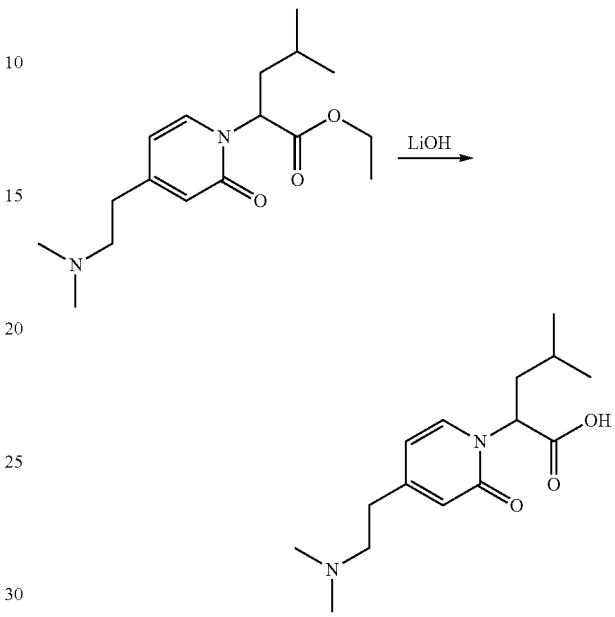

Ethyl 2-(4-(2-(dimethylamino)ethyl)-2-oxopyridin-1(2H)-yl)-4-methylpentanoate (400 mg, 1.3 mmol) was treated with LiOH—H$_2$O (218 mg, 5.2 mmol) in MeOH (4 mL) and H$_2$O (1 mL) at room temperature for 1 hour. The mixture was acidified to pH 4~5 with 1N HCl. The mixture was concentrated in vacuo and the residue was purified by reverse phase HPLC on a C18/40 g column (A: water/0.01% TFA, B: MeOH, 0~100%) to give 2-(4-(2-(dimethylamino)ethyl)-2-oxopyridin-1(2H)-yl)-4-methylpentanoic acid as white solid (310 mg). Yield 85% (ESI 281.2 (M+H)$^+$).

Step 6: (3S)-methyl 3-(2-(4-(2-(dimethylamino)ethyl)-2-oxopyridin-1(2H)-yl)-4-methylpentanamido)-3-(5-(2,6-dimethylphenyl)pyridin-3-yl)propanoate

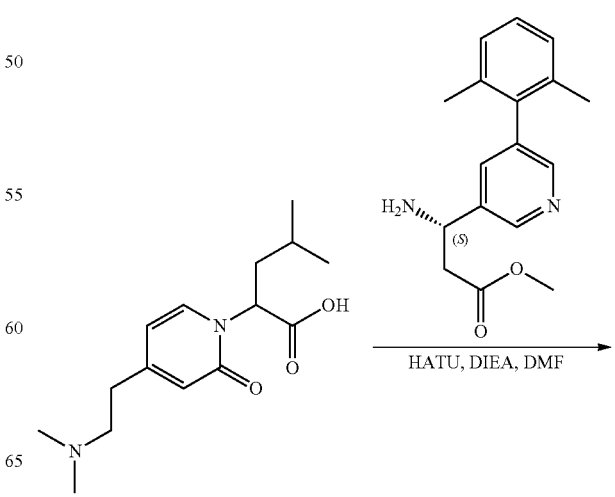

-continued

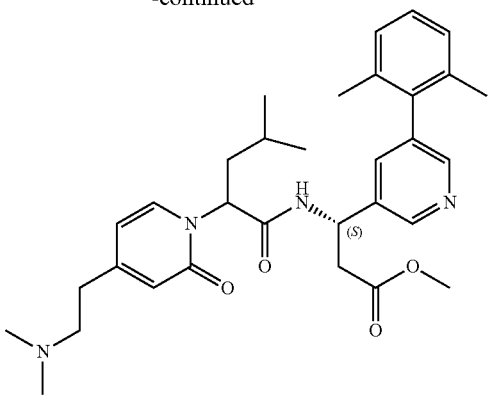

A mixture of 2-(4-(2-(dimethylamino)ethyl)-2-oxopyridin-1(2H)-yl)-4-methylpentanoic acid (230 mg, 0.82 mmol), (S)-methyl 3-amino-3-(5-(2,6-dimethylphenyl)pyridin-3-yl)propanoate (284 mg, 1 mmol), HATU (467 mg, 1.23 mmol) and DIEA (423 mg, 3.28 mmol) in DMF (5 mL) was stirred at room temperature for 1 hour. The mixture was purified by reverse phase HPLC on a C18/40 g column (A: water 10 mM $NH_4HCO_3$, B: MeOH, 0~100%) to give product (3S)-methyl 3-(2-(4-(2-(dimethylamino)ethyl)-2-oxopyridin-1(2H)-yl)-4-methylpentanamido)-3-(5-(2,6-dimethylphenyl)pyridin-3-yl)propanoate as a yellow oil (200 mg). Yield 45% (ESI 547.2 $(M+H)^+$).

Step 7: (3S)-3-(2-(4-(2-(dimethylamino)ethyl)-2-oxopyridin-1(2H)-yl)-4-methylpentanamido)-3-(5-(2,6-dimethylphenyl)pyridin-3-yl)propanoic acid

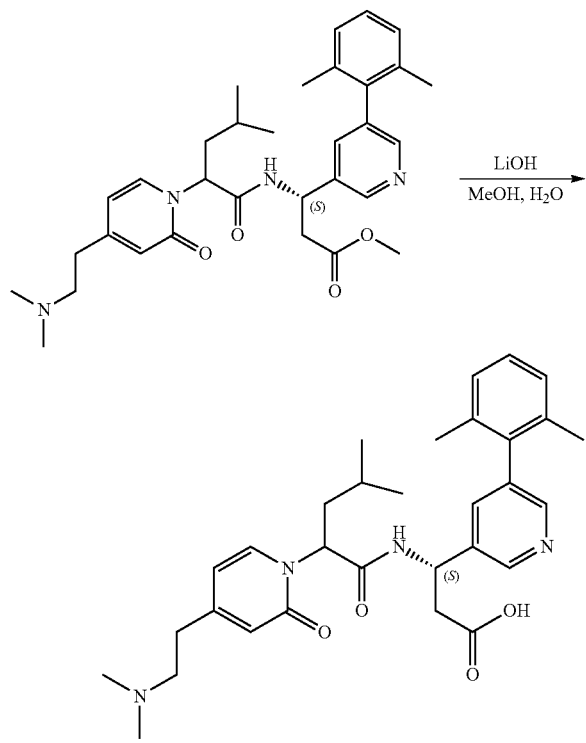

(3S)-methyl 3-(2-(4-(2-(dimethylamino)ethyl)-2-oxopyridin-1(2H)-yl)-4-methylpentanamido)-3-(5-(2,6-dimethylphenyl)pyridin-3-yl)propanoate (200 mg, 0.37 mmol) was treated with LiOH monohydrate (62 mg, 1.48 mmol) in MeOH (4 mL) and $H_2O$ (1 mL) at room temperature for 2 hours. The reaction mixture was acidified to pH 4~5 with 1N HCl. The mixture was removed in vacuo and the residue was purified by prep-HPLC A to give the diastereomeric products BA1 (48.9 mg) and BA2 (53.6 mg) as white solids.

Compound BA1 ESI 533.3 $(M+H)^+$.

1H NMR (500 MHz, MeOD) δ 8.48 (d, J=2.1 Hz, 1H), 8.20 (d, J=1.9 Hz, 1H), 7.70 (d, J=7.2 Hz, 1H), 7.58 (t, J=2.0 Hz, 1H), 7.25-7.19 (m, 1H), 7.17-7.11 (m, 2H), 6.59 (s, 1H), 6.50-6.45 (m, 1H), 5.71-5.60 (m, 1H), 5.19 (t, J=5.2 Hz, 1H), 3.38-3.27 (m, 1H), 3.32-3.28 (m, 1H), 3.03-2.87 (m, 2H), 2.78 (s, 6H), 2.64-2.58 (m, 2H), 2.07-2.00 (m, 2H), 2.00 (d, J=7.0 Hz, 6H), 1.48-1.42 (m, 1H), 0.97-0.87 (m, 6H).

Compound BA2 ESI 533.3 $(M+H)^+$.

1H NMR (500 MHz, MeOD) δ 8.51 (d, J=1.9 Hz, 1H), 8.20 (d, J=1.8 Hz, 1H), 7.71 (d, J=7.2 Hz, 1H), 7.59 (s, 1H), 7.24-7.18 (m, 1H), 7.15 (d, J=8.6 Hz, 2H), 6.59 (s, 1H), 6.52 (d, J=7.1 Hz, 1H), 5.65-5.59 (m, 1H), 5.19 (s, 1H), 3.44 (d, J=7.4 Hz, 1H), 3.34 (s, 1H), 2.96 (s, 2H), 2.80 (s, 6H), 2.67-2.62 (m, 2H), 2.03-1.97 (m, 8H), 1.53-1.39 (m, 1H), 0.95-0.91 (m, 6H).

Preparation of Compounds BB1 and BB2 ((3S)-3-(2-(5-((3,3-difluoroazetidin-1-yl)methyl)-2-oxopyridin-1(2H)-yl)-4-methylpentanamido)-3-(5-(2,6-dimethylphenyl)pyridin-3-yl)propanoic acid)

Step 1: 5-((3,3-difluoroazetidin-1-yl)methyl)pyridin-2(1H)-one

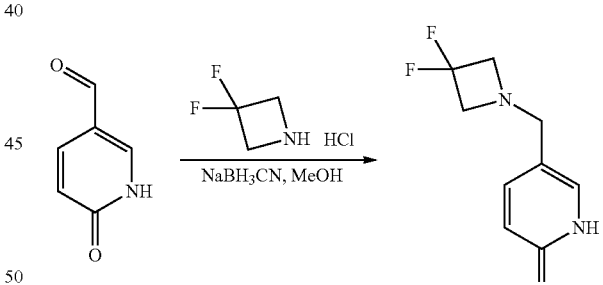

A mixture of 6-oxo-1,6-dihydropyridine-3-carbaldehyde (153 mg, 1.24 mmol) and 3,3-difluoroazetidine hydrochloride (193 mg, 1.49 mmol) in MeOH (3 mL) was stirred at room temperature for 30 mins. $NaBH_3CN$ (231 mg, 3.73 mmol) was added and stirred at room temperature for 1 hour. The solvent was removed in vacuo to provide the crude 5-((3,3-difluoroazetidin-1-yl)methyl)pyridin-2(1H)-one as white solid (248 mg) used without further purification. (ESI 201.1 $(M+H)^+$).

Step 2: ethyl 2-(5-((3,3-difluoroazetidin-1-yl)methyl)-2-oxopyridin-1(2H)-yl)-4-methylpentanoate

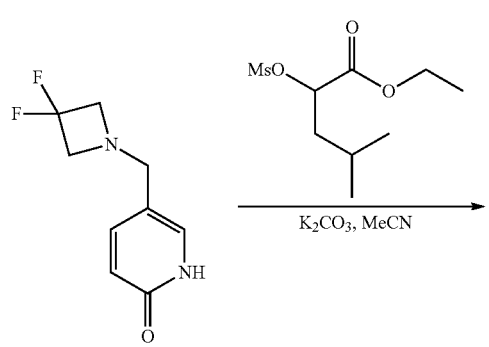

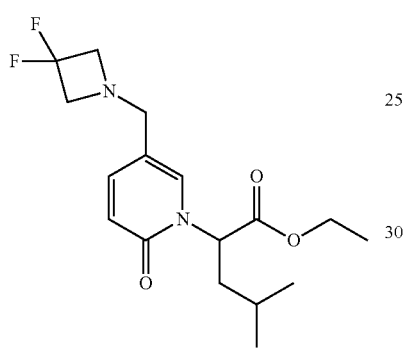

A mixture of 5-((3,3-difluoroazetidin-1-yl)methyl)pyridin-2(1H)-one (248 mg, 1.24 mmol), ethyl 4-methyl-2-(methylsulfonyloxy)pentanoate (443 mg, 1.86 mmol) and K$_2$CO$_3$ (514 mg, 3.72 mmol) in MeCN (5 mL) was stirred at 80° C. overnight. The mixture was filtered and washed with MeCN (5 mL). The filtrate was concentrated in vacuo and the residue was purified by silica gel column (petroleum ether:EtOAc 2:1) to give ethyl 2-(5-((3,3-difluoroazetidin-1-yl)methyl)-2-oxopyridin-1(2H)-yl)-4-methylpentanoate as a colorless oil (150 mg). Yield 36% (ESI 343.1 (M+H)$^+$).

Step 3: 2-(5-((3,3-difluoroazetidin-1-yl)methyl)-2-oxopyridin-1(2H)-yl)-4-methylpentanoic acid

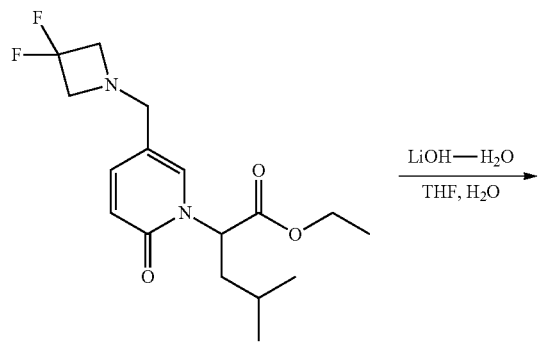

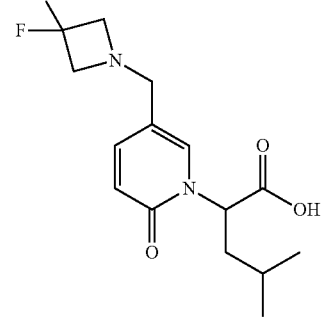

Ethyl 2-(5-((3,3-difluoroazetidin-1-yl)methyl)-2-oxopyridin-1(2H)-yl)-4-methylpentanoate (151 mg, 0.44 mmol) was treated with LiOH—H$_2$O (28 mg, 0.66 mmol) in THF (3 mL) and H$_2$O (0.5 mL) at room temperature for 30 min. The mixture was acidified to pH 4~5 with 1N HCl. The mixture was concentrated in vacuo to provide 2-(5-((3,3-difluoroazetidin-1-yl)methyl)-2-oxopyridin-1(2H)-yl)-4-methylpentanoic acid as white solid (138 mg) used without further purification. Yield 100% (ESI 315.1 (M+H)$^+$).

Step 4: methyl (3S)-3-(2-(5-((3,3-difluoroazetidin-1-yl)methyl)-2-oxopyridin-1(2H)-yl)-4-methylpentanamido)-3-(5-(2,6-dimethylphenyl)pyridin-3-yl)propanoate

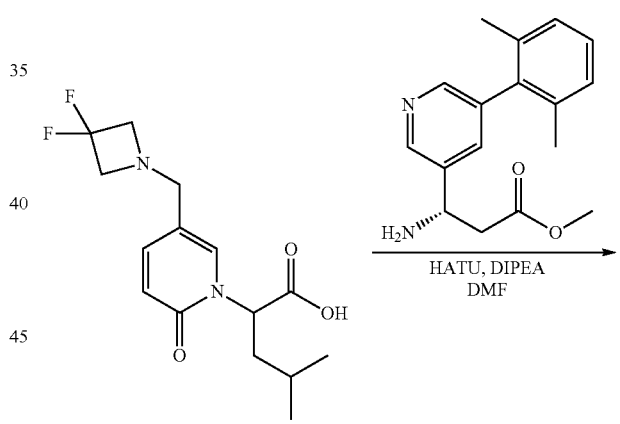

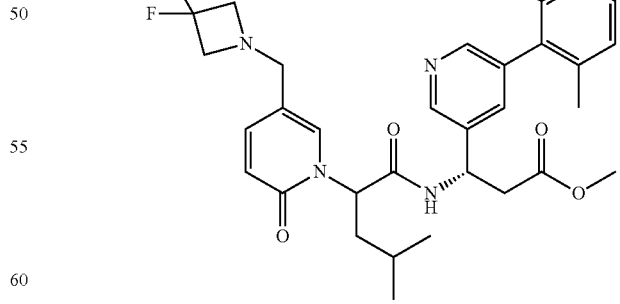

A mixture of 2-(5-((3,3-difluoroazetidin-1-yl)methyl)-2-oxopyridin-1(2H)-yl)-4-methylpentanoic acid (138 mg, 0.44 mmol), methyl (S)-3-amino-3-(5-(2,6-dimethylphenyl)pyridin-3-yl)propanoate (125 mg, 0.44 mmol), HATU (200 mg, 0.53 mmol) and DIEA (171 mg, 1.32 mmol) in DMF (3 mL)

was stirred at room temperature for 30 min. The mixture was poured into water (10 mL) and extracted with EtOAc (20 mL×3). The combined organic layers were washed with brine (20 mL), dried over anhydrous Na$_2$SO$_4$, filtered and concentrated in vacuo. The residue was purified by silica gel column (DCM:MeOH 10:1) to give methyl (3S)-3-(2-(5-((3, 3-difluoroazetidin-1-yl)methyl)-2-oxopyridin-1 (2H)-yl)-4-methylpentanamido)-3-(5-(2,6-dimethylphenyl)pyridin-3-yl)propanoate as a yellow oil (86 mg). Yield 34% (ESI 581.3 (M+H)$^+$).

Step 5: (3S)-3-(2-(5-((3,3-difluoroazetidin-1-yl) methyl)-2-oxopyridin-1(2H)-yl)-4-methylpentanamido)-3-(5-(2,6-dimethylphenyl)pyridin-3-yl)propanoic acid

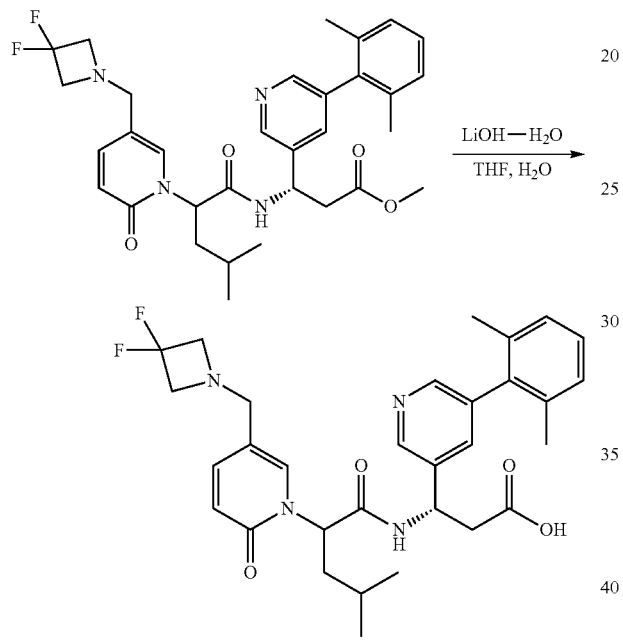

Methyl (3S)-3-(2-(5-((3,3-difluoroazetidin-1-yl)methyl)-2-oxopyridin-1(2H)-yl)-4-methylpentanamido)-3-(5-(2,6-dimethylphenyl)pyridin-3-yl)propanoate (86 mg, 0.15 mmol) was treated with LiOH monohydrate (9 mg, 0.22 mmol) in THF (3 mL) and H$_2$O (0.5 mL) at room temperature for 1 hour. The reaction mixture was acidified to pH 4~5 with 1N HCl aqueous solution, concentrated in vacuo and purified by prep HPLC A to give the diastereomeric products BB1 (10 mg) and BB2 (20 mg) as white solids.

Compound BB1 ESI 567.3 (M+H)$^+$.
$^1$H NMR (400 MHz, MeOD) δ 8.51 (s, 1H), 8.18 (s, 1H), 7.66 (s, 1H), 7.55 (s, 1H), 7.44 (dd, J=9.3, 2.3 Hz, 1H), 7.23-7.15 (m, 1H), 7.14-7.11 (m, 2H), 6.44 (d, J=9.3 Hz, 1H), 5.72 (dd, J=9.5, 6.6 Hz, 1H), 5.41 (t, J=7.3 Hz, 1H), 3.66-3.44 (m, 6H), 2.92 (d, J=7.3 Hz, 2H), 2.08-1.76 (m, 8H), 1.53-1.32 (m, 1H), 1.02-0.89 (t, J=12.0 Hz, 6H).

Compound BB22 ESI 567.3 (M+H)$^+$.
$^1$H NMR (400 MHz, MeOD) δ 8.58 (d, J=1.8 Hz, 1H), 8.26 (s, 1H), 7.67 (d, J=7.2 Hz, 2H), 7.51 (dd, J=9.3, 2.3 Hz, 1H), 7.25-7.18 (m, 1H), 7.15 (d, J=7.4 Hz, 2H), 6.54 (d, J=9.3 Hz, 1H), 5.72 (t, J=8.1 Hz, 1H), 5.40 (t, J=7.4 Hz, 1H), 3.71-3.54 (m, 6H), 2.94-2.88 (m, 2H), 2.01 (s, 6H), 1.83 (t, J=7.5 Hz, 2H), 1.36-1.29 (m, 1H), 0.89 (dd, J=6.5, 4.3 Hz, 6H).

Preparation of Compounds BC1 and BC2 ((3S)-3-(2',6'-dimethyl-[1,1'-biphenyl]-3-yl)-3-(2-(5-((dimethylamino)methyl)-2-oxopyridin-1(2H)-yl)-4-methylpentanamido)propanoic acid)

Step 1: methyl (3S)-3-(2',6'-dimethyl-[1,1'-biphenyl]-3-yl)-3-(2-(5-((dimethylamino)methyl)-2-oxopyridin-1(2H)-yl)-4-methylpentanamido)propanoate

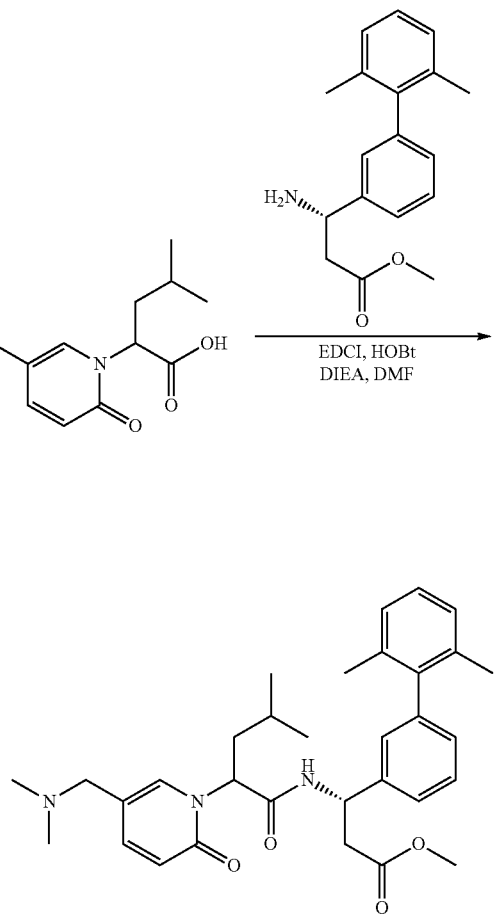

A mixture of 2-(5-((dimethylamino)methyl)-2-oxopyridin-1(2H)-yl)-4-methylpentanoic acid (100 mg, 0.38 mmol), methyl (S)-3-amino-3-(2',6'-dimethyl-[1,1'-biphenyl]-3-yl)propanoate (99 mg, 0.35 mmol), EDCI (81 mg, 0.42 mmol), HOBt (57 mg, 0.42 mmol) and DIEA (136 mg, 1.05 mmol) in DMF (4 mL) was stirred at room temperature for 4 hours. The mixture was poured into water (10 mL) and extracted with EtOAc (20 mL×3). The organic layer was washed with brine (10 mL), dried over anhydrous Na$_2$SO$_4$, filtered and concentrated in vacuo. The residue was purified by reverse phase HPLC on a C18/40 g column (A: water 10 mM NH$_4$HCO$_3$, B: MeOH, 0~100%) to give the diastereomeric products P1 (20 mg) and P2 (35 mg) as colorless oils. Total yield 28% (ESI 532.2 (M+H)$^+$)

Step 2a: (3S)-3-(2',6'-dimethyl-[1,1'-biphenyl]-3-yl)-3-(2-(5-((dimethylamino)methyl)-2-oxopyridin-1(2H)-yl)-4-methylpentanamido)propanoic acid (BC1)

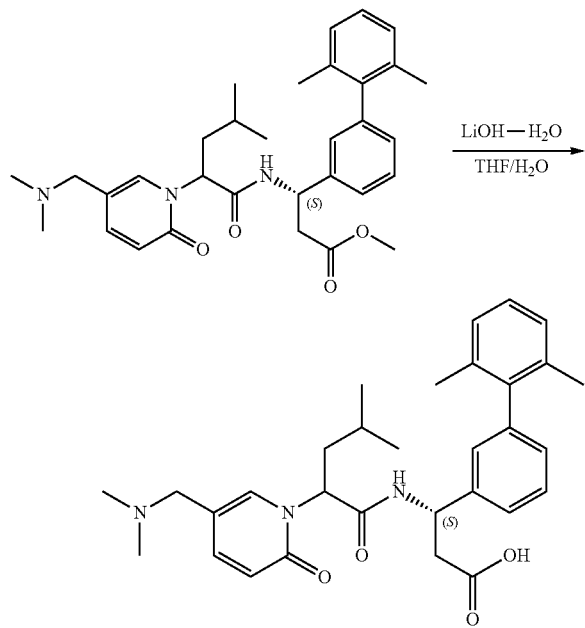

Methyl (3S)-3-(2',6'-dimethyl-[1,1'-biphenyl]-3-yl)-3-(2-(5-((dimethylamino)methyl)-2-oxopyridin-1(2H)-yl)-4-methylpentanamido)propanoate (20 mg, 0.038 mmol) was treated with LiOH—H₂O (8 mg, 0.19 mmol) in methanol (2 mL) and water (0.5 mL) at room temperature for 1 hour. The reaction mixture was acidified to PH 4~5 with 1N HCl. The solvent was removed in vacuo and the residue was purified by prep-HPLC A to give BC1 (10 mg) as a white solid.

Compound BC1 ESI 518.2 (M+H)$^+$ $^1$H NMR (500 MHz, MeOD) δ 7.89 (d, J=2.3 Hz, 1H), 7.51 (dd, J=9.3, 2.5 Hz, 1H), 7.42-7.30 (m, 2H), 7.14-7.07 (m, 4H), 6.99 (d, J=7.4 Hz, 1H), 6.55 (d, J=9.3 Hz, 1H), 5.77 (dd, J=9.5, 6.6 Hz, 1H), 5.33 (dd, J=9.1, 5.3 Hz, 1H), 3.97 (d, J=13.2 Hz, 1H), 3.79 (d, J=13.2 Hz, 1H), 2.84-2.72 (m, 2H), 2.66 (s, 6H), 2.02-1.88 (m, 8H), 1.49-1.36 (m, 1H), 0.96 (d, J=6.5 Hz, 6H).

Step 2b: (3S)-3-(2',6'-dimethyl-[1,1'-biphenyl]-3-yl)-3-(2-(5-((dimethylamino)methyl)-2-oxopyridin-1(2H)-yl)-4-methylpentanamido)propanoic acid (BC22)

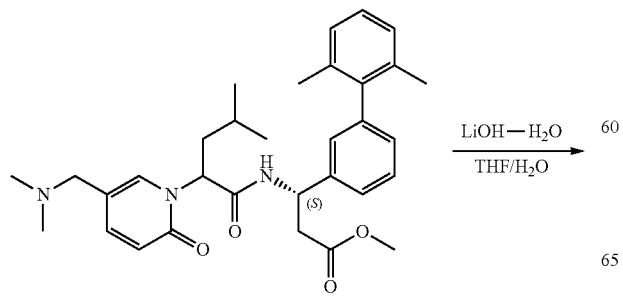

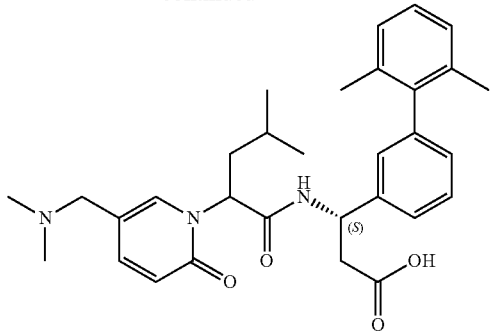

Methyl (3S)-3-(2',6'-dimethyl-[1,1'-biphenyl]-3-yl)-3-(2-(5-((dimethylamino)methyl)-2-oxopyridin-1(2H)-yl)-4-methylpentanamido)propanoate (35 mg, 0.067 mmol) was treated with LiOH—H₂O (14 mg, 0.34 mmol) in methanol (4 mL) and water (1 mL) at room temperature for 1 hour. The reaction mixture was acidified to PH 4~5 with 1N HCl. The solvent was removed in vacuo and the residue was purified by preparatory HPLC A to give the product BC2 (10 mg) as a white solid.

Compound BC2 ESI 518.2 (M+H)$^+$ $^1$H NMR (500 MHz, MeOD) δ 7.80 (d, J=2.4 Hz, 1H), 7.56 (dd, J=9.3, 1.8 Hz, 1H), 7.43 (t, J=7.6 Hz, 1H), 7.34 (d, J=7.8 Hz, 1H), 7.15-7.09 (m, 4H), 7.03 (d, J=7.5 Hz, 1H), 6.58 (d, J=9.3 Hz, 1H), 5.55 (dd, J=11.2, 3.9 Hz, 1H), 5.49 (dd, J=8.5, 5.6 Hz, 1H), 4.22 (d, J=13.3 Hz, 1H), 3.79 (d, J=13.3 Hz, 1H), 2.79 (s, 6H), 2.68 (dd, J=15.1, 4.0 Hz, 1H), 2.54 (dd, J=15.1, 11.3 Hz, 1H), 2.07-2.03 (m, 1H), 2.00 (d, J=7.7 Hz, 6H), 1.58-1.49 (m, 2H), 0.92 (t, J=5.9 Hz, 6H).

Preparation of BD1 and BD2 ((3S)-3-(5-(2,6-dimethylphenyl)pyridin-3-yl)-3-(2-(5-((3-fluoroazetidin-1-yl)methyl)-2-oxopyridin-1(2H)-yl)-4-methylpentanamido)propanoic acid)

Step 1: ethyl 2-(5-formyl-2-oxopyridin-1(2H)-yl)-4-methylpentanoate

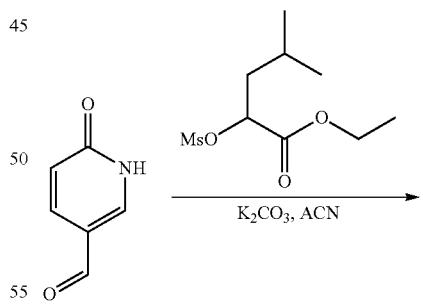

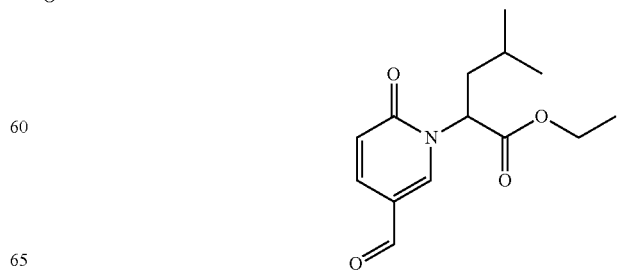

A mixture of 6-oxo-1,6-dihydropyridine-3-carbaldehyde (400 mg, 3.2 mmol), ethyl 4-methyl-2-(methylsulfonyloxy) pentanoate (1 g, 4.2 mmol) and K₂CO₃ (1.1 g, 8 mmol) in MeCN (10 mL) was stirred 80° C. overnight. The mixture was filtered, washed with ACN (5 mL). The filtrate was concentrated in vacuo and purified by silica gel column (pet ether: EtOAc 4:1) to provide ethyl 2-(5-formyl-2-oxopyridin-1(2H)-yl)-4-methylpentanoate as a colorless oil (650 mg). Yield 70% (ESI 266.3 (M+H)⁺).

Step 2: ethyl 2-(5-((3-fluoroazetidin-1-yl)methyl)-2-oxopyridin-1(2H)-yl)-4-methylpentanoate

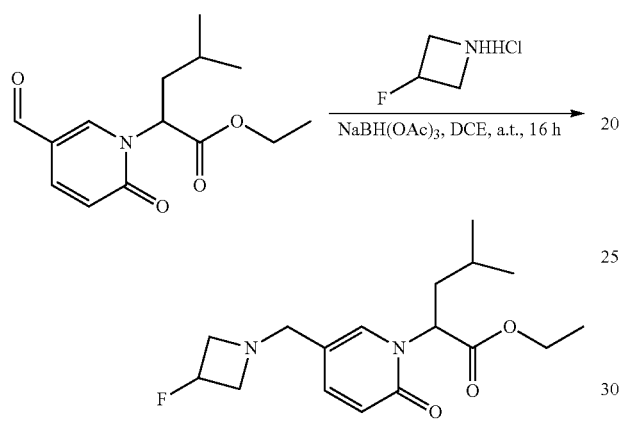

A mixture of ethyl 2-(5-formyl-2-oxopyridin-1(2H)-yl)-4-methylpentanoate (300 mg, 1.13 mmol) and 3-fluoroazetidine hydrochloride (251 mg, 2.26 mmol) in DCE (4 mL) was stirred at room temperature for 30 min. Sodium triacetoxyborohydride (959 mg, 4.52 mmol) was added and stirred at room temperature overnight. The mixture was concentrated in vacuo and purified by silica gel column (DCM:MeOH 10:1) to give ethyl 2-(5-((3-fluoroazetidin-1-yl)methyl)-2-oxopyridin-1(2H)-yl)-4-methylpentanoate as a colorless oil (264 mg). Yield 72% (ESI 325.2 (M+H)⁺).

Step 3: 2-(5-((3-fluoroazetidin-1-yl)methyl)-2-oxopyridin-1(2H)-yl)-4-methylpentanoic acid

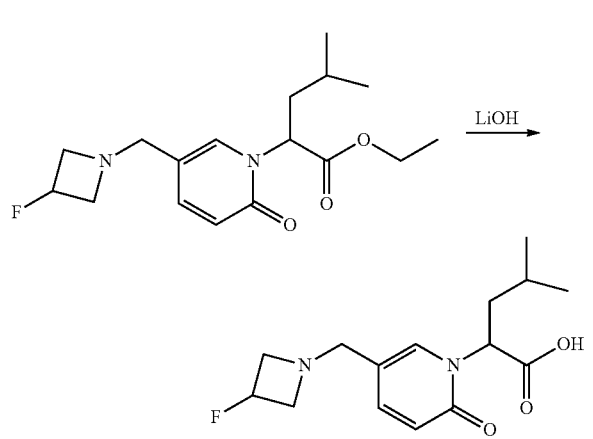

Ethyl 2-(5-((3-fluoroazetidin-1-yl)methyl)-2-oxopyridin-1(2H)-yl)-4-methylpentanoate (264 mg, 0.81 mmol) was treated with LiOH—H₂O (171 mg, 4 mmol) in EtOH (4 mL) and H₂O (1 mL) at room temperature for 2 hours. The mixture was acidified to pH 4~5 with 1N HCl. The mixture was concentrated in vacuo and purified by silica gel column (DCM:MeOH 10:1) to give 2-(5-((3-fluoroazetidin-1-yl)methyl)-2-oxopyridin-1(2H)-yl)-4-methylpentanoic acid as a white solid (217 mg). Yield 90% (ESI 297.1 (M+H)⁺).

Step 4: (3S)-methyl 3-(5-(2,6-dimethylphenyl)pyridin-3-yl)-3-(2-(5-((3-fluoroazetidin-1-yl)methyl)-2-oxopyridin-1(2H)-yl)-4-methylpentanamido)propanoate

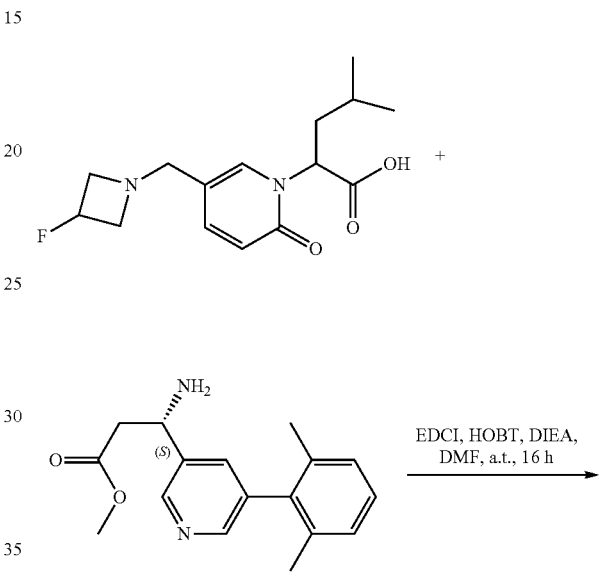

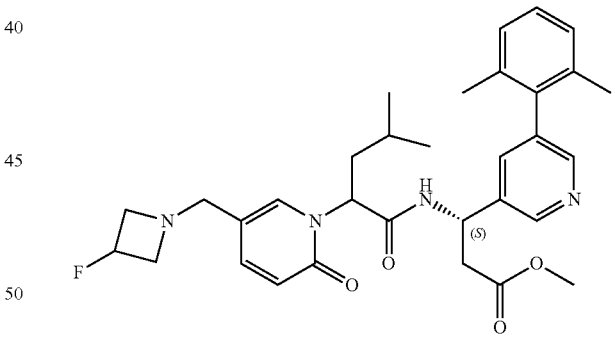

To a solution of 2-(5-((3-fluoroazetidin-1-yl)methyl)-2-oxopyridin-1(2H)-yl)-4-methylpentanoic acid (217 mg, 0.73 mmol) and (S)-methyl 3-amino-3-(5-(2,6-dimethylphenyl)pyridin-3-yl)propanoate (208 mg, 0.73 mmol) in DMF (3 mL) was added EDCI (154 mg, 0.81 mmol), HOBT (109 mg, 0.81 mmol) and DIEA (282 mg, 2.19 mmol). The reaction mixture was stirred at room temperature overnight. The reaction mixture was concentrated and purified by reverse phase HPLC on a C18/80 g column (A: water 10 mM NH₄HCO₃, B: MeOH, 0~100%) to give (3S)-methyl 3-(5-(2,6-dimethylphenyl)pyridin-3-yl)-3-(2-(5-((3-fluoroazetidin-1-yl)methyl)-2-oxopyridin-1(2H)-yl)-4-methylpentanamido)propanoate as a brown solid (288 mg). Yield 70% (ESI 563.2 (M+H)⁺).

Step 5: (3S)-3-(5-(2,6-dimethylphenyl)pyridin-3-yl)-3-(2-(5-((3-fluoroazetidin-1-yl)methyl)-2-oxopyridin-1(2H)-yl)-4-methylpentanamido)propanoic acid

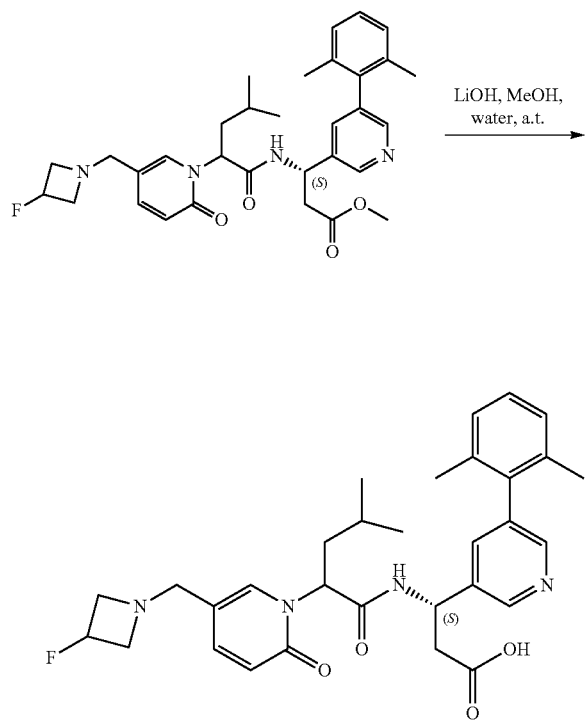

(3S)-methyl 3-(5-(2,6-dimethylphenyl)pyridin-3-yl)-3-(2-(5-((3-fluoroazetidin-1-yl)methyl)-2-oxopyridin-1(2H)-yl)-4-methylpentanamido)propanoate (100 mg, 0.18 mmol) was treated with LiOH—H$_2$O (38 mg, 0.9 mmol) in methanol (3 mL) and water (1 mL) at room temperature for 2 hours. The reaction mixture was acidified to PH 4~5 with 1N HCl. The solvent was removed in vacuo and the residue purified by reverse phase HPLC on a C18/80 g column (A: water 10 mM NH$_4$HCO$_3$, B: ACN, 0-60%) to give the diastereomeric products BD1 (33 mg) and BD2 (35 mg) as white solids.

Compound BD1 ESI 549.3 (M+H)$^+$
1H NMR (400 MHz, MeOD) δ 8.53 (d, J=2.0 Hz, 1H), 8.19 (d, J=1.8 Hz, 1H), 7.73 (s, 1H), 7.59 (t, J=1.9 Hz, 1H), 7.45-7.35 (m, 1H), 7.21-7.19 (m, 1H), 7.17-7.09 (m, 2H), 6.47 (d, J=9.3 Hz, 1H), 5.74-5.65 (m, 1H), 5.47-5.35 (m, 1H), 5.19-5.02 (m, 1H), 3.79-3.66 (m, 2H), 3.65-3.58 (m, 2H), 3.54-3.41 (m, 2H), 2.95-2.81 (m, 2H), 2.05-1.81 (m, 8H), 1.55-1.33 (m, 1H), 0.97-0.88 (m, 6H).

Compound BD2 ESI 549.3 (M+H)$^+$
1H NMR (400 MHz, MeOD) δ 8.59 (d, J=1.9 Hz, 1H), 8.26 (d, J=1.7 Hz, 1H), 7.67 (d, J=2.1 Hz, 2H), 7.56 (d, J=9.3 Hz, 1H), 7.30-7.09 (m, 3H), 6.57 (d, J=9.3 Hz, 1H), 5.62 (t, J=7.5 Hz, 1H), 5.52-5.35 (m, 1H), 5.29-5.15 (m, 1H), 4.22-4.06 (m, 2H), 4.01-3.79 (m, 4H), 2.90-2.67 (m, 2H), 2.09-1.87 (m, 7H), 1.68-1.62 (m, 1H), 1.55-1.33 (m, 1H), 0.91 (d, J=6.5 Hz, 6H).

Preparation of Compounds BE1 and BE2 ((3S)-3-(2',6'-dimethyl-[1,1'-biphenyl]-3-yl)-3-(2-(3-(2-(dimethylamino)ethyl)-2-oxopyridin-1(2H)-yl)-4-methylpentanamido)propanoic acid)

Step 1: ethyl 2-(3-bromo-2-oxopyridin-1(2H)-yl)-4-methylpentanoate

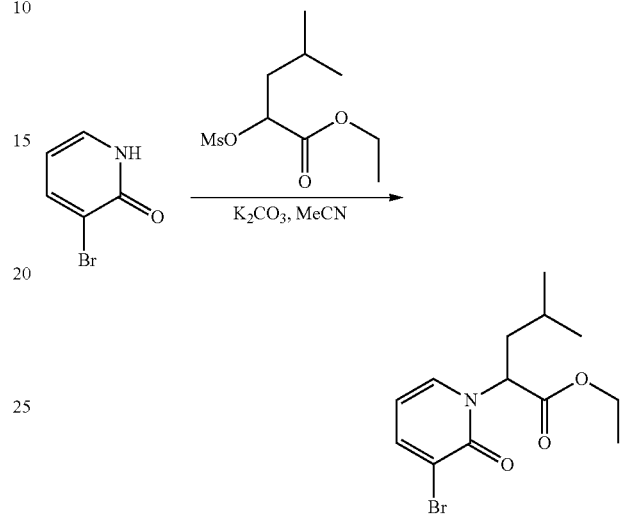

A mixture of 3-bromopyridin-2(1H)-one (1 g, 5.78 mmol), K$_2$CO$_3$ (1.6 g, 11.56 mmol) and ethyl 4-methyl-2-(methylsulfonyloxy)pentanoate (1.65 g, 6.94 mmol) in CH$_3$CN (20 mL) was stirred at 80° C. overnight. The solvent was concentrated in vacuo and purified by silica gel column (petroleum ether:EtOAc 1:1) to give ethyl 2-(3-bromo-2-oxopyridin-1(2H)-yl)-4-methylpentanoate as a white solid (1.6 g). Yield 88% (ESI 316.1 (M+H)$^+$).

Step 2: ethyl 2-(3-(2-(benzyloxycarbonylamino)ethyl)-2-oxopyridin-1(2H)-yl)-4-methylpentanoate

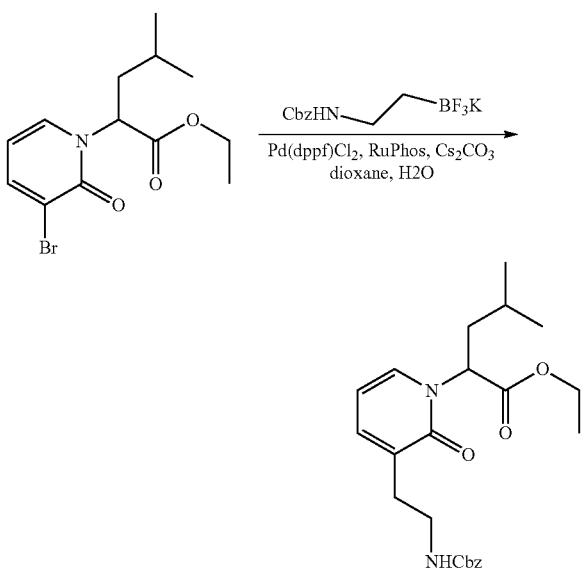

A mixture of ethyl 2-(3-bromo-2-oxopyridin-1(2H)-yl)-4-methylpentanoate (1 g, 3.17 mmol), potassium benzyl N-[2-(trifluoroboryl)ethyl]carbamate (1.08 g, 3.8 mmol), Pd(dppf)Cl₂ (36 mg, 0.16 mmol), Cs₂CO₃ (2 g, 6.34 mmol) and RuPhos (144 mg, 0.32 mmol) in 1,4-dioxane (20 mL) and H₂O (10 mL) was stirred at 110° C. for 2 hours. After completion, the reaction was concentrated and purified by reverse phase HPLC on a C18/40 g column (A: water/0.01% TFA, B: MeOH, 0~100%) to give ethyl 24342-(benzyloxycarbonylamino)ethyl)-2-oxopyridin-1(2H)-yl)-4-methylpentanoate as a yellow oil (1.1 g). Yield 84% (ESI 415.2 (M+H)⁺).

Step 3: ethyl 2-(3-(2-aminoethyl)-2-oxopyridin-1(2H)-yl)-4-methylpentanoate

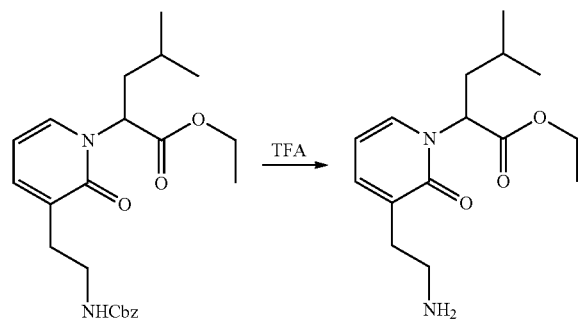 [SMILES: CCOC(=O)C(CC(C)C)n1cccc(CCNC(=O)OCc2ccccc2)c1=O ; CCOC(=O)C(CC(C)C)n1cccc(CCN)c1=O ; "TFA"]

Ethyl 2-(3-(2-(benzyloxycarbonylamino)ethyl)-2-oxopyridin-1(2H)-yl)-4-methylpentanoate (1.07 g, 2.58 mmol) was treated with TFA (20 mL) at 50° C. for 4 hours. The solvent was removed in vacuo and the residue purified by reverse phase HPLC on a C18/40 g column (A: water 10 mM NH₄HCO₃, B: MeOH, 0~100%) to provide ethyl 2-(3-(2-aminoethyl)-2-oxopyridin-1(2H)-yl)-4-methylpentanoate as a yellow oil (0.6 g). Yield 83%. (ESI 281.2 (M+H)⁺).

Step 4: ethyl 2-(3-(2-(dimethylamino)ethyl)-2-oxopyridin-1(2H)-yl)-4-methylpentanoate

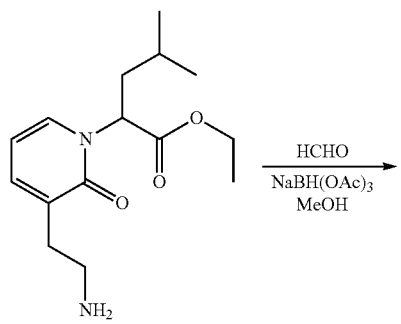

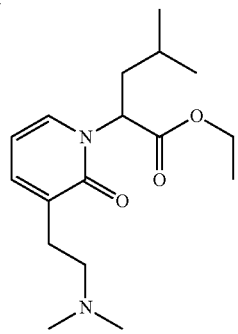

To a mixture of ethyl 2-(3-(2-aminoethyl)-2-oxopyridin-1(2H)-yl)-4-methylpentanoate (600 mg, 2.14 mmol) in MeOH (10 mL) was added HCHO (37% in H₂O, 1 mL). The mixture was stirred at room temperature for 5 mins. NaBH(OAc)₃ (1.81 g, 8.56 mmol) was added and stirred at room temperature for 1 hour. The solvent was removed in vacuo and the residue purified by reverse phase HPLC on a C18/40 g column (A: water 10 mM NH₄HCO₃, B: MeOH, 0~100%) to provide ethyl 2-(3-(2-(dimethylamino)ethyl)-2-oxopyridin-1(2H)-yl)-4-methylpentanoate as yellow oil (600 mg). Yield 91% (ESI 309.2 (M+H)⁺).

Step 5: 2-(3-(2-(dimethylamino)ethyl)-2-oxopyridin-1(2H)-yl)-4-methylpentanoic acid

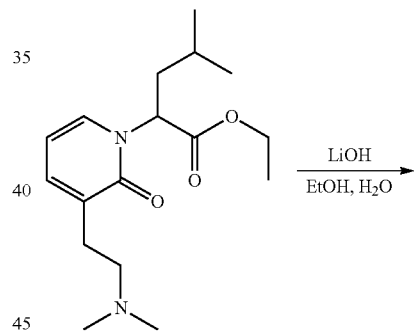

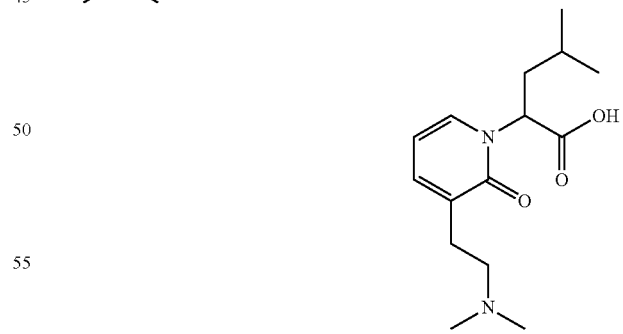

Ethyl 2-(3-(2-(dimethylamino)ethyl)-2-oxopyridin-1(2H)-yl)-4-methylpentanoate (600 mg, 1.95 mmol) was treated with LiOH monohydrate (328 mg, 7.8 mmol) in EtOH (4 mL) and H₂O (1 mL) at room temperature for 1 hour. The mixture was acidified to pH 4~5 with 1N HCl aqueous solution. The mixture was concentrated in vacuo and the residue purified by reverse phase HPLC on a C18/40 g column (A: water/0.01% TFA, B: MeOH, 0~100%) to give 2-(3-(2-(dimethylamino)ethyl)-2-oxopyridin-1(2H)-yl)-4-methylpentanoic acid as white solid (500 mg). Yield 92% (ESI 281.2 (M+H)+).

Step 6: (3S)-methyl 3-(2-(3-(2-(dimethylamino) ethyl)-2-oxopyridin-1(2H)-yl)-4-methylpentanamido)-3-(2',6'-dimethylbiphenyl-3-yl)propanoate Step 7: (3S)-3-(2-(3-(2-(dimethylamino)ethyl)-2-oxopyridin-1(2H)-yl)-4-methylpentanamido)-3-(2',6'-dimethylbiphenyl-3-yl)propanoic acid

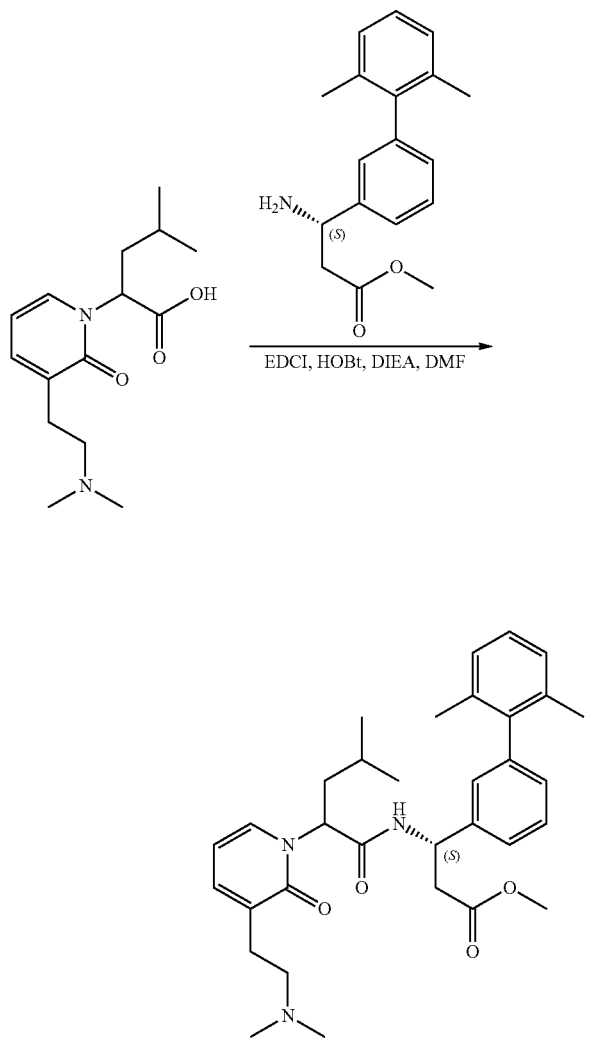

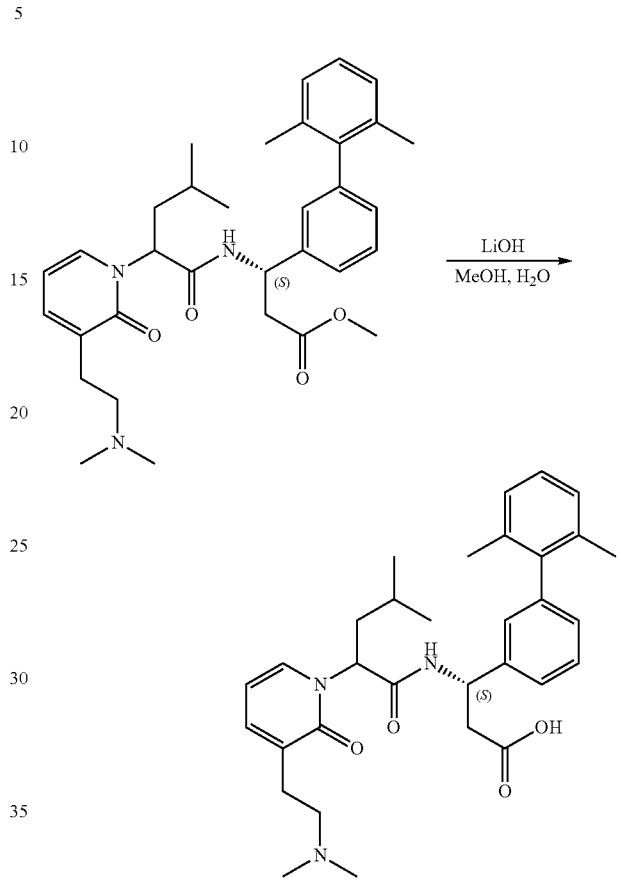

A mixture of 2-(3-(2-(dimethylamino)ethyl)-2-oxopyridin-1(2H)-yl)-4-methylpentanoic acid (150 mg, 0.54 mmol), (S)-methyl 3-amino-3-(2',6'-dimethylbiphenyl-3-yl)propanoate (229 mg, 0.81 mmol), EDCI (206 mg, 1.08 mmol), HOBt (146 mg, 1.08 mmol) and DIEA (279 mg, 2.16 mmol) in DMF (4 mL) was stirred at room temperature for 1 hour. The mixture was purified by reverse phase HPLC on a C18/40 g column (A: water 10 mM NH4HCO3, B: MeOH, 0~100%) to give (3S)-methyl 3-(2-(3-(2-(dimethylamino) ethyl)-2-oxopyridin-1(2H)-yl)-4-methylpentanamido)-3-(2', 6'-dimethylbiphenyl-3-yl)propanoate as a yellow oil (130 mg). Yield 44% (ESI 546.3 (M+H)+).

(3S)-methyl 3-(2-(3-(2-(dimethylamino)ethyl)-2-oxopyridin-1(2H)-yl)-4-methylpentanamido)-3-(2',6'-dimethylbiphenyl-3-yl)propanoate (130 mg, 0.24 mmol) was treated with LiOH monohydrate (40 mg, 0.96 mmol) in MeOH (4 mL) and H2O (1 mL) at room temperature for 1 hour. The reaction mixture was acidified to pH 4~5 with 1N HCl. The mixture was removed in vacuo and the residue purified by prep-HPLC A to give the diastereomeric products BE1 (40 mg) and BE2 (36.4 mg) as white solids.

Compound BE1 ESI 532.3 (M+H)+.

1H NMR (500 MHz, MeOD) δ 7.52-7.50 (m, 1H), 7.49-7.43 (m, 1H), 7.36 (t, J=7.6 Hz, 1H), 7.27 (d, J=7.8 Hz, 1H), 7.18-7.13 (m, 1H), 7.09 (d, J=7.5 Hz, 2H), 6.97 (d, J=7.5 Hz, 1H), 6.89 (s, 1H), 6.23 (t, J=6.9 Hz, 1H), 5.66 (s, 1H), 5.07 (t, J=5.2 Hz, 1H), 3.42-3.35 (m, 1H), 3.17-3.08 (m, 1H), 3.06-2.97 (m, 1H), 2.83-2.75 (m, 7H), 2.67-2.63 (m, 1H), 2.53-2.50 (m, 1H), 2.09-2.02 (m, 2H), 1.97 (s, 3H), 1.92 (s, 3H), 1.42-1.39 (m, 1H), 0.95 (t, J=7.0 Hz, 6H).

Compound BE2 ESI 532.3 (M+H)+.

1H NMR (500 MHz, MeOD) δ 7.65-7.62 (m, 1H), 7.58-7.52 (m, 1H), 7.40 (t, J=7.6 Hz, 1H), 7.32 (d, J=7.8 Hz, 1H), 7.17-7.05 (m, 4H), 7.02 (d, J=7.5 Hz, 1H), 6.45 (t, J=6.9 Hz, 1H), 5.77-5.73 (m, 1H), 5.02 (t, J=4.8 Hz, 1H), 3.52 (t, J=8.9 Hz, 1H), 3.11-3.07 (m, 2H), 2.88-2.78 (m, 1H), 2.66 (s, 6H), 2.52-2.46 (m, 2H), 2.11-2.07 (m, 1H), 2.06-2.01 (m, 4H), 1.99 (s, 3H), 1.49-1.36 (m, 1H), 0.93-0.87 (m, 6H).

Preparation of Compounds BF1 and BF2 ((3S)-3-(5-(2,6-dimethylphenyl)pyridin-3-yl)-3-(4-methyl-2-(5-(morpholinomethyl)-2-oxopyridin-1(2H)-yl)pentanamido)propanoic acid)

Step 1: ethyl 4-methyl-2-(5-(morpholinomethyl)-2-oxopyridin-1(2H)-yl)pentanoate

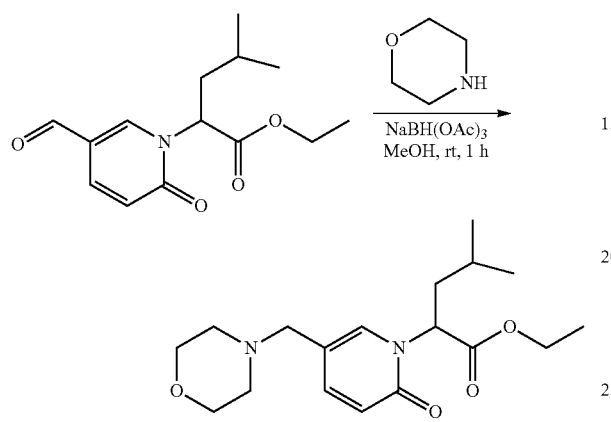

A mixture of ethyl 2-(5-formyl-2-oxopyridin-1(2H)-yl)-4-methylpentanoate (300 mg, 1.13 mmol) and morpholine (147 mg, 1.70 mmol) in DCE (5 mL) was stirred at room temperature for 30 mins. NaBH(OAc)₃ (715 mg, 3.39 mmol) was added and stirred at room temperature for 1 hour. The solvent was removed in vacuo and the residue purified by silica gel column (DCM:MeOH 2:1) to provide ethyl 4-methyl-2-(5-(morpholinomethyl)-2-oxopyridin-1(2H)-yl) pentanoate as yellow oil (150 mg). Yield 39% (ESI 337.2 (M+H)⁺).

Step 2: 4-methyl-2-(5-(morpholinomethyl)-2-oxopyridin-1(2H)-yl)pentanoic acid

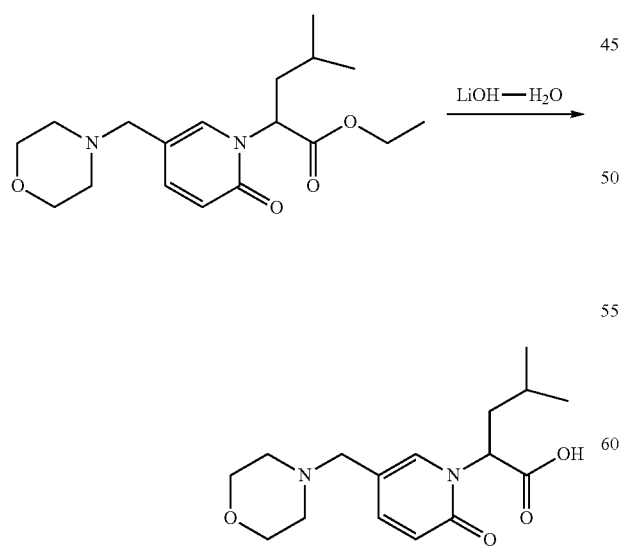

Ethyl 4-methyl-2-(5-(morpholinomethyl)-2-oxopyridin-1 (2H)-yl)pentanoate (150 mg, 0.45 mmol) was treated with LiOH—H₂O (56 mg, 1.34 mmol) in THF (3 mL) and H₂O (0.5 mL) at room temperature for 2 hours. The mixture was acidified to pH=4~5 with 1N HCl. The mixture was concentrated in vacuo and the residue was purified by reverse phase HPLC on a C18/40 g column (A: water 10 mM NH₄HCO₃, B: MeOH, 0~100%) to provide 4-methyl-2-(5-(morpholinomethyl)-2-oxopyridin-1(2H)-yl)pentanoic acid as white solid (110 mg). Yield 80% (ESI 309.3 (M+H)⁺).

Step 3: methyl (3S)-3-(5-(2,6-dimethylphenyl)pyridin-3-yl)-3-(4-methyl-2-(5-(morpholinomethyl)-2-oxopyridin-1(2H)-yl)pentanamido)propanoate

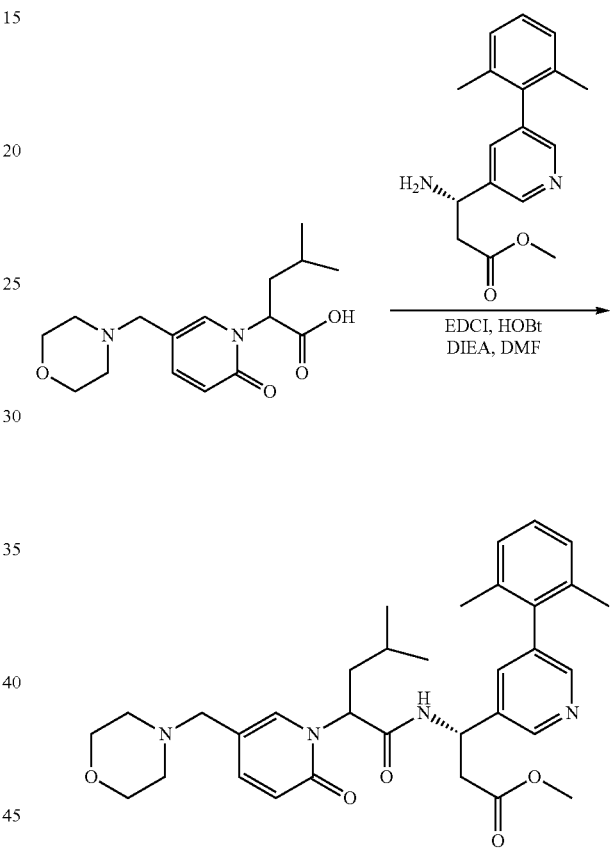

A mixture of 4-methyl-2-(5-(morpholinomethyl)-2-oxopyridin-1(2H)-yl)pentanoic acid (90 mg, 0.29 mmol), methyl (S)-3-amino-3-(5-(2,6-dimethylphenyl)pyridin-3-yl) propanoate (100 mg, 0.35 mmol), EDCI (83 mg, 0.44 mmol), HOBt (59 mg, 0.44 mmol) and DIEA (113 mg, 0.88 mmol) in DMF (3 mL) was stirred at room temperature for 1 hour. The mixture was poured into water (10 mL) and extracted with EtOAc (20 mL×3). The organic layer was washed with brine (20 mL), dried over anhydrous Na₂SO₄, filtered and concentrated in vacuo. The residue was purified by silica gel column (DCM:MeOH 10:1) to give methyl (3 S)-3-(5-(2,6-dimethylphenyl)pyridin-3-yl)-3-(4-methyl-2-(5-(morpholinomethyl)-2-oxopyridin-1(2H)-yl)pentanamido)propanoate as a yellow oil (70 mg). Yield 25% (ESI 575.1 (M+H)⁺).

Step 4: (3S)-3-(5-(2,6-dimethylphenyl)pyridin-3-yl)-3-(4-methyl-2-(5-(morpholinomethyl)-2-oxopyridin-1(2H)-yl)pentanamido)propanoic acid

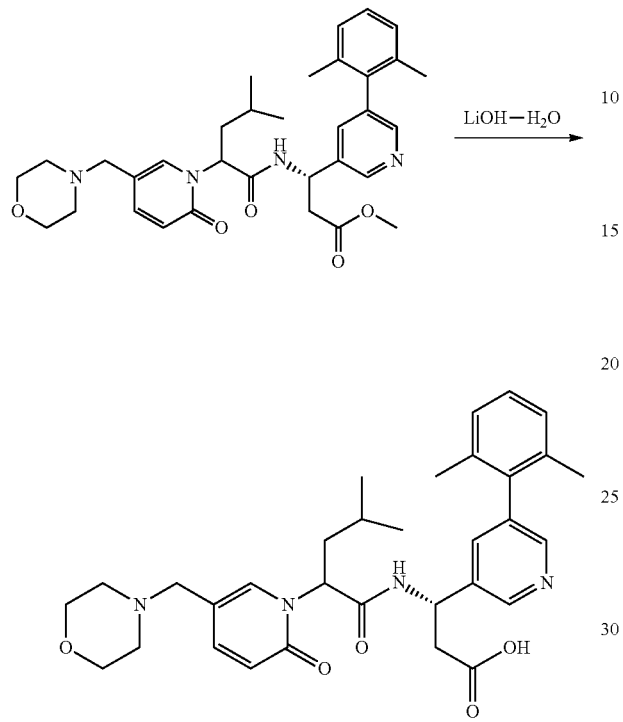

Methyl (3S)-3-(5-(2,6-dimethylphenyl)pyridin-3-yl)-3-(4-methyl-2-(5-(morpholinomethyl)-2-oxopyridin-1(2H)-yl)pentanamido)propanoate (70 mg, 0.12 mmol) was treated with LiOH—H$_2$O (15 mg, 0.36 mmol) in THF (3 mL) and H$_2$O (0.5 mL) at room temperature for 2 hours. The reaction mixture was acidified to pH 4~5 with 1N HCl. The solvent was removed in vacuo and the residue purified by preparatory HPLC A to give the diastereomeric products BF1 (30.1 mg) and BF2 (33.4 mg) as white solids.

Compound BF1 ESI 561.0 (M+H)$^+$.

$^1$H NMR (500 MHz, MeOD) δ 8.53 (d, J=2.1 Hz, 1H), 8.20 (d, J=1.8 Hz, 1H), 7.70 (d, J=2.1 Hz, 1H), 7.58 (d, J=1.9 Hz, 1H), 7.49 (dd, J=9.3, 2.3 Hz, 1H), 7.21 (t, J=7.5 Hz, 1H), 7.16-7.06 (m, 2H), 6.48 (d, J=9.3 Hz, 1H), 5.74 (t, J=8.1 Hz, 1H), 5.45-5.26 (m, 1H), 3.72 (t, J=4.3 Hz, 4H), 3.46 (s, 2H), 2.92 (t, J=7.8 Hz, 2H), 2.59 (s, 4H), 1.99-1.92 (m, 5H), 1.89 (s, 3H), 1.47-1.42 (m, 1H), 0.97 (t, J=6.3 Hz, 6H).

Compounds BF2 ESI 561.1 (M+H)$^+$.

$^1$H NMR (500 MHz, MeOD) δ 8.59 (d, J=2.1 Hz, 1H), 8.26 (d, J=1.9 Hz, 1H), 7.71 (d, J=2.3 Hz, 1H), 7.67 (t, J=2.0 Hz, 1H), 7.57 (dd, J=9.3, 2.4 Hz, 1H), 7.25-7.19 (m, 1H), 7.16 (d, J=7.5 Hz, 2H), 6.57 (d, J=9.3 Hz, 1H), 5.64 (t, J=7.7 Hz, 1H), 5.53-5.50 (m, 1H), 3.86-3.71 (m, 5H), 3.62 (d, J=13.3 Hz, 1H), 2.91-2.79 (m, 5H), 2.74 (dd, J=15.1, 9.4 Hz, 1H), 2.02 (d, J=2.9 Hz, 6H), 1.97-1.91 (m, 1H), 1.75-1.65 (m, 1H), 1.45-1.40 (m, 1H), 0.92 (dd, J=6.6, 2.9 Hz, 6H).

Preparation of Compounds BG1 and BG2 ((3S)-3-(2',6'-dimethyl-[1,1'-biphenyl]-3-yl)-3-(2-(5-(2-(dimethylamino)ethyl)-2-oxopyridin-1(2H)-yl)-4-methylpentanamido)propanoic acid)

Step 1: ethyl 2-(5-(((R)-3-fluoropyrrolidin-1-yl)methyl)-2-oxopyridin-1(2H)-yl)-4-methylpentanoate

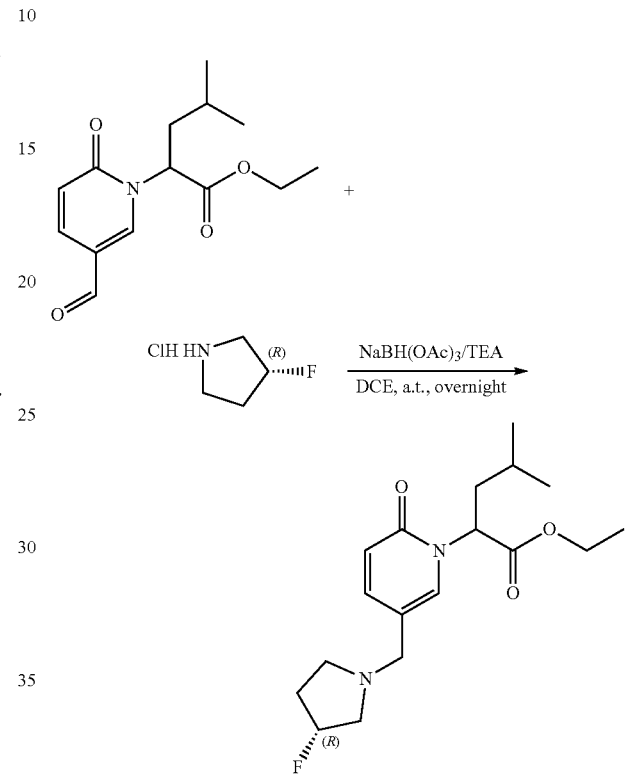

A mixture of ethyl 2-(5-formyl-2-oxopyridin-1(2H)-yl)-4-methylpentanoate (300 mg, 1.13 mmol), (R)-3-fluoropyrrolidine hydrochloride (284 mg, 2.26 mmol) and triethylamine (0.31 mL, 2.26 mmol) in DCE (10 mL) was stirred at room temperature for 30 min. sodium triacetoxyborohydride (959 mg, 4.52 mmol) was added and stirred at room temperature overnight. The mixture was concentrated in vacuo and purified by silica gel column (DCM:MeOH 10:1) to give ethyl 2-(5-(((R)-3-fluoropyrrolidin-1-yl)methyl)-2-oxopyridin-1(2H)-yl)-4-methylpentanoate as a colorless oil (237 mg). Yield 62% (ESI 339.2 (M+H)$^+$).

Step 2: 2-(5-(((R)-3-fluoropyrrolidin-1-yl)methyl)-2-oxopyridin-1(2H)-yl)-4-methylpentanoic acid

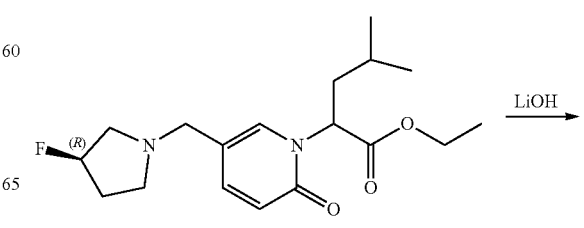

-continued

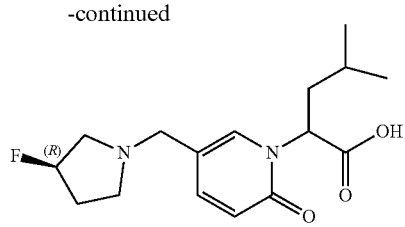

Ethyl 2-(5-(((R)-3-fluoropyrrolidin-1-yl)methyl)-2-oxopyridin-1(2H)-yl)-4-methylpentanoate (426 mg, 1.13 mmol) was treated with LiOH—H₂O (237 mg, 5.65 mmol) in EtOH (6 mL) and H₂O (0.6 mL) at room temperature for 2 hours. The mixture was acidified to pH 4~5 with 1N HCl. The mixture was concentrated in vacuo and the residue purified by silica gel column (DCM:MeOH 10:1) to give 2-(5-(((R)-3-fluoropyrrolidin-1-yl)methyl)-2-oxopyridin-1(2H)-yl)-4-methylpentanoic acid as a white solid (348 mg). Yield 99% (ESI 311.1 (M+H)⁺).

Step 3: methyl (3S)-3-(5-(2,6-dimethylphenyl)pyridin-3-yl)-3-(2-(5-(((R)-3-fluoropyrrolidin-1-yl)methyl)-2-oxopyridin-1(2H)-yl)-4-methylpentanamido)propanoate

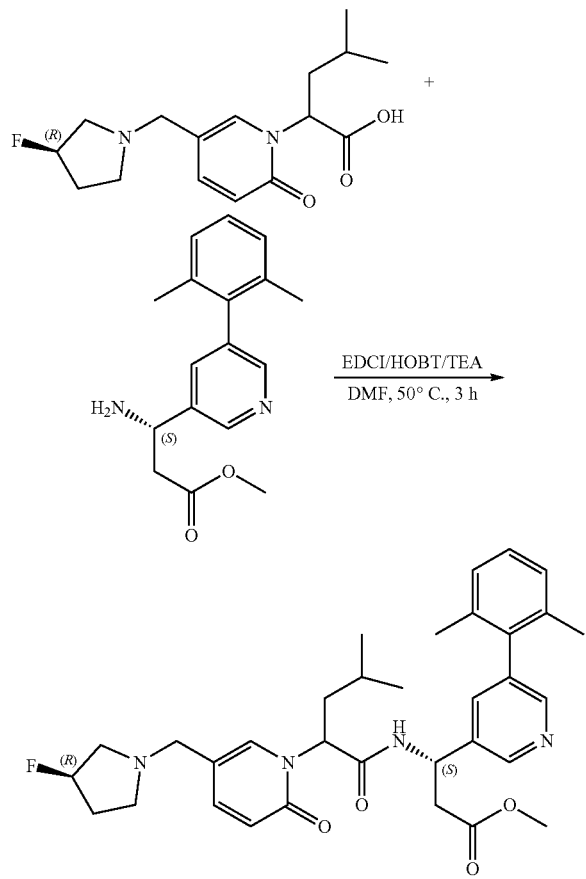

To 1-(3-dimethylaminopropyl)-3-ethylcarbodiimide hydrochloride (247 mg, 1.29 mmol), 1-hydroxybenzotriazole (174 mg, 1.29 mmol) and triethylamine (0.36 mL, 2.58 mmol) was added to a stirring solution of 2-(5-(((R)-3-fluoropyrrolidin-1-yl)methyl)-2-oxopyridin-1(2H)-yl)-4-methylpentanoic acid (200 mg, 0.64 mmol) in N,N-dimethylformamide (3 mL) at ambient temperature. The mixture was stirred at ambient temperature for 30 min. (S)-methyl 3-amino-3-(5-(2,6-dimethylphenyl)pyridin-3-yl)propanoate (183 mg, 0.64 mmol) was added and stirred at ambient temperature for 15 min, then heated to 50° C. for 3 h. After completion, the mixture was concentrated and purified by reverse phase on a C18/80 g column (A: water 10 mM NH₄HCO₃, B: MeOH, 0~100%) to give (3S)-methyl 3-(5-(2,6-dimethylphenyl)pyridin-3-yl)-3-(2-(5-(((R)-3-fluoropyrrolidin-1-yl)methyl)-2-oxopyridin-1(2H)-yl)-4-methylpentanamido)propanoate as a brown solid (285 mg). Yield 77% (ESI 577.0 (M+H)⁺).

Step 4: (3S)-3-(5-(2,6-dimethylphenyl)pyridin-3-yl)-3-(2-(5-(((R)-3-fluoropyrrolidin-1-yl)methyl)-2-oxopyridin-1(2H)-yl)-4-methylpentanamido)propanoic acid

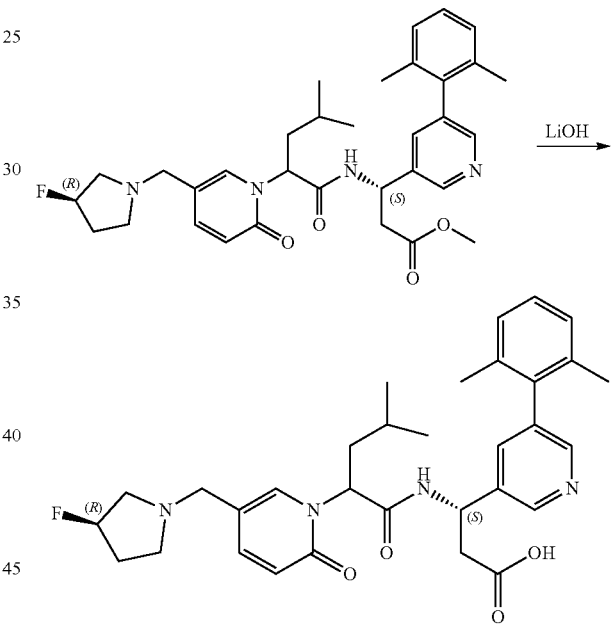

(3S)-methyl 3-(5-(2,6-dimethylphenyl)pyrindin-3-yl)-3-(2-(5-(((R)-3-fluoropyrrolidin-1-yl)methyl)-2-oxopyridin-1(2H)-yl)-4-methylpentanamido)propanoate (285 mg, 0.64 mmol) was treated with LiOH—H₂O (134 mg, 3.20 mmol) in MeOH (6 mL) and H₂O (0.3 mL) at room temperature for 2 hours. The mixture was acidified to pH 4~5 with 1N HCl. The mixture was concentrated in vacuo and the residue purified by prep-HPLC A (30-60% MeCN) to give the products BG1 (66 mg) as a white solid and BG2 (78 mg) as a light-yellow solid.

Compound BG1 ESI 563.0 (M+H)⁺.

¹H NMR (500 MHz, CD₃OD) δ 8.51 (d, J=2.0 Hz, 1H), 8.17 (d, J=2.0 Hz, 1H), 7.77 (d, J=2.0 Hz, 1H), 7.59 (t, J=2.0 Hz, 1H), 7.52-7.43 (m, 1H), 7.19 (t, J=7.5 Hz, 1H), 7.12-7.04 (m, 2H), 6.48-6.38 (m, 1H), 5.73-5.63 (m, 1H), 5.36-5.29 (m, 1H), 5.26-5.21 (m, 1H), 3.80 (d, J=13.0 Hz, 1H), 3.72 (d, J=13.0 Hz, 1H), 3.21-3.13 (m, 1H), 3.12-3.01 (m,

2H), 2.92-2.79 (m, 3H), 2.32-2.07 (m, 2H), 1.97-1.93 (m, 5H), 1.89 (s, 3H), 1.46-1.40 (m, 1H), 0.95-0.91 (m, 6H).

Compound BG2 ESI 563.1 (M+H)+.

$^1$H NMR (500 MHz, CD$_3$OD) δ 8.56 (d, J=1.5 Hz, 1H), 8.23 (d, J=2.0 Hz, 1H), 7.71 (d, J=2.0 Hz, 1H), 7.64 (t, J=1.5 Hz, 1H), 7.61-7.52 (m, 1H), 7.20-7.16 (m, 1H), 7.14 (t, J=7.5 Hz, 2H), 6.57 (d, J=9.0 Hz, 1H), 5.57-5.54 (m, 2H), 5.34 (d, J=53.0 Hz, 1H), 4.16 (d, J=13.0 Hz, 1H), 3.84 (d, J=13.0 Hz, 1H), 3.46 (s, 1H), 3.40-3.33 (m, 2H), 3.92-3.25 (m, 1H), 2.75-2.72 (m, 1H), 2.61-2.58 (m, 1H), 2.38-2.23 (m, 2H), 2.00 (d, J=3.0 Hz, 6H), 1.97 (t, J=7.5 Hz, 1H), 1.62-1.57 (m, 1H), 1.48-1.43 (m, 1H), 0.90 (d, J=6.5 Hz, 6H).

Preparation of Compounds BH1 and BH2 ((3S)-3-(2',6'-dimethyl-[1,1'-biphenyl]-3-yl)-3-(2-(5-(((R)-3-fluoropyrrolidin-1-yl)methyl)-2-oxopyridin-1(2H)-yl)-4-methylpentanamido)propanoic acid)

Step 1: (3S)-methyl 3-(2',6'-dimethylbiphenyl-3-yl)-3-(2-(5-(((R)-3-fluoropyrrolidin-1-yl)methyl)-2-oxopyridin-1(2H)-yl)-4-methylpentanamido)propanoate

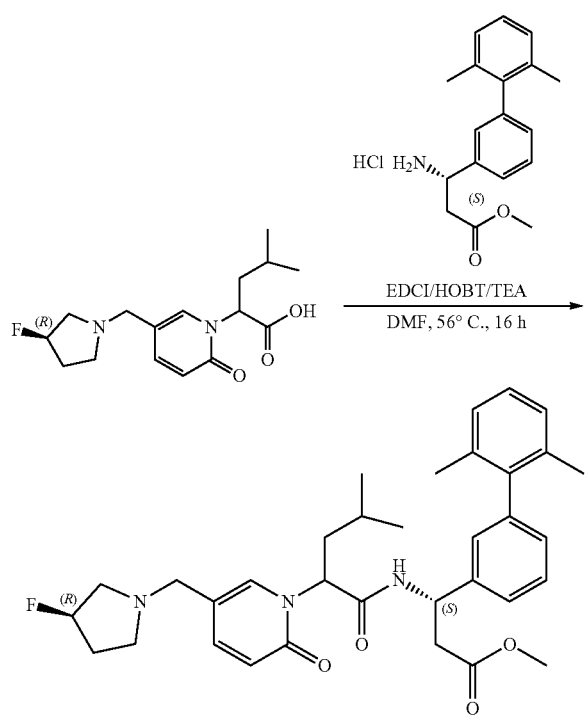

A mixture of 2-(5-(((R)-3-fluoropyrrolidin-1-yl)methyl)-2-oxopyridin-1(2H)-yl)-4-methylpentanoic acid (950 mg, 3.06 mmol), (S)-methyl 3-amino-3-(2',6'-dimethylbiphenyl-3-yl)propanoate hydrochloride (979 mg, 3.06 mmol), 1-(3-dimethylaminopropyl)-3-ethylcarbodiimide hydrochloride (1.17 g, 6.12 mmol), 1-hydroxybenzotriazole (827 mg, 6.12 mmol) and triethylamine (3.40 mL, 24.49 mmol) in N,N-dimethylformamide (15 mL) was stirred at 56° C. overnight. The solvent was removed in vacuo and the residue purified by silica gel column (pet ether:EtOAc 1:1) to give (3S)-methyl 3-(2',6'-dimethylbiphenyl-3-yl)-3-(2-(5-(((R)-3-fluoropyrrolidin-1-yl)methyl)-2-oxopyridin-1(2H)-yl)-4-methylpentanamido)propanoate as a brown solid (1.6 g). Yield 83% (ESI 576.2 (M+H)+).

Step 2: (3S)-3-(2',6'-dimethylbiphenyl-3-yl)-3-(2-(5-(((R)-3-fluoropyrrolidin-1-yl)methyl)-2-oxopyridin-1(2H)-yl)-4-methylpentanamido)propanoic acid

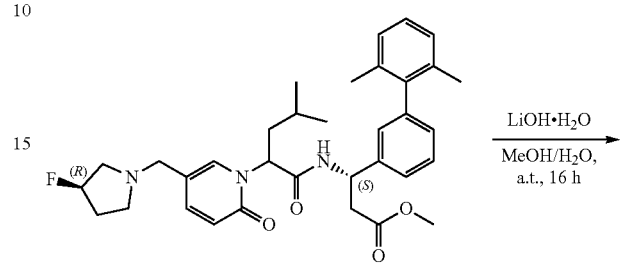

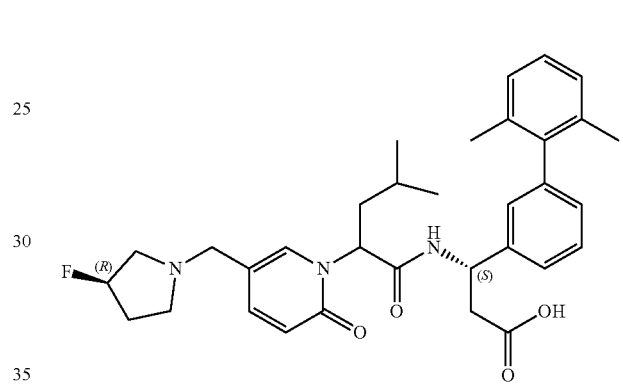

(3 S)-methyl 3-(2',6'-dimethylbiphenyl-3-yl)-3-(2-(5-(((R)-3-fluoropyrrolidin-1-yl)methyl)-2-oxopyridin-1(2H)-yl)-4-methylpentanamido)propanoate (1.6 g, 2.80 mmol) was treated with LiOH—H$_2$O (1.18 g, 28.00 mmol) in MeOH (30 mL) and H$_2$O (3 mL) at room temperature for 16 hours. After completion, the reaction mixture was acidified to pH 4~5 with 1N HCl. The solvent was removed in vacuo and the residue was purified by prep-HPLC A (30-60% MeCN) to give the diastereomeric products BH1 (568 mg) and BH2 (586 mg) as white solids.

Compound BH1 ESI 562.3 (M+H)+. $^1$H NMR (500 MHz, MeOD) δ 7.75 (d, J=2.0 Hz, 1H), 7.50-7.47 (m, 1H), 7.36 (t, J=7.5 Hz, 1H), 7.29 (d, J=8.0 Hz, 1H), 7.11 (t, J=7.5 Hz, 1H), 7.05 (d, J=10.5 Hz, 3H), 6.97 (d, J=7.0 Hz, 1H), 6.48 (d, J=9.5 Hz, 1H), 5.75 (t, J=7.5 Hz, 1H), 5.35-5.31 (m, 1H), 5.23-5.20 (m, 1H), 3.69-3.65 (m, 2H), 3.14-2.94 (m, 3H), 2.86-2.76 (m, 2H), 2.74-2.69 (m, 1H), 2.30-2.17 (m, 1H), 2.14-2.03 (m, 1H), 1.96-1.92 (m, 5H), 1.88 (s, 3H), 1.47-1.39 (m, 1H), 0.95-0.93 (m, 6H).

Compound BH2 ESI 562.2 (M+H)+. $^1$H NMR (500 MHz, MeOD) δ 7.72 (d, J=2.0 Hz, 1H), 7.59-7.54 (m, 1H), 7.41 (t, J=7.5 Hz, 1H), 7.34 (d, J=7.5 Hz, 1H), 7.12 (t, J=7.5 Hz, 2H), 7.07 (d, J=6.0 Hz, 2H), 7.02 (d, J=7.5 Hz, 1H), 6.56 (d, J=9.0 Hz, 1H), 5.54-5.50 (m, 2H), 5.32-5.48 (m, 1H), 4.13 (d, J=13.5 Hz, 1H), 3.81 (d, J=13.0 Hz, 1H), 3.42 (d, J=3.0 Hz, 1H), 3.37-3.33 (m, 2H), 3.26-3.22 (m, 1H), 2.72-2.68 (m, 1H), 2.56-2.52 (m, 1H), 2.36-2.22 (m, 2H), 2.00-1.94 (m, 7H), 1.60-1.54 (m, 1H), 1.49-1.44 (m, 1H), 0.89-0.85 (m, 6H).

Preparation of Compounds BI1 and BI2 ((3S)-3-(2',6'-dimethyl-[1,1'-biphenyl]-3-yl)-3-(2-(4-(2-(dimethylamino)ethyl)-2-oxopyridin-1(2H)-yl)-4-methylpentanamido)propanoic acid)

Step 1: (3S)-ethyl 3-(2-(4-(2-(dimethylamino)ethyl)-2-oxopyridin-1(2H)-yl)-4-methylpentanamido)-3-(2',6'-dimethylbiphenyl-3-yl)propanoate

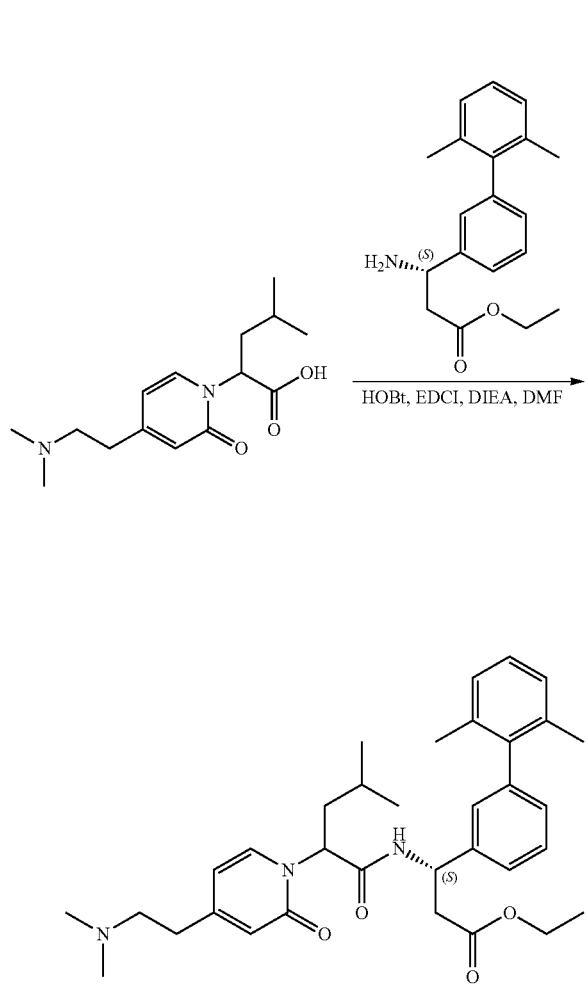

A mixture of 2-(4-(2-(dimethylamino)ethyl)-2-oxopyridin-1(2H)-yl)-4-methylpentanoic acid (182 mg, 0.65 mmol), (S)-ethyl 3-amino-3-(2',6'-dimethylbiphenyl-3-yl)propanoate (150 mg, 0.5 mmol), EDCI (191 mg, 1 mmol), HOBt (135 mg, 1 mmol) and DIEA (258 mg, 7 mmol) in DMF (4 mL) was stirred at 40° C. 4 hours. The mixture was purified by reverse phase HPLC on a C18/40 g column (A: water 10 mM NH$_4$HCO$_3$, B: MeOH, 0~100%) to give (3S)-ethyl 3-(2-(4-(2-(dimethylamino)ethyl)-2-oxopyridin-1(2H)-yl)-4-methylpentanamido)-3-(2',6'-dimethylbiphenyl-3-yl)propanoate as a yellow oil (140 mg). Yield 50% (ESI 560.3 (M+H)$^+$).

Step 2: (3S)-3-(2-(4-(2-(dimethylamino)ethyl)-2-oxopyridin-1(2H)-yl)-4-methylpentanamido)-3-(2',6'-dimethylbiphenyl-3-yl)propanoic acid

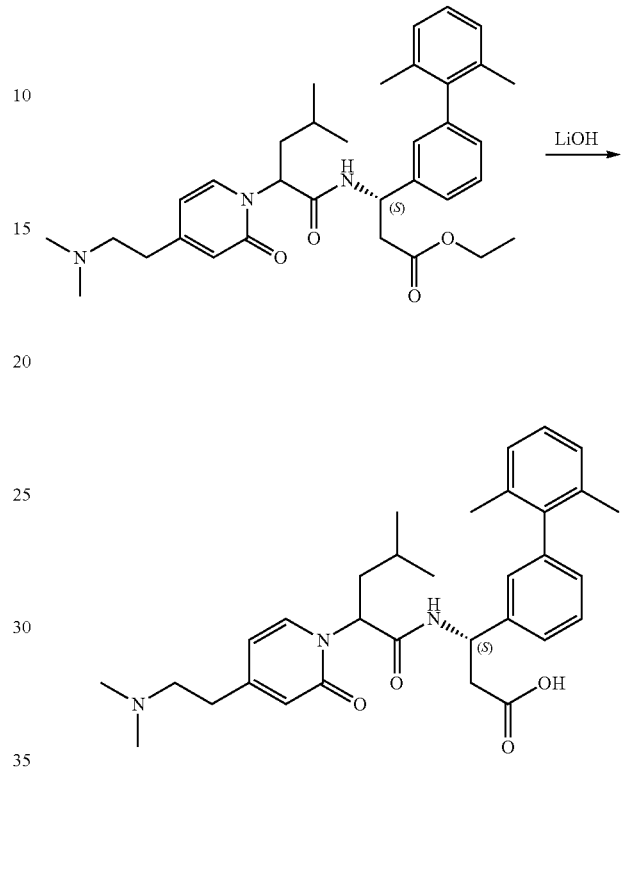

(3S)-ethyl 3-(2-(4-(2-(dimethylamino)ethyl)-2-oxopyridin-1(2H)-yl)-4-methylpentanamido)-3-(2',6'-dimethylbiphenyl-3-yl)propanoate (140 mg, 0.25 mmol) was treated with LiOH—H$_2$O (32 mg, 0.75 mmol) in EtOH (3 mL) and H$_2$O (1 mL) at room temperature for 2 hours. The reaction mixture was acidified to pH 4~5 with 1N HCl. The solvent was removed in vacuo and the residue purified by Prep-HPLC A (30-60% MeCN) to give the diastereomeric products BI1 (44 mg) and BI2 (44 mg) as white solids.

Compound BI1 ESI 532.3 (M+H)$^+$.

1H NMR (500 MHz, MeOD) δ 7.65 (d, J=7.2 Hz, 1H), 7.37 (t, J=7.6 Hz, 1H), 7.27 (d, J=7.8 Hz, 1H), 7.17-7.07 (m, 3H), 7.04 (s, 1H), 6.99 (d, J=7.5 Hz, 1H), 6.59 (s, 1H), 6.44 (d, J=7.1 Hz, 1H), 5.69-5.64 (m, 1H), 5.13 (s, 1H), 3.31-3.21 (m, 2H), 3.01-2.85 (m, 2H), 2.73 (s, 6H), 2.60-2.57 (m, 2H), 2.05-2.01 (m, 2H), 1.98 (s, 6H), 1.48-1.42 (m, 1H), 0.97-0.94 (m, 6H).

Compound BI2 ESI 532.2 (M+H)$^+$.

1H NMR (500 MHz, MeOD) δ 7.69 (d, J=7.2 Hz, 1H), 7.38 (t, J=7.6 Hz, 1H), 7.29 (d, J=7.8 Hz, 1H), 7.18-7.03 (m, 4H), 6.99 (d, J=7.5 Hz, 1H), 6.58 (s, 1H), 6.50 (d, J=6.7 Hz, 1H), 5.65 (s, 1H), 5.15 (s, 1H), 3.39 (s, 1H), 3.29 (s, 1H), 2.94 (s, 2H), 2.77 (s, 6H), 2.58-2.53 (m, 2H), 2.01 (d, J=11.7 Hz, 8H), 1.46 (s, 1H), 0.94-0.90 (m, 6H).

Preparation of Compounds BJ1 and BJ2 ((3S)-3-(2',6'-dimethyl-[1,1'-biphenyl]-3-yl)-3-(2-(5-((3-fluoroazetidin-1-yl)methyl)-2-oxopyridin-1(2H)-yl)-4-methylpentanamido)propanoic acid)

Step 1: ethyl (3S)-ethyl 3-(2',6'-dimethylbiphenyl-3-yl)-3-(2-(5-((3-fluoroazetidin-1-yl)methyl)-2-oxopyridin-1(2H)-yl)-4-methylpentanamido)propanoate

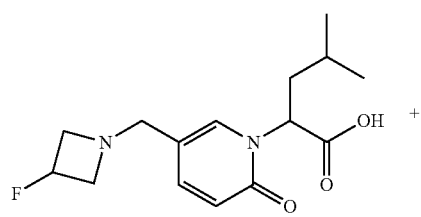

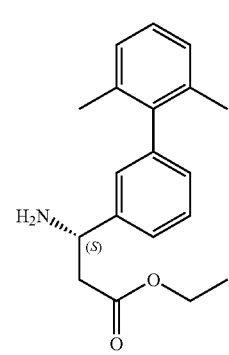

EDCI, HOBT, DIEA, DMF, a.t., 24 h

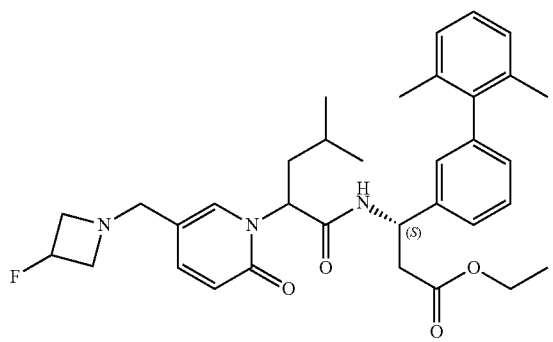

To a solution of 2-(5-((3-fluoroazetidin-1-yl)methyl)-2-oxopyridin-1(2H)-yl)-4-methylpentanoic acid (100 mg, 0.33 mmol) and (S)-ethyl 3-amino-3-(2',6'-dimethylbiphenyl-3-yl)propanoate (99 mg, 0.33 mmol) in DMF (2 mL) was added EDCI (95 mg, 0.5 mmol), HOBT (68 mg, 0.5 mmol) and DIEA (129 mg, 1 mmol). The reaction mixture was stirred at ambient temperature for 16 h. The reaction mixture was concentrated in vacuo and the residue purified by reverse phase HPLC on a C18/80 g column (A: water 10 mM $NH_4HCO_3$, B: MeOH, 0~100%) to give (3S)-ethyl 3-(2',6'-dimethylbiphenyl-3-yl)-3-(2-(5-((3-fluoroazetidin-1-yl)methyl)-2-oxopyridin-1(2H)-yl)-4-methylpentanamido) propanoate as a brown solid (70 mg). Yield 37% (ESI 576.3 $(M+H)^+$).

Step 2: (3S)-3-(2',6'-dimethyl-[1,1'-biphenyl]-3-yl)-3-(2-(5-((3-fluoroazetidin-1-yl)methyl)-2-oxopyridin-1(2H)-yl)-4-methylpentanamido)propanoic acid (3S)-ethyl 3-(2',6'-dimethylbiphenyl-3-yl)-3-(2-(5-((3-fluoroazetidin-1-yl)methyl)-2-oxopyridin-1(2H)-yl)-4-methylpentanamido)propanoate (70 mg, 0.12 mmol) was treated with LiOH—$H_2O$ (38 mg, 0.9 mmol) in methanol (2 mL) and water (1 mL) at ambient temperature for 2 hours. The reaction mixture was acidified to PH 4~5 with 1N HCl. The solvent was removed in vacuo and the residue purified by reverse phase HPLC on a C18/40 g column (A: water 10 mM $NH_4HCO_3$, B: ACN, 0~60%) to give the diastereomeric products BJ1 (24 mg) and BJ2 (30 mg) as white solids.

Compound BJ1 ESI 548.3 $(MH)^+$ 1H NMR (400 MHz, MeOD) δ 7.70 (s, 1H), 7.45-7.26 (m, 3H), 7.15-6.94 (m, 5H), 6.47 (d, J=9.3 Hz, 1H), 5.76 (t, J=8.0 Hz, 1H), 5.38 (t, J=7.3 Hz, 1H), 5.16 (d, J=57.3 Hz, 1H), 3.82-3.66 (m, 2H), 3.57-3.53 (m, 2H), 3.47-3.37 (m, 2H), 2.84-2.81 (m, 2H), 1.94 (m, 8H), 1.50-1.37 (m, 1H), 0.97 (t, J=6.7 Hz, 6H).

Compound BJ2 ESI 548.3 $(M+H)^+$

1H NMR (400 MHz, MeOD) δ 7.67 (d, J=2.3 Hz, 1H), 7.55-7.51 (m, 1H), 7.44 (t, J=7.6 Hz, 1H), 7.36 (d, J=7.8 Hz, 1H), 7.18-7.00 (m, 5H), 6.56 (d, J=9.3 Hz, 1H), 5.59 (t, J=7.6 Hz, 1H), 5.49-5.41 (m, 1H), 5.27-5.24 (m, 1H), 4.09-4.05 (m, 2H), 3.96-3.75 (m, 4H), 2.71-2.67 (m, 2H), 2.04-1.88 (m, 7H), 1.66-1.58 (m, 1H), 1.44-1.38 (m, 1H), 0.91-0.88 (m, 6H).

Preparation of Compounds BK1 and BK2 ((3S)-3-(2',6'-dimethyl-[1,1'-biphenyl]-3-yl)-3-(2-(5-(2-(dimethylamino)ethyl)-2-oxopyridin-1(2H)-yl)-4-methylpentanamido)propanoic acid)

Step 1: methyl (3S)-3-(2',6'-dimethyl-[1,1'-biphenyl]-3-yl)-3-(2-(5-(2-(dimethylamino)ethyl)-2-oxopyridin-1(2H)-yl)-4-methylpentanamido)propanoate

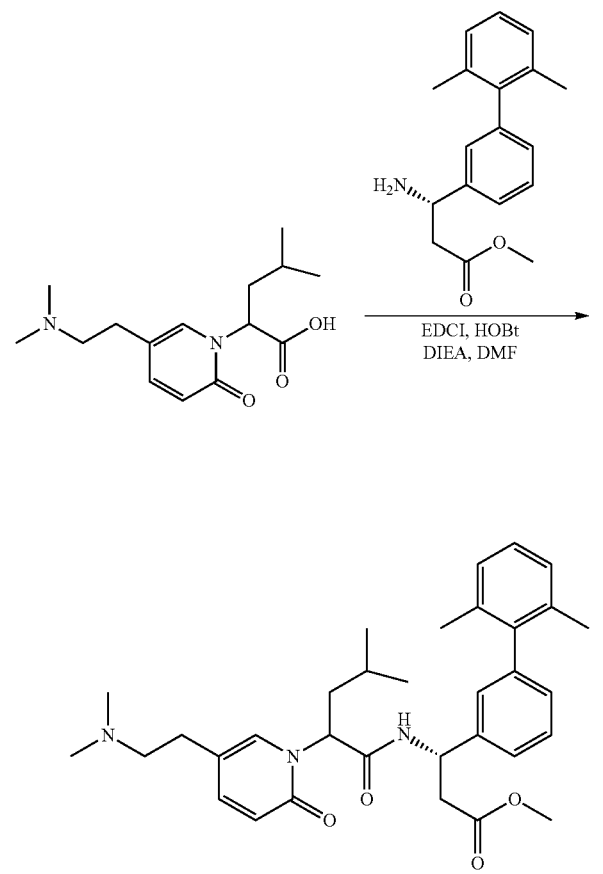

A mixture of 2-(5-(2-(dimethylamino)ethyl)-2-oxopyridin-1(2H)-yl)-4-methylpentanoic acid (80 mg, 0.29 mmol), methyl (S)-3-amino-3-(2',6'-dimethyl-[1,1'-biphenyl]-3-yl)propanoate (96 mg, 0.34 mmol), EDCI (109 mg, 0.57 mmol), HOBt (77 mg, 0.57 mmol) and DIEA (185 mg, 1.43 mmol) in DMF (4 mL) was stirred at room temperature for 4 hours. The mixture was concentrated and purified by reverse phase HPLC on a C18/40 g column (A: water 10 mM $NH_4HCO_3$, B: MeOH, 0~100%) to give methyl (3S)-3-(2',6'-dimethyl-[1,1'-biphenyl]-3-yl)-3-(2-(5-(2-(dimethylamino)ethyl)-2-oxopyridin-1(2H)-yl)-4-methylpentanamido)propanoate as a yellow oil (140 mg). Yield 50% (ESI 546.3 (M+H)+).

Step 2: (3S)-3-(2',6'-dimethyl-[1,1'-biphenyl]-3-yl)-3-(2-(5-(2-(dimethylamino)ethyl)-2-oxopyridin-1(2H)-yl)-4-methylpentanamido)propanoic acid

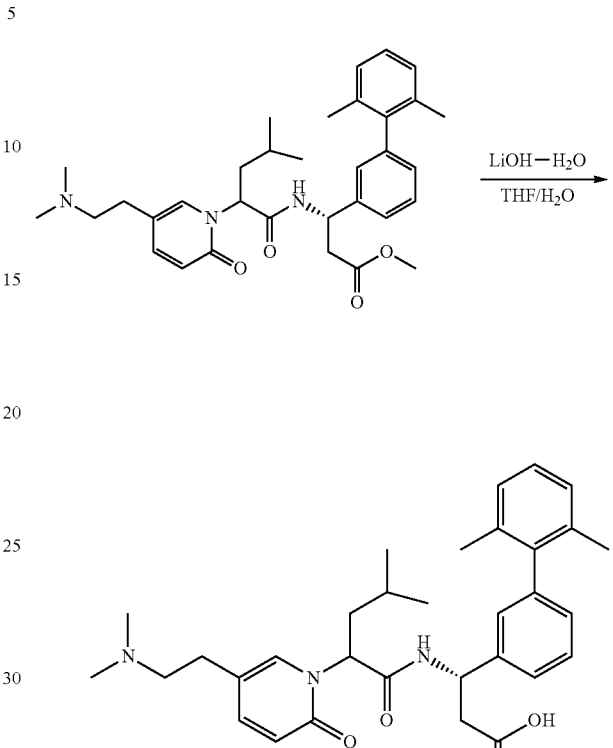

Methyl (3S)-3-(2',6'-dimethyl-[1,1'-biphenyl]-3-yl)-3-(2-(5-(2-(dimethylamino)ethyl)-2-oxopyridin-1(2H)-yl)-4-methylpentanamido)propanoate (140 mg, 0.26 mmol) was treated with LiOH—$H_2O$ (54 mg, 1.28 mmol) in THF (6 mL) and $H_2O$ (1 mL) at room temperature for 2 hours. The reaction mixture was acidified to pH 4~5 with 1N HCl. The solvent was removed in vacuo and the residue was purified by prep-HPLC A to give the diastereomeric products BK1 (25.2 mg) and BK2 (37.3 mg) as white solids.

Compound BK1 ESI 532.2 (M+H)+.
$^1$H NMR (500 MHz, MeOD) δ 7.72 (d, J=2.1 Hz, 1H), 7.56 (dd, J=9.4, 2.3 Hz, 1H), 7.40 (t, J=7.6 Hz, 1H), 7.30 (d, J=7.8 Hz, 1H), 7.16-6.98 (m, 5H), 6.61 (d, J=9.3 Hz, 1H), 5.66 (dd, J=10.6, 5.4 Hz, 1H), 5.16 (t, J=5.3 Hz, 1H), 3.37-3.35 (m, 1H), 3.22-3.14 (m, 1H), 2.95-2.80 (m, 2H), 2.71 (s, 6H), 2.62 (m, 2H), 2.08-1.94 (m, 8H), 1.50-1.40 (m, 1H), 0.95 (dd, J=19.9, 6.6 Hz, 6H).

Compound BK2 ESI 532.3 (M+H)+.
$^1$H NMR (500 MHz, MeOD) δ 7.67 (s, 1H), 7.54 (d, J=9.3 Hz, 1H), 7.41 (t, J=7.6 Hz, 1H), 7.32 (d, J=7.8 Hz, 1H), 7.14-7.08 (m, 4H), 7.02 (d, J=7.5 Hz, 1H), 6.61 (d, J=9.3 Hz, 1H), 5.68-5.59 (m, 1H), 5.38-5.31 (m, 1H), 3.36-3.33 (m, 1H), 3.28-3.25 (m, 1H), 2.95-2.90 (m, 1H), 2.85-2.81 (m, 7H), 2.61 (dd, J=14.8, 4.2 Hz, 1H), 2.52-2.47 (m, 1H), 2.05-1.94 (m, 7H), 1.91-1.81 (m, 1H), 1.43-1.41 (m, 1H), 0.92 (t, J=7.2 Hz, 6H).

301

Preparation of Compounds BL1 and BL2 ((3S)-3-(2-(5-(2-(azetidin-1-yl)ethyl)-2-oxopyridin-1(2H)-yl)-4-methylpentanamido)-3-(4'-fluoro-2',6'-dimethyl-[1,1-biphenyl]-3-yl)propanoic acid)

Step 1: 5-(2-(azetidin-1-yl)ethyl)pyridin-2(1H)-one

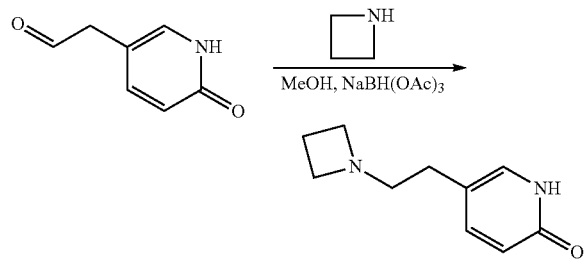

A mixture of methyl 2-(6-oxo-1,6-dihydropyridin-3-yl)acetaldehyde (1.0 g, 7.29 mmol) and azetidine (416 mg, 7.30 mmol) in MeOH (10 mL) was stirred at room temperature for 30 mins. NaBH(OAc)₃ (4.6 g, 21.9 mmol) was added and stirred at room temperature for 1 hour. The solvent was removed in vacuo and the residue purified by silica gel column (DCM:MeOH 2:1) to provide 5-(2-(azetidin-1-yl)ethyl)pyridin-2(1H)-one as yellow oil (800 mg). Yield 62% (ESI 179.1 (M+H)⁺).

Step 2: ethyl 2-(5-(2-(azetidin-1-yl)ethyl)-2-oxopyridin-1(2H)-yl)-4-methylpentanoate

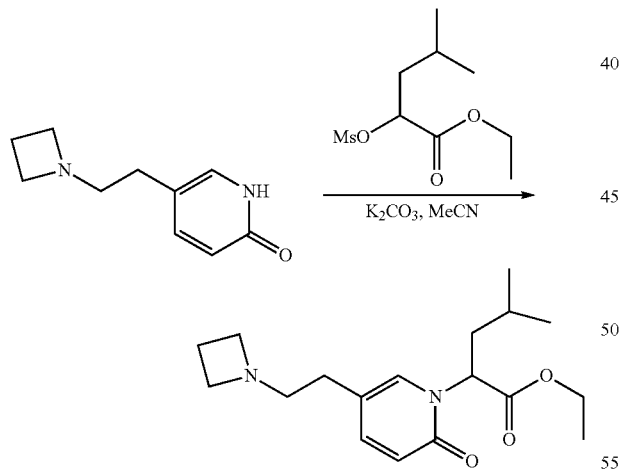

A mixture of 5-(2-(azetidin-1-yl)ethyl)pyridin-2(1H)-one (800 mg, 4.49 mmol), ethyl 4-methyl-2-(methylsulfonyloxy)pentanoate (2.2 g, 6.74 mmol) and K₂CO₃ (1.8 g, 13.47 mmol) in MeCN (40 mL) was stirred at 80° C. overnight. The mixture was filtered and washed with ACN (5 mL). The filtrate was concentrated in vacuo and the residue purified by reverse phase HPLC on a C18/80 g column (A: water/0.01% TFA, B: MeOH, 0~100%) to provide ethyl 2-(5-(2-(azetidin-1-yl)ethyl)-2-oxopyridin-1(2H)-yl)-4-methylpentanoate as a colorless oil (600 mg). Yield 42% (ESI 321.2 (M+H)⁺).

302

Step 3: 2-(5-(2-(azetidin-1-yl)ethyl)-2-oxopyridin-1(2H)-yl)-4-methylpentanoic acid

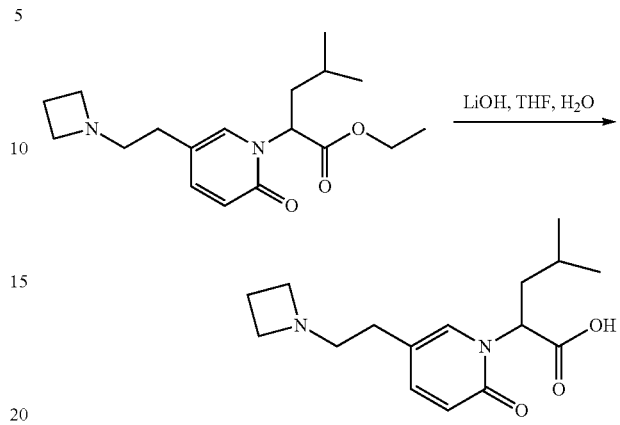

Ethyl 2-(5-(2-(azetidin-1-yl)ethyl)-2-oxopyridin-1(2H)-yl)-4-methylpentanoate (600 mg, 1.88 mmol) was treated with LiOH—H₂O (394 mg, 9.40 mmol) in THF (10 mL) and H₂O (2 mL) at room temperature for 1 hour. The mixture was acidified to pH=4~5 with 1N HCl.

The mixture was concentrated in vacuo and the residue purified by reverse phase HPLC on a C18/40 g column (A: water 10 mM NH₄HCO₃, B: MeOH, 0~100%) to give 24542-(azetidin-1-yl)ethyl)-2-oxopyridin-1(2H)-yl)-4-methylpentanoic acid as red solid (150 mg). Yield 27% (ESI 293.2 (M+H)⁺).

Step 4: ethyl (S)-3-((tert-butoxycarbonyl)amino)-3-(4'-fluoro-2',6'-dimethyl-[1,1-biphenyl]-3-yl)propanoate

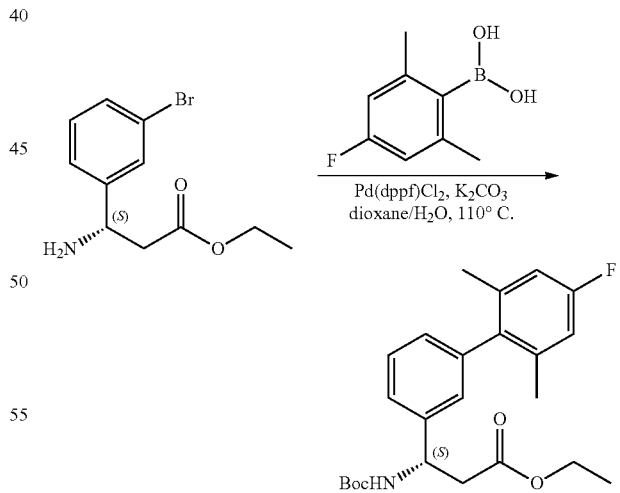

To a mixture of ethyl (S)-3-amino-3-(3-bromophenyl)propanoate (200 mg, 0.54 mmol), (4-fluoro-2,6-dimethylphenyl)boronic acid (110 mg, 0.65 mmol) and K₂CO₃ (224 mg, 1.62 mmol) in dioxane (6 mL) in H₂O (1.5 mL) was added PdCl₂(dppf) (40 mg, 0.054 mmol). The mixture was heated to 110° C. for 2 hours under nitrogen atmosphere. Water (20 mL) was added and the solution was extracted with EtOAc (20 mL×3). The combined organic phases were concentrated in vacuo and the residue purified by silica gel column (15% EtOAc in pet ether) to give ethyl (S)-3-((tert-butoxycarbonyl)amino)-3-(4'-fluoro-2',6'-dimethyl[1,1'-biphenyl]-3-yl)propanoate as a colorless oil (190 mg). Yield 80% (ESI 316.1 [M-100+H]$^+$).

Step 5: ethyl (S)-3-amino-3-(4'-fluoro-2',6'-dimethyl-[1,1'-biphenyl]-3-yl)propanoate

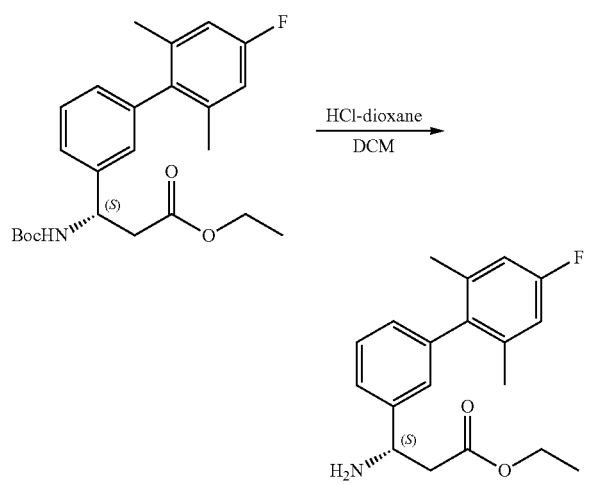

To a mixture of ethyl (S)-3-((tert-butoxycarbonyl)amino)-3-(4'-fluoro-2',6'-dimethyl-[1,1'-biphenyl]-3-yl)propanoate (90 mg, 0.29 mmol) in DCM (3 mL) was added HCl-dioxane (4M, 1 mL). The mixture was stirred at room temperature for 2 hours and concentrated in vacuo to give ethyl (S)-3-amino-3-(4'-fluoro-2',6'-dimethyl-[1,1'-biphenyl]-3-yl)propanoate as a white solid (68 mg) used without further purification. Yield 99% (ESI 316.1 [M+H]+).

Step 6: ethyl (3S)-3-(2-(5-(2-(azetidin-1-yl)ethyl)-2-oxopyridin-1(2H)-yl)-4-methylpentanamido)-3-(4'-fluoro-2',6'-dimethyl-[1,1'-biphenyl]-3-yl)propanoate

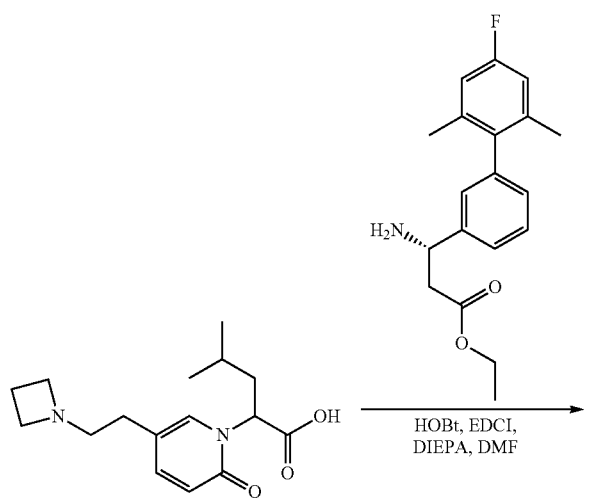

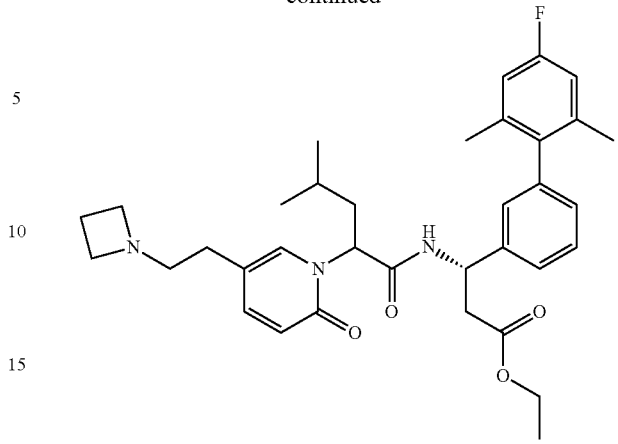

A mixture of 2-(5-(2-(azetidin-1-yl)ethyl)-2-oxopyridin-1(2H)-yl)-4-methylpentanoic acid (53 mg, 0.18 mmol), ethyl (S)-3-amino-3-(4'-fluoro-2',6'-dimethyl-[1,1'-biphenyl]-3-yl)propanoate (68 mg, 0.22 mmol), EDCI (52 mg, 0.27 mmol), HOBt (36 mg, 0.27 mmol) and DIEA (70 mg, 0.54 mmol) in DMF (4 mL) was stirred at room temperature for 6 hours. The mixture was concentrated in vacuo and the residue purified by reverse phase HPLC on a C18/40 g column (A: water 10 mM NH$_4$HCO$_3$, B: MeOH, 0~100%) to give (3S)-3-(2-(5-(2-(azetidin-1-yl)ethyl)-2-oxopyridin-1(2H)-yl)-4-methylpentanamido)-3-(4'-fluoro-2',6'-dimethyl-[1,1'-biphenyl]-3-yl)propanoate as a yellow oil (50 mg). Yield 47% (ESI 590.2 (M+H)$^+$).

Step 8: (3S)-3-(2-(5-(2-(azetidin-1-yl)ethyl)-2-oxopyridin-1(2H)-yl)-4-methylpentanamido)-3-(4'-fluoro-2',6'-dimethyl-[1,1'-biphenyl]-3-yl)propanoic acid

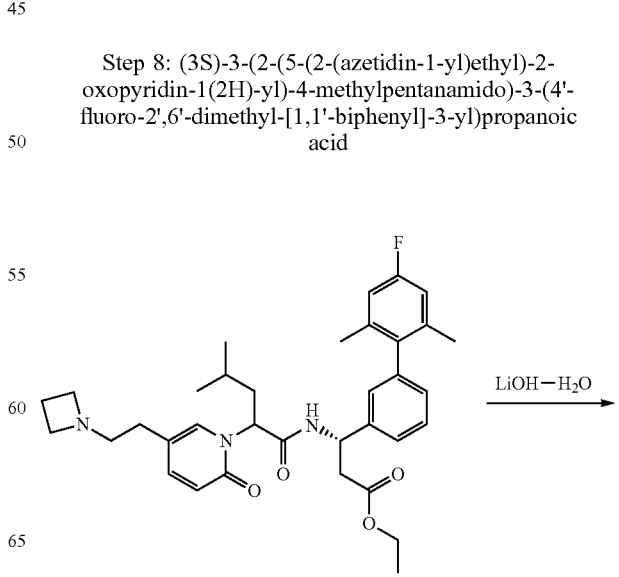

-continued

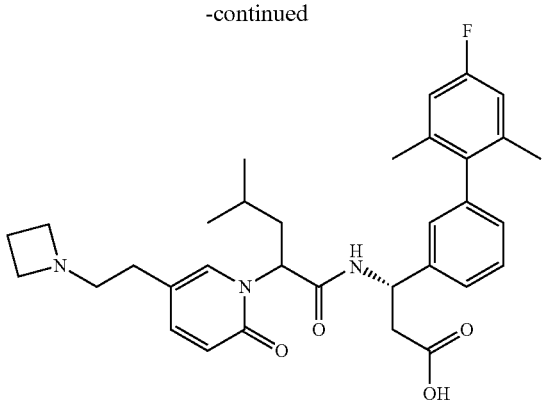

Methyl (3S)-3-(2-(5-(2-(azetidin-1-yl)ethyl)-2-oxopyridin-1(2H)-yl)-4-methylpentanamido)-3-(4'-fluoro-2',6'-dimethyl-[1,1'-biphenyl]-3-yl)propanoate (50 mg, 0.085 mmol) was treated with LiOH—H$_2$O (11 mg, 0.255 mmol) in THF (4 mL) and H$_2$O (1 mL) at room temperature for 3 hours. The reaction mixture was acidified to pH 4~5 with 1N HCl. The solvent was removed in vacuo and the residue purified by preparatory HPLC A to give the diastereomeric products BL1 (7.5 mg) and BL2 (10.5 mg) as white solids.

Compound BL1 ESI 562.2 (M+H)$^+$.

$^1$H NMR (500 MHz, MeOD) δ 7.64 (d, J=2.1 Hz, 1H), 7.52 (dd, J=9.4, 2.4 Hz, 1H), 7.42 (t, J=7.6 Hz, 1H), 7.35 (d, J=7.8 Hz, 1H), 7.09 (s, 1H), 7.01 (d, J=7.5 Hz, 1H), 6.85 (dd, J=9.6, 2.6 Hz, 2H), 6.61 (d, J=9.3 Hz, 1H), 5.63 (dd, J=10.4, 5.2 Hz, 1H), 5.22 (t, J=5.5 Hz, 1H), 4.02-4.01 (m, 2H), 3.89 (q, J=8.5 Hz, 2H), 3.40-3.35 (m, 2H), 2.78-2.75 (m, 2H), 2.67 (d, J=5.6 Hz, 2H), 2.33-2.27 (m, 2H), 2.11-1.94 (m, 8H), 1.49-1.37 (m, 1H), 0.95 (dd, J=17.8, 6.6 Hz, 6H).

Compound BL2 ESI 562.2 (M+H)$^+$.

$^1$H NMR (500 MHz, MeOD) δ 7.55 (d, J=2.1 Hz, 1H), 7.48 (dd, J=9.3, 2.4 Hz, 1H), 7.43 (t, J=7.6 Hz, 1H), 7.35 (d, J=7.8 Hz, 1H), 7.11 (s, 1H), 7.02 (d, J=7.5 Hz, 1H), 6.85 (d, J=9.7 Hz, 2H), 6.60 (d, J=9.3 Hz, 1H), 5.63 (dd, J=8.5, 7.0 Hz, 1H), 5.41 (dd, J=10.0, 3.9 Hz, 1H), 4.17-3.99 (m, 4H), 3.48-3.35 (m, 2H), 2.82-2.60 (m, 3H), 2.55-2.38 (m, 3H), 2.04-1.94 (m, 7H), 1.85-1.76 (m, 1H), 1.52-1.36 (m, 1H), 0.94-0.89 (m, 6H).

Preparation of Compounds BM1 and BM2 ((3S)-3-(2',6'-dimethyl-[1,1'-biphenyl]-3-yl)-3-(2-(5-(2-(dimethylamino)ethyl)-4-methyl-2-oxopyridin-1(2H)-yl)-4-methylpentanamido)propanoic acid)

Step 1: (E)-2-methoxy-5-(2-methoxyvinyl)-4-methylpyridine

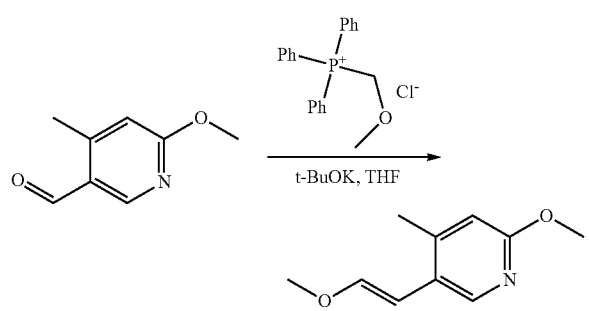

A mixture of (methoxymethyl)triphenyl phosphonium chloride (8.5 g, 24.8 mmol) and t-BuOK (4.6 g, 41.3 mmol) in THF (40 mL) was stirred at room temperature for 20 mins. 6-methoxy-4-methylnicotinaldehyde (2.5 g, 16.5 mmol) in 10 mL of THF was added and mixture stirred at room temperature for 2 hours. The reaction mixture was poured into 40 mL of water and extracted with EtOAc (50 mL×2). The organic phase was concentrated in vacuo and the residue purified by reverse phase HPLC on a C18/40 g column (A: water 10 mM NH$_4$HCO$_3$, B: MeOH, 0~100%) to give (E)-2-methoxy-5-(2-methoxyvinyl)-4-methylpyridine as a colorless oil (1.8 g). Yield 61% (ESI 180.1 (M+H)$^+$).

Step 2: 2-(6-methoxy-4-methylpyridin-3-yl)acetaldehyde

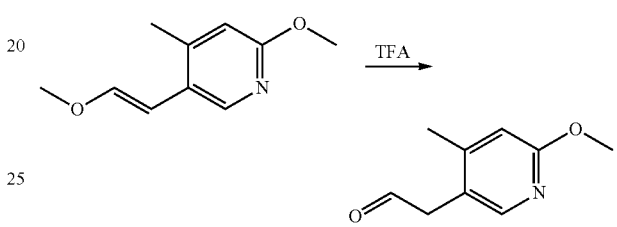

(E)-2-methoxy-5-(2-methoxyvinyl)-4-methylpyridine (1.8 g, 10 mmol) was treated with TFA (20 mL) at room temperature for 4 hours. The solvent was removed in vacuo to provide 2-(6-methoxy-4-methylpyridin-3-yl)acetaldehyde as red oil (1.5 g, crude) used without further purification. (ESI 166.1 (M+H)$^+$).

Step 3: 2-(6-methoxy-4-methylpyridin-3-yl)-N,N-dimethylethanamine

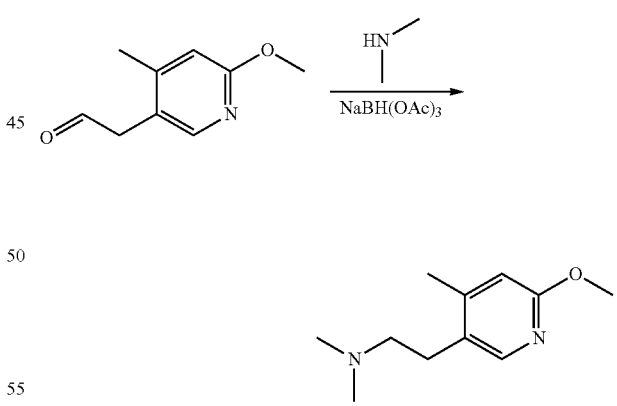

A mixture of 2-(6-methoxy-4-methylpyridin-3-yl)acetaldehyde (1.45 g, 8.78 mmol), dimethylamine (in THF, 17.5 mL, 35.72 mmol) and Achoo (0.8 g, 13.2 mmol) in DCE (30 mL) was stirred at room temperature for 15 mins. NaBH(OAc)$_3$ (3.71 g, 17.5 mmol) was added and stirred at room temperature for 3 hours. The solvent was removed in vacuo and the residue purified by silica gel column (DCM:MeOH 10:1) to provide 2-(6-methoxy-4-methylpyridin-3-yl)-N,N-dimethylethanamine as yellow oil (850 mg). Yield 50% (ESI 195.1 (M+H)$^+$).

307

Step 4: 5-(2-(dimethylamino)ethyl)-4-methylpyridin-2-ol

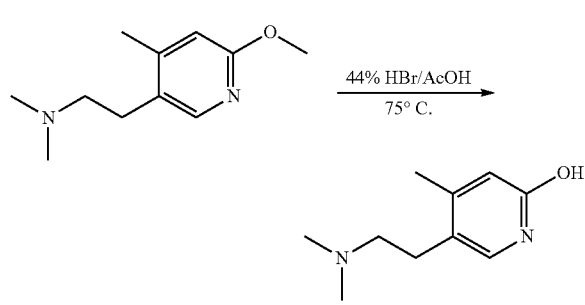

A mixture of 2-(6-methoxy-4-methylpyridin-3-yl)-N,N-dimethylethylamine (850 mg, 4.38 mmol) in HBr/AcOH (20 mL) was heated at 75° C. for 16 h. The solvent was removed in vacuo and the residue purified by reverse phase HPLC on a C18/40 g column (A: water 10 mM NH$_4$HCO$_3$, B: MeOH, 0~100%) to provide 5-(2-(dimethylamino)ethyl)-4-methylpyridin-2-ol as a red solid (650 mg). Yield 82% (ESI 181.1 (M+H)$^+$).

Step 5: ethyl 2-(5-(2-(dimethylamino)ethyl)-4-methyl-2-oxopyridin-1(2H)-yl)-4-methylpentanoate

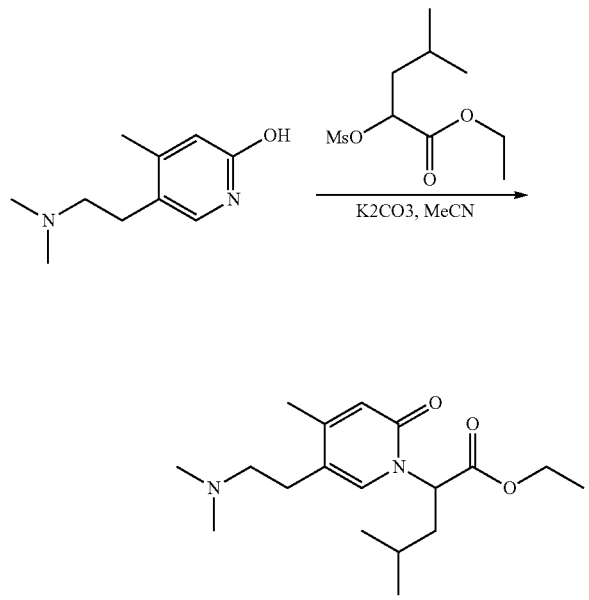

A mixture of 5-(2-(dimethylamino)ethyl)-4-methylpyridin-2-ol (650 g, 3.6 mmol), ethyl 4-methyl-2-(methylsulfonyloxy)pentanoate (1.71 g, 7.2 mmol) and K$_2$CO$_3$ (1.49 g, 10.8 mmol) in MeCN (20 mL) was stirred at 80° C. overnight. The solvent was removed in vacuo and the residue purified by reverse phase HPLC on a C18/40 g column (A: water 10 mM NH$_4$HCO$_3$, B: MeOH, 0~100%) to provide ethyl 2-(5-(2-(dimethylamino)ethyl)-4-methyl-2-oxopyridin-1(2H)-yl)-4-methylpentanoate (500 mg). Yield 43% (ESI 323.2 (M+H)$^+$).

308

Step 6: 2-(5-(2-(dimethylamino)ethyl)-4-methyl-2-oxopyridin-1(2H)-yl)-4-methylpentanoic acid

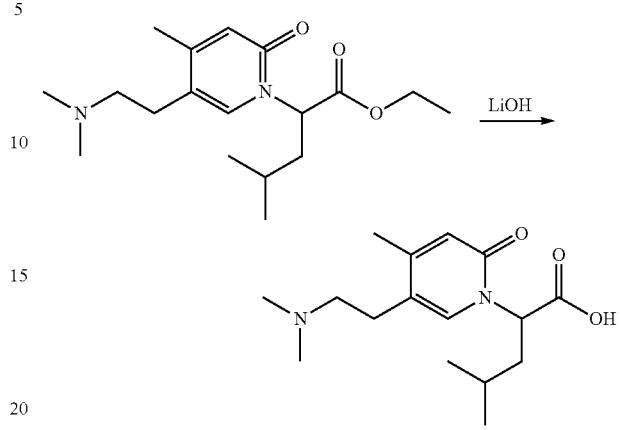

Ethyl 2-(5-(2-(dimethylamino)ethyl)-4-methyl-2-oxopyridin-1(2H)-yl)-4-methylpentanoate (500 mg, 1.55 mmol) was treated with LiOH—H$_2$O (260 mg, 6.2 mmol) in MeOH (10 mL) and H$_2$O (2 mL) at room temperature for 2 hours. The mixture was acidified to pH 4~5 with 1N HCl and purified by reverse phase HPLC on a C18/40 g column (A: water 10 mM NH$_4$HCO$_3$, B: MeOH, 0~100%) to give 2-(5-(2-(dimethylamino)ethyl)-4-methyl-2-oxopyridin-1(2H)-yl)-4-methylpentanoic acid as white solid (420 mg). Yield 92% (ESI 295.2 (M+H)$^+$).

Step 7: (3S)-methyl 3-(2-(3-(2-(dimethylamino)ethyl)-4-methyl-6-oxocyclohexa-2,4-dienyl)-4-methylpentanamido)-3-(2',6'-dimethylbiphenyl-3-yl)propanoate

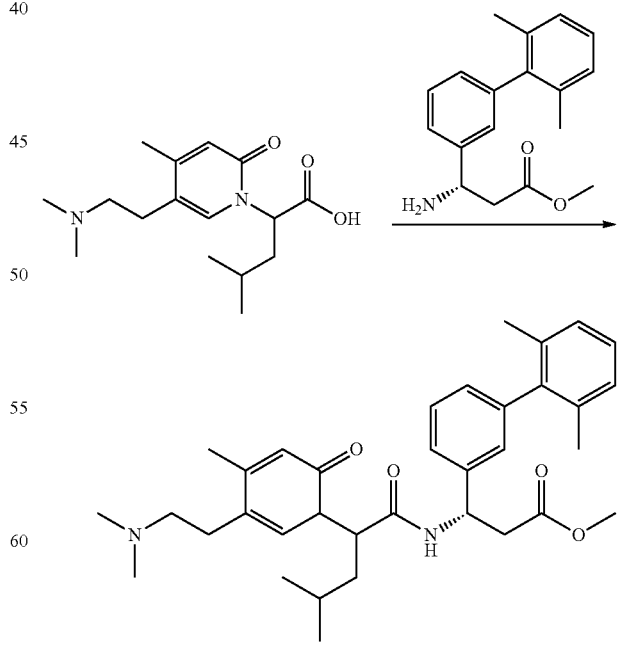

A mixture of 2-(5-(2-(dimethylamino)ethyl)-4-methyl-2-oxopyridin-1(2H)-yl)-4-methylpentanoic acid (100 mg, 0.34 mmol), (S)-methyl 3-amino-3-(2',6'-dimethylbiphenyl-3-yl)propanoate (101 mg, 0.34 mmol), EDCI (130 mg, 0.68 mmol), HOBt (92 mg, 0.68 mmol) and DIEA (175 mg, 1.36 mmol) in DMF (4 mL) was stirred at 40° C. for 2 hours.

The mixture was concentrated and purified by reverse phase HPLC on a C18/40 g column (A: water 10 mM NH$_4$HCO$_3$, B: MeOH, 0~100%) to give (3S)-methyl 3-(2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoate as a red oil (130 mg). Yield 67% (ESI 574.2 (M+H)$^+$).

Step 8: (3S)-3-(2-(5-(2-(dimethylamino)ethyl)-4-methyl-2-oxopyridin-1(2H)-yl)-4-methylpentanamido)-3-(2',6'-dimethylbiphenyl-3-yl)propanoic acid

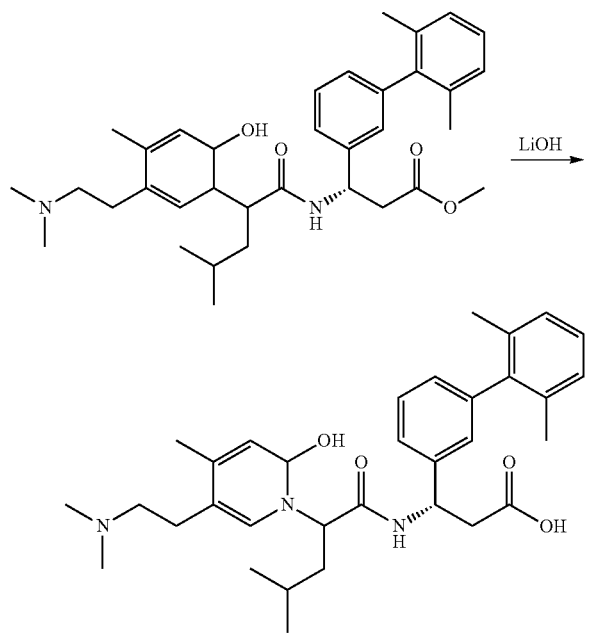

(3 S)-methyl 3-(2-(5-(2-(dimethylamino)ethyl)-4-methyl-2-oxopyridin-1(2H)-yl)-4-methylpentanamido)-3-(2',6'-dimethylbiphenyl-3-yl)propanoate (130 mg, 0.23 mmol) was treated with LiOH—H$_2$O (39 mg, 0.92 mmol) in MeOH (3 mL) and H$_2$O (1 mL) at room temperature for 2 hours. The reaction mixture was acidified to pH 4~5 with 1N HCl. The solvent was removed in vacuo and the residue purified by Prep-HPLC A (30-60% MeCN) to give the diastereomeric products BM1 (36.9 mg) and BM2 (42.3 mg) as white solids.

Compound BM1ESI 546.2 (M+H)$^+$.

$^1$H NMR (500 MHz, MeOD) δ 7.52 (s, 1H), 7.40 (t, J=7.6 Hz, 1H), 7.32 (d, J=7.7 Hz, 1H), 7.17-7.11 (m, 1H), 7.08 (d, J=7.5 Hz, 2H), 7.05 (s, 1H), 7.00 (d, J=7.5 Hz, 1H), 6.38 (s, 1H), 5.65 (t, J=8.1 Hz, 1H), 5.37 (t, J=6.7 Hz, 1H), 5.18 (d, J=57.3 Hz, 1H), 4.01 (d, J=9.4 Hz, 2H), 3.80-3.55 (m, 2H), 3.05 (s, 2H), 2.78 (d, J=6.7 Hz, 2H), 2.66-2.61 (m, 2H), 2.25 (s, 3H), 2.00-1.87 (m, 8H), 1.42-1.38 (m, 1H), 0.95-0.91 (m, 6H).

Compound BM2ESI 546.2 (M+H)$^+$.

1H NMR (500 MHz, MeOD) δ 7.56 (s, 1H), 7.42 (t, J=7.6 Hz, 1H), 7.34 (d, J=7.8 Hz, 1H), 7.12 (m, J=18.3, 11.4, 6.5 Hz, 4H), 7.02 (d, J=7.5 Hz, 1H), 6.46 (s, 1H), 5.62 (t, J=7.7 Hz, 1H), 5.41-5.37 (m, 1H), 3.32-3.26 (m, 1H), 3.24-3.12 (m, 1H), 3.00-2.87 (m, 2H), 2.84 (s, 6H), 2.63-2.58 (m, 1H), 2.58-2.45 (m, 1H), 2.28 (s, 3H), 2.05-1.90 (m, 7H), 1.83-1.70 (m, 1H), 1.49-1.29 (m, 1H), 0.91-0.86 (m, 6H).

Preparation of Compounds BN1 and BN2 ((3S)-3-(2',6'-dimethyl-[1,1'-biphenyl]-3-yl)-3-(2-(5-(2-(3-fluoroazetidin-1-yl)ethyl)-2-oxopyridin-1(2H)-yl)-4-methylpentanamido)propanoic acid)

Step 1: 5-(2-(3-fluoroazetidin-1-yl)ethyl)pyridin-2(1H)-one

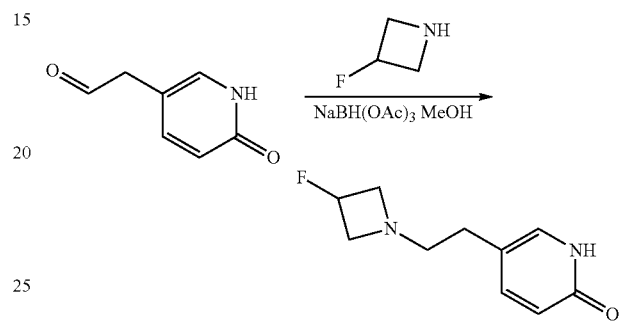

A mixture of 2-(6-oxo-1,6-dihydropyridin-3-yl)acetaldehyde (1.5 g, 11 mmol), AcOH (0.8 g, 13.2 mmol) and 3-fluoroazetidine hydrochloride (1.47 g, 13.2 mmol) in MeOH (30 mL) was stirred at room temperature for 30 mins. NaBH(OAc)$_3$ (4.66 g, 22 mmol) was added and stirred at room temperature for 3 hours. The solvent was removed in vacuo and the residue was purified by reverse phase HPLC on a C18/120 g column (A: water 10 mM NH$_4$HCO$_3$, B: MeOH, 0~100%) to provide 5-(2-(3-fluoroazetidin-1-yl)ethyl)pyridin-2(1H)-one as yellow oil (2 g, crude). (ESI 197.2 (M+H)$^+$).

Step 4: ethyl 2-(5-(2-(3-fluoroazetidin-1-yl)ethyl)-2-oxopyridin-1(2H)-yl)-4-methylpentanoate

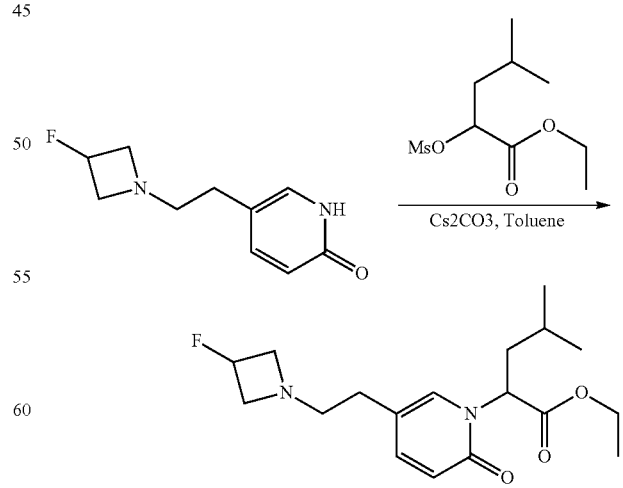

A mixture of 5-(2-(3-fluoroazetidin-1-yl)ethyl)pyridin-2(1H)-one (1.9 g, 9.7 mmol), ethyl 4-methyl-2-(methylsulfonyloxy)pentanoate (3.45 g, 14.5 mmol) and Cs$_2$CO$_3$ (9.5 g, 29.1 mmol) in Toluene (40 mL) was stirred 110° C. overnight. The solvent was removed in vacuo and the residue purified by reverse phase HPLC on a C18/120 g column (A: water 10 mM NH₄HCO₃, B: MeOH, 0~100%) to provide ethyl 2-(5-(2-(3-fluoroazetidin-1-yl)ethyl)-2-oxopyridin-1(2H)-yl)-4-methylpentanoate as a yellow oil (650 mg). Yield 20% (ESI 339.1 (M+H)$^+$).

Step 5: 2-(5-(2-(3-fluoroazetidin-1-yl)ethyl)-2-oxopyridin-1(2H)-yl)-4-methylpentanoic acid

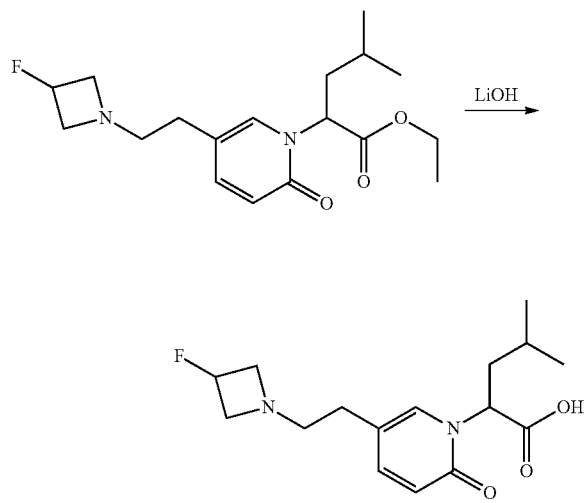

Ethyl 2-(5-(2-(3-fluoroazetidin-1-yl)ethyl)-2-oxopyridin-1(2H)-yl)-4-methylpentanoate (650 mg, 1.92 mmol) was treated with LiOH—H₂O (322 mg, 7.68 mmol) in MeOH (10 mL) and H₂O (2.5 mL) at room temperature for 2 hours. The mixture was acidified to pH=4~5 with 1N HCl, purified by reverse phase HPLC on a C18/40 g column (A: water 10 mM NH₄HCO₃, B: MeOH, 0~100%) to give 2-(5-(2-(3-fluoroazetidin-1-yl)ethyl)-2-oxopyridin-1(2H)-yl)-4-methylpentanoic acid as a white solid (350 mg). Yield 59% (ESI 311.2 (M+H)$^+$).

Step 6: (3S)-methyl 3-(2',6'-dimethylbiphenyl-3-yl)-3-(2-(5-(2-(3-fluoroazetidin-1-yl)ethyl)-2-oxopyridin-1(2H)-yl)-4-methylpentanamido)propanoate

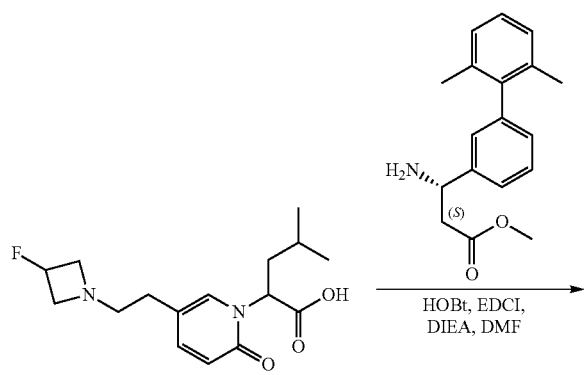

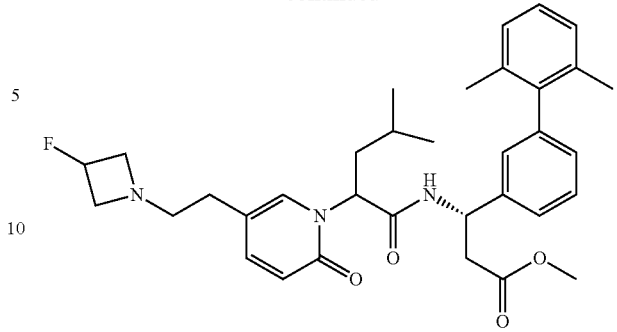

A mixture of 2-(5-(2-(3-fluoroazetidin-1-yl)ethyl)-2-oxopyridin-1(2H)-yl)-4-methylpentanoic acid (120 mg, 0.39 mmol), (S)-methyl 3-amino-3-(2',6'-dimethylbiphenyl-3-yl)propanoate (133 mg, 0.47 mmol), EDCI (150 mg, 0.78 mmol), HOBt (105 mg, 0.78 mmol) and DIEA (201 mg, 1.56 mmol) in DMF (4 mL) was stirred at 45° C. for 2 hours. The mixture was purified by reverse phase HPLC on a C18/40 g column (A: water 10 mM NH₄HCO₃, B: MeOH, 0~100%) to give (3S)-methyl 3-(2',6'-dimethylbiphenyl-3-yl)-3-(2-(5-(2-(3-fluoroazetidin-1-yl)ethyl)-2-oxopyridin-1(2H)-yl)-4-methylpentanamido)propanoate as a oil (120 mg). Yield 52% (ESI 576.2 (M+H)$^+$).

Step 7: (3S)-3-(2',6'-dimethylbiphenyl-3-yl)-3-(2-(5-(2-(3-fluoroazetidin-1-yl)ethyl)-2-oxopyridin-1(2H)-yl)-4-methylpentanamido)propanoic acid

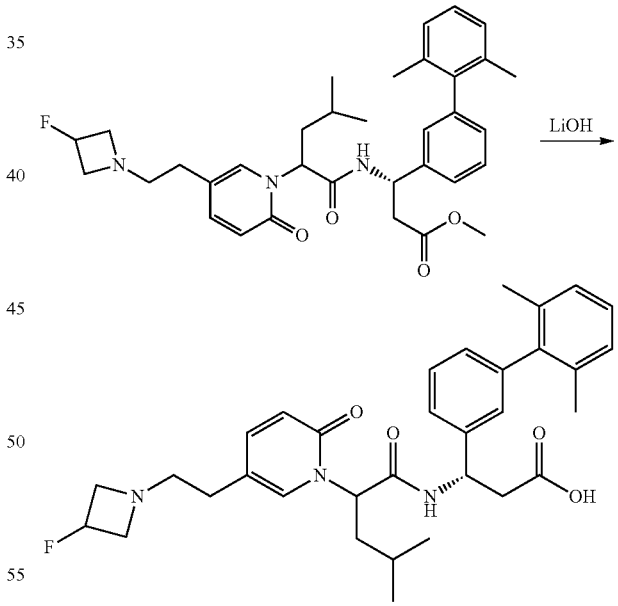

(3S)-methyl 3-(2',6'-dimethylbiphenyl-3-yl)-3-(2-(5-(2-(3-fluoroazetidin-1-yl)ethyl)-2-oxopyridin-1(2H)-yl)-4-methylpentanamido)propanoate (120 mg, 0.2 mmol) was treated with LiOH—H₂O (34 mg, 0.8 mmol) in MeOH (4 mL) and H₂O (1 mL) at room temperature for 2 hours. The reaction mixture was acidified to pH 4~5 with 1N HCl. The solvent was removed in vacuo and the residue purified by preparatory HPLC A (30-60% MeCN) to give the diastereomeric products BN1 (30 mg) and BN2 (34.9 mg) as white solids.

Compound BN1 ESI 562.0 (M+H)⁺.

1H NMR (500 MHz, MeOD) δ 7.59 (d, J=2.0 Hz, 1H), 7.46-7.42 (m, 1H), 7.40 (t, J=7.6 Hz, 1H), 7.31 (d, J=7.8 Hz, 1H), 7.17-7.12 (m, 1H), 7.11-7.06 (m, 2H), 7.04 (s, 1H), 7.01 (d, J=7.5 Hz, 1H), 6.54 (d, J=9.3 Hz, 1H), 5.68 (t, J=8.1 Hz, 1H), 5.28 (t, J=6.2 Hz, 1H), 5.16-5.11 (m, 1H), 4.04-4.00 (m, 2H), 3.78-3.61 (m, 2H), 3.22-3.06 (m, 2H), 2.78-2.69 (m, 2H), 2.65-2.59 (m, 2H), 1.97-1.93 (m, 8H), 1.45-1.39 (m, 1H), 0.95-0.92 (m, 6H).

Compound BN2 ESI 562.0 (M+H)⁺.

1H NMR (500 MHz, MeOD) δ 7.55 (s, 1H), 7.48-7.45 (m, 1H), 7.43 (t, J=7.6 Hz, 1H), 7.34 (d, J=7.8 Hz, 1H), 7.12-7.08 (m, 4H), 7.04 (d, J=7.5 Hz, 1H), 6.59 (d, J=9.3 Hz, 1H), 5.66-5.61 (m, 1H), 5.40-5.36 (m, 1H), 5.37-5.19 (m, 1H), 4.31 (d, J=42.0 Hz, 2H), 3.95 (d, J=10.3 Hz, 2H), 3.32 (s, 2H), 2.79-2.63 (m, 3H), 2.56-2.51 (m, 1H), 2.04-1.91 (m, 7H), 1.86-1.72 (m, 1H), 1.41-1.38 (m, 1H), 0.92-0.88 (m, 6H).

Preparation of Compounds BO1 and BO2 ((3S)-3-(2-(5-(2-(dimethylamino)ethyl)-2-oxo-4-(trifluoromethyl)pyridin-1(2H)-yl)-4-methylpentanamido)-3-(2′,6′-dimethylbiphenyl-3-yl)propanoic acid)

Step 1: (E)-2-methoxy-5-(2-methoxyvinyl)-4-(trifluoromethyl)pyridine

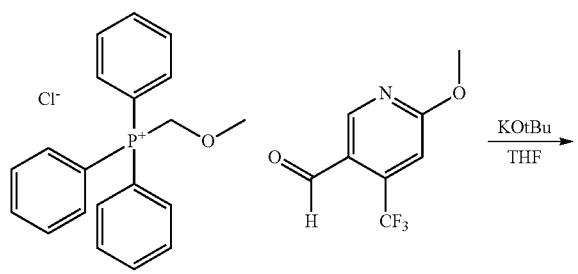

To a solution of (methoxymethyl)triphenylphosphonium chloride (1.0 g, 2.95 mmol) in THF (13.406 mL) at 0 C is added potassium tert-butoxide (376 mg, 3.35 mmol). After stirring the reaction for 1 hour at 0° C., a solution of 6-methoxy-4-(trifluoromethyl)nicotinaldehyde (550 mg, 2.68 mmol) in THF (6.5 mL) was added. The reaction was allowed to stir overnight at room temperature and quenched with a NH₄Cl solution. The mixture was extracted (EtOAc× 3), concentrated and purify by silica gel chromatography (0-100 Ethyl acetate: Hexanes) to provide (E)-2-methoxy-5-(2-methoxyvinyl)-4-(trifluoromethyl)pyridine (450 mgs). Yield 72% (ESI 234.2 (M+H)⁺).

Step 2: 2-(6-methoxy-4-(trifluoromethyl)pyridin-3-yl)acetaldehyde

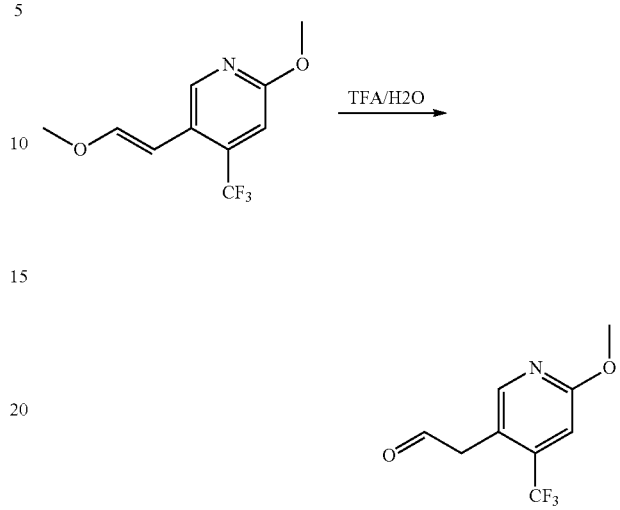

To a solution of (E)-2-methoxy-5-(2-methoxyvinyl)-4-(trifluoromethyl)pyridine (450 mg, 1.930 mmol) in DCM (29.689 mL) was added TFA (0.595 mL, 7.72 mmol) and water (0.591 mL, 32.8 mmol). The reaction was stirred for 18 hrs at 45° C. The reaction was diluted with DCM and quenched with NaHCO₃. The mixture was washed with water, dried with Na₂SO₄, filtered and concentrated to provide 2-(6-methoxy-4-(trifluoromethyl)pyridin-3-yl)acetaldehyde (343 mgs) used without further purification. Yield 81% (ESI 220.18 (M+H)⁺).

Step 3: 2-(6-methoxy-4-(trifluoromethyl)pyridin-3-yl)-N,N-dimethylethan-1-amine

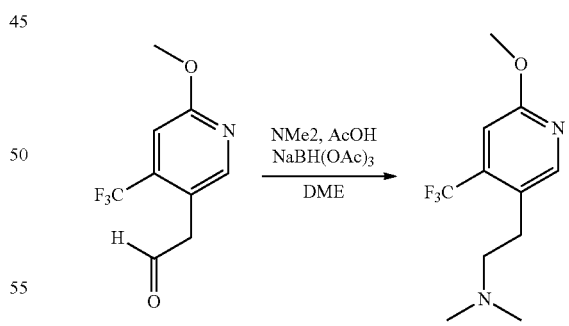

To a solution of 2-(6-methoxy-4-(trifluoromethyl)pyridin-3-yl)acetaldehyde (0.34 g, 1.6 mmol) in DCE (7.8 mL) is added dimethylamine (3.9 mL, 7.8 mmol) and acetic acid (0.05 mL, 0.78 mmol) and stirred for 1 hour. To the solution was added sodium triacetoxyborohydride (0.6 g, 3.1 mmol). The reaction was allowed to stir for 12 hours then concentrated and purify by silica gel chromatography (0~35% DCM (1% TEA):MeOH 0-30%) to provide 2-(6-methoxy-4-(trifluoromethyl)pyridin-3-yl)-N,N-dimethylethan-1-amine (305 mg). Yield 79% (ESI 249.27 (M+H)⁺).

Step 4: 5-(2-(dimethylamino)ethyl)-4-(trifluoromethyl)pyridin-2(1H)-one

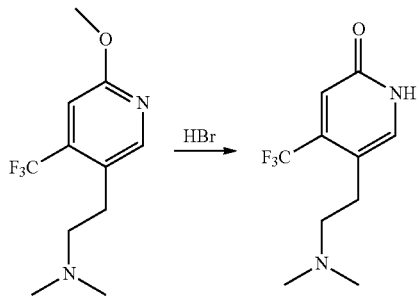 [SMILES: COc1cc(C(F)(F)F)c(CCN(C)C)cn1 ; Br ; CN(C)CCc1c[nH]c(=O)cc1C(F)(F)F]

HBr (33% in Acetic Acid) (4.04 mL, 24.57 mmol) was added to 2-(6-methoxy-4-(trifluoromethyl)pyridin-3-yl)-N,N-dimethylethan-1-amine (0.305 g, 1.229 mmol) and heated to 75° C. in a pressure vessel. After 4 hours, the solvent was removed and the residue purify by silica gel chromatography (0-25% DCM:MeOH with 1% TEA as a modifier) to provide 5-(2-(dimethylamino)ethyl)-4-(trifluoromethyl)pyridin-2(1H)-one (219 mg). Yield 76% (ESI 235.15 (M+H)$^+$). $^1$H NMR (400 MHz, MeOD) δ 7.56 (s, 1H), 6.85 (s, 1H), 2.76 (m, 2H), 2.61 (m, 1H), 2.37 (m, 6H)

Step 5: ethyl 2-(5-(2-(dimethylamino)ethyl)-2-oxo-4-(trifluoromethyl)pyridin-1(2H)-yl)-4-methylpentanoate

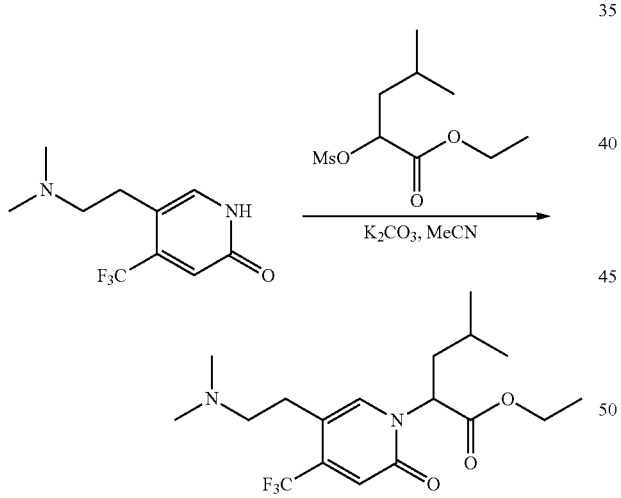

A mixture of 5-(2-(dimethylamino)ethyl)-4-(trifluoromethyl)pyridin-2(1H)-one (685 mg, 2.92 mmol), K$_2$CO$_3$ (1.60 g, 11.55 mmol) and ethyl 4-methyl-2-(methylsulfonyloxy)pentanoate (1.60 g, 6.70 mmol) in CH$_3$CN (60 mL) was stirred at 85° C. overnight. The solvent was concentrated in vacuo and the residue was purified by silica gel column (DCM:MeOH 2:1) to give ethyl 2-(5-(2-(dimethylamino)ethyl)-2-oxo-4-(trifluoromethyl)pyridin-1(2H)-yl)-4-methylpentanoate as brown oil (390 mg). Yield 35% (ESI 377.2 (M+H)$^+$). $^1$H NMR (500 MHz, MeOD) δ 7.84 (s, 1H), 6.68 (s, 1H), 5.51 (dd, J=11.0, 5.0 Hz, 1H), 4.23 (q, J=7.0 Hz, 2H), 2.77 (t, J=8.0 Hz, 2H), 2.53 (t, J=8.0 Hz, 2H), 2.33 (s, 6H), 2.18-2.12 (m, 1H), 2.08-2.02 (m, 1H), 1.46-1.38 (m, 1H), 1.27 (t, J=7.0 Hz, 3H), 0.97 (t, J=7.0 Hz, 6H).

Step 6: 2-(5-(2-(dimethylamino)ethyl)-2-oxo-4-(trifluoromethyl)pyridin-1(2H)-yl)-4-methylpentanoic acid

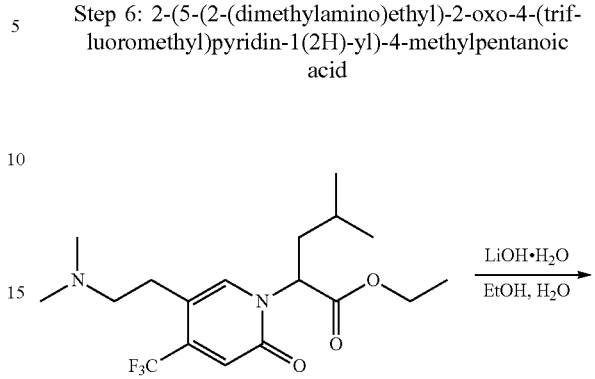

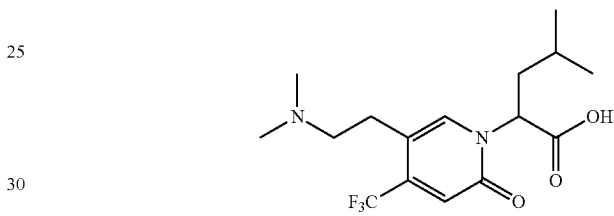

Ethyl 2-(5-(2-(dimethylamino)ethyl)-2-oxo-4-(trifluoromethyl)pyridin-1(2H)-yl)-4-methylpentanoate (390 mg, 1.0 mmol) was treated with LiOH monohydrate (435 mg, 10.36 mmol) in EtOH (10 mL) and H$_2$O (1 mL) at room temperature for 1 hour. The mixture was acidified to pH 4~5 with 1N HCl aqueous solution. The mixture was concentrated in vacuo and purified by silica gel column (MeOH:EtOAc 1:2) to give 2-(5-(2-(dimethylamino)ethyl)-2-oxo-4-(trifluoromethyl)pyridin-1(2H)-yl)-4-methylpentanoic acid as an oil (358 mg). Yield 99% (ESI 349.1 (M+H)$^+$).

Step 7: (3S)-methyl 3-(2-(5-(2-(dimethylamino)ethyl)-2-oxo-4-(trifluoromethyl)pyridin-1(2H)-yl)-4-methylpentanamido)-3-(2',6'-dimethylbiphenyl-3-yl)propanoate

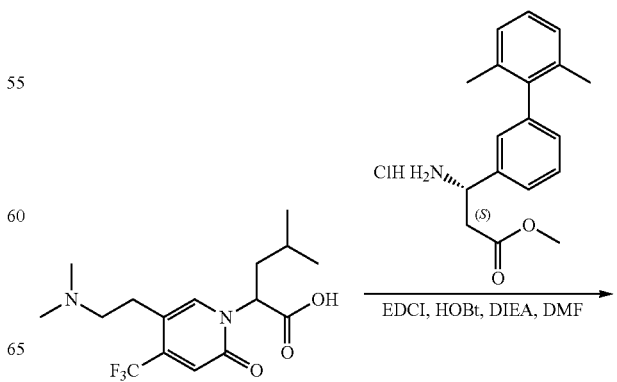

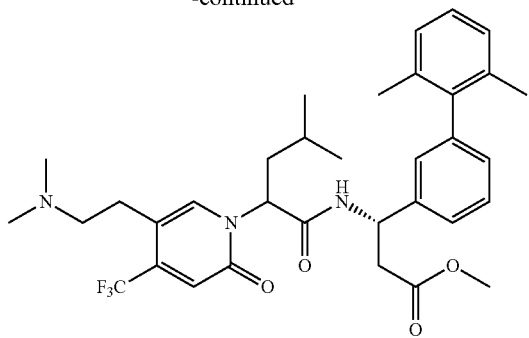

A mixture of 2-(5-(2-(dimethylamino)ethyl)-2-oxo-4-(trifluoromethyl)pyridin-1(2H)-yl)-4-methylpentanoic acid (167 mg, 0.25 mmol), (S)-methyl 3-amino-3-(2',6'-dimethylbiphenyl-3-yl)propanoate hydrochloride (167 mg, 0.52 mmol), EDCI (196 mg, 1.01 mmol), HOBt (135 mg, 1.00 mmol) and DIEA (0.83 mL, 5.00 mmol) in DMF (3 mL) was stirred at room temperature for 9 hours. The mixture was concentrated and purified by reverse phase HPLC on a C18/40 g column (A: water 10 mM $NH_4HCO_3$, B: MeOH, 0~92%) to give (3S)-methyl 3-(2-(5-(2-(dimethylamino)ethyl)-2-oxo-4-(trifluoromethyl)pyridin-1(2H)-yl)-4-methylpentanamido)-3-(2',6'-dimethylbiphenyl-3-yl)propanoate as brown solid (99 mg). Yield 64% (ESI 614.2 $(M+H)^+$).

Step 8: (3S)-3-(2-(5-(2-(dimethylamino)ethyl)-2-oxo-4-(trifluoromethyl)pyridin-1(2H)-yl)-4-methylpentanamido)-3-(2',6'-dimethylbiphenyl-3-yl)propanoic acid

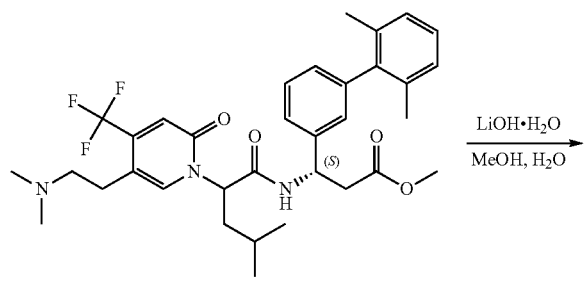

(3S)-methyl 3-(2-(5-(2-(dimethylamino)ethyl)-2-oxo-4-(trifluoromethyl)pyridin-1(2H)-yl)-4-methylpentanamido)-3-(2',6'-dimethylbiphenyl-3-yl)propanoate (99 mg, 0.16 mmol) in MeOH (10 mL) and $H_2O$ (0.1 mL) was treated with LiOH monohydrate (68 mg, 1.62 mmol) at room temperature for 20 hours. The reaction mixture was acidified to pH 4~5 with 1N HCl. The mixture was concentrated in vacuo and purified by prep-HPLC A to give the diastereomeric products BO1 (26 mg) and BO2 (28 mg) as white solids.

Compound BO1 ESI 600.2 $(M+H)^+$.
$^1$H NMR (500 MHz, MeOD) δ 7.89 (s, 1H), 7.36 (t, J=8.0 Hz, 1H), 7.31 (d, J=8.0 Hz, 1H), 7.10 (t, J=7.5 Hz, 1H), 7.05 (m, 3H), 6.96 (d, J=8.0 Hz, 1H), 6.80 (s, 1H), 5.70 (t, J=8.0 Hz, 1H), 5.35 (t, J=7.5 Hz, 1H), 3.07-3.00 (m, 2H), 2.95-2.90 (m, 2H), 2.74-2.69 (m, 8H), 1.98 (t, J=7.5 Hz, 2H), 1.95 (s, 3H), 1.87 (s, 3H), 1.47-1.39 (m, 1H), 0.96 (d, J=6.5 Hz, 3H), 0.94 (d, J=6.5 Hz, 3H).

Compound BO2 ESI 600.2 $(M+H)^+$.
$^1$H NMR (500 MHz, MeOD) δ 7.84 (s, 1H), 7.41 (t, J=7.5 Hz, 1H), 7.34 (d, J=8.0 Hz, 1H), 7.12 (t, J=7.5 Hz, 2H), 7.07 (d, J=7.5 Hz, 2H), 7.02 (d, J=7.0 Hz, 1H), 6.89 (s, 1H), 5.62 (t, J=8.0 Hz, 1H), 5.48-5.45 (m, 1H), 3.27-3.22 (m, 1H), 3.20-3.15 (m, 1H), 2.97 (t, J=7.0 Hz, 2H), 2.79 (s, 6H), 2.67-2.63 (m, 1H), 2.58-2.53 (m, 1H), 2.00-1.94 (m, 7H), 1.74-1.68 (m, 1H), 1.43-1.35 (m, 1H), 0.90-0.88 (m, 6H).

Preparation of Compounds BP1 and BP2 ((3S)-3-(2',6'-dimethyl-[1,1'-biphenyl]-3-yl)-3-(2-(5-(2-(3-fluoroazetidin-1-yl)ethyl)-4-methyl-2-oxopyridin-1(2H)-yl)-4-methylpentanamido)propanoic acid)

Step 1: 6-hydroxy-4-methylnicotinaldehyde

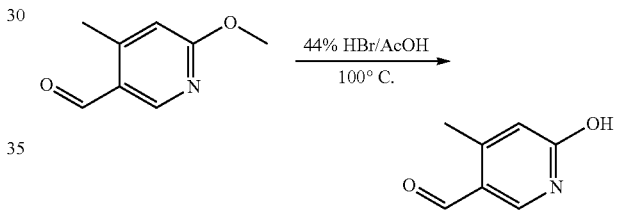

A mixture of 6-methoxy-4-methylnicotinaldehyde (5 g, 33 mmol) in HBr/AcOH (50 mL) was heated at 100° C. for 4 hours. The solvent was removed in vacuo and the residue purified by silica gel column (EtOAc:MeOH 4:1) to provide 6-hydroxy-4-methylnicotinaldehyde as a red solid (6 g, crude). (ESI 138.1 $(M+H)^+$).

Step 2: (E)-5-(2-methoxyvinyl)-4-methylpyridin-2-ol

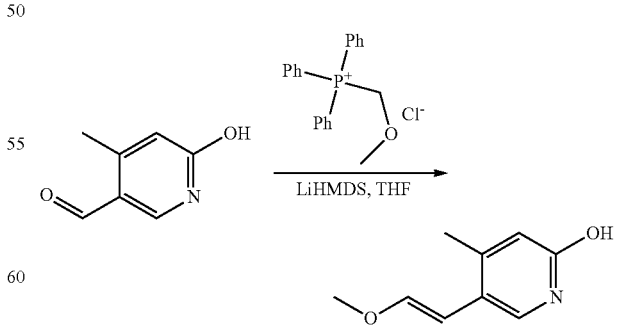

To a mixture of (methoxymethyl)triphenylphosphonium chloride (10.3 g, 30 mmol) in THF (40 mL) under $N_2$ atmosphere at 0° C. was added LiHMDS (38 mL, 50 mmol) dropwise and stirred at 0° C. for 20 mins. 6-hydroxy-4- methylnicotinaldehyde (2.74 g, 20 mmol) was added and the mixture was stirred at room temperature for 3 hours. The reaction mixture was cooled to 0° C. and 40 mL of water was added and stirred at 0° C. for 10 mins. The mixture was concentrated and purified by reverse phase HPLC on a C18/120 g column (A:

water 10 mM NH₄HCO₃, B: MeOH, 0~100%) to give (E)-5-(2-methoxyvinyl)-4-methylpyridin-2-ol as a red oil (1.5 g). Yield 45% (ESI 166.1 (M+H)⁺).

Step 3:
2-(6-hydroxy-4-methylpyridin-3-yl)acetaldehyde

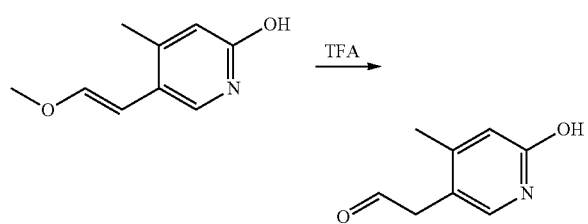

(E)-5-(2-methoxyvinyl)-4-methylpyridin-2-ol (1.5 g, 9.1 mmol) was treated with TFA (15 mL) at room temperature for 3 hours. The solvent was removed in vacuo to provide 2-(6-hydroxy-4-methylpyridin-3-yl)acetaldehyde as red oil (2.2 g, crude) used without further purification. (ESI 152.2 (M+H)⁺).

Step 4: 5-(2-(3-fluoroazetidin-1-yl)ethyl)-4-methylpyridin-2-ol

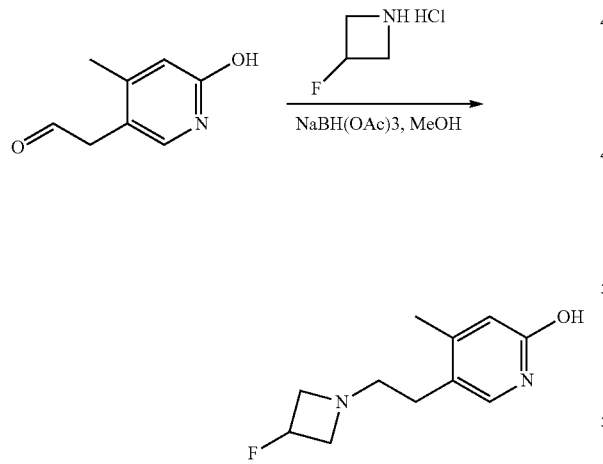

A mixture of 2-(6-hydroxy-4-methylpyridin-3-yl)acetaldehyde (2 g, 13.2 mmol), 3-fluoroazetidine hydrochloride (2.2 g, 19.8 mmol) in MeOH (20 mL) was stirred at room temperature for 30 mins. NaBH(OAc)₃ (5.6 g, 26.4 mmol) was added and stirred at room temperature for 2 hours. The solvent was removed in vacuo and the residue was purified by silica gel column (DCM:MeOH 2:1) to provide 5-(2-(3-fluoroazetidin-1-yl)ethyl)-4-methylpyridin-2-ol as yellow oil (1 g). Yield 36% (ESI 211.1 (M+H)⁺).

Step 5: ethyl 2-(5-(2-(3-fluoroazetidin-1-yl)ethyl)-4-methyl-2-oxopyridin-1(2H)-yl)-4-methylpentanoate

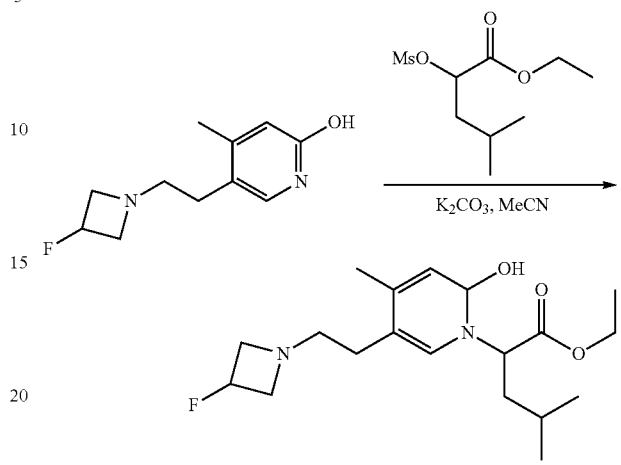

A mixture of methyl 5-(2-(dimethylamino)ethyl)pyridin-2(1H)-one (1 g, 4.76 mmol), ethyl 4-methyl-2-(methylsulfonyloxy)pentanoate (1.36 g, 5.71 mmol) and K₂CO₃(1.97 g, 14.28 mmol) in MeCN (20 mL) was stirred at 85° C. overnight. The solvent was removed in vacuo and the residue purified by silica gel column (DCM:MeOH 1:2) to provide t ethyl 2-(5-(2-(3-fluoroazetidin-1-yl)ethyl)-4-methyl-2-oxopyridin-1(2H)-yl)-4-methylpentanoate as a white solid (500 mg). Yield 30% (ESI 353.2 (M+H)⁺).

Step 6: 2-(5-(2-(3-fluoroazetidin-1-yl)ethyl)-4-methyl-2-oxopyridin-1(2H)-yl)-4-methylpentanoic acid

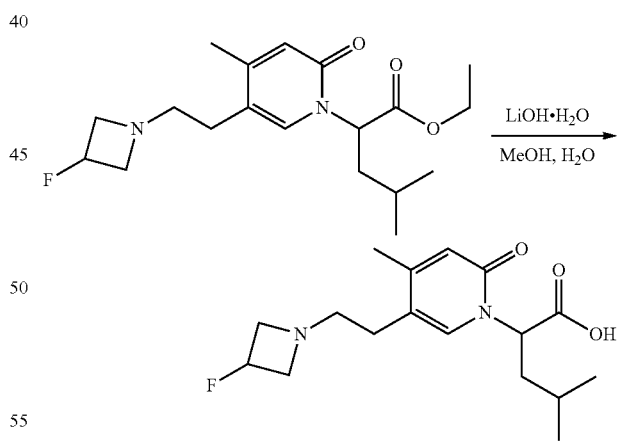

Ethyl 2-(5-(2-(3-fluoroazetidin-1-yl)ethyl)-4-methyl-2-oxopyridin-1(2H)-yl)-4-methylpentanoate (500 mg, 1.42 mmol) was treated with LiOH—H₂O (298 mg, 7.1 mmol) in MeOH (10 mL) and H₂O (2.5 mL) at room temperature for 2 hours. The mixture was acidified to pH 4~5 with 1N HCl, purified by reverse phase HPLC on a C18/40 g column (A: water 10 mM NH₄HCO₃, B: MeOH, 0~100%) to give 2-(5-(2-(3-fluoroazetidin-1-yl)ethyl)-4-methyl-2-oxopyridin-1(2H)-yl)-4-methylpentanoic acid as white solid (360 mg). Yield 78% (ESI 325.1 (M+H)⁺).

Step 7: (3S)-methyl 3-(2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoate

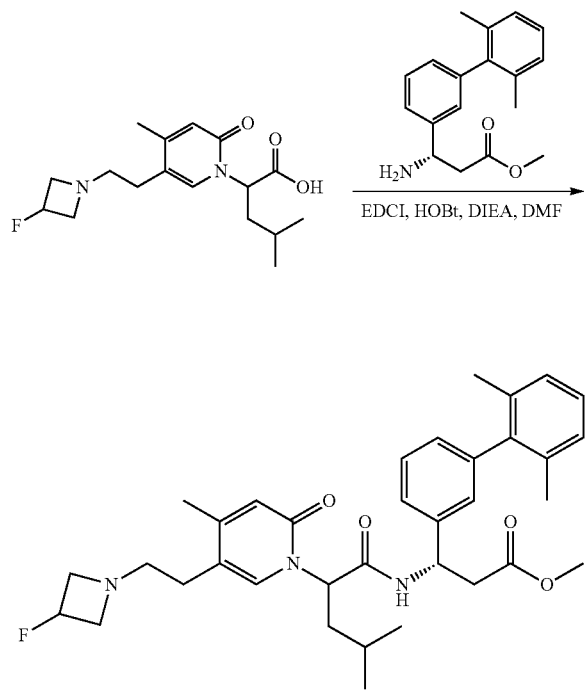

A mixture of 2-(5-(2-(3-fluoroazetidin-1-yl)ethyl)-4-methyl-2-oxopyridin-1(2H)-yl)-4-methylpentanoic acid (150 mg, 0.46 mmol), (S)-methyl 3-amino-3-(2',6'-dimethylbiphenyl-3-yl)propanoate (130 mg, 0.46 mmol), EDCI (177 mg, 0.92 mmol), HOBt (124 mg, 0.92 mmol) and DIEA (237 mg, 1.84 mmol) in DMF (4 mL) was stirred at room temperature 2 hours. The mixture was concentrated and purified by reverse phase HPLC on a C18/40 g column (A: water 10 mM NH$_4$HCO$_3$, B: MeOH, 0~100%) to give (3S)-methyl 3-(2',6'-dimethylbiphenyl-3-yl)-3-(2-(5-(2-((3-fluoroazetidin-1-yl)ethyl)-4-methyl-2-oxopyridin-1(2H)-yl)-4-methylpentanamido)propanoate as a yellow oil (200 mg). Yield 74% (ESI 590.2 (M+H)$^+$).

Step 8: (3S)-3-(2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoic acid

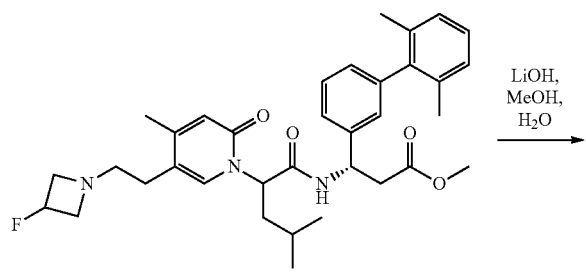

-continued

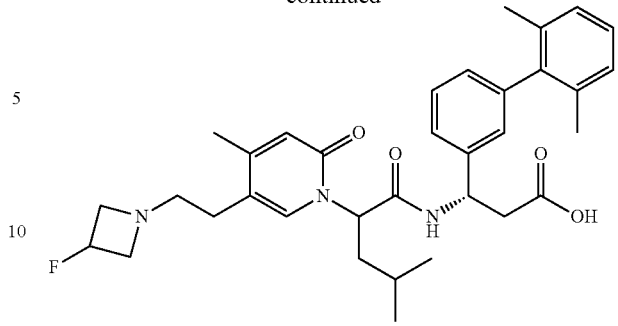

(3S)-methyl 3-(2',6'-dimethylbiphenyl-3-yl)-3-(2-(5-(2-(3-fluoroazetidin-1-yl)ethyl)-4-methyl-2-oxopyridin-1(2H)-yl)-4-methylpentanamido)propanoate (200 mg, 0.34 mmol) was treated with LiOH—H$_2$O (57 mg, 1.36 mmol) in MeOH (4 mL) and H$_2$O (1 mL) at room temperature for 2 hours. The reaction mixture was acidified to pH 4~5 with 1N HCl. The solvent was removed in vacuo and the residue purified by Prep-HPLC A (30-60% MeCN) to give the products BP1 (77 mg) and BP2 (80 mg) as white solids.

Compound BP1 ESI 576.2 (M+H)$^+$.

$^1$H NMR (500 MHz, MeOD) δ 7.52 (s, 1H), 7.40 (t, J=7.6 Hz, 1H), 7.32 (d, J=7.7 Hz, 1H), 7.17-7.11 (m, 1H), 7.08 (d, J=7.5 Hz, 2H), 7.05 (s, 1H), 7.00 (d, J=7.5 Hz, 1H), 6.38 (s, 1H), 5.65 (t, J=8.1 Hz, 1H), 5.37 (t, J=6.7 Hz, 1H), 5.18 (d, J=57.3 Hz, 1H), 4.01 (d, J=9.4 Hz, 2H), 3.80-3.55 (m, 2H), 3.05 (s, 2H), 2.78 (d, J=6.7 Hz, 2H), 2.66-2.61 (m, 2H), 2.25 (s, 3H), 2.00-1.87 (m, 8H), 1.42-1.39 (m, 1H), 0.95-0.92 (m, 6H).

Compound BP2 ESI 576.2 (M+H)$^+$.

1H NMR (500 MHz, MeOD) δ 7.46 (d, J=4.0 Hz, 1H), 7.43 (d, J=7.6 Hz, 1H), 7.35 (d, J=7.9 Hz, 1H), 7.14-7.10 (m, 2H), 7.10 (d, J=6.9 Hz, 2H), 7.04 (d, J=7.5 Hz, 1H), 6.46 (s, 1H), 5.62 (t, J=7.8 Hz, 1H), 5.45-5.41 (m, 1H), 5.31 (d, J=57.6 Hz, 1H), 4.31 (s, 2H), 3.93 (s, 2H), 3.30-3.17 (m, 2H), 2.84 (d, J=15.8 Hz, 1H), 2.73-2.61 (m, 2H), 2.62-2.53 (m, 1H), 2.26 (s, 3H), 2.01 (d, J=2.0 Hz, 6H), 1.93-1.89 (m, 1H), 1.82-1.73 (m, 1H), 1.39-1.35 (m, 1H), 0.91-0.88 (m, 6H).

Preparation of Compounds BQ1 and BQ2 ((3S)-3-(2-(3-(difluoromethyl)-5-(2-(dimethylamino)ethyl)-2-oxopyridin-1(2H)-yl)-4-methylpentanamido)-3-(4'-fluoro-2',6'-dimethyl-[1,1'-biphenyl]-3-yl)propanoic acid)

Step 1: 5-bromo-3-(difluoromethyl)-2-methoxypyridine

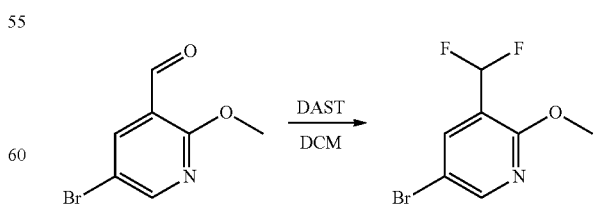

To a mixture of 5-bromo-2-methoxynicotinaldehyde (10.0 g, 46.3 mmol) in dry DCM (100 mL) under N$_2$ at 0° C. was added DAST (29.8 g, 185.2 mmol) and stirred at 0° C. for 2 days. The reaction was quenched with 100 mL of a saturated NaHCO₃ solution. The aqueous layer was extracted with DCM (100 mL×3). The combined organic layers were washed with NaHCO₃(sat, 100 mL) and brine (100 mL), dried over anhydrous Na₂SO₄, filtered and concentrated in vacuo to give 5-bromo-3-(difluoromethyl)-2-methoxypyridine as a yellow oil (11.0 g). Yield 100% (ESI 238.1 (M+H)⁺).

Step 2: 5-bromo-3-(difluoromethyl)pyridin-2-ol

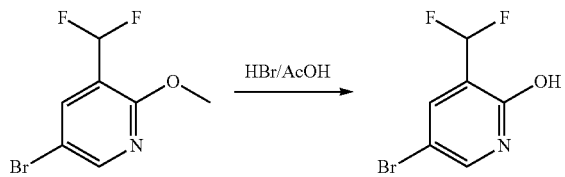

A mixture of 5-bromo-3-(difluoromethyl)-2-methoxypyridine (11.0 g, 46.2 mmol) in HBr (33% in acetic acid, 100 mL) was stirred at room temperature for 5 hours and then at 40° C. for 75 mins. The mixture was concentrated and poured into 100 mL of saturated NaHCO₃ solution and extracted with DCM. The combined organic layers dried over Na₂SO₄ and concentrated in vacuo to give 5-bromo-3-(difluoromethyl)pyridin-2-ol as a white solid (8.5 g) used without further purification. Yield 73.2% (ESI 226.0 (M+H)⁺).

Step 3: ethyl 2-(5-bromo-3-(difluoromethyl)-2-oxopyridin-1(2H)-yl)-4-methylpentanoate

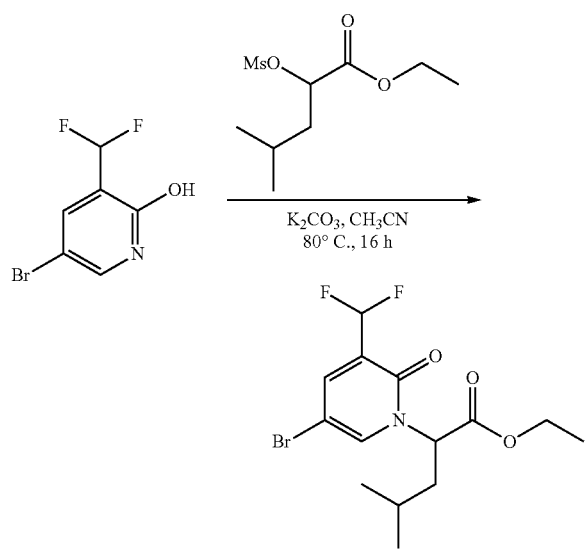

A mixture of 5-bromo-3-(difluoromethyl)pyridin-2-ol (7.0 g, 31.2 mmol), ethyl 4-methyl-2-((methylsulfonyl)oxy)pentanoate (14.0 g, 37.4 mmol) and K₂CO₃ (14.0 g, 62.5 mmol) in ACN (100 mL) was stirred at 80° C. overnight. The mixture was filtered and washed with ACN (20 mL). The filtrate was concentrated in vacuo and the residue purified by silica gel column (pet ether:EtOAc 4:1) to provide ethyl 2-(5-bromo-3-(difluoromethyl)-2-oxopyridin-1(2H)-yl)-4-methylpentanoate as a white solid (10.0 g). Yield 80.3% (ESI 366.0 (M+H)⁺).

Step 4: ethyl 2-(5-allyl-3-(difluoromethyl)-2-oxopyridin-1(2H)-yl)-4-methylpentanoate

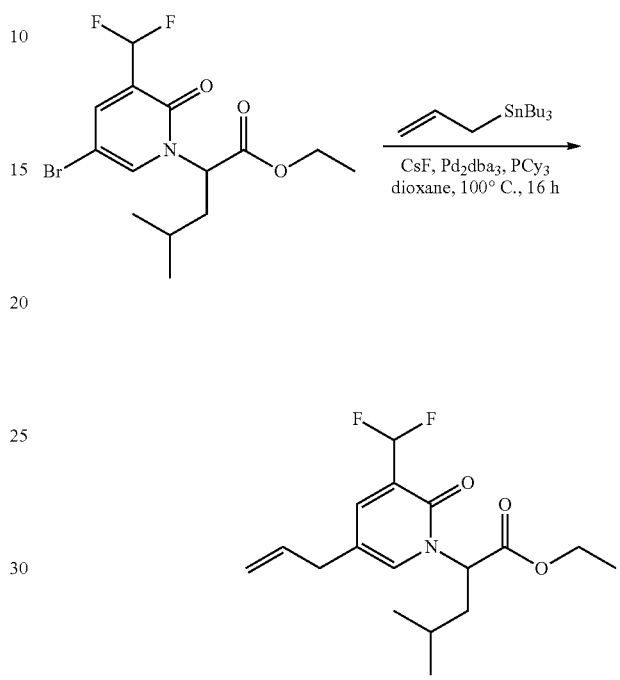

A mixture of ethyl 2-(5-bromo-3-(difluoromethyl)-2-oxopyridin-1(2H)-yl)-4-methylpentanoate (6.0 g, 16.2 mmol), allyltributylstannane (7.0 g, 19.2 mmol), CsF (5.0 g, 32.4 mmol), Pd(dba)₃ (720 mg, 1.62 mmol) and PCy₃ (450 mg, 0.135 mmol) in dioxane (100 mL) was stirred at 100° C. overnight. The mixture was poured into water (200 mL), extracted with EtOAc (100 mL×3). The combined organic layers were washed with brine (200 mL), dried over Na₂SO₄, filtered and concentrated in vacuo. The residue was purified by silica gel column (pet ether:EtOAc 4:1) to give ethyl 2-(5-allyl-3-(difluoromethyl)-2-oxopyridin-1(2H)-yl)-4-methylpentanoate as a white solid (3.0 g). Yield 71.6% (ESI 328.1 (M+H)⁺).

Step 5: ethyl 2-(3-(difluoromethyl)-2-oxo-5-(2-oxoethyl)pyridin-1(2H)-yl)-4-methylpentanoate

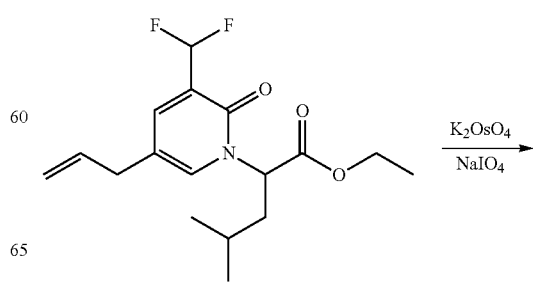

325

-continued

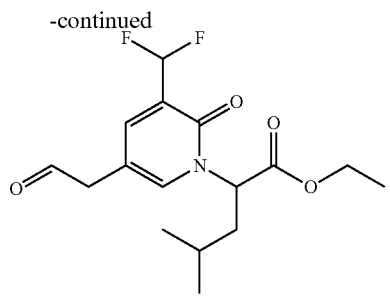

To a mixture of ethyl 2-(5-allyl-3-(difluoromethyl)-2-oxopyridin-1(2H)-yl)-4 (3.0 g, 9.1 mmol) in THF/H$_2$O (2/1, 100 mL) was added K$_2$OsO$_4$ (33.7 mg, 0.09 mmol) and stirred at room temperature for 1 hour. NaIO$_4$ (3.9, 18.3 mmol) was added and the mixture was stirred at room temperature for 2 hours. The mixture was poured into water (200 mL) and extracted with EtOAc (100 mL×3). The combined organic layers were washed brine (200 mL) and dried over Na$_2$SO$_4$, filtered and concentrated in vacuo to give ethyl 2-(3-(difluoromethyl)-2-oxo-5-(2-oxoethyl)pyridin-1(2H)-yl)-4-methylpentanoate as a yellow oil (3.0 g, crude) used without further purification. (ESI 330.1 (M+H)$^+$).

Step 6: ethyl 2-(3-(difluoromethyl)-5-(2-(dimethylamino)ethyl)-2-oxopyridin-1(2H)-yl)-4-methylpentanoate

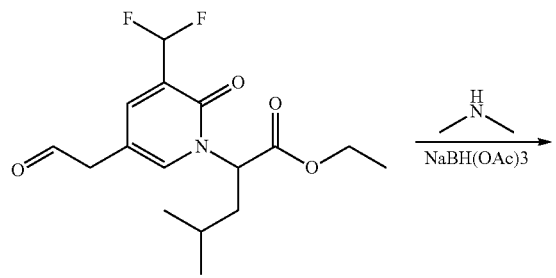

A mixture of ethyl 2-(3-(difluoromethyl)-2-oxo-5-(2-oxoethyl)pyridin-1(2H)-yl)-4-methylpentanoate (3.0 g, 9.1 mmol), dimethylamine (2M in THF, 14 mL, 28 mmol) in DCE (50 ml) was stirred at room temperature for 30 min. NaBH(OAc)$_3$ (3.8 g, 18.2 mmol) was added portion-wise and the reaction was stirred at room temperature overnight. The solvent was concentrated in vacuo and the residue purified by reverse phase HPLC on a C18/120 g column (A: water 10 mM NH$_4$HCO$_3$, B: MeOH, 0~100%) to give ethyl 2-(3-(difluoromethyl)-5-(2-(dimethylamino)ethyl)-2-oxopyridin-1(2H)-yl)-4-methylpentanoate as a yellow oil (2.0 g). Yield 33.6% (ESI 359.2 (M+H)$^+$).

326

Step 7: 2-(3-(difluoromethyl)-5-(2-(dimethylamino)ethyl)-2-oxopyridin-1(2H)-yl)-4-methylpentanoic acid

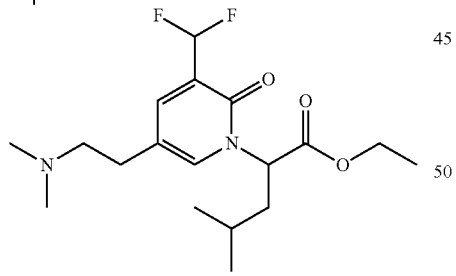

A mixture of ethyl 2-(3-(difluoromethyl)-5-(2-(dimethylamino)ethyl)-2-oxopyridin-1(2H)-yl)-4-methylpentanoate (2.0 g, 5.5 mmol) was treated with LiOH—H$_2$O (40 mg, 1.01 mmol) in THF (20 mL) and water (10 mL) at room temperature for 2 hours. The solvent was removed in vacuo and the residue purified by reverse phase HPLC on a C18/120 g column (A: water 10 mM NH$_4$HCO$_3$, B: MeOH, 0~100%) to give the to give 2-(3-(difluoromethyl)-5-(2-(dimethylamino)ethyl)-2-oxopyridin-1(2H)-yl)-4-methylpentanoic acid as a white solid (1.2 g). Yield 85.6% (ESI 331.1 (M+H)$^+$).

Step 8: ethyl (3S)-3-(2-(3-(difluoromethyl)-5-(2-(dimethylamino)ethyl)-2-oxopyridin-1(2H)-yl)-4-methylpentanamido)-3-(4'-fluoro-2',6'-dimethyl-[1,1'-biphenyl]-3-yl)propanoate

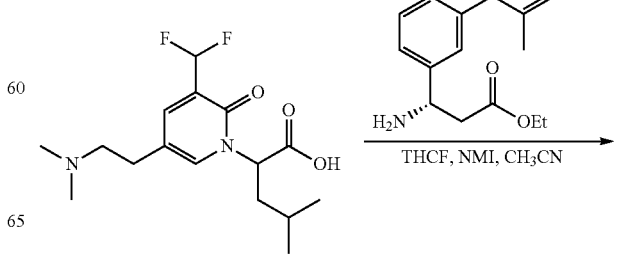

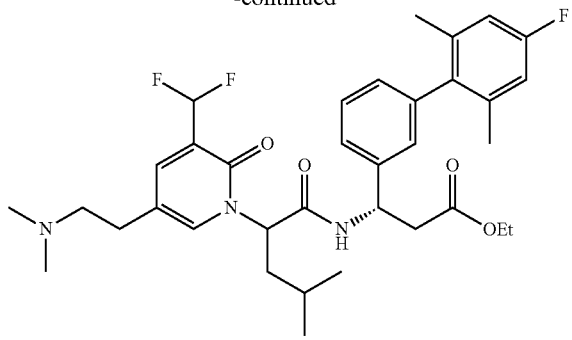

A mixture of 2-(3-(difluoromethyl)-5-(2-(dimethylamino)ethyl)-2-oxopyridin-1(2H)-yl)-4-methylpentanoic acid (120 mg, 0.36 mmol), ethyl (S)-3-amino-3-(4'-fluoro-2',6'-dimethyl-[1,1'-biphenyl]-3-yl)propanoate (137 mg, 0.43 mmol), TCFH (151.2 mg, 0.54 mmol) and NMI (149 mg, 1.8 mmol) in MeCN (5 mL) was stirred at room temperature for 1 hour. The sovent was removed in vacuo and the residue purified by silica gel column (DCM:MeOH 10:1) to give ethyl (3S)-3-(2-(3-(difluoromethyl)-5-(2-(dimethylamino)ethyl)-2-oxopyridin-1 (2H)-yl)-4-methylpentanamido)-3-(4'-fluoro-2',6'-dimethyl-[1,1'-biphenyl]-3-yl)propanoate as a yellow solid (140 mg). Yield 61% (ESI 628 (M+H)$^+$).

Step 12: (3S)-3-(2-(3-(difluoromethyl)-5-(2-(dimethylamino)ethyl)-2-oxopyridin-1(2H)-yl)-4-methylpentanamido)-3-(4'-fluoro-2',6'-dimethyl-[1,1'-biphenyl]-3-yl)propanoic acid

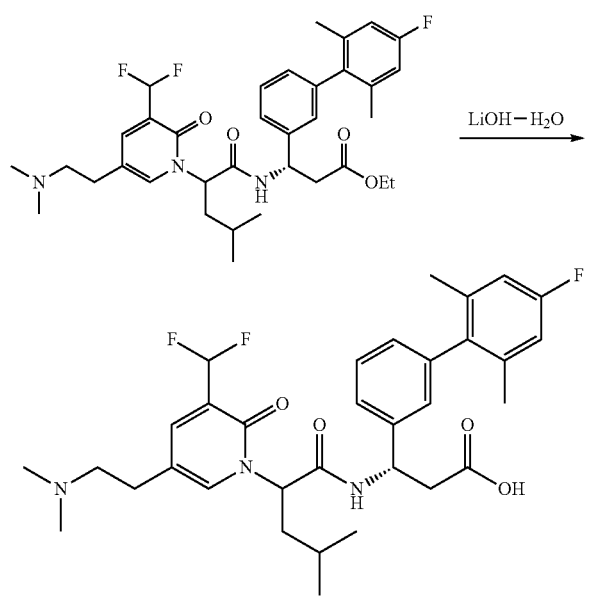

Ethyl (3S)-3-(2-(3-(difluoromethyl)-5-(2-(dimethylamino)ethyl)-2-oxopyridin-1(2H)-yl)-4-methylpentanamido)-3-(4'-fluoro-2',6'-dimethyl-[1,1'-biphenyl]-3-yl)propanoate (140 mg, 0.22 mmol) was treated with LiOH—H$_2$O (46.8 mg, 1.1 mmol) in EtOH (3 mL) and H$_2$O (1 mL) at room temperature for 2 hours. The reaction mixture was acidified to pH 4~5 with 1N HCl. The solvent was removed in vacuo and the residue purified by prep-HPLC A (30-60% MeCN) to give the diastereomeric products BQ1 (11 mg) and BQ2 (14 mg) as white solids.

Compound BQ1 ESI 600.2 (M+H)$^+$. $^1$H NMR (400 MHz, MeOD) δ 7.89 (d, J=15.3 Hz, 2H), 7.39 (t, J=7.6 Hz, 1H), 7.31 (d, J=7.8 Hz, 1H), 7.05 (s, 1H), 7.00-6.96 (m, 1H), 6.74-6.64 (m, 3H), 5.67-5.58 (m, 1H), 5.21 (t, J=5.9 Hz, 1H), 3.23-3.15 (m, 6.4 Hz, 1H), 3.04-2.86 (m, 3H), 2.76 (s, 6H), 2.68-2.59 (m, 2H), 2.03-1.93 (m, 8H), 1.45 (s, 1H), 0.96-0.92 (m, 6H).

Compound BQ2 ESI 600.3 (M+H)$^+$. $^1$H NMR (400 MHz, MeOD) δ 7.84 (d, J=10.8 Hz, 2H), 7.42 (t, J=7.6 Hz, 1H), 7.33 (d, J=7.8 Hz, 1H), 7.08 (s, 1H), 7.01 (d, J=7.5 Hz, 1H), 6.89-6.60 (m, 3H), 5.65-5.58 (m, 1H), 5.38-5.32 (m, 1H), 3.45-3.36 (m, 1H), 3.27-3.19 (m, 1H), 3.00-2.81 (m, 8H), 2.64-2.58 (m, 1H), 2.50-2.42 (m, 1H), 2.05-1.98 (m, 7H), 1.85-1.78 (m, 1H), 1.48-1.39 (m, 1H), 0.96-0.89 (m, 6H).

Example 4: Fluorescence Polarization Assays of Compounds for α4β7 Binding

Fluorescence Polarization (FP) assays were used to measure compound activity through binding competition with the fluorescein-labeled peptide CRSDTLCGE{Lys(FITC)}. In the assay, 6.5 nM of integrin a4b7 was incubated with the test compound in 2 mM manganese chloride, 0.1 mM calcium chloride, 20 mM HEPES buffer at pH 7.3, 150 mM sodium chloride, 0.01% Triton X-100, 2% DMSO, and 3 nM of the fluorescein-labeled peptide. Running the assays in 384-well plates, the integrin protein was pre-incubated with the test compounds for 15 minutes at 22° C. before the fluorescein-labeled peptide was added. After the fluorescein-labeled peptide was added, the assay was incubated at 22° C. for 1 hour and fluorescence polarization was measured. IC$_{50}$ values were determined by nonlinear regression, four-parameter curve fitting.

INCORPORATION BY REFERENCE

All of the U.S. patents and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound represented by formula (I):

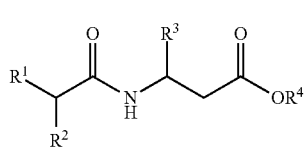

wherein:
R$^1$ is H, alkyl, alkylene-cycloalkyl, heterocyclyl, alkylene-O-alkyl, aryl, heteroaryl, or alkylene-CF$_3$;
R$^2$ is a 6- to 12-membered N-containing heterocyclyl;
R$^3$ is

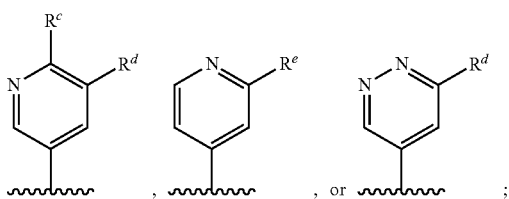

R⁴ is H, or (C₁-C₆)-alkyl;

$R^c$ is H, alkyl, —CF₃, halogen, cycloalkyl, heterocyclyl, or alkylene-CF₃, $R^d$ is aryl, heteroaryl, heterocyclyl, —O-cycloalkyl, —O-aryl, or —O-heterocyclyl; and $R^e$ is aryl, heteroaryl, or heterocyclyl;

or a pharmaceutically acceptable salt thereof;

provided that the compound is not

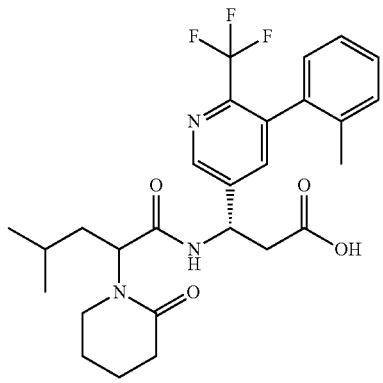

2. The compound of claim 1, wherein $R^2$ is substituted with one or more substituents selected from amino, alkyl and alkoxy.

3. The compound of claim 1, wherein $R^2$ is substituted with one or more substituents selected from amino, alkyl and alkoxy; and
  each alkyl or alkoxy substituent in $R^2$ is independently substituted with one or more substituents selected from morpholino, cyclic amino, and acyclic amino.

4. The compound of claim 1, wherein $R^2$ is substituted with one or more substituents selected from amino, alkyl and alkoxy;
  each alkyl or alkoxy substituent in $R^2$ is independently substituted with one or more substituents selected from alkoxy, fluorine, morpholino, cyclic amino, and acyclic amino;
  and
  each morpholino, cyclic amino, or acyclic amino moiety in $R^2$ is independently substituted with one or more substituents selected from alkoxy and fluorine.

5. The compound of claim 1, wherein $R^1$ is selected from methyl, ethyl, isopropyl, n-propyl, i-butyl, n-butyl, and t-butyl.

6. The compound of claim 5, wherein $R^1$ is i-butyl.

7. The compound of claim 1, wherein $R^2$ is selected from

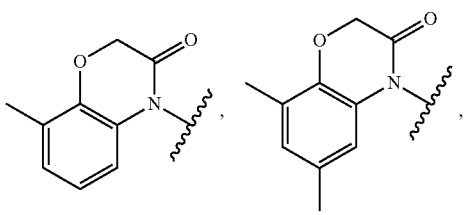

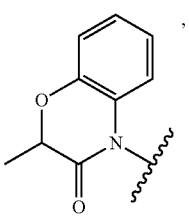

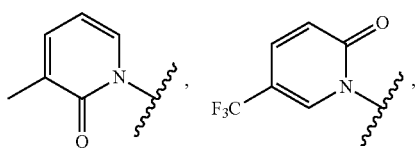

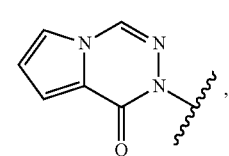

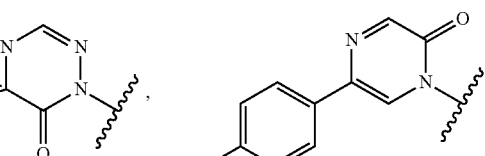

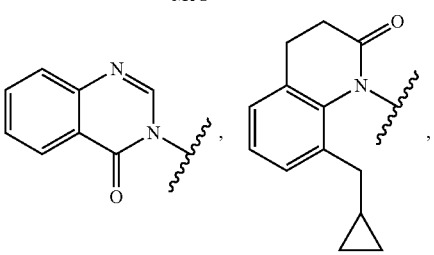

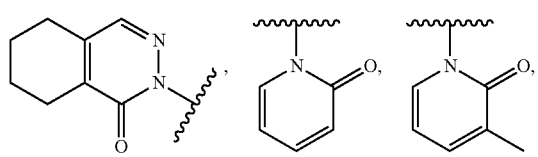

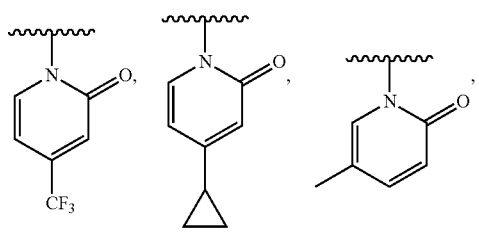

-continued
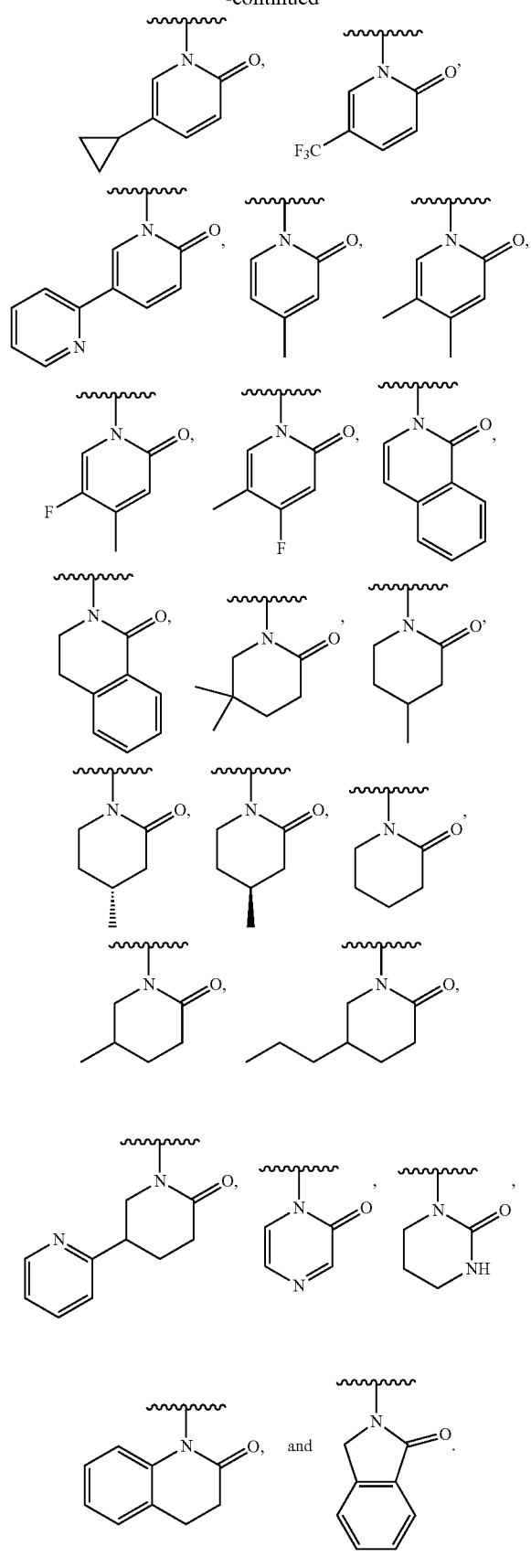
8. The compound of claim 1, wherein $R^2$ is selected from
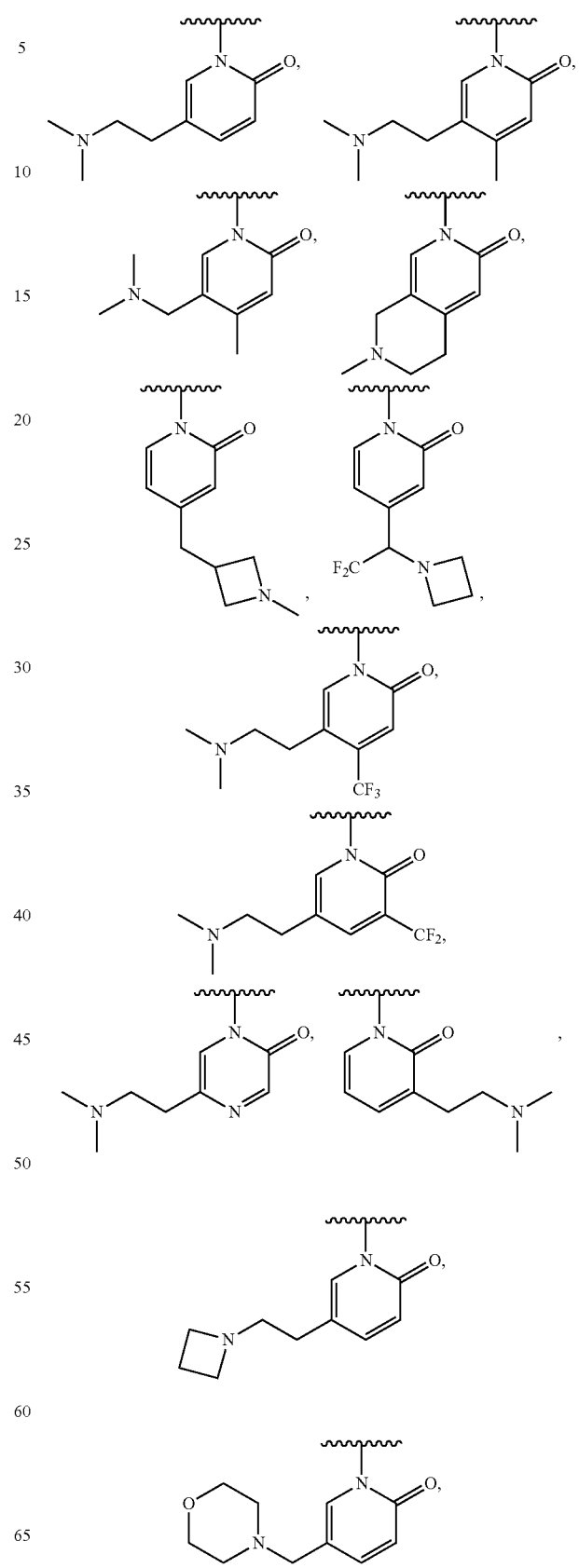

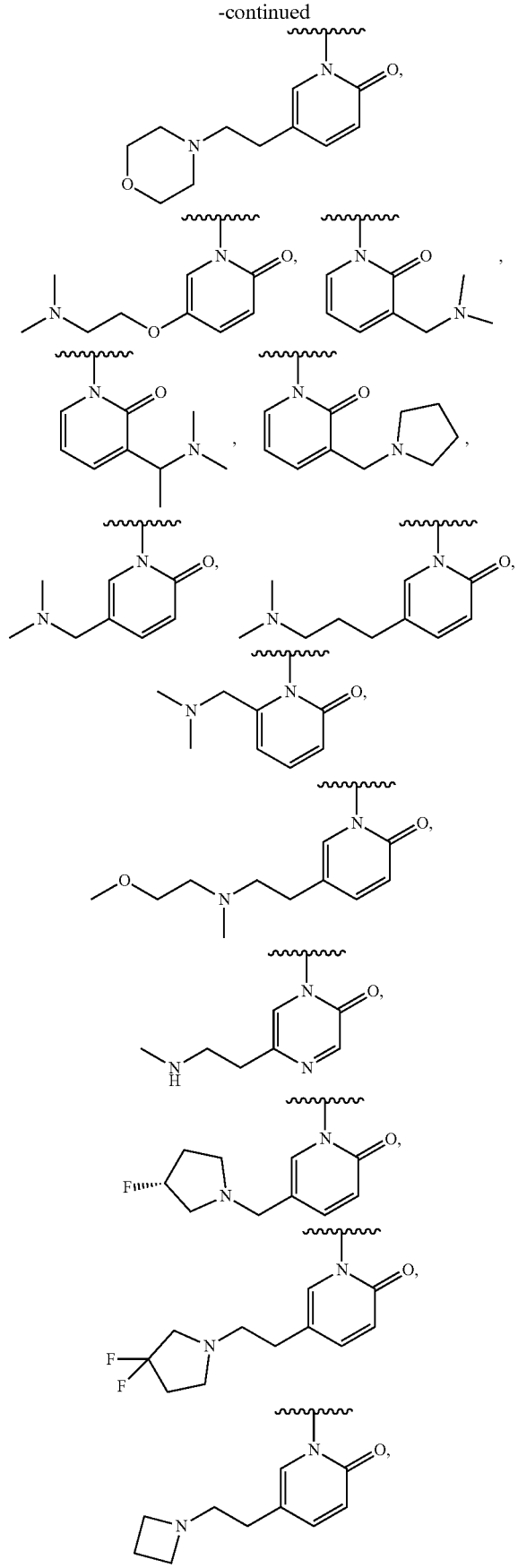
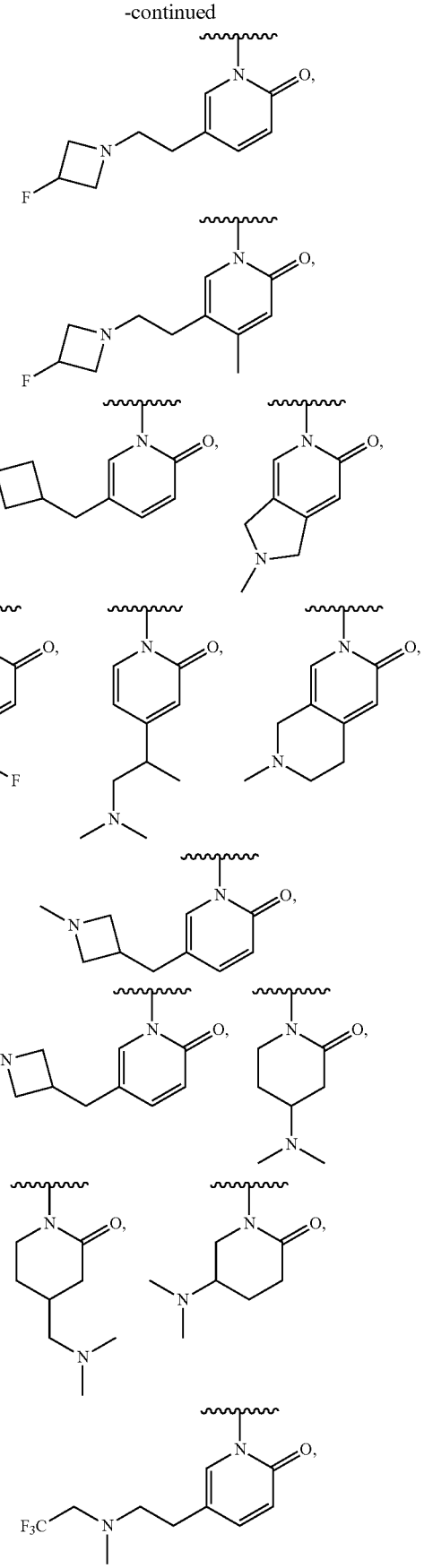

-continued

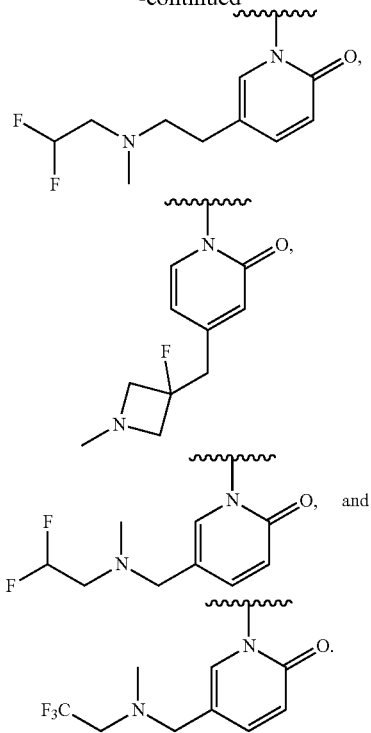

9. The compound of claim 1, wherein $R^4$ is H.
10. The compound of claim 9, wherein
   a. $R^1$ is alkyl;
   b. $R^2$ is optionally substituted with one or more substituents selected from amino, alkyl and alkoxy; and
   c. $R^d$ is aryl, heteroaryl, or heterocyclyl.
11. The compound of claim 10, wherein
   a. $R^1$ is $(C_1\text{-}C_6)$alkyl;
   b. $R^c$ is H, alkyl, or $CF_3$; and
   c. $R^e$ is substituted phenyl or unsubstituted phenyl.
12. The compound of claim 11, wherein
   $R^2$ is substituted with one or more substituents selected from amino, alkyl and alkoxy;
   each alkyl or alkoxy in $R^2$ is independently substituted with one or more substituents selected from alkoxy, fluorine, morpholino, cyclic amino, and acyclic amino; and
   each morpholino, cyclic amino, or acyclic amino in $R^2$ is independently substituted with one or more substituents selected from alkoxy and fluorine.
13. The compound of claim 12, wherein $R^2$ is unsubstituted or substituted pyridinonyl.
14. The compound of claim 12, wherein $R^3$ is

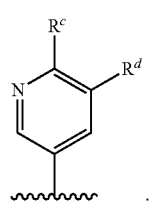

15. The compound of claim 12, wherein $R^3$ is

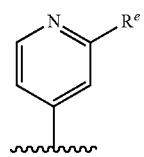

16. The compound of claim 12, wherein $R^3$ is

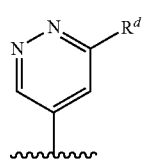

17. The compound of claim 12, wherein $R^d$ is selected from

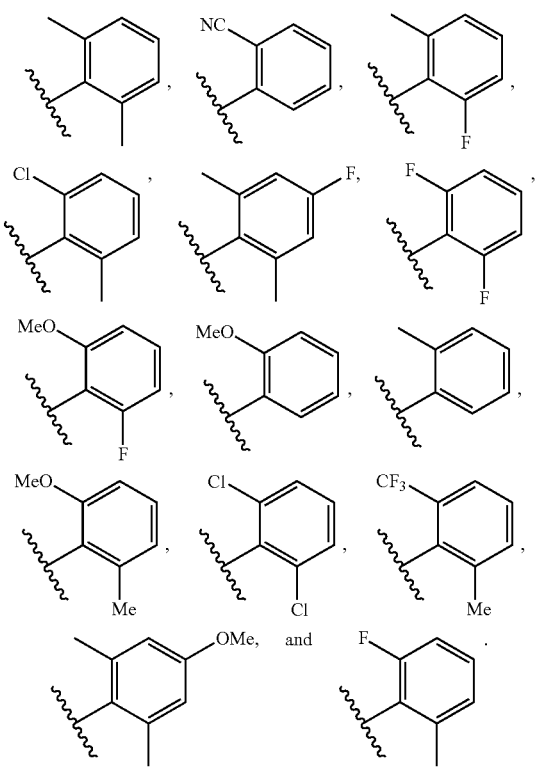

18. The compound of claim 12, wherein $R^d$ is selected from

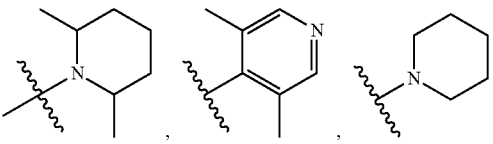

-continued
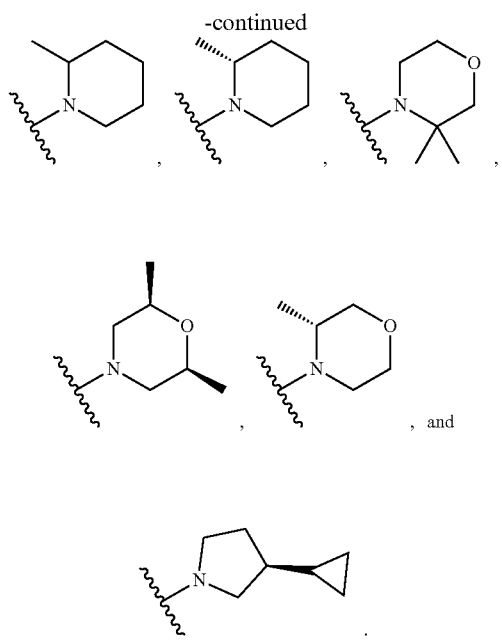
19. The compound of claim 12, wherein
   a. $R^d$ is
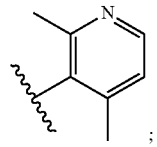 [SMILES: *c1c(C)ccnc1C]
and
   b. $R^e$ is
, , or .
20. A pharmaceutical composition comprising a compound of claim 1, or a pharmaceutically acceptable salt thereof.
* * * * *